US006656700B2

(12) United States Patent
Gu et al.

(10) Patent No.: US 6,656,700 B2

(45) Date of Patent: Dec. 2, 2003

(54) ISOFORMS OF HUMAN PREGNANCY-ASSOCIATED PROTEIN-E

(75) Inventors: Yizhong Gu, Sunnyvale, CA (US); Mark E. Shannon, Livermore, CA (US)

(73) Assignee: Amersham PLC, Buckinghamshire (GB)

(*) Notice: Subject to any disclaimer, the term of this patent is extended or adjusted under 35 U.S.C. 154(b) by 0 days.

(21) Appl. No.: 09/827,998

(22) Filed: Apr. 6, 2001

(65) Prior Publication Data

US 2002/0102252 A1 Aug. 1, 2002

Related U.S. Application Data

(60) Provisional application No. 60/207,456, filed on May 26, 2000, and provisional application No. 60/236,359, filed on Sep. 27, 2000.

(51) Int. Cl.[7] .......................... C12N 9/50; C12N 15/79; C12N 1/21; C12N 5/10; C12Q 1/37

(52) U.S. Cl. ...................... 435/23; 435/219; 435/320.1; 435/325; 435/252.3; 536/23.2; 514/44

(58) Field of Search ....................... 435/23, 219, 320.1, 435/325, 252.3; 536/23.2; 514/44

(56) References Cited

U.S. PATENT DOCUMENTS

| | | | | |
|---|---|---|---|---|
| 3,687,808 | A | 8/1972 | Merigan, Jr. et al. | 435/91.3 |
| 3,980,986 | A | 9/1976 | Baird et al. | 367/82 |
| 4,246,774 | A | 1/1981 | Flesselles et al. | 73/38 |
| 4,469,863 | A | 9/1984 | Ts'o et al. | 536/24.5 |
| 4,476,301 | A | 10/1984 | Imbach et al. | 536/25.2 |
| 4,708,871 | A | 11/1987 | Geysen | 424/186.1 |
| 5,023,243 | A | 6/1991 | Tullis | 514/44 |
| 5,034,506 | A | 7/1991 | Summerton et al. | 528/391 |
| 5,166,315 | A | 11/1992 | Summerton et al. | 528/406 |
| 5,177,196 | A | 1/1993 | Meyer, Jr. et al. | 536/22.1 |
| 5,185,444 | A | 2/1993 | Summerton et al. | 544/81 |
| 5,186,042 | A | 2/1993 | Miyazaki | 73/118.1 |
| 5,188,897 | A | 2/1993 | Suhadolnik et al. | 428/402.2 |
| 5,214,134 | A | 5/1993 | Weis et al. | 536/25.3 |
| 5,216,141 | A | 6/1993 | Benner | 536/27.13 |

(List continued on next page.)

FOREIGN PATENT DOCUMENTS

| | | |
|---|---|---|
| WO | WO 96/18412 | 6/1996 |
| WO | WO 96/32478 | 10/1996 |
| WO | WO 97/19193 | 5/1997 |
| WO | WO 97/34631 | 9/1997 |
| WO | WO 97/43316 | 11/1997 |
| WO | WO 98/12559 | 3/1998 |
| WO | WO 98/59360 | 12/1998 |
| WO | WO 98/59361 | 12/1998 |
| WO | WO 98/59362 | 12/1998 |
| WO | WO 99/58720 | 11/1999 |
| WO | WO 00/15779 | 3/2000 |

OTHER PUBLICATIONS

Witkowski et al. , Biochemistry 38:11643–11650, 1999.*

Broun et al. , Science 282:1315–1317, 1998.*

Van de Loo et al. , Proc. Natl. Acad. Sci. 92:6743–6747, 1995.*

Seffernick et al. , J. Bacteriol. 183(8):2405–2410, 2001.*

Ailor et al., "Overexpression of a Cystolic Chaperone in Insect Cells," *Biotechnology & Bioengineering, vol. 58 No.* 2& 3: pp. 196–203 (Apr. 20/May 5, 1998).

Alers et al., "Universal Linkage System: An Improved Method for Labeling Archival DNA for Comparative Genomic Hybridization," *Genes, Chromosomes, and Cancer vol. 25:* pp. 301–305 (1999).

Allen et al., "Finding Prospective Partners in the Library: The Two–Hybrid System and Phage Display Find a Match," *Trends in Biochemical Science vol. 20:* pp. 511–516 (Dec. 1995).

Aujame et al., "High Affinity Human Antibodies by Phage Display," *Human Antibodies vol. 8 No. 4:* pp. 155–168 (1997).

Baner et al., "More Keys to Padlock Probes: Mechanisms for High–Throughput Nucleic Acid Analysis," *Current Opinion in Biotechnology vol. 12:* pp. 11–15 (2001).

Barbas et al., "Selection of Human Anti–Viral Antibodies," *Trends in Biotechnology vol. 14:* pp. 230–234 (1996).

Becker et al., "High–Efficiency Transformation of Yeast by Electroporation," *Methods in Enzymology vol. 194:* pp. 182–187 (1991).

Brenner et al., "In Vitro Cloning of Complex Mixtures of DNA on Microbeads: Physical Separation of Differentially Expressed cDNAs," Proc. *Nat. Acad. Sci. USA vol. 97 No. 4:* pp. 16650–16670 (2000).

Brett et al., "EST Comparison Indicated 38% of Human mRNAs Contain Possible Alternative Splice Forms," *FEBS Letters vol. 474 No. 1:* pp. 83–86 (2000).

(List continued on next page.)

*Primary Examiner*—Rebecca E. Prouty

(74) *Attorney, Agent, or Firm*—Fish & Neave; Daniel M. Becker; David A. Roise

(57) ABSTRACT

The invention provides isolated nucleic acids that encode three novel isoforms of human pregnancy associated plasma protein E, hPAPP-E, and fragments thereof, vectors for propagating and expressing PAPP-E nucleic acids, host cells comprising the nucleic acids and vectors of the present invention, proteins, protein fragments, and protein fusions of the novel PAPP-E isoforms, and antibodies thereto. The invention further provides transgenic cells and non-human organisms comprising human PAPP-E isoform nucleic acids, and transgenic cells and non-human organisms with targeted disruption of the endogenous orthologue of the human PAPP-E gene. The invention further provides pharmaceutical formulations of the nucleic acids, proteins, and antibodies of the present invention, and diagnostic, investigational, and therapeutic methods based on the PAPP-E nucleic acids, proteins, and antibodies of the present invention.

14 Claims, 28 Drawing Sheets

U.S. PATENT DOCUMENTS 5,235,033 A 8/1993 Summerton et al. ........ 528/391
5,264,423 A 11/1993 Cohen et al. ................ 514/44
5,264,562 A 11/1993 Matteucci ................. 536/23.1
5,264,564 A 11/1993 Matteucci ................. 536/23.1
5,272,071 A 12/1993 Chappel ........................ 435/6
5,276,019 A 1/1994 Cohen et al. ................ 514/44
5,278,302 A 1/1994 Caruthers et al. .......... 536/24.5
5,279,044 A 1/1994 Bremer ........................ 33/706
5,286,717 A 2/1994 Cohen et al. ................ 514/44
5,321,131 A 6/1994 Agrawal et al. ......... 536/25.34
5,399,676 A 3/1995 Froehler .................... 536/23.1
5,405,938 A 4/1995 Summerton et al. ........ 528/406
5,405,939 A 4/1995 Suhadolnik et al. ........ 530/322
5,434,257 A 7/1995 Matteucci et al. ......... 536/24.3
5,445,934 A 8/1995 Fodor et al. ................... 435/6
5,453,496 A 9/1995 Caruthers et al. .......... 536/24.5
5,455,233 A 10/1995 Spielvogel et al. ........... 514/44
5,464,764 A 11/1995 Capecchi et al. .............. 435/6
5,466,677 A 11/1995 Baxter et al. ................. 514/44
5,470,967 A 11/1995 Huie et al. ................. 536/24.3
5,476,925 A 12/1995 Letsinger et al. .......... 536/23.1
5,487,992 A 1/1996 Capecchi et al. .............. 435/6
5,489,677 A 2/1996 Sanghvi et al. ............ 536/22.1
5,519,126 A 5/1996 Hecht ........................ 536/24.3
5,527,695 A 6/1996 Hodges et al. .............. 800/291
5,536,821 A 7/1996 Agrawal et al. ........... 536/22.1
5,538,848 A 7/1996 Livak et al. ................... 435/6
5,539,082 A 7/1996 Nielsen et al. .............. 530/300
5,539,084 A 7/1996 Geysen ....................... 530/334
5,541,306 A 7/1996 Agrawal et al. ........... 536/22.1
5,541,307 A 7/1996 Cook et al. ................ 536/23.1
5,545,806 A 8/1996 Lonberg et al. ................ 800/6
5,545,807 A 8/1996 Surani et al. .................. 800/6
5,550,111 A 8/1996 Suhadolnik et al. .......... 514/44
5,561,225 A 10/1996 Maddry et al. ............ 536/23.1
5,563,253 A 10/1996 Agrawal et al. ........... 536/22.1
5,569,825 A 10/1996 Lonberg et al. ............... 800/18
5,570,694 A 11/1996 Rometsch ................... 600/493
5,571,799 A 11/1996 Tkachuk et al. .............. 514/47
5,587,361 A 12/1996 Cook et al. ................... 514/44
5,589,466 A 12/1996 Feigner et al. ................ 514/44
5,591,669 A 1/1997 Krimpenfort et al. ......... 800/11
5,595,915 A 1/1997 Geysen ....................... 436/518
5,596,086 A 1/1997 Matteucci et al. ......... 536/22.1
5,602,240 A 2/1997 De Mesmaeker et al. . 536/22.1
5,608,046 A 3/1997 Cook et al. ................ 536/23.1
5,610,289 A 3/1997 Cook et al. ............. 536/25.34
5,614,396 A 3/1997 Bradley et al. ............. 435/463
5,618,704 A 4/1997 Sanghvi et al. ............ 435/91.5
5,623,070 A 4/1997 Cook et al. ................ 536/27.6
5,625,048 A 4/1997 Tsien et al. ................ 536/23.4
5,625,050 A 4/1997 Beaton et al. ............. 536/24.1
5,625,126 A 4/1997 Lonberg et al. ............... 800/18
5,627,052 A 5/1997 Schrader .................... 435/69.6
5,627,059 A 5/1997 Capecchi et al. ............. 800/21
5,631,153 A 5/1997 Capecchi et al. .............. 435/6
5,633,360 A 5/1997 Bischofberger et al. ... 536/22.1
5,633,425 A 5/1997 Lonberg et al. ............... 800/18
5,661,016 A 8/1997 Lonberg et al. ............ 435/452
5,663,312 A 9/1997 Chaturvedula ............. 536/22.1
5,677,437 A 10/1997 Teng et al. ................ 536/23.1
5,677,439 A 10/1997 Weis et al. ................ 536/23.1
5,679,647 A 10/1997 Carson et al. ................ 514/44
5,693,761 A 12/1997 Queen et al. ............ 536/23.53
5,714,320 A 2/1998 Kool ............................ 435/6
5,714,331 A 2/1998 Buchardt et al. .............. 435/6
5,719,262 A 2/1998 Buchardt et al. ........... 530/300
5,723,591 A 3/1998 Livak et al. ............... 536/22.1
5,731,181 A 3/1998 Kmiec ........................... 435/6
5,741,668 A 4/1998 Ward et al. ................ 435/69.1
5,744,305 A 4/1998 Fodor et al. ................... 435/6
5,756,325 A 5/1998 Kmiec ........................ 435/463
5,760,012 A 6/1998 Kmiec .......................... 514/44
5,766,886 A 6/1998 Studnicka et al. ....... 435/70.21
5,770,196 A 6/1998 Studnicka ................ 424/133.1
5,770,429 A 6/1998 Lonberg et al. ............. 435/328
5,777,079 A 7/1998 Tsien et al. ................. 530/350
5,780,296 A 7/1998 Holloman et al. ....... 435/320.1
5,783,674 A 7/1998 Geysen ....................... 530/413
5,789,650 A 8/1998 Lonberg et al. ............... 800/18
5,795,972 A 8/1998 Kmiec ....................... 536/23.1
5,804,387 A 9/1998 Cormack et al. .............. 435/6
5,804,566 A 9/1998 Carson et al. ................ 514/44
5,807,715 A 9/1998 Morrison et al. .......... 435/69.6
5,814,318 A 9/1998 Lonberg et al. .......... 424/184.1
5,821,123 A 10/1998 Studnicka ................... 435/328
5,821,337 A 10/1998 Carter et al. ............. 530/387.3
5,824,269 A 10/1998 Kosaka et al. ................ 422/73
5,830,877 A 11/1998 Carson et al. ................ 514/44
5,843,913 A 12/1998 Li et al. ....................... 514/44
5,846,726 A 12/1998 Nadeau et al. ................. 435/6
5,854,033 A 12/1998 Lizardi ...................... 435/91.2
5,869,619 A 2/1999 Studnicka ................ 530/387.3
5,871,984 A 2/1999 Kmiec ........................ 435/463
5,874,299 A 2/1999 Lonberg et al. .......... 435/320.1
5,874,304 A 2/1999 Zolotukhin et al. ......... 435/366
5,877,397 A 3/1999 Lonberg et al. ............... 800/18
5,880,104 A 3/1999 Li et al. ....................... 514/44
5,888,983 A 3/1999 Kmiec et al. ................. 514/44
5,889,351 A 3/1999 Okumura et al. ........... 310/321
5,925,517 A 7/1999 Tyagi et al. ................... 435/6
5,930,143 A 7/1999 Savazzi ...................... 700/195
5,939,598 A 8/1999 Kucherlapati et al. ........ 800/25
5,945,339 A 8/1999 Holloman et al. .......... 435/477
5,958,891 A 9/1999 Hsu et al. ..................... 514/44
5,968,750 A 10/1999 Zolotukhin et al. ............ 435/6
5,981,214 A 11/1999 Skoultchi .................. 435/69.1
5,984,175 A 11/1999 Popp .......................... 235/375
5,985,847 A 11/1999 Carson et al. ................ 514/44
6,001,233 A 12/1999 Levy .......................... 204/618
6,004,744 A 12/1999 Goelet et al. .................. 435/5
6,004,752 A 12/1999 Loewy et al. .................. 435/6
6,013,256 A 1/2000 Light et al. ............. 424/133.1
6,016,191 A 1/2000 Ramos et al. ................. 356/70
6,017,897 A 1/2000 Li et al. ....................... 514/44
6,025,201 A 2/2000 Zelmanovic et al. ......... 436/63
6,027,881 A 2/2000 Pavlakis et al. ............... 435/6
6,042,549 A 3/2000 Amano et al. .............. 600/500
6,046,800 A 4/2000 Ohtomo et al. .......... 356/141.1
6,048,524 A 4/2000 Selden et al. ............ 424/93.21
6,051,831 A 4/2000 Koster ........................ 250/281
6,054,297 A 4/2000 Carter et al. ............... 435/69.6
6,054,321 A 4/2000 Tsien et al. ................... 436/86
6,063,630 A 5/2000 Treco et al. ................ 435/463
6,066,476 A 5/2000 Tsien et al. ................ 435/69.7
6,075,181 A 6/2000 Kucherlapati et al. ........ 800/25
6,090,919 A 7/2000 Cormack et al. ........... 530/350
6,096,865 A 8/2000 Michaels .................... 530/350
6,110,898 A 8/2000 Malone et al. ................ 514/44
6,114,598 A 9/2000 Kucherlapati et al. ........ 800/18
6,124,128 A 9/2000 Tsien et al. ............ 435/252.33
6,150,584 A 11/2000 Kucherlapati et al. ........ 800/18
6,162,963 A 12/2000 Kucherlapati et al. ........ 800/18
6,180,370 B1 1/2001 Queen et al. .............. 435/69.6
6,180,377 B1 1/2001 Morgan et al. .......... 424/133.1
6,187,305 B1 2/2001 Treco et al. ............. 424/93.21
6,204,061 B1 3/2001 Capecchi et al. ........... 435/463
6,204,250 B1 3/2001 Bot et al. ..................... 514/44

OTHER PUBLICATIONS

Chan et al., "Triplex DNA: Fundamentals, Advances, and Potential Applications for Gene Therapy," *Mol. Med. vol. 75 No. 4:* pp. 267–282 (1997).

Chen et al., "Herbicide Resistance from a Divide EPSPS Protein: The Split Synechocystis DnaE Intein as an In Vivo Affinity Domain," *Gene vol. 263:* pp. 39–48 (2001).

Chenchik et al., "Full Length cDNA Cloning and Determination of mRNA 5' and 3' Ends by Amplification of Adaptor–Ligated cDNA," *BioTechniques vol. 21:* pp. 526–532 (1996).

Co et al., "Humanized Antibodies for Therapy," *Nature vol. 351:* pp. 501–502 (Jun. 6, 1991).

Cormack et al., "FACS–Optimized Mutants of the Green Fluorescent Protein (GFP)," *Gene vol. 173:* pp. 33–38 (1996).

Culver et al., "Correction of Chromosomal Point Mutations in Human Cells with Bifunctional Oligonucleotides," *Nature Biotechnology vol. 17 No. 10:* pp. 989–993 (1999).

Cunningham et al., "High Resolution Epitope Mapping of hGH–Receptor Interactions by Alanine–Scanning Mutagenesis," *Science vol. 244 No. 4908:* pp. 1081–1085 (Jun. 2, 1989).

de Kruif et al., "New Perspectives on Recombinant Human Antibodies," *Immunology Today vol. 17 No. 10:* pp. 453–455 (1996).

Delgado et al., "The Uses and Properties of PEG–Linked Proteins," *Critical Reviews in Therapeutic Drug Carrier Systems vol. 9 Nos. 3& 4:* pp. 249–304 (1992).

DeSantis et al., "Chemical Modification of Enzymes for Enhanced Functionality," *Current Opinion in Biotechnology vol. 10:* pp. 324–330 (1999).

Drees, Becky L., "Progress and Variation in Two–Hybrid and Three–Hybrid Technologies," *Current Opinion in Chemical Biology vol. 3:* pp. 64–70 (1999).

Edelman et al., "Obtaining a Functional Recombinant Anti–Rhesus (D) Antibody Using the Baculovirus–Insect Cell Expression System," *Immunology vol. 91:* pp. 13–19 (1997).

Eldin et al., "High–Level Secretion of Two Antibody Single Chain Fv Fragments by *Pichia Pastroris,*" *Journal of Immunological Methods vol. 201:* pp. 67–75 (1997).

Escude et al., "Padlock Oligonucleotides for Duplex DNA Based on Sequence–Specific Triple Helix Formation," *Proc. Nat. Acad. Sci. USA vol. 96 No. 19:* pp. 10603–10607 (1999).

Farr et al., "Pregnancy Associated Plasma Protein–E (PAPP–E)," *Biochimica et Biophysical Acta vol. 1493:* pp. 356–362 (2000).

Fashena et al., "The Continued Evolution of Two–Hybrid Screening Approches in Yeast: How to Outwit Different Preys with Different Baits," *Gene vol. 250:* pp. 1–14 (2000).

Fields et al., "The Two–Hybrid System: an Assay for Protein–Protein Interactions," *Trends in Genetics vol. 10 No. 8:* pp. 286–292 (Aug. 1994).

Finn et al., "Synthesis and Properties of DNA–PNA Chimeric Oligomers," *Nucleic Acids Research vol. 24:* pp. 3357–3363 (1996).

Fischer et al., "Molecular Farming of Recombinant Antibodies in Plants," *Biol. Chem. vol. 380:* pp. 825–839 (Jul./Aug. 1999).

Fischer et al., "Antibody Production by Molecular Farming in Plants," *Journal of Biological Regulators and Homeostatic Agents vol. 14 No. 2:* pp. 83–92 (2000).

Fischer et al., "Towards Molecular Farming in the Future: Transient Protein Expression in Plants," *Biotechnol. Appl. Biochem.* vol. 30: pp. 113–116 (1999).

Fischer et al., "Towards Molecular Farming in the Future: *Pichia Pastoris*–Based Production of Single–Chain Antibody Fragments," *Biotechnol. Appl. Biochem.* vol. 30: pp. 117–120 (1999).

Fox, "Targeting DNA with Triplexes," *Current Medical Chemistry vol 7 No. 1:* pp. 17–37 (2000).

Frenken et al., "Recent Advances in the Large–Scale Production of Antibody Fragments Using Lower Eukaryotic Microorganisms," *Res. Immunol. vol. 149:* pp. 589–599 (1998).

Freyre et al., "Very High Expression of an Anti–Carcinoembryonic Antigen Single Chain Fv Antibody Fragment in the Yeast *Pichia Pastoris,*" *Journal of Biotechnology vol. 76:* pp. 157–163 (2000).

Gamper et al., "The DNA Strand of Chimeric RNA/DNA Oligonucleotides Can Direct Gene Repair/Conversion Activity in Mammalian and Plant Cell–Free Extracts," *Nucleic Acids Research vol. 28 No. 21:* pp. 4332–4339 (2000).

Gautheret et al., "Alternate Polyadenylation in Human mRNAs: A Large–Scale Analysis by Est Clustering," *Genome Research vol. 8:* pp. 524–530 (1998).

Gavilondo et al., "Antibody Engineering at the Millennium," *Biotechniques vol. 29:* pp. 128–138 (2000).

Geysen et al., "Use of Peptide Synthesis to Probe Viral Antignes for Epitopes to a Resolution of a Single Amino Acid," *Proc. Nat. Aca. Sci. USA vol. 81:* pp. 3998–4002 (1984).

Giddings et al., "Transgenic Plants as Factories for Biopharmaceuticals," *Nature Biotechnology vol. 18:* pp. 1151–1155 (2000).

Gonnet et al., "Exhaustive Matching of the Entire Protein Sequence Database," *Science vol. 256 No. 5062:* pp. 1443–1445 (1992).

Griffiths et al., "Strategies for Selection of Antibodies by Phage Display," *Current Opinion in Biotechnology vol. 9:* pp. 102–108 (1998).

Hanke, "Alternative Splicing of Human Genes: More the Rule than the Exception?" *Trends in Genetics vol. 15 No. 1:* pp. 389–390 (1999).

Heid et al., "Real Time Quantitative PCR," *Genome Research vol. 6 No. 10:* pp. 986–994 (1996).

Heikal et al., "Molecular Spectroscopy and Dynamics on Intrinsically Fluorescent Proteins: Coral red (dsRed) and Yellow (Citrine)," *Proc. Natl. Acad. Sci. USA vol. 97:* pp. 11996–12001 (2000).

Heim et al., "Engineering Green Fluorescent Protein for Improved Brightness, Longer Wavelengths and Fluorescence Resonance Energy Transfer," *Current Biology vol. 6:* pp. 178–182 (1996).

Henegariu et al., "Custom Fluorescent–Nucleotide Synthesis as an Alternative Method for Nucleic Acid Labeling," *Nature Biotechnology vol. 18:* pp. 345–348 (2000).

Henikoff et al., "Amino Acid Substitution Matrices from Protein Blocks," *Proc. Natl. Acad. Sci. USA vol. 89:* pp. 10915–10919 (Nov. 1992).

Holland et al., "Detection of Specific Polymerase Chain reaction Product by Utilizing the 5'→3' Exonculease Activity of *Thermus Aquaticus* DNA Polymerase," *Proc. Natl. Acad. Sci. USA vol. 88:* pp. 7276–7280 (1991).

Hoogenboom et al., "Antibody Phage Display Technology and its Applications," *Immunotechnology, vol. 4:* pp. 1–20 (1998).

Hoogenboom, "Designing and Optimizing Library Selection Strategies for Generating High–Affinity Antibodies," *Trends in Biotechnology* vol. 15:pp. 62–70 (Feb. 1997).

Hourvitz et al., "Pregnancy–Associated Plasma Protein–A Gene Expression in Human Ovaries is Restricted to Healthy Follicles and Corpora Lutea," *Journal of Clinical Endocrinology and Metabolism vol. 85:* pp. 4916–4920 (2000).

Hsu et al., "Coexpression of Molecular Chaperone BiP Improves Immunogloblin Solubility and IgG Secretion from *Trichoplusia ni* Insect Cells," *Biotechnol. Prog. vol. 13:* pp. 96–104 (1997).

Hudson, "Recombinant Antibody Fragments," *Current Opinion in Biotechnology vol. 9:pp.* 395–402 (1998).

International Human Genome Sequencing Consortium, *Nature vol. 409:* pp. 860–921 (Feb. 15, 2001).

Jelsma et al., "Increased Labeling of DNA Probes For In Situ Hybridization With the Universal Linkage System (ULS)," *Journal of NIH Research vol. 5:* p. 82 (1994).

Jin et al., "High Resolution Functional Analysis of Antibody–Antigen Interactions," *J. Mol. Biol.* vol. 226: pp. 851–865 (1992).

Kochetkova et al., "Triplex–Forming Oligonucleotides and Their Use in the Analysis of Gene Transcription," *Mehods in Molecular Biology vol. 130:* pp. 189–201 (2000).

Kole et al., "Protein–Tyrosine Phosphatase Inhibition by a Peptide Containing the Phosphotryosyl Mimetic, L–O–Malonyltyrosine," *Biochemical & Biophysical Research Communicatons vol. 209 No. 3:* pp. 817–821 (1995).

Kostrikis et al., "Spectral Genotyping of Human Alleles," *Science vol. 279:* pp. 1228–1229 (1998).

Kricka et al., "Comparison of 5–Hydroxy–2, 3–Dihydrophthalazine–1, 4–Dione and Luminol as Co–Substrates for Detection of Horseradish Peroxidase in Enhanced Chemiluminescent Reactions," *Journal of Immunoassay vol. 17:* pp. 67–83 (1996).

Kuimelis et al., "Structural Analogues of TaqMan Probes for Real–Time Quantitative PCR," *Nucleic Acids Symposium Series No. 37:* pp. 255–256 (1997).

Lander et al., "The Chipping Forecast," *Supplement to Nature Genetics vol. 21 No. 1:* pp. 1–60 (Jan. 1999).

Larsen et al., "Antisense Properties of Peptide Nucleic Acid," *Biochimica et Biophysical Acta 1489:* pp. 159–166 (1999).

Lauffer et al., "MS–325: Albumin–Targeted Contrast Agent for MR Angiography," *Radiology* vol. 207 No. 2: pp. 529–538 (1998).

Lawrence et al., "The Insulin–Like Growth Factor (IGF)–Dependent IGF Binding Protein–4 Protease Secreted by Human Fibroblasts is Pregnancy–Associated Plasma Protein–A," *Proc. Nat. Acad. Sci. USA vol. 96:* pp. 3149–3153 (1999).

Lerner, "Tapping the Immunological Repertoire to Produce Antibodies of Predetermined Specificity," *Nature vol. 299:* pp. 592–596 (1982).

Li et al., "Deletions of the *Aequorea Victoria* Fluorescent Protein Define the Minimal Domain Required for Fluorescence," *Journal of Biological Chemistry vol. 272:* pp. 28545–28549 (1997).

Li et al., "Production of Functional Antibodies Generated in a Nonlytic Insect Cell Expression System," *Protein Expression and Purification vol. 21:* pp. 121–128 (2001).

Liang et al., "Gene Index Analysis of the Human Genome Estimates Approximately 120,000 Genes," *Nature Genetics vol. 25 No. 2:* pp. 239–240 (2000).

Liu et al., "Progress Toward the Evolution of an Organism with an Expanded Genetic Code," *Proc. Natl. Acad. Sci. USA vol. 96:* pp. 4780–4785 (1999).

Lizardi et al., "Mutation Detection and Single–Molecule Counting Using Isothermal Rolling–Circle Amplification," *Nature Genetics vol. 19:* pp. 225–232 (1998).

Luban et al., "The Yeast Two–Hybrid System for Studying Protein–Protein Interactions," *Current Opinions in Biotechnology vol. 6:* pp. 59–64 (1995).

Lundqvist et al., "Influence of Different Luminols on the Characteristics of the Chemiluminescence Reaction in Human Neutrophils," *J. Biolumin. Chemilumin. vol. 10:* pp. 353–359 (1995).

Ma et al., "Plant Antibodies for Immunotherapy," *Plant Physiology vol. 109:* pp. 341–346 (1995).

Marras et al., "Multiplex detection of Single–Nucleotide Variations Using Molecular Beacons," *Genetic Analysis: Biomolecular Engineering vol. 14:* pp. 151–156 (1999).

Mendelsohn et al., "Applictions of Interaction Traps/Two–Hybrid Systems to Biotechnology Research, " *Current Opinion in Biotechnology vol. 5:* pp. 482–486 (1994).

Merchant et al., "Recent Advancements in Surface–Enhanced Laser Desorption/Ionization–Time of Flight–Mass Spectrometry," *Electrophoresis vol. 21:* pp. 1164–1177 (2000).

Merk et al., "Cell–Free Expression of Two Single–Chain Monoclonal Antibodies Against Lysozyme: Effect of Domain Arrangement on the Expression," *J. Biochem. vol. 125 No. 2:* pp. 328–333 (1999).

Mironov et al. "Frequent Alternative Splicing of Human Genes," *Genome Research vol. 9:* pp. 1288–1293 (1999).

Misra et al., "Polyamide Nucleic Acid–DNA Chimera Lacking the Phosphate Backbone are Novel Primers for Polymerase Reaction Catalyzed by DNA Polymerases," *Biochemistry vol. 37:* pp. 1917–1925 (1998).

Miyawaki et al., "Fluorescent Indicators for Ca2+ Based on Green Fluorescent Proteins and Calmodulin," *Nature vol. 388:* pp. 882–887 (1997).

Morrison et al., "Chimeric Human Antibody Molecules: Mouse Antigen–Binding Domains with Human constant Region Domains," *Proc. Natl. Acad. Sci. USA vol. 81:* pp. 6851–6855 (1984).

Nesbit et al., "Production of a Functional Monoclonal Antibody Recognizing Human Colorectal Carcinoma Cells from a Baculovirus Expression System," *Journal of Immunological Methods* vol. 151: pp. 201–208 (1992).

Nielsen, "Peptide Nucleic Acids as Therapeutic Agents," *Current Opinion in Structural Biology vol. 9:* pp. 353–357 (1999).

Nielsen, "Applications of Peptide Nucleic Acids," *Current Opinion in Biotechnology vol. 10:* pp. 71–75 (1999).

Nielsen et al., "Peptide Nucleic Acids: On the Road to New Gene Therapeutic Drugs," *Pharmacology & Toxicology vol. 86:* pp. 3–7 (2000).

Nilsson et al., "Padlock Probes: Cirularizing Oligonucleotides for Localized DNA Detection," *Science vol. 265 No. 5181:* pp. 2085–2088 (1994).

Ong et al., "First Trimester Maternal Serum Free Beta Human Chorionic Gonadotrophin and Pregnancy Associated Plasma Protein A as Predictors of Pregnancy Complications," *British Journal of Obstetrics and Gynaecology vol. 107::* pp. 1265–1270 (Oct. 2000).

Ormo et al., "Crystal Structure of the Aequorea Victoria Green Fluorescent Protein," *Science vol. 273:* pp. 1392–1395 (Sep. 6, 1996).

Overgaard et al., "Expression of Recombinant Human Pregnancy Associated Plasma Protein–A and Identification of the Proform of Eosinophil Major Basic Protein as Its Physiological Inhibitor," *Journal of Biological Chemistry vol. 275 No. 40:* pp. 31128–31133 (Oct. 6, 2000).

Palm et al., "Spectral Variants of Green Fluorescent Protein," in *Green Fluorescent Proteins,* Conn (ed.), *Methods in Enzymology vol. 302:* pp. 378–394 (1999).

Penn et al., "Mining the Human Genome Using Microarrays of Open Reading Frames," *Nature Genetics vol. 26:* pp. 315–318 (2000).

Pennell et al., "In Vitro Production of Recombinant Antibody Fragments in *Picia Pastoris," Research in Immunology vol. 149 No. 6:* pp. 599–603 (1998).

Pollock et al., "Transgenic Milk as a Method for the Production of Recombinant Antibodies," *Journal of Immunological Methods vol. 231:* pp. 147–157 (1999).

Posnett et al., "A Novel Method for Producing Anti–Peptide Antibodies," *Journal of Biological Chemistry vol. 263:* pp. 1719–1725 (1988).

Praseuth et al., "Triple Helix Formation and the Antigene Strategy for Sequence–Specific Control of Gene Expression," *Biochimica et Biophysical Acta 1489 vol. 1:* pp. 181–206 (1999).

Rader et al., "Phase Display of Combinatorial Antibody Libraries," *Current Opinion in Biotechnology vol. 8:* pp. 503–508 (1997).

Ray et al., "Peptide Nucleic Acid (PNA): Its Medical and Biotechnical Applications and Promise for the Future," *FASEB Journal vol. 14 No. 9:* pp. 1041–1060 (2000).

Riechmann et al., "Reshaping Human Antibodies for Therapy," *Nature vol. 332:* pp. 323–327 (Mar. 24, 1988).

Russell, D.A., "Feasibility of Antibody Production in Plants for Human Therapeutic Use," *Current Topics in Microbiology & Immunology vol. 240:* pp. 119–138 (1999).

Ryabova et al., "Functional Antibody Production Using Cell–Free Translation: Effects of Protein Disulfide Isomerase and Chaperones," *Nature Biotechnology vol. 15:* pp. 79–84 (1997).

Schiestl et al., "High Efficiency Transformation of Intact Yeast Cells Using Single Stranded Nucleic Acids as a Carrier," *Current Genetics vol. 16 Nos. 5& 6:* pp. 339–346 (1989).

Schmucker et al., "Drosophilia Dscam Is an Axon Guidance Receptor Exhibiting Extraordinary Molecular Diversity," *Cell vol. 101:* p. 671 (2000).

Schoner et al., "Translation of a Synthetic Two–Cistron mRNA in *Escherichia coli," Proc. Natl. Acad. Sci. USA vol. 83:* pp. 8506–8510 (1986).

Schweitzer et al., "Combining Nucleic Acid Amplification and Detection," *Current Opinion in Biotechnology vol. 12 No. 1:* pp. 21–27 (2001).

Scott et al., "Cellular Camouflage: Fooling the Immune System with Polymers," *Current Pharmaceutical Design vol.* 4: pp. 423–438 (1998).

Sharon et al., "Expression of a VHCK Chimaeric Protein in Mouse Myeloma Cells," *Nature* vol. 309: pp. 364–367 (1984).

Shinnick et al., "Synthetic Peptide Immunogens as Vaccines," *Annual Review of Microbiology vol. 37:* pp. 425–446 (1983).

Shusta et al., "Increasing the Secretory Capacity of *Saccharomyces Cerevisiae* for Production of Single–Chain Antibody Fragments," *Nature Biotechnology vol. 16:* pp. 773–777 (Aug. 1998).

Sidhu, Sachdev S., "Phage Display in Pharmaceutical Biotechnology," *Current Opinion in Biotechnology vol. 11:* pp. 610–616 (2000).

Sokol et al., "Real Time Detection of DNA–RNA Hybridization in Living Cells," *Proc. Natl. Acad. Sci. USA vol.* 95: pp. 11538–11543 (1998).

Spencer et al., "Second Trimester Levels of Pregnancy Associated Plasma Protien–A in Cases of Trisomy 18," *Prentatal Diagnostics vol. 19:* pp. 1127–1134 (1999).

Stocker et al., "The Metzincins—Topological and Sequential Relations between the Astacins, Adamalysins, Serralysins, and Matrixins (Collagenases) Define a Superfamily of Zinc–Peptidases," *Protein Science vol. 4:* pp. 823–840 (1995).

Sutcliffe et al., "Antibodies that React with Predetermined Sites on Proteins," *Science vol. 219:* pp. 660–666 (1983).

Takahashi et al., "Production of Humanized Fab Fragment Against Human High Affinity IgE Receptor in *Pichia Pastoris," Biosci. Biotechnol. Biochem. vol. 64 No. 10:* pp. 2138–2144 (2000).

Takeda et al., "Construction of Chimaeric Processed Immunoglobulin Genes Contianing Mouse Variable and Human constant Region Sequences," *Nature vol. 314:* pp. 452–454 (Apr. 1985).

Tam et al., "Synthetic Peptide Vaccine Design: Synthesis and Properties of a High–Density Multiple Antigenic Peptide System," *Proc. Natl. Acad. Sci. USA vol. 85:* pp. 5409–5413 (1988).

Tatiana et al., "Blast 2 Sequences—A New Tool for Comparing Protein and Nucleotide Sequences," *FEMS Microbiology Letters vol. 174:* pp. 247–250 (1999).

Thorpe et al., "Bioluminescense and Chemiluminescence," *Methods in Enzymology vol. 133:* pp. 331–353 (1986).

Topcu et al., "The Yeast Two–Hybrid System and Its Pharmaceutical Significance," *Pharmaceutical Research vol. 17 No. 9:* pp. 1049–1055 (2000).

Tul et al., "Screening for Trisomy 18 by Fetal Nuchal Translucency and Maternal Serum Free Beta–hCG and PAPP–A at 1–14 Weeks of Gestation." *Prenatal Diagnostics vol. 19:* pp. 1035–1042 (1999).

Tyagi et al., "Molecular Beacons: Probes that Fluoresce upon Hybridization," *Nature Biotechnology vol. 14:* pp. 303–308 (1996).

Tyagi et al., "Multicolor Molecular Beacons for Allele Discrimination, " *Nature Biotechnology vol. 16:* pp. 49–53 (1998).

Van Belkum et al., "Non–Isotopic Labeling of DNA by Newly Developed Hapten–Containing Platinum Compounds," *BioTechniques vol. 16:* pp. 148–153 (1994).

Verma et al., "Antibody Engineering: Comparison of Bacterial, Yeast, Insect and Mammalian Expression Systems," *Journal of Immunological Methods vol. 216:* pp. 165–181 (1998).

Wald et al., "Serum Screening for Down's Syndrome Between 8 and 14 Weeks of Pregnancy," *British Journal of Obstetrics and Gynaecology vol. 103 No. 5:* pp. 407–412 (1996).

Weiss et al., "Rapid Mapping of Protein Functional Epitopes by Combinatorial Alanine Scanning," *Proc. Natl. Acad. Sci. USA vol. 97:* pp. 8950–8954 (2000).

Winter et al., "Making Antibodies by Phage Display Technology," *Annual Review of Immunology:* pp. 433–455 (1994).

* cited by examiner

PAPP-Ea nt: SEQ ID NO:1
aa: SEQ ID NO:3

```
ccccaagcatcaaactgaaggaaacattctaaccttcacagacagactggag   52
gctggatggggacctggctgaagacatctggagaatgaaagttaagtaccag  104
cttgcatttttgtgcccctagattattttgcattttaaaataagaagcatc  156
aaattgcgtgtctctgtgtaaaagttctagcaatttgttttaaggtgaactt  208
attttggcttagggactacaaaaagagaaggtaattcctagggaaggaagaa  260
gagaaagaaatgaaaattagagaataagattattttgaatgacttcaggtag  312
cgaggagtgtgtgtttgtgagtgtgtatttgagagacttggctcatgcctgt  364
gggtcttctcttctagtatcagtgaggggagggattactgaagaagaagggg  416
ggaaaaaaaaagaaagaaatctgagctttctgggaggaaattcaaaggaacc  468
aagagaaattaacttcgttctgcaaggactaaagtacagcaagaggagagag  520
gtcaagcgagaagcgtgcgggaagcacatgccctggggaggcatagaagcca  572
cactggcagagcggccagcacaggtagccagcagaggcattcttggggctat  624
ttgaaaaagtttggtctgtgaacaaaacagtttccctggtgactgcaaatcc  676
attgctagctgcctctttctcgtctgcccatcactctggtgtggtacccaga  728
                                       M   M   C      3
agttgacttctggttctgtagaaagagctaggggaggt ATG ATG TGC  775

 L   K   I   L   R   I   S   L   A   I   L   A   G    16
TTA AAG ATC CTA AGA ATA AGC CTG GCG ATT TTG GCT GGG  814

           |→ BEGIN PAPP-Ef CLONE
 W   A   L | C   S   A   N   S   E   L   G   W   T    29
TGG GCA CTC|TGT TCT GCC AAC TCT GAG CTG GGC TGG ACA  853
           |→ BEGIN PAPP-Ef CLONE

 R   K   K   S   L   V   E   R   E   H   L   N   Q    42
CGC AAG AAA TCC TTG GTT GAG AGG GAA CAC CTG AAT CAG  892
```

FIG. 3A

```
 V   L   L   E   G   E   R   C   W   L   G   A   K      55
GTG CTG TTG GAA GGA GAA CGT TGT TGG CTG GGG GCC AAG    931

 V   R   R   P   R   A   S   P   Q   H   H   L   F      68
GTT CGA AGA CCC AGA GCT TCT CCA CAG CAT CAC CTC TTT    970

 G   V   Y   P   S   R   A   G   N   Y   L   R   P      81
GGA GTC TAC CCC AGC AGG GCT GGG AAC TAC CTA AGG CCC   1009

 Y   P   V   G   E   Q   E   I   H   H   T   G   R      94
TAC CCC GTG GGG GAG CAA GAA ATC CAT CAT ACA GGA CGC   1048

 S   K   P   D   T   E   G   N   A   V   S   L   V     107
AGC AAA CCA GAC ACT GAA GGA AAT GCT GTG AGC CTT GTT   1087

 P   P   D   L   T   E   N   P   A   G   L   R   G     120
CCC CCA GAC CTG ACT GAA AAT CCA GCA GGA CTG AGG GGT   1126

 A   V   E   E   P   A   A   P   W   V   G   D   S     133
GCA GTT GAA GAG CCG GCT GCC CCA TGG GTA GGG GAT AGT   1165

 P   I   G   Q   S   E   L   L   G   D   D   D   A     146
CCT ATT GGG CAA TCT GAG CTG CTG GGA GAT GAT GAC GCT   1204

 Y   L   G   N   Q   R   S   K   E   S   L   G   E     159
TAT CTC GGC AAT CAA AGA TCC AAG GAG TCT CTA GGT GAG   1243

                                |→ BEGIN PAPP-Ef TRANSLATION
 A   G   I   Q   K   G   S   A  | M   A   A   T   T     172
GCC GGG ATT CAG AAA GGC TCA GCC|ATG GCT GCC ACT ACT   1282
                                |→ BEGIN PAPP-Ef TRANSLATION

 T   T   A   I   F   T   T   L   N   E   P   K   P     185
ACC ACC GCC ATT TTC ACA ACC CTG AAC GAA CCC AAA CCA   1321

 E   T   Q   R   R   G   W   A   K   S   R   Q   R     198
GAG ACC CAA AGG AGG GGC TGG GCC AAG TCC AGG CAG CGT   1360

 R   Q   V   W   K   R   R   A   E   D   G   Q   G     211
CGC CAA GTG TGG AAG AGG CGG GCG GAA GAT GGG CAG GGA   1399

 D   S   G   I   S   S   H   F   Q   P   W   P   K     224
GAC TCC GGT ATC TCT TCA CAT TTC CAA CCT TGG CCC AAG   1438

 H   S   L   K   H   R   V   K   K   S   P   P   E     237
CAT TCC CTT AAA CAC AGG GTC AAA AAG AGT CCA CCG GAG   1477

 E   S   N   Q   N   G   G   E   G   S   Y   R   E     250
```

```
GAA AGC AAC CAA AAT GGT GGA GAG GGC TCC TAC CGA GAA  1516

 A   E   T   F   N   S   Q   V   G   L   P   I   L    263
GCA GAG ACC TTT AAG TCC CAA GTA GGA CTG CCC ATC TTA  1555

 Y   F   S   G   R   R   E   R   L   L   L   R   P    276
TAC TTC TCT GGG AGG CGG GAG CGG CTG CTG CTG CGT CCA  1594

 E   V   L   A   E   I   P   R   E   A   F   T   V    289
GAA GTG CTG GCT GAG ATT CCC CGG GAG GCG TTC ACA GTG  1633

 E   A   W   V   K   P   E   G   G   Q   N   N   P    302
GAA GCC TGG GTT AAA CCG GAG GGA GGA CAG AAC AAC CCA  1672

 A   I   I   A   G   V   F   D   N   C   S   H   T    315
GCC ATC ATC GCA GGT GTG TTT GAT AAC TGC TCC CAC ACT  1711

 V   S   D   K   G   W   A   L   G   I   R   S   G    328
GTC AGT GAC AAA GGC TGG GCC CTG GGG ATC CGC TCA GGG  1750

 K   D   K   G   K   R   D   A   R   F   F   F   S    341
AAG GAC AAG GGA AAG CGG GAT GCT CGC TTC TTC TTC TCC  1789

 L   C   T   D   R   V   K   K   A   T   I   L   I    354
CTC TGC ACC GAC CGC GTG AAG AAA GCC ACC ATC TTG ATT  1828

 S   H   S   R   Y   Q   P   G   T   W   T   H   V    367
AGC CAC AGT CGC TAC CAA CCA GGC ACA TGG ACC CAT GTG  1867

 A   A   T   Y   D   G   R   H   M   A   L   Y   V    380
GCA GCC ACT TAC GAT GGA CGG CAC ATG GCC CTG TAT GTG  1906

 D   G   T   Q   V   A   S   S   L   D   Q   S   G    393
GAT GGC ACT CAG GTG GCT AGC AGT CTA GAC CAG TCT GGT  1945

 P   L   N   S   P   F   M   A   S   C   R   S   L    406
CCC CTG AAC AGC CCC TTC ATG GCA TCT TGC CGC TCT TTG  1984

 L   L   G   G   D   S   S   E   D   G   H   Y   F    419
CTC CTG GGG GGA GAC AGC TCT GAG GAT GGG CAC TAT TTC  2023

 R   G   H   L   G   T   L   V   F   W   S   T   A    432
CGT GGA CAC CTG GGC ACA CTG GTT TTC TGG TCG ACC GCC  2062

 L   P   Q   S   H   F   Q   H   S   S   Q   H   S    445
CTG CCA CAA AGC CAT TTT CAG CAC AGT TCT CAG CAT TCA  2101

 S   E   E   E   E   A   T   D   L   V   L   T   A    458
AGT GAG GAG GAG GAA GCG ACT GAC TTG GTC CTG ACA GCG  2140
```

FIG. 3C

```
 S   F   E   P   V   N   T   E   W   V   P   F   R    471
AGC TTT GAG CCT GTG AAC ACA GAG TGG GTT CCC TTT AGA  2179

 D   E   K   Y   P   R   L   E   V   L   Q   G   F    484
GAT GAG AAG TAC CCA CGA CTT GAG GTT CTC CAG GGC TTT  2218

 E   P   E   P   E   I   L   S   P   L   Q   P   P    497
GAG CCA GAG CCT GAG ATT CTG TCG CCT TTG CAG CCC CCA  2257

 L   C   G   Q   T   V   C   D   N   V   E   L   I    510
CTC TGT GGG CAA ACA GTC TGT GAC AAT GTG GAA TTG ATC  2296

 S   Q   Y   N   G   Y   W   P   L   R   G   E   K    523
TCC CAG TAC AAT GGA TAC TGG CCC CTT CGG GGA GAG AAG  2335

 V   I   R   Y   Q   V   V   N   I   C   D   D   E    536
GTG ATA CGC TAC CAG GTG GTG AAC ATC TGT GAT GAT GAG  2374

 G   L   N   P   I   V   S   E   E   Q   I   R   L    549
GGC CTA AAC CCC ATT GTG AGT GAG GAG CAG ATT CGT CTG  2413

 Q   H   E   A   L   N   E   A   F   S   R   Y   N    562
CAG CAC GAG GCA CTG AAT GAG GCC TTC AGC CGC TAC AAC  2452

 I   S   W   Q   L   S   V   H   Q   V   H   N   S    575
ATC AGC TGG CAG CTG AGC GTC CAC CAG GTC CAC AAT TCC  2491

 T   L   R   H   R   V   V   L   V   N   C   E   P    588
ACC CTG CGA CAC CGG GTT GTG CTT GTG AAC TGT GAG CCC  2530

 S   K   I   G   N   D   H   C   D   P   E   C   E    601
AGC AAG ATT GGC AAT GAC CAT TGT GAC CCC GAG TGT GAG  2569

 H   P   L   T   G   Y   D   G   G   D   C   R   L    614
CAC CCA CTC ACA GGC TAT GAT GGG GGT GAC TGC CGC CTG  2608

 Q   G   R   C   Y   S   W   N   R   R   D   G   L    627
CAG GGC CGC TGC TAC TCC TGG AAC CGC AGG GAT GGG CTC  2647

 C   H   V   E   C   N   N   M   L   N   D   F   D    640
TGT CAC GTG GAG TGT AAC AAC ATG CTG AAC GAC TTT GAC  2686

 D   G   D   C   C   D   P   Q   V   A   D   V   R    653
GAC GGA GAC TGC TGC GAC CCC CAG GTG GCT GAT GTG CGC  2725

 K   T   C   F   D   P   D   S   P   K   R   A   Y    666
AAG ACC TGC TTT GAC CCT GAC TCA CCC AAG AGG GCA TAC  2764
```

FIG. 3D

```
 M   S   V   K   E   L   K   E   A   L   Q   L   N     679
ATG AGT GTG AAG GAG CTG AAG GAG GCC CTG CAG CTG AAC    2803

 S   T   H   F   L   N   I   Y   F   A   S   S   V     692
AGT ACT CAC TTC CTC AAC ATC TAC TTT GCC AGC TCA GTG    2842

 R   E   D   L   A   G   A   A   T   W   P   W   D     705
CGG GAA GAC CTT GCA GGT GCT GCC ACC TGG CCT TGG GAC    2881

 K   D   A   V   T   H   L   G   G   I   V   L   S     718
AAG GAC GCT GTC ACT CAC CTG GGT GGC ATT GTC CTC AGC    2920

 P   A   Y   Y   G   M   P   G   H   T   D   T   M     731
CCA GCA TAT TAT GGG ATG CCT GGC CAC ACC GAC ACC ATG    2959

 I   H   E   V   G   H   V   L   G   L   Y   H   V     744
ATC CAT GAA GTG GGA CAT GTT CTG GGA CTC TAC CAT GTC    2998

 F   K   G   V   S   E   R   E   S   C   N   D   P     757
TTT AAA GGA GTC AGT GAA AGA GAA TCC TGC AAT GAC CCC    3037

 C   K   E   T   V   P   S   M   E   T   G   D   L     770
TGC AAG GAG ACA GTG CCA TCC ATG GAA ACG GGA GAC CTC    3076

 C   A   D   T   A   P   T   P   K   S   E   L   C     783
TGT GCC GAC ACC GCC CCC ACT CCC AAG AGT GAG CTG TGC    3115

 R   E   P   E   P   T   S   D   T   C   G   F   T     796
CGG GAA CCA GAG CCC ACT AGT GAC ACC TGT GGC TTC ACT    3154

 R   F   P   G   A   P   F   T   N   Y   M   S   Y     809
CGC TTC CCA GGG GCT CCG TTC ACC AAC TAC ATG AGC TAC    3193

 T   D   D   N   C   T   D   N   F   T   P   N   Q     822
ACG GAT GAT AAC TGC ACT GAC AAC TTC ACT CCT AAC CAA    3232

 V   A   R   M   H   C   Y   L   D   L   V   Y   Q     835
GTG GCC CGA ATG CAT TGC TAT TTG GAC CTA GTC TAT CAG    3271

 Q   W   T   E   S   R   K   P   T   P   I   P   I     848
CAG TGG ACT GAA AGC AGA AAG CCC ACC CCC ATC CCC ATT    3310

 P   P   M   V   I   G   Q   T   N   K   S   L   T     861
CCA CCT ATG GTC ATC GGA CAG ACC AAC AAG TCC CTC ACT    3349

 I   H   W   L   P   P   I   S   G   V   V   Y   D     874
ATC CAC TGG CTG CCT CCT ATT AGT GGA GTT GTA TAT GAC    3388

 R   A   S   G   S   L   C   G   A   C   T   E   D     887
```

AGG GCC TCA GGC AGC TTG TGT GGC GCT TGC ACT GAA GAT 3427

G T F R Q Y V H T A S S R 900
GGG ACC TTT CGT CAG TAT GTG CAC ACA GCT TCC TCC CGG 3466

R V C D S S G Y W T P E E 913
CGG GTG TGT GAC TCC TCA GGT TAT TGG ACC CCA GAG GAG 3505

A V G P P D V D Q P C E P 926
GCT GTG GGG CCT CCT GAT GTG GAT CAG CCC TGC GAG CCA 3544

S L Q A W S P E V H L Y H 939
AGC TTA CAG GCC TGG AGC CCT GAG GTC CAC CTG TAC CAC 3583

M N M T V P C P T E G C S 952
ATG AAC ATG ACG GTC CCC TGC CCC ACA GAA GGC TGT AGC 3622

L E L L F Q H P V Q A D T 965
TTG GAG CTG CTC TTC CAA CAC CCG GTC CAA GCC GAC ACC 3661

L T L W V T S F F M E S S 978
CTC ACC CTG TGG GTC ACT TCC TTC TTC ATG GAG TCC TCG 3700

Q V L F D T E I L L E N K 991
CAG GTC CTC TTT GAC ACA GAG ATC TTG CTG GAA AAC AAG 3739

E S V H L G P L D T F C D 1004
GAG TCA GTG CAC CTG GGC CCC TTA GAC ACT TTC TGT GAC 3778

I P L T I K L H V D G K V 1017
ATC CCA CTC ACC ATC AAA CTG CAC GTG GAT GGG AAG GTG 3817

S G V K V Y T F D E R I E 1030
TCG GGG GTG AAA GTC TAC ACC TTT GAT GAG AGG ATA GAG 3856

I D A A L L T S Q P H S P 1043
ATT GAT GCA GCA CTC CTG ACT TCT CAG CCC CAC AGT CCC 3895

L C S G C R P V R Y Q V L 1056
TTG TGC TCT GGC TGC AGG CCT GTG AGG TAC CAG GTT CTC 3934

R D P P F A S G L P V V V 1069
CGC GAT CCC CCA TTT GCC AGT GGT TTG CCC GTG GTG GTG 3973

T H S H R K F T D V E V T 1082
ACA CAT TCT CAC AGG AAG TTC ACG GAC GTG GAG GTC ACA 4012

P G Q M Y Q Y Q V L A E A 1095
CCT GGA CAG ATG TAT CAG TAC CAA GTT CTA GCT GAA GCT 4051

FIG. 3F

```
 G   G   E   L   G   E   A   S   P   P   L   N   H   1108
GGA GGA GAA CTG GGA GAA GCT TCG CCT CCT CTG AAC CAC  4090

 I   H   G   A   P   Y   C   G   D   G   K   V   S   1121
ATT CAT GGA GCT CCT TAT TGT GGA GAT GGG AAG GTG TCA  4129

 E   R   L   G   E   E   C   D   D   G   D   L   V   1134
GAG AGA CTG GGA GAA GAG TGT GAT GAT GGA GAC CTT GTG  4168

 S   G   D   G   C   S   K   V   C   E   L   E   E   1147
AGC GGA GAT GGC TGC TCC AAG GTG TGT GAG CTG GAG GAA  4207

 G   F   N   C   V   G   E   P   S   L   C   Y   M   1160
GGT TTC AAC TGT GTA GGA GAG CCA AGC CTT TGC TAC ATG  4246

 Y   E   G   D   G   I   C   E   P   F   E   R   K   1173
TAT GAG GGA GAT GGC ATA TGT GAA CCT TTT GAG AGA AAA  4285

 T   S   I   V   D   C   G   I   Y   T   P   K   G   1186
ACC AGC ATT GTA GAC TGT GGC ATC TAC ACT CCC AAA GGA  4324

 Y   L   D   Q   W   A   T   R   A   Y   S   S   H   1199
TAC TTG GAT CAA TGG GCT ACC CGG GCT TAC TCC TCT CAT  4363

 E   D   K   K   K   C   P   V   S   L   V   T   G   1212
GAA GAC AAG AAG AAG TGT CCT GTT TCC TTG GTA ACT GGA  4402

 E   P   H   S   L   I   C   T   S   Y   H   P   D   1225
GAA CCT CAT TCC CTA ATT TGC ACA TCA TAC CAT CCA GAT  4441

 L   P   N   H   R   P   L   T   G   W   F   P   C   1238
TTA CCC AAC CAC CGT CCC CTA ACT GGC TGG TTT CCC TGT  4480

 V   A   S   E   N   E   T   Q   D   D   R   S   E   1251
GTT GCC AGT GAA AAT GAA ACT CAG GAT GAC AGG AGT GAA  4519

 Q   P   E   G   S   L   K   K   E   D   E   V   W   1264
CAG CCA GAA GGT AGC CTG AAG AAA GAG GAT GAG GTT TGG  4558

 L   K   V   C   F   N   R   P   G   E   A   R   A   1277
CTC AAA GTG TGT TTC AAT AGA CCA GGA GAG GCC AGA GCA  4597

 I   F   I   F   L   T   T   D   G   L   V   P   G   1290
ATT TTT ATT TTT TTG ACA ACT GAT GGC CTA GTT CCC GGA  4636

 E   H   Q   Q   P   T   V   T   L   Y   L   T   D   1303
GAG CAT CAG CAG CCG ACA GTG ACT CTC TAC CTG ACC GAT  4675
```

FIG. 3G

```
 V   R   G   S   N   H   S   L   G   T   Y   G   L   1316
GTC CGT GGA AGC AAC CAC TCT CTT GGA ACC TAT GGA CTG  4714

 S   C   Q   H   N   P   L   I   I   N   V   T   H   1329
TCA TGC CAG CAT AAT CCA CTG ATT ATC AAT GTG ACC CAT  4753

 H   Q   N   V   L   F   H   H   T   T   S   V   L   1342
CAC CAG AAT GTC CTT TTC CAC CAT ACC ACC TCA GTG CTG  4792

 P   N   F   S   S   P   R   V   G   I   S   A   V   1355
CCG AAT TTC TCA TCC CCA CGG GTC GGC ATC TCA GCT GTG  4831

 A   L   R   T   S   S   R   I   G   L   S   A   P   1368
GCT CTA AGG ACA TCC TCC CGC ATT GGT CTT TCG GCT CCC  4870

 S   N   C   I   S   E   D   E   G   Q   N   H   Q   1381
AGT AAC TGC ATC TCA GAG GAC GAG GGG CAG AAT CAT CAG  4909

 G   Q   S   C   I   H   R   P   C   G   K   Q   D   1394
GGA CAG AGC TGT ATC CAT CGG CCC TGT GGG AAG CAG GAC  4948

 S   C   P   S   L   L   L   D   H   A   D   V   V   1407
AGC TGT CCG TCA TTG CTG CTT GAT CAT GCT GAT GTG GTG  4987

 N   C   T   S   I   G   P   G   L   M   K   C   A   1420
AAC TGT ACC TCT ATA GGC CCA GGT CTC ATG AAG TGT GCT  5026

 I   T   C   Q   R   G   F   A   L   Q   A   S   S   1433
ATC ACT TGT CAA AGG GGA TTT GCC CTT CAG GCC AGC AGT  5065

 G   Q   Y   I   R   P   M   Q   K   E   I   L   L   1446
GGG CAG TAC ATC AGG CCC ATG CAG AAG GAA ATT CTG CTC  5104

 T   C   S   S   G   H   W   D   Q   N   V   S   C   1459
ACA TGT TCT TCT GGG CAC TGG GAC CAG AAT GTG AGC TGC  5143

 L   P   V   D   C   G   V   P   D   P   S   L   V   1472
CTT CCC GTG GAC TGC GGT GTT CCC GAC CCG TCT TTG GTG  5182

 N   Y   A   N   F   S   C   S   E   G   T   K   F   1485
AAC TAT GCA AAC TTC TCC TGC TCA GAG GGA ACC AAA TTT  5221

 L   K   R   C   S   I   S   C   V   P   P   A   K   1498
CTG AAA CGC TGC TCA ATC TCT TGT GTC CCA CCA GCC AAG  5260

 L   Q   G   L   S   P   W   L   T   C   L   E   D   1511
CTG CAA GGA CTG AGC CCA TGG CTG ACA TGT CTT GAA GAT  5299

 G   L   W   S   L   P   E   V   Y   C   K   L   E   1524
```

```
GGT CTC TGG TCT CTC CCT GAA GTC TAC TGC AAG TTG GAG  5338

 C   D   A   P   P   I   I   L   N   A   N   L   L   1537
TGT GAT GCT CCC CCT ATT ATT CTG ATT GCC AAC TTG CTC  5377

 L   P   H   C   L   Q   D   N   H   D   V   G   T   1550
CTG CCT CAC TGC CTC CAG GAC AAC CAC GAC GTG GGC ACC  5416

 I   C   K   Y   E   C   K   P   G   Y   Y   V   A   1563
ATC TGC AAA TAT GAA TGC AAA CCA GGG TAC TAT GTG GCA  5455

 E   S   A   E   G   K   V   R   N   K   L   L   K   1576
GAA AGT GCA GAG GGT AAA GTC AGG AAC AAG CTC CTG AAG  5494

 I   Q   C   L   E   G   G   I   W   E   Q   G   S   1589
ATA CAA TGC CTG GAA GGT GGA ATC TGG GAG CAA GGC AGC  5533

 C   I   P   V   V   C   E   P   P   P   P   V   F   1602
TGC ATT CCT GTG GTG TGT GAG CCA CCC CCT CCT GTG TTT  5572

 E   G   M   Y   E   C   T   N   G   F   S   L   D   1615
GAA GGC ATG TAT GAA TGT ACC AAT GGC TTC AGC CTG GAC  5611

 S   Q   C   V   L   N   C   N   Q   E   R   E   K   1628
AGC CAG TGT GTG CTC AAC TGT AAC CAG GAA CGT GAA AAG  5650

 L   P   I   L   C   T   K   E   G   L   W   T   Q   1641
CTT CCC ATC CTC TGC ACT AAA GAG GGC CTG TGG ACC CAG  5689

 E   F   K   L   C   E   N   L   Q   G   E   C   P   1654
GAG TTT AAG TTG TGT GAG ATT CTG CAA GGA GAA TGC CCA  5728

 P   P   P   S   E   L   N   S   V   E   Y   K   C   1667
CCA CCC CCC TCA GAG CTG AAT TCT GTG GAG TAC AAA TGT  5767

 E   Q   G   Y   G   I   G   A   V   C   S   P   L   1680
GAA CAA GGA TAT GGG ATT GGT GCA GTG TGT TCC CCA TTG  5806

 C   V   I   P   P   S   D   P   V   M   L   P   E   1693
TGT GTA ATC CCC CCC AGT GAC CCC GTG ATG CTA CCT GAG  5845

 N   I   T   A   D   T   L   E   H   W   M   E   P   1706
AAT ATC ACT GCT GAC ACT CTG GAG CAC TGG ATG GAA CCT  5884

 V   K   V   Q   S   I   V   C   T   G   R   R   Q   1719
GTC AAA GTC CAG AGC ATT GTG TGC ACT GGC CGG CGT CAA  5923

 W   H   P   D   P   V   L   V   H   C   I   Q   S   1732
TGG CAC CCA GAC CCC GTC TTA GTC CAC TGC ATC CAG TCA  5962
```

FIG. 3I

```
 C   E   P   F   Q   A   N   G   W   C   D   T   I   1745
TGT GAG CCC TTC CAA GCA AAT GGT TGG TGT GAC ACT ATC  6001

 N   N   R   A   Y   C   H   Y   D   G   G   D   C   1758
AAC AAC CGA GCC TAC TGC CAC TAT GAC GGG GGA GAC TGC  6040

 C   S   S   T   L   S   S   K   K   V   I   P   F   1771
TGC TCT TCC ACA CTC TCC TCC AAG AAG GTC ATT CCA TTT  6079

 A   A   D   C   D   L   D   E   C   T   C   R   D   1784
GCT GCT GAC TGT GAC CTG GAT GAG TGC ACC TGC CGG GAC  6118

 P   K   A   E   E   N   Q   *                       1792
CCC AAG GCA GAA GAA AAT CAG TAA  ctgtgggaacaagcccctc 6161

cctccactgcctcagaggcagtaagaaagagaggccgacccaggaggaaaca 6213

aagggtgaatgaagaagaacaatcatgaaatggaagaaggaggaagagcatg 6265

aaggatcttataagaaatgcaagaggatattgataggtgtgaactagttcat 6317

caagtagcccaagtaggagagaatcataggcaaaagtttctttaaagtggca 6369

                            END PAPP-Ef CLONE      ←|
gttgattaacatggaaggggaaatatgatagatatataaggaccctcc    | tccc 6421
                            END PAPP-Ef CLONE      ←|

tcacttatattctattaaatcctatcctcaactcttgccctgctctccgctc 6473

cacccccctgccaactactcagtcccacccaacttgtaaaccaataccaaaat 6525

actagaggagaagttggcagggatactgttaatacccattttgaatggattg 6577

ccatctttcagagcttgtctgctctcaactggctctttttctttttgtgtag 6629

tttccaatgaataatgaagttagttattaattctttataagtatttaaacat 6681

aattatataaatatattatatatattaaaaaaaaaaaa               6719
```

FIG. 3J

PAPP-Eb nt: SEQ ID NO:8
aa: SEQ ID NO:10

```
 M   M   C   L   K   I   L   R   I   S   L   A   I      13
ATG ATG TGC TTA AAG ATC CTA AGA ATA AGC CTG GCG ATT     39

                        |→ BEGIN PAPP-Ef CLONE
 L   A   G   W   A   L  | C   S   A   N   S   E   L     26
TTG GCT GGG TGG GCA CTC|TGT TCT GCC AAC TCT GAG CTG     78
                        |→ BEGIN PAPP-Ef CLONE

 G   W   T   R   K   K   S   L   V   E   R   E   H      39
GGC TGG ACA CGC AAG AAA TCC TTG GTT GAG AGG GAA CAC    117

 L   N   Q   V   L   L   E   G   E   R   C   W   L      52
CTG AAT CAG GTG CTG TTG GAA GGA GAA CGT TGT TGG CTG    156

 G   A   K   V   R   R   P   R   A   S   P   Q   H      65
GGG GCC AAG GTT CGA AGA CCC AGA GCT TCT CCA CAG CAT    195

 H   L   F   G   V   Y   P   S   R   A   G   N   Y      78
CAC CTC TTT GGA GTC TAC CCC AGC AGG GCT GGG AAC TAC    234

 L   R   P   Y   P   V   G   E   Q   E   I   H   H      91
CTA AGG CCC TAC CCC GTG GGG GAG CAA GAA ATC CAT CAT    273

 T   G   R   S   K   P   D   T   E   G   N   A   V     104
ACA GGA CGC AGC AAA CCA GAC ACT GAA GGA AAT GCT GTG    312

 S   L   V   P   P   D   L   T   E   N   P   A   G     117
AGC CTT GTT CCC CCA GAC CTG ACT GAA AAT CCA GCA GGA    351

 L   R   G   A   V   E   E   P   A   A   P   W   V     130
CTG AGG GGT GCA GTT GAA GAG CCG GCT GCC CCA TGG GTA    390

 G   D   S   P   I   G   Q   S   E   L   L   G   D     143
GGG GAT AGT CCT ATT GGG CAA TCT GAG CTG CTG GGA GAT    429

 D   D   A   Y   L   G   N   Q   R   S   K   E   S     156
GAT GAC GCT TAT CTC GGC AAT CAA AGA TCC AAG GAG TCT    468

 L   G   E   A   G   I   Q   K   G   S   A   M   A     169
CTA GGT GAG GCC GGG ATT CAG AAA GGC TCA GCC ATG GCT    507

 A   T   T   T   T   A   I   F   T   T   L   N   E     182
```

```
GCC ACT ACT ACC ACC GCC ATT TTC ACA ACC CTG AAC GAA   546

 P   K   P   E   T   Q   R   R   G   W   A   K   S    195
CCC AAA CCA GAG ACC CAA AGG AGG GGC TGG GCC AAG TCC   585

 R   Q   R   R   Q   V   W   K   R   R   A   E   D    208
AGG CAG CGT CGC CAA GTG TGG AAG AGG CGG GCG GAA GAT   624

 G   Q   G   D   S   G   I   S   S   H   F   Q   P    221
GGG CAG GGA GAC TCC GGT ATC TCT TCA CAT TTC CAA CCT   663

 W   P   K   H   S   L   K   H   R   V   K   K   S    234
TGG CCC AAG CAT TCC CTT AAA CAC AGG GTC AAA AAG AGT   702

 P   P   E   E   S   N   Q   N   G   G   E   G   S    247
CCA CCG GAG GAA AGC AAC CAA AAT GGT GGA GAG GGC TCC   741

 Y   R   E   A   E   T   F   N   S   Q   V   G   L    260
TAC CGA GAA GCA GAG ACC TTT AAC TCC CAA GTA GGA CTG   780

 P   I   L   Y   F   S   G   R   R   E   R   L   L    273
CCC ATC TTA TAC TTC TCT GGG AGG CGG GAG CGG CTG CTG   819

 L   R   P   E   V   L   A   E   I   P   R   E   A    286
CTG CGT CCA GAA GTG CTG GCT GAG ATT CCC CGG GAG GCG   858

 F   T   V   E   A   W   V   K   P   E   G   G   Q    299
TTC ACA GTG GAA GCC TGG GTT AAA CCG GAG GGA GGA CAG   897

 N   N   P   A   I   I   A   G   V   F   D   N   C    312
AAC AAC CCA GCC ATC ATC GCA GGT GTG TTT GAT AAC TGC   936

 S   H   T   V   S   D   K   G   W   A   L   G   I    325
TCC CAC ACT GTC AGT GAC AAA GGC TGG GCC CTG GGG ATC   975

 R   S   G   K   D   K   G   K   R   D   A   R   F    338
CGC TCA GGG AAG GAC AAG GGA AAG CGG GAT GCT CGC TTC  1014

 F   F   S   L   C   T   D   R   V   K   K   A   T    351
TTC TTC TCC CTC TGC ACC GAC CGC GTG AAG AAA GCC ACC  1053

 I   L   I   S   H   S   R   Y   Q   P   G   T   W    364
ATC TTG ATT AGC CAC AGT CGC TAC CAA CCA GGC ACA TGG  1092

 T   H   V   A   A   T   Y   D   G   R   H   M   A    377
ACC CAT GTG GCA GCC ACT TAC GAT GGA CGG CAC ATG GCC  1131

 L   Y   V   D   G   T   Q   V   A   S   S   L   D    390
```

```
CTG TAT GTG GAT GGC ACT CAG GTG GCT AGC AGT CTA GAC   1170
 Q   S   G   P   L   N   S   P   F   M   A   S   C    403
CAG TCT GGT CCC CTG AAC AGC CCC TTC ATG GCA TCT TGC   1209
 R   S   L   L   L   G   G   D   S   S   E   D   G    416
CGC TCT TTG CTC CTG GGG GGA GAC AGC TCT GAG GAT GGG   1248
 H   Y   F   R   G   H   L   G   T   L   V   F   W    429
CAC TAT TTC CGT GGA CAC CTG GGC ACA CTG GTT TTC TGG   1287
 S   T   A   L   P   Q   S   H   F   Q   H   S   S    442
TCG ACC GCC CTG CCA CAA AGC CAT TTT CAG CAC AGT TCT   1326
 Q   H   S   S   E   E   E   E   A   T   D   L   V    455
CAG CAT TCA AGT GAG GAG GAG GAA GCG ACT GAC TTG GTC   1365
 L   T   A   S   F   E   P   V   N   T   E   W   V    468
CTG ACA GCG AGC TTT GAG CCT GTG AAC ACA GAG TGG GTT   1404
 P   F   R   D   E   K   Y   P   R   L   E   V   L    481
CCC TTT AGA GAT GAG AAG TAC CCA CGA CTT GAG GTT CTC   1443
 Q   G   F   E   P   E   P   E   I   L   S   P   L    494
CAG GGC TTT GAG CCA GAG CCT GAG ATT CTG TCG CCT TTG   1482
 Q   P   P   L   C   G   Q   T   V   C   D   N   V    507
CAG CCC CCA CTC TGT GGG CAA ACA GTC TGT GAC AAT GTG   1521
 E   L   I   S   Q   Y   N   G   Y   W   P   L   R    520
GAA TTG ATC TCC CAG TAC AAT GGA TAC TGG CCC CTT CGG   1560
 G   E   K   V   I   R   Y   Q   V   V   N   I   C    533
GGA GAG AAG GTG ATA CGC TAC CAG GTG GTG AAC ATC TGT   1599
 D   D   E   G   L   N   P   I   V   S   E   E   Q    546
GAT GAT GAG GGC CTA AAC CCC ATT GTG AGT GAG GAG CAG   1638
 I   R   L   Q   H   E   A   L   N   E   A   F   S    559
ATT CGT CTG CAG CAC GAG GCA CTG AAT GAG GCC TTC AGC   1677
 R   Y   N   I   S   W   Q   L   S   V   H   Q   V    572
CGC TAC AAC ATC AGC TGG CAG CTG AGC GTC CAC CAG GTC   1716
 H   N   S   T   L   R   H   R   V   V   L   V   N    585
CAC AAT TCC ACC CTG CGA CAC CGG GTT GTG CTT GTG AAC   1755
     C   E   P   S   K   I   G   N   D   H   C   D   P   598
```

FIG. 4C

```
TGT GAG CCC AGC AAG ATT GGC AAT GAC CAT TGT GAC CCC  1794

 E   C   E   H   P   L   T   G   Y   D   G   G   D    611
GAG TGT GAG CAC CCA CTC ACA GGC TAT GAT GGG GGT GAC  1833

 C   R   L   Q   G   R   C   Y   S   W   N   R   R    624
TGC CGC CTG CAG GGC CGC TGC TAC TCC TGG AAC CGC AGG  1872

 D   G   L   C   H   V   E   C   N   N   M   L   N    637
GAT GGG CTC TGT CAC GTG GAG TGT AAC AAC ATG CTG AAC  1911

 D   F   D   D   G   D   C   C   D   P   Q   V   A    650
GAC TTT GAC GAC GGA GAC TGC TGC GAC CCC CAG GTG GCT  1950

 D   V   R   K   T   C   F   D   P   D   S   P   K    663
GAT GTG CGC AAG ACC TGC TTT GAC CCT GAC TCA CCC AAG  1989

 R   A   Y   M   S   V   K   E   L   K   E   A   L    676
AGG GCA TAC ATG AGT GTG AAG GAG CTG AAG GAG GCC CTG  2028

 Q   L   N   S   T   H   F   L   N   I   Y   F   A    689
CAG CTG AAC AGT ACT CAC TTC CTC AAC ATC TAC TTT GCC  2067

 S   S   V   R   E   D   L   A   G   A   A   T   W    702
AGC TCA GTG CGG GAA GAC CTT GCA GGT GCT GCC ACC TGG  2106

 P   W   D   K   D   A   V   T   H   L   G   G   I    715
CCT TGG GAC AAG GAC GCT GTC ACT CAC CTG GGT GGC ATT  2145

 V   L   S   P   A   Y   Y   G   M   P   G   H   T    728
GTC CTC AGC CCA GCA TAT TAT GGG ATG CCT GGC CAC ACC  2184

 D   T   M   I   H   E   V   G   H   V   L   G   L    741
GAC ACC ATG ATC CAT GAA GTG GGA CAT GTT CTG GGA CTC  2223

 Y   H   V   F   K   G   V   S   E   R   E   S   C    754
TAC CAT GTC TTT AAA GGA GTC AGT GAA AGA GAA TCC TGC  2262

 N   D   P   C   K   E   T   V   P   S   M   E   T    767
AAT GAC CCC TGC AAG GAG ACA GTG CCA TCC ATG GAA ACG  2301

 G   D   L   C   A   D   T   A   P   T   P   K   S    780
GGA GAC CTC TGT GCC GAC ACC GCC CCC ACT CCC AAG AGT  2340

 E   L   C   R   E   P   E   P   T   S   D   T   C    793
GAG CTG TGC CGG GAA CCA GAG CCC ACT AGT GAC ACC TGT  2379

 G   F   T   R   F   P   G   A   P   F   T   N   Y    806
```

```
GGC TTC ACT CGC TTC CCA GGG GCT CCG TTC ACC AAC TAC  2418

 M   S   Y   T   D   D   N   C   T   D   N   F   T    819
ATG AGC TAC ACG GAT GAT AAC TGC ACT GAC AAC TTC ACT  2457

 P   N   Q   V   A   R   M   H   C   Y   L   D   L    832
CCT AAC CAA GTG GCC CGA ATG CAT TGC TAT TTG GAC CTA  2496

 V   Y   Q   Q   W   T   E   S   R   K   P   T   P    845
GTC TAT CAG CAG TGG ACT GAA AGC AGA AAG CCC ACC CCC  2535

 I   P   I   P   P   M   V   I   G   Q   T   N   K    858
ATC CCC ATT CCA CCT ATG GTC ATC GGA CAG ACC AAC AAG  2574

 S   L   T   I   H   W   L   P   P   I   S   G   V    871
TCC CTC ACT ATC CAC TGG CTG CCT CCT ATT AGT GGA GTT  2613

 V   Y   D   R   A   S   G   S   L   C   G   A   C    884
GTA TAT GAC AGG GCC TCA GGC AGC TTG TGT GGC GCT TGC  2652

 T   E   D   G   T   F   R   Q   Y   V   H   T   A    897
ACT GAA GAT GGG ACC TTT CGT CAG TAT GTG CAC ACA GCT  2691

 S   S   R   R   V   C   D   S   S   G   Y   W   T    910
TCC TCC CGG CGG GTG TGT GAC TCC TCA GGT TAT TGG ACC  2730

 P   E   E   A   V   G   P   P   D   V   D   Q   P    923
CCA GAG GAG GCT GTG GGG CCT CCT GAT GTG GAT CAG CCC  2769

 C   E   P   S   L   Q   A   W   S   P   E   V   H    936
TGC GAG CCA AGC TTA CAG GCC TGG AGC CCT GAG GTC CAC  2808

 L   Y   H   M   N   M   T   V   P   C   P   T   E    949
CTG TAC CAC ATG AAC ATG ACG GTC CCC TGC CCC ACA GAA  2847

 G   C   S   L   E   L   L   F   Q   H   P   V   Q    962
GGC TGT AGC TTG GAG CTG CTC TTC CAA CAC CCG GTC CAA  2886

 A   D   T   L   T   L   W   V   T   S   F   F   M    975
GCC GAC ACC CTC ACC CTG TGG GTC ACT TCC TTC TTC ATG  2925

 E   S   S   Q   V   L   F   D   T   E   I   L   L    988
GAG TCC TCG CAG GTC CTC TTT GAC ACA GAG ATC TTG CTG  2964

 E   N   K   E   S   V   H   L   G   P   L   D   T   1001
GAA AAC AAG GAG TCA GTG CAC CTG GGC CCC TTA GAC ACT  3003

 F   C   D   I   P   L   T   I   K   L   H   V   D   1014
```

```
                TTC TGT GAC ATC CCA CTC ACC ATC AAA CTC CAC GTG GAT   3042
 G   K   V   S   G   V   K   V   Y   T   F   D   E   1027
GGG AAG GTG TCG GGG GTG AAA GTC TAC ACC TTT GAT GAG   3081
 R   I   E   I   D   A   A   L   L   T   S   Q   P   1040
AGG ATA GAG ATT GAT GCA GCA CTC CTG ACT TCT CAG CCC   3120
 H   S   P   L   C   S   G   C   R   P   V   R   Y   1053
CAC AGT CCC TTG TGC TCT GGC TGC AGG CCT GTG AGG TAC   3159
 Q   V   L   R   D   P   P   F   A   S   G   L   P   1066
CAG GTT CTC CGC GAT CCC CCA TTT GCC AGT GGT TTG CCC   3198
 V   V   V   T   H   S   G   R   K   F   T   D   V   1079
GTG GTG GTG ACA CAT TCT CAC AGG AAG TTC ACG GAC GTG   3237
 E   V   T   P   G   Q   M   Y   Q   Y   Q   V   L   1092
GAG GTC ACA CCT GGA CAG ATG TAT CAG TAC CAA GTT CTA   3276
 A   E   A   G   G   E   L   G   E   A   S   P   P   1105
GCT GAA GCT GGA GGA GAA CTG GGA GAA GCT TCG CCT CCT   3315
 L   N   H   I   H   G   A   P   Y   C   G   D   G   1118
CTG AAC CAC ATT CAT GGA GCT CCT TAT TGT GGA GAT GGG   3354
 K   V   S   E   R   L   G   E   E   C   D   D   G   1131
AAG GTG TCA GAG AGA CTG GGA GAA GAG TGT GAT GAT GGA   3393
 D   L   V   S   G   D   G   C   S   K   V   C   E   1144
GAC CTT GTG AGC GGA GAT GGC TGC TCC AAG GTG TGT GAG   3432
 L   E   E   G   F   N   C   V   G   E   P   S   L   1157
CTG GAG GAA GGT TTC AAC TGT GTA GGA GAG CCA AGC CTT   3471
 C   Y   M   Y   E   G   D   G   I   C   E   P   F   1170
TGC TAC ATG TAT GAG GGA GAT GGC ATA TGT GAA CCT TTT   3510
 E   R   K   T   S   I   V   D   C   G   I   Y   T   1183
GAG AGA AAA ACC AGC ATT GTA GAC TGT GGC ATC TAC ACT   3549
 P   K   G   Y   L   D   Q   W   A   T   R   A   Y   1196
CCC AAA GGA TAC TTG GAT CAA TGG GCT ACC CGG GCT TAC   3588
 S   S   H   E   D   K   K   K   C   P   V   S   L   1209
TCC TCT CAT GAA GAC AAG AAG AAG TGT CCT GTT TCC TTG   3627
 V   T   G   E   P   H   S   L   I   C   T   S   Y   1222
```

FIG. 4F

```
GTA ACT GGA GAA CCT CAT TCC CTA ATT TGC ACA TCA TAC  3666

 H   P   D   L   P   N   H   R   P   L   T   G   W   1235
CAT CCA GAT TTA CCC AAC CAC CGT CCC CTA ACT GGC TGG  3705

 F   P   C   V   A   S   E   N   E   T   Q   D   D   1248
TTT CCC TGT GTT GCC AGT GAA AAT GAA ACT CAG GAT GAC  3744

 R   S   E   Q   P   E   G   S   L   K   K   E   D   1261
AGG AGT GAA CAG CCA GAA GGT AGC CTG AAG AAA GAG GAT  3783

 E   V   W   L   K   V   C   F   N   R   P   G   E   1274
GAG GTT TGG CTC AAA GTG TGT TTC AAT AGA CCA GGA GAG  3822

 A   R   A   I   F   I   F   L   T   T   D   G   L   1287
GCC AGA GCA ATT TTT ATT TTT TTG ACA ACT GAT GGC CTA  3861

 V   P   G   E   H   Q   Q   P   T   V   T   L   Y   1300
GTT CCC GGA GAG CAT CAG CAG CCG ACA GTG ACT CTC TAC  3900

 L   T   D   V   R   G   S   N   H   S   L   G   T   1313
CTG ACC GAT GTC CGT GGA AGC AAC CAC TCT CTT GGA ACC  3939

 Y   G   L   S   C   Q   H   N   P   L   I   I   N   1326
TAT GGA CTG TCA TGC CAG CAT AAT CCA CTG ATT ATC AAT  3978

 V   T   H   H   Q   N   V   L   F   H   H   T   T   1339
GTG ACC CAT CAC CAG AAT GTC CTT TTC CAC CAT ACC ACC  4017

 S   V   L   P   N   F   S   S   P   R   V   G   I   1352
TCA GTG CTG CCG AAT TTC TCA TCC CCA CGG GTC GGC ATC  4056

 S   A   V   A   L   R   T   S   S   R   I   G   L   1365
TCA GCT GTG GCT CTA AGG ACA TCC TCC CGC ATT GGT CTT  4095

 S   A   P   S   N   C   I   S   E   D   E   G   Q   1378
TCG GCT CCC AGT AAC TGC ATC TCA GAG GAC GAG GGG CAG  4134

 N   H   Q   G   Q   S   C   I   H   R   P   C   G   1391
AAT CAT CAG GGA CAG AGC TGT ATC CAT CGG CCC TGT GGG  4173

 K   Q   D   S   C   P   S   L   L   L   D   H   A   1404
AAG CAG GAC AGC TGT CCG TCA TTG CTG CTT GAT CAT GCT  4212

 D   V   V   N   C   T   S   I   G   P   G   L   M   1417
GAT GTG GTG AAC TGT ACC TCT ATA GGC CCA GGT CTC ATG  4251

 K   C   A   I   T   C   Q   R   G   F   A   L   Q   1430
```

```
                    AAG TGT GCT ATC ACT TGT CAA AGG GGA TTT GCC CTT CAG  4290
 A   S   S   G   Q   Y   I   R   P   M   Q   K   E  1443
GCC AGC AGT GGG CAG TAC ATC AGG CCC ATG CAG AAG GAA  4329
 I   L   L   T   C   S   S   G   H   W   D   Q   N  1456
ATT CTG CTC ACA TGT TCT TCT GGG CAC TGG GAC CAG ATT  4368
 V   S   C   L   P   V   D   C   G   V   P   D   P  1469
GTG AGC TGC CTT CCC GTG GAC TGC GGT GTT CCC GAC CCG  4407
 S   L   V   N   Y   A   N   F   S   C   S   E   G  1482
TCT TTG GTG AAC TAT GCA AAC TTC TCC TGC TCA GAG GGA  4486
 T   K   F   L   K   R   C   S   I   S   C   V   P  1495
ACC AAA TTT CTG AAA CGC TGC TCA ATC TCT TGT GTC CCA  4485
 P   A   K   L   Q   G   L   S   P   W   L   T   C  1508
CCA GCC AAG CTG CAA GGA CTG AGC CCA TGG CTG ACA TGT  4524
 L   E   D   G   L   W   S   L   P   E   V   Y   C  1521
CTT GAA GAT GGT CTC TGG TCT CTC CCT GAA GTC TAC TGC  4563
 K   L   E   C   D   A   P   P   I   I   L   N   A  1534
AAG TTG GAG TGT GAT GCT CCC CCT ATT ATT CTG AAT GCC  4602
 N   L   L   L   P   H   C   L   Q   D   N   H   D  1547
AAC TTG CTC CTG CCT CAC TGC CTC CAG GAC AAC CAC GAC  4641
 V   G   T   I   C   K   Y   E   C   K   P   G   Y  1560
GTG GGC ACC ATC TGC AAA TAT GAA TGC AAA CCA GGG TAC  4680
 Y   V   A   E   S   A   E   G   K   V   R   N   K  1573
TAT GTG GCA GAA AGT GCA GAG GGT AAA GTC AGG AAC AAG  4719
 L   L   K   I   Q   C   L   E   G   G   I   W   E  1586
CTC CTG AAG ATA CAA TGC CTG GAA GGT GGA ATC TGG GAG  4758
 Q   G   S   C   I   P   V   V   C   E   P   P   P  1599
CAA GGC AGC TGC ATT CCT GTG GTG TGT GAG CCA CCC CCT  4797
 P   V   F   E   G   M   Y   E   C   T   N   G   F  1612
CCT GTG TTT GAA GGC ATG TAT GAA TGT ACC AAT GGC TTC  4836
 S   L   D   S   Q   C   V   L   N   C   N   Q   E  1625
AGC CTG GAC AGC CAG TGT GTG CTC AAC TGT AAC CAG AAA  4875
 R   E   K   L   P   I   L   C   T   K   E   G   L  1638
```

FIG. 4H

```
CGT GAA AAG CTT CCC ATC CTC TGC ACT AAA GAG GGC CTG   4914

 W   T   Q   E   F   K   L   C   E   N   L   Q   G    1651
TGG ACC CAG GAG TTT AAG TTG TGT GAG AAT CTG CAA GGA   4953

 E   C   P   P   P   P   S   E   L   N   S   V   E    1664
GAA TGC CCA CCA CCC CCC TCA GAG CTG AAT TCT GTG GAG   4992

 Y   K   C   X   Q   G   Y   G   I   G   A   V   C    1677
TAC AAA TGT GAR CAA GGA TAT GGG ATT GGT GCA GTG TGT   5031

 S   P   L   C   V   I   P   P   S   D   P   V   M    1690
TCC CCA TTG TGT GTA ATC CCC CCC AGT GAC CCC GTG ATG   5070

 L   P   E   N   I   T   A   D   T   L   E   H   W    1703
CTA CCT GAG AAT ATC ACT GCT GAC ACT CTG GAG CAC TGG   5109

 M   E   P   V   K   V   Q   S   I   V   C   T   G    1716
ATG GAA CCT GTC AAA GTC CAG AGC ATT GTG TGC ACT GGC   5148

 R   R   Q   W   H   P   D   P   V   L   V   H   C    1729
CGG CGT CAA TGG CAC CCA GAC CCC GTC TTA GTC CAC TGC   5187

                    |→ EXON 21
 I   Q   S   C   E |V   I   S   Q   L   L   L   L    1742
ATC CAG TCA TGT GAG|GTC ATA AGC CAG TTG TTG CTG CTT   5226
                    |→ EXON 21

 V   F   P   L   S   Q   Q   E   H   T   Y   A   T    1755
GTG TTC CCA TTG TCC CAG CAA GAA CAC ACG TAT GCT ACA   5265

                    EXON 21 ←|→ FRAME SHIFT
 Y   L   Q   S   K   I   V   |A   L   P   S   R   W    1768
TAT CTG CAA TCC AAA ATT GTT G| CC CTT CCA AGC AGA TGG   5304
                    EXON 21 ←|→ FRAME SHIFT

 L   V   *                                            1771
TTG GTG TGA  cactatcaacaaccgagcctactgccactatgacggggg 5352

agactgctgctcttccacactctcctccaagaaggtcattccatttgctgct 5404

gactgtgacctggatgagtgcacctgccgggaccccaaggcagaagaaaatc 5456

agtaa                                                 5461
```

FIG. 4I

PAPP-Ec nt: SEQ ID NO:15
aa: SEQ ID NO:16

```
 M   M   C   L   K   I   L   R   I   S   L   A   I     13
ATG ATG TGC TTA AAG ATC CTA AGA ATA AGC CTG GCG ATT    39

                        |→ BEGIN PAPP-Ef CLONE
 L   A   G   W   A   L  | C   S   A   N   S   E   L   26
TTG GCT GGG TGG GCA CTC |TGT TCT GCC AAC TCT GAG CTG   78
                        |→ BEGIN PAPP-Ef CLONE

 G   W   T   R   K   K   S   L   V   E   R   E   H     39
GGC TGG ACA CGC AAG AAA TCC TTG GTT GAG AGG GAA CAC   117

 L   N   Q   V   L   L   E   G   E   R   C   W   L     52
CTG AAT CAG GTG CTG TTG GAA GGA GAA CGT TGT TGG CTG   156

 G   A   K   V   R   R   P   R   A   S   P   Q   H     65
GGG GCC AAG GTT CGA AGA CCC AGA GCT TCT CCA CAG CAT   195

 H   L   F   G   V   Y   P   S   R   A   G   N   Y     78
CAC CTC TTT GGA GTC TAC CCC AGC AGG GCT GGG AAC TAC   234

 L   R   P   Y   P   V   G   E   Q   E   I   H   H     91
CTA AGG CCC TAC CCC GTG GGG GAG CAA GAA ATC CAT CAT   273

 T   G   R   S   K   P   D   T   E   G   N   A   V    104
ACA GGA CGC AGC AAA CCA GAC ACT GAA GGA AAT GCT GTG   312

 S   L   V   P   P   D   L   T   E   N   P   A   G    117
AGC CTT GTT CCC CCA GAC CTG ACT GAA AAT CCA GCA GGA   351

 L   R   G   A   V   E   E   P   A   A   P   W   V    130
CTG AGG GGT GCA GTT GAA GAG CCG GCT GCC CCA TGG GTA   390

 G   D   S   P   I   G   Q   S   E   L   L   G   D    143
GGG GAT AGT CCT ATT GGG CAA TCT GAG CTG CTG GGA GAT   429

 D   D   A   Y   L   G   N   Q   R   S   K   E   S    156
GAT GAC GCT TAT CTC GGC AAT CAA AGA TCC AAG GAG TCT   468

 L   G   E   A   G   I   Q   K   G   S   A   M   A    169
CTA GGT GAG GCC GGG ATT CAG AAA GGC TCA GCC ATG GCT   507
```

FIG. 5A

```
 A   T   T   T   T   A   I   F   T   T   L   N   E    182
GCC ACT ACT ACC ACC GCC ATT TTC ACA ACC CTG AAC GAA   546

 P   K   P   E   T   Q   R   R   G   W   A   K   S    195
CCC AAA CCA GAG ACC CAA AGG AGG GGC TGG GCC AAG TCC   585

 R   Q   R   R   Q   V   W   K   R   R   A   E   D    208
AGG CAG CGT CGC CAA GTG TGG AAG AGG CGG GCG GAA GAT   624

 G   Q   G   D   S   G   I   S   S   H   F   Q   P    221
GGG CAG GGA GAC TCC GGT ATC TCT TCA CAT TTC CAA CCT   663

 W   P   K   H   S   L   K   H   G   V   K   K   S    234
TGG CCC AAG CAT TCC CTT AAA CAC GGG GTC AAA AAG AGT   702

 P   P   E   E   S   N   Q   N   G   G   E   G   S    247
CCA CCG GAG GAA AGC AAC CAA AAT GGT GGA GAG GGC TCC   741

 Y   R   E   A   E   T   F   N   S   Q   V   G   L    260
TAC CGA GAA GCA GAG ACC TTT AAC TCC CAA GTA GGA CTG   780

 P   I   L   Y   F   S   G   R   R   E   R   L   L    273
CCC ATC TTA TAC TTC TCT GGG AGG CGG GAG CGG CTG CTG   819

 L   R   P   E   V   L   A   E   I   P   R   E   A    286
CTG CGT CCA GAA GTG CTG GCT GAG ATT CCC CGG GAG GCG   858

 F   T   V   E   A   W   V   K   P   E   G   G   Q    299
TTC ACA GTG GAA GCC TGG GTT AAA CCG GAG GGA GGA CAG   897

                                ∇ DELETION OF PAPP-Ea
                                      aa 308-413
 N   N   P   A   I   I   A   G | G   I   V   L   S    312
AAC AAC CCA GCC ATC ATC GCA GGT|GGC ATT GTC CTC AGC   936
                                |
                                Δ DELETION OF PAPP-Ea
                                      aa 308-413

 P   A   Y   Y   G   M   P   G   H   T   D   T   M    325
CCA GCA TAT TAT GGG ATG CCT GGC CAC ACC GAC ACC ATG   975

 I   H   E   V   G   H   V   L   G   L   Y   H   V    338
ATC CAT GAA GTG GGA CAT GTT CTG GGA CTC TAC CAT GTC  1014

 F   K   G   V   S   E   R   E   S   C   N   D   P    351
TTT AAA GGA GTC AGT GAA AGA GAA TCC TGC AAT GAC CCC  1053
```

FIG. 5B

```
 C   K   E   T   V   P   S   M   E   T   G   D   L    364
TGC AAG GAG ACA GTG CCA TCC ATG GAA ACG GGA GAC CTC  1092

 C   A   D   T   A   P   T   P   K   S   E   L   C    377
TGT GCC GAC ACC GCC CCC ACT CCC AAG AGT GAG CTG TGC  1131

 R   E   P   E   P   T   S   D   T   C   G   F   T    390
CGG GAA CCA GAG CCC ACT AGT GAC ACC TGT GGC TTC ACT  1170

 R   F   P   G   A   P   F   T   N   Y   M   S   Y    403
CGC TTC CCA GGG GCT CCG TTC ACC AAC TAC ATG AGC TAC  1209

 T   D   D   N   C   T   D   N   F   T   P   N   Q    416
ACG GAT GAT AAC TGC ACT GAC AAC TTC ACT CCT AAC CAA  1248

 V   A   R   M   H   C   Y   L   D   L   V   Y   Q    429
GTG GCC CGA ATG CAT TGC TAT TTG GAC CTA GTC TAT CAG  1287

 Q   W   T   E   S   R   K   P   T   P   I   P   I    442
CAG TGG ACT GAA AGC AGA AAG CCC ACC CCC ATC CCC ATT  1326

 P   P   M   V   I   G   Q   T   N   K   S   L   T    455
CCA CCT ATG GTC ATC GGA CAG ACC AAC AAG TCC CTC ACT  1365

 I   H   W   L   P   P   I   S   G   V   V   Y   D    468
ATC CAC TGG CTG CCT CCT ATT AGT GGA GTT GTA TAT GAC  1404

 R   A   S   G   S   L   C   G   A   C   T   E   D    481
AGG GCC TCA GGC AGC TTG TGT GGC GCT TGC ACT GAA GAT  1443

 G   T   F   R   Q   Y   V   H   T   A   S   S   R    494
GGG ACC TTT CGT CAG TAT GTG CAC ACA GCT TCC TCC CGG  1482

 R   V   C   D   S   S   G   Y   W   T   P   E   E    507
CGG GTG TGT GAC TCC TCA GGT TAT TGG ACC CCA GAG GAG  1521

 A   V   G   P   P   D   V   D   Q   P   C   E   P    520
GCT GTG GGG CCT CCT GAT GTG GAT CAG CCC TGC GAG CCA  1560

 S   L   Q   A   W   S   P   E   V   H   L   Y   H    533
AGC TTA CAG GCC TGG AGC CCT GAG GTC CAC CTG TAC CAC  1599

 M   N   M   T   V   P   C   P   T   E   G   C   S    546
ATG AAC ATG ACG GTC CCC TGC CCC ACA GAA GGC TGT AGC  1638

 L   E   L   L   F   Q   H   P   V   Q   A   D   T    559
TTG GAG CTG CTC TTC CAA CAC CCG GTC CAA GCC GAC ACC  1677
```

FIG. 5C

```
L   T   L   W   V   T   S   F   F   M   E   S   S    572
CTC ACC CTG TGG GTC ACT TCC TTC TTC ATG GAG TCC TCG 1716

Q   V   L   F   D   T   E   I   L   L   E   N   K    585
CAG GTC CTC TTT GAC ACA GAG ATC TTG CTG GAA AAC AAG 1755

E   S   V   H   L   G   P   L   D   T   F   C   D    598
GAG TCA GTG CAC CTG GGC CCC TTA GAC ACT TTC TGT GAC 1794

I   P   L   T   I   K   L   H   V   D   G   K   V    611
ATC CCA CTC ACC ATC AAA CTG CAC GTG GAT GGG AAG GTG 1833

S   G   V   K   V   Y   T   F   D   E   R   I   E    624
TCG GGG GTG AAA GTC TAC ACC TTT GAT GAG AGG ATA GAG 1872

I   D   A   A   L   L   T   S   Q   P   H   S   P    637
ATT GAT GCA GCA CTC CTG ACT TCT CAG CCC CAC AGT CCC 1911

L   C   S   G   C   R   P   V   R   Y   Q   V   L    650
TTG TGC TCT GGC TGC AGG CCT GTG AGG TAC CAG GTT CTC 1950

R   D   P   P   F   A   S   G   L   P   V   V   V    663
CGC GAT CCC CCA TTT GCC AGT GGT TTG CCC GTG GTG GTG 1989

T   H   S   H   R   K   F   T   D   V   E   V   T    676
ACA CAT TCT CAC AGG AAG TTC ACG GAC GTG GAG GTC ACA 2028

P   G   Q   M   Y   Q   Y   Q   V   L   A   E   A    689
CCT GGA CAG ATG TAT CAG TAC CAA GTT CTA GCT GAA GCT 2067

G   G   E   L   G   E   A   S   P   P   L   N   H    702
GGA GGA GAA CTG GGA GAA GCT TCG CCT CCT CTG AAC CAC 2106

I   H   G   A   P   Y   C   G   D   G   K   V   S    715
ATT CAT GGA GCT CCT TAT TGT GGA GAT GGG AAG GTG TCA 2145

E   R   L   G   E   E   C   D   D   G   D   L   V    728
GAG AGA CTG GGA GAA GAG TGT GAT GAT GGA GAC CTT GTG 2184

S   G   D   G   C   S   K   V   C   E   L   E   E    741
AGC GGA GAT GGC TGC TCC AAG GTG TGT GAG CTG GAG GAA 2223

G   F   N   C   V   G   E   P   S   L   C   Y   M    754
GGT TTC AAC TGT GTA GGA GAG CCA AGC CTT TGC TAC ATG 2262

Y   E   G   D   G   I   C   E   P   F   E   R   K    767
TAT GAG GGA GAT GGC ATA TGT GAA CCT TTT GAG AGA AAA 2301
```

FIG. 5D

```
 T   S   I   V   D   C   G   I   Y   T   P   K   G    780
ACC AGC ATT GTA GAC TGT GGC ATC TAC ACT CCC AAA GGA  2340

 Y   L   D   Q   W   A   T   R   A   Y   S   S   H    793
TAC TTG GAT CAA TGG GCT ACC CGG GCT TAC TCC TCT CAT  2379

 E   D   K   K   K   C   P   V   S   L   V   T   G    806
GAA GAC AAG AAG AAG TGT CCT GTT TCC TTG GTA ACT GGA  2418

 E   P   H   S   L   I   R   T   S   Y   H   P   D    819
GAA CCT CAT TCC CTA ATT CGC ACA TCA TAC CAT CCA GAT  2457

 L   P   N   H   R   P   L   T   G   W   F   P   C    832
TTA CCC AAC CAC CGT CCC CTA ACT GGC TGG TTT CCC TGT  2496

 V   A   S   E   N   E   T   Q   D   D   R   S   E    845
GTT GCC AGT GAA AAT GAA ACT CAG GAT GAC AGG AGT GAA  2535

 Q   P   E   G   S   L   K   K   E   D   E   V   W    858
CAG CCA GAA GGT AGC CTG AAG AAA GAG GAT GAG GTT TGG  2574

 L   K   V   C   F   N   R   P   G   E   A   R   A    871
CTC AAA GTG TGT TTC AAT AGA CCA GGA GAG GCC AGA GCA  2613

 I   F   I   F   L   T   T   D   G   L   V   P   G    884
ATT TTT ATT TTT TTG ACA ACT GAT GGC CTA GTT CCC GGA  2652

 E   H   Q   Q   P   T   V   T   L   Y   L   T   D    897
GAG CAT CAG CAG CCG ACA GTG ACT CTC TAC CTG ACC GAT  2691

 V   R   G   S   N   H   S   L   G   T   Y   G   L    910
GTC CGT GGA AGC AAC CAC TCT CTT GGA ACC TAT GGA CTG  2730

 S   C   Q   H   N   P   L   I   I   N   V   T   H    923
TCA TGC CAG CAC AAT CCA CTG ATT ATC AAT GTG ACC CAT  2769

 H   Q   N   V   L   F   R   H   T   T   S   V   L    936
CAC CAG AAT GTC CTT TTC CGC CAT ACC ACC TCA GTG CTG  2808

 L   N   F   S   S   P   R   V   G   I   S   A   V    949
CTG AAT TTC TCA TCC CCA CGG GTC GGC ATC TCA GCT GTG  2847

 A   L   R   T   S   S   R   I   G   L   S   A   P    962
GCT CTA AGG ACA TCC TCC CGC ATT GGT CTC TCG GCT CCC  2886

 S   N   C   I   S   E   D   E   G   Q   N   H   Q    975
AGT AAC TGC ATC TCA GAG GAC GAG GGG CAG AAT CAT CAG  2925
```

FIG. 5E

```
 G   Q   S   C   I   H   R   P   C   G   K   Q   D    988
GGA CAG AGC TGT ATC CAT CGG CCC TGT GGG AAG CAG GAC  2964

 S   C   P   S   L   L   L   D   H   A   D   V   V   1001
AGC TGT CCG TCA TTG CTG CTT GAT CAT GCT GAT GTG GTG  3003

 N   C   T   S   I   G   P   G   L   M   K   C   A   1014
AAC TGT ACC TCT ATA GGC CCA GGT CTC ATG AAG TGT GCT  3042

 T   T   C   Q   R   G   F   A   L   Q   A   S   S   1027
ACC ACT TGT CAA AGG GGA TTT GCC CTT CAG GCC AGC AGT  3081

 E   Q   Y   I   R   L   M   Q   K   E   I   L   L   1040
GAG CAG TAC ATC AGG CTC ATG CAG AAG GAG ATT CTG CTC  3120

 T   C   S   S   G   H   W   D   Q   N   V   S   C   1053
ACA TGT TCT TCT GGG CAC TGG GAC CAG AAT GTG AGC TGC  3159

 L   P   V   D   C   G   V   P   D   P   S   L   V   1066
CTT CCC GTG GAC TGC GGT GTT CCC GAC CCG TCT TTG GTG  3198

 N   Y   A   N   F   S   C   S   E   G   T   K   F   1079
AAC TAT GCA AAC TTC TCC TGC TCA GAG GGA ACC AAA TTT  3237

 L   K   R   C   S   I   S   C   V   P   P   A   K   1092
CTG AAA CGC TGC TCA ATC TCT TGT GTC CCA CCA GCC AAG  3276

 L   Q   G   L   S   P   W   L   T   C   L   E   D   1105
CTG CAA GGA CTG AGC CCA TGG CTG ACA TGT CTT GAA GAT  3315

 G   L   W   S   L   P   E   V   Y   C   K   L   E   1118
GGT CTC TGG TCT CTC CCT GAA GTC TAC TGC AAG TTG GAG  3354

 C   D   A   P   P   I   I   L   N   A   N   L   L   1131
TGT GAT GCT CCC CCT ATT ATT CTG AAT GCC AAC TTG CTC  3393

 L   P   H   C   L   Q   D   N   H   D   V   G   T   1144
CTG CCT CAC TGC CTC CAG GAC AAC CAC GAC GTG GGC ACC  3432

 I   C   K   Y   E   C   K   P   G   Y   Y   V   A   1157
ATC TGC AAA TAT GAA TGC AAA CCA GGG TAC TAT GTG GCA  3471

 E   S   A   E   G   K   V   R   N   K   L   L   K   1170
GAA AGT GCA GAG GGT AAA GTC AGG AAC AAG CTC CTG AAG  3510

 I   Q   C   L   E   G   G   I   W   E   Q   G   S   1183
ATA CAA TGC CTG GAA GGT GGA ATC TGG GAG CAA GGC AGC  3549
```

FIG. 5F

```
 C   I   P   V   V   C   E   P   P   P   P   V   F   1196
TGC ATT CCT GTG GTG TGT GAG CCA CCC CCT CCT GTG TTT  3588

 E   G   M   Y   E   C   T   N   G   F   S   L   D   1209
GAA GGC ATG TAT GAA TGT ACC AAT GGC TTC AGC CTG GAC  3627

 S   Q   C   V   L   N   C   N   Q   E   R   E   K   1222
AGC CAG TGT GTG CTC AAC TGT AAC CAG GAA CGT GAA AAG  3666

 L   P   I   L   C   T   K   E   G   L   W   T   Q   1235
CTT CCC ATC CTC TGC ACT AAA GAG GGC CTG TGG ACC CAG  3705

 E   F   K   L   C   E   N   L   Q   G   E   C   P   1248
GAG TTT AAG TTG TGT GAG AAT CTG CAA GGA GAA TGC CCG  3744

 P   P   P   S   E   L   N   S   V   E   Y   K   C   1261
CCA CCC CCC TCA GAG CTG AAT TCT GTG GAG TAC AAA TGT  3783

 E   Q   G   Y   G   I   G   A   V   C   S   P   L   1274
GAA CAA GGA TAT GGG ATT GGT GCA GTG TGT TCC CCA TTG  3822

 C   V   I   P   P   S   D   P   V   M   L   P   E   1287
TGT GTA ATC CCC CCC AGT GAC CCC GTG ATG CTA CCT GAG  3861

 N   I   T   A   D   T   L   E   H   W   M   E   P   1300
AAT ATC ACT GCT GAC ACT CTG GAG CAC TGG ATG GAA CCT  3900

 V   K   V   Q   S   I   V   C   T   G   R   R   Q   1313
GTC AAA GTC CAG AGC ATT GTG TGC ACT GGC CGG CGT CAA  3939

 W   H   P   D   P   V   L   V   H   C   I   Q   S   1326
TGG CAC CCA GAC CCC GTC TTA GTC CAC TGC ATC CAG TCA  3978

 C   E   P   F   Q   A   D   G   W   C   D   T   I   1339
TGT GAG CCC TTC CAA GCA GAT GGT TGG TGT GAC ACT ATC  4017

 N   N   R   A   Y   C   H   Y   D   G   G   D   C   1352
AAC AAC CGA GCC TAC TGC CAC TAT GAC GGG GGA GAC TGC  4056

 C   S   S   T   L   S   S   K   K   V   I   P   F   1365
TGC TCT TCC ACA CTC TCC TCC AAG AAG GTC ATT CCA TTT  4095

 A   A   D   C   D   L   D   E   C   T   C   R   D   1378
GCT GCT GAC TGT GAC CTG GAT GAG TGC ACC TGC CGG GAC  4134

 P   K   A   E   E   N   Q   *                       1386
CCC AAG GCA GAA GAA AAT CAG TAA                      4158
```

FIG. 5G

SEQUENCE LISTING

```
<160> NUMBER OF SEQ ID NOS: 1881

<210> SEQ ID NO 1
<211> LENGTH: 6719
<212> TYPE: DNA
<213> ORGANISM: Homo sapiens

<400> SEQUENCE: 1

ccccaagcat caaactgaag gaaacattct aaccttcaca gacagactgg aggctggatg      60

gggacctggc tgaagacatc tggagaatga aagttaagta ccagcttgca tttttgtgcc     120

cctagattat ttttgcattt taaaataaga agcatcaaat tgcgtgtctc tgtgtaaaag     180

ttctagcaat ttgttttaag gtgaacttat tttggcttag ggactacaaa aagagaaggt     240

aattcctagg gaaggaagaa gagaaagaaa tgaaaattag agaataagat tattttgaat     300
```

-continued

```
gacttcaggt agcgaggagt gtgtgtttgt gagtgtgtat ttgagagact tggctcatgc    360
ctgtgggtct tctcttctag tatcagtgag gggagggatt actgaagaag aaggggggaa    420
aaaaaaagaa agaaatctga gctttctggg aggaaattca aaggaaccaa gagaaattaa    480
cttcgttctg caaggactaa agtacagcaa gaggagagag gtcaagcgag aagcgtgcgg    540
gaagcacatg ccctggggag gcatagaagc cacactggca gagcggccag cacaggtagc    600
cagcagaggc attcttgggg ctatttgaaa aagtttggtc tgtgaacaaa acagtttccc    660
tggtgactgc aaatccattg ctagctgcct ctttctcgtc tgcccatcac tctggtgtgg    720
tacccagaag ttgacttctg gttctgtaga aagagctagg ggaggtatga tgtgcttaaa    780
gatcctaaga ataagcctgg cgattttggc tgggtgggca ctctgttctg ccaactctga    840
gctgggctgg acacgcaaga aatccttggt tgagagggaa cacctgaatc aggtgctgtt    900
ggaaggagaa cgttgttggc tgggggccaa ggttcgaaga cccagagctt ctccacagca    960
tcacctcttt ggagtctacc ccagcagggc tgggaactac ctaaggccct accccgtggg   1020
ggagcaagaa atccatcata caggacgcag caaaccagac actgaaggaa atgctgtgag   1080
ccttgttccc ccagacctga ctgaaaatcc agcaggactg aggggtgcag ttgaagagcc   1140
ggctgcccca tgggtagggg atagtcctat tgggcaatct gagctgctgg gagatgatga   1200
cgcttatctc ggcaatcaaa gatccaagga gtctctaggt gaggccggga ttcagaaagg   1260
ctcagccatg gctgccacta ctaccaccgc cattttcaca accctgaacg aacccaaacc   1320
agagacccaa aggaggggct gggccaagtc caggcagcgt cgccaagtgt ggaagaggcg   1380
ggcggaagat gggcagggag actccggtat ctcttcacat ttccaacctt ggcccaagca   1440
ttcccttaaa cacagggtca aaaagagtcc accggaggaa agcaaccaaa atggtggaga   1500
gggctcctac cgagaagcag agacctttaa ctcccaagta ggactgccca tcttatactt   1560
ctctgggagg cgggagcggc tgctgctgcg tccagaagtg ctggctgaga ttccccggga   1620
ggcgttcaca gtggaagcct gggttaaacc ggagggagga cagaacaacc cagccatcat   1680
cgcaggtgtg tttgataact gctcccacac tgtcagtgac aaaggctggg ccctggggat   1740
ccgctcaggg aaggacaagg gaaagcggga tgctcgcttc ttcttctccc tctgcaccga   1800
ccgcgtgaag aaagccacca tcttgattag ccacagtcgc taccaaccag gcacatggac   1860
ccatgtggca gccacttacg atggacggca catggccctg tatgtggatg gcactcaggt   1920
ggctagcagt ctagaccagt ctggtcccct gaacagcccc ttcatggcat cttgccgctc   1980
tttgctcctg gggggagaca gctctgagga tgggcactat ttccgtggac acctgggcac   2040
actggttttc tggtcgaccg ccctgccaca aagccatttt cagcacagtt ctcagcattc   2100
aagtgaggag gaggaagcga ctgacttggt cctgacagcg agctttgagc ctgtgaacac   2160
agagtgggtt ccctttagag atgagaagta cccacgactt gaggttctcc agggctttga   2220
gccagagcct gagattctgt cgcctttgca gcccccactc tgtgggcaaa cagtctgtga   2280
caatgtggaa ttgatctccc agtacaatgg atactggccc cttcggggag agaaggtgat   2340
acgctaccag gtggtgaaca tctgtgatga tgagggccta aaccccattg tgagtgagga   2400
gcagattcgt ctgcagcacg aggcactgaa tgaggccttc agccgctaca acatcagctg   2460
gcagctgagc gtccaccagg tccacaattc caccctgcga caccgggttg tgcttgtgaa   2520
ctgtgagccc agcaagattg gcaatgacca ttgtgacccc gagtgtgagc acccactcac   2580
aggctatgat gggggtgact gccgcctgca gggccgctgc tactcctgga accgcaggga   2640
```

-continued

```
tgggctctgt cacgtggagt gtaacaacat gctgaacgac tttgacgacg gagactgctg   2700
cgacccccag gtggctgatg tgcgcaagac ctgctttgac cctgactcac ccaagagggc   2760
atacatgagt gtgaaggagc tgaaggaggc cctgcagctg aacagtactc acttcctcaa   2820
catctacttt gccagctcag tgcgggaaga ccttgcaggt gctgccacct ggccttggga   2880
caaggacgct gtcactcacc tgggtggcat tgtcctcagc ccagcatatt atgggatgcc   2940
tggccacacc gacaccatga tccatgaagt gggacatgtt ctgggactct accatgtctt   3000
taaaggagtc agtgaaagag aatcctgcaa tgacccctgc aaggagacag tgccatccat   3060
ggaaacggga gacctctgtg ccgacaccgc ccccactccc aagagtgagc tgtgccggga   3120
accagagccc actagtgaca cctgtggctt cactcgcttc ccaggggctc cgttcaccaa   3180
ctacatgagc tacacggatg ataactgcac tgacaacttc actcctaacc aagtggcccg   3240
aatgcattgc tatttggacc tagtctatca gcagtggact gaaagcagaa agcccacccc   3300
catccccatt ccacctatgg tcatcggaca gaccaacaag tccctcacta tccactggct   3360
gcctcctatt agtggagttg tatatgacag ggcctcaggc agcttgtgtg gcgcttgcac   3420
tgaagatggg acctttcgtc agtatgtgca cacagcttcc tcccggcggg tgtgtgactc   3480
ctcaggttat tggaccccag aggaggctgt ggggcctcct gatgtggatc agccctgcga   3540
gccaagctta caggcctgga gccctgaggt ccacctgtac cacatgaaca tgacggtccc   3600
ctgccccaca gaaggctgta gcttggagct gctcttccaa cacccggtcc aagccgacac   3660
cctcaccctg tgggtcactt ccttcttcat ggagtcctcg caggtcctct ttgacacaga   3720
gatcttgctg gaaaacaagg agtcagtgca cctgggcccc ttagacactt tctgtgacat   3780
cccactcacc atcaaactgc acgtggatgg gaaggtgtcg gggtgaaag tctacacctt   3840
tgatgagagg atagagattg atgcagcact cctgacttct cagccccaca gtcccttgtg   3900
ctctggctgc aggcctgtga ggtaccaggt tctccgcgat cccccatttg ccagtggttt   3960
gcccgtggtg gtgacacatt ctcacaggaa gttcacggac gtggaggtca cacctggaca   4020
gatgtatcag taccaagttc tagctgaagc tggaggagaa ctgggagaag cttcgcctcc   4080
tctgaaccac attcatggag ctccttattg tggagatggg aaggtgtcag agagactggg   4140
agaagagtgt gatgatggag accttgtgag cggagatggc tgctccaagg tgtgtgagct   4200
ggaggaaggt ttcaactgtg taggagagcc aagcctttgc tacatgtatg agggagatgg   4260
catatgtgaa ccttttgaga gaaaaaccag cattgtagac tgtggcatct acactcccaa   4320
aggatacttg gatcaatggg ctacccgggc ttactcctct catgaagaca agaagaagtg   4380
tcctgtttcc ttggtaactg gagaacctca ttccctaatt tgcacatcat accatccaga   4440
tttacccaac caccgtcccc taactggctg gtttccctgt gttgccagtg aaaatgaaac   4500
tcaggatgac aggagtgaac agccagaagg tagcctgaag aaagaggatg aggtttggct   4560
caaagtgtgt ttcaatagac caggagaggc cagagcaatt tttatttttt tgacaactga   4620
tggcctagtt cccggagagc atcagcagcc gacagtgact ctctacctga ccgatgtccg   4680
tggaagcaac cactctcttg gaacctatgg actgtcatgc cagcataatc cactgattat   4740
caatgtgacc catcaccaga atgtcctttt ccaccatacc acctcagtgc tgccgaattt   4800
ctcatcccca cgggtcggca tctcagctgt ggctctaagg acatcctccc gcattggtct   4860
ttcggctccc agtaactgca tctcagagga cgaggggcag aatcatcagg gacagagctg   4920
tatccatcgg ccctgtggga agcaggacag ctgtccgtca ttgctgcttg atcatgctga   4980
tgtggtgaac tgtacctcta taggcccagg tctcatgaag tgtgctatca cttgtcaaag   5040
```

-continued gggatttgcc cttcaggcca gcagtgggca gtacatcagg cccatgcaga aggaaattct 5100
gctcacatgt tcttctgggc actgggacca gaatgtgagc tgccttcccg tggactgcgg 5160
tgttcccgac ccgtctttgg tgaactatgc aaacttctcc tgctcagagg gaaccaaatt 5220
tctgaaacgc tgctcaatct cttgtgtccc accagccaag ctgcaaggac tgagcccatg 5280
gctgacatgt cttgaagatg gtctctggtc tctccctgaa gtctactgca agttggagtg 5340
tgatgctccc cctattattc tgaatgccaa cttgctcctg cctcactgcc tccaggacaa 5400
ccacgacgtg ggcaccatct gcaaatatga atgcaaacca gggtactatg tggcagaaag 5460
tgcagagggt aaagtcagga acaagctcct gaagatacaa tgcctggaag gtggaatctg 5520
ggagcaaggc agctgcattc ctgtggtgtg tgagccaccc cctcctgtgt ttgaaggcat 5580
gtatgaatgt accaatggct tcagcctgga cagccagtgt gtgctcaact gtaaccagga 5640
acgtgaaaag cttcccatcc tctgcactaa agagggcctg tggacccagg agtttaagtt 5700
gtgtgagaat ctgcaaggag aatgcccacc acccccctca gagctgaatt ctgtggagta 5760
caaatgtgaa caaggatatg ggattggtgc agtgtgttcc ccattgtgtg taatcccccc 5820
cagtgacccc gtgatgctac ctgagaatat cactgctgac actctggagc actggatgga 5880
acctgtcaaa gtccagagca ttgtgtgcac tggccggcgt caatggcacc cagaccccgt 5940
cttagtccac tgcatccagt catgtgagcc cttccaagca aatggttggt gtgacactat 6000
caacaaccga gcctactgcc actatgacgg gggagactgc tgctcttcca cactctcctc 6060
caagaaggtc attccatttg ctgctgactg tgacctggat gagtgcacct gccgggaccc 6120
caaggcagaa gaaaatcagt aactgtggga acaagcccct ccctccactg cctcagaggc 6180
agtaagaaag agaggccgac ccaggaggaa acaaagggtg aatgaagaag aacaatcatg 6240
aaatggaaga aggaggaaga gcatgaagga tcttataaga aatgcaagag gatattgata 6300
ggtgtgaact agttcatcaa gtagcccaag taggagagaa tcataggcaa aagtttcttt 6360
aaagtggcag ttgattaaca tggaagggga aatatgatag atatataagg accctcctcc 6420
ctcacttata ttctattaaa tcctatcctc aactcttgcc ctgctctccg ctccaccccc 6480
tgccaactac tcagtcccac ccaacttgta aaccaatacc aaaatactag aggagaagtt 6540
ggcagggata ctgttaatac ccattttgaa tggattgcca tctttcagag cttgtctgct 6600
ctcaactggc tctttttctt tttgtgtagt ttccaatgaa taatgaagtt agttattaat 6660
tctttataag tatttaaaca taattatata aatatattat atatattaaa aaaaaaaaa 6719

<210> SEQ ID NO 2
<211> LENGTH: 5376
<212> TYPE: DNA
<213> ORGANISM: Homo sapiens

<400> SEQUENCE: 2
atgatgtgct taaagatcct aagaataagc ctggcgattt tggctgggtg ggcactctgt 60
tctgccaact ctgagctggg ctggacacgc aagaaatcct tggttgagag ggaacacctg 120
aatcaggtgc tgttggaagg agaacgttgt tggctggggg ccaaggttcg aagacccaga 180
gcttctccac agcatcacct ctttggagtc taccccagca gggctgggaa ctacctaagg 240
ccctaccccg tgggggagca agaaatccat catacaggac gcagcaaacc agacactgaa 300
ggaaatgctg tgagccttgt tcccccagac ctgactgaaa atccagcagg actgaggggt 360
gcagttgaag agccggctgc cccatgggta ggggatagtc ctattgggca atctgagctg 420

-continued

```
ctgggagatg atgacgctta tctcggcaat caaagatcca aggagtctct aggtgaggcc    480
gggattcaga aaggctcagc catggctgcc actactacca ccgccatttt cacaaccctg    540
aacgaaccca aaccagagac ccaaaggagg ggctgggcca agtccaggca gcgtcgccaa    600
gtgtggaaga ggcgggcgga agatgggcag ggagactccg gtatctcttc acatttccaa    660
ccttggccca agcattccct taaacacagg gtcaaaaaga gtccaccgga ggaaagcaac    720
caaaatggtg gagagggctc ctaccgagaa gcagagacct ttaactccca agtaggactg    780
cccatcttat acttctctgg gaggcgggag cggctgctgc tgcgtccaga agtgctggct    840
gagattcccc gggaggcgtt cacagtggaa gcctgggtta aaccggaggg aggacagaac    900
aacccagcca tcatcgcagg tgtgtttgat aactgctccc acactgtcag tgacaaaggc    960
tgggccctgg ggatccgctc agggaaggac aagggaaagc gggatgctcg cttcttcttc   1020
tccctctgca ccgaccgcgt gaagaaagcc accatcttga ttagccacag tcgctaccaa   1080
ccaggcacat ggacccatgt ggcagccact tacgatggac ggcacatggc cctgtatgtg   1140
gatggcactc aggtggctag cagtctagac cagtctggtc ccctgaacag cccctteatg   1200
gcatcttgcc gctctttgct cctgggggga gacagctctg aggatgggca ctatttccgt   1260
ggacacctgg gcacactggt tttctggtcg accgccctgc cacaaagcca ttttcagcac   1320
agttctcagc attcaagtga ggaggaggaa gcgactgact tggtcctgac agcgagcttt   1380
gagcctgtga acacagagtg ggttcccttt agagatgaga agtacccacg acttgaggtt   1440
ctccagggct ttgagccaga gcctgagatt ctgtcgcctt tgcagccccc actctgtggg   1500
caaacagtct gtgacaatgt ggaattgatc tcccagtaca atggatactg gccccttcgg   1560
ggagagaagg tgatacgcta ccaggtggtg aacatctgtg atgatgaggg cctaaacccc   1620
attgtgagtg aggagcagat tcgtctgcag cacgaggcac tgaatgaggc cttcagccgc   1680
tacaacatca gctggcagct gagcgtccac caggtccaca attccaccct gcgacaccgg   1740
gttgtgcttg tgaactgtga gcccagcaag attggcaatg accattgtga ccccgagtgt   1800
gagcacccac tcacaggcta tgatgggggt gactgccgcc tgcagggccg ctgctactcc   1860
tggaaccgca gggatgggct ctgtcacgtg gagtgtaaca acatgctgaa cgactttgac   1920
gacggagact gctgcgaccc ccaggtggct gatgtgcgca agacctgctt tgaccctgac   1980
tcacccaaga gggcatacat gagtgtgaag gagctgaagg aggccctgca gctgaacagt   2040
actcacttcc tcaacatcta ctttgccagc tcagtgcggg aagaccttgc aggtgctgcc   2100
acctggcctt gggacaagga cgctgtcact cacctgggtg gcattgtcct cagcccagca   2160
tattatggga tgcctggcca caccgacacc atgatccatg aagtgggaca tgttctggga   2220
ctctaccatg tctttaaagg agtcagtgaa agagaatcct gcaatgaccc ctgcaaggag   2280
acagtgccat ccatggaaac gggagacctc tgtgccgaca ccgcccccac tcccaagagt   2340
gagctgtgcc gggaaccaga gcccactagt gacacctgtg gcttcactcg cttcccaggg   2400
gctccgttca ccaactacat gagctacacg gatgataact gcactgacaa cttcactcct   2460
aaccaagtgg cccgaatgca ttgctatttg gacctagtct atcagcagtg gactgaaagc   2520
agaaagccca cccccatccc cattccacct atggtcatcg gacagaccaa caagtccctc   2580
actatccact ggctgcctcc tattagtgga gttgtatatg acagggcctc aggcagcttg   2640
tgtggcgctt gcactgaaga tgggaccttt cgtcagtatg tgcacacagc ttcctcccgg   2700
cgggtgtgtg actcctcagg ttattggacc ccagaggagg ctgtggggcc tcctgatgtg   2760
gatcagccct gcgagccaag cttacaggcc tggagccctg aggtccacct gtaccacatg   2820
```

-continued

```
aacatgacgg tcccctgccc cacagaaggc tgtagcttgg agctgctctt ccaacacccg   2880
gtccaagccg acaccctcac cctgtgggtc acttccttct tcatggagtc ctcgcaggtc   2940
ctctttgaca cagagatctt gctggaaaac aaggagtcag tgcacctggg ccccttagac   3000
actttctgtg acatcccact caccatcaaa ctgcacgtgg atgggaaggt gtcgggggtg   3060
aaagtctaca cctttgatga gaggatagag attgatgcag cactcctgac ttctcagccc   3120
cacagtccct tgtgctctgg ctgcaggcct gtgaggtacc aggttctccg cgatcccca   3180
tttgccagtg gtttgcccgt ggtggtgaca cattctcaca ggaagttcac ggacgtggag   3240
gtcacacctg gacagatgta tcagtaccaa gttctagctg aagctggagg agaactggga   3300
gaagcttcgc ctcctctgaa ccacattcat ggagctcctt attgtggaga tgggaaggtg   3360
tcagagagac tgggagaaga gtgtgatgat ggagaccttg tgagcggaga tggctgctcc   3420
aaggtgtgtg agctggagga aggtttcaac tgtgtaggag agccaagcct ttgctacatg   3480
tatgagggag atggcatatg tgaacctttt gagagaaaaa ccagcattgt agactgtggc   3540
atctacactc ccaaaggata cttggatcaa tgggctaccc gggcttactc ctctcatgaa   3600
gacaagaaga agtgtcctgt ttccttggta actggagaac ctcattccct aatttgcaca   3660
tcataccatc cagatttacc caaccaccgt cccctaactg gctggtttcc ctgtgttgcc   3720
agtgaaaatg aaactcagga tgacaggagt gaacagccag aaggtagcct gaagaaagag   3780
gatgaggttt ggctcaaagt gtgtttcaat agaccaggag aggccagagc aatttttatt   3840
tttttgacaa ctgatggcct agttcccgga gagcatcagc agccgacagt gactctctac   3900
ctgaccgatg tccgtggaag caaccactct cttggaacct atggactgtc atgccagcat   3960
aatccactga ttatcaatgt gacccatcac cagaatgtcc ttttccacca taccacctca   4020
gtgctgccga atttctcatc cccacgggtc ggcatctcag ctgtggctct aaggacatcc   4080
tcccgcattg gtctttcggc tcccagtaac tgcatctcag aggacgaggg gcagaatcat   4140
cagggacaga gctgtatcca tcggccctgt gggaagcagg acagctgtcc gtcattgctg   4200
cttgatcatg ctgatgtggt gaactgtacc tctataggcc caggtctcat gaagtgtgct   4260
atcacttgtc aaaggggatt tgcccttcag gccagcagtg ggcagtacat caggcccatg   4320
cagaaggaaa ttctgctcac atgttcttct gggcactggg accagaatgt gagctgcctt   4380
cccgtggact gcggtgttcc cgacccgtct ttggtgaact atgcaaactt ctcctgctca   4440
gagggaacca aatttctgaa acgctgctca atctcttgtg tcccaccagc caagctgcaa   4500
ggactgagcc catggctgac atgtcttgaa gatggtctct ggtctctccc tgaagtctac   4560
tgcaagttgg agtgtgatgc tccccctatt attctgaatg ccaacttgct cctgcctcac   4620
tgcctccagg acaaccacga cgtgggcacc atctgcaaat atgaatgcaa accagggtac   4680
tatgtggcag aaagtgcaga gggtaaagtc aggaacaagc tcctgaagat acaatgcctg   4740
gaaggtggaa tctgggagca aggcagctgc attcctgtgg tgtgtgagcc accccctcct   4800
gtgtttgaag gcatgtatga atgtaccaat ggcttcagcc tggacagcca gtgtgtgctc   4860
aactgtaacc aggaacgtga aaagcttccc atcctctgca ctaaagaggg cctgtggacc   4920
caggagttta agttgtgtga gaatctgcaa ggagaatgcc caccaccccc ctcagagctg   4980
aattctgtgg agtacaaatg tgaacaagga tatgggattg gtgcagtgtg ttccccattg   5040
tgtgtaatcc cccccagtga ccccgtgatg ctacctgaga atatcactgc tgacactctg   5100
gagcactgga tggaacctgt caaagtccag agcattgtgt gcactggccg gcgtcaatgg   5160
```

-continued

```
cacccagacc ccgtcttagt ccactgcatc cagtcatgtg agcccttcca agcaaatggt   5220

tggtgtgaca ctatcaacaa ccgagcctac tgccactatg acgggggaga ctgctgctct   5280

tccacactct cctccaagaa ggtcattcca tttgctgctg actgtgacct ggatgagtgc   5340

acctgccggg accccaaggc agaagaaaat cagtaa                             5376


<210> SEQ ID NO 3w
<211> LENGTH: 1791
<212> TYPE: PRT
<213> ORGANISM: Homo sapiens

<400> SEQUENCE: 3

Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
                85                  90                  95

Pro Asp Thr Glu Gly Asn Ala Val Ser Leu Val Pro Pro Asp Leu Thr
            100                 105                 110

Glu Asn Pro Ala Gly Leu Arg Gly Ala Val Glu Glu Pro Ala Ala Pro
        115                 120                 125

Trp Val Gly Asp Ser Pro Ile Gly Gln Ser Glu Leu Leu Gly Asp Asp
    130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Thr Ala Ile
                165                 170                 175

Phe Thr Thr Leu Asn Glu Pro Lys Pro Glu Thr Gln Arg Arg Gly Trp
            180                 185                 190

Ala Lys Ser Arg Gln Arg Arg Gln Val Trp Lys Arg Arg Ala Glu Asp
        195                 200                 205

Gly Gln Gly Asp Ser Gly Ile Ser Ser His Phe Gln Pro Trp Pro Lys
    210                 215                 220

His Ser Leu Lys His Arg Val Lys Lys Ser Pro Pro Glu Glu Ser Asn
225                 230                 235                 240

Gln Asn Gly Gly Glu Gly Ser Tyr Arg Glu Ala Glu Thr Phe Asn Ser
                245                 250                 255

Gln Val Gly Leu Pro Ile Leu Tyr Phe Ser Gly Arg Arg Glu Arg Leu
            260                 265                 270

Leu Leu Arg Pro Glu Val Leu Ala Glu Ile Pro Arg Glu Ala Phe Thr
        275                 280                 285

Val Glu Ala Trp Val Lys Pro Glu Gly Gly Gln Asn Asn Pro Ala Ile
    290                 295                 300

Ile Ala Gly Val Phe Asp Asn Cys Ser His Thr Val Ser Asp Lys Gly
305                 310                 315                 320

Trp Ala Leu Gly Ile Arg Ser Gly Lys Asp Lys Gly Lys Arg Asp Ala
                325                 330                 335
```

-continued

```
Arg Phe Phe Phe Ser Leu Cys Thr Asp Arg Val Lys Lys Ala Thr Ile
            340                 345                 350

Leu Ile Ser His Ser Arg Tyr Gln Pro Gly Thr Trp Thr His Val Ala
        355                 360                 365

Ala Thr Tyr Asp Gly Arg His Met Ala Leu Tyr Val Asp Gly Thr Gln
    370                 375                 380

Val Ala Ser Ser Leu Asp Gln Ser Gly Pro Leu Asn Ser Pro Phe Met
385                 390                 395                 400

Ala Ser Cys Arg Ser Leu Leu Leu Gly Gly Asp Ser Ser Glu Asp Gly
                405                 410                 415

His Tyr Phe Arg Gly His Leu Gly Thr Leu Val Phe Trp Ser Thr Ala
            420                 425                 430

Leu Pro Gln Ser His Phe Gln His Ser Ser Gln His Ser Ser Glu Glu
        435                 440                 445

Glu Glu Ala Thr Asp Leu Val Leu Thr Ala Ser Phe Glu Pro Val Asn
    450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
                485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
        515                 520                 525

Val Val Asn Ile Cys Asp Asp Glu Gly Leu Asn Pro Ile Val Ser Glu
    530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
                565                 570                 575

Leu Arg His Arg Val Val Leu Val Asn Cys Glu Pro Ser Lys Ile Gly
            580                 585                 590

Asn Asp His Cys Asp Pro Glu Cys Glu His Pro Leu Thr Gly Tyr Asp
        595                 600                 605

Gly Gly Asp Cys Arg Leu Gln Gly Arg Cys Tyr Ser Trp Asn Arg Arg
    610                 615                 620

Asp Gly Leu Cys His Val Glu Cys Asn Asn Met Leu Asn Asp Phe Asp
625                 630                 635                 640

Asp Gly Asp Cys Cys Asp Pro Gln Val Ala Asp Val Arg Lys Thr Cys
                645                 650                 655

Phe Asp Pro Asp Ser Pro Lys Arg Ala Tyr Met Ser Val Lys Glu Leu
            660                 665                 670

Lys Glu Ala Leu Gln Leu Asn Ser Thr His Phe Leu Asn Ile Tyr Phe
        675                 680                 685

Ala Ser Ser Val Arg Glu Asp Leu Ala Gly Ala Ala Thr Trp Pro Trp
    690                 695                 700

Asp Lys Asp Ala Val Thr His Leu Gly Gly Ile Val Leu Ser Pro Ala
705                 710                 715                 720

Tyr Tyr Gly Met Pro Gly His Thr Asp Thr Met Ile His Glu Val Gly
                725                 730                 735

His Val Leu Gly Leu Tyr His Val Phe Lys Gly Val Ser Glu Arg Glu
            740                 745                 750

Ser Cys Asn Asp Pro Cys Lys Glu Thr Val Pro Ser Met Glu Thr Gly
```

-continued

```
        755                 760                 765

Asp Leu Cys Ala Asp Thr Ala Pro Thr Pro Lys Ser Glu Leu Cys Arg
    770                 775                 780

Glu Pro Glu Pro Thr Ser Asp Thr Cys Gly Phe Thr Arg Phe Pro Gly
785                 790                 795                 800

Ala Pro Phe Thr Asn Tyr Met Ser Tyr Thr Asp Asp Asn Cys Thr Asp
                805                 810                 815

Asn Phe Thr Pro Asn Gln Val Ala Arg Met His Cys Tyr Leu Asp Leu
            820                 825                 830

Val Tyr Gln Gln Trp Thr Glu Ser Arg Lys Pro Thr Pro Ile Pro Ile
        835                 840                 845

Pro Pro Met Val Ile Gly Gln Thr Asn Lys Ser Leu Thr Ile His Trp
    850                 855                 860

Leu Pro Pro Ile Ser Gly Val Val Tyr Asp Arg Ala Ser Gly Ser Leu
865                 870                 875                 880

Cys Gly Ala Cys Thr Glu Asp Gly Thr Phe Arg Gln Tyr Val His Thr
                885                 890                 895

Ala Ser Ser Arg Arg Val Cys Asp Ser Ser Gly Tyr Trp Thr Pro Glu
            900                 905                 910

Glu Ala Val Gly Pro Pro Asp Val Asp Gln Pro Cys Glu Pro Ser Leu
        915                 920                 925

Gln Ala Trp Ser Pro Glu Val His Leu Tyr His Met Asn Met Thr Val
    930                 935                 940

Pro Cys Pro Thr Glu Gly Cys Ser Leu Glu Leu Leu Phe Gln His Pro
945                 950                 955                 960

Val Gln Ala Asp Thr Leu Thr Leu Trp Val Thr Ser Phe Phe Met Glu
                965                 970                 975

Ser Ser Gln Val Leu Phe Asp Thr Glu Ile Leu Leu Glu Asn Lys Glu
            980                 985                 990

Ser Val His Leu Gly Pro Leu Asp Thr Phe Cys Asp Ile Pro Leu Thr
        995                 1000                1005

Ile Lys Leu His Val Asp Gly Lys Val Ser Gly Val Lys Val Tyr Thr
    1010                1015                1020

Phe Asp Glu Arg Ile Glu Ile Asp Ala Ala Leu Leu Thr Ser Gln Pro
1025                1030                1035                1040

His Ser Pro Leu Cys Ser Gly Cys Arg Pro Val Arg Tyr Gln Val Leu
                1045                1050                1055

Arg Asp Pro Pro Phe Ala Ser Gly Leu Pro Val Val Val Thr His Ser
            1060                1065                1070

His Arg Lys Phe Thr Asp Val Glu Val Thr Pro Gly Gln Met Tyr Gln
        1075                1080                1085

Tyr Gln Val Leu Ala Glu Ala Gly Gly Glu Leu Gly Glu Ala Ser Pro
    1090                1095                1100

Pro Leu Asn His Ile His Gly Ala Pro Tyr Cys Gly Asp Gly Lys Val
1105                1110                1115                1120

Ser Glu Arg Leu Gly Glu Glu Cys Asp Asp Gly Asp Leu Val Ser Gly
                1125                1130                1135

Asp Gly Cys Ser Lys Val Cys Glu Leu Glu Glu Gly Phe Asn Cys Val
            1140                1145                1150

Gly Glu Pro Ser Leu Cys Tyr Met Tyr Glu Gly Asp Gly Ile Cys Glu
        1155                1160                1165

Pro Phe Glu Arg Lys Thr Ser Ile Val Asp Cys Gly Ile Tyr Thr Pro
    1170                1175                1180
```

-continued

```
Lys Gly Tyr Leu Asp Gln Trp Ala Thr Arg Ala Tyr Ser Ser His Glu
1185                1190                1195                1200

Asp Lys Lys Lys Cys Pro Val Ser Leu Val Thr Gly Glu Pro His Ser
                1205                1210                1215

Leu Ile Cys Thr Ser Tyr His Pro Asp Leu Pro Asn His Arg Pro Leu
            1220                1225                1230

Thr Gly Trp Phe Pro Cys Val Ala Ser Glu Asn Glu Thr Gln Asp Asp
        1235                1240                1245

Arg Ser Glu Gln Pro Glu Gly Ser Leu Lys Lys Glu Asp Glu Val Trp
    1250                1255                1260

Leu Lys Val Cys Phe Asn Arg Pro Gly Glu Ala Arg Ala Ile Phe Ile
1265                1270                1275                1280

Phe Leu Thr Thr Asp Gly Leu Val Pro Gly Glu His Gln Gln Pro Thr
                1285                1290                1295

Val Thr Leu Tyr Leu Thr Asp Val Arg Gly Ser Asn His Ser Leu Gly
            1300                1305                1310

Thr Tyr Gly Leu Ser Cys Gln His Asn Pro Leu Ile Ile Asn Val Thr
        1315                1320                1325

His His Gln Asn Val Leu Phe His His Thr Thr Ser Val Leu Pro Asn
    1330                1335                1340

Phe Ser Ser Pro Arg Val Gly Ile Ser Ala Val Ala Leu Arg Thr Ser
1345                1350                1355                1360

Ser Arg Ile Gly Leu Ser Ala Pro Ser Asn Cys Ile Ser Glu Asp Glu
                1365                1370                1375

Gly Gln Asn His Gln Gly Gln Ser Cys Ile His Arg Pro Cys Gly Lys
            1380                1385                1390

Gln Asp Ser Cys Pro Ser Leu Leu Leu Asp His Ala Asp Val Val Asn
        1395                1400                1405

Cys Thr Ser Ile Gly Pro Gly Leu Met Lys Cys Ala Ile Thr Cys Gln
    1410                1415                1420

Arg Gly Phe Ala Leu Gln Ala Ser Ser Gly Gln Tyr Ile Arg Pro Met
1425                1430                1435                1440

Gln Lys Glu Ile Leu Leu Thr Cys Ser Ser Gly His Trp Asp Gln Asn
                1445                1450                1455

Val Ser Cys Leu Pro Val Asp Cys Gly Val Pro Asp Pro Ser Leu Val
            1460                1465                1470

Asn Tyr Ala Asn Phe Ser Cys Ser Glu Gly Thr Lys Phe Leu Lys Arg
        1475                1480                1485

Cys Ser Ile Ser Cys Val Pro Pro Ala Lys Leu Gln Gly Leu Ser Pro
    1490                1495                1500

Trp Leu Thr Cys Leu Glu Asp Gly Leu Trp Ser Leu Pro Glu Val Tyr
1505                1510                1515                1520

Cys Lys Leu Glu Cys Asp Ala Pro Pro Ile Ile Leu Asn Ala Asn Leu
                1525                1530                1535

Leu Leu Pro His Cys Leu Gln Asp Asn His Asp Val Gly Thr Ile Cys
            1540                1545                1550

Lys Tyr Glu Cys Lys Pro Gly Tyr Tyr Val Ala Glu Ser Ala Glu Gly
        1555                1560                1565

Lys Val Arg Asn Lys Leu Leu Lys Ile Gln Cys Leu Glu Gly Gly Ile
    1570                1575                1580

Trp Glu Gln Gly Ser Cys Ile Pro Val Val Cys Glu Pro Pro Pro Pro
1585                1590                1595                1600
```

-continued

Val Phe Glu Gly Met Tyr Glu Cys Thr Asn Gly Phe Ser Leu Asp Ser
1605 1610 1615

Gln Cys Val Leu Asn Cys Asn Gln Glu Arg Glu Lys Leu Pro Ile Leu
1620 1625 1630

Cys Thr Lys Glu Gly Leu Trp Thr Gln Glu Phe Lys Leu Cys Glu Asn
1635 1640 1645

Leu Gln Gly Glu Cys Pro Pro Pro Pro Ser Glu Leu Asn Ser Val Glu
1650 1655 1660

Tyr Lys Cys Glu Gln Gly Tyr Gly Ile Gly Ala Val Cys Ser Pro Leu
1665 1670 1675 1680

Cys Val Ile Pro Pro Ser Asp Pro Val Met Leu Pro Glu Asn Ile Thr
1685 1690 1695

Ala Asp Thr Leu Glu His Trp Met Glu Pro Val Lys Val Gln Ser Ile
1700 1705 1710

Val Cys Thr Gly Arg Arg Gln Trp His Pro Asp Pro Val Leu Val His
1715 1720 1725

Cys Ile Gln Ser Cys Glu Pro Phe Gln Ala Asn Gly Trp Cys Asp Thr
1730 1735 1740

Ile Asn Asn Arg Ala Tyr Cys His Tyr Asp Gly Gly Asp Cys Cys Ser
1745 1750 1755 1760

Ser Thr Leu Ser Ser Lys Lys Val Ile Pro Phe Ala Ala Asp Cys Asp
1765 1770 1775

Leu Asp Glu Cys Thr Cys Arg Asp Pro Lys Ala Glu Glu Asn Gln
1780 1785 1790

<210> SEQ ID NO 4
<211> LENGTH: 823
<212> TYPE: DNA
<213> ORGANISM: Homo sapiens

<400> SEQUENCE: 4
ccccaagcat caaactgaag gaaacattct aaccttcaca gacagactgg aggctggatg 60
gggacctggc tgaagacatc tggagaatga aagttaagta ccagcttgca tttttgtgcc 120
cctagattat ttttgcattt taaaataaga agcatcaaat tgcgtgtctc tgtgtaaaag 180
ttctagcaat ttgttttaag gtgaacttat tttggcttag ggactacaaa aagagaaggt 240
aattcctagg gaaggaagaa gagaaagaaa tgaaaattag agaataagat tattttgaat 300
gacttcaggt agcgaggagt gtgtgtttgt gagtgtgtat ttgagagact tggctcatgc 360
ctgtgggtct tctcttctag tatcagtgag gggagggatt actgaagaag aagggggggaa 420 aaaaaaagaa agaaatctga gctttctggg aggaaattca aaggaaccaa gagaaattaa 480
cttcgttctg caaggactaa agtacagcaa gaggagagag gtcaagcgag aagcgtgcgg 540
gaagcacatg ccctggggag gcatagaagc cacactggca gagcggccag cacaggtagc 600
cagcagaggc attcttgggg ctatttgaaa aagtttggtc tgtgaacaaa acagtttccc 660
tggtgactgc aaatccattg ctagctgcct ctttctcgtc tgcccatcac tctggtgtgg 720
tacccagaag ttgacttctg gttctgtaga aagagctagg ggaggtatga tgtgcttaaa 780
gatcctaaga ataagcctgg cgattttggc tgggtgggca ctc 823

<210> SEQ ID NO 5
<211> LENGTH: 766
<212> TYPE: DNA
<213> ORGANISM: Homo sapiens -continued

<400> SEQUENCE: 5
ccccaagcat caaactgaag gaaacattct aaccttcaca gacagactgg aggctggatg 60
gggacctggc tgaagacatc tggagaatga aagttaagta ccagcttgca tttttgtgcc 120
cctagattat ttttgcattt taaaataaga agcatcaaat tgcgtgtctc tgtgtaaaag 180
ttctagcaat ttgttttaag gtgaacttat tttggcttag ggactacaaa aagagaaggt 240
aattcctagg gaaggaagaa gagaaagaaa tgaaaattag agaataagat tattttgaat 300
gacttcaggt agcgaggagt gtgtgtttgt gagtgtgtat ttgagagact tggctcatgc 360
ctgtgggtct tctcttctag tatcagtgag gggagggatt actgaagaag aagggggaa 420 aaaaaaagaa agaaatctga gctttctggg aggaaattca aaggaaccaa gagaaattaa 480
cttcgttctg caaggactaa agtacagcaa gaggagagag gtcaagcgag aagcgtgcgg 540
gaagcacatg ccctggggag gcatagaagc cacactggca gagcggccag cacaggtagc 600
cagcagaggc attcttgggg ctatttgaaa aagtttggtc tgtgaacaaa acagtttccc 660
tggtgactgc aaatccattg ctagctgcct ctttctcgtc tgcccatcac tctggtgtgg 720
tacccagaag ttgacttctg gttctgtaga aagagctagg ggaggt 766

<210> SEQ ID NO 6
<211> LENGTH: 57
<212> TYPE: DNA
<213> ORGANISM: Homo sapiens

<400> SEQUENCE: 6
atgatgtgct taaagatcct aagaataagc ctggcgattt tggctgggtg ggcactc 57

<210> SEQ ID NO 7
<211> LENGTH: 19
<212> TYPE: PRT
<213> ORGANISM: Homo sapiens

<400> SEQUENCE: 7

Met Met Cys Leu Lys Ile Leu Arg Ile Ser Leu Ala Ile Leu Ala Gly
1 5 10 15

Trp Ala Leu

<210> SEQ ID NO 8
<211> LENGTH: 5461
<212> TYPE: DNA
<213> ORGANISM: Homo sapiens

<400> SEQUENCE: 8
atgatgtgct taaagatcct aagaataagc ctggcgattt tggctgggtg ggcactctgt 60
tctgccaact ctgagctggg ctggacacgc aagaaatcct tggttgagag ggaacacctg 120
aatcaggtgc tgttggaagg agaacgttgt tggctggggg ccaaggttcg aagacccaga 180
gcttctccac agcatcacct ctttggagtc taccccagca gggctgggaa ctacctaagg 240
ccctaccccg tgggggagca agaaatccat catacaggac gcagcaaacc agacactgaa 300
ggaaatgctg tgagccttgt tcccccagac ctgactgaaa atccagcagg actgaggggt 360
gcagttgaag agccggctgc cccatgggta ggggatagtc ctattgggca atctgagctg 420
ctgggagatg atgacgctta tctcggcaat caaagatcca aggagtctct aggtgaggcc 480
gggattcaga aaggctcagc catggctgcc actactacca ccgccatttt cacaaccctg 540
aacgaaccca aaccagagac ccaaaggagg ggctgggcca agtccaggca gcgtcgccaa 600

-continued

```
gtgtggaaga ggcgggcgga agatgggcag ggagactccg gtatctcttc acatttccaa    660
ccttggccca agcattccct taaacacagg gtcaaaaaga gtccaccgga ggaaagcaac    720
caaaatggtg gagagggctc ctaccgagaa gcagagacct ttaactccca agtaggactg    780
cccatcttat acttctctgg gaggcgggag cggctgctgc tgcgtccaga agtgctggct    840
gagattcccc gggaggcgtt cacagtggaa gcctgggtta aaccggaggg aggacagaac    900
aacccagcca tcatcgcagg tgtgtttgat aactgctccc acactgtcag tgacaaaggc    960
tgggccctgg ggatccgctc agggaaggac aagggaaagc gggatgctcg cttcttcttc   1020
tccctctgca ccgaccgcgt gaagaaagcc accatcttga ttagccacag tcgctaccaa   1080
ccaggcacat ggacccatgt ggcagccact tacgatggac ggcacatggc cctgtatgtg   1140
gatggcactc aggtggctag cagtctagac cagtctggtc ccctgaacag ccccttcatg   1200
gcatcttgcc gctctttgct cctgggggga gacagctctg aggatgggca ctatttccgt   1260
ggacacctgg gcacactggt tttctggtcg accgccctgc cacaaagcca ttttcagcac   1320
agttctcagc attcaagtga ggaggaggaa gcgactgact tggtcctgac agcgagcttt   1380
gagcctgtga acacagagtg ggttcccttt agagatgaga agtacccacg acttgaggtt   1440
ctccagggct ttgagccaga gcctgagatt ctgtcgcctt tgcagccccc actctgtggg   1500
caaacagtct gtgacaatgt ggaattgatc tcccagtaca atggatactg gccccttcgg   1560
ggagagaagg tgatacgcta ccaggtggtg aacatctgtg atgatgaggg cctaaacccc   1620
attgtgagtg aggagcagat tcgtctgcag cacgaggcac tgaatgaggc cttcagccgc   1680
tacaacatca gctggcagct gagcgtccac caggtccaca attccaccct gcgacaccgg   1740
gttgtgcttg tgaactgtga gcccagcaag attggcaatg accattgtga ccccgagtgt   1800
gagcacccac tcacaggcta tgatgggggt gactgccgcc tgcagggccg ctgctactcc   1860
tggaaccgca gggatgggct ctgtcacgtg gagtgtaaca acatgctgaa cgactttgac   1920
gacggagact gctgcgaccc ccaggtggct gatgtgcgca agacctgctt tgaccctgac   1980
tcacccaaga gggcatacat gagtgtgaag gagctgaagg aggccctgca gctgaacagt   2040
actcacttcc tcaacatcta ctttgccagc tcagtgcggg aagaccttgc aggtgctgcc   2100
acctggcctt gggacaagga cgctgtcact cacctgggtg gcattgtcct cagcccagca   2160
tattatggga tgcctggcca caccgacacc atgatccatg aagtgggaca tgttctggga   2220
ctctaccatg tctttaaagg agtcagtgaa agagaatcct gcaatgaccc ctgcaaggag   2280
acagtgccat ccatggaaac gggagacctc tgtgccgaca ccgcccccac tcccaagagt   2340
gagctgtgcc gggaaccaga gcccactagt gacacctgtg gcttcactcg cttcccaggg   2400
gctccgttca ccaactacat gagctacacg gatgataact gcactgacaa cttcactcct   2460
aaccaagtgg cccgaatgca ttgctatttg gacctagtct atcagcagtg gactgaaagc   2520
agaaagccca cccccatccc cattccacct atggtcatcg gacagaccaa caagtccctc   2580
actatccact ggctgcctcc tattagtgga gttgtatatg acagggcctc aggcagcttg   2640
tgtggcgctt gcactgaaga tgggaccttt cgtcagtatg tgcacacagc ttcctcccgg   2700
cgggtgtgtg actcctcagg ttattggacc ccagaggagg ctgtggggcc tcctgatgtg   2760
gatcagccct gcgagccaag cttacaggcc tggagccctg aggtccacct gtaccacatg   2820
aacatgacgg tcccctgccc cacagaaggc tgtagcttgg agctgctctt ccaacacccg   2880
gtccaagccg acaccctcac cctgtgggtc acttccttct tcatggagtc ctcgcaggtc   2940
ctctttgaca cagagatctt gctggaaaac aaggagtcag tgcacctggg ccccttagac   3000
```

-continued

```
actttctgtg acatcccact caccatcaaa ctgcacgtgg atgggaaggt gtcgggggtg   3060
aaagtctaca cctttgatga gaggatagag attgatgcag cactcctgac ttctcagccc   3120
cacagtccct tgtgctctgg ctgcaggcct gtgaggtacc aggttctccg cgatccccca   3180
tttgccagtg gtttgcccgt ggtggtgaca cattctcaca ggaagttcac ggacgtggag   3240
gtcacacctg gacagatgta tcagtaccaa gttctagctg aagctggagg agaactggga   3300
gaagcttcgc ctcctctgaa ccacattcat ggagctcctt attgtggaga tgggaaggtg   3360
tcagagagac tgggagaaga gtgtgatgat ggagaccttg tgagcggaga tggctgctcc   3420
aaggtgtgtg agctggagga aggtttcaac tgtgtaggag agccaagcct ttgctacatg   3480
tatgagggag atggcatatg tgaacctttt gagagaaaaa ccagcattgt agactgtggc   3540
atctacactc ccaaaggata cttggatcaa tgggctaccc gggcttactc ctctcatgaa   3600
gacaagaaga agtgtcctgt ttccttggta actggagaac ctcattccct aatttgcaca   3660
tcataccatc cagatttacc caaccaccgt cccctaactg gctggtttcc ctgtgttgcc   3720
agtgaaaatg aaactcagga tgacaggagt gaacagccag aaggtagcct gaagaaagag   3780
gatgaggttt ggctcaaagt gtgtttcaat agaccaggag aggccagagc aatttttatt   3840
tttttgacaa ctgatggcct agttcccgga gagcatcagc agccgacagt gactctctac   3900
ctgaccgatg tccgtggaag caaccactct cttggaacct atggactgtc atgccagcat   3960
aatccactga ttatcaatgt gacccatcac cagaatgtcc ttttccacca taccacctca   4020
gtgctgccga atttctcatc ccccacgggtc ggcatctcag ctgtggctct aaggacatcc   4080
tcccgcattg gtctttcggc tcccagtaac tgcatctcag aggacgaggg gcagaatcat   4140
cagggacaga gctgtatcca tcggccctgt gggaagcagg acagctgtcc gtcattgctg   4200
cttgatcatg ctgatgtggt gaactgtacc tctataggcc caggtctcat gaagtgtgct   4260
atcacttgtc aaaggggatt tgcccttcag gccagcagtg ggcagtacat caggcccatg   4320
cagaaggaaa ttctgctcac atgttcttct gggcactggg accagaatgt gagctgcctt   4380
cccgtggact gcggtgttcc cgacccgtct ttggtgaact atgcaaactt ctcctgctca   4440
gagggaacca aatttctgaa acgctgctca atctcttgtg tcccaccagc caagctgcaa   4500
ggactgagcc catggctgac atgtcttgaa gatggtctct ggtctctccc tgaagtctac   4560
tgcaagttgg agtgtgatgc tcccccctatt attctgaatg ccaacttgct cctgcctcac   4620
tgcctccagg acaaccacga cgtgggcacc atctgcaaat atgaatgcaa accagggtac   4680
tatgtggcag aaagtgcaga gggtaaagtc aggaacaagc tcctgaagat acaatgcctg   4740
gaaggtggaa tctgggagca aggcagctgc attcctgtgg tgtgtgagcc accccctcct   4800
gtgtttgaag gcatgtatga atgtaccaat ggcttcagcc tggacagcca gtgtgtgctc   4860
aactgtaacc aggaacgtga aaagcttccc atcctctgca ctaaagaggg cctgtggacc   4920
caggagttta agttgtgtga gaatctgcaa ggagaatgcc caccaccccc ctcagagctg   4980
aattctgtgg agtacaaatg tgarcaagga tatgggattg gtgcagtgtg ttccccattg   5040
tgtgtaatcc cccccagtga ccccgtgatg ctacctgaga atatcactgc tgacactctg   5100
gagcactgga tggaacctgt caaagtccag agcattgtgt gcactggccg gcgtcaatgg   5160
cacccagacc ccgtcttagt ccactgcatc cagtcatgtg aggtcataag ccagttgttg   5220
ctgcttgtgt tcccattgtc ccagcaagaa cacacgtatg ctacatatct gcaatccaaa   5280
attgttgccc ttccaagcag atggttggtg tgacactatc aacaaccgag cctactgcca   5340
```

-continued

```
ctatgacggg ggagactgct gctcttccac actctcctcc aagaaggtca ttccatttgc   5400

tgctgactgt gacctggatg agtgcacctg ccgggacccc aaggcagaag aaaatcagta   5460

a                                                                    5461
```

<210> SEQ ID NO 9
<211> LENGTH: 5313
<212> TYPE: DNA
<213> ORGANISM: Homo sapiens

<400> SEQUENCE: 9

```
atgatgtgct taaagatcct aagaataagc ctggcgattt tggctgggtg ggcactctgt     60

tctgccaact ctgagctggg ctggacacgc aagaaatcct tggttgagag ggaacacctg    120

aatcaggtgc tgttggaagg agaacgttgt tggctggggg ccaaggttcg aagacccaga    180

gcttctccac agcatcacct ctttggagtc taccccagca gggctgggaa ctacctaagg    240

ccctaccccg tgggggagca agaaatccat catacaggac gcagcaaacc agacactgaa    300

ggaaatgctg tgagccttgt tcccccagac ctgactgaaa atccagcagg actgaggggt    360

gcagttgaag agccggctgc cccatgggta ggggatagtc ctattgggca atctgagctg    420

ctgggagatg atgacgctta tctcggcaat caaagatcca aggagtctct aggtgaggcc    480

gggattcaga aaggctcagc catggctgcc actactacca ccgccatttt cacaaccctg    540

aacgaaccca aaccagagac ccaaaggagg ggctgggcca agtccaggca gcgtcgccaa    600

gtgtggaaga ggcgggcgga agatgggcag ggagactccg gtatctcttc acatttccaa    660

ccttggccca agcattccct taaacacagg gtcaaaaaga gtccaccgga ggaaagcaac    720

caaaatggtg gagagggctc ctaccgagaa gcagagacct ttaactccca agtaggactg    780

cccatcttat acttctctgg gaggcgggag cggctgctgc tgcgtccaga agtgctggct    840

gagattcccc gggaggcgtt cacagtggaa gcctgggtta aaccggaggg aggacagaac    900

aacccagcca tcatcgcagg tgtgtttgat aactgctccc acactgtcag tgacaaaggc    960

tgggccctgg ggatccgctc agggaaggac aagggaaagc gggatgctcg cttcttcttc   1020

tccctctgca ccgaccgcgt gaagaaagcc accatcttga ttagccacag tcgctaccaa   1080

ccaggcacat ggacccatgt ggcagccact tacgatggac ggcacatggc cctgtatgtg   1140

gatggcactc aggtggctag cagtctagac cagtctggtc ccctgaacag cccctcatg    1200

gcatcttgcc gctctttgct cctgggggga gacagctctg aggatgggca ctatttccgt   1260

ggacacctgg gcacactggt tttctggtcg accgccctgc cacaaagcca ttttcagcac   1320

agttctcagc attcaagtga ggaggaggaa gcgactgact tggtcctgac agcgagcttt   1380

gagcctgtga acacagagtg ggttcccttt agagatgaga agtacccacg acttgaggtt   1440

ctccagggct ttgagccaga gcctgagatt ctgtcgcctt tgcagccccc actctgtggg   1500

caaacagtct gtgacaatgt ggaattgatc tcccagtaca atggatactg gccccttcgg   1560

ggagagaagg tgatacgcta ccaggtggtg aacatctgtg atgatgaggg cctaaacccc   1620

attgtgagtg aggagcagat tcgtctgcag cacgaggcac tgaatgaggc cttcagccgc   1680

tacaacatca gctggcagct gagcgtccac caggtccaca attccaccct gcgacaccgg   1740

gttgtgcttg tgaactgtga gcccagcaag attggcaatg accattgtga ccccgagtgt   1800

gagcacccac tcacaggcta tgatgggggt gactgccgcc tgcagggccg ctgctactcc   1860

tggaaccgca gggatgggct ctgtcacgtg gagtgtaaca acatgctgaa cgactttgac   1920
```

-continued

```
gacggagact gctgcgaccc ccaggtggct gatgtgcgca agacctgctt tgaccctgac   1980
tcacccaaga gggcatacat gagtgtgaag gagctgaagg aggccctgca gctgaacagt   2040
actcacttcc tcaacatcta ctttgccagc tcagtgcggg aagaccttgc aggtgctgcc   2100
acctggcctt gggacaagga cgctgtcact cacctgggtg gcattgtcct cagcccagca   2160
tattatggga tgcctggcca caccgacacc atgatccatg aagtgggaca tgttctggga   2220
ctctaccatg tctttaaagg agtcagtgaa agagaatcct gcaatgaccc ctgcaaggag   2280
acagtgccat ccatggaaac gggagacctc tgtgccgaca ccgcccccac tcccaagagt   2340
gagctgtgcc gggaaccaga gcccactagt gacacctgtg gcttcactcg cttcccaggg   2400
gctccgttca ccaactacat gagctacacg gatgataact gcactgacaa cttcactcct   2460
aaccaagtgg cccgaatgca ttgctatttg gacctagtct atcagcagtg gactgaaagc   2520
agaaagccca cccccatccc cattccacct atggtcatcg gacagaccaa caagtccctc   2580
actatccact ggctgcctcc tattagtgga gttgtatatg acagggcctc aggcagcttg   2640
tgtggcgctt gcactgaaga tgggaccttt cgtcagtatg tgcacacagc ttcctcccgg   2700
cgggtgtgtg actcctcagg ttattggacc ccagaggagg ctgtggggcc tcctgatgtg   2760
gatcagccct gcgagccaag cttacaggcc tggagccctg aggtccacct gtaccacatg   2820
aacatgacgg tcccctgccc cacagaaggc tgtagcttgg agctgctctt ccaacacccg   2880
gtccaagccg acaccctcac cctgtgggtc acttccttct tcatggagtc ctcgcaggtc   2940
ctctttgaca cagagatctt gctggaaaac aaggagtcag tgcacctggg cccccttagac   3000
actttctgtg acatcccact caccatcaaa ctgcacgtgg atgggaaggt gtcgggggtg   3060
aaagtctaca cctttgatga gaggatagag attgatgcag cactcctgac ttctcagccc   3120
cacagtccct tgtgctctgg ctgcaggcct gtgaggtacc aggttctccg cgatccccca   3180
tttgccagtg gtttgcccgt ggtggtgaca cattctcaca ggaagttcac ggacgtggag   3240
gtcacacctg gacagatgta tcagtaccaa gttctagctg aagctggagg agaactggga   3300
gaagcttcgc ctcctctgaa ccacattcat ggagctcctt attgtggaga tgggaaggtg   3360
tcagagagac tgggagaaga gtgtgatgat ggagaccttg tgagcggaga tggctgctcc   3420
aaggtgtgtg agctggagga aggtttcaac tgtgtaggag agccaagcct ttgctacatg   3480
tatgagggag atggcatatg tgaacctttt gagagaaaaa ccagcattgt agactgtggc   3540
atctacactc ccaaaggata cttggatcaa tgggctaccc gggcttactc ctctcatgaa   3600
gacaagaaga agtgtcctgt ttccttggta actggagaac ctcattccct aatttgcaca   3660
tcataccatc cagatttacc caaccaccgt cccctaactg gctggtttcc ctgtgttgcc   3720
agtgaaaatg aaactcagga tgacaggagt gaacagccag aaggtagcct gaagaaagag   3780
gatgaggttt ggctcaaagt gtgtttcaat agaccaggag aggccagagc aatttttatt   3840
tttttgacaa ctgatggcct agttcccgga gagcatcagc agccgacagt gactctctac   3900
ctgaccgatg tccgtggaag caaccactct cttggaacct atggactgtc atgccagcat   3960
aatccactga ttatcaatgt gacccatcac cagaatgtcc ttttccacca taccacctca   4020
gtgctgccga atttctcatc cccacgggtc ggcatctcag ctgtggctct aaggacatcc   4080
tcccgcattg gtctttcggc tcccagtaac tgcatctcag aggacgaggg gcagaatcat   4140
cagggacaga gctgtatcca tcggccctgt gggaagcagg acagctgtcc gtcattgctg   4200
cttgatcatg ctgatgtggt gaactgtacc tctataggcc caggtctcat gaagtgtgct   4260
atcacttgtc aaaggggatt tgcccttcag gccagcagtg ggcagtacat caggcccatg   4320
```

-continued cagaaggaaa ttctgctcac atgttcttct gggcactggg accagaatgt gagctgcctt 4380
cccgtggact gcggtgttcc cgacccgtct ttggtgaact atgcaaactt ctcctgctca 4440
gagggaacca aatttctgaa acgctgctca atctcttgtg tcccaccagc caagctgcaa 4500
ggactgagcc catggctgac atgtcttgaa gatggtctct ggtctctccc tgaagtctac 4560
tgcaagttgg agtgtgatgc tccccctatt attctgaatg ccaacttgct cctgcctcac 4620
tgcctccagg acaaccacga cgtgggcacc atctgcaaat atgaatgcaa accagggtac 4680
tatgtggcag aaagtgcaga gggtaaagtc aggaacaagc tcctgaagat acaatgcctg 4740
gaaggtggaa tctgggagca aggcagctgc attcctgtgg tgtgtgagcc accccctcct 4800
gtgtttgaag gcatgtatga atgtaccaat ggcttcagcc tggacagcca gtgtgtgctc 4860
aactgtaacc aggaacgtga aaagcttccc atcctctgca ctaaagaggg cctgtggacc 4920
caggagttta agttgtgtga gaatctgcaa ggagaatgcc caccaccccc ctcagagctg 4980
aattctgtgg agtacaaatg tgarcaagga tatgggattg gtgcagtgtg ttccccattg 5040
tgtgtaatcc cccccagtga ccccgtgatg ctacctgaga atatcactgc tgacactctg 5100
gagcactgga tggaacctgt caaagtccag agcattgtgt gcactggccg gcgtcaatgg 5160
cacccagacc ccgtcttagt ccactgcatc cagtcatgtg aggtcataag ccagttgttg 5220
ctgcttgtgt tcccattgtc ccagcaagaa cacacgtatg ctacatatct gcaatccaaa 5280
attgttgccc ttccaagcag atggttggtg tga 5313

<210> SEQ ID NO 10
<211> LENGTH: 1770
<212> TYPE: PRT
<213> ORGANISM: Homo sapiens

<400> SEQUENCE: 10

Met Met Cys Leu Lys Ile Leu Arg Ile Ser Leu Ala Ile Leu Ala Gly
5 10 15

Trp Ala Leu Cys Ser Ala Asn Ser Glu Leu Gly Trp Thr Arg Lys Lys
20 25 30

Ser Leu Val Glu Arg Glu His Leu Asn Gln Val Leu Leu Glu Gly Glu
35 40 45

Arg Cys Trp Leu Gly Ala Lys Val Arg Arg Pro Arg Ala Ser Pro Gln
50 55 60

His His Leu Phe Gly Val Tyr Pro Ser Arg Ala Gly Asn Tyr Leu Arg
65 70 75 80

Pro Tyr Pro Val Gly Glu Gln Glu Ile His His Thr Gly Arg Ser Lys
85 90 95

Pro Asp Thr Glu Gly Asn Ala Val Ser Leu Val Pro Pro Asp Leu Thr
100 105 110

Glu Asn Pro Ala Gly Leu Arg Gly Ala Val Glu Glu Pro Ala Ala Pro
115 120 125

Trp Val Gly Asp Ser Pro Ile Gly Gln Ser Glu Leu Leu Gly Asp Asp
130 135 140

Asp Ala Tyr Leu Gly Asn Gln Arg Ser Lys Glu Ser Leu Gly Glu Ala
145 150 155 160

Gly Ile Gln Lys Gly Ser Ala Met Ala Ala Thr Thr Thr Thr Ala Ile
165 170 175

Phe Thr Thr Leu Asn Glu Pro Lys Pro Glu Thr Gln Arg Arg Gly Trp
180 185 190

-continued

```
Ala Lys Ser Arg Gln Arg Arg Gln Val Trp Lys Arg Arg Ala Glu Asp
        195                 200                 205

Gly Gln Gly Asp Ser Gly Ile Ser Ser His Phe Gln Pro Trp Pro Lys
    210                 215                 220

His Ser Leu Lys His Arg Val Lys Lys Ser Pro Pro Glu Glu Ser Asn
225                 230                 235                 240

Gln Asn Gly Gly Glu Gly Ser Tyr Arg Glu Ala Glu Thr Phe Asn Ser
                245                 250                 255

Gln Val Gly Leu Pro Ile Leu Tyr Phe Ser Gly Arg Arg Glu Arg Leu
            260                 265                 270

Leu Leu Arg Pro Glu Val Leu Ala Glu Ile Pro Arg Glu Ala Phe Thr
        275                 280                 285

Val Glu Ala Trp Val Lys Pro Glu Gly Gly Gln Asn Asn Pro Ala Ile
    290                 295                 300

Ile Ala Gly Val Phe Asp Asn Cys Ser His Thr Val Ser Asp Lys Gly
305                 310                 315                 320

Trp Ala Leu Gly Ile Arg Ser Gly Lys Asp Lys Gly Lys Arg Asp Ala
                325                 330                 335

Arg Phe Phe Phe Ser Leu Cys Thr Asp Arg Val Lys Lys Ala Thr Ile
            340                 345                 350

Leu Ile Ser His Ser Arg Tyr Gln Pro Gly Thr Trp Thr His Val Ala
        355                 360                 365

Ala Thr Tyr Asp Gly Arg His Met Ala Leu Tyr Val Asp Gly Thr Gln
    370                 375                 380

Val Ala Ser Ser Leu Asp Gln Ser Gly Pro Leu Asn Ser Pro Phe Met
385                 390                 395                 400

Ala Ser Cys Arg Ser Leu Leu Leu Gly Gly Asp Ser Ser Glu Asp Gly
                405                 410                 415

His Tyr Phe Arg Gly His Leu Gly Thr Leu Val Phe Trp Ser Thr Ala
            420                 425                 430

Leu Pro Gln Ser His Phe Gln His Ser Ser Gln His Ser Ser Glu Glu
        435                 440                 445

Glu Glu Ala Thr Asp Leu Val Leu Thr Ala Ser Phe Glu Pro Val Asn
    450                 455                 460

Thr Glu Trp Val Pro Phe Arg Asp Glu Lys Tyr Pro Arg Leu Glu Val
465                 470                 475                 480

Leu Gln Gly Phe Glu Pro Glu Pro Glu Ile Leu Ser Pro Leu Gln Pro
                485                 490                 495

Pro Leu Cys Gly Gln Thr Val Cys Asp Asn Val Glu Leu Ile Ser Gln
            500                 505                 510

Tyr Asn Gly Tyr Trp Pro Leu Arg Gly Glu Lys Val Ile Arg Tyr Gln
        515                 520                 525

Val Val Asn Ile Cys Asp Asp Glu Gly Leu Asn Pro Ile Val Ser Glu
    530                 535                 540

Glu Gln Ile Arg Leu Gln His Glu Ala Leu Asn Glu Ala Phe Ser Arg
545                 550                 555                 560

Tyr Asn Ile Ser Trp Gln Leu Ser Val His Gln Val His Asn Ser Thr
                565                 570                 575

Leu Arg His Arg Val Val Leu Val Asn Cys Glu Pro Ser Lys Ile Gly
            580                 585                 590

Asn Asp His Cys Asp Pro Glu Cys Glu His Pro Leu Thr Gly Tyr Asp
        595                 600                 605

Gly Gly Asp Cys Arg Leu Gln Gly Arg Cys Tyr Ser Trp Asn Arg Arg
```

-continued

```
    610                 615                 620

Asp Gly Leu Cys His Val Glu Cys Asn Asn Met Leu Asn Asp Phe Asp
625                 630                 635                 640

Asp Gly Asp Cys Cys Asp Pro Gln Val Ala Asp Val Arg Lys Thr Cys
                645                 650                 655

Phe Asp Pro Asp Ser Pro Lys Arg Ala Tyr Met Ser Val Lys Glu Leu
            660                 665                 670

Lys Glu Ala Leu Gln Leu Asn Ser Thr His Phe Leu Asn Ile Tyr Phe
        675                 680                 685

Ala Ser Ser Val Arg Glu Asp Leu Ala Gly Ala Ala Thr Trp Pro Trp
    690                 695                 700

Asp Lys Asp Ala Val Thr His Leu Gly Gly Ile Val Leu Ser Pro Ala
705                 710                 715                 720

Tyr Tyr Gly Met Pro Gly His Thr Asp Thr Met Ile His Glu Val Gly
                725                 730                 735

His Val Leu Gly Leu Tyr His Val Phe Lys Gly Val Ser Glu Arg Glu
            740                 745                 750

Ser Cys Asn Asp Pro Cys Lys Glu Thr Val Pro Ser Met Glu Thr Gly
        755                 760                 765

Asp Leu Cys Ala Asp Thr Ala Pro Thr Pro Lys Ser Glu Leu Cys Arg
    770                 775                 780

Glu Pro Glu Pro Thr Ser Asp Thr Cys Gly Phe Thr Arg Phe Pro Gly
785                 790                 795                 800

Ala Pro Phe Thr Asn Tyr Met Ser Tyr Thr Asp Asp Asn Cys Thr Asp
                805                 810                 815

Asn Phe Thr Pro Asn Gln Val Ala Arg Met His Cys Tyr Leu Asp Leu
            820                 825                 830

Val Tyr Gln Gln Trp Thr Glu Ser Arg Lys Pro Thr Pro Ile Pro Ile
        835                 840                 845

Pro Pro Met Val Ile Gly Gln Thr Asn Lys Ser Leu Thr Ile His Trp
    850                 855                 860

Leu Pro Pro Ile Ser Gly Val Val Tyr Asp Arg Ala Ser Gly Ser Leu
865                 870                 875                 880

Cys Gly Ala Cys Thr Glu Asp Gly Thr Phe Arg Gln Tyr Val His Thr
                885                 890                 895

Ala Ser Ser Arg Arg Val Cys Asp Ser Ser Gly Tyr Trp Thr Pro Glu
            900                 905                 910

Glu Ala Val Gly Pro Pro Asp Val Asp Gln Pro Cys Glu Pro Ser Leu
        915                 920                 925

Gln Ala Trp Ser Pro Glu Val His Leu Tyr His Met Asn Met Thr Val
    930                 935                 940

Pro Cys Pro Thr Glu Gly Cys Ser Leu Glu Leu Leu Phe Gln His Pro
945                 950                 955                 960

Val Gln Ala Asp Thr Leu Thr Leu Trp Val Thr Ser Phe Phe Met Glu
                965                 970                 975

Ser Ser Gln Val Leu Phe Asp Thr Glu Ile Leu Leu Glu Asn Lys Glu
            980                 985                 990

Ser Val His Leu Gly Pro Leu Asp Thr Phe Cys Asp Ile Pro Leu Thr
        995                 1000                1005

Ile Lys Leu His Val Asp Gly Lys Val Ser Gly Val Lys Val Tyr Thr
    1010                1015                1020

Phe Asp Glu Arg Ile Glu Ile Asp Ala Ala Leu Leu Thr Ser Gln Pro
1025                1030                1035                1040
```

-continued

```
His Ser Pro Leu Cys Ser Gly Cys Arg Pro Val Arg Tyr Gln Val Leu
                1045                1050                1055

Arg Asp Pro Pro Phe Ala Ser Gly Leu Pro Val Val Val Thr His Ser
            1060                1065                1070

His Arg Lys Phe Thr Asp Val Glu Val Thr Pro Gly Gln Met Tyr Gln
        1075                1080                1085

Tyr Gln Val Leu Ala Glu Ala Gly Gly Glu Leu Gly Glu Ala Ser Pro
    1090                1095                1100

Pro Leu Asn His Ile His Gly Ala Pro Tyr Cys Gly Asp Gly Lys Val
1105                1110                1115                1120

Ser Glu Arg Leu Gly Glu Glu Cys Asp Asp Gly Asp Leu Val Ser Gly
                1125                1130                1135

Asp Gly Cys Ser Lys Val Cys Glu Leu Glu Glu Gly Phe Asn Cys Val
            1140                1145                1150

Gly Glu Pro Ser Leu Cys Tyr Met Tyr Glu Gly Asp Gly Ile Cys Glu
        1155                1160                1165

Pro Phe Glu Arg Lys Thr Ser Ile Val Asp Cys Gly Ile Tyr Thr Pro
    1170                1175                1180

Lys Gly Tyr Leu Asp Gln Trp Ala Thr Arg Ala Tyr Ser Ser His Glu
1185                1190                1195                1200

Asp Lys Lys Lys Cys Pro Val Ser Leu Val Thr Gly Glu Pro His Ser
                1205                1210                1215

Leu Ile Cys Thr Ser Tyr His Pro Asp Leu Pro Asn His Arg Pro Leu
            1220                1225                1230

Thr Gly Trp Phe Pro Cys Val Ala Ser Glu Asn Glu Thr Gln Asp Asp
        1235                1240                1245

Arg Ser Glu Gln Pro Glu Gly Ser Leu Lys Lys Glu Asp Glu Val Trp
    1250                1255                1260

Leu Lys Val Cys Phe Asn Arg Pro Gly Glu Ala Arg Ala Ile Phe Ile
1265                1270                1275                1280

Phe Leu Thr Thr Asp Gly Leu Val Pro Gly Glu His Gln Gln Pro Thr
                1285                1290                1295

Val Thr Leu Tyr Leu Thr Asp Val Arg Gly Ser Asn His Ser Leu Gly
            1300                1305                1310

Thr Tyr Gly Leu Ser Cys Gln His Asn Pro Leu Ile Ile Asn Val Thr
        1315                1320                1325

His His Gln Asn Val Leu Phe His His Thr Thr Ser Val Leu Pro Asn
    1330                1335                1340

Phe Ser Ser Pro Arg Val Gly Ile Ser Ala Val Ala Leu Arg Thr Ser
1345                1350                1355                1360

Ser Arg Ile Gly Leu Ser Ala Pro Ser Asn Cys Ile Ser Glu Asp Glu
                1365                1370                1375

Gly Gln Asn His Gln Gly Gln Ser Cys Ile His Arg Pro Cys Gly Lys
            1380                1385                1390

Gln Asp Ser Cys Pro Ser Leu Leu Leu Asp His Ala Asp Val Val Asn
        1395                1400                1405

Cys Thr Ser Ile Gly Pro Gly Leu Met Lys Cys Ala Ile Thr Cys Gln
    1410                1415                1420

Arg Gly Phe Ala Leu Gln Ala Ser Ser Gly Gln Tyr Ile Arg Pro Met
1425                1430                1435                1440

Gln Lys Glu Ile Leu Leu Thr Cys Ser Ser Gly His Trp Asp Gln Asn
                1445                1450                1455
```

-continued

```
Val Ser Cys Leu Pro Val Asp Cys Gly Val Pro Asp Pro Ser Leu Val
            1460                1465                1470

Asn Tyr Ala Asn Phe Ser Cys Ser Glu Gly Thr Lys Phe Leu Lys Arg
        1475                1480                1485

Cys Ser Ile Ser Cys Val Pro Pro Ala Lys Leu Gln Gly Leu Ser Pro
    1490                1495                1500

Trp Leu Thr Cys Leu Glu Asp Gly Leu Trp Ser Leu Pro Glu Val Tyr
1505                1510                1515                1520

Cys Lys Leu Glu Cys Asp Ala Pro Pro Ile Ile Leu Asn Ala Asn Leu
                1525                1530                1535

Leu Leu Pro His Cys Leu Gln Asp Asn His Asp Val Gly Thr Ile Cys
            1540                1545                1550

Lys Tyr Glu Cys Lys Pro Gly Tyr Tyr Val Ala Glu Ser Ala Glu Gly
        1555                1560                1565

Lys Val Arg Asn Lys Leu Leu Lys Ile Gln Cys Leu Glu Gly Gly Ile
    1570                1575                1580

Trp Glu Gln Gly Ser Cys Ile Pro Val Val Cys Glu Pro Pro Pro Pro
1585                1590                1595                1600

Val Phe Glu Gly Met Tyr Glu Cys Thr Asn Gly Phe Ser Leu Asp Ser
                1605                1610                1615

Gln Cys Val Leu Asn Cys Asn Gln Glu Arg Glu Lys Leu Pro Ile Leu
            1620                1625                1630

Cys Thr Lys Glu Gly Leu Trp Thr Gln Glu Phe Lys Leu Cys Glu Asn
        1635                1640                1645

Leu Gln Gly Glu Cys Pro Pro Pro Pro Ser Glu Leu Asn Ser Val Glu
    1650                1655                1660

Tyr Lys Cys Glu Gln Gly Tyr Gly Ile Gly Ala Val Cys Ser Pro Leu
1665                1670                1675                1680

Cys Val Ile Pro Pro Ser Asp Pro Val Met Leu Pro Glu Asn Ile Thr
                1685                1690                1695

Ala Asp Thr Leu Glu His Trp Met Glu Pro Val Lys Val Gln Ser Ile
            1700                1705                1710

Val Cys Thr Gly Arg Arg Gln Trp His Pro Asp Pro Val Leu Val His
        1715                1720                1725

Cys Ile Gln Ser Cys Glu Val Ile Ser Gln Leu Leu Leu Leu Val Phe
    1730                1735                1740

Pro Leu Ser Gln Gln Glu His Thr Tyr Ala Thr Tyr Leu Gln Ser Lys
1745                1750                1755                1760

Ile Val Ala Leu Pro Ser Arg Trp Leu Val
                1765                1770
```

<210> SEQ ID NO 11
<211> LENGTH: 85
<212> TYPE: DNA
<213> ORGANISM: Homo sapiens

<400> SEQUENCE: 11

```
gtcataagcc agttgttgct gcttgtgttc ccattgtccc agcaagaaca cacgtatgct     60

acatatctgc aatccaaaat tgttg                                           85
```

<210> SEQ ID NO 12
<211> LENGTH: 28
<212> TYPE: PRT
<213> ORGANISM: Homo sapiens

<400> SEQUENCE: 12

-continued

```
Val Ile Ser Gln Leu Leu Leu Leu Val Phe Pro Leu Ser Gln Gln Glu
1               5                   10                  15

His Thr Tyr Ala Thr Tyr Leu Gln Ser Lys Ile Val
            20                  25


<210> SEQ ID NO 13
<211> LENGTH: 8
<212> TYPE: PRT
<213> ORGANISM: Homo sapiens

<400> SEQUENCE: 13

Ala Leu Pro Ser Arg Trp Leu Val
1               5


<210> SEQ ID NO 14
<211> LENGTH: 36
<212> TYPE: PRT
<213> ORGANISM: Homo sapiens

<400> SEQUENCE: 14

Val Ile Ser Gln Leu Leu Leu Leu Val Phe Pro Leu Ser Gln Gln Glu
1               5                   10                  15

His Thr Tyr Ala Thr Tyr Leu Gln Ser Lys Ile Val Ala Leu Pro Ser
            20                  25                  30

Arg Trp Leu Val
        35


<210> SEQ ID NO 15
<211> LENGTH: 4158
<212> TYPE: DNA
<213> ORGANISM: Homo sapiens

<400> SEQUENCE: 15

atgatgtgct taaagatcct aagaataagc ctggcgattt tggctgggtg ggcactctgt     60

tctgccaact ctgagctggg ctggacacgc aagaaatcct tggttgagag ggaacacctg    120

aatcaggtgc tgttggaagg agaacgttgt tggctggggg ccaaggttcg aagacccaga    180

gcttctccac agcatcacct ctttggagtc taccccagca gggctgggaa ctacctaagg    240

ccctaccccg tgggggagca agaaatccat catacaggac gcagcaaacc agacactgaa    300

ggaaatgctg tgagccttgt tccccccagac ctgactgaaa atccagcagg actgaggggt    360

gcagttgaag agccggctgc cccatgggta ggggatagtc ctattgggca atctgagctg    420

ctgggagatg atgacgctta tctcggcaat caaagatcca aggagtctct aggtgaggcc    480

gggattcaga aaggctcagc catggctgcc actactacca ccgccatttt cacaaccctg    540

aacgaaccca aaccagagac ccaaaggagg ggctgggcca agtccaggca gcgtcgccaa    600

gtgtggaaga ggcgggcgga agatgggcag ggagactccg gtatctcttc acatttccaa    660

ccttggccca agcattccct taaacacggg gtcaaaaaga gtccaccgga ggaaagcaac    720

caaaatggtg gagagggctc ctaccgagaa gcagagacct ttaactccca agtaggactg    780

cccatcttat acttctctgg gaggcgggag cggctgctgc tgcgtccaga agtgctggct    840

gagattcccc gggaggcgtt cacagtggaa gcctgggtta aaccggaggg aggacagaac    900

aacccagcca tcatcgcagg tggcattgtc ctcagcccag catattatgg gatgcctggc    960

cacaccgaca ccatgatcca tgaagtggga catgttctgg gactctacca tgtctttaaa   1020

ggagtcagtg aaagagaatc ctgcaatgac ccctgcaagg agacagtgcc atccatggaa   1080
```

-continued

```
acgggagacc tctgtgccga caccgccccc actcccaaga gtgagctgtg ccgggaacca   1140
gagcccacta gtgacacctg tggcttcact cgcttcccag gggctccgtt caccaactac   1200
atgagctaca cggatgataa ctgcactgac aacttcactc ctaaccaagt ggcccgaatg   1260
cattgctatt tggacctagt ctatcagcag tggactgaaa gcagaaagcc cacccccatc   1320
cccattccac ctatggtcat cggacagacc aacaagtccc tcactatcca ctggctgcct   1380
cctattagtg gagttgtata tgacagggcc tcaggcagct tgtgtggcgc ttgcactgaa   1440
gatgggacct ttcgtcagta tgtgcacaca gcttcctccc ggcgggtgtg tgactcctca   1500
ggttattgga ccccagagga ggctgtgggg cctcctgatg tggatcagcc ctgcgagcca   1560
agcttacagg cctggagccc tgaggtccac ctgtaccaca tgaacatgac ggtcccctgc   1620
cccacagaag gctgtagctt ggagctgctc ttccaacacc cggtccaagc cgacaccctc   1680
accctgtggg tcacttcctt cttcatggag tcctcgcagg tcctctttga cacagagatc   1740
ttgctggaaa acaaggagtc agtgcacctg ggccccttag acactttctg tgacatccca   1800
ctcaccatca aactgcacgt ggatgggaag gtgtcggggg tgaaagtcta cacctttgat   1860
gagaggatag agattgatgc agcactcctg acttctcagc cccacagtcc cttgtgctct   1920
ggctgcaggc ctgtgaggta ccaggttctc cgcgatcccc catttgccag tggtttgccc   1980
gtggtggtga cacattctca caggaagttc acggacgtgg aggtcacacc tggacagatg   2040
tatcagtacc aagttctagc tgaagctgga ggagaactgg gagaagcttc gcctcctctg   2100
aaccacattc atggagctcc ttattgtgga gatgggaagg tgtcagagag actgggagaa   2160
gagtgtgatg atggagacct tgtgagcgga gatggctgct ccaaggtgtg tgagctggag   2220
gaaggtttca actgtgtagg agagccaagc ctttgctaca tgtatgaggg agatggcata   2280
tgtgaacctt ttgagagaaa aaccagcatt gtagactgtg gcatctacac tcccaaagga   2340
tacttggatc aatgggctac ccgggcttac tcctctcatg aagacaagaa gaagtgtcct   2400
gtttccttgg taactggaga acctcattcc ctaattcgca catcatacca tccagattta   2460
cccaaccacc gtcccctaac tggctggttt ccctgtgttg ccagtgaaaa tgaaactcag   2520
gatgacagga gtgaacagcc agaaggtagc ctgaagaaag aggatgaggt ttggctcaaa   2580
gtgtgtttca atagaccagg agaggccaga gcaattttta ttttttttgac aactgatggc   2640
ctagttcccg gagagcatca gcagccgaca gtgactctct acctgaccga tgtccgtgga   2700
agcaaccact ctcttggaac ctatggactg tcatgccagc acaatccact gattatcaat   2760
gtgacccatc accagaatgt ccttttccgc cataccacct cagtgctgct gaatttctca   2820
tccccacggg tcggcatctc agctgtggct ctaaggacat cctcccgcat tggtctctcg   2880
gctcccagta actgcatctc agaggacgag gggcagaatc atcagggaca gagctgtatc   2940
catcggccct gtgggaagca ggacagctgt ccgtcattgc tgcttgatca tgctgatgtg   3000
gtgaactgta cctctatagg cccaggtctc atgaagtgtg ctaccacttg tcaaagggga   3060
tttgcccttc aggccagcag tgagcagtac atcaggctca tgcagaagga gattctgctc   3120
acatgttctt ctgggcactg ggaccagaat gtgagctgcc ttcccgtgga ctgcggtgtt   3180
cccgacccgt ctttggtgaa ctatgcaaac ttctcctgct cagagggaac caaatttctg   3240
aaacgctgct caatctcttg tgtcccacca gccaagctgc aaggactgag cccatggctg   3300
acatgtcttg aagatggtct ctggtctctc cctgaagtct actgcaagtt ggagtgtgat   3360
gctcccccta ttattctgaa tgccaacttg ctcctgcctc actgcctcca ggacaaccac   3420
gacgtgggca ccatctgcaa atatgaatgc aaaccagggt actatgtggc agaaagtgca   3480
```

-continued

```
gagggtaaag tcaggaacaa gctcctgaag atacaatgcc tggaaggtgg aatctgggag   3540

caaggcagct gcattcctgt ggtgtgtgag ccaccccctc ctgtgtttga aggcatgtat   3600

gaatgtacca atggcttcag cctggacagc cagtgtgtgc tcaactgtaa ccaggaacgt   3660

gaaaagcttc ccatcctctg cactaaagag ggcctgtgga cccaggagtt taagttgtgt   3720

gagaatctgc aaggagaatg cccgccaccc ccctcagagc tgaattctgt ggagtacaaa   3780

tgtgaacaag gatatgggat tggtgcagtg tgttccccat tgtgtgtaat ccccccccagt   3840

gaccccgtga tgctacctga gaatatcact gctgacactc tggagcactg gatggaacct   3900

gtcaaagtcc agagcattgt gtgcactggc cggcgtcaat ggcacccaga ccccgtctta   3960

gtccactgca tccagtcatg tgagcccttc caagcagatg gttggtgtga cactatcaac   4020

aaccgagcct actgccacta tgacgggga gactgctgct cttccacact ctcctccaag   4080

aaggtcattc catttgctgc tgactgtgac ctggatgagt gcacctgccg ggaccccaag   4140

gcagaagaaa atcagtaa                                                 4158


<210> SEQ ID NO 16
<211> LENGTH: 1385
<212> TYPE: PRT
<213> ORGANISM: Homo sapiens

<400> SEQUENCE: 16

Met Met Cys Leu Lys Ile Leu Arg Ile Ser Leu Ala Ile Leu Ala Gly
1               5                   10                  15

Trp Ala Leu Cys Ser Ala Asn Ser Glu Leu Gly Trp Thr Arg Lys Lys
            20                  25                  30

Ser Leu Val Glu Arg Glu His Leu Asn Gln Val Leu Leu Glu Gly Glu
        35                  40                  45

Arg Cys Trp Leu Gly Ala Lys Val Arg Arg Pro Arg Ala Ser Pro Gln
    50                  55                  60

His His Leu Phe Gly Val Tyr Pro Ser Arg Ala Gly Asn Tyr Leu Arg
65                  70                  75                  80

Pro Tyr Pro Val Gly Glu Gln Glu Ile His His Thr Gly Arg Ser Lys
                85                  90                  95

Pro Asp Thr Glu Gly Asn Ala Val Ser Leu Val Pro Pro Asp Leu Thr
            100                 105                 110

Glu Asn Pro Ala Gly Leu Arg Gly Ala Val Glu Glu Pro Ala Ala Pro
        115                 120                 125

Trp Val Gly Asp Ser Pro Ile Gly Gln Ser Glu Leu Leu Gly Asp Asp
    130                 135                 140

Asp Ala Tyr Leu Gly Asn Gln Arg Ser Lys Glu Ser Leu Gly Glu Ala
145                 150                 155                 160

Gly Ile Gln Lys Gly Ser Ala Met Ala Ala Thr Thr Thr Thr Ala Ile
                165                 170                 175

Phe Thr Thr Leu Asn Glu Pro Lys Pro Glu Thr Gln Arg Arg Gly Trp
            180                 185                 190

Ala Lys Ser Arg Gln Arg Arg Gln Val Trp Lys Arg Arg Ala Glu Asp
        195                 200                 205

Gly Gln Gly Asp Ser Gly Ile Ser Ser His Phe Gln Pro Trp Pro Lys
    210                 215                 220

His Ser Leu Lys His Gly Val Lys Lys Ser Pro Pro Glu Glu Ser Asn
225                 230                 235                 240

Gln Asn Gly Gly Glu Gly Ser Tyr Arg Glu Ala Glu Thr Phe Asn Ser
```

-continued

```
                245                 250                 255

Gln Val Gly Leu Pro Ile Leu Tyr Phe Ser Gly Arg Arg Glu Arg Leu
            260                 265                 270

Leu Leu Arg Pro Glu Val Leu Ala Glu Ile Pro Arg Glu Ala Phe Thr
        275                 280                 285

Val Glu Ala Trp Val Lys Pro Glu Gly Gly Gln Asn Asn Pro Ala Ile
    290                 295                 300

Ile Ala Gly Gly Ile Val Leu Ser Pro Ala Tyr Tyr Gly Met Pro Gly
305                 310                 315                 320

His Thr Asp Thr Met Ile His Glu Val Gly His Val Leu Gly Leu Tyr
                325                 330                 335

His Val Phe Lys Gly Val Ser Glu Arg Glu Ser Cys Asn Asp Pro Cys
            340                 345                 350

Lys Glu Thr Val Pro Ser Met Glu Thr Gly Asp Leu Cys Ala Asp Thr
        355                 360                 365

Ala Pro Thr Pro Lys Ser Glu Leu Cys Arg Glu Pro Glu Pro Thr Ser
    370                 375                 380

Asp Thr Cys Gly Phe Thr Arg Phe Pro Gly Ala Pro Phe Thr Asn Tyr
385                 390                 395                 400

Met Ser Tyr Thr Asp Asp Asn Cys Thr Asp Asn Phe Thr Pro Asn Gln
                405                 410                 415

Val Ala Arg Met His Cys Tyr Leu Asp Leu Val Tyr Gln Gln Trp Thr
            420                 425                 430

Glu Ser Arg Lys Pro Thr Pro Ile Pro Ile Pro Pro Met Val Ile Gly
        435                 440                 445

Gln Thr Asn Lys Ser Leu Thr Ile His Trp Leu Pro Pro Ile Ser Gly
    450                 455                 460

Val Val Tyr Asp Arg Ala Ser Gly Ser Leu Cys Gly Ala Cys Thr Glu
465                 470                 475                 480

Asp Gly Thr Phe Arg Gln Tyr Val His Thr Ala Ser Ser Arg Arg Val
                485                 490                 495

Cys Asp Ser Ser Gly Tyr Trp Thr Pro Glu Glu Ala Val Gly Pro Pro
            500                 505                 510

Asp Val Asp Gln Pro Cys Glu Pro Ser Leu Gln Ala Trp Ser Pro Glu
        515                 520                 525

Val His Leu Tyr His Met Asn Met Thr Val Pro Cys Pro Thr Glu Gly
    530                 535                 540

Cys Ser Leu Glu Leu Leu Phe Gln His Pro Val Gln Ala Asp Thr Leu
545                 550                 555                 560

Thr Leu Trp Val Thr Ser Phe Phe Met Glu Ser Ser Gln Val Leu Phe
                565                 570                 575

Asp Thr Glu Ile Leu Leu Glu Asn Lys Glu Ser Val His Leu Gly Pro
            580                 585                 590

Leu Asp Thr Phe Cys Asp Ile Pro Leu Thr Ile Lys Leu His Val Asp
        595                 600                 605

Gly Lys Val Ser Gly Val Lys Val Tyr Thr Phe Asp Glu Arg Ile Glu
    610                 615                 620

Ile Asp Ala Ala Leu Leu Thr Ser Gln Pro His Ser Pro Leu Cys Ser
625                 630                 635                 640

Gly Cys Arg Pro Val Arg Tyr Gln Val Leu Arg Asp Pro Pro Phe Ala
                645                 650                 655

Ser Gly Leu Pro Val Val Val Thr His Ser His Arg Lys Phe Thr Asp
            660                 665                 670
```

-continued

```
Val Glu Val Thr Pro Gly Gln Met Tyr Gln Tyr Gln Val Leu Ala Glu
        675                 680                 685

Ala Gly Gly Glu Leu Gly Glu Ala Ser Pro Pro Leu Asn His Ile His
    690                 695                 700

Gly Ala Pro Tyr Cys Gly Asp Gly Lys Val Ser Glu Arg Leu Gly Glu
705                 710                 715                 720

Glu Cys Asp Asp Gly Asp Leu Val Ser Gly Asp Gly Cys Ser Lys Val
                725                 730                 735

Cys Glu Leu Glu Glu Gly Phe Asn Cys Val Gly Glu Pro Ser Leu Cys
            740                 745                 750

Tyr Met Tyr Glu Gly Asp Gly Ile Cys Glu Pro Phe Glu Arg Lys Thr
        755                 760                 765

Ser Ile Val Asp Cys Gly Ile Tyr Thr Pro Lys Gly Tyr Leu Asp Gln
    770                 775                 780

Trp Ala Thr Arg Ala Tyr Ser Ser His Glu Asp Lys Lys Lys Cys Pro
785                 790                 795                 800

Val Ser Leu Val Thr Gly Glu Pro His Ser Leu Ile Arg Thr Ser Tyr
                805                 810                 815

His Pro Asp Leu Pro Asn His Arg Pro Leu Thr Gly Trp Phe Pro Cys
            820                 825                 830

Val Ala Ser Glu Asn Glu Thr Gln Asp Asp Arg Ser Glu Gln Pro Glu
        835                 840                 845

Gly Ser Leu Lys Lys Glu Asp Glu Val Trp Leu Lys Val Cys Phe Asn
    850                 855                 860

Arg Pro Gly Glu Ala Arg Ala Ile Phe Ile Phe Leu Thr Thr Asp Gly
865                 870                 875                 880

Leu Val Pro Gly Glu His Gln Gln Pro Thr Val Thr Leu Tyr Leu Thr
                885                 890                 895

Asp Val Arg Gly Ser Asn His Ser Leu Gly Thr Tyr Gly Leu Ser Cys
            900                 905                 910

Gln His Asn Pro Leu Ile Ile Asn Val Thr His His Gln Asn Val Leu
        915                 920                 925

Phe Arg His Thr Thr Ser Val Leu Leu Asn Phe Ser Ser Pro Arg Val
    930                 935                 940

Gly Ile Ser Ala Val Ala Leu Arg Thr Ser Ser Arg Ile Gly Leu Ser
945                 950                 955                 960

Ala Pro Ser Asn Cys Ile Ser Glu Asp Glu Gly Gln Asn His Gln Gly
                965                 970                 975

Gln Ser Cys Ile His Arg Pro Cys Gly Lys Gln Asp Ser Cys Pro Ser
            980                 985                 990

Leu Leu Leu Asp His Ala Asp Val Val Asn Cys Thr Ser Ile Gly Pro
        995                 1000                1005

Gly Leu Met Lys Cys Ala Thr Thr Cys Gln Arg Gly Phe Ala Leu Gln
    1010                1015                1020

Ala Ser Ser Glu Gln Tyr Ile Arg Leu Met Gln Lys Glu Ile Leu Leu
1025                1030                1035                1040

Thr Cys Ser Ser Gly His Trp Asp Gln Asn Val Ser Cys Leu Pro Val
                1045                1050                1055

Asp Cys Gly Val Pro Asp Pro Ser Leu Val Asn Tyr Ala Asn Phe Ser
            1060                1065                1070

Cys Ser Glu Gly Thr Lys Phe Leu Lys Arg Cys Ser Ile Ser Cys Val
        1075                1080                1085
```

-continued

```
Pro Pro Ala Lys Leu Gln Gly Leu Ser Pro Trp Leu Thr Cys Leu Glu
    1090                1095                1100

Asp Gly Leu Trp Ser Leu Pro Glu Val Tyr Cys Lys Leu Glu Cys Asp
1105                1110                1115                1120

Ala Pro Pro Ile Ile Leu Asn Ala Asn Leu Leu Leu Pro His Cys Leu
                1125                1130                1135

Gln Asp Asn His Asp Val Gly Thr Ile Cys Lys Tyr Glu Cys Lys Pro
            1140                1145                1150

Gly Tyr Tyr Val Ala Glu Ser Ala Glu Gly Lys Val Arg Asn Lys Leu
        1155                1160                1165

Leu Lys Ile Gln Cys Leu Glu Gly Gly Ile Trp Glu Gln Gly Ser Cys
    1170                1175                1180

Ile Pro Val Val Cys Glu Pro Pro Pro Pro Val Phe Glu Gly Met Tyr
1185                1190                1195                1200

Glu Cys Thr Asn Gly Phe Ser Leu Asp Ser Gln Cys Val Leu Asn Cys
                1205                1210                1215

Asn Gln Glu Arg Glu Lys Leu Pro Ile Leu Cys Thr Lys Glu Gly Leu
            1220                1225                1230

Trp Thr Gln Glu Phe Lys Leu Cys Glu Asn Leu Gln Gly Glu Cys Pro
        1235                1240                1245

Pro Pro Pro Ser Glu Leu Asn Ser Val Glu Tyr Lys Cys Glu Gln Gly
    1250                1255                1260

Tyr Gly Ile Gly Ala Val Cys Ser Pro Leu Cys Val Ile Pro Pro Ser
1265                1270                1275                1280

Asp Pro Val Met Leu Pro Glu Asn Ile Thr Ala Asp Thr Leu Glu His
                1285                1290                1295

Trp Met Glu Pro Val Lys Val Gln Ser Ile Val Cys Thr Gly Arg Arg
            1300                1305                1310

Gln Trp His Pro Asp Pro Val Leu Val His Cys Ile Gln Ser Cys Glu
        1315                1320                1325

Pro Phe Gln Ala Asp Gly Trp Cys Asp Thr Ile Asn Asn Arg Ala Tyr
    1330                1335                1340

Cys His Tyr Asp Gly Gly Asp Cys Cys Ser Ser Thr Leu Ser Ser Lys
1345                1350                1355                1360

Lys Val Ile Pro Phe Ala Ala Asp Cys Asp Leu Asp Glu Cys Thr Cys
                1365                1370                1375

Arg Asp Pro Lys Ala Glu Glu Asn Gln
            1380                1385


<210> SEQ ID NO 17
<211> LENGTH: 60
<212> TYPE: DNA
<213> ORGANISM: Homo sapiens

<400> SEQUENCE: 17

ggacagaaca acccagccat catcgcaggt ggcattgtcc tcagcccagc atattatggg     60


<210> SEQ ID NO 18
<211> LENGTH: 20
<212> TYPE: PRT
<213> ORGANISM: Homo sapiens

<400> SEQUENCE: 18

Gly Gln Asn Asn Pro Ala Ile Ile Ala Gly Gly Ile Val Leu Ser Pro
1               5                   10                  15

Ala Tyr Tyr Gly
```

-continued

20

<210> SEQ ID NO 19
<211> LENGTH: 1685
<212> TYPE: DNA
<213> ORGANISM: Homo sapiens

<400> SEQUENCE: 19

```
ccccaagcat caaactgaag gaaacattct aaccttcaca gacagactgg aggctggatg      60

gggacctggc tgaagacatc tggagaatga aagttaagta ccagcttgca tttttgtgcc     120

cctagattat ttttgcattt taaaataaga agcatcaaat tgcgtgtctc tgtgtaaaag     180

ttctagcaat ttgttttaag gtgaacttat tttggcttag ggactacaaa aagagaaggt     240

aattcctagg gaaggaagaa gagaaagaaa tgaaaattag agaataagat tattttgaat     300

gacttcaggt agcgaggagt gtgtgtttgt gagtgtgtat ttgagagact tggctcatgc     360

ctgtgggtct tctcttctag tatcagtgag gggagggatt actgaagaag aagggggg aa     420

aaaaaaagaa agaaatctga gctttctggg aggaaattca aaggaaccaa gagaaattaa     480

cttcgttctg caaggactaa agtacagcaa gaggagagag gtcaagcgag aagcgtgcgg     540

gaagcacatg ccctggggag gcatagaagc cacactggca gagcggccag cacaggtagc     600

cagcagaggc attcttgggg ctatttgaaa aagtttggtc tgtgaacaaa acagtttccc     660

tggtgactgc aaatccattg ctagctgcct ctttctcgtc tgcccatcac tctggtgtgg     720

tacccagaag ttgacttctg gttctgtaga aagagctagg ggaggtatga tgtgcttaaa     780

gatcctaaga ataagcctgg cgattttggc tgggtgggca ctctgttctg ccaactctga     840

gctgggctgg acacgcaaga aatccttggt tgagagggaa cacctgaatc aggtgctgtt     900

ggaaggagaa cgttgttggc tgggggccaa ggttcgaaga cccagagctt ctccacagca     960

tcacctcttt ggagtctacc ccagcagggc tgggaactac ctaaggccct accccgtggg    1020

ggagcaagaa atccatcata caggacgcag caaaccagac actgaaggaa atgctgtgag    1080

ccttgttccc ccagacctga ctgaaaatcc agcaggactg aggggtgcag ttgaagagcc    1140

ggctgcccca tgggtagggg atagtcctat tgggcaatct gagctgctgg gagatgatga    1200

cgcttatctc ggcaatcaaa gatccaagga gtctctaggt gaggccggga ttcagaaagg    1260

ctcagccatg gctgccacta ctaccaccgc cattttcaca accctgaacg aacccaaacc    1320

agagacccaa aggaggggct gggccaagtc caggcagcgt cgccaagtgt ggaagaggcg    1380

ggcggaagat gggcagggag actccggtat ctcttcacat ttccaacctt ggcccaagca    1440

ttcccttaaa cacagggtca aaaagagtcc accggaggaa agcaaccaaa atggtggaga    1500

gggctcctac cgagaagcag agacctttaa ctcccaagta ggactgccca tcttatactt    1560

ctctgggagg cgggagcggc tgctgctgcg tccagaagtg ctggctgaga ttccccggga    1620

ggcgttcaca gtggaagcct gggttaaacc ggagggagga cagaacaacc cagccatcat    1680

cgcag                                                                1685
```

<210> SEQ ID NO 20
<211> LENGTH: 1072
<212> TYPE: DNA
<213> ORGANISM: Homo sapiens

<400> SEQUENCE: 20

```
gtgtgtttga taactgctcc cacactgtca gtgacaaagg ctgggccctg gggatccgct      60

cagggaagga caagggaaag cgggatgctc gcttcttctt ctccctctgc accgaccgcg     120
```

-continued tgaagaaagc caccatcttg attagccaca gtcgctacca accaggcaca tggacccatg 180
tggcagccac ttacgatgga cggcacatgg ccctgtatgt ggatggcact caggtggcta 240
gcagtctaga ccagtctggt cccctgaaca gccccttcat ggcatcttgc cgctctttgc 300
tcctgggggg agacagctct gaggatgggc actatttccg tggacacctg ggcacactgg 360
ttttctggtc gaccgccctg ccacaaagcc attttcagca cagttctcag cattcaagtg 420
aggaggagga agcgactgac ttggtcctga cagcgagctt tgagcctgtg aacacagagt 480
gggttccctt tagagatgag aagtacccac gacttgaggt tctccagggc tttgagccag 540
agcctgagat tctgtcgcct ttgcagcccc cactctgtgg gcaaacagtc tgtgacaatg 600
tggaattgat ctcccagtac aatggatact ggccccttcg gggagagaag gtgatacgct 660
accaggtggt gaacatctgt gatgatgagg gcctaaaccc cattgtgagt gaggagcaga 720
ttcgtctgca gcacgaggca ctgaatgagg ccttcagccg ctacaacatc agctggcagc 780
tgagcgtcca ccaggtccac aattccaccc tgcgacaccg ggttgtgctt gtgaactgtg 840
agcccagcaa gattggcaat gaccattgtg accccgagtg tgagcaccca ctcacaggct 900
atgatggggg tgactgccgc ctgcagggcc gctgctactc ctggaaccgc agggatgggc 960
tctgtcacgt ggagtgtaac aacatgctga acgactttga cgacggagac tgctgcgacc 1020
cccaggtggc tgatgtgcgc aagacctgct ttgaccctga ctcacccaag ag 1072

<210> SEQ ID NO 21
<211> LENGTH: 146
<212> TYPE: DNA
<213> ORGANISM: Homo sapiens

<400> SEQUENCE: 21
ggcatacatg agtgtgaagg agctgaagga ggccctgcag ctgaacagta ctcacttcct 60
caacatctac tttgccagct cagtgcggga agaccttgca ggtgctgcca cctggccttg 120
ggacaaggac gctgtcactc acctgg 146

<210> SEQ ID NO 22
<211> LENGTH: 294
<212> TYPE: DNA
<213> ORGANISM: Homo sapiens

<400> SEQUENCE: 22
gtggcattgt cctcagccca gcatattatg ggatgcctgg ccacaccgac accatgatcc 60
atgaagtggg acatgttctg ggactctacc atgtctttaa aggagtcagt gaaagagaat 120
cctgcaatga cccctgcaag gagacagtgc catccatgga aacgggagac ctctgtgccg 180
acaccgcccc cactcccaag agtgagctgt gccgggaacc agagcccact agtgacacct 240
gtggcttcac tcgcttccca ggggctccgt tcaccaacta catgagctac acgg 294

<210> SEQ ID NO 23
<211> LENGTH: 193
<212> TYPE: DNA
<213> ORGANISM: Homo sapiens

<400> SEQUENCE: 23
atgataactg cactgacaac ttcactccta accaagtggc ccgaatgcat tgctatttgg 60
acctagtcta tcagcagtgg actgaaagca gaaagcccac ccccatcccc attccaccta 120
tggtcatcgg acagaccaac aagtccctca ctatccactg gctgcctcct attagtggag 180

-continued

```
ttgtatatga cag                                                        193


<210> SEQ ID NO 24
<211> LENGTH: 122
<212> TYPE: DNA
<213> ORGANISM: Homo sapiens

<400> SEQUENCE: 24

ggcctcaggc agcttgtgtg gcgcttgcac tgaagatggg acctttcgtc agtatgtgca      60

cacagcttcc tcccggcggg tgtgtgactc ctcaggttat tggaccccag aggaggctgt     120

gg                                                                    122


<210> SEQ ID NO 25
<211> LENGTH: 490
<212> TYPE: DNA
<213> ORGANISM: Homo sapiens

<400> SEQUENCE: 25

ggcctcctga tgtggatcag ccctgcgagc caagcttaca ggcctggagc cctgaggtcc      60

acctgtacca catgaacatg acggtcccct gccccacaga aggctgtagc ttggagctgc     120

tcttccaaca cccggtccaa gccgacaccc tcaccctgtg ggtcacttcc ttcttcatgg     180

agtcctcgca ggtcctcttt gacacagaga tcttgctgga aaacaaggag tcagtgcacc     240

tgggcccctt agacactttc tgtgacatcc cactcaccat caaactgcac gtggatggga     300

aggtgtcggg ggtgaaagtc tacacctttg atgagaggat agagattgat gcagcactcc     360

tgacttctca gccccacagt cccttgtgct ctggctgcag gcctgtgagg taccaggttc     420

tccgcgatcc cccatttgcc agtggtttgc ccgtggtggt gacacattct cacaggaagt     480

tcacggacgt                                                            490


<210> SEQ ID NO 26
<211> LENGTH: 129
<212> TYPE: DNA
<213> ORGANISM: Homo sapiens

<400> SEQUENCE: 26

ggaggtcaca cctggacaga tgtatcagta ccaagttcta gctgaagctg gaggagaact      60

gggagaagct tcgcctcctc tgaaccacat tcatggagct ccttattgtg gagatgggaa     120

ggtgtcaga                                                             129


<210> SEQ ID NO 27
<211> LENGTH: 92
<212> TYPE: DNA
<213> ORGANISM: Homo sapiens

<400> SEQUENCE: 27

gagactggga gaagagtgtg atgatggaga ccttgtgagc ggagatggct gctccaaggt      60

gtgtgagctg gaggaaggtt tcaactgtgt ag                                   92


<210> SEQ ID NO 28
<211> LENGTH: 194
<212> TYPE: DNA
<213> ORGANISM: Homo sapiens

<400> SEQUENCE: 28

gagagccaag cctttgctac atgtatgagg gagatggcat atgtgaacct tttgagagaa      60

aaaccagcat tgtagactgt ggcatctaca ctcccaaagg atacttggat caatgggcta     120
```

-continued cccgggctta ctcctctcat gaagacaaga agaagtgtcc tgtttccttg gtaactggag 180
aacctcattc ccta 194

<210> SEQ ID NO 29
<211> LENGTH: 147
<212> TYPE: DNA
<213> ORGANISM: Homo sapiens

<400> SEQUENCE: 29
atttgcacat cataccatcc agatttaccc aaccaccgtc ccctaactgg ctggtttccc 60
tgtgttgcca gtgaaaatga aactcaggat gacaggagtg aacagccaga aggtagcctg 120
aagaaagagg atgaggtttg gctcaaa 147

<210> SEQ ID NO 30
<211> LENGTH: 136
<212> TYPE: DNA
<213> ORGANISM: Homo sapiens

<400> SEQUENCE: 30
gtgtgtttca atagaccagg agaggccaga gcaattttta tttttttgac aactgatggc 60
ctagttcccg gagagcatca gcagccgaca gtgactctct acctgaccga tgtccgtgga 120
agcaaccact ctcttg 136

<210> SEQ ID NO 31
<211> LENGTH: 217
<212> TYPE: DNA
<213> ORGANISM: Homo sapiens

<400> SEQUENCE: 31
gaacctatgg actgtcatgc cagcataatc cactgattat caatgtgacc catcaccaga 60
atgtcctttt ccaccatacc acctcagtgc tgccgaattt ctcatcccca cgggtcggca 120
tctcagctgt ggctctaagg acatcctccc gcattggtct ttcggctccc agtaactgca 180
tctcagagga cgaggggcag aatcatcagg gacagag 217

<210> SEQ ID NO 32
<211> LENGTH: 172
<212> TYPE: DNA
<213> ORGANISM: Homo sapiens

<400> SEQUENCE: 32
ctgtatccat cggccctgtg ggaagcagga cagctgtccg tcattgctgc ttgatcatgc 60
tgatgtggtg aactgtacct ctataggccc aggtctcatg aagtgtgcta tcacttgtca 120
aaggggattt gcccttcagg ccagcagtgg gcagtacatc aggcccatgc ag 172

<210> SEQ ID NO 33
<211> LENGTH: 178
<212> TYPE: DNA
<213> ORGANISM: Homo sapiens

<400> SEQUENCE: 33
aaggaaattc tgctcacatg ttcttctggg cactgggacc agaatgtgag ctgccttccc 60
gtggactgcg gtgttcccga cccgtctttg gtgaactatg caaacttctc ctgctcagag 120
ggaaccaaat ttctgaaacg ctgctcaatc tcttgtgtcc caccagccaa gctgcaag 178

<210> SEQ ID NO 34

-continued

<211> LENGTH: 214
<212> TYPE: DNA
<213> ORGANISM: Homo sapiens

<400> SEQUENCE: 34
gactgagccc atggctgaca tgtcttgaag atggtctctg gtctctccct gaagtctact 60
gcaagttgga gtgtgatgct ccccctatta ttctgaatgc caacttgctc ctgcctcact 120
gcctccagga caaccacgac gtgggcacca tctgcaaata tgaatgcaaa ccagggtact 180
atgtggcaga aagtgcagag ggtaaagtca ggaa 214

<210> SEQ ID NO 35
<211> LENGTH: 169
<212> TYPE: DNA
<213> ORGANISM: Homo sapiens

<400> SEQUENCE: 35
caagctcctg aagatacaat gcctggaagg tggaatctgg gagcaaggca gctgcattcc 60
tgtggtgtgt gagccacccc ctcctgtgtt tgaaggcatg tatgaatgta ccaatggctt 120
cagcctggac agccagtgtg tgctcaactg taaccaggaa cgtgaaaag 169

<210> SEQ ID NO 36
<211> LENGTH: 136
<212> TYPE: DNA
<213> ORGANISM: Homo sapiens

<400> SEQUENCE: 36
cttcccatcc tctgcactaa agagggcctg tggacccagg agtttaagtt gtgtgagaat 60
ctgcaaggag aatgcccacc acccccctca gagctgaatt ctgtggagta caaatgtgaa 120
caaggatatg ggattg 136

<210> SEQ ID NO 37
<211> LENGTH: 110
<212> TYPE: DNA
<213> ORGANISM: Homo sapiens

<400> SEQUENCE: 37
gtgcagtgtg ttccccattg tgtgtaatcc cccccagtga ccccgtgatg ctacctgaga 60
atatcactgc tgacactctg gagcactgga tggaacctgt caaagtccag 110

<210> SEQ ID NO 38
<211> LENGTH: 72
<212> TYPE: DNA
<213> ORGANISM: Homo sapiens

<400> SEQUENCE: 38
agcattgtgt gcactggccg gcgtcaatgg cacccagacc ccgtcttagt ccactgcatc 60
cagtcatgtg ag 72

<210> SEQ ID NO 39
<211> LENGTH: 85
<212> TYPE: DNA
<213> ORGANISM: Homo sapiens

<400> SEQUENCE: 39
gtcataagcc agttgttgct gcttgtgttc ccattgtccc agcaagaaca cacgtatgct 60
acatatctgc aatccaaaat tgttg 85

-continued

<210> SEQ ID NO 40
<211> LENGTH: 99
<212> TYPE: DNA
<213> ORGANISM: Homo sapiens

<400> SEQUENCE: 40 ccctccaag caaatggttg gtgtgacact atcaacaacc gagcctactg ccactatgac 60
gggggagact gctgctcttc cacactctcc tccaagaag 99

<210> SEQ ID NO 41
<211> LENGTH: 640
<212> TYPE: DNA
<213> ORGANISM: Homo sapiens

<400> SEQUENCE: 41
gtcattccat ttgctgctga ctgtgacctg gatgagtgca cctgccggga ccccaaggca 60
gaagaaaatc agtaactgtg ggaacaagcc cctccctcca ctgcctcaga ggcagtaaga 120
aagagaggcc gacccaggag gaaacaaagg gtgaatgaag aagaacaatc atgaaatgga 180
agaaggagga agagcatgaa ggatcttata agaaatgcaa gaggatattg ataggtgtga 240
actagttcat caagtagccc aagtaggaga gaatcatagg caaaagtttc tttaaagtgg 300
cagttgatta acatggaagg ggaaatatga tagatatata aggaccctcc tccctcactt 360
atattctatt aaatcctatc ctcaactctt gccctgctct ccgctccacc ccctgccaac 420
tactcagtcc cacccaactt gtaaaccaat accaaaatac tagaggagaa gttggcaggg 480
atactgttaa tacccatttt gaatggattg ccatctttca gagcttgtct gctctcaact 540
ggctcttttt ctttttgtgt agtttccaat gaataatgaa gttagttatt aattctttat 600
aagtatttaa acataattat ataaatatat tatatatatt 640

<210> SEQ ID NO 42
<211> LENGTH: 500
<212> TYPE: DNA
<213> ORGANISM: Homo sapiens

<400> SEQUENCE: 42
tatttgaaaa agtttggtct gtgaacaaaa cagtttccct ggtgactgca aatccattgc 60
tagctgcctc tttctcgtct gcccatcact ctggtgtggt acccagaagt tgacttctgg 120
ttctgtagaa agagctaggg gaggtatgat gtgcttaaag atcctaagaa taagcctggc 180
gattttggct gggtgggcac tctgttctgc caactctgag ctgggctgga cacgcaagaa 240
atccttggtt gagagggaac acctgaatca ggtgctgttg gaaggagaac gttgttggct 300
gggggccaag gttcgaagac ccagagcttc tccacagcat cacctctttg gagtctaccc 360
cagcagggct gggaactacc taaggcccta ccccgtgggg gagcaagaaa tccatcatac 420
aggacgcagc aaaccagaca ctgaaggaaa tgctgtgagc cttgttcccc cagacctgac 480
tgaaaatcca gcaggactga 500

<210> SEQ ID NO 43
<211> LENGTH: 500
<212> TYPE: DNA
<213> ORGANISM: Homo sapiens

<400> SEQUENCE: 43
gaacagcccc ttcatggcat cttgccgctc tttgctcctg gggggagaca gctctgagga 60
tgggcactat ttccgtggac acctgggcac actggttttc tggtcgaccg ccctgccaca 120

-continued

```
aagccatttt cagcacagtt ctcagcattc aagtgaggag gaggaagcga ctgacttggt    180

cctgacagcg agctttgagc ctgtgaacac agagtgggtt ccctttagag atgagaagta    240

cccacgactt gaggttctcc agggctttga gccagagcct gagattctgt cgcctttgca    300

gcccccactc tgtgggcaaa cagtctgtga caatgtggaa ttgatctccc agtacaatgg    360

atactggccc cttcggggag agaaggtgat acgctaccag gtggtgaaca tctgtgatga    420

tgagggccta aaccccattg tgagtgagga gcagattcgt ctgcagcacg aggcactgaa    480

tgaggccttc agccgctaca                                                500


<210> SEQ ID NO 44
<211> LENGTH: 500
<212> TYPE: DNA
<213> ORGANISM: Homo sapiens

<400> SEQUENCE: 44

aatgtgtatt agtgcctttt cttctggtct tcatgacagg ctggtctctg ccccatgccc     60

ctccaaaagg taatgctggc tgggagtgcc attagaatct gattaggtct ggctctgcta    120

ttctctaagt accaattctt tgctgtgaca ttttttcatc ttgcatgctc tctagggcat    180

acatgagtgt gaaggagctg aaggaggccc tgcagctgaa cagtactcac ttcctcaaca    240

tctactttgc cagctcagtg cgggaagacc ttgcaggtgc tgccacctgg ccttgggaca    300

aggacgctgt cactcacctg ggtaagtgaa atgaagacca aacatagtag gaaaaaaaca    360

aagaaggctg aaggaagctt gcgaaagtaa gtttggggaa aaaagaaaga cagagaaaaa    420

gtgaatttac acagtgaatt aactgctttg tgctgagaat ggcacttagt agagcctgtc    480

aaaatgtttc aatatagaca                                                500


<210> SEQ ID NO 45
<211> LENGTH: 500
<212> TYPE: DNA
<213> ORGANISM: Homo sapiens

<400> SEQUENCE: 45

gtttatcaga aaacataatt aaggattgga gagctattca ttctgtgctc tgaaaggctt     60

ttcaaaactt tcattgcagg tggcattgtc ctcagcccag catattatgg gatgcctggc    120

cacaccgaca ccatgatcca tgaagtggga catgttctgg gactctacca tgtctttaaa    180

ggagtcagtg aaagagaatc ctgcaatgac ccctgcaagg agacagtgcc atccatggaa    240

acgggagacc tctgtgccga caccgccccc actcccaaga gtgagctgtg ccgggaacca    300

gagcccacta gtgacacctg tggcttcact cgcttcccag gggctccgtt caccaactac    360

atgagctaca cgggtatcac cactgtcttg ttttgttttc tgttaagaat acatgggggc    420

ctttgagagc tgggagggtg gaggtgtggg agctgatggg agaatgatta agtggtcatt    480

tgtgtcggag agttgaagtg                                                500


<210> SEQ ID NO 46
<211> LENGTH: 500
<212> TYPE: DNA
<213> ORGANISM: Homo sapiens

<400> SEQUENCE: 46

agaccctttc tggaacagat tgcatttgtt cattcattca acaagtaagt gctcattgag     60

cctaataagt taactcagcc atgaacaaga cacaaattta tccctgcctt ggtggacttg    120

atgggttaaa atctccatct cttgtgccac ctttttttgtc tccacagatg ataactgcac    180
```

-continued tgacaacttc actcctaacc aagtggcccg aatgcattgc tatttggacc tagtctatca 240
gcagtggact gaaagcagaa agcccacccc catccccatt ccacctatgg tcatcggaca 300
gaccaacaag tccctcacta tccactggct gcctcctatt agtggagttg tatatgacag 360
gtgagagagg cactggctgt gggtgagctg gcttatttct ctgtggcatt tcatatgaat 420
gaggggaaga atatgaatcc aggggaactc caatttggaa gtataaatgt gtgcaccact 480
gctcagagct gctgctccag 500

<210> SEQ ID NO 47
<211> LENGTH: 500
<212> TYPE: DNA
<213> ORGANISM: Homo sapiens

<400> SEQUENCE: 47
caaagatgag gtccacacaa gaaaaaacga ttgagataca gttgttctta gttactctct 60
aggtccttac taaccatcaa cccctgccct ccccacacaa aggtctttct aattttctta 120
tcccaactca tctgatggac tctcctcatc tcccatctcc atccctttat ctccccaggg 180
cctcaggcag cttgtgtggc gcttgcactg aagatgggac ctttcgtcag tatgtgcaca 240
cagcttcctc ccggcgggtg tgtgactcct caggttattg gaccccagag gaggctgtgg 300
gtaaagtacc atgacatttt ttctttatac cctggtgacc actgaggatg ggggtggagg 360
taaagagtgg agtagtgaca tggtgacaaa aaggcaatgt atgtgtatgt gtgtgtgtgt 420
gtgtgtgtgt gtgtgtgtgt gtgtgttttg ctggatatct tttggagctg cctggtgccg 480
ctgtgtgcag aatgttccat 500

<210> SEQ ID NO 48
<211> LENGTH: 500
<212> TYPE: DNA
<213> ORGANISM: Homo sapiens

<400> SEQUENCE: 48
ccccccaggg cctcctgatg tggatcagcc ctgcgagcca agcttacagg cctggagccc 60
tgaggtccac ctgtaccaca tgaacatgac ggtcccctgc cccacagaag gctgtagctt 120
ggagctgctc ttccaacacc cggtccaagc cgacaccctc accctgtggg tcacttcctt 180
cttcatggag tcctcgcagg tcctctttga cacagagatc ttgctggaaa acaaggagtc 240
agtgcacctg ggccccttag acactttctg tgacatccca ctcaccatca aactgcacgt 300
ggatgggaag gtgtcggggg tgaaagtcta cacctttgat gagaggatag agattgatgc 360
agcactcctg acttctcagc cccacagtcc cttgtgctct ggctgcaggc ctgtgaggta 420
ccaggttctc cgcgatcccc catttgccag tggtttgccc gtggtggtga cacattctca 480
caggaagttc acggacgtgt 500

<210> SEQ ID NO 49
<211> LENGTH: 500
<212> TYPE: DNA
<213> ORGANISM: Homo sapiens

<400> SEQUENCE: 49
atctttgttt tagacaatgc agcgtatgtt taacctttat gtttcccata atatttccct 60
tcaacttctg tgaaccatca acaaaggacc cagggcatgc ctcactttgt ggctgtagtg 120
gtcacaaacc ctttggtttc cacagggagg tcacacctgg acagatgtat cagtaccaag 180

-continued

```
ttctagctga agctggagga gaactgggag aagcttcgcc tcctctgaac cacattcatg    240

gagctcctta ttgtggagat gggaaggtgt cagagtgagt attttgtgtg tgtgtgtgtg    300

tgtgtgtgtg tgtgtgtgag agagagagag agagagagag agagggaggg agagagagca    360

gggacactgt tctctaaaca gaagtttcag gagtttgact tgttttggaa atgtagggag    420

caaggcacca tttgattcta gtgttgaaat tctaaaatct gggacttggt tgtgtcaggt    480

cttgagatct ggcatctcta                                                500
```

<210> SEQ ID NO 50
<211> LENGTH: 500
<212> TYPE: DNA
<213> ORGANISM: Homo sapiens

<400> SEQUENCE: 50

```
attgcttaaa ttgtatctac tttatatatc catatgtttg tttctatttt ctgtaaaagc     60

attcttctag ctcctacttt tttccaactt gcacttttta atatatactg agaaattgta    120

agaattttaa atgatggtag ctaaacaaga aaatttgtgt gtatgtgtta tatatgcata    180

tatattttac cctctaggag actgggagaa gagtgtgatg atggagacct tgtgagcgga    240

gatggctgct ccaaggtgtg tgagctggag gaaggtttca actgtgtagg taagttcaag    300

agtttcagtc taagattgtg tcctactttt agaggtgtat tattttgtga gttcttgata    360

tcctgtaaca tctagcttag tgattataat aataacctct gatgtgtccc ttgtatgcca    420

ggcatgaatt gtttcacagg tattatctca gtcaatcctt agaataactg gggaagacaa    480

agtgaggcac agagcttaaa                                                500
```

<210> SEQ ID NO 51
<211> LENGTH: 500
<212> TYPE: DNA
<213> ORGANISM: Homo sapiens

<400> SEQUENCE: 51

```
gtaggcatta gactggcagg caattgcaga attctcttca gtgggctgga gaagaagtgt     60

tgtggacatt cccatgttca ttttttttcat gacatttatg aaaacacttt ttctgtgtca    120

cacaatattt cttggcagga gagccaagcc tttgctacat gtatgaggga gatggcatat    180

gtgaaccttt tgagagaaaa accagcattg tagactgtgg catctacact cccaaaggat    240

acttggatca atgggctacc cgggcttact cctctcatga agacaagaag aagtgtcctg    300

tttccttggt aactggagaa cctcattccc tagtaagtta agccagatga atagagtcga    360

gcctgcgcaa aattgtaaag tgactccccc tatgcttaca cttggggtct atgtttggat    420

aattaaaaga agaagtaagg agttagaagc cctagggaac attactggat ctgccagcat    480

tgctattaca attacatgat                                                500
```

<210> SEQ ID NO 52
<211> LENGTH: 500
<212> TYPE: DNA
<213> ORGANISM: Homo sapiens

<400> SEQUENCE: 52

```
gcactgagaa attcttcaat gttgagaaaa gttttctgcc aataatgtga tcattaggca     60

ttcagaaaga gagaacaact ttgctttgag ctggagagtt tcattgtcct tacttatatc    120

ttcacactcc acacttcaaa ttgttggttg aaattgtatt tcagatttgc acatcatacc    180
```

-continued atccagattt acccaaccac cgtcccctaa ctggctggtt tccctgtgtt gccagtgaaa 240
atgaaactca ggatgacagg agtgaacagc cagaaggtag cctgaagaaa gaggatgagg 300
tttggctcaa agtaagtggc ccaaatgttt cttttgtgca tgtgaaaggt gtaagcatat 360
gtgtgtgtgt gtgtgtgtgt gtgtgtgtaa atggtgcatt tggatgactt gtcagaaaat 420
tttcttttgt tatctcaaag tgttaatatt ttgagtttat tttcacctct ctgtattgtg 480
gacttctttc tgttaataca 500

<210> SEQ ID NO 53
<211> LENGTH: 500
<212> TYPE: DNA
<213> ORGANISM: Homo sapiens

<400> SEQUENCE: 53
tttctgtgtc tactccatat ttttagcatt tataaaaaaa atggaagctc ttactttata 60
aatagtgagc tctctaagaa gaataaaaat tgtatagcac atgtcttgat agctcaatgg 120
aaataatgac ttatacataa atgtgcttat gcttaggtgt gtttcaatag accaggagag 180
gccagagcaa tttttatttt tttgacaact gatggcctag ttcccggaga gcatcagcag 240
ccgacagtga ctctctacct gaccgatgtc cgtggaagca accactctct tggtgagtct 300
gacaaatatc cctttagggt cactagagga caacccggta gacccagaag tcagcttgat 360
gtctgtcttt tatgttgtct gggatcttgc ctacatcata catctaggtt ttggcatcat 420
acacctatta agaggataaa atgaatacaa gatatggaaa catggtacta acaatggctg 480
aaaatatgat tcatctccgt 500

<210> SEQ ID NO 54
<211> LENGTH: 500
<212> TYPE: DNA
<213> ORGANISM: Homo sapiens

<400> SEQUENCE: 54
atctaggttt tggcatcata cacctattaa gaggataaaa tgaatacaag atatggaaac 60
atggtactaa caatggctga aaatatgatt catctccgtt tatcttcagg aacctatgga 120
ctgtcatgcc agcataatcc actgattatc aatgtgaccc atcaccagaa tgtccttttc 180
caccatacca cctcagtgct gctgaatttc tcatccccac gggtcggcat ctcagctgtg 240
gctctaagga catcctcccg cattggtctt tcggctccca gtaactgcat ctcagaggac 300
gaggggcaga atcatcaggg acagaggtac aaacttccct ttctttcttt tgtttccttt 360
tcttgtggct ctaatgattg gctcacattt acatagtgtt atgtatagag tgtttgctca 420
atcactaact gaaaaatgaa tttaggaact actaaaaaga cataggaagc aagcaaagaa 480
taatttgtgg aaggcatact 500

<210> SEQ ID NO 55
<211> LENGTH: 500
<212> TYPE: DNA
<213> ORGANISM: Homo sapiens

<400> SEQUENCE: 55
aaaaaaggtg atgagttaaa tatcagtttt ggagaaaatt gttctctctg gtttaggagc 60
cctcccagat ggagctgcaa agtcattgct cctccttact ggttctcaac cagtcctaag 120
atggttctat ttctcttatc ccagctgtat ccatcggccc tgtgggaagc aggacagctg 180
tccgtcattg ctgcttgatc atgctgatgt ggtgaactgt acctctatag gcccaggtct 240

-continued

```
catgaagtgt gctatcactt gtcaaagggg atttgccctt caggccagca gtgggcagta    300

catcaggccc atgcaggtga gttgaaagaa cactatcacc aggaccaagt tcctgggaag    360

gggaggtatt cacactcttc tctctggctc cacagggaaa gagcagatgt ttttaaacca    420

tttgaaagca aaacatgggg gctctaacaa gcagagagaa tgatggctta atagaaatgc    480

aaggtatata aaagcatgta                                                500


<210> SEQ ID NO 56
<211> LENGTH: 500
<212> TYPE: DNA
<213> ORGANISM: Homo sapiens

<400> SEQUENCE: 56

gagggagaaa ggcaaaataa tttgtcccgt tttaaatgtt tagacagata atcaccaaga     60

ctcttctaaa gcctggaaac tactctgata cgccttttaa tgtgactttg acagaagcaa    120

tttctctgtt tctagaagga aattctgctc acatgttctt ctgggcactg ggaccagaat    180

gtgagctgcc ttcccgtgga ctgcggtgtt cccgacccgt ctttggtgaa ctatgcaaac    240

ttctcctgct cagagggaac caaatttctg aaacgctgct caatctcttg tgtcccacca    300

gccaagctgc aaggtattgt ctggtcaacc aggaactgta tgcaagttct ctgccatccc    360

tcgctcttga gggtactttg ggactctttt cgttacccca acacctttcc tatttgctcc    420

actgtgtcac catcttctga taactccaga aaagtcccaa aaggcaacac cactctttgt    480

ccccaactac ttgaaaggat                                                500


<210> SEQ ID NO 57
<211> LENGTH: 500
<212> TYPE: DNA
<213> ORGANISM: Homo sapiens

<400> SEQUENCE: 57

tgggattttt gagatgctac tcaagaaaga ataatatgac ttttgaaagg caccagtaag     60

ttcagaggtt tttatttcat ctgctatgat tatctttctg ggctctctgt tctgagcatc    120

ttgtgcttct ctttcctgga gtcaggactg agcccatggc tgacatgtct tgaagatggt    180

ctctggtctc tccctgaagt ctactgcaag ttggagtgtg atgctccccc tattattctg    240

aatgccaact tgctcctgcc tcactgcctc caggacaacc acgacgtggg caccatctgc    300

aaatatgaat gcaaaccagg gtactatgtg gcagaaagtg cagagggtaa agtcaggaag    360

taagttgaat gttcctggtc tttggagttc tacctacctc gctgcttgtt atgtttgttt    420

ttctgtataa tctctcttta cctgcagggc tatattctcc agtcatgaca ggcaggcaac    480

ctgctgtgct ttctgtaaat                                                500


<210> SEQ ID NO 58
<211> LENGTH: 500
<212> TYPE: DNA
<213> ORGANISM: Homo sapiens

<400> SEQUENCE: 58

atttactact actttgaata ataaatgaac attactattt ttagttccat gatttagaaa     60

ttagcctagg acagtgggac atatggctca caagaaccat ctgtccctgc ctatttgcta    120

attcttatgc catattgctg aggatcaagt ctttcatgac cttcttgaaa gattctgatg    180

agctattttt gttttatgtt ttatcagcaa gctcctgaag atacaatgcc tggaaggtgg    240
```

-continued

```
aatctgggag caaggcagct gcattcctgt ggtgtgtgag ccaccccctc ctgtgtttga    300

aggcatgtat gaatgtacca atggcttcag cctggacagc cagtgtgtgc tcaactgtaa    360

ccaggaacgt gaaaaggtaa ggaacatttt ttgaacttat tttcatcagg ctgtgctcta    420

atcttgatgc ccaatccaag aaatttgaga aatgaaattt ctaaagaatt ccaacaggca    480

gggacttggg attctaatcg                                                500
```

<210> SEQ ID NO 59
<211> LENGTH: 500
<212> TYPE: DNA
<213> ORGANISM: Homo sapiens

<400> SEQUENCE: 59

```
ttttttttt ttttttttt ggccagtaac aatatgttgt ttcaatagtg tcttttggtc       60

caggttctag aactggagaa tactaccact taatcagacc actttttca actctcaata     120

aagttaacaa aacaataatt aagatgttta cttttgatat tctagcttcc catcctctgc    180

actaaagagg gcctgtggac ccaggagttt aagttgtgtg agaatctgca aggagaatgc    240

ccaccacccc cctcagagct gaattctgtg gagtacaaat gtgaacaagg atatgggatt    300

ggtaaggata ggagtgaatc ttaaagtcaa tttctatgtc attcttttat taagcacagc    360

tgaatttttt ttaattttat ttatttttgt cagacggagt cttgctctgt cgcccaggct    420

ggggtgcagt ggcacagtct cagctcactg caacctccat ttcccgggtt caagcaattc    480

tcctgcctca gcctcccaag                                                500
```

<210> SEQ ID NO 60
<211> LENGTH: 500
<212> TYPE: DNA
<213> ORGANISM: Homo sapiens

<400> SEQUENCE: 60

```
agttgagtta ggttggggca gagtctcttt accaattagt gtgaaggtat tcctacagga     60

acacagtaga tgaatatcag ccctgcctac aacgtcataa tatggtgacc catgatgaaa    120

gcagttgttc tttaaaaact caaagctatt gattcctgaa agaaaaagaa tgagatctgg    180

gaagttcaag tctctgctgt aaacttctgt tctttcaggt gcagtgtgtt ccccattgtg    240

tgtaatcccc cccagtgacc ccgtgatgct acctgagaat atcactgctg acactctgga    300

gcactggatg gaacctgtca aagtccaggt gaggaaaggg acattgttat gtgccaaaga    360

catgagtctg ctgagcaaca cttggagcat tattttttgg agtaatttca gaggctttca    420

aagcatcctc aaagcaaaca accacatgga ttattcctag aaagaaggat taaacattga    480

aaagaaaaaa gagggaagct                                                500
```

<210> SEQ ID NO 61
<211> LENGTH: 500
<212> TYPE: DNA
<213> ORGANISM: Homo sapiens

<400> SEQUENCE: 61

```
tgagacttcc tgcctgaacc acatctgtca gggtgggcag tgtgcacggg aaaggctaga     60

tagccccaat ccactttatg ggacacaatt agaaactagc tgcttgagaa atggagttgg    120

actcctgtgg tgagctcagg atttgcccct tctcacacac aacaaatgtc tttaattttg    180

ttttctgttt ttcccgtctt tccccttaga gcattgtgtg cactggccgg cgtcaatggc    240

acccagaccc cgtcttagtc cactgcatcc agtcatgtga ggtaagatag cctccccttc    300
```

-continued cccaactcag actagagaac tcaggtggat ttaacttatg gagcttgaat ccttctaatt 360
taggacctgg tccctctcct attcctctgt cctttgttta acttcttaaa ttaagttggt 420
tccacgatct taaatttaca gaaattagga gttctgattt ttgttttgtt ttagcaaaat 480
ctttggagat ccactttaaa 500

<210> SEQ ID NO 62
<211> LENGTH: 500
<212> TYPE: DNA
<213> ORGANISM: Homo sapiens

<400> SEQUENCE: 62
gagtgcctca ttcattattt ctcccaataa gcccaaggca gtaaatccac cagctcagta 60
tcctcagccc atattgccct tcatgttact tcagcacttt tgtttgcatc atattctctt 120
ggcataagga tttgctttca attatccact attctgtgct gcttatgttt tctgaggtgc 180
cactaagact ttctttaaaa actcttatct aaataattcc atcttcttat gttaggtcat 240
aagccagttg ttgctgcttg tgttcccatt gtcccagcaa gaacacacgt atgctacata 300
tctgcaatcc aaaattgttg gtacgttcaa ttctattttt ctagttgttg cttgcatttg 360
gcctttgaga cctgaatact ccttgtatct tctgtttctt tcgtaaactg catatgggca 420
aggaatggca acttagttaa tggaaaactt ttgaagtcaa acgaccctag attccaatcc 480
tgggtcagct gagtagtgtg 500

<210> SEQ ID NO 63
<211> LENGTH: 500
<212> TYPE: DNA
<213> ORGANISM: Homo sapiens

<400> SEQUENCE: 63
ggagcagtgc tgccagtgaa atgtgacaat tccttggacc tagtggtctt gagatttttt 60
caacttcttg caaatattag gtcaatttgt gtcctgcacc ttgggtgctt ttctgtaata 120
tctctggagc tgtatggatt acgctgggat gggaggagtg gcagagtcaa acaagacata 180
ataaggctat actgagatgt tgccttctaa cctccctaca gcccttccaa gcagatggtt 240
ggtgtgacac tatcaacaac cgagcctact gccactatga cgggggagac tgctgctctt 300
ccacactctc ctccaagaag gtgagtgaga gaacctgggg atgggggagg cagtggcttc 360
aggaataaag gcagggtctt cagctagctc tcattcatgg tgtgtaataa tgggtttgta 420
ttcaacaatt aggagggaat tataatgaac aaacattgga gcttctaaag tgacagggtt 480
aagggtagca taggttctta 500

<210> SEQ ID NO 64
<211> LENGTH: 500
<212> TYPE: DNA
<213> ORGANISM: Homo sapiens

<400> SEQUENCE: 64
gtgacctgga tgagtgcacc tgccgggacc ccaaggcaga agaaaatcag taactgtggg 60
aacaagcccc tccctccact gcctcagagg cagtaagaaa gagaggccga cccaggagga 120
aacaaagggt gaatgaagaa gaacaatcat gaaatggaag aaggaggaag agcatgaagg 180
atcttataag aaatgcaaga ggatattgat aggtgtgaac tagttcatca agtagcccaa 240
gtaggagaga atcataggca aaagtttctt taaagtggca gttgattaac atggaagggg 300

-continued

```
aaatatgata gatatataag gaccctcctc cctcacttat attctattaa atcctatcct    360

caactcttgc cctgctctcc gctccacccc ctgccaacta ctcagtccca cccaacttgt    420

aaaccaatac caaaatacta gaggagaagt tggcagggat actgttaata cccattttga    480

atggattgcc atctttcaga                                                500


<210> SEQ ID NO 65
<211> LENGTH: 1000
<212> TYPE: DNA
<213> ORGANISM: Homo sapiens

<400> SEQUENCE: 65

tcttccccat cctttccatc catttcaaat caattggaaa catggttcct tgggtctagc     60

tgttcatttt tgtaaattac ttattttgaa catctcattg tttatttgct cactcagcat    120

atggtgactt ttagtaactt cagattgaga aacttctgag ataaaaagga gacctatgta    180

gtatgaattc atggcatttc catttagtac ttctcacagc aggatacttg atttctcctt    240

tctcccatgt ccgatttaaa gtgaatttaa gatattgttc ttttaaatcc ccaatgattg    300

aacaaagtaa gaaaaaatac tttgttttgt ttgtgacaaa acaaaagaaa aatacaaggg    360

atccctaaaa ggttagtgtg ggcttattag gcagtaggta gatctgttca cagtaagtgt    420

gtgtgtgtgt gtgtgtgtgt gtgtgagaga gagagagaga gagagaggga gaatacacac    480

agagaagagt actccaaaac actattgatt ttttgctatt gattgtgtag gctgcggctg    540

ctgaaagaga aagcccgaga tgtttactgg ggaaaccaag agtagcgtct gtcccctgtg    600

ccttggtgag gtgggtaggt tttcaggagg aaggagggga cagggaggag taggtggagt    660

gatgcattga acttactagc tttgacatca tcattgtctt taaatgaaaa caaaaacaaa    720

aacaaaaaca aaaaacaaga agatatttac aggcagacag aaagggagcc aaggggagca    780

ggagagactg gagagaacag gtcccctgaa gtgtatgctc ttctttttgc tcttttcccg    840

atcttcccag gaacccacaa gactcccaga aggtgaagtt aagagctccc agactcataa    900

ggttattaga acagcaaact ggcaccccaa agaactttac ggagacttgc aacctatcaa    960

caagttggat gagggattaa aagccttcaa caaccaacaa                         1000


<210> SEQ ID NO 66
<211> LENGTH: 17
<212> TYPE: DNA
<213> ORGANISM: Homo sapiens

<400> SEQUENCE: 66

ccccaagcat caaactg                                                    17


<210> SEQ ID NO 67
<211> LENGTH: 17
<212> TYPE: DNA
<213> ORGANISM: Homo sapiens

<400> SEQUENCE: 67

cccaagcatc aaactga                                                    17


<210> SEQ ID NO 68
<211> LENGTH: 17
<212> TYPE: DNA
<213> ORGANISM: Homo sapiens

<400> SEQUENCE: 68

ccaagcatca aactgaa                                                    17
```

<210> SEQ ID NO 69
<211> LENGTH: 17
<212> TYPE: DNA
<213> ORGANISM: Homo sapiens

<400> SEQUENCE: 69
caagcatcaa actgaag 17

<210> SEQ ID NO 70
<211> LENGTH: 17
<212> TYPE: DNA
<213> ORGANISM: Homo sapiens

<400> SEQUENCE: 70
aagcatcaaa ctgaagg 17

<210> SEQ ID NO 71
<211> LENGTH: 17
<212> TYPE: DNA
<213> ORGANISM: Homo sapiens

<400> SEQUENCE: 71
agcatcaaac tgaagga 17

<210> SEQ ID NO 72
<211> LENGTH: 17
<212> TYPE: DNA
<213> ORGANISM: Homo sapiens

<400> SEQUENCE: 72
gcatcaaact gaaggaa 17

<210> SEQ ID NO 73
<211> LENGTH: 17
<212> TYPE: DNA
<213> ORGANISM: Homo sapiens

<400> SEQUENCE: 73
catcaaactg aaggaaa 17

<210> SEQ ID NO 74
<211> LENGTH: 17
<212> TYPE: DNA
<213> ORGANISM: Homo sapiens

<400> SEQUENCE: 74
atcaaactga aggaaac 17

<210> SEQ ID NO 75
<211> LENGTH: 17
<212> TYPE: DNA
<213> ORGANISM: Homo sapiens

<400> SEQUENCE: 75
tcaaactgaa ggaaaca 17

<210> SEQ ID NO 76
<211> LENGTH: 17
<212> TYPE: DNA
<213> ORGANISM: Homo sapiens

<400> SEQUENCE: 76

-continued caaactgaag gaaacat 17

<210> SEQ ID NO 77
<211> LENGTH: 17
<212> TYPE: DNA
<213> ORGANISM: Homo sapiens

<400> SEQUENCE: 77
aaactgaagg aaacatt 17

<210> SEQ ID NO 78
<211> LENGTH: 17
<212> TYPE: DNA
<213> ORGANISM: Homo sapiens

<400> SEQUENCE: 78
aactgaagga aacattc 17

<210> SEQ ID NO 79
<211> LENGTH: 17
<212> TYPE: DNA
<213> ORGANISM: Homo sapiens

<400> SEQUENCE: 79
actgaaggaa acattct 17

<210> SEQ ID NO 80
<211> LENGTH: 17
<212> TYPE: DNA
<213> ORGANISM: Homo sapiens

<400> SEQUENCE: 80
ctgaaggaaa cattcta 17

<210> SEQ ID NO 81
<211> LENGTH: 17
<212> TYPE: DNA
<213> ORGANISM: Homo sapiens

<400> SEQUENCE: 81
tgaaggaaac attctaa 17

<210> SEQ ID NO 82
<211> LENGTH: 17
<212> TYPE: DNA
<213> ORGANISM: Homo sapiens

<400> SEQUENCE: 82
gaaggaaaca ttctaac 17

<210> SEQ ID NO 83
<211> LENGTH: 17
<212> TYPE: DNA
<213> ORGANISM: Homo sapiens

<400> SEQUENCE: 83
aaggaaacat tctaacc 17

<210> SEQ ID NO 84
<211> LENGTH: 17
<212> TYPE: DNA
<213> ORGANISM: Homo sapiens

<400> SEQUENCE: 84

-continued aggaaacatt ctaacct 17

<210> SEQ ID NO 85
<211> LENGTH: 17
<212> TYPE: DNA
<213> ORGANISM: Homo sapiens

<400> SEQUENCE: 85
ggaaacattc taacctt 17

<210> SEQ ID NO 86
<211> LENGTH: 17
<212> TYPE: DNA
<213> ORGANISM: Homo sapiens

<400> SEQUENCE: 86
gaaacattct aaccttc 17

<210> SEQ ID NO 87
<211> LENGTH: 17
<212> TYPE: DNA
<213> ORGANISM: Homo sapiens

<400> SEQUENCE: 87
aaacattcta accttca 17

<210> SEQ ID NO 88
<211> LENGTH: 17
<212> TYPE: DNA
<213> ORGANISM: Homo sapiens

<400> SEQUENCE: 88
aacattctaa ccttcac 17

<210> SEQ ID NO 89
<211> LENGTH: 17
<212> TYPE: DNA
<213> ORGANISM: Homo sapiens

<400> SEQUENCE: 89
acattctaac cttcaca 17

<210> SEQ ID NO 90
<211> LENGTH: 17
<212> TYPE: DNA
<213> ORGANISM: Homo sapiens

<400> SEQUENCE: 90
cattctaacc ttcacag 17

<210> SEQ ID NO 91
<211> LENGTH: 17
<212> TYPE: DNA
<213> ORGANISM: Homo sapiens

<400> SEQUENCE: 91
attctaacct tcacaga 17

<210> SEQ ID NO 92
<211> LENGTH: 17
<212> TYPE: DNA
<213> ORGANISM: Homo sapiens -continued

<400> SEQUENCE: 92
ttctaacctt cacagac 17

<210> SEQ ID NO 93
<211> LENGTH: 17
<212> TYPE: DNA
<213> ORGANISM: Homo sapiens

<400> SEQUENCE: 93
tctaaccttc acagaca 17

<210> SEQ ID NO 94
<211> LENGTH: 17
<212> TYPE: DNA
<213> ORGANISM: Homo sapiens

<400> SEQUENCE: 94
ctaaccttca cagacag 17

<210> SEQ ID NO 95
<211> LENGTH: 17
<212> TYPE: DNA
<213> ORGANISM: Homo sapiens

<400> SEQUENCE: 95
taaccttcac agacaga 17

<210> SEQ ID NO 96
<211> LENGTH: 17
<212> TYPE: DNA
<213> ORGANISM: Homo sapiens

<400> SEQUENCE: 96
aaccttcaca gacagac 17

<210> SEQ ID NO 97
<211> LENGTH: 17
<212> TYPE: DNA
<213> ORGANISM: Homo sapiens

<400> SEQUENCE: 97
accttcacag acagact 17

<210> SEQ ID NO 98
<211> LENGTH: 17
<212> TYPE: DNA
<213> ORGANISM: Homo sapiens

<400> SEQUENCE: 98
ccttcacaga cagactg 17

<210> SEQ ID NO 99
<211> LENGTH: 17
<212> TYPE: DNA
<213> ORGANISM: Homo sapiens

<400> SEQUENCE: 99
cttcacagac agactgg 17

<210> SEQ ID NO 100
<211> LENGTH: 17
<212> TYPE: DNA
<213> ORGANISM: Homo sapiens -continued

<400> SEQUENCE: 100
ttcacagaca gactgga 17

<210> SEQ ID NO 101
<211> LENGTH: 17
<212> TYPE: DNA
<213> ORGANISM: Homo sapiens

<400> SEQUENCE: 101
tcacagacag actggag 17

<210> SEQ ID NO 102
<211> LENGTH: 17
<212> TYPE: DNA
<213> ORGANISM: Homo sapiens

<400> SEQUENCE: 102
cacagacaga ctggagg 17

<210> SEQ ID NO 103
<211> LENGTH: 17
<212> TYPE: DNA
<213> ORGANISM: Homo sapiens

<400> SEQUENCE: 103
acagacagac tggaggc 17

<210> SEQ ID NO 104
<211> LENGTH: 17
<212> TYPE: DNA
<213> ORGANISM: Homo sapiens

<400> SEQUENCE: 104
cagacagact ggaggct 17

<210> SEQ ID NO 105
<211> LENGTH: 17
<212> TYPE: DNA
<213> ORGANISM: Homo sapiens

<400> SEQUENCE: 105
agacagactg gaggctg 17

<210> SEQ ID NO 106
<211> LENGTH: 17
<212> TYPE: DNA
<213> ORGANISM: Homo sapiens

<400> SEQUENCE: 106
gacagactgg aggctgg 17

<210> SEQ ID NO 107
<211> LENGTH: 17
<212> TYPE: DNA
<213> ORGANISM: Homo sapiens

<400> SEQUENCE: 107
acagactgga ggctgga 17

<210> SEQ ID NO 108
<211> LENGTH: 17
<212> TYPE: DNA

-continued

<213> ORGANISM: Homo sapiens

<400> SEQUENCE: 108
cagactggag gctggat 17

<210> SEQ ID NO 109
<211> LENGTH: 17
<212> TYPE: DNA
<213> ORGANISM: Homo sapiens

<400> SEQUENCE: 109
agactggagg ctggatg 17

<210> SEQ ID NO 110
<211> LENGTH: 17
<212> TYPE: DNA
<213> ORGANISM: Homo sapiens

<400> SEQUENCE: 110
gactggaggc tggatgg 17

<210> SEQ ID NO 111
<211> LENGTH: 17
<212> TYPE: DNA
<213> ORGANISM: Homo sapiens

<400> SEQUENCE: 111
actggaggct ggatggg 17

<210> SEQ ID NO 112
<211> LENGTH: 17
<212> TYPE: DNA
<213> ORGANISM: Homo sapiens

<400> SEQUENCE: 112
ctggaggctg gatgggg 17

<210> SEQ ID NO 113
<211> LENGTH: 17
<212> TYPE: DNA
<213> ORGANISM: Homo sapiens

<400> SEQUENCE: 113
tggaggctgg atgggga 17

<210> SEQ ID NO 114
<211> LENGTH: 17
<212> TYPE: DNA
<213> ORGANISM: Homo sapiens

<400> SEQUENCE: 114
ggaggctgga tggggac 17

<210> SEQ ID NO 115
<211> LENGTH: 17
<212> TYPE: DNA
<213> ORGANISM: Homo sapiens

<400> SEQUENCE: 115
gaggctggat ggggacc 17

<210> SEQ ID NO 116
<211> LENGTH: 17

-continued

<212> TYPE: DNA
<213> ORGANISM: Homo sapiens

<400> SEQUENCE: 116
aggctggatg gggacct 17

<210> SEQ ID NO 117
<211> LENGTH: 17
<212> TYPE: DNA
<213> ORGANISM: Homo sapiens

<400> SEQUENCE: 117
ggctggatgg ggacctg 17

<210> SEQ ID NO 118
<211> LENGTH: 17
<212> TYPE: DNA
<213> ORGANISM: Homo sapiens

<400> SEQUENCE: 118
gctggatggg gacctgg 17

<210> SEQ ID NO 119
<211> LENGTH: 17
<212> TYPE: DNA
<213> ORGANISM: Homo sapiens

<400> SEQUENCE: 119
ctggatgggg acctggc 17

<210> SEQ ID NO 120
<211> LENGTH: 17
<212> TYPE: DNA
<213> ORGANISM: Homo sapiens

<400> SEQUENCE: 120
tggatgggga cctggct 17

<210> SEQ ID NO 121
<211> LENGTH: 17
<212> TYPE: DNA
<213> ORGANISM: Homo sapiens

<400> SEQUENCE: 121
ggatggggac ctggctg 17

<210> SEQ ID NO 122
<211> LENGTH: 17
<212> TYPE: DNA
<213> ORGANISM: Homo sapiens

<400> SEQUENCE: 122
gatggggacc tggctga 17

<210> SEQ ID NO 123
<211> LENGTH: 17
<212> TYPE: DNA
<213> ORGANISM: Homo sapiens

<400> SEQUENCE: 123
atggggacct ggctgaa 17

<210> SEQ ID NO 124

-continued

<211> LENGTH: 17
<212> TYPE: DNA
<213> ORGANISM: Homo sapiens

<400> SEQUENCE: 124
tggggacctg gctgaag 17

<210> SEQ ID NO 125
<211> LENGTH: 17
<212> TYPE: DNA
<213> ORGANISM: Homo sapiens

<400> SEQUENCE: 125
ggggacctgg ctgaaga 17

<210> SEQ ID NO 126
<211> LENGTH: 17
<212> TYPE: DNA
<213> ORGANISM: Homo sapiens

<400> SEQUENCE: 126
gggacctggc tgaagac 17

<210> SEQ ID NO 127
<211> LENGTH: 17
<212> TYPE: DNA
<213> ORGANISM: Homo sapiens

<400> SEQUENCE: 127
ggacctggct gaagaca 17

<210> SEQ ID NO 128
<211> LENGTH: 17
<212> TYPE: DNA
<213> ORGANISM: Homo sapiens

<400> SEQUENCE: 128
gacctggctg aagacat 17

<210> SEQ ID NO 129
<211> LENGTH: 17
<212> TYPE: DNA
<213> ORGANISM: Homo sapiens

<400> SEQUENCE: 129
acctggctga agacatc 17

<210> SEQ ID NO 130
<211> LENGTH: 17
<212> TYPE: DNA
<213> ORGANISM: Homo sapiens

<400> SEQUENCE: 130
cctggctgaa gacatct 17

<210> SEQ ID NO 131
<211> LENGTH: 17
<212> TYPE: DNA
<213> ORGANISM: Homo sapiens

<400> SEQUENCE: 131
ctggctgaag acatctg 17

-continued

<210> SEQ ID NO 132
<211> LENGTH: 17
<212> TYPE: DNA
<213> ORGANISM: Homo sapiens

<400> SEQUENCE: 132
tggctgaaga catctgg 17

<210> SEQ ID NO 133
<211> LENGTH: 17
<212> TYPE: DNA
<213> ORGANISM: Homo sapiens

<400> SEQUENCE: 133
ggctgaagac atctgga 17

<210> SEQ ID NO 134
<211> LENGTH: 17
<212> TYPE: DNA
<213> ORGANISM: Homo sapiens

<400> SEQUENCE: 134
gctgaagaca tctggag 17

<210> SEQ ID NO 135
<211> LENGTH: 17
<212> TYPE: DNA
<213> ORGANISM: Homo sapiens

<400> SEQUENCE: 135
ctgaagacat ctggaga 17

<210> SEQ ID NO 136
<211> LENGTH: 17
<212> TYPE: DNA
<213> ORGANISM: Homo sapiens

<400> SEQUENCE: 136
tgaagacatc tggagaa 17

<210> SEQ ID NO 137
<211> LENGTH: 17
<212> TYPE: DNA
<213> ORGANISM: Homo sapiens

<400> SEQUENCE: 137
gaagacatct ggagaat 17

<210> SEQ ID NO 138
<211> LENGTH: 17
<212> TYPE: DNA
<213> ORGANISM: Homo sapiens

<400> SEQUENCE: 138
aagacatctg gagaatg 17

<210> SEQ ID NO 139
<211> LENGTH: 17
<212> TYPE: DNA
<213> ORGANISM: Homo sapiens

<400> SEQUENCE: 139
agacatctgg agaatga 17

-continued

<210> SEQ ID NO 140
<211> LENGTH: 17
<212> TYPE: DNA
<213> ORGANISM: Homo sapiens

<400> SEQUENCE: 140
gacatctgga gaatgaa 17

<210> SEQ ID NO 141
<211> LENGTH: 17
<212> TYPE: DNA
<213> ORGANISM: Homo sapiens

<400> SEQUENCE: 141
acatctggag aatgaaa 17

<210> SEQ ID NO 142
<211> LENGTH: 17
<212> TYPE: DNA
<213> ORGANISM: Homo sapiens

<400> SEQUENCE: 142
catctggaga atgaaag 17

<210> SEQ ID NO 143
<211> LENGTH: 17
<212> TYPE: DNA
<213> ORGANISM: Homo sapiens

<400> SEQUENCE: 143
atctggagaa tgaaagt 17

<210> SEQ ID NO 144
<211> LENGTH: 17
<212> TYPE: DNA
<213> ORGANISM: Homo sapiens

<400> SEQUENCE: 144
tctggagaat gaaagtt 17

<210> SEQ ID NO 145
<211> LENGTH: 17
<212> TYPE: DNA
<213> ORGANISM: Homo sapiens

<400> SEQUENCE: 145
ctggagaatg aaagtta 17

<210> SEQ ID NO 146
<211> LENGTH: 17
<212> TYPE: DNA
<213> ORGANISM: Homo sapiens

<400> SEQUENCE: 146
tggagaatga aagttaa 17

<210> SEQ ID NO 147
<211> LENGTH: 17
<212> TYPE: DNA
<213> ORGANISM: Homo sapiens

<400> SEQUENCE: 147
ggagaatgaa agttaag 17

-continued

<210> SEQ ID NO 148
<211> LENGTH: 17
<212> TYPE: DNA
<213> ORGANISM: Homo sapiens

<400> SEQUENCE: 148
gagaatgaaa gttaagt 17

<210> SEQ ID NO 149
<211> LENGTH: 17
<212> TYPE: DNA
<213> ORGANISM: Homo sapiens

<400> SEQUENCE: 149
agaatgaaag ttaagta 17

<210> SEQ ID NO 150
<211> LENGTH: 17
<212> TYPE: DNA
<213> ORGANISM: Homo sapiens

<400> SEQUENCE: 150
gaatgaaagt taagtac 17

<210> SEQ ID NO 151
<211> LENGTH: 17
<212> TYPE: DNA
<213> ORGANISM: Homo sapiens

<400> SEQUENCE: 151
aatgaaagtt aagtacc 17

<210> SEQ ID NO 152
<211> LENGTH: 17
<212> TYPE: DNA
<213> ORGANISM: Homo sapiens

<400> SEQUENCE: 152
atgaaagtta agtacca 17

<210> SEQ ID NO 153
<211> LENGTH: 17
<212> TYPE: DNA
<213> ORGANISM: Homo sapiens

<400> SEQUENCE: 153
tgaaagttaa gtaccag 17

<210> SEQ ID NO 154
<211> LENGTH: 17
<212> TYPE: DNA
<213> ORGANISM: Homo sapiens

<400> SEQUENCE: 154
gaaagttaag taccagc 17

<210> SEQ ID NO 155
<211> LENGTH: 17
<212> TYPE: DNA
<213> ORGANISM: Homo sapiens

<400> SEQUENCE: 155

-continued aaagttaagt accagct 17

<210> SEQ ID NO 156
<211> LENGTH: 17
<212> TYPE: DNA
<213> ORGANISM: Homo sapiens

<400> SEQUENCE: 156
aagttaagta ccagctt 17

<210> SEQ ID NO 157
<211> LENGTH: 17
<212> TYPE: DNA
<213> ORGANISM: Homo sapiens

<400> SEQUENCE: 157
agttaagtac cagcttg 17

<210> SEQ ID NO 158
<211> LENGTH: 17
<212> TYPE: DNA
<213> ORGANISM: Homo sapiens

<400> SEQUENCE: 158
gttaagtacc agcttgc 17

<210> SEQ ID NO 159
<211> LENGTH: 17
<212> TYPE: DNA
<213> ORGANISM: Homo sapiens

<400> SEQUENCE: 159
ttaagtacca gcttgca 17

<210> SEQ ID NO 160
<211> LENGTH: 17
<212> TYPE: DNA
<213> ORGANISM: Homo sapiens

<400> SEQUENCE: 160
taagtaccag cttgcat 17

<210> SEQ ID NO 161
<211> LENGTH: 17
<212> TYPE: DNA
<213> ORGANISM: Homo sapiens

<400> SEQUENCE: 161
aagtaccagc ttgcatt 17

<210> SEQ ID NO 162
<211> LENGTH: 17
<212> TYPE: DNA
<213> ORGANISM: Homo sapiens

<400> SEQUENCE: 162
agtaccagct tgcattt 17

<210> SEQ ID NO 163
<211> LENGTH: 17
<212> TYPE: DNA
<213> ORGANISM: Homo sapiens

<400> SEQUENCE: 163

-continued gtaccagctt gcatttt 17

<210> SEQ ID NO 164
<211> LENGTH: 17
<212> TYPE: DNA
<213> ORGANISM: Homo sapiens

<400> SEQUENCE: 164
taccagcttg cattttt 17

<210> SEQ ID NO 165
<211> LENGTH: 17
<212> TYPE: DNA
<213> ORGANISM: Homo sapiens

<400> SEQUENCE: 165
accagcttgc atttttg 17

<210> SEQ ID NO 166
<211> LENGTH: 17
<212> TYPE: DNA
<213> ORGANISM: Homo sapiens

<400> SEQUENCE: 166
ccagcttgca tttttgt 17

<210> SEQ ID NO 167
<211> LENGTH: 17
<212> TYPE: DNA
<213> ORGANISM: Homo sapiens

<400> SEQUENCE: 167
cagcttgcat ttttgtg 17

<210> SEQ ID NO 168
<211> LENGTH: 17
<212> TYPE: DNA
<213> ORGANISM: Homo sapiens

<400> SEQUENCE: 168
agcttgcatt tttgtgc 17

<210> SEQ ID NO 169
<211> LENGTH: 17
<212> TYPE: DNA
<213> ORGANISM: Homo sapiens

<400> SEQUENCE: 169
gcttgcattt ttgtgcc 17

<210> SEQ ID NO 170
<211> LENGTH: 17
<212> TYPE: DNA
<213> ORGANISM: Homo sapiens

<400> SEQUENCE: 170
cttgcatttt tgtgccc 17

<210> SEQ ID NO 171
<211> LENGTH: 17
<212> TYPE: DNA
<213> ORGANISM: Homo sapiens -continued

<400> SEQUENCE: 171
ttgcattttt gtgcccc 17

<210> SEQ ID NO 172
<211> LENGTH: 17
<212> TYPE: DNA
<213> ORGANISM: Homo sapiens

<400> SEQUENCE: 172
tgcatttttg tgcccct 17

<210> SEQ ID NO 173
<211> LENGTH: 17
<212> TYPE: DNA
<213> ORGANISM: Homo sapiens

<400> SEQUENCE: 173
gcatttttgt gccccta 17

<210> SEQ ID NO 174
<211> LENGTH: 17
<212> TYPE: DNA
<213> ORGANISM: Homo sapiens

<400> SEQUENCE: 174
catttttgtg cccctag 17

<210> SEQ ID NO 175
<211> LENGTH: 17
<212> TYPE: DNA
<213> ORGANISM: Homo sapiens

<400> SEQUENCE: 175
atttttgtgc ccctaga 17

<210> SEQ ID NO 176
<211> LENGTH: 17
<212> TYPE: DNA
<213> ORGANISM: Homo sapiens

<400> SEQUENCE: 176
tttttgtgcc cctagat 17

<210> SEQ ID NO 177
<211> LENGTH: 17
<212> TYPE: DNA
<213> ORGANISM: Homo sapiens

<400> SEQUENCE: 177
ttttgtgccc ctagatt 17

<210> SEQ ID NO 178
<211> LENGTH: 17
<212> TYPE: DNA
<213> ORGANISM: Homo sapiens

<400> SEQUENCE: 178
tttgtgcccc tagatta 17

<210> SEQ ID NO 179
<211> LENGTH: 17
<212> TYPE: DNA
<213> ORGANISM: Homo sapiens -continued

<400> SEQUENCE: 179
ttgtgcccct agattat 17

<210> SEQ ID NO 180
<211> LENGTH: 17
<212> TYPE: DNA
<213> ORGANISM: Homo sapiens

<400> SEQUENCE: 180
tgtgccccta gattatt 17

<210> SEQ ID NO 181
<211> LENGTH: 17
<212> TYPE: DNA
<213> ORGANISM: Homo sapiens

<400> SEQUENCE: 181
gtgcccctag attattt 17

<210> SEQ ID NO 182
<211> LENGTH: 17
<212> TYPE: DNA
<213> ORGANISM: Homo sapiens

<400> SEQUENCE: 182
tgcccctaga ttatttt 17

<210> SEQ ID NO 183
<211> LENGTH: 17
<212> TYPE: DNA
<213> ORGANISM: Homo sapiens

<400> SEQUENCE: 183
gcccctagat tattttt 17

<210> SEQ ID NO 184
<211> LENGTH: 17
<212> TYPE: DNA
<213> ORGANISM: Homo sapiens

<400> SEQUENCE: 184
cccctagatt atttttg 17

<210> SEQ ID NO 185
<211> LENGTH: 17
<212> TYPE: DNA
<213> ORGANISM: Homo sapiens

<400> SEQUENCE: 185
ccctagatta tttttgc 17

<210> SEQ ID NO 186
<211> LENGTH: 17
<212> TYPE: DNA
<213> ORGANISM: Homo sapiens

<400> SEQUENCE: 186
cctagattat ttttgca 17

<210> SEQ ID NO 187
<211> LENGTH: 17
<212> TYPE: DNA

-continued

<213> ORGANISM: Homo sapiens

<400> SEQUENCE: 187
ctagattatt tttgcat 17

<210> SEQ ID NO 188
<211> LENGTH: 17
<212> TYPE: DNA
<213> ORGANISM: Homo sapiens

<400> SEQUENCE: 188
tagattattt ttgcatt 17

<210> SEQ ID NO 189
<211> LENGTH: 17
<212> TYPE: DNA
<213> ORGANISM: Homo sapiens

<400> SEQUENCE: 189
agattatttt tgcattt 17

<210> SEQ ID NO 190
<211> LENGTH: 17
<212> TYPE: DNA
<213> ORGANISM: Homo sapiens

<400> SEQUENCE: 190
gattattttt gcatttt 17

<210> SEQ ID NO 191
<211> LENGTH: 17
<212> TYPE: DNA
<213> ORGANISM: Homo sapiens

<400> SEQUENCE: 191
attatttttg catttta 17

<210> SEQ ID NO 192
<211> LENGTH: 17
<212> TYPE: DNA
<213> ORGANISM: Homo sapiens

<400> SEQUENCE: 192
ttatttttgc attttaa 17

<210> SEQ ID NO 193
<211> LENGTH: 17
<212> TYPE: DNA
<213> ORGANISM: Homo sapiens

<400> SEQUENCE: 193
tatttttgca ttttaaa 17

<210> SEQ ID NO 194
<211> LENGTH: 17
<212> TYPE: DNA
<213> ORGANISM: Homo sapiens

<400> SEQUENCE: 194
atttttgcat tttaaaa 17

<210> SEQ ID NO 195
<211> LENGTH: 17

-continued

<212> TYPE: DNA
<213> ORGANISM: Homo sapiens

<400> SEQUENCE: 195
tttttgcatt ttaaaat 17

<210> SEQ ID NO 196
<211> LENGTH: 17
<212> TYPE: DNA
<213> ORGANISM: Homo sapiens

<400> SEQUENCE: 196
ttttgcattt taaaata 17

<210> SEQ ID NO 197
<211> LENGTH: 17
<212> TYPE: DNA
<213> ORGANISM: Homo sapiens

<400> SEQUENCE: 197
tttgcatttt aaaataa 17

<210> SEQ ID NO 198
<211> LENGTH: 17
<212> TYPE: DNA
<213> ORGANISM: Homo sapiens

<400> SEQUENCE: 198
ttgcatttta aaataag 17

<210> SEQ ID NO 199
<211> LENGTH: 17
<212> TYPE: DNA
<213> ORGANISM: Homo sapiens

<400> SEQUENCE: 199
tgcattttaa aataaga 17

<210> SEQ ID NO 200
<211> LENGTH: 17
<212> TYPE: DNA
<213> ORGANISM: Homo sapiens

<400> SEQUENCE: 200
gcattttaaa ataagaa 17

<210> SEQ ID NO 201
<211> LENGTH: 17
<212> TYPE: DNA
<213> ORGANISM: Homo sapiens

<400> SEQUENCE: 201
cattttaaaa taagaag 17

<210> SEQ ID NO 202
<211> LENGTH: 17
<212> TYPE: DNA
<213> ORGANISM: Homo sapiens

<400> SEQUENCE: 202
attttaaaat aagaagc 17

<210> SEQ ID NO 203

-continued

<211> LENGTH: 17
<212> TYPE: DNA
<213> ORGANISM: Homo sapiens

<400> SEQUENCE: 203
ttttaaaata agaagca 17

<210> SEQ ID NO 204
<211> LENGTH: 17
<212> TYPE: DNA
<213> ORGANISM: Homo sapiens

<400> SEQUENCE: 204
tttaaaataa gaagcat 17

<210> SEQ ID NO 205
<211> LENGTH: 17
<212> TYPE: DNA
<213> ORGANISM: Homo sapiens

<400> SEQUENCE: 205
ttaaaataag aagcatc 17

<210> SEQ ID NO 206
<211> LENGTH: 17
<212> TYPE: DNA
<213> ORGANISM: Homo sapiens

<400> SEQUENCE: 206
taaaataaga agcatca 17

<210> SEQ ID NO 207
<211> LENGTH: 17
<212> TYPE: DNA
<213> ORGANISM: Homo sapiens

<400> SEQUENCE: 207
aaaataagaa gcatcaa 17

<210> SEQ ID NO 208
<211> LENGTH: 17
<212> TYPE: DNA
<213> ORGANISM: Homo sapiens

<400> SEQUENCE: 208
aaataagaag catcaaa 17

<210> SEQ ID NO 209
<211> LENGTH: 17
<212> TYPE: DNA
<213> ORGANISM: Homo sapiens

<400> SEQUENCE: 209
aataagaagc atcaaat 17

<210> SEQ ID NO 210
<211> LENGTH: 17
<212> TYPE: DNA
<213> ORGANISM: Homo sapiens

<400> SEQUENCE: 210
ataagaagca tcaaatt 17

-continued

<210> SEQ ID NO 211
<211> LENGTH: 17
<212> TYPE: DNA
<213> ORGANISM: Homo sapiens

<400> SEQUENCE: 211
taagaagcat caaattg 17

<210> SEQ ID NO 212
<211> LENGTH: 17
<212> TYPE: DNA
<213> ORGANISM: Homo sapiens

<400> SEQUENCE: 212
aagaagcatc aaattgc 17

<210> SEQ ID NO 213
<211> LENGTH: 17
<212> TYPE: DNA
<213> ORGANISM: Homo sapiens

<400> SEQUENCE: 213
agaagcatca aattgcg 17

<210> SEQ ID NO 214
<211> LENGTH: 17
<212> TYPE: DNA
<213> ORGANISM: Homo sapiens

<400> SEQUENCE: 214
gaagcatcaa attgcgt 17

<210> SEQ ID NO 215
<211> LENGTH: 17
<212> TYPE: DNA
<213> ORGANISM: Homo sapiens

<400> SEQUENCE: 215
aagcatcaaa ttgcgtg 17

<210> SEQ ID NO 216
<211> LENGTH: 17
<212> TYPE: DNA
<213> ORGANISM: Homo sapiens

<400> SEQUENCE: 216
agcatcaaat tgcgtgt 17

<210> SEQ ID NO 217
<211> LENGTH: 17
<212> TYPE: DNA
<213> ORGANISM: Homo sapiens

<400> SEQUENCE: 217
gcatcaaatt gcgtgtc 17

<210> SEQ ID NO 218
<211> LENGTH: 17
<212> TYPE: DNA
<213> ORGANISM: Homo sapiens

<400> SEQUENCE: 218
catcaaattg cgtgtct 17

-continued

<210> SEQ ID NO 219
<211> LENGTH: 17
<212> TYPE: DNA
<213> ORGANISM: Homo sapiens

<400> SEQUENCE: 219
atcaaattgc gtgtctc 17

<210> SEQ ID NO 220
<211> LENGTH: 17
<212> TYPE: DNA
<213> ORGANISM: Homo sapiens

<400> SEQUENCE: 220
tcaaattgcg tgtctct 17

<210> SEQ ID NO 221
<211> LENGTH: 17
<212> TYPE: DNA
<213> ORGANISM: Homo sapiens

<400> SEQUENCE: 221
caaattgcgt gtctctg 17

<210> SEQ ID NO 222
<211> LENGTH: 17
<212> TYPE: DNA
<213> ORGANISM: Homo sapiens

<400> SEQUENCE: 222
aaattgcgtg tctctgt 17

<210> SEQ ID NO 223
<211> LENGTH: 17
<212> TYPE: DNA
<213> ORGANISM: Homo sapiens

<400> SEQUENCE: 223
aattgcgtgt ctctgtg 17

<210> SEQ ID NO 224
<211> LENGTH: 17
<212> TYPE: DNA
<213> ORGANISM: Homo sapiens

<400> SEQUENCE: 224
attgcgtgtc tctgtgt 17

<210> SEQ ID NO 225
<211> LENGTH: 17
<212> TYPE: DNA
<213> ORGANISM: Homo sapiens

<400> SEQUENCE: 225
ttgcgtgtct ctgtgta 17

<210> SEQ ID NO 226
<211> LENGTH: 17
<212> TYPE: DNA
<213> ORGANISM: Homo sapiens

<400> SEQUENCE: 226
tgcgtgtctc tgtgtaa 17

-continued

<210> SEQ ID NO 227
<211> LENGTH: 17
<212> TYPE: DNA
<213> ORGANISM: Homo sapiens

<400> SEQUENCE: 227
gcgtgtctct gtgtaaa 17

<210> SEQ ID NO 228
<211> LENGTH: 17
<212> TYPE: DNA
<213> ORGANISM: Homo sapiens

<400> SEQUENCE: 228
cgtgtctctg tgtaaaa 17

<210> SEQ ID NO 229
<211> LENGTH: 17
<212> TYPE: DNA
<213> ORGANISM: Homo sapiens

<400> SEQUENCE: 229
gtgtctctgt gtaaaag 17

<210> SEQ ID NO 230
<211> LENGTH: 17
<212> TYPE: DNA
<213> ORGANISM: Homo sapiens

<400> SEQUENCE: 230
tgtctctgtg taaaagt 17

<210> SEQ ID NO 231
<211> LENGTH: 17
<212> TYPE: DNA
<213> ORGANISM: Homo sapiens

<400> SEQUENCE: 231
gtctctgtgt aaaagtt 17

<210> SEQ ID NO 232
<211> LENGTH: 17
<212> TYPE: DNA
<213> ORGANISM: Homo sapiens

<400> SEQUENCE: 232
tctctgtgta aaagttc 17

<210> SEQ ID NO 233
<211> LENGTH: 17
<212> TYPE: DNA
<213> ORGANISM: Homo sapiens

<400> SEQUENCE: 233
ctctgtgtaa aagttct 17

<210> SEQ ID NO 234
<211> LENGTH: 17
<212> TYPE: DNA
<213> ORGANISM: Homo sapiens

<400> SEQUENCE: 234

-continued tctgtgtaaa agttcta 17

<210> SEQ ID NO 235
<211> LENGTH: 17
<212> TYPE: DNA
<213> ORGANISM: Homo sapiens

<400> SEQUENCE: 235
ctgtgtaaaa gttctag 17

<210> SEQ ID NO 236
<211> LENGTH: 17
<212> TYPE: DNA
<213> ORGANISM: Homo sapiens

<400> SEQUENCE: 236
tgtgtaaaag ttctagc 17

<210> SEQ ID NO 237
<211> LENGTH: 17
<212> TYPE: DNA
<213> ORGANISM: Homo sapiens

<400> SEQUENCE: 237
gtgtaaaagt tctagca 17

<210> SEQ ID NO 238
<211> LENGTH: 17
<212> TYPE: DNA
<213> ORGANISM: Homo sapiens

<400> SEQUENCE: 238
tgtaaaagtt ctagcaa 17

<210> SEQ ID NO 239
<211> LENGTH: 17
<212> TYPE: DNA
<213> ORGANISM: Homo sapiens

<400> SEQUENCE: 239
gtaaaagttc tagcaat 17

<210> SEQ ID NO 240
<211> LENGTH: 17
<212> TYPE: DNA
<213> ORGANISM: Homo sapiens

<400> SEQUENCE: 240
taaaagttct agcaatt 17

<210> SEQ ID NO 241
<211> LENGTH: 17
<212> TYPE: DNA
<213> ORGANISM: Homo sapiens

<400> SEQUENCE: 241
aaaagttcta gcaattt 17

<210> SEQ ID NO 242
<211> LENGTH: 17
<212> TYPE: DNA
<213> ORGANISM: Homo sapiens

<400> SEQUENCE: 242

-continued aaagttctag caatttg 17

<210> SEQ ID NO 243
<211> LENGTH: 17
<212> TYPE: DNA
<213> ORGANISM: Homo sapiens

<400> SEQUENCE: 243
aagttctagc aatttgt 17

<210> SEQ ID NO 244
<211> LENGTH: 17
<212> TYPE: DNA
<213> ORGANISM: Homo sapiens

<400> SEQUENCE: 244
agttctagca atttgtt 17

<210> SEQ ID NO 245
<211> LENGTH: 17
<212> TYPE: DNA
<213> ORGANISM: Homo sapiens

<400> SEQUENCE: 245
gttctagcaa tttgttt 17

<210> SEQ ID NO 246
<211> LENGTH: 17
<212> TYPE: DNA
<213> ORGANISM: Homo sapiens

<400> SEQUENCE: 246
ttctagcaat ttgtttt 17

<210> SEQ ID NO 247
<211> LENGTH: 17
<212> TYPE: DNA
<213> ORGANISM: Homo sapiens

<400> SEQUENCE: 247
tctagcaatt tgtttta 17

<210> SEQ ID NO 248
<211> LENGTH: 17
<212> TYPE: DNA
<213> ORGANISM: Homo sapiens

<400> SEQUENCE: 248
ctagcaattt gttttaa 17

<210> SEQ ID NO 249
<211> LENGTH: 17
<212> TYPE: DNA
<213> ORGANISM: Homo sapiens

<400> SEQUENCE: 249
tagcaatttg ttttaag 17

<210> SEQ ID NO 250
<211> LENGTH: 17
<212> TYPE: DNA
<213> ORGANISM: Homo sapiens -continued

<400> SEQUENCE: 250
agcaatttgt tttaagg 17

<210> SEQ ID NO 251
<211> LENGTH: 17
<212> TYPE: DNA
<213> ORGANISM: Homo sapiens

<400> SEQUENCE: 251
gcaatttgtt ttaaggt 17

<210> SEQ ID NO 252
<211> LENGTH: 17
<212> TYPE: DNA
<213> ORGANISM: Homo sapiens

<400> SEQUENCE: 252
caatttgttt taaggtg 17

<210> SEQ ID NO 253
<211> LENGTH: 17
<212> TYPE: DNA
<213> ORGANISM: Homo sapiens

<400> SEQUENCE: 253
aatttgtttt aaggtga 17

<210> SEQ ID NO 254
<211> LENGTH: 17
<212> TYPE: DNA
<213> ORGANISM: Homo sapiens

<400> SEQUENCE: 254
atttgtttta aggtgaa 17

<210> SEQ ID NO 255
<211> LENGTH: 17
<212> TYPE: DNA
<213> ORGANISM: Homo sapiens

<400> SEQUENCE: 255
tttgttttaa ggtgaac 17

<210> SEQ ID NO 256
<211> LENGTH: 17
<212> TYPE: DNA
<213> ORGANISM: Homo sapiens

<400> SEQUENCE: 256
ttgttttaag gtgaact 17

<210> SEQ ID NO 257
<211> LENGTH: 17
<212> TYPE: DNA
<213> ORGANISM: Homo sapiens

<400> SEQUENCE: 257
tgttttaagg tgaactt 17

<210> SEQ ID NO 258
<211> LENGTH: 17
<212> TYPE: DNA
<213> ORGANISM: Homo sapiens -continued

<400> SEQUENCE: 258
gttttaaggt gaactta 17

<210> SEQ ID NO 259
<211> LENGTH: 17
<212> TYPE: DNA
<213> ORGANISM: Homo sapiens

<400> SEQUENCE: 259
ttttaaggtg aacttat 17

<210> SEQ ID NO 260
<211> LENGTH: 17
<212> TYPE: DNA
<213> ORGANISM: Homo sapiens

<400> SEQUENCE: 260
tttaaggtga acttatt 17

<210> SEQ ID NO 261
<211> LENGTH: 17
<212> TYPE: DNA
<213> ORGANISM: Homo sapiens

<400> SEQUENCE: 261
ttaaggtgaa cttattt 17

<210> SEQ ID NO 262
<211> LENGTH: 17
<212> TYPE: DNA
<213> ORGANISM: Homo sapiens

<400> SEQUENCE: 262
taaggtgaac ttatttt 17

<210> SEQ ID NO 263
<211> LENGTH: 17
<212> TYPE: DNA
<213> ORGANISM: Homo sapiens

<400> SEQUENCE: 263
aaggtgaact tattttg 17

<210> SEQ ID NO 264
<211> LENGTH: 17
<212> TYPE: DNA
<213> ORGANISM: Homo sapiens

<400> SEQUENCE: 264
aggtgaactt attttgg 17

<210> SEQ ID NO 265
<211> LENGTH: 17
<212> TYPE: DNA
<213> ORGANISM: Homo sapiens

<400> SEQUENCE: 265
ggtgaactta ttttggc 17

<210> SEQ ID NO 266
<211> LENGTH: 17
<212> TYPE: DNA

-continued

<213> ORGANISM: Homo sapiens

<400> SEQUENCE: 266
gtgaacttat tttggct 17

<210> SEQ ID NO 267
<211> LENGTH: 17
<212> TYPE: DNA
<213> ORGANISM: Homo sapiens

<400> SEQUENCE: 267
tgaacttatt ttggctt 17

<210> SEQ ID NO 268
<211> LENGTH: 17
<212> TYPE: DNA
<213> ORGANISM: Homo sapiens

<400> SEQUENCE: 268
gaacttattt tggctta 17

<210> SEQ ID NO 269
<211> LENGTH: 17
<212> TYPE: DNA
<213> ORGANISM: Homo sapiens

<400> SEQUENCE: 269
aacttatttt ggcttag 17

<210> SEQ ID NO 270
<211> LENGTH: 17
<212> TYPE: DNA
<213> ORGANISM: Homo sapiens

<400> SEQUENCE: 270
acttattttg gcttagg 17

<210> SEQ ID NO 271
<211> LENGTH: 17
<212> TYPE: DNA
<213> ORGANISM: Homo sapiens

<400> SEQUENCE: 271
cttattttgg cttaggg 17

<210> SEQ ID NO 272
<211> LENGTH: 17
<212> TYPE: DNA
<213> ORGANISM: Homo sapiens

<400> SEQUENCE: 272
ttattttggc ttaggga 17

<210> SEQ ID NO 273
<211> LENGTH: 17
<212> TYPE: DNA
<213> ORGANISM: Homo sapiens

<400> SEQUENCE: 273
tattttggct tagggac 17

<210> SEQ ID NO 274
<211> LENGTH: 17

-continued

<212> TYPE: DNA
<213> ORGANISM: Homo sapiens

<400> SEQUENCE: 274
attttggctt agggact 17

<210> SEQ ID NO 275
<211> LENGTH: 17
<212> TYPE: DNA
<213> ORGANISM: Homo sapiens

<400> SEQUENCE: 275
ttttggctta gggacta 17

<210> SEQ ID NO 276
<211> LENGTH: 17
<212> TYPE: DNA
<213> ORGANISM: Homo sapiens

<400> SEQUENCE: 276
tttggcttag ggactac 17

<210> SEQ ID NO 277
<211> LENGTH: 17
<212> TYPE: DNA
<213> ORGANISM: Homo sapiens

<400> SEQUENCE: 277
ttggcttagg gactaca 17

<210> SEQ ID NO 278
<211> LENGTH: 17
<212> TYPE: DNA
<213> ORGANISM: Homo sapiens

<400> SEQUENCE: 278
tggcttaggg actacaa 17

<210> SEQ ID NO 279
<211> LENGTH: 17
<212> TYPE: DNA
<213> ORGANISM: Homo sapiens

<400> SEQUENCE: 279
ggcttaggga ctacaaa 17

<210> SEQ ID NO 280
<211> LENGTH: 17
<212> TYPE: DNA
<213> ORGANISM: Homo sapiens

<400> SEQUENCE: 280
gcttagggac tacaaaa 17

<210> SEQ ID NO 281
<211> LENGTH: 17
<212> TYPE: DNA
<213> ORGANISM: Homo sapiens

<400> SEQUENCE: 281
cttagggact acaaaaa 17

<210> SEQ ID NO 282

-continued

<211> LENGTH: 17
<212> TYPE: DNA
<213> ORGANISM: Homo sapiens

<400> SEQUENCE: 282
ttagggacta caaaaag 17

<210> SEQ ID NO 283
<211> LENGTH: 17
<212> TYPE: DNA
<213> ORGANISM: Homo sapiens

<400> SEQUENCE: 283
tagggactac aaaaaga 17

<210> SEQ ID NO 284
<211> LENGTH: 17
<212> TYPE: DNA
<213> ORGANISM: Homo sapiens

<400> SEQUENCE: 284
agggactaca aaaagag 17

<210> SEQ ID NO 285
<211> LENGTH: 17
<212> TYPE: DNA
<213> ORGANISM: Homo sapiens

<400> SEQUENCE: 285
gggactacaa aaagaga 17

<210> SEQ ID NO 286
<211> LENGTH: 17
<212> TYPE: DNA
<213> ORGANISM: Homo sapiens

<400> SEQUENCE: 286
ggactacaaa aagagaa 17

<210> SEQ ID NO 287
<211> LENGTH: 17
<212> TYPE: DNA
<213> ORGANISM: Homo sapiens

<400> SEQUENCE: 287
gactacaaaa agagaag 17

<210> SEQ ID NO 288
<211> LENGTH: 17
<212> TYPE: DNA
<213> ORGANISM: Homo sapiens

<400> SEQUENCE: 288
actacaaaaa gagaagg 17

<210> SEQ ID NO 289
<211> LENGTH: 17
<212> TYPE: DNA
<213> ORGANISM: Homo sapiens

<400> SEQUENCE: 289
ctacaaaaag agaaggt 17

-continued

<210> SEQ ID NO 290
<211> LENGTH: 17
<212> TYPE: DNA
<213> ORGANISM: Homo sapiens

<400> SEQUENCE: 290
tacaaaaaga gaaggta 17

<210> SEQ ID NO 291
<211> LENGTH: 17
<212> TYPE: DNA
<213> ORGANISM: Homo sapiens

<400> SEQUENCE: 291
acaaaaagag aaggtaa 17

<210> SEQ ID NO 292
<211> LENGTH: 17
<212> TYPE: DNA
<213> ORGANISM: Homo sapiens

<400> SEQUENCE: 292
caaaaagaga aggtaat 17

<210> SEQ ID NO 293
<211> LENGTH: 17
<212> TYPE: DNA
<213> ORGANISM: Homo sapiens

<400> SEQUENCE: 293
aaaaagagaa ggtaatt 17

<210> SEQ ID NO 294
<211> LENGTH: 17
<212> TYPE: DNA
<213> ORGANISM: Homo sapiens

<400> SEQUENCE: 294
aaaagagaag gtaattc 17

<210> SEQ ID NO 295
<211> LENGTH: 17
<212> TYPE: DNA
<213> ORGANISM: Homo sapiens

<400> SEQUENCE: 295
aaagagaagg taattcc 17

<210> SEQ ID NO 296
<211> LENGTH: 17
<212> TYPE: DNA
<213> ORGANISM: Homo sapiens

<400> SEQUENCE: 296
aagagaaggt aattcct 17

<210> SEQ ID NO 297
<211> LENGTH: 17
<212> TYPE: DNA
<213> ORGANISM: Homo sapiens

<400> SEQUENCE: 297
agagaaggta attccta 17

-continued

<210> SEQ ID NO 298
<211> LENGTH: 17
<212> TYPE: DNA
<213> ORGANISM: Homo sapiens

<400> SEQUENCE: 298
gagaaggtaa ttcctag 17

<210> SEQ ID NO 299
<211> LENGTH: 17
<212> TYPE: DNA
<213> ORGANISM: Homo sapiens

<400> SEQUENCE: 299
agaaggtaat tcctagg 17

<210> SEQ ID NO 300
<211> LENGTH: 17
<212> TYPE: DNA
<213> ORGANISM: Homo sapiens

<400> SEQUENCE: 300
gaaggtaatt cctaggg 17

<210> SEQ ID NO 301
<211> LENGTH: 17
<212> TYPE: DNA
<213> ORGANISM: Homo sapiens

<400> SEQUENCE: 301
aaggtaattc ctaggga 17

<210> SEQ ID NO 302
<211> LENGTH: 17
<212> TYPE: DNA
<213> ORGANISM: Homo sapiens

<400> SEQUENCE: 302
aggtaattcc tagggaa 17

<210> SEQ ID NO 303
<211> LENGTH: 17
<212> TYPE: DNA
<213> ORGANISM: Homo sapiens

<400> SEQUENCE: 303
ggtaattcct agggaag 17

<210> SEQ ID NO 304
<211> LENGTH: 17
<212> TYPE: DNA
<213> ORGANISM: Homo sapiens

<400> SEQUENCE: 304
gtaattccta gggaagg 17

<210> SEQ ID NO 305
<211> LENGTH: 17
<212> TYPE: DNA
<213> ORGANISM: Homo sapiens

<400> SEQUENCE: 305
taattcctag ggaagga 17

-continued

<210> SEQ ID NO 306
<211> LENGTH: 17
<212> TYPE: DNA
<213> ORGANISM: Homo sapiens

<400> SEQUENCE: 306
aattcctagg gaaggaa 17

<210> SEQ ID NO 307
<211> LENGTH: 17
<212> TYPE: DNA
<213> ORGANISM: Homo sapiens

<400> SEQUENCE: 307
attcctaggg aaggaag 17

<210> SEQ ID NO 308
<211> LENGTH: 17
<212> TYPE: DNA
<213> ORGANISM: Homo sapiens

<400> SEQUENCE: 308
ttcctaggga aggaaga 17

<210> SEQ ID NO 309
<211> LENGTH: 17
<212> TYPE: DNA
<213> ORGANISM: Homo sapiens

<400> SEQUENCE: 309
tcctagggaa ggaagaa 17

<210> SEQ ID NO 310
<211> LENGTH: 17
<212> TYPE: DNA
<213> ORGANISM: Homo sapiens

<400> SEQUENCE: 310
cctagggaag gaagaag 17

<210> SEQ ID NO 311
<211> LENGTH: 17
<212> TYPE: DNA
<213> ORGANISM: Homo sapiens

<400> SEQUENCE: 311
ctagggaagg aagaaga 17

<210> SEQ ID NO 312
<211> LENGTH: 17
<212> TYPE: DNA
<213> ORGANISM: Homo sapiens

<400> SEQUENCE: 312
tagggaagga agaagag 17

<210> SEQ ID NO 313
<211> LENGTH: 17
<212> TYPE: DNA
<213> ORGANISM: Homo sapiens

<400> SEQUENCE: 313

-continued agggaaggaa gaagaga 17

<210> SEQ ID NO 314
<211> LENGTH: 17
<212> TYPE: DNA
<213> ORGANISM: Homo sapiens

<400> SEQUENCE: 314
gggaaggaag aagagaa 17

<210> SEQ ID NO 315
<211> LENGTH: 17
<212> TYPE: DNA
<213> ORGANISM: Homo sapiens

<400> SEQUENCE: 315
ggaaggaaga agagaaa 17

<210> SEQ ID NO 316
<211> LENGTH: 17
<212> TYPE: DNA
<213> ORGANISM: Homo sapiens

<400> SEQUENCE: 316
gaaggaagaa gagaaag 17

<210> SEQ ID NO 317
<211> LENGTH: 17
<212> TYPE: DNA
<213> ORGANISM: Homo sapiens

<400> SEQUENCE: 317
aaggaagaag agaaaga 17

<210> SEQ ID NO 318
<211> LENGTH: 17
<212> TYPE: DNA
<213> ORGANISM: Homo sapiens

<400> SEQUENCE: 318
aggaagaaga gaaagaa 17

<210> SEQ ID NO 319
<211> LENGTH: 17
<212> TYPE: DNA
<213> ORGANISM: Homo sapiens

<400> SEQUENCE: 319
ggaagaagag aaagaaa 17

<210> SEQ ID NO 320
<211> LENGTH: 17
<212> TYPE: DNA
<213> ORGANISM: Homo sapiens

<400> SEQUENCE: 320
gaagaagaga aagaaat 17

<210> SEQ ID NO 321
<211> LENGTH: 17
<212> TYPE: DNA
<213> ORGANISM: Homo sapiens

<400> SEQUENCE: 321

-continued aagaagagaa agaaatg 17

<210> SEQ ID NO 322
<211> LENGTH: 17
<212> TYPE: DNA
<213> ORGANISM: Homo sapiens

<400> SEQUENCE: 322
agaagagaaa gaaatga 17

<210> SEQ ID NO 323
<211> LENGTH: 17
<212> TYPE: DNA
<213> ORGANISM: Homo sapiens

<400> SEQUENCE: 323
gaagagaaag aaatgaa 17

<210> SEQ ID NO 324
<211> LENGTH: 17
<212> TYPE: DNA
<213> ORGANISM: Homo sapiens

<400> SEQUENCE: 324
aagagaaaga aatgaaa 17

<210> SEQ ID NO 325
<211> LENGTH: 17
<212> TYPE: DNA
<213> ORGANISM: Homo sapiens

<400> SEQUENCE: 325
agagaaagaa atgaaaa 17

<210> SEQ ID NO 326
<211> LENGTH: 17
<212> TYPE: DNA
<213> ORGANISM: Homo sapiens

<400> SEQUENCE: 326
gagaaagaaa tgaaaat 17

<210> SEQ ID NO 327
<211> LENGTH: 17
<212> TYPE: DNA
<213> ORGANISM: Homo sapiens

<400> SEQUENCE: 327
agaaagaaat gaaaatt 17

<210> SEQ ID NO 328
<211> LENGTH: 17
<212> TYPE: DNA
<213> ORGANISM: Homo sapiens

<400> SEQUENCE: 328
gaaagaaatg aaaatta 17

<210> SEQ ID NO 329
<211> LENGTH: 17
<212> TYPE: DNA
<213> ORGANISM: Homo sapiens -continued

<400> SEQUENCE: 329
aaagaaatga aaattag 17

<210> SEQ ID NO 330
<211> LENGTH: 17
<212> TYPE: DNA
<213> ORGANISM: Homo sapiens

<400> SEQUENCE: 330
aagaaatgaa aattaga 17

<210> SEQ ID NO 331
<211> LENGTH: 17
<212> TYPE: DNA
<213> ORGANISM: Homo sapiens

<400> SEQUENCE: 331
agaaatgaaa attagag 17

<210> SEQ ID NO 332
<211> LENGTH: 17
<212> TYPE: DNA
<213> ORGANISM: Homo sapiens

<400> SEQUENCE: 332
gaaatgaaaa ttagaga 17

<210> SEQ ID NO 333
<211> LENGTH: 17
<212> TYPE: DNA
<213> ORGANISM: Homo sapiens

<400> SEQUENCE: 333
aaatgaaaat tagagaa 17

<210> SEQ ID NO 334
<211> LENGTH: 17
<212> TYPE: DNA
<213> ORGANISM: Homo sapiens

<400> SEQUENCE: 334
aatgaaaatt agagaat 17

<210> SEQ ID NO 335
<211> LENGTH: 17
<212> TYPE: DNA
<213> ORGANISM: Homo sapiens

<400> SEQUENCE: 335
atgaaaatta gagaata 17

<210> SEQ ID NO 336
<211> LENGTH: 17
<212> TYPE: DNA
<213> ORGANISM: Homo sapiens

<400> SEQUENCE: 336
tgaaaattag agaataa 17

<210> SEQ ID NO 337
<211> LENGTH: 17
<212> TYPE: DNA
<213> ORGANISM: Homo sapiens -continued

<400> SEQUENCE: 337
gaaaattaga gaataag 17

<210> SEQ ID NO 338
<211> LENGTH: 17
<212> TYPE: DNA
<213> ORGANISM: Homo sapiens

<400> SEQUENCE: 338
aaaattagag aataaga 17

<210> SEQ ID NO 339
<211> LENGTH: 17
<212> TYPE: DNA
<213> ORGANISM: Homo sapiens

<400> SEQUENCE: 339
aaattagaga ataagat 17

<210> SEQ ID NO 340
<211> LENGTH: 17
<212> TYPE: DNA
<213> ORGANISM: Homo sapiens

<400> SEQUENCE: 340
aattagagaa taagatt 17

<210> SEQ ID NO 341
<211> LENGTH: 17
<212> TYPE: DNA
<213> ORGANISM: Homo sapiens

<400> SEQUENCE: 341
attagagaat aagatta 17

<210> SEQ ID NO 342
<211> LENGTH: 17
<212> TYPE: DNA
<213> ORGANISM: Homo sapiens

<400> SEQUENCE: 342
ttagagaata agattat 17

<210> SEQ ID NO 343
<211> LENGTH: 17
<212> TYPE: DNA
<213> ORGANISM: Homo sapiens

<400> SEQUENCE: 343
tagagaataa gattatt 17

<210> SEQ ID NO 344
<211> LENGTH: 17
<212> TYPE: DNA
<213> ORGANISM: Homo sapiens

<400> SEQUENCE: 344
agagaataag attattt 17

<210> SEQ ID NO 345
<211> LENGTH: 17
<212> TYPE: DNA

-continued

<213> ORGANISM: Homo sapiens

<400> SEQUENCE: 345
gagaataaga ttatttt 17

<210> SEQ ID NO 346
<211> LENGTH: 17
<212> TYPE: DNA
<213> ORGANISM: Homo sapiens

<400> SEQUENCE: 346
agaataagat tattttg 17

<210> SEQ ID NO 347
<211> LENGTH: 17
<212> TYPE: DNA
<213> ORGANISM: Homo sapiens

<400> SEQUENCE: 347
gaataagatt attttga 17

<210> SEQ ID NO 348
<211> LENGTH: 17
<212> TYPE: DNA
<213> ORGANISM: Homo sapiens

<400> SEQUENCE: 348
aataagatta ttttgaa 17

<210> SEQ ID NO 349
<211> LENGTH: 17
<212> TYPE: DNA
<213> ORGANISM: Homo sapiens

<400> SEQUENCE: 349
ataagattat tttgaat 17

<210> SEQ ID NO 350
<211> LENGTH: 17
<212> TYPE: DNA
<213> ORGANISM: Homo sapiens

<400> SEQUENCE: 350
taagattatt ttgaatg 17

<210> SEQ ID NO 351
<211> LENGTH: 17
<212> TYPE: DNA
<213> ORGANISM: Homo sapiens

<400> SEQUENCE: 351
aagattattt tgaatga 17

<210> SEQ ID NO 352
<211> LENGTH: 17
<212> TYPE: DNA
<213> ORGANISM: Homo sapiens

<400> SEQUENCE: 352
agattatttt gaatgac 17

<210> SEQ ID NO 353
<211> LENGTH: 17

-continued

<212> TYPE: DNA
<213> ORGANISM: Homo sapiens

<400> SEQUENCE: 353
gattattttg aatgact 17

<210> SEQ ID NO 354
<211> LENGTH: 17
<212> TYPE: DNA
<213> ORGANISM: Homo sapiens

<400> SEQUENCE: 354
attattttga atgactt 17

<210> SEQ ID NO 355
<211> LENGTH: 17
<212> TYPE: DNA
<213> ORGANISM: Homo sapiens

<400> SEQUENCE: 355
ttattttgaa tgacttc 17

<210> SEQ ID NO 356
<211> LENGTH: 17
<212> TYPE: DNA
<213> ORGANISM: Homo sapiens

<400> SEQUENCE: 356
tattttgaat gacttca 17

<210> SEQ ID NO 357
<211> LENGTH: 17
<212> TYPE: DNA
<213> ORGANISM: Homo sapiens

<400> SEQUENCE: 357
attttgaatg acttcag 17

<210> SEQ ID NO 358
<211> LENGTH: 17
<212> TYPE: DNA
<213> ORGANISM: Homo sapiens

<400> SEQUENCE: 358
ttttgaatga cttcagg 17

<210> SEQ ID NO 359
<211> LENGTH: 17
<212> TYPE: DNA
<213> ORGANISM: Homo sapiens

<400> SEQUENCE: 359
tttgaatgac ttcaggt 17

<210> SEQ ID NO 360
<211> LENGTH: 17
<212> TYPE: DNA
<213> ORGANISM: Homo sapiens

<400> SEQUENCE: 360
ttgaatgact tcaggta 17

<210> SEQ ID NO 361

-continued

<211> LENGTH: 17
<212> TYPE: DNA
<213> ORGANISM: Homo sapiens

<400> SEQUENCE: 361
tgaatgactt caggtag 17

<210> SEQ ID NO 362
<211> LENGTH: 17
<212> TYPE: DNA
<213> ORGANISM: Homo sapiens

<400> SEQUENCE: 362
gaatgacttc aggtagc 17

<210> SEQ ID NO 363
<211> LENGTH: 17
<212> TYPE: DNA
<213> ORGANISM: Homo sapiens

<400> SEQUENCE: 363
aatgacttca ggtagcg 17

<210> SEQ ID NO 364
<211> LENGTH: 17
<212> TYPE: DNA
<213> ORGANISM: Homo sapiens

<400> SEQUENCE: 364
atgacttcag gtagcga 17

<210> SEQ ID NO 365
<211> LENGTH: 17
<212> TYPE: DNA
<213> ORGANISM: Homo sapiens

<400> SEQUENCE: 365
tgacttcagg tagcgag 17

<210> SEQ ID NO 366
<211> LENGTH: 17
<212> TYPE: DNA
<213> ORGANISM: Homo sapiens

<400> SEQUENCE: 366
gacttcaggt agcgagg 17

<210> SEQ ID NO 367
<211> LENGTH: 17
<212> TYPE: DNA
<213> ORGANISM: Homo sapiens

<400> SEQUENCE: 367
acttcaggta gcgagga 17

<210> SEQ ID NO 368
<211> LENGTH: 17
<212> TYPE: DNA
<213> ORGANISM: Homo sapiens

<400> SEQUENCE: 368
cttcaggtag cgaggag 17

-continued

<210> SEQ ID NO 369
<211> LENGTH: 17
<212> TYPE: DNA
<213> ORGANISM: Homo sapiens

<400> SEQUENCE: 369
ttcaggtagc gaggagt 17

<210> SEQ ID NO 370
<211> LENGTH: 17
<212> TYPE: DNA
<213> ORGANISM: Homo sapiens

<400> SEQUENCE: 370
tcaggtagcg aggagtg 17

<210> SEQ ID NO 371
<211> LENGTH: 17
<212> TYPE: DNA
<213> ORGANISM: Homo sapiens

<400> SEQUENCE: 371
caggtagcga ggagtgt 17

<210> SEQ ID NO 372
<211> LENGTH: 17
<212> TYPE: DNA
<213> ORGANISM: Homo sapiens

<400> SEQUENCE: 372
aggtagcgag gagtgtg 17

<210> SEQ ID NO 373
<211> LENGTH: 17
<212> TYPE: DNA
<213> ORGANISM: Homo sapiens

<400> SEQUENCE: 373
ggtagcgagg agtgtgt 17

<210> SEQ ID NO 374
<211> LENGTH: 17
<212> TYPE: DNA
<213> ORGANISM: Homo sapiens

<400> SEQUENCE: 374
gtagcgagga gtgtgtg 17

<210> SEQ ID NO 375
<211> LENGTH: 17
<212> TYPE: DNA
<213> ORGANISM: Homo sapiens

<400> SEQUENCE: 375
tagcgaggag tgtgtgt 17

<210> SEQ ID NO 376
<211> LENGTH: 17
<212> TYPE: DNA
<213> ORGANISM: Homo sapiens

<400> SEQUENCE: 376
agcgaggagt gtgtgtt 17

-continued

<210> SEQ ID NO 377
<211> LENGTH: 17
<212> TYPE: DNA
<213> ORGANISM: Homo sapiens

<400> SEQUENCE: 377
gcgaggagtg tgtgttt 17

<210> SEQ ID NO 378
<211> LENGTH: 17
<212> TYPE: DNA
<213> ORGANISM: Homo sapiens

<400> SEQUENCE: 378
cgaggagtgt gtgtttg 17

<210> SEQ ID NO 379
<211> LENGTH: 17
<212> TYPE: DNA
<213> ORGANISM: Homo sapiens

<400> SEQUENCE: 379
gaggagtgtg tgtttgt 17

<210> SEQ ID NO 380
<211> LENGTH: 17
<212> TYPE: DNA
<213> ORGANISM: Homo sapiens

<400> SEQUENCE: 380
aggagtgtgt gtttgtg 17

<210> SEQ ID NO 381
<211> LENGTH: 17
<212> TYPE: DNA
<213> ORGANISM: Homo sapiens

<400> SEQUENCE: 381
ggagtgtgtg tttgtga 17

<210> SEQ ID NO 382
<211> LENGTH: 17
<212> TYPE: DNA
<213> ORGANISM: Homo sapiens

<400> SEQUENCE: 382
gagtgtgtgt ttgtgag 17

<210> SEQ ID NO 383
<211> LENGTH: 17
<212> TYPE: DNA
<213> ORGANISM: Homo sapiens

<400> SEQUENCE: 383
agtgtgtgtt tgtgagt 17

<210> SEQ ID NO 384
<211> LENGTH: 17
<212> TYPE: DNA
<213> ORGANISM: Homo sapiens

<400> SEQUENCE: 384
gtgtgtgttt gtgagtg 17

-continued

<210> SEQ ID NO 385
<211> LENGTH: 17
<212> TYPE: DNA
<213> ORGANISM: Homo sapiens

<400> SEQUENCE: 385
tgtgtgtttg tgagtgt 17

<210> SEQ ID NO 386
<211> LENGTH: 17
<212> TYPE: DNA
<213> ORGANISM: Homo sapiens

<400> SEQUENCE: 386
gtgtgtttgt gagtgtg 17

<210> SEQ ID NO 387
<211> LENGTH: 17
<212> TYPE: DNA
<213> ORGANISM: Homo sapiens

<400> SEQUENCE: 387
tgtgtttgtg agtgtgt 17

<210> SEQ ID NO 388
<211> LENGTH: 17
<212> TYPE: DNA
<213> ORGANISM: Homo sapiens

<400> SEQUENCE: 388
gtgtttgtga gtgtgta 17

<210> SEQ ID NO 389
<211> LENGTH: 17
<212> TYPE: DNA
<213> ORGANISM: Homo sapiens

<400> SEQUENCE: 389
tgtttgtgag tgtgtat 17

<210> SEQ ID NO 390
<211> LENGTH: 17
<212> TYPE: DNA
<213> ORGANISM: Homo sapiens

<400> SEQUENCE: 390
gtttgtgagt gtgtatt 17

<210> SEQ ID NO 391
<211> LENGTH: 17
<212> TYPE: DNA
<213> ORGANISM: Homo sapiens

<400> SEQUENCE: 391
tttgtgagtg tgtattt 17

<210> SEQ ID NO 392
<211> LENGTH: 17
<212> TYPE: DNA
<213> ORGANISM: Homo sapiens

<400> SEQUENCE: 392

-continued ttgtgagtgt gtatttg 17

<210> SEQ ID NO 393
<211> LENGTH: 17
<212> TYPE: DNA
<213> ORGANISM: Homo sapiens

<400> SEQUENCE: 393
tgtgagtgtg tatttga 17

<210> SEQ ID NO 394
<211> LENGTH: 17
<212> TYPE: DNA
<213> ORGANISM: Homo sapiens

<400> SEQUENCE: 394
gtgagtgtgt atttgag 17

<210> SEQ ID NO 395
<211> LENGTH: 17
<212> TYPE: DNA
<213> ORGANISM: Homo sapiens

<400> SEQUENCE: 395
tgagtgtgta tttgaga 17

<210> SEQ ID NO 396
<211> LENGTH: 17
<212> TYPE: DNA
<213> ORGANISM: Homo sapiens

<400> SEQUENCE: 396
gagtgtgtat ttgagag 17

<210> SEQ ID NO 397
<211> LENGTH: 17
<212> TYPE: DNA
<213> ORGANISM: Homo sapiens

<400> SEQUENCE: 397
agtgtgtatt tgagaga 17

<210> SEQ ID NO 398
<211> LENGTH: 17
<212> TYPE: DNA
<213> ORGANISM: Homo sapiens

<400> SEQUENCE: 398
gtgtgtattt gagagac 17

<210> SEQ ID NO 399
<211> LENGTH: 17
<212> TYPE: DNA
<213> ORGANISM: Homo sapiens

<400> SEQUENCE: 399
tgtgtatttg agagact 17

<210> SEQ ID NO 400
<211> LENGTH: 17
<212> TYPE: DNA
<213> ORGANISM: Homo sapiens

<400> SEQUENCE: 400

-continued gtgtatttga gagactt 17

<210> SEQ ID NO 401
<211> LENGTH: 17
<212> TYPE: DNA
<213> ORGANISM: Homo sapiens

<400> SEQUENCE: 401
tgtatttgag agacttg 17

<210> SEQ ID NO 402
<211> LENGTH: 17
<212> TYPE: DNA
<213> ORGANISM: Homo sapiens

<400> SEQUENCE: 402
gtatttgaga gacttgg 17

<210> SEQ ID NO 403
<211> LENGTH: 17
<212> TYPE: DNA
<213> ORGANISM: Homo sapiens

<400> SEQUENCE: 403
tatttgagag acttggc 17

<210> SEQ ID NO 404
<211> LENGTH: 17
<212> TYPE: DNA
<213> ORGANISM: Homo sapiens

<400> SEQUENCE: 404
atttgagaga cttggct 17

<210> SEQ ID NO 405
<211> LENGTH: 17
<212> TYPE: DNA
<213> ORGANISM: Homo sapiens

<400> SEQUENCE: 405
tttgagagac ttggctc 17

<210> SEQ ID NO 406
<211> LENGTH: 17
<212> TYPE: DNA
<213> ORGANISM: Homo sapiens

<400> SEQUENCE: 406
ttgagagact tggctca 17

<210> SEQ ID NO 407
<211> LENGTH: 17
<212> TYPE: DNA
<213> ORGANISM: Homo sapiens

<400> SEQUENCE: 407
tgagagactt ggctcat 17

<210> SEQ ID NO 408
<211> LENGTH: 17
<212> TYPE: DNA
<213> ORGANISM: Homo sapiens -continued

<400> SEQUENCE: 408
gagagacttg gctcatg 17

<210> SEQ ID NO 409
<211> LENGTH: 17
<212> TYPE: DNA
<213> ORGANISM: Homo sapiens

<400> SEQUENCE: 409
agagacttgg ctcatgc 17

<210> SEQ ID NO 410
<211> LENGTH: 17
<212> TYPE: DNA
<213> ORGANISM: Homo sapiens

<400> SEQUENCE: 410
gagacttggc tcatgcc 17

<210> SEQ ID NO 411
<211> LENGTH: 17
<212> TYPE: DNA
<213> ORGANISM: Homo sapiens

<400> SEQUENCE: 411
agacttggct catgcct 17

<210> SEQ ID NO 412
<211> LENGTH: 17
<212> TYPE: DNA
<213> ORGANISM: Homo sapiens

<400> SEQUENCE: 412
gacttggctc atgcctg 17

<210> SEQ ID NO 413
<211> LENGTH: 17
<212> TYPE: DNA
<213> ORGANISM: Homo sapiens

<400> SEQUENCE: 413
acttggctca tgcctgt 17

<210> SEQ ID NO 414
<211> LENGTH: 17
<212> TYPE: DNA
<213> ORGANISM: Homo sapiens

<400> SEQUENCE: 414
cttggctcat gcctgtg 17

<210> SEQ ID NO 415
<211> LENGTH: 17
<212> TYPE: DNA
<213> ORGANISM: Homo sapiens

<400> SEQUENCE: 415
ttggctcatg cctgtgg 17

<210> SEQ ID NO 416
<211> LENGTH: 17
<212> TYPE: DNA
<213> ORGANISM: Homo sapiens -continued

<400> SEQUENCE: 416
tggctcatgc ctgtggg 17

<210> SEQ ID NO 417
<211> LENGTH: 17
<212> TYPE: DNA
<213> ORGANISM: Homo sapiens

<400> SEQUENCE: 417
ggctcatgcc tgtgggt 17

<210> SEQ ID NO 418
<211> LENGTH: 17
<212> TYPE: DNA
<213> ORGANISM: Homo sapiens

<400> SEQUENCE: 418
gctcatgcct gtgggtc 17

<210> SEQ ID NO 419
<211> LENGTH: 17
<212> TYPE: DNA
<213> ORGANISM: Homo sapiens

<400> SEQUENCE: 419
ctcatgcctg tgggtct 17

<210> SEQ ID NO 420
<211> LENGTH: 17
<212> TYPE: DNA
<213> ORGANISM: Homo sapiens

<400> SEQUENCE: 420
tcatgcctgt gggtctt 17

<210> SEQ ID NO 421
<211> LENGTH: 17
<212> TYPE: DNA
<213> ORGANISM: Homo sapiens

<400> SEQUENCE: 421
catgcctgtg ggtcttc 17

<210> SEQ ID NO 422
<211> LENGTH: 17
<212> TYPE: DNA
<213> ORGANISM: Homo sapiens

<400> SEQUENCE: 422
atgcctgtgg gtcttct 17

<210> SEQ ID NO 423
<211> LENGTH: 17
<212> TYPE: DNA
<213> ORGANISM: Homo sapiens

<400> SEQUENCE: 423
tgcctgtggg tcttctc 17

<210> SEQ ID NO 424
<211> LENGTH: 17
<212> TYPE: DNA

-continued

<213> ORGANISM: Homo sapiens

<400> SEQUENCE: 424
gcctgtgggt cttctct 17

<210> SEQ ID NO 425
<211> LENGTH: 17
<212> TYPE: DNA
<213> ORGANISM: Homo sapiens

<400> SEQUENCE: 425
cctgtgggtc ttctctt 17

<210> SEQ ID NO 426
<211> LENGTH: 17
<212> TYPE: DNA
<213> ORGANISM: Homo sapiens

<400> SEQUENCE: 426
ctgtgggtct tctcttc 17

<210> SEQ ID NO 427
<211> LENGTH: 17
<212> TYPE: DNA
<213> ORGANISM: Homo sapiens

<400> SEQUENCE: 427
tgtgggtctt ctcttct 17

<210> SEQ ID NO 428
<211> LENGTH: 17
<212> TYPE: DNA
<213> ORGANISM: Homo sapiens

<400> SEQUENCE: 428
gtgggtcttc tcttcta 17

<210> SEQ ID NO 429
<211> LENGTH: 17
<212> TYPE: DNA
<213> ORGANISM: Homo sapiens

<400> SEQUENCE: 429
tgggtcttct cttctag 17

<210> SEQ ID NO 430
<211> LENGTH: 17
<212> TYPE: DNA
<213> ORGANISM: Homo sapiens

<400> SEQUENCE: 430
gggtcttctc ttctagt 17

<210> SEQ ID NO 431
<211> LENGTH: 17
<212> TYPE: DNA
<213> ORGANISM: Homo sapiens

<400> SEQUENCE: 431
ggtcttctct tctagta 17

<210> SEQ ID NO 432
<211> LENGTH: 17

-continued

<212> TYPE: DNA
<213> ORGANISM: Homo sapiens

<400> SEQUENCE: 432
gtcttctctt ctagtat 17

<210> SEQ ID NO 433
<211> LENGTH: 17
<212> TYPE: DNA
<213> ORGANISM: Homo sapiens

<400> SEQUENCE: 433
tcttctcttc tagtatc 17

<210> SEQ ID NO 434
<211> LENGTH: 17
<212> TYPE: DNA
<213> ORGANISM: Homo sapiens

<400> SEQUENCE: 434
cttctcttct agtatca 17

<210> SEQ ID NO 435
<211> LENGTH: 17
<212> TYPE: DNA
<213> ORGANISM: Homo sapiens

<400> SEQUENCE: 435
ttctcttcta gtatcag 17

<210> SEQ ID NO 436
<211> LENGTH: 17
<212> TYPE: DNA
<213> ORGANISM: Homo sapiens

<400> SEQUENCE: 436
tctcttctag tatcagt 17

<210> SEQ ID NO 437
<211> LENGTH: 17
<212> TYPE: DNA
<213> ORGANISM: Homo sapiens

<400> SEQUENCE: 437
ctcttctagt atcagtg 17

<210> SEQ ID NO 438
<211> LENGTH: 17
<212> TYPE: DNA
<213> ORGANISM: Homo sapiens

<400> SEQUENCE: 438
tcttctagta tcagtga 17

<210> SEQ ID NO 439
<211> LENGTH: 17
<212> TYPE: DNA
<213> ORGANISM: Homo sapiens

<400> SEQUENCE: 439
cttctagtat cagtgag 17

<210> SEQ ID NO 440

-continued

<211> LENGTH: 17
<212> TYPE: DNA
<213> ORGANISM: Homo sapiens

<400> SEQUENCE: 440
ttctagtatc agtgagg 17

<210> SEQ ID NO 441
<211> LENGTH: 17
<212> TYPE: DNA
<213> ORGANISM: Homo sapiens

<400> SEQUENCE: 441
tctagtatca gtgaggg 17

<210> SEQ ID NO 442
<211> LENGTH: 17
<212> TYPE: DNA
<213> ORGANISM: Homo sapiens

<400> SEQUENCE: 442
ctagtatcag tgagggg 17

<210> SEQ ID NO 443
<211> LENGTH: 17
<212> TYPE: DNA
<213> ORGANISM: Homo sapiens

<400> SEQUENCE: 443
tagtatcagt gagggga 17

<210> SEQ ID NO 444
<211> LENGTH: 17
<212> TYPE: DNA
<213> ORGANISM: Homo sapiens

<400> SEQUENCE: 444
agtatcagtg aggggag 17

<210> SEQ ID NO 445
<211> LENGTH: 17
<212> TYPE: DNA
<213> ORGANISM: Homo sapiens

<400> SEQUENCE: 445
gtatcagtga ggggagg 17

<210> SEQ ID NO 446
<211> LENGTH: 17
<212> TYPE: DNA
<213> ORGANISM: Homo sapiens

<400> SEQUENCE: 446
tatcagtgag gggaggg 17

<210> SEQ ID NO 447
<211> LENGTH: 17
<212> TYPE: DNA
<213> ORGANISM: Homo sapiens

<400> SEQUENCE: 447
atcagtgagg ggaggga 17

-continued

<210> SEQ ID NO 448
<211> LENGTH: 17
<212> TYPE: DNA
<213> ORGANISM: Homo sapiens

<400> SEQUENCE: 448
tcagtgaggg gagggat 17

<210> SEQ ID NO 449
<211> LENGTH: 17
<212> TYPE: DNA
<213> ORGANISM: Homo sapiens

<400> SEQUENCE: 449
cagtgagggg agggatt 17

<210> SEQ ID NO 450
<211> LENGTH: 17
<212> TYPE: DNA
<213> ORGANISM: Homo sapiens

<400> SEQUENCE: 450
agtgagggga gggatta 17

<210> SEQ ID NO 451
<211> LENGTH: 17
<212> TYPE: DNA
<213> ORGANISM: Homo sapiens

<400> SEQUENCE: 451
gtgaggggag ggattac 17

<210> SEQ ID NO 452
<211> LENGTH: 17
<212> TYPE: DNA
<213> ORGANISM: Homo sapiens

<400> SEQUENCE: 452
tgaggggagg gattact 17

<210> SEQ ID NO 453
<211> LENGTH: 17
<212> TYPE: DNA
<213> ORGANISM: Homo sapiens

<400> SEQUENCE: 453
gaggggaggg attactg 17

<210> SEQ ID NO 454
<211> LENGTH: 17
<212> TYPE: DNA
<213> ORGANISM: Homo sapiens

<400> SEQUENCE: 454
aggggaggga ttactga 17

<210> SEQ ID NO 455
<211> LENGTH: 17
<212> TYPE: DNA
<213> ORGANISM: Homo sapiens

<400> SEQUENCE: 455
ggggagggat tactgaa 17

-continued

<210> SEQ ID NO 456
<211> LENGTH: 17
<212> TYPE: DNA
<213> ORGANISM: Homo sapiens

<400> SEQUENCE: 456
gggagggatt actgaag 17

<210> SEQ ID NO 457
<211> LENGTH: 17
<212> TYPE: DNA
<213> ORGANISM: Homo sapiens

<400> SEQUENCE: 457
ggagggatta ctgaaga 17

<210> SEQ ID NO 458
<211> LENGTH: 17
<212> TYPE: DNA
<213> ORGANISM: Homo sapiens

<400> SEQUENCE: 458
gagggattac tgaagaa 17

<210> SEQ ID NO 459
<211> LENGTH: 17
<212> TYPE: DNA
<213> ORGANISM: Homo sapiens

<400> SEQUENCE: 459
agggattact gaagaag 17

<210> SEQ ID NO 460
<211> LENGTH: 17
<212> TYPE: DNA
<213> ORGANISM: Homo sapiens

<400> SEQUENCE: 460
gggattactg aagaaga 17

<210> SEQ ID NO 461
<211> LENGTH: 17
<212> TYPE: DNA
<213> ORGANISM: Homo sapiens

<400> SEQUENCE: 461
ggattactga agaagaa 17

<210> SEQ ID NO 462
<211> LENGTH: 17
<212> TYPE: DNA
<213> ORGANISM: Homo sapiens

<400> SEQUENCE: 462
gattactgaa gaagaag 17

<210> SEQ ID NO 463
<211> LENGTH: 17
<212> TYPE: DNA
<213> ORGANISM: Homo sapiens

<400> SEQUENCE: 463
attactgaag aagaagg 17

-continued

<210> SEQ ID NO 464
<211> LENGTH: 17
<212> TYPE: DNA
<213> ORGANISM: Homo sapiens

<400> SEQUENCE: 464
ttactgaaga agaaggg 17

<210> SEQ ID NO 465
<211> LENGTH: 17
<212> TYPE: DNA
<213> ORGANISM: Homo sapiens

<400> SEQUENCE: 465
tactgaagaa gaagggg 17

<210> SEQ ID NO 466
<211> LENGTH: 17
<212> TYPE: DNA
<213> ORGANISM: Homo sapiens

<400> SEQUENCE: 466
actgaagaag aaggggg 17

<210> SEQ ID NO 467
<211> LENGTH: 17
<212> TYPE: DNA
<213> ORGANISM: Homo sapiens

<400> SEQUENCE: 467
ctgaagaaga aggggg 17

<210> SEQ ID NO 468
<211> LENGTH: 17
<212> TYPE: DNA
<213> ORGANISM: Homo sapiens

<400> SEQUENCE: 468
tgaagaagaa gggggga 17

<210> SEQ ID NO 469
<211> LENGTH: 17
<212> TYPE: DNA
<213> ORGANISM: Homo sapiens

<400> SEQUENCE: 469
gaagaagaag gggggaa 17

<210> SEQ ID NO 470
<211> LENGTH: 17
<212> TYPE: DNA
<213> ORGANISM: Homo sapiens

<400> SEQUENCE: 470
aagaagaagg ggggaaa 17

<210> SEQ ID NO 471
<211> LENGTH: 17
<212> TYPE: DNA
<213> ORGANISM: Homo sapiens

<400> SEQUENCE: 471

-continued agaagaaggg gggaaaa 17

<210> SEQ ID NO 472
<211> LENGTH: 17
<212> TYPE: DNA
<213> ORGANISM: Homo sapiens

<400> SEQUENCE: 472
gaagaagggg ggaaaaa 17

<210> SEQ ID NO 473
<211> LENGTH: 17
<212> TYPE: DNA
<213> ORGANISM: Homo sapiens

<400> SEQUENCE: 473
aagaaggggg gaaaaaa 17

<210> SEQ ID NO 474
<211> LENGTH: 17
<212> TYPE: DNA
<213> ORGANISM: Homo sapiens

<400> SEQUENCE: 474
agaagggggg aaaaaaa 17

<210> SEQ ID NO 475
<211> LENGTH: 17
<212> TYPE: DNA
<213> ORGANISM: Homo sapiens

<400> SEQUENCE: 475
gaagggggga aaaaaaa 17

<210> SEQ ID NO 476
<211> LENGTH: 17
<212> TYPE: DNA
<213> ORGANISM: Homo sapiens

<400> SEQUENCE: 476
aaggggggaa aaaaaaa 17

<210> SEQ ID NO 477
<211> LENGTH: 17
<212> TYPE: DNA
<213> ORGANISM: Homo sapiens

<400> SEQUENCE: 477
aggggggaaa aaaaaag 17

<210> SEQ ID NO 478
<211> LENGTH: 17
<212> TYPE: DNA
<213> ORGANISM: Homo sapiens

<400> SEQUENCE: 478
ggggggaaaa aaaaaga 17

<210> SEQ ID NO 479
<211> LENGTH: 17
<212> TYPE: DNA
<213> ORGANISM: Homo sapiens

<400> SEQUENCE: 479

-continued gggggaaaaa aaaagaa 17

<210> SEQ ID NO 480
<211> LENGTH: 17
<212> TYPE: DNA
<213> ORGANISM: Homo sapiens

<400> SEQUENCE: 480
ggggaaaaaa aaagaaa 17

<210> SEQ ID NO 481
<211> LENGTH: 17
<212> TYPE: DNA
<213> ORGANISM: Homo sapiens

<400> SEQUENCE: 481
gggaaaaaaa aagaaag 17

<210> SEQ ID NO 482
<211> LENGTH: 17
<212> TYPE: DNA
<213> ORGANISM: Homo sapiens

<400> SEQUENCE: 482
ggaaaaaaaa agaaaga 17

<210> SEQ ID NO 483
<211> LENGTH: 17
<212> TYPE: DNA
<213> ORGANISM: Homo sapiens

<400> SEQUENCE: 483
gaaaaaaaaa gaaagaa 17

<210> SEQ ID NO 484
<211> LENGTH: 17
<212> TYPE: DNA
<213> ORGANISM: Homo sapiens

<400> SEQUENCE: 484
aaaaaaaaag aaagaaa 17

<210> SEQ ID NO 485
<211> LENGTH: 17
<212> TYPE: DNA
<213> ORGANISM: Homo sapiens

<400> SEQUENCE: 485
aaaaaaaaga aagaaat 17

<210> SEQ ID NO 486
<211> LENGTH: 17
<212> TYPE: DNA
<213> ORGANISM: Homo sapiens

<400> SEQUENCE: 486
aaaaaaagaa agaaatc 17

<210> SEQ ID NO 487
<211> LENGTH: 17
<212> TYPE: DNA
<213> ORGANISM: Homo sapiens -continued

<400> SEQUENCE: 487
aaaaaagaaa gaaatct 17

<210> SEQ ID NO 488
<211> LENGTH: 17
<212> TYPE: DNA
<213> ORGANISM: Homo sapiens

<400> SEQUENCE: 488
aaaaagaaag aaatctg 17

<210> SEQ ID NO 489
<211> LENGTH: 17
<212> TYPE: DNA
<213> ORGANISM: Homo sapiens

<400> SEQUENCE: 489
aaaagaaaga aatctga 17

<210> SEQ ID NO 490
<211> LENGTH: 17
<212> TYPE: DNA
<213> ORGANISM: Homo sapiens

<400> SEQUENCE: 490
aaagaaagaa atctgag 17

<210> SEQ ID NO 491
<211> LENGTH: 17
<212> TYPE: DNA
<213> ORGANISM: Homo sapiens

<400> SEQUENCE: 491
aagaaagaaa tctgagc 17

<210> SEQ ID NO 492
<211> LENGTH: 17
<212> TYPE: DNA
<213> ORGANISM: Homo sapiens

<400> SEQUENCE: 492
agaaagaaat ctgagct 17

<210> SEQ ID NO 493
<211> LENGTH: 17
<212> TYPE: DNA
<213> ORGANISM: Homo sapiens

<400> SEQUENCE: 493
gaaagaaatc tgagctt 17

<210> SEQ ID NO 494
<211> LENGTH: 17
<212> TYPE: DNA
<213> ORGANISM: Homo sapiens

<400> SEQUENCE: 494
aaagaaatct gagcttt 17

<210> SEQ ID NO 495
<211> LENGTH: 17
<212> TYPE: DNA
<213> ORGANISM: Homo sapiens -continued

<400> SEQUENCE: 495
aagaaatctg agctttc 17

<210> SEQ ID NO 496
<211> LENGTH: 17
<212> TYPE: DNA
<213> ORGANISM: Homo sapiens

<400> SEQUENCE: 496
agaaatctga gctttct 17

<210> SEQ ID NO 497
<211> LENGTH: 17
<212> TYPE: DNA
<213> ORGANISM: Homo sapiens

<400> SEQUENCE: 497
gaaatctgag ctttctg 17

<210> SEQ ID NO 498
<211> LENGTH: 17
<212> TYPE: DNA
<213> ORGANISM: Homo sapiens

<400> SEQUENCE: 498
aaatctgagc tttctgg 17

<210> SEQ ID NO 499
<211> LENGTH: 17
<212> TYPE: DNA
<213> ORGANISM: Homo sapiens

<400> SEQUENCE: 499
aatctgagct ttctggg 17

<210> SEQ ID NO 500
<211> LENGTH: 17
<212> TYPE: DNA
<213> ORGANISM: Homo sapiens

<400> SEQUENCE: 500
atctgagctt tctggga 17

<210> SEQ ID NO 501
<211> LENGTH: 17
<212> TYPE: DNA
<213> ORGANISM: Homo sapiens

<400> SEQUENCE: 501
tctgagcttt ctgggag 17

<210> SEQ ID NO 502
<211> LENGTH: 17
<212> TYPE: DNA
<213> ORGANISM: Homo sapiens

<400> SEQUENCE: 502
ctgagctttc tgggagg 17

<210> SEQ ID NO 503
<211> LENGTH: 17
<212> TYPE: DNA

-continued

<213> ORGANISM: Homo sapiens

<400> SEQUENCE: 503
tgagctttct gggagga 17

<210> SEQ ID NO 504
<211> LENGTH: 17
<212> TYPE: DNA
<213> ORGANISM: Homo sapiens

<400> SEQUENCE: 504
gagctttctg ggaggaa 17

<210> SEQ ID NO 505
<211> LENGTH: 17
<212> TYPE: DNA
<213> ORGANISM: Homo sapiens

<400> SEQUENCE: 505
agctttctgg gaggaaa 17

<210> SEQ ID NO 506
<211> LENGTH: 17
<212> TYPE: DNA
<213> ORGANISM: Homo sapiens

<400> SEQUENCE: 506
gctttctggg aggaaat 17

<210> SEQ ID NO 507
<211> LENGTH: 17
<212> TYPE: DNA
<213> ORGANISM: Homo sapiens

<400> SEQUENCE: 507
ctttctggga ggaaatt 17

<210> SEQ ID NO 508
<211> LENGTH: 17
<212> TYPE: DNA
<213> ORGANISM: Homo sapiens

<400> SEQUENCE: 508
tttctgggag gaaattc 17

<210> SEQ ID NO 509
<211> LENGTH: 17
<212> TYPE: DNA
<213> ORGANISM: Homo sapiens

<400> SEQUENCE: 509
ttctgggagg aaattca 17

<210> SEQ ID NO 510
<211> LENGTH: 17
<212> TYPE: DNA
<213> ORGANISM: Homo sapiens

<400> SEQUENCE: 510
tctgggagga aattcaa 17

<210> SEQ ID NO 511
<211> LENGTH: 17

-continued

<212> TYPE: DNA
<213> ORGANISM: Homo sapiens

<400> SEQUENCE: 511
ctgggaggaa attcaaa 17

<210> SEQ ID NO 512
<211> LENGTH: 17
<212> TYPE: DNA
<213> ORGANISM: Homo sapiens

<400> SEQUENCE: 512
tgggaggaaa ttcaaag 17

<210> SEQ ID NO 513
<211> LENGTH: 17
<212> TYPE: DNA
<213> ORGANISM: Homo sapiens

<400> SEQUENCE: 513
gggaggaaat tcaaagg 17

<210> SEQ ID NO 514
<211> LENGTH: 17
<212> TYPE: DNA
<213> ORGANISM: Homo sapiens

<400> SEQUENCE: 514
ggaggaaatt caaagga 17

<210> SEQ ID NO 515
<211> LENGTH: 17
<212> TYPE: DNA
<213> ORGANISM: Homo sapiens

<400> SEQUENCE: 515
gaggaaattc aaaggaa 17

<210> SEQ ID NO 516
<211> LENGTH: 17
<212> TYPE: DNA
<213> ORGANISM: Homo sapiens

<400> SEQUENCE: 516
aggaaattca aaggaac 17

<210> SEQ ID NO 517
<211> LENGTH: 17
<212> TYPE: DNA
<213> ORGANISM: Homo sapiens

<400> SEQUENCE: 517
ggaaattcaa aggaacc 17

<210> SEQ ID NO 518
<211> LENGTH: 17
<212> TYPE: DNA
<213> ORGANISM: Homo sapiens

<400> SEQUENCE: 518
gaaattcaaa ggaacca 17

<210> SEQ ID NO 519

-continued

<211> LENGTH: 17
<212> TYPE: DNA
<213> ORGANISM: Homo sapiens

<400> SEQUENCE: 519
aaattcaaag gaaccaa 17

<210> SEQ ID NO 520
<211> LENGTH: 17
<212> TYPE: DNA
<213> ORGANISM: Homo sapiens

<400> SEQUENCE: 520
aattcaaagg aaccaag 17

<210> SEQ ID NO 521
<211> LENGTH: 17
<212> TYPE: DNA
<213> ORGANISM: Homo sapiens

<400> SEQUENCE: 521
attcaaagga accaaga 17

<210> SEQ ID NO 522
<211> LENGTH: 17
<212> TYPE: DNA
<213> ORGANISM: Homo sapiens

<400> SEQUENCE: 522
ttcaaaggaa ccaagag 17

<210> SEQ ID NO 523
<211> LENGTH: 17
<212> TYPE: DNA
<213> ORGANISM: Homo sapiens

<400> SEQUENCE: 523
tcaaaggaac caagaga 17

<210> SEQ ID NO 524
<211> LENGTH: 17
<212> TYPE: DNA
<213> ORGANISM: Homo sapiens

<400> SEQUENCE: 524
caaaggaacc aagagaa 17

<210> SEQ ID NO 525
<211> LENGTH: 17
<212> TYPE: DNA
<213> ORGANISM: Homo sapiens

<400> SEQUENCE: 525
aaaggaacca agagaaa 17

<210> SEQ ID NO 526
<211> LENGTH: 17
<212> TYPE: DNA
<213> ORGANISM: Homo sapiens

<400> SEQUENCE: 526
aaggaaccaa gagaaat 17

-continued

<210> SEQ ID NO 527
<211> LENGTH: 17
<212> TYPE: DNA
<213> ORGANISM: Homo sapiens

<400> SEQUENCE: 527
aggaaccaag agaaatt 17

<210> SEQ ID NO 528
<211> LENGTH: 17
<212> TYPE: DNA
<213> ORGANISM: Homo sapiens

<400> SEQUENCE: 528
ggaaccaaga gaaatta 17

<210> SEQ ID NO 529
<211> LENGTH: 17
<212> TYPE: DNA
<213> ORGANISM: Homo sapiens

<400> SEQUENCE: 529
gaaccaagag aaattaa 17

<210> SEQ ID NO 530
<211> LENGTH: 17
<212> TYPE: DNA
<213> ORGANISM: Homo sapiens

<400> SEQUENCE: 530
aaccaagaga aattaac 17

<210> SEQ ID NO 531
<211> LENGTH: 17
<212> TYPE: DNA
<213> ORGANISM: Homo sapiens

<400> SEQUENCE: 531
accaagagaa attaact 17

<210> SEQ ID NO 532
<211> LENGTH: 17
<212> TYPE: DNA
<213> ORGANISM: Homo sapiens

<400> SEQUENCE: 532
ccaagagaaa ttaactt 17

<210> SEQ ID NO 533
<211> LENGTH: 17
<212> TYPE: DNA
<213> ORGANISM: Homo sapiens

<400> SEQUENCE: 533
caagagaaat taacttc 17

<210> SEQ ID NO 534
<211> LENGTH: 17
<212> TYPE: DNA
<213> ORGANISM: Homo sapiens

<400> SEQUENCE: 534
aagagaaatt aacttcg 17

-continued

<210> SEQ ID NO 535
<211> LENGTH: 17
<212> TYPE: DNA
<213> ORGANISM: Homo sapiens

<400> SEQUENCE: 535
agagaaatta acttcgt 17

<210> SEQ ID NO 536
<211> LENGTH: 17
<212> TYPE: DNA
<213> ORGANISM: Homo sapiens

<400> SEQUENCE: 536
gagaaattaa cttcgtt 17

<210> SEQ ID NO 537
<211> LENGTH: 17
<212> TYPE: DNA
<213> ORGANISM: Homo sapiens

<400> SEQUENCE: 537
agaaattaac ttcgttc 17

<210> SEQ ID NO 538
<211> LENGTH: 17
<212> TYPE: DNA
<213> ORGANISM: Homo sapiens

<400> SEQUENCE: 538
gaaattaact tcgttct 17

<210> SEQ ID NO 539
<211> LENGTH: 17
<212> TYPE: DNA
<213> ORGANISM: Homo sapiens

<400> SEQUENCE: 539
aaattaactt cgttctg 17

<210> SEQ ID NO 540
<211> LENGTH: 17
<212> TYPE: DNA
<213> ORGANISM: Homo sapiens

<400> SEQUENCE: 540
aattaacttc gttctgc 17

<210> SEQ ID NO 541
<211> LENGTH: 17
<212> TYPE: DNA
<213> ORGANISM: Homo sapiens

<400> SEQUENCE: 541
attaacttcg ttctgca 17

<210> SEQ ID NO 542
<211> LENGTH: 17
<212> TYPE: DNA
<213> ORGANISM: Homo sapiens

<400> SEQUENCE: 542
ttaacttcgt tctgcaa 17

-continued

<210> SEQ ID NO 543
<211> LENGTH: 17
<212> TYPE: DNA
<213> ORGANISM: Homo sapiens

<400> SEQUENCE: 543
taacttcgtt ctgcaag 17

<210> SEQ ID NO 544
<211> LENGTH: 17
<212> TYPE: DNA
<213> ORGANISM: Homo sapiens

<400> SEQUENCE: 544
aacttcgttc tgcaagg 17

<210> SEQ ID NO 545
<211> LENGTH: 17
<212> TYPE: DNA
<213> ORGANISM: Homo sapiens

<400> SEQUENCE: 545
acttcgttct gcaagga 17

<210> SEQ ID NO 546
<211> LENGTH: 17
<212> TYPE: DNA
<213> ORGANISM: Homo sapiens

<400> SEQUENCE: 546
cttcgttctg caaggac 17

<210> SEQ ID NO 547
<211> LENGTH: 17
<212> TYPE: DNA
<213> ORGANISM: Homo sapiens

<400> SEQUENCE: 547
ttcgttctgc aaggact 17

<210> SEQ ID NO 548
<211> LENGTH: 17
<212> TYPE: DNA
<213> ORGANISM: Homo sapiens

<400> SEQUENCE: 548
tcgttctgca aggacta 17

<210> SEQ ID NO 549
<211> LENGTH: 17
<212> TYPE: DNA
<213> ORGANISM: Homo sapiens

<400> SEQUENCE: 549
cgttctgcaa ggactaa 17

<210> SEQ ID NO 550
<211> LENGTH: 17
<212> TYPE: DNA
<213> ORGANISM: Homo sapiens

<400> SEQUENCE: 550

-continued gttctgcaag gactaaa 17

<210> SEQ ID NO 551
<211> LENGTH: 17
<212> TYPE: DNA
<213> ORGANISM: Homo sapiens

<400> SEQUENCE: 551
ttctgcaagg actaaag 17

<210> SEQ ID NO 552
<211> LENGTH: 17
<212> TYPE: DNA
<213> ORGANISM: Homo sapiens

<400> SEQUENCE: 552
tctgcaagga ctaaagt 17

<210> SEQ ID NO 553
<211> LENGTH: 17
<212> TYPE: DNA
<213> ORGANISM: Homo sapiens

<400> SEQUENCE: 553
ctgcaaggac taaagta 17

<210> SEQ ID NO 554
<211> LENGTH: 17
<212> TYPE: DNA
<213> ORGANISM: Homo sapiens

<400> SEQUENCE: 554
tgcaaggact aaagtac 17

<210> SEQ ID NO 555
<211> LENGTH: 17
<212> TYPE: DNA
<213> ORGANISM: Homo sapiens

<400> SEQUENCE: 555
gcaaggacta aagtaca 17

<210> SEQ ID NO 556
<211> LENGTH: 17
<212> TYPE: DNA
<213> ORGANISM: Homo sapiens

<400> SEQUENCE: 556
caaggactaa agtacag 17

<210> SEQ ID NO 557
<211> LENGTH: 17
<212> TYPE: DNA
<213> ORGANISM: Homo sapiens

<400> SEQUENCE: 557
aaggactaaa gtacagc 17

<210> SEQ ID NO 558
<211> LENGTH: 17
<212> TYPE: DNA
<213> ORGANISM: Homo sapiens

<400> SEQUENCE: 558

-continued aggactaaag tacagca 17

<210> SEQ ID NO 559
<211> LENGTH: 17
<212> TYPE: DNA
<213> ORGANISM: Homo sapiens

<400> SEQUENCE: 559
ggactaaagt acagcaa 17

<210> SEQ ID NO 560
<211> LENGTH: 17
<212> TYPE: DNA
<213> ORGANISM: Homo sapiens

<400> SEQUENCE: 560
gactaaagta cagcaag 17

<210> SEQ ID NO 561
<211> LENGTH: 17
<212> TYPE: DNA
<213> ORGANISM: Homo sapiens

<400> SEQUENCE: 561
actaaagtac agcaaga 17

<210> SEQ ID NO 562
<211> LENGTH: 17
<212> TYPE: DNA
<213> ORGANISM: Homo sapiens

<400> SEQUENCE: 562
ctaaagtaca gcaagag 17

<210> SEQ ID NO 563
<211> LENGTH: 17
<212> TYPE: DNA
<213> ORGANISM: Homo sapiens

<400> SEQUENCE: 563
taaagtacag caagagg 17

<210> SEQ ID NO 564
<211> LENGTH: 17
<212> TYPE: DNA
<213> ORGANISM: Homo sapiens

<400> SEQUENCE: 564
aaagtacagc aagagga 17

<210> SEQ ID NO 565
<211> LENGTH: 17
<212> TYPE: DNA
<213> ORGANISM: Homo sapiens

<400> SEQUENCE: 565
aagtacagca agaggag 17

<210> SEQ ID NO 566
<211> LENGTH: 17
<212> TYPE: DNA
<213> ORGANISM: Homo sapiens -continued

<400> SEQUENCE: 566
agtacagcaa gaggaga 17

<210> SEQ ID NO 567
<211> LENGTH: 17
<212> TYPE: DNA
<213> ORGANISM: Homo sapiens

<400> SEQUENCE: 567
gtacagcaag aggagag 17

<210> SEQ ID NO 568
<211> LENGTH: 17
<212> TYPE: DNA
<213> ORGANISM: Homo sapiens

<400> SEQUENCE: 568
tacagcaaga ggagaga 17

<210> SEQ ID NO 569
<211> LENGTH: 17
<212> TYPE: DNA
<213> ORGANISM: Homo sapiens

<400> SEQUENCE: 569
acagcaagag gagagag 17

<210> SEQ ID NO 570
<211> LENGTH: 17
<212> TYPE: DNA
<213> ORGANISM: Homo sapiens

<400> SEQUENCE: 570
cagcaagagg agagagg 17

<210> SEQ ID NO 571
<211> LENGTH: 17
<212> TYPE: DNA
<213> ORGANISM: Homo sapiens

<400> SEQUENCE: 571
agcaagagga gagaggt 17

<210> SEQ ID NO 572
<211> LENGTH: 17
<212> TYPE: DNA
<213> ORGANISM: Homo sapiens

<400> SEQUENCE: 572
gcaagaggag agaggtc 17

<210> SEQ ID NO 573
<211> LENGTH: 17
<212> TYPE: DNA
<213> ORGANISM: Homo sapiens

<400> SEQUENCE: 573
caagaggaga gaggtca 17

<210> SEQ ID NO 574
<211> LENGTH: 17
<212> TYPE: DNA
<213> ORGANISM: Homo sapiens

<400> SEQUENCE: 574
aagaggagag aggtcaa 17

<210> SEQ ID NO 575
<211> LENGTH: 17
<212> TYPE: DNA
<213> ORGANISM: Homo sapiens

<400> SEQUENCE: 575
agaggagaga ggtcaag 17

<210> SEQ ID NO 576
<211> LENGTH: 17
<212> TYPE: DNA
<213> ORGANISM: Homo sapiens

<400> SEQUENCE: 576
gaggagagag gtcaagc 17

<210> SEQ ID NO 577
<211> LENGTH: 17
<212> TYPE: DNA
<213> ORGANISM: Homo sapiens

<400> SEQUENCE: 577
aggagagagg tcaagcg 17

<210> SEQ ID NO 578
<211> LENGTH: 17
<212> TYPE: DNA
<213> ORGANISM: Homo sapiens

<400> SEQUENCE: 578
ggagagaggt caagcga 17

<210> SEQ ID NO 579
<211> LENGTH: 17
<212> TYPE: DNA
<213> ORGANISM: Homo sapiens

<400> SEQUENCE: 579
gagagaggtc aagcgag 17

<210> SEQ ID NO 580
<211> LENGTH: 17
<212> TYPE: DNA
<213> ORGANISM: Homo sapiens

<400> SEQUENCE: 580
agagaggtca agcgaga 17

<210> SEQ ID NO 581
<211> LENGTH: 17
<212> TYPE: DNA
<213> ORGANISM: Homo sapiens

<400> SEQUENCE: 581
gagaggtcaa gcgagaa 17

<210> SEQ ID NO 582
<211> LENGTH: 17
<212> TYPE: DNA

-continued

<213> ORGANISM: Homo sapiens

<400> SEQUENCE: 582
agaggtcaag cgagaag 17

<210> SEQ ID NO 583
<211> LENGTH: 17
<212> TYPE: DNA
<213> ORGANISM: Homo sapiens

<400> SEQUENCE: 583
gaggtcaagc gagaagc 17

<210> SEQ ID NO 584
<211> LENGTH: 17
<212> TYPE: DNA
<213> ORGANISM: Homo sapiens

<400> SEQUENCE: 584
aggtcaagcg agaagcg 17

<210> SEQ ID NO 585
<211> LENGTH: 17
<212> TYPE: DNA
<213> ORGANISM: Homo sapiens

<400> SEQUENCE: 585
ggtcaagcga gaagcgt 17

<210> SEQ ID NO 586
<211> LENGTH: 17
<212> TYPE: DNA
<213> ORGANISM: Homo sapiens

<400> SEQUENCE: 586
gtcaagcgag aagcgtg 17

<210> SEQ ID NO 587
<211> LENGTH: 17
<212> TYPE: DNA
<213> ORGANISM: Homo sapiens

<400> SEQUENCE: 587
tcaagcgaga agcgtgc 17

<210> SEQ ID NO 588
<211> LENGTH: 17
<212> TYPE: DNA
<213> ORGANISM: Homo sapiens

<400> SEQUENCE: 588
caagcgagaa gcgtgcg 17

<210> SEQ ID NO 589
<211> LENGTH: 17
<212> TYPE: DNA
<213> ORGANISM: Homo sapiens

<400> SEQUENCE: 589
aagcgagaag cgtgcgg 17

<210> SEQ ID NO 590
<211> LENGTH: 17

-continued

<212> TYPE: DNA
<213> ORGANISM: Homo sapiens

<400> SEQUENCE: 590
agcgagaagc gtgcggg 17

<210> SEQ ID NO 591
<211> LENGTH: 17
<212> TYPE: DNA
<213> ORGANISM: Homo sapiens

<400> SEQUENCE: 591
gcgagaagcg tgcggga 17

<210> SEQ ID NO 592
<211> LENGTH: 17
<212> TYPE: DNA
<213> ORGANISM: Homo sapiens

<400> SEQUENCE: 592
cgagaagcgt gcgggaa 17

<210> SEQ ID NO 593
<211> LENGTH: 17
<212> TYPE: DNA
<213> ORGANISM: Homo sapiens

<400> SEQUENCE: 593
gagaagcgtg cgggaag 17

<210> SEQ ID NO 594
<211> LENGTH: 17
<212> TYPE: DNA
<213> ORGANISM: Homo sapiens

<400> SEQUENCE: 594
agaagcgtgc gggaagc 17

<210> SEQ ID NO 595
<211> LENGTH: 17
<212> TYPE: DNA
<213> ORGANISM: Homo sapiens

<400> SEQUENCE: 595
gaagcgtgcg ggaagca 17

<210> SEQ ID NO 596
<211> LENGTH: 17
<212> TYPE: DNA
<213> ORGANISM: Homo sapiens

<400> SEQUENCE: 596
aagcgtgcgg gaagcac 17

<210> SEQ ID NO 597
<211> LENGTH: 17
<212> TYPE: DNA
<213> ORGANISM: Homo sapiens

<400> SEQUENCE: 597
agcgtgcggg aagcaca 17

<210> SEQ ID NO 598

-continued

<211> LENGTH: 17
<212> TYPE: DNA
<213> ORGANISM: Homo sapiens

<400> SEQUENCE: 598
gcgtgcggga agcacat 17

<210> SEQ ID NO 599
<211> LENGTH: 17
<212> TYPE: DNA
<213> ORGANISM: Homo sapiens

<400> SEQUENCE: 599
cgtgcgggaa gcacatg 17

<210> SEQ ID NO 600
<211> LENGTH: 17
<212> TYPE: DNA
<213> ORGANISM: Homo sapiens

<400> SEQUENCE: 600
gtgcgggaag cacatgc 17

<210> SEQ ID NO 601
<211> LENGTH: 17
<212> TYPE: DNA
<213> ORGANISM: Homo sapiens

<400> SEQUENCE: 601
tgcgggaagc acatgcc 17

<210> SEQ ID NO 602
<211> LENGTH: 17
<212> TYPE: DNA
<213> ORGANISM: Homo sapiens

<400> SEQUENCE: 602
gcgggaagca catgccc 17

<210> SEQ ID NO 603
<211> LENGTH: 17
<212> TYPE: DNA
<213> ORGANISM: Homo sapiens

<400> SEQUENCE: 603
cgggaagcac atgccct 17

<210> SEQ ID NO 604
<211> LENGTH: 17
<212> TYPE: DNA
<213> ORGANISM: Homo sapiens

<400> SEQUENCE: 604
gggaagcaca tgccctg 17

<210> SEQ ID NO 605
<211> LENGTH: 17
<212> TYPE: DNA
<213> ORGANISM: Homo sapiens

<400> SEQUENCE: 605
ggaagcacat gccctgg 17

-continued

<210> SEQ ID NO 606
<211> LENGTH: 17
<212> TYPE: DNA
<213> ORGANISM: Homo sapiens

<400> SEQUENCE: 606
gaagcacatg ccctggg 17

<210> SEQ ID NO 607
<211> LENGTH: 17
<212> TYPE: DNA
<213> ORGANISM: Homo sapiens

<400> SEQUENCE: 607
aagcacatgc cctgggg 17

<210> SEQ ID NO 608
<211> LENGTH: 17
<212> TYPE: DNA
<213> ORGANISM: Homo sapiens

<400> SEQUENCE: 608
agcacatgcc ctgggga 17

<210> SEQ ID NO 609
<211> LENGTH: 17
<212> TYPE: DNA
<213> ORGANISM: Homo sapiens

<400> SEQUENCE: 609
gcacatgccc tggggag 17

<210> SEQ ID NO 610
<211> LENGTH: 17
<212> TYPE: DNA
<213> ORGANISM: Homo sapiens

<400> SEQUENCE: 610
cacatgccct ggggagg 17

<210> SEQ ID NO 611
<211> LENGTH: 17
<212> TYPE: DNA
<213> ORGANISM: Homo sapiens

<400> SEQUENCE: 611
acatgccctg gggaggc 17

<210> SEQ ID NO 612
<211> LENGTH: 17
<212> TYPE: DNA
<213> ORGANISM: Homo sapiens

<400> SEQUENCE: 612
catgccctgg ggaggca 17

<210> SEQ ID NO 613
<211> LENGTH: 17
<212> TYPE: DNA
<213> ORGANISM: Homo sapiens

<400> SEQUENCE: 613
atgccctggg gaggcat 17

-continued

<210> SEQ ID NO 614
<211> LENGTH: 17
<212> TYPE: DNA
<213> ORGANISM: Homo sapiens

<400> SEQUENCE: 614
tgccctgggg aggcata 17

<210> SEQ ID NO 615
<211> LENGTH: 17
<212> TYPE: DNA
<213> ORGANISM: Homo sapiens

<400> SEQUENCE: 615
gccctgggga ggcatag 17

<210> SEQ ID NO 616
<211> LENGTH: 17
<212> TYPE: DNA
<213> ORGANISM: Homo sapiens

<400> SEQUENCE: 616
ccctggggag gcataga 17

<210> SEQ ID NO 617
<211> LENGTH: 17
<212> TYPE: DNA
<213> ORGANISM: Homo sapiens

<400> SEQUENCE: 617
cctggggagg catagaa 17

<210> SEQ ID NO 618
<211> LENGTH: 17
<212> TYPE: DNA
<213> ORGANISM: Homo sapiens

<400> SEQUENCE: 618
ctggggaggc atagaag 17

<210> SEQ ID NO 619
<211> LENGTH: 17
<212> TYPE: DNA
<213> ORGANISM: Homo sapiens

<400> SEQUENCE: 619
tggggaggca tagaagc 17

<210> SEQ ID NO 620
<211> LENGTH: 17
<212> TYPE: DNA
<213> ORGANISM: Homo sapiens

<400> SEQUENCE: 620
ggggaggcat agaagcc 17

<210> SEQ ID NO 621
<211> LENGTH: 17
<212> TYPE: DNA
<213> ORGANISM: Homo sapiens

<400> SEQUENCE: 621
gggaggcata gaagcca 17

<210> SEQ ID NO 622
<211> LENGTH: 17
<212> TYPE: DNA
<213> ORGANISM: Homo sapiens

<400> SEQUENCE: 622
ggaggcatag aagccac 17

<210> SEQ ID NO 623
<211> LENGTH: 17
<212> TYPE: DNA
<213> ORGANISM: Homo sapiens

<400> SEQUENCE: 623
gaggcataga agccaca 17

<210> SEQ ID NO 624
<211> LENGTH: 17
<212> TYPE: DNA
<213> ORGANISM: Homo sapiens

<400> SEQUENCE: 624
aggcatagaa gccacac 17

<210> SEQ ID NO 625
<211> LENGTH: 17
<212> TYPE: DNA
<213> ORGANISM: Homo sapiens

<400> SEQUENCE: 625
ggcatagaag ccacact 17

<210> SEQ ID NO 626
<211> LENGTH: 17
<212> TYPE: DNA
<213> ORGANISM: Homo sapiens

<400> SEQUENCE: 626
gcatagaagc cacactg 17

<210> SEQ ID NO 627
<211> LENGTH: 17
<212> TYPE: DNA
<213> ORGANISM: Homo sapiens

<400> SEQUENCE: 627
catagaagcc acactgg 17

<210> SEQ ID NO 628
<211> LENGTH: 17
<212> TYPE: DNA
<213> ORGANISM: Homo sapiens

<400> SEQUENCE: 628
atagaagcca cactggc 17

<210> SEQ ID NO 629
<211> LENGTH: 17
<212> TYPE: DNA
<213> ORGANISM: Homo sapiens

<400> SEQUENCE: 629

-continued tagaagccac actggca 17

<210> SEQ ID NO 630
<211> LENGTH: 17
<212> TYPE: DNA
<213> ORGANISM: Homo sapiens

<400> SEQUENCE: 630
agaagccaca ctggcag 17

<210> SEQ ID NO 631
<211> LENGTH: 17
<212> TYPE: DNA
<213> ORGANISM: Homo sapiens

<400> SEQUENCE: 631
gaagccacac tggcaga 17

<210> SEQ ID NO 632
<211> LENGTH: 17
<212> TYPE: DNA
<213> ORGANISM: Homo sapiens

<400> SEQUENCE: 632
aagccacact ggcagag 17

<210> SEQ ID NO 633
<211> LENGTH: 17
<212> TYPE: DNA
<213> ORGANISM: Homo sapiens

<400> SEQUENCE: 633
agccacactg gcagagc 17

<210> SEQ ID NO 634
<211> LENGTH: 17
<212> TYPE: DNA
<213> ORGANISM: Homo sapiens

<400> SEQUENCE: 634
gccacactgg cagagcg 17

<210> SEQ ID NO 635
<211> LENGTH: 17
<212> TYPE: DNA
<213> ORGANISM: Homo sapiens

<400> SEQUENCE: 635
ccacactggc agagcgg 17

<210> SEQ ID NO 636
<211> LENGTH: 17
<212> TYPE: DNA
<213> ORGANISM: Homo sapiens

<400> SEQUENCE: 636
cacactggca gagcggc 17

<210> SEQ ID NO 637
<211> LENGTH: 17
<212> TYPE: DNA
<213> ORGANISM: Homo sapiens

<400> SEQUENCE: 637

-continued acactggcag agcggcc 17

<210> SEQ ID NO 638
<211> LENGTH: 17
<212> TYPE: DNA
<213> ORGANISM: Homo sapiens

<400> SEQUENCE: 638
cactggcaga gcggcca 17

<210> SEQ ID NO 639
<211> LENGTH: 17
<212> TYPE: DNA
<213> ORGANISM: Homo sapiens

<400> SEQUENCE: 639
actggcagag cggccag 17

<210> SEQ ID NO 640
<211> LENGTH: 17
<212> TYPE: DNA
<213> ORGANISM: Homo sapiens

<400> SEQUENCE: 640
ctggcagagc ggccagc 17

<210> SEQ ID NO 641
<211> LENGTH: 17
<212> TYPE: DNA
<213> ORGANISM: Homo sapiens

<400> SEQUENCE: 641
tggcagagcg gccagca 17

<210> SEQ ID NO 642
<211> LENGTH: 17
<212> TYPE: DNA
<213> ORGANISM: Homo sapiens

<400> SEQUENCE: 642
ggcagagcgg ccagcac 17

<210> SEQ ID NO 643
<211> LENGTH: 17
<212> TYPE: DNA
<213> ORGANISM: Homo sapiens

<400> SEQUENCE: 643
gcagagcggc cagcaca 17

<210> SEQ ID NO 644
<211> LENGTH: 17
<212> TYPE: DNA
<213> ORGANISM: Homo sapiens

<400> SEQUENCE: 644
cagagcggcc agcacag 17

<210> SEQ ID NO 645
<211> LENGTH: 17
<212> TYPE: DNA
<213> ORGANISM: Homo sapiens -continued

<400> SEQUENCE: 645
agagcggcca gcacagg 17

<210> SEQ ID NO 646
<211> LENGTH: 17
<212> TYPE: DNA
<213> ORGANISM: Homo sapiens

<400> SEQUENCE: 646
gagcggccag cacaggt 17

<210> SEQ ID NO 647
<211> LENGTH: 17
<212> TYPE: DNA
<213> ORGANISM: Homo sapiens

<400> SEQUENCE: 647
agcggccagc acaggta 17

<210> SEQ ID NO 648
<211> LENGTH: 17
<212> TYPE: DNA
<213> ORGANISM: Homo sapiens

<400> SEQUENCE: 648
gcggccagca caggtag 17

<210> SEQ ID NO 649
<211> LENGTH: 17
<212> TYPE: DNA
<213> ORGANISM: Homo sapiens

<400> SEQUENCE: 649
cggccagcac aggtagc 17

<210> SEQ ID NO 650
<211> LENGTH: 17
<212> TYPE: DNA
<213> ORGANISM: Homo sapiens

<400> SEQUENCE: 650
ggccagcaca ggtagcc 17

<210> SEQ ID NO 651
<211> LENGTH: 17
<212> TYPE: DNA
<213> ORGANISM: Homo sapiens

<400> SEQUENCE: 651
gccagcacag gtagcca 17

<210> SEQ ID NO 652
<211> LENGTH: 17
<212> TYPE: DNA
<213> ORGANISM: Homo sapiens

<400> SEQUENCE: 652
ccagcacagg tagccag 17

<210> SEQ ID NO 653
<211> LENGTH: 17
<212> TYPE: DNA
<213> ORGANISM: Homo sapiens -continued

<400> SEQUENCE: 653
cagcacaggt agccagc 17

<210> SEQ ID NO 654
<211> LENGTH: 17
<212> TYPE: DNA
<213> ORGANISM: Homo sapiens

<400> SEQUENCE: 654
agcacaggta gccagca 17

<210> SEQ ID NO 655
<211> LENGTH: 17
<212> TYPE: DNA
<213> ORGANISM: Homo sapiens

<400> SEQUENCE: 655
gcacaggtag ccagcag 17

<210> SEQ ID NO 656
<211> LENGTH: 17
<212> TYPE: DNA
<213> ORGANISM: Homo sapiens

<400> SEQUENCE: 656
cacaggtagc cagcaga 17

<210> SEQ ID NO 657
<211> LENGTH: 17
<212> TYPE: DNA
<213> ORGANISM: Homo sapiens

<400> SEQUENCE: 657
acaggtagcc agcagag 17

<210> SEQ ID NO 658
<211> LENGTH: 17
<212> TYPE: DNA
<213> ORGANISM: Homo sapiens

<400> SEQUENCE: 658
caggtagcca gcagagg 17

<210> SEQ ID NO 659
<211> LENGTH: 17
<212> TYPE: DNA
<213> ORGANISM: Homo sapiens

<400> SEQUENCE: 659
aggtagccag cagaggc 17

<210> SEQ ID NO 660
<211> LENGTH: 17
<212> TYPE: DNA
<213> ORGANISM: Homo sapiens

<400> SEQUENCE: 660
ggtagccagc agaggca 17

<210> SEQ ID NO 661
<211> LENGTH: 17
<212> TYPE: DNA

-continued

<213> ORGANISM: Homo sapiens

<400> SEQUENCE: 661
gtagccagca gaggcat 17

<210> SEQ ID NO 662
<211> LENGTH: 17
<212> TYPE: DNA
<213> ORGANISM: Homo sapiens

<400> SEQUENCE: 662 agccagcag aggcatt 17

<210> SEQ ID NO 663
<211> LENGTH: 17
<212> TYPE: DNA
<213> ORGANISM: Homo sapiens

<400> SEQUENCE: 663
agccagcaga ggcattc 17

<210> SEQ ID NO 664
<211> LENGTH: 17
<212> TYPE: DNA
<213> ORGANISM: Homo sapiens

<400> SEQUENCE: 664
gccagcagag gcattct 17

<210> SEQ ID NO 665
<211> LENGTH: 17
<212> TYPE: DNA
<213> ORGANISM: Homo sapiens

<400> SEQUENCE: 665
ccagcagagg cattctt 17

<210> SEQ ID NO 666
<211> LENGTH: 17
<212> TYPE: DNA
<213> ORGANISM: Homo sapiens

<400> SEQUENCE: 666
cagcagaggc attcttg 17

<210> SEQ ID NO 667
<211> LENGTH: 17
<212> TYPE: DNA
<213> ORGANISM: Homo sapiens

<400> SEQUENCE: 667
agcagaggca ttcttgg 17

<210> SEQ ID NO 668
<211> LENGTH: 17
<212> TYPE: DNA
<213> ORGANISM: Homo sapiens

<400> SEQUENCE: 668
gcagaggcat tcttggg 17

<210> SEQ ID NO 669
<211> LENGTH: 17

-continued

<212> TYPE: DNA
<213> ORGANISM: Homo sapiens

<400> SEQUENCE: 669
cagaggcatt cttgggg 17

<210> SEQ ID NO 670
<211> LENGTH: 17
<212> TYPE: DNA
<213> ORGANISM: Homo sapiens

<400> SEQUENCE: 670
agaggcattc ttggggc 17

<210> SEQ ID NO 671
<211> LENGTH: 17
<212> TYPE: DNA
<213> ORGANISM: Homo sapiens

<400> SEQUENCE: 671
gaggcattct tggggct 17

<210> SEQ ID NO 672
<211> LENGTH: 17
<212> TYPE: DNA
<213> ORGANISM: Homo sapiens

<400> SEQUENCE: 672
aggcattctt ggggcta 17

<210> SEQ ID NO 673
<211> LENGTH: 17
<212> TYPE: DNA
<213> ORGANISM: Homo sapiens

<400> SEQUENCE: 673
ggcattcttg gggctat 17

<210> SEQ ID NO 674
<211> LENGTH: 17
<212> TYPE: DNA
<213> ORGANISM: Homo sapiens

<400> SEQUENCE: 674
gcattcttgg ggctatt 17

<210> SEQ ID NO 675
<211> LENGTH: 17
<212> TYPE: DNA
<213> ORGANISM: Homo sapiens

<400> SEQUENCE: 675
cattcttggg gctattt 17

<210> SEQ ID NO 676
<211> LENGTH: 17
<212> TYPE: DNA
<213> ORGANISM: Homo sapiens

<400> SEQUENCE: 676
attcttgggg ctatttg 17

<210> SEQ ID NO 677

-continued

<211> LENGTH: 17
<212> TYPE: DNA
<213> ORGANISM: Homo sapiens

<400> SEQUENCE: 677
ttcttggggc tatttga 17

<210> SEQ ID NO 678
<211> LENGTH: 17
<212> TYPE: DNA
<213> ORGANISM: Homo sapiens

<400> SEQUENCE: 678
tcttggggct atttgaa 17

<210> SEQ ID NO 679
<211> LENGTH: 17
<212> TYPE: DNA
<213> ORGANISM: Homo sapiens

<400> SEQUENCE: 679
cttggggcta tttgaaa 17

<210> SEQ ID NO 680
<211> LENGTH: 17
<212> TYPE: DNA
<213> ORGANISM: Homo sapiens

<400> SEQUENCE: 680
ttggggctat ttgaaaa 17

<210> SEQ ID NO 681
<211> LENGTH: 17
<212> TYPE: DNA
<213> ORGANISM: Homo sapiens

<400> SEQUENCE: 681
tggggctatt tgaaaaa 17

<210> SEQ ID NO 682
<211> LENGTH: 17
<212> TYPE: DNA
<213> ORGANISM: Homo sapiens

<400> SEQUENCE: 682
ggggctattt gaaaaag 17

<210> SEQ ID NO 683
<211> LENGTH: 17
<212> TYPE: DNA
<213> ORGANISM: Homo sapiens

<400> SEQUENCE: 683
gggctatttg aaaaagt 17

<210> SEQ ID NO 684
<211> LENGTH: 17
<212> TYPE: DNA
<213> ORGANISM: Homo sapiens

<400> SEQUENCE: 684
ggctatttga aaaagtt 17

-continued

<210> SEQ ID NO 685
<211> LENGTH: 17
<212> TYPE: DNA
<213> ORGANISM: Homo sapiens

<400> SEQUENCE: 685
gctatttgaa aaagttt 17

<210> SEQ ID NO 686
<211> LENGTH: 17
<212> TYPE: DNA
<213> ORGANISM: Homo sapiens

<400> SEQUENCE: 686
ctatttgaaa aagtttg 17

<210> SEQ ID NO 687
<211> LENGTH: 17
<212> TYPE: DNA
<213> ORGANISM: Homo sapiens

<400> SEQUENCE: 687
tatttgaaaa agtttgg 17

<210> SEQ ID NO 688
<211> LENGTH: 17
<212> TYPE: DNA
<213> ORGANISM: Homo sapiens

<400> SEQUENCE: 688
atttgaaaaa gtttggt 17

<210> SEQ ID NO 689
<211> LENGTH: 17
<212> TYPE: DNA
<213> ORGANISM: Homo sapiens

<400> SEQUENCE: 689
tttgaaaaag tttggtc 17

<210> SEQ ID NO 690
<211> LENGTH: 17
<212> TYPE: DNA
<213> ORGANISM: Homo sapiens

<400> SEQUENCE: 690
ttgaaaaagt ttggtct 17

<210> SEQ ID NO 691
<211> LENGTH: 17
<212> TYPE: DNA
<213> ORGANISM: Homo sapiens

<400> SEQUENCE: 691
tgaaaaagtt tggtctg 17

<210> SEQ ID NO 692
<211> LENGTH: 17
<212> TYPE: DNA
<213> ORGANISM: Homo sapiens

<400> SEQUENCE: 692
gaaaaagttt ggtctgt 17

-continued

<210> SEQ ID NO 693
<211> LENGTH: 17
<212> TYPE: DNA
<213> ORGANISM: Homo sapiens

<400> SEQUENCE: 693
aaaaagtttg gtctgtg 17

<210> SEQ ID NO 694
<211> LENGTH: 17
<212> TYPE: DNA
<213> ORGANISM: Homo sapiens

<400> SEQUENCE: 694
aaaagtttgg tctgtga 17

<210> SEQ ID NO 695
<211> LENGTH: 17
<212> TYPE: DNA
<213> ORGANISM: Homo sapiens

<400> SEQUENCE: 695
aaagtttggt ctgtgaa 17

<210> SEQ ID NO 696
<211> LENGTH: 17
<212> TYPE: DNA
<213> ORGANISM: Homo sapiens

<400> SEQUENCE: 696
aagtttggtc tgtgaac 17

<210> SEQ ID NO 697
<211> LENGTH: 17
<212> TYPE: DNA
<213> ORGANISM: Homo sapiens

<400> SEQUENCE: 697
agtttggtct gtgaaca 17

<210> SEQ ID NO 698
<211> LENGTH: 17
<212> TYPE: DNA
<213> ORGANISM: Homo sapiens

<400> SEQUENCE: 698
gtttggtctg tgaacaa 17

<210> SEQ ID NO 699
<211> LENGTH: 17
<212> TYPE: DNA
<213> ORGANISM: Homo sapiens

<400> SEQUENCE: 699
tttggtctgt gaacaaa 17

<210> SEQ ID NO 700
<211> LENGTH: 17
<212> TYPE: DNA
<213> ORGANISM: Homo sapiens

<400> SEQUENCE: 700
ttggtctgtg aacaaaa 17

-continued

<210> SEQ ID NO 701
<211> LENGTH: 17
<212> TYPE: DNA
<213> ORGANISM: Homo sapiens

<400> SEQUENCE: 701
tggtctgtga acaaaac 17

<210> SEQ ID NO 702
<211> LENGTH: 17
<212> TYPE: DNA
<213> ORGANISM: Homo sapiens

<400> SEQUENCE: 702
ggtctgtgaa caaaaca 17

<210> SEQ ID NO 703
<211> LENGTH: 17
<212> TYPE: DNA
<213> ORGANISM: Homo sapiens

<400> SEQUENCE: 703
gtctgtgaac aaaacag 17

<210> SEQ ID NO 704
<211> LENGTH: 17
<212> TYPE: DNA
<213> ORGANISM: Homo sapiens

<400> SEQUENCE: 704
tctgtgaaca aaacagt 17

<210> SEQ ID NO 705
<211> LENGTH: 17
<212> TYPE: DNA
<213> ORGANISM: Homo sapiens

<400> SEQUENCE: 705
ctgtgaacaa aacagtt 17

<210> SEQ ID NO 706
<211> LENGTH: 17
<212> TYPE: DNA
<213> ORGANISM: Homo sapiens

<400> SEQUENCE: 706
tgtgaacaaa acagttt 17

<210> SEQ ID NO 707
<211> LENGTH: 17
<212> TYPE: DNA
<213> ORGANISM: Homo sapiens

<400> SEQUENCE: 707
gtgaacaaaa cagtttc 17

<210> SEQ ID NO 708
<211> LENGTH: 17
<212> TYPE: DNA
<213> ORGANISM: Homo sapiens

<400> SEQUENCE: 708

-continued tgaacaaaac agtttcc 17

<210> SEQ ID NO 709
<211> LENGTH: 17
<212> TYPE: DNA
<213> ORGANISM: Homo sapiens

<400> SEQUENCE: 709
gaacaaaaca gtttccc 17

<210> SEQ ID NO 710
<211> LENGTH: 17
<212> TYPE: DNA
<213> ORGANISM: Homo sapiens

<400> SEQUENCE: 710
aacaaaacag tttccct 17

<210> SEQ ID NO 711
<211> LENGTH: 17
<212> TYPE: DNA
<213> ORGANISM: Homo sapiens

<400> SEQUENCE: 711
acaaaacagt ttccctg 17

<210> SEQ ID NO 712
<211> LENGTH: 17
<212> TYPE: DNA
<213> ORGANISM: Homo sapiens

<400> SEQUENCE: 712
caaaacagtt tccctgg 17

<210> SEQ ID NO 713
<211> LENGTH: 17
<212> TYPE: DNA
<213> ORGANISM: Homo sapiens

<400> SEQUENCE: 713
aaaacagttt ccctggt 17

<210> SEQ ID NO 714
<211> LENGTH: 17
<212> TYPE: DNA
<213> ORGANISM: Homo sapiens

<400> SEQUENCE: 714
aaacagtttc cctggtg 17

<210> SEQ ID NO 715
<211> LENGTH: 17
<212> TYPE: DNA
<213> ORGANISM: Homo sapiens

<400> SEQUENCE: 715
aacagtttcc ctggtga 17

<210> SEQ ID NO 716
<211> LENGTH: 17
<212> TYPE: DNA
<213> ORGANISM: Homo sapiens

<400> SEQUENCE: 716

-continued acagtttccc tggtgac 17

<210> SEQ ID NO 717
<211> LENGTH: 17
<212> TYPE: DNA
<213> ORGANISM: Homo sapiens

<400> SEQUENCE: 717
cagtttccct ggtgact 17

<210> SEQ ID NO 718
<211> LENGTH: 17
<212> TYPE: DNA
<213> ORGANISM: Homo sapiens

<400> SEQUENCE: 718
agtttccctg gtgactg 17

<210> SEQ ID NO 719
<211> LENGTH: 17
<212> TYPE: DNA
<213> ORGANISM: Homo sapiens

<400> SEQUENCE: 719
gtttccctgg tgactgc 17

<210> SEQ ID NO 720
<211> LENGTH: 17
<212> TYPE: DNA
<213> ORGANISM: Homo sapiens

<400> SEQUENCE: 720
tttccctggt gactgca 17

<210> SEQ ID NO 721
<211> LENGTH: 17
<212> TYPE: DNA
<213> ORGANISM: Homo sapiens

<400> SEQUENCE: 721
ttccctggtg actgcaa 17

<210> SEQ ID NO 722
<211> LENGTH: 17
<212> TYPE: DNA
<213> ORGANISM: Homo sapiens

<400> SEQUENCE: 722
tccctggtga ctgcaaa 17

<210> SEQ ID NO 723
<211> LENGTH: 17
<212> TYPE: DNA
<213> ORGANISM: Homo sapiens

<400> SEQUENCE: 723
ccctggtgac tgcaaat 17

<210> SEQ ID NO 724
<211> LENGTH: 17
<212> TYPE: DNA
<213> ORGANISM: Homo sapiens -continued

<400> SEQUENCE: 724
cctggtgact gcaaatc 17

<210> SEQ ID NO 725
<211> LENGTH: 17
<212> TYPE: DNA
<213> ORGANISM: Homo sapiens

<400> SEQUENCE: 725
ctggtgactg caaatcc 17

<210> SEQ ID NO 726
<211> LENGTH: 17
<212> TYPE: DNA
<213> ORGANISM: Homo sapiens

<400> SEQUENCE: 726
tggtgactgc aaatcca 17

<210> SEQ ID NO 727
<211> LENGTH: 17
<212> TYPE: DNA
<213> ORGANISM: Homo sapiens

<400> SEQUENCE: 727
ggtgactgca aatccat 17

<210> SEQ ID NO 728
<211> LENGTH: 17
<212> TYPE: DNA
<213> ORGANISM: Homo sapiens

<400> SEQUENCE: 728
gtgactgcaa atccatt 17

<210> SEQ ID NO 729
<211> LENGTH: 17
<212> TYPE: DNA
<213> ORGANISM: Homo sapiens

<400> SEQUENCE: 729
tgactgcaaa tccattg 17

<210> SEQ ID NO 730
<211> LENGTH: 17
<212> TYPE: DNA
<213> ORGANISM: Homo sapiens

<400> SEQUENCE: 730
gactgcaaat ccattgc 17

<210> SEQ ID NO 731
<211> LENGTH: 17
<212> TYPE: DNA
<213> ORGANISM: Homo sapiens

<400> SEQUENCE: 731
actgcaaatc cattgct 17

<210> SEQ ID NO 732
<211> LENGTH: 17
<212> TYPE: DNA
<213> ORGANISM: Homo sapiens -continued

<400> SEQUENCE: 732
ctgcaaatcc attgcta 17

<210> SEQ ID NO 733
<211> LENGTH: 17
<212> TYPE: DNA
<213> ORGANISM: Homo sapiens

<400> SEQUENCE: 733
tgcaaatcca ttgctag 17

<210> SEQ ID NO 734
<211> LENGTH: 17
<212> TYPE: DNA
<213> ORGANISM: Homo sapiens

<400> SEQUENCE: 734
gcaaatccat tgctagc 17

<210> SEQ ID NO 735
<211> LENGTH: 17
<212> TYPE: DNA
<213> ORGANISM: Homo sapiens

<400> SEQUENCE: 735
caaatccatt gctagct 17

<210> SEQ ID NO 736
<211> LENGTH: 17
<212> TYPE: DNA
<213> ORGANISM: Homo sapiens

<400> SEQUENCE: 736
aaatccattg ctagctg 17

<210> SEQ ID NO 737
<211> LENGTH: 17
<212> TYPE: DNA
<213> ORGANISM: Homo sapiens

<400> SEQUENCE: 737
aatccattgc tagctgc 17

<210> SEQ ID NO 738
<211> LENGTH: 17
<212> TYPE: DNA
<213> ORGANISM: Homo sapiens

<400> SEQUENCE: 738
atccattgct agctgcc 17

<210> SEQ ID NO 739
<211> LENGTH: 17
<212> TYPE: DNA
<213> ORGANISM: Homo sapiens

<400> SEQUENCE: 739
tccattgcta gctgcct 17

<210> SEQ ID NO 740
<211> LENGTH: 17
<212> TYPE: DNA

-continued

<213> ORGANISM: Homo sapiens

<400> SEQUENCE: 740
ccattgctag ctgcctc 17

<210> SEQ ID NO 741
<211> LENGTH: 17
<212> TYPE: DNA
<213> ORGANISM: Homo sapiens

<400> SEQUENCE: 741
cattgctagc tgcctct 17

<210> SEQ ID NO 742
<211> LENGTH: 17
<212> TYPE: DNA
<213> ORGANISM: Homo sapiens

<400> SEQUENCE: 742
attgctagct gcctctt 17

<210> SEQ ID NO 743
<211> LENGTH: 17
<212> TYPE: DNA
<213> ORGANISM: Homo sapiens

<400> SEQUENCE: 743
ttgctagctg cctcttt 17

<210> SEQ ID NO 744
<211> LENGTH: 17
<212> TYPE: DNA
<213> ORGANISM: Homo sapiens

<400> SEQUENCE: 744
tgctagctgc ctctttc 17

<210> SEQ ID NO 745
<211> LENGTH: 17
<212> TYPE: DNA
<213> ORGANISM: Homo sapiens

<400> SEQUENCE: 745
gctagctgcc tctttct 17

<210> SEQ ID NO 746
<211> LENGTH: 17
<212> TYPE: DNA
<213> ORGANISM: Homo sapiens

<400> SEQUENCE: 746
ctagctgcct ctttctc 17

<210> SEQ ID NO 747
<211> LENGTH: 17
<212> TYPE: DNA
<213> ORGANISM: Homo sapiens

<400> SEQUENCE: 747
tagctgcctc tttctcg 17

<210> SEQ ID NO 748
<211> LENGTH: 17

-continued

<212> TYPE: DNA
<213> ORGANISM: Homo sapiens

<400> SEQUENCE: 748
agctgcctct ttctcgt 17

<210> SEQ ID NO 749
<211> LENGTH: 17
<212> TYPE: DNA
<213> ORGANISM: Homo sapiens

<400> SEQUENCE: 749
gctgcctctt tctcgtc 17

<210> SEQ ID NO 750
<211> LENGTH: 17
<212> TYPE: DNA
<213> ORGANISM: Homo sapiens

<400> SEQUENCE: 750
ctgcctcttt ctcgtct 17

<210> SEQ ID NO 751
<211> LENGTH: 17
<212> TYPE: DNA
<213> ORGANISM: Homo sapiens

<400> SEQUENCE: 751
tgcctctttc tcgtctg 17

<210> SEQ ID NO 752
<211> LENGTH: 17
<212> TYPE: DNA
<213> ORGANISM: Homo sapiens

<400> SEQUENCE: 752
gcctctttct cgtctgc 17

<210> SEQ ID NO 753
<211> LENGTH: 17
<212> TYPE: DNA
<213> ORGANISM: Homo sapiens

<400> SEQUENCE: 753
cctctttctc gtctgcc 17

<210> SEQ ID NO 754
<211> LENGTH: 17
<212> TYPE: DNA
<213> ORGANISM: Homo sapiens

<400> SEQUENCE: 754
ctctttctcg tctgccc 17

<210> SEQ ID NO 755
<211> LENGTH: 17
<212> TYPE: DNA
<213> ORGANISM: Homo sapiens

<400> SEQUENCE: 755
tctttctcgt ctgccca 17

<210> SEQ ID NO 756

-continued

<211> LENGTH: 17
<212> TYPE: DNA
<213> ORGANISM: Homo sapiens

<400> SEQUENCE: 756
ctttctcgtc tgcccat 17

<210> SEQ ID NO 757
<211> LENGTH: 17
<212> TYPE: DNA
<213> ORGANISM: Homo sapiens

<400> SEQUENCE: 757
tttctcgtct gcccatc 17

<210> SEQ ID NO 758
<211> LENGTH: 17
<212> TYPE: DNA
<213> ORGANISM: Homo sapiens

<400> SEQUENCE: 758
ttctcgtctg cccatca 17

<210> SEQ ID NO 759
<211> LENGTH: 17
<212> TYPE: DNA
<213> ORGANISM: Homo sapiens

<400> SEQUENCE: 759
tctcgtctgc ccatcac 17

<210> SEQ ID NO 760
<211> LENGTH: 17
<212> TYPE: DNA
<213> ORGANISM: Homo sapiens

<400> SEQUENCE: 760
ctcgtctgcc catcact 17

<210> SEQ ID NO 761
<211> LENGTH: 17
<212> TYPE: DNA
<213> ORGANISM: Homo sapiens

<400> SEQUENCE: 761
tcgtctgccc atcactc 17

<210> SEQ ID NO 762
<211> LENGTH: 17
<212> TYPE: DNA
<213> ORGANISM: Homo sapiens

<400> SEQUENCE: 762
cgtctgccca tcactct 17

<210> SEQ ID NO 763
<211> LENGTH: 17
<212> TYPE: DNA
<213> ORGANISM: Homo sapiens

<400> SEQUENCE: 763
gtctgcccat cactctg 17

-continued

<210> SEQ ID NO 764
<211> LENGTH: 17
<212> TYPE: DNA
<213> ORGANISM: Homo sapiens

<400> SEQUENCE: 764
tctgcccatc actctgg 17

<210> SEQ ID NO 765
<211> LENGTH: 17
<212> TYPE: DNA
<213> ORGANISM: Homo sapiens

<400> SEQUENCE: 765
ctgcccatca ctctggt 17

<210> SEQ ID NO 766
<211> LENGTH: 17
<212> TYPE: DNA
<213> ORGANISM: Homo sapiens

<400> SEQUENCE: 766
tgcccatcac tctggtg 17

<210> SEQ ID NO 767
<211> LENGTH: 17
<212> TYPE: DNA
<213> ORGANISM: Homo sapiens

<400> SEQUENCE: 767
gcccatcact ctggtgt 17

<210> SEQ ID NO 768
<211> LENGTH: 17
<212> TYPE: DNA
<213> ORGANISM: Homo sapiens

<400> SEQUENCE: 768
cccatcactc tggtgtg 17

<210> SEQ ID NO 769
<211> LENGTH: 17
<212> TYPE: DNA
<213> ORGANISM: Homo sapiens

<400> SEQUENCE: 769
ccatcactct ggtgtgg 17

<210> SEQ ID NO 770
<211> LENGTH: 17
<212> TYPE: DNA
<213> ORGANISM: Homo sapiens

<400> SEQUENCE: 770
catcactctg gtgtggt 17

<210> SEQ ID NO 771
<211> LENGTH: 17
<212> TYPE: DNA
<213> ORGANISM: Homo sapiens

<400> SEQUENCE: 771
atcactctgg tgtggta 17

-continued

<210> SEQ ID NO 772
<211> LENGTH: 17
<212> TYPE: DNA
<213> ORGANISM: Homo sapiens

<400> SEQUENCE: 772
tcactctggt gtggtac 17

<210> SEQ ID NO 773
<211> LENGTH: 17
<212> TYPE: DNA
<213> ORGANISM: Homo sapiens

<400> SEQUENCE: 773
cactctggtg tggtacc 17

<210> SEQ ID NO 774
<211> LENGTH: 17
<212> TYPE: DNA
<213> ORGANISM: Homo sapiens

<400> SEQUENCE: 774
actctggtgt ggtaccc 17

<210> SEQ ID NO 775
<211> LENGTH: 17
<212> TYPE: DNA
<213> ORGANISM: Homo sapiens

<400> SEQUENCE: 775
ctctggtgtg gtaccca 17

<210> SEQ ID NO 776
<211> LENGTH: 17
<212> TYPE: DNA
<213> ORGANISM: Homo sapiens

<400> SEQUENCE: 776
tctggtgtgg tacccag 17

<210> SEQ ID NO 777
<211> LENGTH: 17
<212> TYPE: DNA
<213> ORGANISM: Homo sapiens

<400> SEQUENCE: 777
ctggtgtggt acccaga 17

<210> SEQ ID NO 778
<211> LENGTH: 17
<212> TYPE: DNA
<213> ORGANISM: Homo sapiens

<400> SEQUENCE: 778
tggtgtggta cccagaa 17

<210> SEQ ID NO 779
<211> LENGTH: 17
<212> TYPE: DNA
<213> ORGANISM: Homo sapiens

<400> SEQUENCE: 779
ggtgtggtac ccagaag 17

-continued

<210> SEQ ID NO 780
<211> LENGTH: 17
<212> TYPE: DNA
<213> ORGANISM: Homo sapiens

<400> SEQUENCE: 780
gtgtggtacc cagaagt 17

<210> SEQ ID NO 781
<211> LENGTH: 17
<212> TYPE: DNA
<213> ORGANISM: Homo sapiens

<400> SEQUENCE: 781
tgtggtaccc agaagtt 17

<210> SEQ ID NO 782
<211> LENGTH: 17
<212> TYPE: DNA
<213> ORGANISM: Homo sapiens

<400> SEQUENCE: 782
gtggtaccca gaagttg 17

<210> SEQ ID NO 783
<211> LENGTH: 17
<212> TYPE: DNA
<213> ORGANISM: Homo sapiens

<400> SEQUENCE: 783
tggtacccag aagttga 17

<210> SEQ ID NO 784
<211> LENGTH: 17
<212> TYPE: DNA
<213> ORGANISM: Homo sapiens

<400> SEQUENCE: 784
ggtacccaga agttgac 17

<210> SEQ ID NO 785
<211> LENGTH: 17
<212> TYPE: DNA
<213> ORGANISM: Homo sapiens

<400> SEQUENCE: 785
gtacccagaa gttgact 17

<210> SEQ ID NO 786
<211> LENGTH: 17
<212> TYPE: DNA
<213> ORGANISM: Homo sapiens

<400> SEQUENCE: 786
tacccagaag ttgactt 17

<210> SEQ ID NO 787
<211> LENGTH: 17
<212> TYPE: DNA
<213> ORGANISM: Homo sapiens

<400> SEQUENCE: 787

-continued acccagaagt tgacttc 17

<210> SEQ ID NO 788
<211> LENGTH: 17
<212> TYPE: DNA
<213> ORGANISM: Homo sapiens

<400> SEQUENCE: 788
cccagaagtt gacttct 17

<210> SEQ ID NO 789
<211> LENGTH: 17
<212> TYPE: DNA
<213> ORGANISM: Homo sapiens

<400> SEQUENCE: 789
ccagaagttg acttctg 17

<210> SEQ ID NO 790
<211> LENGTH: 17
<212> TYPE: DNA
<213> ORGANISM: Homo sapiens

<400> SEQUENCE: 790
cagaagttga cttctgg 17

<210> SEQ ID NO 791
<211> LENGTH: 17
<212> TYPE: DNA
<213> ORGANISM: Homo sapiens

<400> SEQUENCE: 791
agaagttgac ttctggt 17

<210> SEQ ID NO 792
<211> LENGTH: 17
<212> TYPE: DNA
<213> ORGANISM: Homo sapiens

<400> SEQUENCE: 792
gaagttgact tctggtt 17

<210> SEQ ID NO 793
<211> LENGTH: 17
<212> TYPE: DNA
<213> ORGANISM: Homo sapiens

<400> SEQUENCE: 793
aagttgactt ctggttc 17

<210> SEQ ID NO 794
<211> LENGTH: 17
<212> TYPE: DNA
<213> ORGANISM: Homo sapiens

<400> SEQUENCE: 794
agttgacttc tggttct 17

<210> SEQ ID NO 795
<211> LENGTH: 17
<212> TYPE: DNA
<213> ORGANISM: Homo sapiens

<400> SEQUENCE: 795

-continued gttgacttct ggttctg 17

<210> SEQ ID NO 796
<211> LENGTH: 17
<212> TYPE: DNA
<213> ORGANISM: Homo sapiens

<400> SEQUENCE: 796
ttgacttctg gttctgt 17

<210> SEQ ID NO 797
<211> LENGTH: 17
<212> TYPE: DNA
<213> ORGANISM: Homo sapiens

<400> SEQUENCE: 797
tgacttctgg ttctgta 17

<210> SEQ ID NO 798
<211> LENGTH: 17
<212> TYPE: DNA
<213> ORGANISM: Homo sapiens

<400> SEQUENCE: 798
gacttctggt tctgtag 17

<210> SEQ ID NO 799
<211> LENGTH: 17
<212> TYPE: DNA
<213> ORGANISM: Homo sapiens

<400> SEQUENCE: 799
acttctggtt ctgtaga 17

<210> SEQ ID NO 800
<211> LENGTH: 17
<212> TYPE: DNA
<213> ORGANISM: Homo sapiens

<400> SEQUENCE: 800
cttctggttc tgtagaa 17

<210> SEQ ID NO 801
<211> LENGTH: 17
<212> TYPE: DNA
<213> ORGANISM: Homo sapiens

<400> SEQUENCE: 801
ttctggttct gtagaaa 17

<210> SEQ ID NO 802
<211> LENGTH: 17
<212> TYPE: DNA
<213> ORGANISM: Homo sapiens

<400> SEQUENCE: 802
tctggttctg tagaaag 17

<210> SEQ ID NO 803
<211> LENGTH: 17
<212> TYPE: DNA
<213> ORGANISM: Homo sapiens -continued

<400> SEQUENCE: 803
ctggttctgt agaaaga 17

<210> SEQ ID NO 804
<211> LENGTH: 17
<212> TYPE: DNA
<213> ORGANISM: Homo sapiens

<400> SEQUENCE: 804
tggttctgta gaaagag 17

<210> SEQ ID NO 805
<211> LENGTH: 17
<212> TYPE: DNA
<213> ORGANISM: Homo sapiens

<400> SEQUENCE: 805
ggttctgtag aaagagc 17

<210> SEQ ID NO 806
<211> LENGTH: 17
<212> TYPE: DNA
<213> ORGANISM: Homo sapiens

<400> SEQUENCE: 806
gttctgtaga aagagct 17

<210> SEQ ID NO 807
<211> LENGTH: 17
<212> TYPE: DNA
<213> ORGANISM: Homo sapiens

<400> SEQUENCE: 807
ttctgtagaa agagcta 17

<210> SEQ ID NO 808
<211> LENGTH: 17
<212> TYPE: DNA
<213> ORGANISM: Homo sapiens

<400> SEQUENCE: 808
tctgtagaaa gagctag 17

<210> SEQ ID NO 809
<211> LENGTH: 17
<212> TYPE: DNA
<213> ORGANISM: Homo sapiens

<400> SEQUENCE: 809
ctgtagaaag agctagg 17

<210> SEQ ID NO 810
<211> LENGTH: 17
<212> TYPE: DNA
<213> ORGANISM: Homo sapiens

<400> SEQUENCE: 810
tgtagaaaga gctaggg 17

<210> SEQ ID NO 811
<211> LENGTH: 17
<212> TYPE: DNA
<213> ORGANISM: Homo sapiens -continued

<400> SEQUENCE: 811
gtagaaagag ctagggg 17

<210> SEQ ID NO 812
<211> LENGTH: 17
<212> TYPE: DNA
<213> ORGANISM: Homo sapiens

<400> SEQUENCE: 812
tagaaagagc tagggga 17

<210> SEQ ID NO 813
<211> LENGTH: 17
<212> TYPE: DNA
<213> ORGANISM: Homo sapiens

<400> SEQUENCE: 813
agaaagagct aggggag 17

<210> SEQ ID NO 814
<211> LENGTH: 17
<212> TYPE: DNA
<213> ORGANISM: Homo sapiens

<400> SEQUENCE: 814
gaaagagcta ggggagg 17

<210> SEQ ID NO 815
<211> LENGTH: 17
<212> TYPE: DNA
<213> ORGANISM: Homo sapiens

<400> SEQUENCE: 815
aaagagctag gggaggt 17

<210> SEQ ID NO 816
<211> LENGTH: 17
<212> TYPE: DNA
<213> ORGANISM: Homo sapiens

<400> SEQUENCE: 816
aagagctagg ggaggta 17

<210> SEQ ID NO 817
<211> LENGTH: 17
<212> TYPE: DNA
<213> ORGANISM: Homo sapiens

<400> SEQUENCE: 817
agagctaggg gaggtat 17

<210> SEQ ID NO 818
<211> LENGTH: 17
<212> TYPE: DNA
<213> ORGANISM: Homo sapiens

<400> SEQUENCE: 818
gagctagggg aggtatg 17

<210> SEQ ID NO 819
<211> LENGTH: 17
<212> TYPE: DNA

-continued

<213> ORGANISM: Homo sapiens

<400> SEQUENCE: 819
agctagggga ggtatga 17

<210> SEQ ID NO 820
<211> LENGTH: 17
<212> TYPE: DNA
<213> ORGANISM: Homo sapiens

<400> SEQUENCE: 820
gctaggggag gtatgat 17

<210> SEQ ID NO 821
<211> LENGTH: 17
<212> TYPE: DNA
<213> ORGANISM: Homo sapiens

<400> SEQUENCE: 821
ctaggggagg tatgatg 17

<210> SEQ ID NO 822
<211> LENGTH: 17
<212> TYPE: DNA
<213> ORGANISM: Homo sapiens

<400> SEQUENCE: 822
taggggaggt atgatgt 17

<210> SEQ ID NO 823
<211> LENGTH: 17
<212> TYPE: DNA
<213> ORGANISM: Homo sapiens

<400> SEQUENCE: 823
aggggaggta tgatgtg 17

<210> SEQ ID NO 824
<211> LENGTH: 17
<212> TYPE: DNA
<213> ORGANISM: Homo sapiens

<400> SEQUENCE: 824
ggggaggtat gatgtgc 17

<210> SEQ ID NO 825
<211> LENGTH: 17
<212> TYPE: DNA
<213> ORGANISM: Homo sapiens

<400> SEQUENCE: 825
gggaggtatg atgtgct 17

<210> SEQ ID NO 826
<211> LENGTH: 17
<212> TYPE: DNA
<213> ORGANISM: Homo sapiens

<400> SEQUENCE: 826
ggaggtatga tgtgctt 17

<210> SEQ ID NO 827
<211> LENGTH: 17

-continued

<212> TYPE: DNA
<213> ORGANISM: Homo sapiens

<400> SEQUENCE: 827
gaggtatgat gtgctta 17

<210> SEQ ID NO 828
<211> LENGTH: 17
<212> TYPE: DNA
<213> ORGANISM: Homo sapiens

<400> SEQUENCE: 828
aggtatgatg tgcttaa 17

<210> SEQ ID NO 829
<211> LENGTH: 17
<212> TYPE: DNA
<213> ORGANISM: Homo sapiens

<400> SEQUENCE: 829
ggtatgatgt gcttaaa 17

<210> SEQ ID NO 830
<211> LENGTH: 17
<212> TYPE: DNA
<213> ORGANISM: Homo sapiens

<400> SEQUENCE: 830
gtatgatgtg cttaaag 17

<210> SEQ ID NO 831
<211> LENGTH: 17
<212> TYPE: DNA
<213> ORGANISM: Homo sapiens

<400> SEQUENCE: 831
tatgatgtgc ttaaaga 17

<210> SEQ ID NO 832
<211> LENGTH: 17
<212> TYPE: DNA
<213> ORGANISM: Homo sapiens

<400> SEQUENCE: 832
atgatgtgct taaagat 17

<210> SEQ ID NO 833
<211> LENGTH: 17
<212> TYPE: DNA
<213> ORGANISM: Homo sapiens

<400> SEQUENCE: 833
tgatgtgctt aaagatc 17

<210> SEQ ID NO 834
<211> LENGTH: 17
<212> TYPE: DNA
<213> ORGANISM: Homo sapiens

<400> SEQUENCE: 834
gatgtgctta aagatcc 17

<210> SEQ ID NO 835

-continued

<211> LENGTH: 17
<212> TYPE: DNA
<213> ORGANISM: Homo sapiens

<400> SEQUENCE: 835
atgtgcttaa agatcct 17

<210> SEQ ID NO 836
<211> LENGTH: 17
<212> TYPE: DNA
<213> ORGANISM: Homo sapiens

<400> SEQUENCE: 836
tgtgcttaaa gatccta 17

<210> SEQ ID NO 837
<211> LENGTH: 17
<212> TYPE: DNA
<213> ORGANISM: Homo sapiens

<400> SEQUENCE: 837
gtgcttaaag atcctaa 17

<210> SEQ ID NO 838
<211> LENGTH: 17
<212> TYPE: DNA
<213> ORGANISM: Homo sapiens

<400> SEQUENCE: 838
tgcttaaaga tcctaag 17

<210> SEQ ID NO 839
<211> LENGTH: 17
<212> TYPE: DNA
<213> ORGANISM: Homo sapiens

<400> SEQUENCE: 839
gcttaaagat cctaaga 17

<210> SEQ ID NO 840
<211> LENGTH: 17
<212> TYPE: DNA
<213> ORGANISM: Homo sapiens

<400> SEQUENCE: 840
cttaaagatc ctaagaa 17

<210> SEQ ID NO 841
<211> LENGTH: 17
<212> TYPE: DNA
<213> ORGANISM: Homo sapiens

<400> SEQUENCE: 841
ttaaagatcc taagaat 17

<210> SEQ ID NO 842
<211> LENGTH: 17
<212> TYPE: DNA
<213> ORGANISM: Homo sapiens

<400> SEQUENCE: 842
taaagatcct aagaata 17

-continued

<210> SEQ ID NO 843
<211> LENGTH: 17
<212> TYPE: DNA
<213> ORGANISM: Homo sapiens

<400> SEQUENCE: 843
aaagatccta agaataa 17

<210> SEQ ID NO 844
<211> LENGTH: 17
<212> TYPE: DNA
<213> ORGANISM: Homo sapiens

<400> SEQUENCE: 844
aagatcctaa gaataag 17

<210> SEQ ID NO 845
<211> LENGTH: 17
<212> TYPE: DNA
<213> ORGANISM: Homo sapiens

<400> SEQUENCE: 845
agatcctaag aataagc 17

<210> SEQ ID NO 846
<211> LENGTH: 17
<212> TYPE: DNA
<213> ORGANISM: Homo sapiens

<400> SEQUENCE: 846
gatcctaaga ataagcc 17

<210> SEQ ID NO 847
<211> LENGTH: 17
<212> TYPE: DNA
<213> ORGANISM: Homo sapiens

<400> SEQUENCE: 847
atcctaagaa taagcct 17

<210> SEQ ID NO 848
<211> LENGTH: 17
<212> TYPE: DNA
<213> ORGANISM: Homo sapiens

<400> SEQUENCE: 848
tcctaagaat aagcctg 17

<210> SEQ ID NO 849
<211> LENGTH: 17
<212> TYPE: DNA
<213> ORGANISM: Homo sapiens

<400> SEQUENCE: 849
cctaagaata agcctgg 17

<210> SEQ ID NO 850
<211> LENGTH: 17
<212> TYPE: DNA
<213> ORGANISM: Homo sapiens

<400> SEQUENCE: 850
ctaagaataa gcctggc 17

<210> SEQ ID NO 851
<211> LENGTH: 17
<212> TYPE: DNA
<213> ORGANISM: Homo sapiens

<400> SEQUENCE: 851
taagaataag cctggcg 17

<210> SEQ ID NO 852
<211> LENGTH: 17
<212> TYPE: DNA
<213> ORGANISM: Homo sapiens

<400> SEQUENCE: 852
aagaataagc ctggcga 17

<210> SEQ ID NO 853
<211> LENGTH: 17
<212> TYPE: DNA
<213> ORGANISM: Homo sapiens

<400> SEQUENCE: 853
agaataagcc tggcgat 17

<210> SEQ ID NO 854
<211> LENGTH: 17
<212> TYPE: DNA
<213> ORGANISM: Homo sapiens

<400> SEQUENCE: 854
gaataagcct ggcgatt 17

<210> SEQ ID NO 855
<211> LENGTH: 17
<212> TYPE: DNA
<213> ORGANISM: Homo sapiens

<400> SEQUENCE: 855
aataagcctg gcgattt 17

<210> SEQ ID NO 856
<211> LENGTH: 17
<212> TYPE: DNA
<213> ORGANISM: Homo sapiens

<400> SEQUENCE: 856
ataagcctgg cgatttt 17

<210> SEQ ID NO 857
<211> LENGTH: 17
<212> TYPE: DNA
<213> ORGANISM: Homo sapiens

<400> SEQUENCE: 857
taagcctggc gattttg 17

<210> SEQ ID NO 858
<211> LENGTH: 17
<212> TYPE: DNA
<213> ORGANISM: Homo sapiens

<400> SEQUENCE: 858
aagcctggcg attttgg 17

-continued

<210> SEQ ID NO 859
<211> LENGTH: 17
<212> TYPE: DNA
<213> ORGANISM: Homo sapiens

<400> SEQUENCE: 859
agcctggcga ttttggc 17

<210> SEQ ID NO 860
<211> LENGTH: 17
<212> TYPE: DNA
<213> ORGANISM: Homo sapiens

<400> SEQUENCE: 860
gcctggcgat tttggct 17

<210> SEQ ID NO 861
<211> LENGTH: 17
<212> TYPE: DNA
<213> ORGANISM: Homo sapiens

<400> SEQUENCE: 861
cctggcgatt ttggctg 17

<210> SEQ ID NO 862
<211> LENGTH: 17
<212> TYPE: DNA
<213> ORGANISM: Homo sapiens

<400> SEQUENCE: 862
ctggcgattt tggctgg 17

<210> SEQ ID NO 863
<211> LENGTH: 17
<212> TYPE: DNA
<213> ORGANISM: Homo sapiens

<400> SEQUENCE: 863
tggcgatttt ggctggg 17

<210> SEQ ID NO 864
<211> LENGTH: 17
<212> TYPE: DNA
<213> ORGANISM: Homo sapiens

<400> SEQUENCE: 864
ggcgattttg gctgggt 17

<210> SEQ ID NO 865
<211> LENGTH: 17
<212> TYPE: DNA
<213> ORGANISM: Homo sapiens

<400> SEQUENCE: 865
gcgattttgg ctgggtg 17

<210> SEQ ID NO 866
<211> LENGTH: 17
<212> TYPE: DNA
<213> ORGANISM: Homo sapiens

<400> SEQUENCE: 866

-continued cgattttggc tgggtgg 17

<210> SEQ ID NO 867
<211> LENGTH: 17
<212> TYPE: DNA
<213> ORGANISM: Homo sapiens

<400> SEQUENCE: 867
gattttggct gggtggg 17

<210> SEQ ID NO 868
<211> LENGTH: 17
<212> TYPE: DNA
<213> ORGANISM: Homo sapiens

<400> SEQUENCE: 868
attttggctg ggtgggc 17

<210> SEQ ID NO 869
<211> LENGTH: 17
<212> TYPE: DNA
<213> ORGANISM: Homo sapiens

<400> SEQUENCE: 869
ttttggctgg gtgggca 17

<210> SEQ ID NO 870
<211> LENGTH: 17
<212> TYPE: DNA
<213> ORGANISM: Homo sapiens

<400> SEQUENCE: 870
tttggctggg tgggcac 17

<210> SEQ ID NO 871
<211> LENGTH: 17
<212> TYPE: DNA
<213> ORGANISM: Homo sapiens

<400> SEQUENCE: 871
ttggctgggt gggcact 17

<210> SEQ ID NO 872
<211> LENGTH: 17
<212> TYPE: DNA
<213> ORGANISM: Homo sapiens

<400> SEQUENCE: 872
tggctgggtg ggcactc 17

<210> SEQ ID NO 873
<211> LENGTH: 17
<212> TYPE: DNA
<213> ORGANISM: Homo sapiens

<400> SEQUENCE: 873
ggctgggtgg gcactct 17

<210> SEQ ID NO 874
<211> LENGTH: 17
<212> TYPE: DNA
<213> ORGANISM: Homo sapiens

<400> SEQUENCE: 874

-continued gctgggtggg cactctg 17

<210> SEQ ID NO 875
<211> LENGTH: 17
<212> TYPE: DNA
<213> ORGANISM: Homo sapiens

<400> SEQUENCE: 875
ctgggtgggc actctgt 17

<210> SEQ ID NO 876
<211> LENGTH: 17
<212> TYPE: DNA
<213> ORGANISM: Homo sapiens

<400> SEQUENCE: 876
tgggtgggca ctctgtt 17

<210> SEQ ID NO 877
<211> LENGTH: 17
<212> TYPE: DNA
<213> ORGANISM: Homo sapiens

<400> SEQUENCE: 877
gggtgggcac tctgttc 17

<210> SEQ ID NO 878
<211> LENGTH: 17
<212> TYPE: DNA
<213> ORGANISM: Homo sapiens

<400> SEQUENCE: 878
ggtgggcact ctgttct 17

<210> SEQ ID NO 879
<211> LENGTH: 17
<212> TYPE: DNA
<213> ORGANISM: Homo sapiens

<400> SEQUENCE: 879
gtgggcactc tgttctg 17

<210> SEQ ID NO 880
<211> LENGTH: 17
<212> TYPE: DNA
<213> ORGANISM: Homo sapiens

<400> SEQUENCE: 880
tgggcactct gttctgc 17

<210> SEQ ID NO 881
<211> LENGTH: 17
<212> TYPE: DNA
<213> ORGANISM: Homo sapiens

<400> SEQUENCE: 881
gggcactctg ttctgcc 17

<210> SEQ ID NO 882
<211> LENGTH: 17
<212> TYPE: DNA
<213> ORGANISM: Homo sapiens -continued

<400> SEQUENCE: 882
ggcactctgt tctgcca 17

<210> SEQ ID NO 883
<211> LENGTH: 17
<212> TYPE: DNA
<213> ORGANISM: Homo sapiens

<400> SEQUENCE: 883
gcactctgtt ctgccaa 17

<210> SEQ ID NO 884
<211> LENGTH: 17
<212> TYPE: DNA
<213> ORGANISM: Homo sapiens

<400> SEQUENCE: 884
cactctgttc tgccaac 17

<210> SEQ ID NO 885
<211> LENGTH: 17
<212> TYPE: DNA
<213> ORGANISM: Homo sapiens

<400> SEQUENCE: 885
actctgttct gccaact 17

<210> SEQ ID NO 886
<211> LENGTH: 17
<212> TYPE: DNA
<213> ORGANISM: Homo sapiens

<400> SEQUENCE: 886
ctctgttctg ccaactc 17

<210> SEQ ID NO 887
<211> LENGTH: 17
<212> TYPE: DNA
<213> ORGANISM: Homo sapiens

<400> SEQUENCE: 887
tctgttctgc caactct 17

<210> SEQ ID NO 888
<211> LENGTH: 17
<212> TYPE: DNA
<213> ORGANISM: Homo sapiens

<400> SEQUENCE: 888
ctgttctgcc aactctg 17

<210> SEQ ID NO 889
<211> LENGTH: 25
<212> TYPE: DNA
<213> ORGANISM: Homo sapiens

<400> SEQUENCE: 889
ccccaagcat caaactgaag gaaac 25

<210> SEQ ID NO 890
<211> LENGTH: 25
<212> TYPE: DNA
<213> ORGANISM: Homo sapiens -continued

<400> SEQUENCE: 890
cccaagcatc aaactgaagg aaaca 25

<210> SEQ ID NO 891
<211> LENGTH: 25
<212> TYPE: DNA
<213> ORGANISM: Homo sapiens

<400> SEQUENCE: 891
ccaagcatca aactgaagga aacat 25

<210> SEQ ID NO 892
<211> LENGTH: 25
<212> TYPE: DNA
<213> ORGANISM: Homo sapiens

<400> SEQUENCE: 892
caagcatcaa actgaaggaa acatt 25

<210> SEQ ID NO 893
<211> LENGTH: 25
<212> TYPE: DNA
<213> ORGANISM: Homo sapiens

<400> SEQUENCE: 893
aagcatcaaa ctgaaggaaa cattc 25

<210> SEQ ID NO 894
<211> LENGTH: 25
<212> TYPE: DNA
<213> ORGANISM: Homo sapiens

<400> SEQUENCE: 894
agcatcaaac tgaaggaaac attct 25

<210> SEQ ID NO 895
<211> LENGTH: 25
<212> TYPE: DNA
<213> ORGANISM: Homo sapiens

<400> SEQUENCE: 895
gcatcaaact gaaggaaaca ttcta 25

<210> SEQ ID NO 896
<211> LENGTH: 25
<212> TYPE: DNA
<213> ORGANISM: Homo sapiens

<400> SEQUENCE: 896
catcaaactg aaggaaacat tctaa 25

<210> SEQ ID NO 897
<211> LENGTH: 25
<212> TYPE: DNA
<213> ORGANISM: Homo sapiens

<400> SEQUENCE: 897
atcaaactga aggaaacatt ctaac 25

<210> SEQ ID NO 898
<211> LENGTH: 25
<212> TYPE: DNA

-continued

<213> ORGANISM: Homo sapiens

<400> SEQUENCE: 898
tcaaactgaa ggaaacattc taacc 25

<210> SEQ ID NO 899
<211> LENGTH: 25
<212> TYPE: DNA
<213> ORGANISM: Homo sapiens

<400> SEQUENCE: 899
caaactgaag gaaacattct aacct 25

<210> SEQ ID NO 900
<211> LENGTH: 25
<212> TYPE: DNA
<213> ORGANISM: Homo sapiens

<400> SEQUENCE: 900
aaactgaagg aaacattcta acctt 25

<210> SEQ ID NO 901
<211> LENGTH: 25
<212> TYPE: DNA
<213> ORGANISM: Homo sapiens

<400> SEQUENCE: 901
aactgaagga aacattctaa ccttc 25

<210> SEQ ID NO 902
<211> LENGTH: 25
<212> TYPE: DNA
<213> ORGANISM: Homo sapiens

<400> SEQUENCE: 902
actgaaggaa acattctaac cttca 25

<210> SEQ ID NO 903
<211> LENGTH: 25
<212> TYPE: DNA
<213> ORGANISM: Homo sapiens

<400> SEQUENCE: 903
ctgaaggaaa cattctaacc ttcac 25

<210> SEQ ID NO 904
<211> LENGTH: 25
<212> TYPE: DNA
<213> ORGANISM: Homo sapiens

<400> SEQUENCE: 904
tgaaggaaac attctaacct tcaca 25

<210> SEQ ID NO 905
<211> LENGTH: 25
<212> TYPE: DNA
<213> ORGANISM: Homo sapiens

<400> SEQUENCE: 905
gaaggaaaca ttctaacctt cacag 25

<210> SEQ ID NO 906
<211> LENGTH: 25

-continued

<212> TYPE: DNA
<213> ORGANISM: Homo sapiens

<400> SEQUENCE: 906
aaggaaacat tctaaccttc acaga 25

<210> SEQ ID NO 907
<211> LENGTH: 25
<212> TYPE: DNA
<213> ORGANISM: Homo sapiens

<400> SEQUENCE: 907
aggaaacatt ctaaccttca cagac 25

<210> SEQ ID NO 908
<211> LENGTH: 25
<212> TYPE: DNA
<213> ORGANISM: Homo sapiens

<400> SEQUENCE: 908
ggaaacattc taaccttcac agaca 25

<210> SEQ ID NO 909
<211> LENGTH: 25
<212> TYPE: DNA
<213> ORGANISM: Homo sapiens

<400> SEQUENCE: 909
gaaacattct aaccttcaca gacag 25

<210> SEQ ID NO 910
<211> LENGTH: 25
<212> TYPE: DNA
<213> ORGANISM: Homo sapiens

<400> SEQUENCE: 910
aaacattcta accttcacag acaga 25

<210> SEQ ID NO 911
<211> LENGTH: 25
<212> TYPE: DNA
<213> ORGANISM: Homo sapiens

<400> SEQUENCE: 911
aacattctaa ccttcacaga cagac 25

<210> SEQ ID NO 912
<211> LENGTH: 25
<212> TYPE: DNA
<213> ORGANISM: Homo sapiens

<400> SEQUENCE: 912
acattctaac cttcacagac agact 25

<210> SEQ ID NO 913
<211> LENGTH: 25
<212> TYPE: DNA
<213> ORGANISM: Homo sapiens

<400> SEQUENCE: 913
cattctaacc ttcacagaca gactg 25

<210> SEQ ID NO 914

-continued

<211> LENGTH: 25
<212> TYPE: DNA
<213> ORGANISM: Homo sapiens

<400> SEQUENCE: 914
attctaacct tcacagacag actgg 25

<210> SEQ ID NO 915
<211> LENGTH: 25
<212> TYPE: DNA
<213> ORGANISM: Homo sapiens

<400> SEQUENCE: 915
ttctaacctt cacagacaga ctgga 25

<210> SEQ ID NO 916
<211> LENGTH: 25
<212> TYPE: DNA
<213> ORGANISM: Homo sapiens

<400> SEQUENCE: 916
tctaaccttc acagacagac tggag 25

<210> SEQ ID NO 917
<211> LENGTH: 25
<212> TYPE: DNA
<213> ORGANISM: Homo sapiens

<400> SEQUENCE: 917
ctaaccttca cagacagact ggagg 25

<210> SEQ ID NO 918
<211> LENGTH: 25
<212> TYPE: DNA
<213> ORGANISM: Homo sapiens

<400> SEQUENCE: 918
taaccttcac agacagactg gaggc 25

<210> SEQ ID NO 919
<211> LENGTH: 25
<212> TYPE: DNA
<213> ORGANISM: Homo sapiens

<400> SEQUENCE: 919
aaccttcaca gacagactgg aggct 25

<210> SEQ ID NO 920
<211> LENGTH: 25
<212> TYPE: DNA
<213> ORGANISM: Homo sapiens

<400> SEQUENCE: 920
accttcacag acagactgga ggctg 25

<210> SEQ ID NO 921
<211> LENGTH: 25
<212> TYPE: DNA
<213> ORGANISM: Homo sapiens

<400> SEQUENCE: 921
ccttcacaga cagactggag gctgg 25

-continued

<210> SEQ ID NO 922
<211> LENGTH: 25
<212> TYPE: DNA
<213> ORGANISM: Homo sapiens

<400> SEQUENCE: 922
cttcacagac agactggagg ctgga 25

<210> SEQ ID NO 923
<211> LENGTH: 25
<212> TYPE: DNA
<213> ORGANISM: Homo sapiens

<400> SEQUENCE: 923
ttcacagaca gactggaggc tggat 25

<210> SEQ ID NO 924
<211> LENGTH: 25
<212> TYPE: DNA
<213> ORGANISM: Homo sapiens

<400> SEQUENCE: 924
tcacagacag actggaggct ggatg 25

<210> SEQ ID NO 925
<211> LENGTH: 25
<212> TYPE: DNA
<213> ORGANISM: Homo sapiens

<400> SEQUENCE: 925
cacagacaga ctggaggctg gatgg 25

<210> SEQ ID NO 926
<211> LENGTH: 25
<212> TYPE: DNA
<213> ORGANISM: Homo sapiens

<400> SEQUENCE: 926
acagacagac tggaggctgg atggg 25

<210> SEQ ID NO 927
<211> LENGTH: 25
<212> TYPE: DNA
<213> ORGANISM: Homo sapiens

<400> SEQUENCE: 927
cagacagact ggaggctgga tgggg 25

<210> SEQ ID NO 928
<211> LENGTH: 25
<212> TYPE: DNA
<213> ORGANISM: Homo sapiens

<400> SEQUENCE: 928
agacagactg gaggctggat gggga 25

<210> SEQ ID NO 929
<211> LENGTH: 25
<212> TYPE: DNA
<213> ORGANISM: Homo sapiens

<400> SEQUENCE: 929
gacagactgg aggctggatg gggac 25

-continued

<210> SEQ ID NO 930
<211> LENGTH: 25
<212> TYPE: DNA
<213> ORGANISM: Homo sapiens

<400> SEQUENCE: 930
acagactgga ggctggatgg ggacc 25

<210> SEQ ID NO 931
<211> LENGTH: 25
<212> TYPE: DNA
<213> ORGANISM: Homo sapiens

<400> SEQUENCE: 931
cagactggag gctggatggg gacct 25

<210> SEQ ID NO 932
<211> LENGTH: 25
<212> TYPE: DNA
<213> ORGANISM: Homo sapiens

<400> SEQUENCE: 932
agactggagg ctggatgggg acctg 25

<210> SEQ ID NO 933
<211> LENGTH: 25
<212> TYPE: DNA
<213> ORGANISM: Homo sapiens

<400> SEQUENCE: 933
gactggaggc tggatgggga cctgg 25

<210> SEQ ID NO 934
<211> LENGTH: 25
<212> TYPE: DNA
<213> ORGANISM: Homo sapiens

<400> SEQUENCE: 934
actggaggct ggatggggac ctggc 25

<210> SEQ ID NO 935
<211> LENGTH: 25
<212> TYPE: DNA
<213> ORGANISM: Homo sapiens

<400> SEQUENCE: 935
ctggaggctg gatggggacc tggct 25

<210> SEQ ID NO 936
<211> LENGTH: 25
<212> TYPE: DNA
<213> ORGANISM: Homo sapiens

<400> SEQUENCE: 936
tggaggctgg atggggacct ggctg 25

<210> SEQ ID NO 937
<211> LENGTH: 25
<212> TYPE: DNA
<213> ORGANISM: Homo sapiens

<400> SEQUENCE: 937
ggaggctgga tggggacctg gctga 25

-continued

<210> SEQ ID NO 938
<211> LENGTH: 25
<212> TYPE: DNA
<213> ORGANISM: Homo sapiens

<400> SEQUENCE: 938
gaggctggat ggggacctgg ctgaa 25

<210> SEQ ID NO 939
<211> LENGTH: 25
<212> TYPE: DNA
<213> ORGANISM: Homo sapiens

<400> SEQUENCE: 939
aggctggatg gggacctggc tgaag 25

<210> SEQ ID NO 940
<211> LENGTH: 25
<212> TYPE: DNA
<213> ORGANISM: Homo sapiens

<400> SEQUENCE: 940
ggctggatgg ggacctggct gaaga 25

<210> SEQ ID NO 941
<211> LENGTH: 25
<212> TYPE: DNA
<213> ORGANISM: Homo sapiens

<400> SEQUENCE: 941
gctggatggg gacctggctg aagac 25

<210> SEQ ID NO 942
<211> LENGTH: 25
<212> TYPE: DNA
<213> ORGANISM: Homo sapiens

<400> SEQUENCE: 942
ctggatgggg acctggctga agaca 25

<210> SEQ ID NO 943
<211> LENGTH: 25
<212> TYPE: DNA
<213> ORGANISM: Homo sapiens

<400> SEQUENCE: 943
tggatgggga cctggctgaa gacat 25

<210> SEQ ID NO 944
<211> LENGTH: 25
<212> TYPE: DNA
<213> ORGANISM: Homo sapiens

<400> SEQUENCE: 944
ggatggggac ctggctgaag acatc 25

<210> SEQ ID NO 945
<211> LENGTH: 25
<212> TYPE: DNA
<213> ORGANISM: Homo sapiens

<400> SEQUENCE: 945

-continued gatggggacc tggctgaaga catct 25

<210> SEQ ID NO 946
<211> LENGTH: 25
<212> TYPE: DNA
<213> ORGANISM: Homo sapiens

<400> SEQUENCE: 946
atggggacct ggctgaagac atctg 25

<210> SEQ ID NO 947
<211> LENGTH: 25
<212> TYPE: DNA
<213> ORGANISM: Homo sapiens

<400> SEQUENCE: 947
tggggacctg gctgaagaca tctgg 25

<210> SEQ ID NO 948
<211> LENGTH: 25
<212> TYPE: DNA
<213> ORGANISM: Homo sapiens

<400> SEQUENCE: 948
ggggacctgg ctgaagacat ctgga 25

<210> SEQ ID NO 949
<211> LENGTH: 25
<212> TYPE: DNA
<213> ORGANISM: Homo sapiens

<400> SEQUENCE: 949
gggacctggc tgaagacatc tggag 25

<210> SEQ ID NO 950
<211> LENGTH: 25
<212> TYPE: DNA
<213> ORGANISM: Homo sapiens

<400> SEQUENCE: 950
ggacctggct gaagacatct ggaga 25

<210> SEQ ID NO 951
<211> LENGTH: 25
<212> TYPE: DNA
<213> ORGANISM: Homo sapiens

<400> SEQUENCE: 951
gacctggctg aagacatctg gagaa 25

<210> SEQ ID NO 952
<211> LENGTH: 25
<212> TYPE: DNA
<213> ORGANISM: Homo sapiens

<400> SEQUENCE: 952
acctggctga agacatctgg agaat 25

<210> SEQ ID NO 953
<211> LENGTH: 25
<212> TYPE: DNA
<213> ORGANISM: Homo sapiens

<400> SEQUENCE: 953

-continued cctggctgaa gacatctgga gaatg 25

<210> SEQ ID NO 954
<211> LENGTH: 25
<212> TYPE: DNA
<213> ORGANISM: Homo sapiens

<400> SEQUENCE: 954
ctggctgaag acatctggag aatga 25

<210> SEQ ID NO 955
<211> LENGTH: 25
<212> TYPE: DNA
<213> ORGANISM: Homo sapiens

<400> SEQUENCE: 955
tggctgaaga catctggaga atgaa 25

<210> SEQ ID NO 956
<211> LENGTH: 25
<212> TYPE: DNA
<213> ORGANISM: Homo sapiens

<400> SEQUENCE: 956
ggctgaagac atctggagaa tgaaa 25

<210> SEQ ID NO 957
<211> LENGTH: 25
<212> TYPE: DNA
<213> ORGANISM: Homo sapiens

<400> SEQUENCE: 957
gctgaagaca tctggagaat gaaag 25

<210> SEQ ID NO 958
<211> LENGTH: 25
<212> TYPE: DNA
<213> ORGANISM: Homo sapiens

<400> SEQUENCE: 958
ctgaagacat ctggagaatg aaagt 25

<210> SEQ ID NO 959
<211> LENGTH: 25
<212> TYPE: DNA
<213> ORGANISM: Homo sapiens

<400> SEQUENCE: 959
tgaagacatc tggagaatga aagtt 25

<210> SEQ ID NO 960
<211> LENGTH: 25
<212> TYPE: DNA
<213> ORGANISM: Homo sapiens

<400> SEQUENCE: 960
gaagacatct ggagaatgaa agtta 25

<210> SEQ ID NO 961
<211> LENGTH: 25
<212> TYPE: DNA
<213> ORGANISM: Homo sapiens -continued

<400> SEQUENCE: 961
aagacatctg gagaatgaaa gttaa 25

<210> SEQ ID NO 962
<211> LENGTH: 25
<212> TYPE: DNA
<213> ORGANISM: Homo sapiens

<400> SEQUENCE: 962
agacatctgg agaatgaaag ttaag 25

<210> SEQ ID NO 963
<211> LENGTH: 25
<212> TYPE: DNA
<213> ORGANISM: Homo sapiens

<400> SEQUENCE: 963
gacatctgga gaatgaaagt taagt 25

<210> SEQ ID NO 964
<211> LENGTH: 25
<212> TYPE: DNA
<213> ORGANISM: Homo sapiens

<400> SEQUENCE: 964
acatctggag aatgaaagtt aagta 25

<210> SEQ ID NO 965
<211> LENGTH: 25
<212> TYPE: DNA
<213> ORGANISM: Homo sapiens

<400> SEQUENCE: 965
catctggaga atgaaagtta agtac 25

<210> SEQ ID NO 966
<211> LENGTH: 25
<212> TYPE: DNA
<213> ORGANISM: Homo sapiens

<400> SEQUENCE: 966
atctggagaa tgaaagttaa gtacc 25

<210> SEQ ID NO 967
<211> LENGTH: 25
<212> TYPE: DNA
<213> ORGANISM: Homo sapiens

<400> SEQUENCE: 967
tctggagaat gaaagttaag tacca 25

<210> SEQ ID NO 968
<211> LENGTH: 25
<212> TYPE: DNA
<213> ORGANISM: Homo sapiens

<400> SEQUENCE: 968
ctggagaatg aaagttaagt accag 25

<210> SEQ ID NO 969
<211> LENGTH: 25
<212> TYPE: DNA
<213> ORGANISM: Homo sapiens

<400> SEQUENCE: 969
tggagaatga aagttaagta ccagc 25

<210> SEQ ID NO 970
<211> LENGTH: 25
<212> TYPE: DNA
<213> ORGANISM: Homo sapiens

<400> SEQUENCE: 970
ggagaatgaa agttaagtac cagct 25

<210> SEQ ID NO 971
<211> LENGTH: 25
<212> TYPE: DNA
<213> ORGANISM: Homo sapiens

<400> SEQUENCE: 971
gagaatgaaa gttaagtacc agctt 25

<210> SEQ ID NO 972
<211> LENGTH: 25
<212> TYPE: DNA
<213> ORGANISM: Homo sapiens

<400> SEQUENCE: 972
agaatgaaag ttaagtacca gcttg 25

<210> SEQ ID NO 973
<211> LENGTH: 25
<212> TYPE: DNA
<213> ORGANISM: Homo sapiens

<400> SEQUENCE: 973
gaatgaaagt taagtaccag cttgc 25

<210> SEQ ID NO 974
<211> LENGTH: 25
<212> TYPE: DNA
<213> ORGANISM: Homo sapiens

<400> SEQUENCE: 974
aatgaaagtt aagtaccagc ttgca 25

<210> SEQ ID NO 975
<211> LENGTH: 25
<212> TYPE: DNA
<213> ORGANISM: Homo sapiens

<400> SEQUENCE: 975
atgaaagtta agtaccagct tgcat 25

<210> SEQ ID NO 976
<211> LENGTH: 25
<212> TYPE: DNA
<213> ORGANISM: Homo sapiens

<400> SEQUENCE: 976
tgaaagttaa gtaccagctt gcatt 25

<210> SEQ ID NO 977
<211> LENGTH: 25
<212> TYPE: DNA

-continued

<213> ORGANISM: Homo sapiens

<400> SEQUENCE: 977
gaaagttaag taccagcttg cattt 25

<210> SEQ ID NO 978
<211> LENGTH: 25
<212> TYPE: DNA
<213> ORGANISM: Homo sapiens

<400> SEQUENCE: 978
aaagttaagt accagcttgc atttt 25

<210> SEQ ID NO 979
<211> LENGTH: 25
<212> TYPE: DNA
<213> ORGANISM: Homo sapiens

<400> SEQUENCE: 979
aagttaagta ccagcttgca ttttt 25

<210> SEQ ID NO 980
<211> LENGTH: 25
<212> TYPE: DNA
<213> ORGANISM: Homo sapiens

<400> SEQUENCE: 980
agttaagtac cagcttgcat ttttg 25

<210> SEQ ID NO 981
<211> LENGTH: 25
<212> TYPE: DNA
<213> ORGANISM: Homo sapiens

<400> SEQUENCE: 981
gttaagtacc agcttgcatt tttgt 25

<210> SEQ ID NO 982
<211> LENGTH: 25
<212> TYPE: DNA
<213> ORGANISM: Homo sapiens

<400> SEQUENCE: 982
ttaagtacca gcttgcattt ttgtg 25

<210> SEQ ID NO 983
<211> LENGTH: 25
<212> TYPE: DNA
<213> ORGANISM: Homo sapiens

<400> SEQUENCE: 983
taagtaccag cttgcatttt tgtgc 25

<210> SEQ ID NO 984
<211> LENGTH: 25
<212> TYPE: DNA
<213> ORGANISM: Homo sapiens

<400> SEQUENCE: 984
aagtaccagc ttgcattttt gtgcc 25

<210> SEQ ID NO 985
<211> LENGTH: 25

-continued

<212> TYPE: DNA
<213> ORGANISM: Homo sapiens

<400> SEQUENCE: 985
agtaccagct tgcatttttg tgccc 25

<210> SEQ ID NO 986
<211> LENGTH: 25
<212> TYPE: DNA
<213> ORGANISM: Homo sapiens

<400> SEQUENCE: 986
gtaccagctt gcatttttgt gcccc 25

<210> SEQ ID NO 987
<211> LENGTH: 25
<212> TYPE: DNA
<213> ORGANISM: Homo sapiens

<400> SEQUENCE: 987
taccagcttg catttttgtg cccct 25

<210> SEQ ID NO 988
<211> LENGTH: 25
<212> TYPE: DNA
<213> ORGANISM: Homo sapiens

<400> SEQUENCE: 988
accagcttgc atttttgtgc cccta 25

<210> SEQ ID NO 989
<211> LENGTH: 25
<212> TYPE: DNA
<213> ORGANISM: Homo sapiens

<400> SEQUENCE: 989
ccagcttgca tttttgtgcc cctag 25

<210> SEQ ID NO 990
<211> LENGTH: 25
<212> TYPE: DNA
<213> ORGANISM: Homo sapiens

<400> SEQUENCE: 990
cagcttgcat ttttgtgccc ctaga 25

<210> SEQ ID NO 991
<211> LENGTH: 25
<212> TYPE: DNA
<213> ORGANISM: Homo sapiens

<400> SEQUENCE: 991
agcttgcatt tttgtgcccc tagat 25

<210> SEQ ID NO 992
<211> LENGTH: 25
<212> TYPE: DNA
<213> ORGANISM: Homo sapiens

<400> SEQUENCE: 992
gcttgcattt ttgtgcccct agatt 25

<210> SEQ ID NO 993

-continued

<211> LENGTH: 25
<212> TYPE: DNA
<213> ORGANISM: Homo sapiens

<400> SEQUENCE: 993
cttgcatttt tgtgcccta gatta 25

<210> SEQ ID NO 994
<211> LENGTH: 25
<212> TYPE: DNA
<213> ORGANISM: Homo sapiens

<400> SEQUENCE: 994
ttgcattttt gtgcccctag attat 25

<210> SEQ ID NO 995
<211> LENGTH: 25
<212> TYPE: DNA
<213> ORGANISM: Homo sapiens

<400> SEQUENCE: 995
tgcatttttg tgcccctaga ttatt 25

<210> SEQ ID NO 996
<211> LENGTH: 25
<212> TYPE: DNA
<213> ORGANISM: Homo sapiens

<400> SEQUENCE: 996
gcatttttgt gcccctagat tattt 25

<210> SEQ ID NO 997
<211> LENGTH: 25
<212> TYPE: DNA
<213> ORGANISM: Homo sapiens

<400> SEQUENCE: 997
catttttgtg cccctagatt atttt 25

<210> SEQ ID NO 998
<211> LENGTH: 25
<212> TYPE: DNA
<213> ORGANISM: Homo sapiens

<400> SEQUENCE: 998
atttttgtgc ccctagatta ttttt 25

<210> SEQ ID NO 999
<211> LENGTH: 25
<212> TYPE: DNA
<213> ORGANISM: Homo sapiens

<400> SEQUENCE: 999
tttttgtgcc cctagattat ttttg 25

<210> SEQ ID NO 1000
<211> LENGTH: 25
<212> TYPE: DNA
<213> ORGANISM: Homo sapiens

<400> SEQUENCE: 1000
ttttgtgccc ctagattatt tttgc 25

<210> SEQ ID NO 1001
<211> LENGTH: 25
<212> TYPE: DNA
<213> ORGANISM: Homo sapiens

<400> SEQUENCE: 1001
tttgtgcccc tagattattt ttgca 25

<210> SEQ ID NO 1002
<211> LENGTH: 25
<212> TYPE: DNA
<213> ORGANISM: Homo sapiens

<400> SEQUENCE: 1002
ttgtgcccct agattatttt tgcat 25

<210> SEQ ID NO 1003
<211> LENGTH: 25
<212> TYPE: DNA
<213> ORGANISM: Homo sapiens

<400> SEQUENCE: 1003
tgtgccccta gattattttt gcatt 25

<210> SEQ ID NO 1004
<211> LENGTH: 25
<212> TYPE: DNA
<213> ORGANISM: Homo sapiens

<400> SEQUENCE: 1004
gtgcccctag attatttttg cattt 25

<210> SEQ ID NO 1005
<211> LENGTH: 25
<212> TYPE: DNA
<213> ORGANISM: Homo sapiens

<400> SEQUENCE: 1005
tgcccctaga ttatttttgc atttt 25

<210> SEQ ID NO 1006
<211> LENGTH: 25
<212> TYPE: DNA
<213> ORGANISM: Homo sapiens

<400> SEQUENCE: 1006
gcccctagat tatttttgca tttta 25

<210> SEQ ID NO 1007
<211> LENGTH: 25
<212> TYPE: DNA
<213> ORGANISM: Homo sapiens

<400> SEQUENCE: 1007
cccctagatt atttttgcat tttaa 25

<210> SEQ ID NO 1008
<211> LENGTH: 25
<212> TYPE: DNA
<213> ORGANISM: Homo sapiens

<400> SEQUENCE: 1008
ccctagatta tttttgcatt ttaaa 25

-continued

<210> SEQ ID NO 1009
<211> LENGTH: 25
<212> TYPE: DNA
<213> ORGANISM: Homo sapiens

<400> SEQUENCE: 1009
cctagattat ttttgcattt taaaa 25

<210> SEQ ID NO 1010
<211> LENGTH: 25
<212> TYPE: DNA
<213> ORGANISM: Homo sapiens

<400> SEQUENCE: 1010
ctagattatt tttgcatttt aaaat 25

<210> SEQ ID NO 1011
<211> LENGTH: 25
<212> TYPE: DNA
<213> ORGANISM: Homo sapiens

<400> SEQUENCE: 1011
tagattattt ttgcatttta aaata 25

<210> SEQ ID NO 1012
<211> LENGTH: 25
<212> TYPE: DNA
<213> ORGANISM: Homo sapiens

<400> SEQUENCE: 1012
agattatttt tgcattttaa aataa 25

<210> SEQ ID NO 1013
<211> LENGTH: 25
<212> TYPE: DNA
<213> ORGANISM: Homo sapiens

<400> SEQUENCE: 1013
gattattttt gcattttaaa ataag 25

<210> SEQ ID NO 1014
<211> LENGTH: 25
<212> TYPE: DNA
<213> ORGANISM: Homo sapiens

<400> SEQUENCE: 1014
attatttttg cattttaaaa taaga 25

<210> SEQ ID NO 1015
<211> LENGTH: 25
<212> TYPE: DNA
<213> ORGANISM: Homo sapiens

<400> SEQUENCE: 1015
ttatttttgc attttaaaat aagaa 25

<210> SEQ ID NO 1016
<211> LENGTH: 25
<212> TYPE: DNA
<213> ORGANISM: Homo sapiens

<400> SEQUENCE: 1016
tatttttgca ttttaaaata agaag 25

-continued

<210> SEQ ID NO 1017
<211> LENGTH: 25
<212> TYPE: DNA
<213> ORGANISM: Homo sapiens

<400> SEQUENCE: 1017
atttttgcat tttaaaataa gaagc 25

<210> SEQ ID NO 1018
<211> LENGTH: 25
<212> TYPE: DNA
<213> ORGANISM: Homo sapiens

<400> SEQUENCE: 1018
tttttgcatt ttaaaataag aagca 25

<210> SEQ ID NO 1019
<211> LENGTH: 25
<212> TYPE: DNA
<213> ORGANISM: Homo sapiens

<400> SEQUENCE: 1019
ttttgcattt taaaataaga agcat 25

<210> SEQ ID NO 1020
<211> LENGTH: 25
<212> TYPE: DNA
<213> ORGANISM: Homo sapiens

<400> SEQUENCE: 1020
tttgcatttt aaaataagaa gcatc 25

<210> SEQ ID NO 1021
<211> LENGTH: 25
<212> TYPE: DNA
<213> ORGANISM: Homo sapiens

<400> SEQUENCE: 1021
ttgcatttta aaataagaag catca 25

<210> SEQ ID NO 1022
<211> LENGTH: 25
<212> TYPE: DNA
<213> ORGANISM: Homo sapiens

<400> SEQUENCE: 1022
tgcattttaa aataagaagc atcaa 25

<210> SEQ ID NO 1023
<211> LENGTH: 25
<212> TYPE: DNA
<213> ORGANISM: Homo sapiens

<400> SEQUENCE: 1023
gcattttaaa ataagaagca tcaaa 25

<210> SEQ ID NO 1024
<211> LENGTH: 25
<212> TYPE: DNA
<213> ORGANISM: Homo sapiens

<400> SEQUENCE: 1024

-continued cattttaaaa taagaagcat caaat 25

<210> SEQ ID NO 1025
<211> LENGTH: 25
<212> TYPE: DNA
<213> ORGANISM: Homo sapiens

<400> SEQUENCE: 1025
attttaaaat aagaagcatc aaatt 25

<210> SEQ ID NO 1026
<211> LENGTH: 25
<212> TYPE: DNA
<213> ORGANISM: Homo sapiens

<400> SEQUENCE: 1026
ttttaaaata agaagcatca aattg 25

<210> SEQ ID NO 1027
<211> LENGTH: 25
<212> TYPE: DNA
<213> ORGANISM: Homo sapiens

<400> SEQUENCE: 1027
tttaaaataa gaagcatcaa attgc 25

<210> SEQ ID NO 1028
<211> LENGTH: 25
<212> TYPE: DNA
<213> ORGANISM: Homo sapiens

<400> SEQUENCE: 1028
ttaaaataag aagcatcaaa ttgcg 25

<210> SEQ ID NO 1029
<211> LENGTH: 25
<212> TYPE: DNA
<213> ORGANISM: Homo sapiens

<400> SEQUENCE: 1029
taaaataaga agcatcaaat tgcgt 25

<210> SEQ ID NO 1030
<211> LENGTH: 25
<212> TYPE: DNA
<213> ORGANISM: Homo sapiens

<400> SEQUENCE: 1030
aaaataagaa gcatcaaatt gcgtg 25

<210> SEQ ID NO 1031
<211> LENGTH: 25
<212> TYPE: DNA
<213> ORGANISM: Homo sapiens

<400> SEQUENCE: 1031
aaataagaag catcaaattg cgtgt 25

<210> SEQ ID NO 1032
<211> LENGTH: 25
<212> TYPE: DNA
<213> ORGANISM: Homo sapiens

<400> SEQUENCE: 1032

-continued aataagaagc atcaaattgc gtgtc 25

<210> SEQ ID NO 1033
<211> LENGTH: 25
<212> TYPE: DNA
<213> ORGANISM: Homo sapiens

<400> SEQUENCE: 1033
ataagaagca tcaaattgcg tgtct 25

<210> SEQ ID NO 1034
<211> LENGTH: 25
<212> TYPE: DNA
<213> ORGANISM: Homo sapiens

<400> SEQUENCE: 1034
taagaagcat caaattgcgt gtctc 25

<210> SEQ ID NO 1035
<211> LENGTH: 25
<212> TYPE: DNA
<213> ORGANISM: Homo sapiens

<400> SEQUENCE: 1035
aagaagcatc aaattgcgtg tctct 25

<210> SEQ ID NO 1036
<211> LENGTH: 25
<212> TYPE: DNA
<213> ORGANISM: Homo sapiens

<400> SEQUENCE: 1036
agaagcatca aattgcgtgt ctctg 25

<210> SEQ ID NO 1037
<211> LENGTH: 25
<212> TYPE: DNA
<213> ORGANISM: Homo sapiens

<400> SEQUENCE: 1037
gaagcatcaa attgcgtgtc tctgt 25

<210> SEQ ID NO 1038
<211> LENGTH: 25
<212> TYPE: DNA
<213> ORGANISM: Homo sapiens

<400> SEQUENCE: 1038
aagcatcaaa ttgcgtgtct ctgtg 25

<210> SEQ ID NO 1039
<211> LENGTH: 25
<212> TYPE: DNA
<213> ORGANISM: Homo sapiens

<400> SEQUENCE: 1039
agcatcaaat tgcgtgtctc tgtgt 25

<210> SEQ ID NO 1040
<211> LENGTH: 25
<212> TYPE: DNA
<213> ORGANISM: Homo sapiens -continued

<400> SEQUENCE: 1040
gcatcaaatt gcgtgtctct gtgta 25

<210> SEQ ID NO 1041
<211> LENGTH: 25
<212> TYPE: DNA
<213> ORGANISM: Homo sapiens

<400> SEQUENCE: 1041
catcaaattg cgtgtctctg tgtaa 25

<210> SEQ ID NO 1042
<211> LENGTH: 25
<212> TYPE: DNA
<213> ORGANISM: Homo sapiens

<400> SEQUENCE: 1042
atcaaattgc gtgtctctgt gtaaa 25

<210> SEQ ID NO 1043
<211> LENGTH: 25
<212> TYPE: DNA
<213> ORGANISM: Homo sapiens

<400> SEQUENCE: 1043
tcaaattgcg tgtctctgtg taaaa 25

<210> SEQ ID NO 1044
<211> LENGTH: 25
<212> TYPE: DNA
<213> ORGANISM: Homo sapiens

<400> SEQUENCE: 1044
caaattgcgt gtctctgtgt aaaag 25

<210> SEQ ID NO 1045
<211> LENGTH: 25
<212> TYPE: DNA
<213> ORGANISM: Homo sapiens

<400> SEQUENCE: 1045
aaattgcgtg tctctgtgta aaagt 25

<210> SEQ ID NO 1046
<211> LENGTH: 25
<212> TYPE: DNA
<213> ORGANISM: Homo sapiens

<400> SEQUENCE: 1046
aattgcgtgt ctctgtgtaa aagtt 25

<210> SEQ ID NO 1047
<211> LENGTH: 25
<212> TYPE: DNA
<213> ORGANISM: Homo sapiens

<400> SEQUENCE: 1047
attgcgtgtc tctgtgtaaa agttc 25

<210> SEQ ID NO 1048
<211> LENGTH: 25
<212> TYPE: DNA
<213> ORGANISM: Homo sapiens -continued

<400> SEQUENCE: 1048
ttgcgtgtct ctgtgtaaaa gttct 25

<210> SEQ ID NO 1049
<211> LENGTH: 25
<212> TYPE: DNA
<213> ORGANISM: Homo sapiens

<400> SEQUENCE: 1049
tgcgtgtctc tgtgtaaaag ttcta 25

<210> SEQ ID NO 1050
<211> LENGTH: 25
<212> TYPE: DNA
<213> ORGANISM: Homo sapiens

<400> SEQUENCE: 1050
gcgtgtctct gtgtaaaagt tctag 25

<210> SEQ ID NO 1051
<211> LENGTH: 25
<212> TYPE: DNA
<213> ORGANISM: Homo sapiens

<400> SEQUENCE: 1051
cgtgtctctg tgtaaaagtt ctagc 25

<210> SEQ ID NO 1052
<211> LENGTH: 25
<212> TYPE: DNA
<213> ORGANISM: Homo sapiens

<400> SEQUENCE: 1052
gtgtctctgt gtaaaagttc tagca 25

<210> SEQ ID NO 1053
<211> LENGTH: 25
<212> TYPE: DNA
<213> ORGANISM: Homo sapiens

<400> SEQUENCE: 1053
tgtctctgtg taaaagttct agcaa 25

<210> SEQ ID NO 1054
<211> LENGTH: 25
<212> TYPE: DNA
<213> ORGANISM: Homo sapiens

<400> SEQUENCE: 1054
gtctctgtgt aaaagttcta gcaat 25

<210> SEQ ID NO 1055
<211> LENGTH: 25
<212> TYPE: DNA
<213> ORGANISM: Homo sapiens

<400> SEQUENCE: 1055
tctctgtgta aaagttctag caatt 25

<210> SEQ ID NO 1056
<211> LENGTH: 25
<212> TYPE: DNA

-continued

<213> ORGANISM: Homo sapiens

<400> SEQUENCE: 1056
ctctgtgtaa aagttctagc aattt 25

<210> SEQ ID NO 1057
<211> LENGTH: 25
<212> TYPE: DNA
<213> ORGANISM: Homo sapiens

<400> SEQUENCE: 1057
tctgtgtaaa agttctagca atttg 25

<210> SEQ ID NO 1058
<211> LENGTH: 25
<212> TYPE: DNA
<213> ORGANISM: Homo sapiens

<400> SEQUENCE: 1058
ctgtgtaaaa gttctagcaa tttgt 25

<210> SEQ ID NO 1059
<211> LENGTH: 25
<212> TYPE: DNA
<213> ORGANISM: Homo sapiens

<400> SEQUENCE: 1059
tgtgtaaaag ttctagcaat ttgtt 25

<210> SEQ ID NO 1060
<211> LENGTH: 25
<212> TYPE: DNA
<213> ORGANISM: Homo sapiens

<400> SEQUENCE: 1060
gtgtaaaagt tctagcaatt tgttt 25

<210> SEQ ID NO 1061
<211> LENGTH: 25
<212> TYPE: DNA
<213> ORGANISM: Homo sapiens

<400> SEQUENCE: 1061
tgtaaaagtt ctagcaattt gtttt 25

<210> SEQ ID NO 1062
<211> LENGTH: 25
<212> TYPE: DNA
<213> ORGANISM: Homo sapiens

<400> SEQUENCE: 1062
gtaaaagttc tagcaatttg tttta 25

<210> SEQ ID NO 1063
<211> LENGTH: 25
<212> TYPE: DNA
<213> ORGANISM: Homo sapiens

<400> SEQUENCE: 1063
taaaagttct agcaatttgt tttaa 25

<210> SEQ ID NO 1064
<211> LENGTH: 25

-continued

<212> TYPE: DNA
<213> ORGANISM: Homo sapiens

<400> SEQUENCE: 1064
aaaagttcta gcaatttgtt ttaag 25

<210> SEQ ID NO 1065
<211> LENGTH: 25
<212> TYPE: DNA
<213> ORGANISM: Homo sapiens

<400> SEQUENCE: 1065
aaagttctag caatttgttt taagg 25

<210> SEQ ID NO 1066
<211> LENGTH: 25
<212> TYPE: DNA
<213> ORGANISM: Homo sapiens

<400> SEQUENCE: 1066
aagttctagc aatttgtttt aaggt 25

<210> SEQ ID NO 1067
<211> LENGTH: 25
<212> TYPE: DNA
<213> ORGANISM: Homo sapiens

<400> SEQUENCE: 1067
agttctagca atttgtttta aggtg 25

<210> SEQ ID NO 1068
<211> LENGTH: 25
<212> TYPE: DNA
<213> ORGANISM: Homo sapiens

<400> SEQUENCE: 1068
gttctagcaa tttgttttaa ggtga 25

<210> SEQ ID NO 1069
<211> LENGTH: 25
<212> TYPE: DNA
<213> ORGANISM: Homo sapiens

<400> SEQUENCE: 1069
ttctagcaat ttgttttaag gtgaa 25

<210> SEQ ID NO 1070
<211> LENGTH: 25
<212> TYPE: DNA
<213> ORGANISM: Homo sapiens

<400> SEQUENCE: 1070
tctagcaatt tgttttaagg tgaac 25

<210> SEQ ID NO 1071
<211> LENGTH: 25
<212> TYPE: DNA
<213> ORGANISM: Homo sapiens

<400> SEQUENCE: 1071
ctagcaattt gttttaaggt gaact 25

<210> SEQ ID NO 1072

-continued

<211> LENGTH: 25
<212> TYPE: DNA
<213> ORGANISM: Homo sapiens

<400> SEQUENCE: 1072
tagcaatttg ttttaaggtg aactt 25

<210> SEQ ID NO 1073
<211> LENGTH: 25
<212> TYPE: DNA
<213> ORGANISM: Homo sapiens

<400> SEQUENCE: 1073
agcaatttgt tttaaggtga actta 25

<210> SEQ ID NO 1074
<211> LENGTH: 25
<212> TYPE: DNA
<213> ORGANISM: Homo sapiens

<400> SEQUENCE: 1074
gcaatttgtt ttaaggtgaa cttat 25

<210> SEQ ID NO 1075
<211> LENGTH: 25
<212> TYPE: DNA
<213> ORGANISM: Homo sapiens

<400> SEQUENCE: 1075
caatttgttt taaggtgaac ttatt 25

<210> SEQ ID NO 1076
<211> LENGTH: 25
<212> TYPE: DNA
<213> ORGANISM: Homo sapiens

<400> SEQUENCE: 1076
aatttgtttt aaggtgaact tattt 25

<210> SEQ ID NO 1077
<211> LENGTH: 25
<212> TYPE: DNA
<213> ORGANISM: Homo sapiens

<400> SEQUENCE: 1077
atttgtttta aggtgaactt atttt 25

<210> SEQ ID NO 1078
<211> LENGTH: 25
<212> TYPE: DNA
<213> ORGANISM: Homo sapiens

<400> SEQUENCE: 1078
tttgttttaa ggtgaactta ttttg 25

<210> SEQ ID NO 1079
<211> LENGTH: 25
<212> TYPE: DNA
<213> ORGANISM: Homo sapiens

<400> SEQUENCE: 1079
ttgttttaag gtgaacttat tttgg 25

-continued

<210> SEQ ID NO 1080
<211> LENGTH: 25
<212> TYPE: DNA
<213> ORGANISM: Homo sapiens

<400> SEQUENCE: 1080
tgttttaagg tgaacttatt ttggc 25

<210> SEQ ID NO 1081
<211> LENGTH: 25
<212> TYPE: DNA
<213> ORGANISM: Homo sapiens

<400> SEQUENCE: 1081
gttttaaggt gaacttattt tggct 25

<210> SEQ ID NO 1082
<211> LENGTH: 25
<212> TYPE: DNA
<213> ORGANISM: Homo sapiens

<400> SEQUENCE: 1082
ttttaaggtg aacttatttt ggctt 25

<210> SEQ ID NO 1083
<211> LENGTH: 25
<212> TYPE: DNA
<213> ORGANISM: Homo sapiens

<400> SEQUENCE: 1083
tttaaggtga acttattttg gctta 25

<210> SEQ ID NO 1084
<211> LENGTH: 25
<212> TYPE: DNA
<213> ORGANISM: Homo sapiens

<400> SEQUENCE: 1084
ttaaggtgaa cttattttgg cttag 25

<210> SEQ ID NO 1085
<211> LENGTH: 25
<212> TYPE: DNA
<213> ORGANISM: Homo sapiens

<400> SEQUENCE: 1085
taaggtgaac ttattttggc ttagg 25

<210> SEQ ID NO 1086
<211> LENGTH: 25
<212> TYPE: DNA
<213> ORGANISM: Homo sapiens

<400> SEQUENCE: 1086
aaggtgaact tattttggct taggg 25

<210> SEQ ID NO 1087
<211> LENGTH: 25
<212> TYPE: DNA
<213> ORGANISM: Homo sapiens

<400> SEQUENCE: 1087
aggtgaactt attttggctt aggga 25

-continued

<210> SEQ ID NO 1088
<211> LENGTH: 25
<212> TYPE: DNA
<213> ORGANISM: Homo sapiens

<400> SEQUENCE: 1088
ggtgaactta ttttggctta gggac 25

<210> SEQ ID NO 1089
<211> LENGTH: 25
<212> TYPE: DNA
<213> ORGANISM: Homo sapiens

<400> SEQUENCE: 1089
gtgaacttat tttggcttag ggact 25

<210> SEQ ID NO 1090
<211> LENGTH: 25
<212> TYPE: DNA
<213> ORGANISM: Homo sapiens

<400> SEQUENCE: 1090
tgaacttatt ttggcttagg gacta 25

<210> SEQ ID NO 1091
<211> LENGTH: 25
<212> TYPE: DNA
<213> ORGANISM: Homo sapiens

<400> SEQUENCE: 1091
gaacttattt tggcttaggg actac 25

<210> SEQ ID NO 1092
<211> LENGTH: 25
<212> TYPE: DNA
<213> ORGANISM: Homo sapiens

<400> SEQUENCE: 1092
aacttatttt ggcttaggga ctaca 25

<210> SEQ ID NO 1093
<211> LENGTH: 25
<212> TYPE: DNA
<213> ORGANISM: Homo sapiens

<400> SEQUENCE: 1093
acttattttg gcttagggac tacaa 25

<210> SEQ ID NO 1094
<211> LENGTH: 25
<212> TYPE: DNA
<213> ORGANISM: Homo sapiens

<400> SEQUENCE: 1094
cttattttgg cttagggact acaaa 25

<210> SEQ ID NO 1095
<211> LENGTH: 25
<212> TYPE: DNA
<213> ORGANISM: Homo sapiens

<400> SEQUENCE: 1095
ttattttggc ttagggacta caaaa 25

-continued

<210> SEQ ID NO 1096
<211> LENGTH: 25
<212> TYPE: DNA
<213> ORGANISM: Homo sapiens

<400> SEQUENCE: 1096
tattttggct tagggactac aaaaa 25

<210> SEQ ID NO 1097
<211> LENGTH: 25
<212> TYPE: DNA
<213> ORGANISM: Homo sapiens

<400> SEQUENCE: 1097
attttggctt agggactaca aaaag 25

<210> SEQ ID NO 1098
<211> LENGTH: 25
<212> TYPE: DNA
<213> ORGANISM: Homo sapiens

<400> SEQUENCE: 1098
ttttggctta gggactacaa aaaga 25

<210> SEQ ID NO 1099
<211> LENGTH: 25
<212> TYPE: DNA
<213> ORGANISM: Homo sapiens

<400> SEQUENCE: 1099
tttggcttag ggactacaaa aagag 25

<210> SEQ ID NO 1100
<211> LENGTH: 25
<212> TYPE: DNA
<213> ORGANISM: Homo sapiens

<400> SEQUENCE: 1100
ttggcttagg gactacaaaa agaga 25

<210> SEQ ID NO 1101
<211> LENGTH: 25
<212> TYPE: DNA
<213> ORGANISM: Homo sapiens

<400> SEQUENCE: 1101
tggcttaggg actacaaaaa gagaa 25

<210> SEQ ID NO 1102
<211> LENGTH: 25
<212> TYPE: DNA
<213> ORGANISM: Homo sapiens

<400> SEQUENCE: 1102
ggcttaggga ctacaaaaag agaag 25

<210> SEQ ID NO 1103
<211> LENGTH: 25
<212> TYPE: DNA
<213> ORGANISM: Homo sapiens

<400> SEQUENCE: 1103

-continued gcttagggac tacaaaaaga gaagg 25

<210> SEQ ID NO 1104
<211> LENGTH: 25
<212> TYPE: DNA
<213> ORGANISM: Homo sapiens

<400> SEQUENCE: 1104
cttagggact acaaaaagag aaggt 25

<210> SEQ ID NO 1105
<211> LENGTH: 25
<212> TYPE: DNA
<213> ORGANISM: Homo sapiens

<400> SEQUENCE: 1105
ttagggacta caaaaagaga aggta 25

<210> SEQ ID NO 1106
<211> LENGTH: 25
<212> TYPE: DNA
<213> ORGANISM: Homo sapiens

<400> SEQUENCE: 1106
tagggactac aaaaagagaa ggtaa 25

<210> SEQ ID NO 1107
<211> LENGTH: 25
<212> TYPE: DNA
<213> ORGANISM: Homo sapiens

<400> SEQUENCE: 1107
agggactaca aaaagagaag gtaat 25

<210> SEQ ID NO 1108
<211> LENGTH: 25
<212> TYPE: DNA
<213> ORGANISM: Homo sapiens

<400> SEQUENCE: 1108
gggactacaa aaagagaagg taatt 25

<210> SEQ ID NO 1109
<211> LENGTH: 25
<212> TYPE: DNA
<213> ORGANISM: Homo sapiens

<400> SEQUENCE: 1109
ggactacaaa aagagaaggt aattc 25

<210> SEQ ID NO 1110
<211> LENGTH: 25
<212> TYPE: DNA
<213> ORGANISM: Homo sapiens

<400> SEQUENCE: 1110
gactacaaaa agagaaggta attcc 25

<210> SEQ ID NO 1111
<211> LENGTH: 25
<212> TYPE: DNA
<213> ORGANISM: Homo sapiens

<400> SEQUENCE: 1111

-continued actacaaaaa gagaaggtaa ttcct 25

<210> SEQ ID NO 1112
<211> LENGTH: 25
<212> TYPE: DNA
<213> ORGANISM: Homo sapiens

<400> SEQUENCE: 1112
ctacaaaaag agaaggtaat tccta 25

<210> SEQ ID NO 1113
<211> LENGTH: 25
<212> TYPE: DNA
<213> ORGANISM: Homo sapiens

<400> SEQUENCE: 1113
tacaaaaaga gaaggtaatt cctag 25

<210> SEQ ID NO 1114
<211> LENGTH: 25
<212> TYPE: DNA
<213> ORGANISM: Homo sapiens

<400> SEQUENCE: 1114
acaaaaagag aaggtaattc ctagg 25

<210> SEQ ID NO 1115
<211> LENGTH: 25
<212> TYPE: DNA
<213> ORGANISM: Homo sapiens

<400> SEQUENCE: 1115
caaaaagaga aggtaattcc taggg 25

<210> SEQ ID NO 1116
<211> LENGTH: 25
<212> TYPE: DNA
<213> ORGANISM: Homo sapiens

<400> SEQUENCE: 1116
aaaaagagaa ggtaattcct aggga 25

<210> SEQ ID NO 1117
<211> LENGTH: 25
<212> TYPE: DNA
<213> ORGANISM: Homo sapiens

<400> SEQUENCE: 1117
aaaagagaag gtaattccta gggaa 25

<210> SEQ ID NO 1118
<211> LENGTH: 25
<212> TYPE: DNA
<213> ORGANISM: Homo sapiens

<400> SEQUENCE: 1118
aaagagaagg taattcctag ggaag 25

<210> SEQ ID NO 1119
<211> LENGTH: 25
<212> TYPE: DNA
<213> ORGANISM: Homo sapiens -continued

<400> SEQUENCE: 1119
aagagaaggt aattcctagg gaagg 25

<210> SEQ ID NO 1120
<211> LENGTH: 25
<212> TYPE: DNA
<213> ORGANISM: Homo sapiens

<400> SEQUENCE: 1120
agagaaggta attcctaggg aagga 25

<210> SEQ ID NO 1121
<211> LENGTH: 25
<212> TYPE: DNA
<213> ORGANISM: Homo sapiens

<400> SEQUENCE: 1121
gagaaggtaa ttcctaggga aggaa 25

<210> SEQ ID NO 1122
<211> LENGTH: 25
<212> TYPE: DNA
<213> ORGANISM: Homo sapiens

<400> SEQUENCE: 1122
agaaggtaat tcctagggaa ggaag 25

<210> SEQ ID NO 1123
<211> LENGTH: 25
<212> TYPE: DNA
<213> ORGANISM: Homo sapiens

<400> SEQUENCE: 1123
gaaggtaatt cctagggaag gaaga 25

<210> SEQ ID NO 1124
<211> LENGTH: 25
<212> TYPE: DNA
<213> ORGANISM: Homo sapiens

<400> SEQUENCE: 1124
aaggtaattc ctagggaagg aagaa 25

<210> SEQ ID NO 1125
<211> LENGTH: 25
<212> TYPE: DNA
<213> ORGANISM: Homo sapiens

<400> SEQUENCE: 1125
aggtaattcc tagggaagga agaag 25

<210> SEQ ID NO 1126
<211> LENGTH: 25
<212> TYPE: DNA
<213> ORGANISM: Homo sapiens

<400> SEQUENCE: 1126
ggtaattcct agggaaggaa gaaga 25

<210> SEQ ID NO 1127
<211> LENGTH: 25
<212> TYPE: DNA
<213> ORGANISM: Homo sapiens -continued

<400> SEQUENCE: 1127
gtaattccta gggaaggaag aagag 25

<210> SEQ ID NO 1128
<211> LENGTH: 25
<212> TYPE: DNA
<213> ORGANISM: Homo sapiens

<400> SEQUENCE: 1128
taattcctag ggaaggaaga agaga 25

<210> SEQ ID NO 1129
<211> LENGTH: 25
<212> TYPE: DNA
<213> ORGANISM: Homo sapiens

<400> SEQUENCE: 1129
aattcctagg gaaggaagaa gagaa 25

<210> SEQ ID NO 1130
<211> LENGTH: 25
<212> TYPE: DNA
<213> ORGANISM: Homo sapiens

<400> SEQUENCE: 1130
attcctaggg aaggaagaag agaaa 25

<210> SEQ ID NO 1131
<211> LENGTH: 25
<212> TYPE: DNA
<213> ORGANISM: Homo sapiens

<400> SEQUENCE: 1131
ttcctaggga aggaagaaga gaaag 25

<210> SEQ ID NO 1132
<211> LENGTH: 25
<212> TYPE: DNA
<213> ORGANISM: Homo sapiens

<400> SEQUENCE: 1132
tcctagggaa ggaagaagag aaaga 25

<210> SEQ ID NO 1133
<211> LENGTH: 25
<212> TYPE: DNA
<213> ORGANISM: Homo sapiens

<400> SEQUENCE: 1133
cctagggaag gaagaagaga aagaa 25

<210> SEQ ID NO 1134
<211> LENGTH: 25
<212> TYPE: DNA
<213> ORGANISM: Homo sapiens

<400> SEQUENCE: 1134
ctagggaagg aagaagagaa agaaa 25

<210> SEQ ID NO 1135
<211> LENGTH: 25
<212> TYPE: DNA

-continued

<213> ORGANISM: Homo sapiens

<400> SEQUENCE: 1135
tagggaagga agaagagaaa gaaat 25

<210> SEQ ID NO 1136
<211> LENGTH: 25
<212> TYPE: DNA
<213> ORGANISM: Homo sapiens

<400> SEQUENCE: 1136
agggaaggaa gaagagaaag aaatg 25

<210> SEQ ID NO 1137
<211> LENGTH: 25
<212> TYPE: DNA
<213> ORGANISM: Homo sapiens

<400> SEQUENCE: 1137
gggaaggaag aagagaaaga aatga 25

<210> SEQ ID NO 1138
<211> LENGTH: 25
<212> TYPE: DNA
<213> ORGANISM: Homo sapiens

<400> SEQUENCE: 1138
ggaaggaaga agagaaagaa atgaa 25

<210> SEQ ID NO 1139
<211> LENGTH: 25
<212> TYPE: DNA
<213> ORGANISM: Homo sapiens

<400> SEQUENCE: 1139
gaaggaagaa gagaaagaaa tgaaa 25

<210> SEQ ID NO 1140
<211> LENGTH: 25
<212> TYPE: DNA
<213> ORGANISM: Homo sapiens

<400> SEQUENCE: 1140
aaggaagaag agaaagaaat gaaaa 25

<210> SEQ ID NO 1141
<211> LENGTH: 25
<212> TYPE: DNA
<213> ORGANISM: Homo sapiens

<400> SEQUENCE: 1141
aggaagaaga gaaagaaatg aaaat 25

<210> SEQ ID NO 1142
<211> LENGTH: 25
<212> TYPE: DNA
<213> ORGANISM: Homo sapiens

<400> SEQUENCE: 1142
ggaagaagag aaagaaatga aaatt 25

<210> SEQ ID NO 1143
<211> LENGTH: 25

-continued

<212> TYPE: DNA
<213> ORGANISM: Homo sapiens

<400> SEQUENCE: 1143
gaagaagaga aagaaatgaa aatta 25

<210> SEQ ID NO 1144
<211> LENGTH: 25
<212> TYPE: DNA
<213> ORGANISM: Homo sapiens

<400> SEQUENCE: 1144
aagaagagaa agaaatgaaa attag 25

<210> SEQ ID NO 1145
<211> LENGTH: 25
<212> TYPE: DNA
<213> ORGANISM: Homo sapiens

<400> SEQUENCE: 1145
agaagagaaa gaaatgaaaa ttaga 25

<210> SEQ ID NO 1146
<211> LENGTH: 25
<212> TYPE: DNA
<213> ORGANISM: Homo sapiens

<400> SEQUENCE: 1146
gaagagaaag aaatgaaaat tagag 25

<210> SEQ ID NO 1147
<211> LENGTH: 25
<212> TYPE: DNA
<213> ORGANISM: Homo sapiens

<400> SEQUENCE: 1147
aagagaaaga aatgaaaatt agaga 25

<210> SEQ ID NO 1148
<211> LENGTH: 25
<212> TYPE: DNA
<213> ORGANISM: Homo sapiens

<400> SEQUENCE: 1148
agagaaagaa atgaaaatta gagaa 25

<210> SEQ ID NO 1149
<211> LENGTH: 25
<212> TYPE: DNA
<213> ORGANISM: Homo sapiens

<400> SEQUENCE: 1149
gagaaagaaa tgaaaattag agaat 25

<210> SEQ ID NO 1150
<211> LENGTH: 25
<212> TYPE: DNA
<213> ORGANISM: Homo sapiens

<400> SEQUENCE: 1150
agaaagaaat gaaaattaga gaata 25

<210> SEQ ID NO 1151

-continued

<211> LENGTH: 25
<212> TYPE: DNA
<213> ORGANISM: Homo sapiens

<400> SEQUENCE: 1151
gaaagaaatg aaaattagag aataa 25

<210> SEQ ID NO 1152
<211> LENGTH: 25
<212> TYPE: DNA
<213> ORGANISM: Homo sapiens

<400> SEQUENCE: 1152
aaagaaatga aaattagaga ataag 25

<210> SEQ ID NO 1153
<211> LENGTH: 25
<212> TYPE: DNA
<213> ORGANISM: Homo sapiens

<400> SEQUENCE: 1153
aagaaatgaa aattagagaa taaga 25

<210> SEQ ID NO 1154
<211> LENGTH: 25
<212> TYPE: DNA
<213> ORGANISM: Homo sapiens

<400> SEQUENCE: 1154
agaaatgaaa attagagaat aagat 25

<210> SEQ ID NO 1155
<211> LENGTH: 25
<212> TYPE: DNA
<213> ORGANISM: Homo sapiens

<400> SEQUENCE: 1155
gaaatgaaaa ttagagaata agatt 25

<210> SEQ ID NO 1156
<211> LENGTH: 25
<212> TYPE: DNA
<213> ORGANISM: Homo sapiens

<400> SEQUENCE: 1156
aaatgaaaat tagagaataa gatta 25

<210> SEQ ID NO 1157
<211> LENGTH: 25
<212> TYPE: DNA
<213> ORGANISM: Homo sapiens

<400> SEQUENCE: 1157
aatgaaaatt agagaataag attat 25

<210> SEQ ID NO 1158
<211> LENGTH: 25
<212> TYPE: DNA
<213> ORGANISM: Homo sapiens

<400> SEQUENCE: 1158
atgaaaatta gagaataaga ttatt 25

-continued

<210> SEQ ID NO 1159
<211> LENGTH: 25
<212> TYPE: DNA
<213> ORGANISM: Homo sapiens

<400> SEQUENCE: 1159
tgaaaattag agaataagat tattt 25

<210> SEQ ID NO 1160
<211> LENGTH: 25
<212> TYPE: DNA
<213> ORGANISM: Homo sapiens

<400> SEQUENCE: 1160
gaaaattaga gaataagatt atttt 25

<210> SEQ ID NO 1161
<211> LENGTH: 25
<212> TYPE: DNA
<213> ORGANISM: Homo sapiens

<400> SEQUENCE: 1161
aaaattagag aataagatta ttttg 25

<210> SEQ ID NO 1162
<211> LENGTH: 25
<212> TYPE: DNA
<213> ORGANISM: Homo sapiens

<400> SEQUENCE: 1162
aaattagaga ataagattat tttga 25

<210> SEQ ID NO 1163
<211> LENGTH: 25
<212> TYPE: DNA
<213> ORGANISM: Homo sapiens

<400> SEQUENCE: 1163
aattagagaa taagattatt ttgaa 25

<210> SEQ ID NO 1164
<211> LENGTH: 25
<212> TYPE: DNA
<213> ORGANISM: Homo sapiens

<400> SEQUENCE: 1164
attagagaat aagattattt tgaat 25

<210> SEQ ID NO 1165
<211> LENGTH: 25
<212> TYPE: DNA
<213> ORGANISM: Homo sapiens

<400> SEQUENCE: 1165
ttagagaata agattatttt gaatg 25

<210> SEQ ID NO 1166
<211> LENGTH: 25
<212> TYPE: DNA
<213> ORGANISM: Homo sapiens

<400> SEQUENCE: 1166
tagagaataa gattattttg aatga 25

-continued

<210> SEQ ID NO 1167
<211> LENGTH: 25
<212> TYPE: DNA
<213> ORGANISM: Homo sapiens

<400> SEQUENCE: 1167
agagaataag attattttga atgac 25

<210> SEQ ID NO 1168
<211> LENGTH: 25
<212> TYPE: DNA
<213> ORGANISM: Homo sapiens

<400> SEQUENCE: 1168
gagaataaga ttattttgaa tgact 25

<210> SEQ ID NO 1169
<211> LENGTH: 25
<212> TYPE: DNA
<213> ORGANISM: Homo sapiens

<400> SEQUENCE: 1169
agaataagat tattttgaat gactt 25

<210> SEQ ID NO 1170
<211> LENGTH: 25
<212> TYPE: DNA
<213> ORGANISM: Homo sapiens

<400> SEQUENCE: 1170
gaataagatt attttgaatg acttc 25

<210> SEQ ID NO 1171
<211> LENGTH: 25
<212> TYPE: DNA
<213> ORGANISM: Homo sapiens

<400> SEQUENCE: 1171
aataagatta ttttgaatga cttca 25

<210> SEQ ID NO 1172
<211> LENGTH: 25
<212> TYPE: DNA
<213> ORGANISM: Homo sapiens

<400> SEQUENCE: 1172
ataagattat tttgaatgac ttcag 25

<210> SEQ ID NO 1173
<211> LENGTH: 25
<212> TYPE: DNA
<213> ORGANISM: Homo sapiens

<400> SEQUENCE: 1173
taagattatt ttgaatgact tcagg 25

<210> SEQ ID NO 1174
<211> LENGTH: 25
<212> TYPE: DNA
<213> ORGANISM: Homo sapiens

<400> SEQUENCE: 1174
aagattattt tgaatgactt caggt 25

<210> SEQ ID NO 1175
<211> LENGTH: 25
<212> TYPE: DNA
<213> ORGANISM: Homo sapiens

<400> SEQUENCE: 1175
agattatttt gaatgacttc aggta 25

<210> SEQ ID NO 1176
<211> LENGTH: 25
<212> TYPE: DNA
<213> ORGANISM: Homo sapiens

<400> SEQUENCE: 1176
gattattttg aatgacttca ggtag 25

<210> SEQ ID NO 1177
<211> LENGTH: 25
<212> TYPE: DNA
<213> ORGANISM: Homo sapiens

<400> SEQUENCE: 1177
attattttga atgacttcag gtagc 25

<210> SEQ ID NO 1178
<211> LENGTH: 25
<212> TYPE: DNA
<213> ORGANISM: Homo sapiens

<400> SEQUENCE: 1178
ttattttgaa tgacttcagg tagcg 25

<210> SEQ ID NO 1179
<211> LENGTH: 25
<212> TYPE: DNA
<213> ORGANISM: Homo sapiens

<400> SEQUENCE: 1179
tattttgaat gacttcaggt agcga 25

<210> SEQ ID NO 1180
<211> LENGTH: 25
<212> TYPE: DNA
<213> ORGANISM: Homo sapiens

<400> SEQUENCE: 1180
attttgaatg acttcaggta gcgag 25

<210> SEQ ID NO 1181
<211> LENGTH: 25
<212> TYPE: DNA
<213> ORGANISM: Homo sapiens

<400> SEQUENCE: 1181
ttttgaatga cttcaggtag cgagg 25

<210> SEQ ID NO 1182
<211> LENGTH: 25
<212> TYPE: DNA
<213> ORGANISM: Homo sapiens

<400> SEQUENCE: 1182

-continued tttgaatgac ttcaggtagc gagga 25

<210> SEQ ID NO 1183
<211> LENGTH: 25
<212> TYPE: DNA
<213> ORGANISM: Homo sapiens

<400> SEQUENCE: 1183
ttgaatgact tcaggtagcg aggag 25

<210> SEQ ID NO 1184
<211> LENGTH: 25
<212> TYPE: DNA
<213> ORGANISM: Homo sapiens

<400> SEQUENCE: 1184
tgaatgactt caggtagcga ggagt 25

<210> SEQ ID NO 1185
<211> LENGTH: 25
<212> TYPE: DNA
<213> ORGANISM: Homo sapiens

<400> SEQUENCE: 1185
gaatgacttc aggtagcgag gagtg 25

<210> SEQ ID NO 1186
<211> LENGTH: 25
<212> TYPE: DNA
<213> ORGANISM: Homo sapiens

<400> SEQUENCE: 1186
aatgacttca ggtagcgagg agtgt 25

<210> SEQ ID NO 1187
<211> LENGTH: 25
<212> TYPE: DNA
<213> ORGANISM: Homo sapiens

<400> SEQUENCE: 1187
atgacttcag gtagcgagga gtgtg 25

<210> SEQ ID NO 1188
<211> LENGTH: 25
<212> TYPE: DNA
<213> ORGANISM: Homo sapiens

<400> SEQUENCE: 1188
tgacttcagg tagcgaggag tgtgt 25

<210> SEQ ID NO 1189
<211> LENGTH: 25
<212> TYPE: DNA
<213> ORGANISM: Homo sapiens

<400> SEQUENCE: 1189
gacttcaggt agcgaggagt gtgtg 25

<210> SEQ ID NO 1190
<211> LENGTH: 25
<212> TYPE: DNA
<213> ORGANISM: Homo sapiens

<400> SEQUENCE: 1190

```
acttcaggta gcgaggagtg tgtgt                                              25

<210> SEQ ID NO 1191
<211> LENGTH: 25
<212> TYPE: DNA
<213> ORGANISM: Homo sapiens

<400> SEQUENCE: 1191

cttcaggtag cgaggagtgt gtgtt                                              25

<210> SEQ ID NO 1192
<211> LENGTH: 25
<212> TYPE: DNA
<213> ORGANISM: Homo sapiens

<400> SEQUENCE: 1192

ttcaggtagc gaggagtgtg tgttt                                              25

<210> SEQ ID NO 1193
<211> LENGTH: 25
<212> TYPE: DNA
<213> ORGANISM: Homo sapiens

<400> SEQUENCE: 1193

tcaggtagcg aggagtgtgt gtttg                                              25

<210> SEQ ID NO 1194
<211> LENGTH: 25
<212> TYPE: DNA
<213> ORGANISM: Homo sapiens

<400> SEQUENCE: 1194

caggtagcga ggagtgtgtg tttgt                                              25

<210> SEQ ID NO 1195
<211> LENGTH: 25
<212> TYPE: DNA
<213> ORGANISM: Homo sapiens

<400> SEQUENCE: 1195

aggtagcgag gagtgtgtgt ttgtg                                              25

<210> SEQ ID NO 1196
<211> LENGTH: 25
<212> TYPE: DNA
<213> ORGANISM: Homo sapiens

<400> SEQUENCE: 1196

ggtagcgagg agtgtgtgtt tgtga                                              25

<210> SEQ ID NO 1197
<211> LENGTH: 25
<212> TYPE: DNA
<213> ORGANISM: Homo sapiens

<400> SEQUENCE: 1197

gtagcgagga gtgtgtgttt gtgag                                              25

<210> SEQ ID NO 1198
<211> LENGTH: 25
<212> TYPE: DNA
<213> ORGANISM: Homo sapiens
```

-continued

<400> SEQUENCE: 1198
tagcgaggag tgtgtgtttg tgagt 25

<210> SEQ ID NO 1199
<211> LENGTH: 25
<212> TYPE: DNA
<213> ORGANISM: Homo sapiens

<400> SEQUENCE: 1199
agcgaggagt gtgtgtttgt gagtg 25

<210> SEQ ID NO 1200
<211> LENGTH: 25
<212> TYPE: DNA
<213> ORGANISM: Homo sapiens

<400> SEQUENCE: 1200
gcgaggagtg tgtgtttgtg agtgt 25

<210> SEQ ID NO 1201
<211> LENGTH: 25
<212> TYPE: DNA
<213> ORGANISM: Homo sapiens

<400> SEQUENCE: 1201
cgaggagtgt gtgtttgtga gtgtg 25

<210> SEQ ID NO 1202
<211> LENGTH: 25
<212> TYPE: DNA
<213> ORGANISM: Homo sapiens

<400> SEQUENCE: 1202
gaggagtgtg tgtttgtgag tgtgt 25

<210> SEQ ID NO 1203
<211> LENGTH: 25
<212> TYPE: DNA
<213> ORGANISM: Homo sapiens

<400> SEQUENCE: 1203
aggagtgtgt gtttgtgagt gtgta 25

<210> SEQ ID NO 1204
<211> LENGTH: 25
<212> TYPE: DNA
<213> ORGANISM: Homo sapiens

<400> SEQUENCE: 1204
ggagtgtgtg tttgtgagtg tgtat 25

<210> SEQ ID NO 1205
<211> LENGTH: 25
<212> TYPE: DNA
<213> ORGANISM: Homo sapiens

<400> SEQUENCE: 1205
gagtgtgtgt ttgtgagtgt gtatt 25

<210> SEQ ID NO 1206
<211> LENGTH: 25
<212> TYPE: DNA
<213> ORGANISM: Homo sapiens

<400> SEQUENCE: 1206
agtgtgtgtt tgtgagtgtg tattt 25

<210> SEQ ID NO 1207
<211> LENGTH: 25
<212> TYPE: DNA
<213> ORGANISM: Homo sapiens

<400> SEQUENCE: 1207
gtgtgtgttt gtgagtgtgt atttg 25

<210> SEQ ID NO 1208
<211> LENGTH: 25
<212> TYPE: DNA
<213> ORGANISM: Homo sapiens

<400> SEQUENCE: 1208
tgtgtgtttg tgagtgtgta tttga 25

<210> SEQ ID NO 1209
<211> LENGTH: 25
<212> TYPE: DNA
<213> ORGANISM: Homo sapiens

<400> SEQUENCE: 1209
gtgtgtttgt gagtgtgtat ttgag 25

<210> SEQ ID NO 1210
<211> LENGTH: 25
<212> TYPE: DNA
<213> ORGANISM: Homo sapiens

<400> SEQUENCE: 1210
tgtgtttgtg agtgtgtatt tgaga 25

<210> SEQ ID NO 1211
<211> LENGTH: 25
<212> TYPE: DNA
<213> ORGANISM: Homo sapiens

<400> SEQUENCE: 1211
gtgtttgtga gtgtgtattt gagag 25

<210> SEQ ID NO 1212
<211> LENGTH: 25
<212> TYPE: DNA
<213> ORGANISM: Homo sapiens

<400> SEQUENCE: 1212
tgtttgtgag tgtgtatttg agaga 25

<210> SEQ ID NO 1213
<211> LENGTH: 25
<212> TYPE: DNA
<213> ORGANISM: Homo sapiens

<400> SEQUENCE: 1213
gtttgtgagt gtgtatttga gagac 25

<210> SEQ ID NO 1214
<211> LENGTH: 25
<212> TYPE: DNA

-continued

<213> ORGANISM: Homo sapiens

<400> SEQUENCE: 1214
tttgtgagtg tgtatttgag agact 25

<210> SEQ ID NO 1215
<211> LENGTH: 25
<212> TYPE: DNA
<213> ORGANISM: Homo sapiens

<400> SEQUENCE: 1215
ttgtgagtgt gtatttgaga gactt 25

<210> SEQ ID NO 1216
<211> LENGTH: 25
<212> TYPE: DNA
<213> ORGANISM: Homo sapiens

<400> SEQUENCE: 1216
tgtgagtgtg tatttgagag acttg 25

<210> SEQ ID NO 1217
<211> LENGTH: 25
<212> TYPE: DNA
<213> ORGANISM: Homo sapiens

<400> SEQUENCE: 1217
gtgagtgtgt atttgagaga cttgg 25

<210> SEQ ID NO 1218
<211> LENGTH: 25
<212> TYPE: DNA
<213> ORGANISM: Homo sapiens

<400> SEQUENCE: 1218
tgagtgtgta tttgagagac ttggc 25

<210> SEQ ID NO 1219
<211> LENGTH: 25
<212> TYPE: DNA
<213> ORGANISM: Homo sapiens

<400> SEQUENCE: 1219
gagtgtgtat ttgagagact tggct 25

<210> SEQ ID NO 1220
<211> LENGTH: 25
<212> TYPE: DNA
<213> ORGANISM: Homo sapiens

<400> SEQUENCE: 1220
agtgtgtatt tgagagactt ggctc 25

<210> SEQ ID NO 1221
<211> LENGTH: 25
<212> TYPE: DNA
<213> ORGANISM: Homo sapiens

<400> SEQUENCE: 1221
gtgtgtattt gagagacttg gctca 25

<210> SEQ ID NO 1222
<211> LENGTH: 25

-continued

<212> TYPE: DNA
<213> ORGANISM: Homo sapiens

<400> SEQUENCE: 1222
tgtgtatttg agagacttgg ctcat 25

<210> SEQ ID NO 1223
<211> LENGTH: 25
<212> TYPE: DNA
<213> ORGANISM: Homo sapiens

<400> SEQUENCE: 1223
gtgtatttga gagacttggc tcatg 25

<210> SEQ ID NO 1224
<211> LENGTH: 25
<212> TYPE: DNA
<213> ORGANISM: Homo sapiens

<400> SEQUENCE: 1224
tgtatttgag agacttggct catgc 25

<210> SEQ ID NO 1225
<211> LENGTH: 25
<212> TYPE: DNA
<213> ORGANISM: Homo sapiens

<400> SEQUENCE: 1225
gtatttgaga gacttggctc atgcc 25

<210> SEQ ID NO 1226
<211> LENGTH: 25
<212> TYPE: DNA
<213> ORGANISM: Homo sapiens

<400> SEQUENCE: 1226
tatttgagag acttggctca tgcct 25

<210> SEQ ID NO 1227
<211> LENGTH: 25
<212> TYPE: DNA
<213> ORGANISM: Homo sapiens

<400> SEQUENCE: 1227
atttgagaga cttggctcat gcctg 25

<210> SEQ ID NO 1228
<211> LENGTH: 25
<212> TYPE: DNA
<213> ORGANISM: Homo sapiens

<400> SEQUENCE: 1228
tttgagagac ttggctcatg cctgt 25

<210> SEQ ID NO 1229
<211> LENGTH: 25
<212> TYPE: DNA
<213> ORGANISM: Homo sapiens

<400> SEQUENCE: 1229
ttgagagact tggctcatgc ctgtg 25

<210> SEQ ID NO 1230

-continued

<211> LENGTH: 25
<212> TYPE: DNA
<213> ORGANISM: Homo sapiens

<400> SEQUENCE: 1230
tgagagactt ggctcatgcc tgtgg 25

<210> SEQ ID NO 1231
<211> LENGTH: 25
<212> TYPE: DNA
<213> ORGANISM: Homo sapiens

<400> SEQUENCE: 1231
gagagacttg gctcatgcct gtggg 25

<210> SEQ ID NO 1232
<211> LENGTH: 25
<212> TYPE: DNA
<213> ORGANISM: Homo sapiens

<400> SEQUENCE: 1232
agagacttgg ctcatgcctg tgggt 25

<210> SEQ ID NO 1233
<211> LENGTH: 25
<212> TYPE: DNA
<213> ORGANISM: Homo sapiens

<400> SEQUENCE: 1233
gagacttggc tcatgcctgt gggtc 25

<210> SEQ ID NO 1234
<211> LENGTH: 25
<212> TYPE: DNA
<213> ORGANISM: Homo sapiens

<400> SEQUENCE: 1234
agacttggct catgcctgtg ggtct 25

<210> SEQ ID NO 1235
<211> LENGTH: 25
<212> TYPE: DNA
<213> ORGANISM: Homo sapiens

<400> SEQUENCE: 1235
gacttggctc atgcctgtgg gtctt 25

<210> SEQ ID NO 1236
<211> LENGTH: 25
<212> TYPE: DNA
<213> ORGANISM: Homo sapiens

<400> SEQUENCE: 1236
acttggctca tgcctgtggg tcttc 25

<210> SEQ ID NO 1237
<211> LENGTH: 25
<212> TYPE: DNA
<213> ORGANISM: Homo sapiens

<400> SEQUENCE: 1237
cttggctcat gcctgtgggt cttct 25

-continued

<210> SEQ ID NO 1238
<211> LENGTH: 25
<212> TYPE: DNA
<213> ORGANISM: Homo sapiens

<400> SEQUENCE: 1238
ttggctcatg cctgtgggtc ttctc 25

<210> SEQ ID NO 1239
<211> LENGTH: 25
<212> TYPE: DNA
<213> ORGANISM: Homo sapiens

<400> SEQUENCE: 1239
tggctcatgc ctgtgggtct tctct 25

<210> SEQ ID NO 1240
<211> LENGTH: 25
<212> TYPE: DNA
<213> ORGANISM: Homo sapiens

<400> SEQUENCE: 1240
ggctcatgcc tgtgggtctt ctctt 25

<210> SEQ ID NO 1241
<211> LENGTH: 25
<212> TYPE: DNA
<213> ORGANISM: Homo sapiens

<400> SEQUENCE: 1241
gctcatgcct gtgggtcttc tcttc 25

<210> SEQ ID NO 1242
<211> LENGTH: 25
<212> TYPE: DNA
<213> ORGANISM: Homo sapiens

<400> SEQUENCE: 1242
ctcatgcctg tgggtcttct cttct 25

<210> SEQ ID NO 1243
<211> LENGTH: 25
<212> TYPE: DNA
<213> ORGANISM: Homo sapiens

<400> SEQUENCE: 1243
tcatgcctgt gggtcttctc ttcta 25

<210> SEQ ID NO 1244
<211> LENGTH: 25
<212> TYPE: DNA
<213> ORGANISM: Homo sapiens

<400> SEQUENCE: 1244
catgcctgtg ggtcttctct tctag 25

<210> SEQ ID NO 1245
<211> LENGTH: 25
<212> TYPE: DNA
<213> ORGANISM: Homo sapiens

<400> SEQUENCE: 1245
atgcctgtgg gtcttctctt ctagt 25

-continued

<210> SEQ ID NO 1246
<211> LENGTH: 25
<212> TYPE: DNA
<213> ORGANISM: Homo sapiens

<400> SEQUENCE: 1246
tgcctgtggg tcttctcttc tagta 25

<210> SEQ ID NO 1247
<211> LENGTH: 25
<212> TYPE: DNA
<213> ORGANISM: Homo sapiens

<400> SEQUENCE: 1247
gcctgtgggt cttctcttct agtat 25

<210> SEQ ID NO 1248
<211> LENGTH: 25
<212> TYPE: DNA
<213> ORGANISM: Homo sapiens

<400> SEQUENCE: 1248
cctgtgggtc ttctcttcta gtatc 25

<210> SEQ ID NO 1249
<211> LENGTH: 25
<212> TYPE: DNA
<213> ORGANISM: Homo sapiens

<400> SEQUENCE: 1249
ctgtgggtct tctcttctag tatca 25

<210> SEQ ID NO 1250
<211> LENGTH: 25
<212> TYPE: DNA
<213> ORGANISM: Homo sapiens

<400> SEQUENCE: 1250
tgtgggtctt ctcttctagt atcag 25

<210> SEQ ID NO 1251
<211> LENGTH: 25
<212> TYPE: DNA
<213> ORGANISM: Homo sapiens

<400> SEQUENCE: 1251
gtgggtcttc tcttctagta tcagt 25

<210> SEQ ID NO 1252
<211> LENGTH: 25
<212> TYPE: DNA
<213> ORGANISM: Homo sapiens

<400> SEQUENCE: 1252
tgggtcttct cttctagtat cagtg 25

<210> SEQ ID NO 1253
<211> LENGTH: 25
<212> TYPE: DNA
<213> ORGANISM: Homo sapiens

<400> SEQUENCE: 1253
gggtcttctc ttctagtatc agtga 25

-continued

<210> SEQ ID NO 1254
<211> LENGTH: 25
<212> TYPE: DNA
<213> ORGANISM: Homo sapiens

<400> SEQUENCE: 1254
ggtcttctct tctagtatca gtgag 25

<210> SEQ ID NO 1255
<211> LENGTH: 25
<212> TYPE: DNA
<213> ORGANISM: Homo sapiens

<400> SEQUENCE: 1255
gtcttctctt ctagtatcag tgagg 25

<210> SEQ ID NO 1256
<211> LENGTH: 25
<212> TYPE: DNA
<213> ORGANISM: Homo sapiens

<400> SEQUENCE: 1256
tcttctcttc tagtatcagt gaggg 25

<210> SEQ ID NO 1257
<211> LENGTH: 25
<212> TYPE: DNA
<213> ORGANISM: Homo sapiens

<400> SEQUENCE: 1257
cttctcttct agtatcagtg agggg 25

<210> SEQ ID NO 1258
<211> LENGTH: 25
<212> TYPE: DNA
<213> ORGANISM: Homo sapiens

<400> SEQUENCE: 1258
ttctcttcta gtatcagtga gggga 25

<210> SEQ ID NO 1259
<211> LENGTH: 25
<212> TYPE: DNA
<213> ORGANISM: Homo sapiens

<400> SEQUENCE: 1259
tctcttctag tatcagtgag gggag 25

<210> SEQ ID NO 1260
<211> LENGTH: 25
<212> TYPE: DNA
<213> ORGANISM: Homo sapiens

<400> SEQUENCE: 1260
ctcttctagt atcagtgagg ggagg 25

<210> SEQ ID NO 1261
<211> LENGTH: 25
<212> TYPE: DNA
<213> ORGANISM: Homo sapiens

<400> SEQUENCE: 1261

-continued tcttctagta tcagtgaggg gaggg 25

<210> SEQ ID NO 1262
<211> LENGTH: 25
<212> TYPE: DNA
<213> ORGANISM: Homo sapiens

<400> SEQUENCE: 1262
cttctagtat cagtgagggg aggga 25

<210> SEQ ID NO 1263
<211> LENGTH: 25
<212> TYPE: DNA
<213> ORGANISM: Homo sapiens

<400> SEQUENCE: 1263
ttctagtatc agtgagggga gggat 25

<210> SEQ ID NO 1264
<211> LENGTH: 25
<212> TYPE: DNA
<213> ORGANISM: Homo sapiens

<400> SEQUENCE: 1264
tctagtatca gtgaggggag ggatt 25

<210> SEQ ID NO 1265
<211> LENGTH: 25
<212> TYPE: DNA
<213> ORGANISM: Homo sapiens

<400> SEQUENCE: 1265
ctagtatcag tgaggggagg gatta 25

<210> SEQ ID NO 1266
<211> LENGTH: 25
<212> TYPE: DNA
<213> ORGANISM: Homo sapiens

<400> SEQUENCE: 1266
tagtatcagt gaggggaggg attac 25

<210> SEQ ID NO 1267
<211> LENGTH: 25
<212> TYPE: DNA
<213> ORGANISM: Homo sapiens

<400> SEQUENCE: 1267
agtatcagtg aggggaggga ttact 25

<210> SEQ ID NO 1268
<211> LENGTH: 25
<212> TYPE: DNA
<213> ORGANISM: Homo sapiens

<400> SEQUENCE: 1268
gtatcagtga ggggagggat tactg 25

<210> SEQ ID NO 1269
<211> LENGTH: 25
<212> TYPE: DNA
<213> ORGANISM: Homo sapiens

<400> SEQUENCE: 1269

-continued tatcagtgag gggagggatt actga 25

<210> SEQ ID NO 1270
<211> LENGTH: 25
<212> TYPE: DNA
<213> ORGANISM: Homo sapiens

<400> SEQUENCE: 1270
atcagtgagg ggagggatta ctgaa 25

<210> SEQ ID NO 1271
<211> LENGTH: 25
<212> TYPE: DNA
<213> ORGANISM: Homo sapiens

<400> SEQUENCE: 1271
tcagtgaggg gagggattac tgaag 25

<210> SEQ ID NO 1272
<211> LENGTH: 25
<212> TYPE: DNA
<213> ORGANISM: Homo sapiens

<400> SEQUENCE: 1272
cagtgagggg agggattact gaaga 25

<210> SEQ ID NO 1273
<211> LENGTH: 25
<212> TYPE: DNA
<213> ORGANISM: Homo sapiens

<400> SEQUENCE: 1273
agtgagggga gggattactg aagaa 25

<210> SEQ ID NO 1274
<211> LENGTH: 25
<212> TYPE: DNA
<213> ORGANISM: Homo sapiens

<400> SEQUENCE: 1274
gtgaggggag ggattactga agaag 25

<210> SEQ ID NO 1275
<211> LENGTH: 25
<212> TYPE: DNA
<213> ORGANISM: Homo sapiens

<400> SEQUENCE: 1275
tgaggggagg gattactgaa gaaga 25

<210> SEQ ID NO 1276
<211> LENGTH: 25
<212> TYPE: DNA
<213> ORGANISM: Homo sapiens

<400> SEQUENCE: 1276
gaggggaggg attactgaag aagaa 25

<210> SEQ ID NO 1277
<211> LENGTH: 25
<212> TYPE: DNA
<213> ORGANISM: Homo sapiens -continued

<400> SEQUENCE: 1277
aggggaggga ttactgaaga agaag 25

<210> SEQ ID NO 1278
<211> LENGTH: 25
<212> TYPE: DNA
<213> ORGANISM: Homo sapiens

<400> SEQUENCE: 1278
ggggagggat tactgaagaa gaagg 25

<210> SEQ ID NO 1279
<211> LENGTH: 25
<212> TYPE: DNA
<213> ORGANISM: Homo sapiens

<400> SEQUENCE: 1279
gggagggatt actgaagaag aaggg 25

<210> SEQ ID NO 1280
<211> LENGTH: 25
<212> TYPE: DNA
<213> ORGANISM: Homo sapiens

<400> SEQUENCE: 1280
ggagggatta ctgaagaaga agggg 25

<210> SEQ ID NO 1281
<211> LENGTH: 25
<212> TYPE: DNA
<213> ORGANISM: Homo sapiens

<400> SEQUENCE: 1281
gagggattac tgaagaagaa ggggg 25

<210> SEQ ID NO 1282
<211> LENGTH: 25
<212> TYPE: DNA
<213> ORGANISM: Homo sapiens

<400> SEQUENCE: 1282
agggattact gaagaagaag ggggg 25

<210> SEQ ID NO 1283
<211> LENGTH: 25
<212> TYPE: DNA
<213> ORGANISM: Homo sapiens

<400> SEQUENCE: 1283
gggattactg aagaagaagg gggga 25

<210> SEQ ID NO 1284
<211> LENGTH: 25
<212> TYPE: DNA
<213> ORGANISM: Homo sapiens

<400> SEQUENCE: 1284
ggattactga agaagaaggg gggaa 25

<210> SEQ ID NO 1285
<211> LENGTH: 25
<212> TYPE: DNA
<213> ORGANISM: Homo sapiens -continued

<400> SEQUENCE: 1285
gattactgaa gaagaagggg ggaaa                                              25

<210> SEQ ID NO 1286
<211> LENGTH: 25
<212> TYPE: DNA
<213> ORGANISM: Homo sapiens

<400> SEQUENCE: 1286
attactgaag aagaaggggg gaaaa                                              25

<210> SEQ ID NO 1287
<211> LENGTH: 25
<212> TYPE: DNA
<213> ORGANISM: Homo sapiens

<400> SEQUENCE: 1287
ttactgaaga agaaggggggg aaaaa                                             25

<210> SEQ ID NO 1288
<211> LENGTH: 25
<212> TYPE: DNA
<213> ORGANISM: Homo sapiens

<400> SEQUENCE: 1288
tactgaagaa gaagggggga aaaaa                                              25

<210> SEQ ID NO 1289
<211> LENGTH: 25
<212> TYPE: DNA
<213> ORGANISM: Homo sapiens

<400> SEQUENCE: 1289
actgaagaag aaggggggaa aaaaa                                              25

<210> SEQ ID NO 1290
<211> LENGTH: 25
<212> TYPE: DNA
<213> ORGANISM: Homo sapiens

<400> SEQUENCE: 1290
ctgaagaaga aggggggaaa aaaaa                                              25

<210> SEQ ID NO 1291
<211> LENGTH: 25
<212> TYPE: DNA
<213> ORGANISM: Homo sapiens

<400> SEQUENCE: 1291
tgaagaagaa ggggggaaaa aaaaa                                              25

<210> SEQ ID NO 1292
<211> LENGTH: 25
<212> TYPE: DNA
<213> ORGANISM: Homo sapiens

<400> SEQUENCE: 1292
gaagaagaag gggggaaaaa aaaag                                              25

<210> SEQ ID NO 1293
<211> LENGTH: 25
<212> TYPE: DNA

-continued

<213> ORGANISM: Homo sapiens

<400> SEQUENCE: 1293
aagaagaagg ggggaaaaaa aaaga 25

<210> SEQ ID NO 1294
<211> LENGTH: 25
<212> TYPE: DNA
<213> ORGANISM: Homo sapiens

<400> SEQUENCE: 1294
agaagaaggg gggaaaaaaa aagaa 25

<210> SEQ ID NO 1295
<211> LENGTH: 25
<212> TYPE: DNA
<213> ORGANISM: Homo sapiens

<400> SEQUENCE: 1295
gaagaagggg ggaaaaaaaa agaaa 25

<210> SEQ ID NO 1296
<211> LENGTH: 25
<212> TYPE: DNA
<213> ORGANISM: Homo sapiens

<400> SEQUENCE: 1296
aagaaggggg gaaaaaaaaa gaaag 25

<210> SEQ ID NO 1297
<211> LENGTH: 25
<212> TYPE: DNA
<213> ORGANISM: Homo sapiens

<400> SEQUENCE: 1297
agaagggggg aaaaaaaaag aaaga 25

<210> SEQ ID NO 1298
<211> LENGTH: 25
<212> TYPE: DNA
<213> ORGANISM: Homo sapiens

<400> SEQUENCE: 1298
gaagggggga aaaaaaaaga aagaa 25

<210> SEQ ID NO 1299
<211> LENGTH: 25
<212> TYPE: DNA
<213> ORGANISM: Homo sapiens

<400> SEQUENCE: 1299
aaggggggaa aaaaaaagaa agaaa 25

<210> SEQ ID NO 1300
<211> LENGTH: 25
<212> TYPE: DNA
<213> ORGANISM: Homo sapiens

<400> SEQUENCE: 1300 agggggaaa aaaaaagaaa gaaat 25

<210> SEQ ID NO 1301
<211> LENGTH: 25

-continued

<212> TYPE: DNA
<213> ORGANISM: Homo sapiens

<400> SEQUENCE: 1301
ggggggaaaa aaaaagaaag aaatc 25

<210> SEQ ID NO 1302
<211> LENGTH: 25
<212> TYPE: DNA
<213> ORGANISM: Homo sapiens

<400> SEQUENCE: 1302
gggggaaaaa aaaagaaaga aatct 25

<210> SEQ ID NO 1303
<211> LENGTH: 25
<212> TYPE: DNA
<213> ORGANISM: Homo sapiens

<400> SEQUENCE: 1303
ggggaaaaaa aaagaaagaa atctg 25

<210> SEQ ID NO 1304
<211> LENGTH: 25
<212> TYPE: DNA
<213> ORGANISM: Homo sapiens

<400> SEQUENCE: 1304
gggaaaaaaa aagaaagaaa tctga 25

<210> SEQ ID NO 1305
<211> LENGTH: 25
<212> TYPE: DNA
<213> ORGANISM: Homo sapiens

<400> SEQUENCE: 1305
ggaaaaaaaa agaaagaaat ctgag 25

<210> SEQ ID NO 1306
<211> LENGTH: 25
<212> TYPE: DNA
<213> ORGANISM: Homo sapiens

<400> SEQUENCE: 1306
gaaaaaaaaa gaaagaaatc tgagc 25

<210> SEQ ID NO 1307
<211> LENGTH: 25
<212> TYPE: DNA
<213> ORGANISM: Homo sapiens

<400> SEQUENCE: 1307
aaaaaaaaag aaagaaatct gagct 25

<210> SEQ ID NO 1308
<211> LENGTH: 25
<212> TYPE: DNA
<213> ORGANISM: Homo sapiens

<400> SEQUENCE: 1308
aaaaaaaaga aagaaatctg agctt 25

<210> SEQ ID NO 1309

-continued

<211> LENGTH: 25
<212> TYPE: DNA
<213> ORGANISM: Homo sapiens

<400> SEQUENCE: 1309
aaaaaaagaa agaaatctga gcttt 25

<210> SEQ ID NO 1310
<211> LENGTH: 25
<212> TYPE: DNA
<213> ORGANISM: Homo sapiens

<400> SEQUENCE: 1310
aaaaaagaaa gaaatctgag ctttc 25

<210> SEQ ID NO 1311
<211> LENGTH: 25
<212> TYPE: DNA
<213> ORGANISM: Homo sapiens

<400> SEQUENCE: 1311
aaaaagaaag aaatctgagc tttct 25

<210> SEQ ID NO 1312
<211> LENGTH: 25
<212> TYPE: DNA
<213> ORGANISM: Homo sapiens

<400> SEQUENCE: 1312
aaaagaaaga aatctgagct ttctg 25

<210> SEQ ID NO 1313
<211> LENGTH: 25
<212> TYPE: DNA
<213> ORGANISM: Homo sapiens

<400> SEQUENCE: 1313
aaagaaagaa atctgagctt tctgg 25

<210> SEQ ID NO 1314
<211> LENGTH: 25
<212> TYPE: DNA
<213> ORGANISM: Homo sapiens

<400> SEQUENCE: 1314
aagaaagaaa tctgagcttt ctggg 25

<210> SEQ ID NO 1315
<211> LENGTH: 25
<212> TYPE: DNA
<213> ORGANISM: Homo sapiens

<400> SEQUENCE: 1315
agaaagaaat ctgagctttc tggga 25

<210> SEQ ID NO 1316
<211> LENGTH: 25
<212> TYPE: DNA
<213> ORGANISM: Homo sapiens

<400> SEQUENCE: 1316
gaaagaaatc tgagctttct gggag 25

-continued

<210> SEQ ID NO 1317
<211> LENGTH: 25
<212> TYPE: DNA
<213> ORGANISM: Homo sapiens

<400> SEQUENCE: 1317
aaagaaatct gagctttctg ggagg 25

<210> SEQ ID NO 1318
<211> LENGTH: 25
<212> TYPE: DNA
<213> ORGANISM: Homo sapiens

<400> SEQUENCE: 1318
aagaaatctg agctttctgg gagga 25

<210> SEQ ID NO 1319
<211> LENGTH: 25
<212> TYPE: DNA
<213> ORGANISM: Homo sapiens

<400> SEQUENCE: 1319
agaaatctga gctttctggg aggaa 25

<210> SEQ ID NO 1320
<211> LENGTH: 25
<212> TYPE: DNA
<213> ORGANISM: Homo sapiens

<400> SEQUENCE: 1320
gaaatctgag ctttctggga ggaaa 25

<210> SEQ ID NO 1321
<211> LENGTH: 25
<212> TYPE: DNA
<213> ORGANISM: Homo sapiens

<400> SEQUENCE: 1321
aaatctgagc tttctgggag gaaat 25

<210> SEQ ID NO 1322
<211> LENGTH: 25
<212> TYPE: DNA
<213> ORGANISM: Homo sapiens

<400> SEQUENCE: 1322
aatctgagct ttctgggagg aaatt 25

<210> SEQ ID NO 1323
<211> LENGTH: 25
<212> TYPE: DNA
<213> ORGANISM: Homo sapiens

<400> SEQUENCE: 1323
atctgagctt tctgggagga aattc 25

<210> SEQ ID NO 1324
<211> LENGTH: 25
<212> TYPE: DNA
<213> ORGANISM: Homo sapiens

<400> SEQUENCE: 1324
tctgagcttt ctgggaggaa attca 25

<210> SEQ ID NO 1325
<211> LENGTH: 25
<212> TYPE: DNA
<213> ORGANISM: Homo sapiens

<400> SEQUENCE: 1325
ctgagctttc tgggaggaaa ttcaa 25

<210> SEQ ID NO 1326
<211> LENGTH: 25
<212> TYPE: DNA
<213> ORGANISM: Homo sapiens

<400> SEQUENCE: 1326
tgagctttct gggaggaaat tcaaa 25

<210> SEQ ID NO 1327
<211> LENGTH: 25
<212> TYPE: DNA
<213> ORGANISM: Homo sapiens

<400> SEQUENCE: 1327
gagctttctg ggaggaaatt caaag 25

<210> SEQ ID NO 1328
<211> LENGTH: 25
<212> TYPE: DNA
<213> ORGANISM: Homo sapiens

<400> SEQUENCE: 1328
agctttctgg gaggaaattc aaagg 25

<210> SEQ ID NO 1329
<211> LENGTH: 25
<212> TYPE: DNA
<213> ORGANISM: Homo sapiens

<400> SEQUENCE: 1329
gctttctggg aggaaattca aagga 25

<210> SEQ ID NO 1330
<211> LENGTH: 25
<212> TYPE: DNA
<213> ORGANISM: Homo sapiens

<400> SEQUENCE: 1330
ctttctggga ggaaattcaa aggaa 25

<210> SEQ ID NO 1331
<211> LENGTH: 25
<212> TYPE: DNA
<213> ORGANISM: Homo sapiens

<400> SEQUENCE: 1331
tttctgggag gaaattcaaa ggaac 25

<210> SEQ ID NO 1332
<211> LENGTH: 25
<212> TYPE: DNA
<213> ORGANISM: Homo sapiens

<400> SEQUENCE: 1332
ttctgggagg aaattcaaag gaacc 25

<210> SEQ ID NO 1333
<211> LENGTH: 25
<212> TYPE: DNA
<213> ORGANISM: Homo sapiens

<400> SEQUENCE: 1333
tctgggagga aattcaaagg aacca 25

<210> SEQ ID NO 1334
<211> LENGTH: 25
<212> TYPE: DNA
<213> ORGANISM: Homo sapiens

<400> SEQUENCE: 1334
ctgggaggaa attcaaagga accaa 25

<210> SEQ ID NO 1335
<211> LENGTH: 25
<212> TYPE: DNA
<213> ORGANISM: Homo sapiens

<400> SEQUENCE: 1335
tgggaggaaa ttcaaaggaa ccaag 25

<210> SEQ ID NO 1336
<211> LENGTH: 25
<212> TYPE: DNA
<213> ORGANISM: Homo sapiens

<400> SEQUENCE: 1336
gggaggaaat tcaaaggaac caaga 25

<210> SEQ ID NO 1337
<211> LENGTH: 25
<212> TYPE: DNA
<213> ORGANISM: Homo sapiens

<400> SEQUENCE: 1337
ggaggaaatt caaaggaacc aagag 25

<210> SEQ ID NO 1338
<211> LENGTH: 25
<212> TYPE: DNA
<213> ORGANISM: Homo sapiens

<400> SEQUENCE: 1338
gaggaaattc aaaggaacca agaga 25

<210> SEQ ID NO 1339
<211> LENGTH: 25
<212> TYPE: DNA
<213> ORGANISM: Homo sapiens

<400> SEQUENCE: 1339
aggaaattca aaggaaccaa gagaa 25

<210> SEQ ID NO 1340
<211> LENGTH: 25
<212> TYPE: DNA
<213> ORGANISM: Homo sapiens

<400> SEQUENCE: 1340

-continued ggaaattcaa aggaaccaag agaaa 25

<210> SEQ ID NO 1341
<211> LENGTH: 25
<212> TYPE: DNA
<213> ORGANISM: Homo sapiens

<400> SEQUENCE: 1341
gaaattcaaa ggaaccaaga gaaat 25

<210> SEQ ID NO 1342
<211> LENGTH: 25
<212> TYPE: DNA
<213> ORGANISM: Homo sapiens

<400> SEQUENCE: 1342
aaattcaaag gaaccaagag aaatt 25

<210> SEQ ID NO 1343
<211> LENGTH: 25
<212> TYPE: DNA
<213> ORGANISM: Homo sapiens

<400> SEQUENCE: 1343
aattcaaagg aaccaagaga aatta 25

<210> SEQ ID NO 1344
<211> LENGTH: 25
<212> TYPE: DNA
<213> ORGANISM: Homo sapiens

<400> SEQUENCE: 1344
attcaaagga accaagagaa attaa 25

<210> SEQ ID NO 1345
<211> LENGTH: 25
<212> TYPE: DNA
<213> ORGANISM: Homo sapiens

<400> SEQUENCE: 1345
ttcaaaggaa ccaagagaaa ttaac 25

<210> SEQ ID NO 1346
<211> LENGTH: 25
<212> TYPE: DNA
<213> ORGANISM: Homo sapiens

<400> SEQUENCE: 1346
tcaaaggaac caagagaaat taact 25

<210> SEQ ID NO 1347
<211> LENGTH: 25
<212> TYPE: DNA
<213> ORGANISM: Homo sapiens

<400> SEQUENCE: 1347
caaaggaacc aagagaaatt aactt 25

<210> SEQ ID NO 1348
<211> LENGTH: 25
<212> TYPE: DNA
<213> ORGANISM: Homo sapiens

<400> SEQUENCE: 1348

-continued aaaggaacca agagaaatta acttc 25

<210> SEQ ID NO 1349
<211> LENGTH: 25
<212> TYPE: DNA
<213> ORGANISM: Homo sapiens

<400> SEQUENCE: 1349
aaggaaccaa gagaaattaa cttcg 25

<210> SEQ ID NO 1350
<211> LENGTH: 25
<212> TYPE: DNA
<213> ORGANISM: Homo sapiens

<400> SEQUENCE: 1350
aggaaccaag agaaattaac ttcgt 25

<210> SEQ ID NO 1351
<211> LENGTH: 25
<212> TYPE: DNA
<213> ORGANISM: Homo sapiens

<400> SEQUENCE: 1351
ggaaccaaga gaaattaact tcgtt 25

<210> SEQ ID NO 1352
<211> LENGTH: 25
<212> TYPE: DNA
<213> ORGANISM: Homo sapiens

<400> SEQUENCE: 1352
gaaccaagag aaattaactt cgttc 25

<210> SEQ ID NO 1353
<211> LENGTH: 25
<212> TYPE: DNA
<213> ORGANISM: Homo sapiens

<400> SEQUENCE: 1353
aaccaagaga aattaacttc gttct 25

<210> SEQ ID NO 1354
<211> LENGTH: 25
<212> TYPE: DNA
<213> ORGANISM: Homo sapiens

<400> SEQUENCE: 1354
accaagagaa attaacttcg ttctg 25

<210> SEQ ID NO 1355
<211> LENGTH: 25
<212> TYPE: DNA
<213> ORGANISM: Homo sapiens

<400> SEQUENCE: 1355
ccaagagaaa ttaacttcgt tctgc 25

<210> SEQ ID NO 1356
<211> LENGTH: 25
<212> TYPE: DNA
<213> ORGANISM: Homo sapiens -continued

<400> SEQUENCE: 1356
caagagaaat taacttcgtt ctgca 25

<210> SEQ ID NO 1357
<211> LENGTH: 25
<212> TYPE: DNA
<213> ORGANISM: Homo sapiens

<400> SEQUENCE: 1357
aagagaaatt aacttcgttc tgcaa 25

<210> SEQ ID NO 1358
<211> LENGTH: 25
<212> TYPE: DNA
<213> ORGANISM: Homo sapiens

<400> SEQUENCE: 1358
agagaaatta acttcgttct gcaag 25

<210> SEQ ID NO 1359
<211> LENGTH: 25
<212> TYPE: DNA
<213> ORGANISM: Homo sapiens

<400> SEQUENCE: 1359
gagaaattaa cttcgttctg caagg 25

<210> SEQ ID NO 1360
<211> LENGTH: 25
<212> TYPE: DNA
<213> ORGANISM: Homo sapiens

<400> SEQUENCE: 1360
agaaattaac ttcgttctgc aagga 25

<210> SEQ ID NO 1361
<211> LENGTH: 25
<212> TYPE: DNA
<213> ORGANISM: Homo sapiens

<400> SEQUENCE: 1361
gaaattaact tcgttctgca aggac 25

<210> SEQ ID NO 1362
<211> LENGTH: 25
<212> TYPE: DNA
<213> ORGANISM: Homo sapiens

<400> SEQUENCE: 1362
aaattaactt cgttctgcaa ggact 25

<210> SEQ ID NO 1363
<211> LENGTH: 25
<212> TYPE: DNA
<213> ORGANISM: Homo sapiens

<400> SEQUENCE: 1363
aattaacttc gttctgcaag gacta 25

<210> SEQ ID NO 1364
<211> LENGTH: 25
<212> TYPE: DNA
<213> ORGANISM: Homo sapiens -continued

<400> SEQUENCE: 1364
attaacttcg ttctgcaagg actaa 25

<210> SEQ ID NO 1365
<211> LENGTH: 25
<212> TYPE: DNA
<213> ORGANISM: Homo sapiens

<400> SEQUENCE: 1365
ttaacttcgt tctgcaagga ctaaa 25

<210> SEQ ID NO 1366
<211> LENGTH: 25
<212> TYPE: DNA
<213> ORGANISM: Homo sapiens

<400> SEQUENCE: 1366
taacttcgtt ctgcaaggac taaag 25

<210> SEQ ID NO 1367
<211> LENGTH: 25
<212> TYPE: DNA
<213> ORGANISM: Homo sapiens

<400> SEQUENCE: 1367
aacttcgttc tgcaaggact aaagt 25

<210> SEQ ID NO 1368
<211> LENGTH: 25
<212> TYPE: DNA
<213> ORGANISM: Homo sapiens

<400> SEQUENCE: 1368
acttcgttct gcaaggacta aagta 25

<210> SEQ ID NO 1369
<211> LENGTH: 25
<212> TYPE: DNA
<213> ORGANISM: Homo sapiens

<400> SEQUENCE: 1369
cttcgttctg caaggactaa agtac 25

<210> SEQ ID NO 1370
<211> LENGTH: 25
<212> TYPE: DNA
<213> ORGANISM: Homo sapiens

<400> SEQUENCE: 1370
ttcgttctgc aaggactaaa gtaca 25

<210> SEQ ID NO 1371
<211> LENGTH: 25
<212> TYPE: DNA
<213> ORGANISM: Homo sapiens

<400> SEQUENCE: 1371
tcgttctgca aggactaaag tacag 25

<210> SEQ ID NO 1372
<211> LENGTH: 25
<212> TYPE: DNA

-continued

<213> ORGANISM: Homo sapiens

<400> SEQUENCE: 1372
cgttctgcaa ggactaaagt acagc 25

<210> SEQ ID NO 1373
<211> LENGTH: 25
<212> TYPE: DNA
<213> ORGANISM: Homo sapiens

<400> SEQUENCE: 1373
gttctgcaag gactaaagta cagca 25

<210> SEQ ID NO 1374
<211> LENGTH: 25
<212> TYPE: DNA
<213> ORGANISM: Homo sapiens

<400> SEQUENCE: 1374
ttctgcaagg actaaagtac agcaa 25

<210> SEQ ID NO 1375
<211> LENGTH: 25
<212> TYPE: DNA
<213> ORGANISM: Homo sapiens

<400> SEQUENCE: 1375
tctgcaagga ctaaagtaca gcaag 25

<210> SEQ ID NO 1376
<211> LENGTH: 25
<212> TYPE: DNA
<213> ORGANISM: Homo sapiens

<400> SEQUENCE: 1376
ctgcaaggac taaagtacag caaga 25

<210> SEQ ID NO 1377
<211> LENGTH: 25
<212> TYPE: DNA
<213> ORGANISM: Homo sapiens

<400> SEQUENCE: 1377
tgcaaggact aaagtacagc aagag 25

<210> SEQ ID NO 1378
<211> LENGTH: 25
<212> TYPE: DNA
<213> ORGANISM: Homo sapiens

<400> SEQUENCE: 1378
gcaaggacta aagtacagca agagg 25

<210> SEQ ID NO 1379
<211> LENGTH: 25
<212> TYPE: DNA
<213> ORGANISM: Homo sapiens

<400> SEQUENCE: 1379
caaggactaa agtacagcaa gagga 25

<210> SEQ ID NO 1380
<211> LENGTH: 25

-continued

<212> TYPE: DNA
<213> ORGANISM: Homo sapiens

<400> SEQUENCE: 1380
aaggactaaa gtacagcaag aggag 25

<210> SEQ ID NO 1381
<211> LENGTH: 25
<212> TYPE: DNA
<213> ORGANISM: Homo sapiens

<400> SEQUENCE: 1381
aggactaaag tacagcaaga ggaga 25

<210> SEQ ID NO 1382
<211> LENGTH: 25
<212> TYPE: DNA
<213> ORGANISM: Homo sapiens

<400> SEQUENCE: 1382
ggactaaagt acagcaagag gagag 25

<210> SEQ ID NO 1383
<211> LENGTH: 25
<212> TYPE: DNA
<213> ORGANISM: Homo sapiens

<400> SEQUENCE: 1383
gactaaagta cagcaagagg agaga 25

<210> SEQ ID NO 1384
<211> LENGTH: 25
<212> TYPE: DNA
<213> ORGANISM: Homo sapiens

<400> SEQUENCE: 1384
actaaagtac agcaagagga gagag 25

<210> SEQ ID NO 1385
<211> LENGTH: 25
<212> TYPE: DNA
<213> ORGANISM: Homo sapiens

<400> SEQUENCE: 1385
ctaaagtaca gcaagaggag agagg 25

<210> SEQ ID NO 1386
<211> LENGTH: 25
<212> TYPE: DNA
<213> ORGANISM: Homo sapiens

<400> SEQUENCE: 1386
taaagtacag caagaggaga gaggt 25

<210> SEQ ID NO 1387
<211> LENGTH: 25
<212> TYPE: DNA
<213> ORGANISM: Homo sapiens

<400> SEQUENCE: 1387
aaagtacagc aagaggagag aggtc 25

<210> SEQ ID NO 1388

-continued

<211> LENGTH: 25
<212> TYPE: DNA
<213> ORGANISM: Homo sapiens

<400> SEQUENCE: 1388
aagtacagca agaggagaga ggtca 25

<210> SEQ ID NO 1389
<211> LENGTH: 25
<212> TYPE: DNA
<213> ORGANISM: Homo sapiens

<400> SEQUENCE: 1389
agtacagcaa gaggagagag gtcaa 25

<210> SEQ ID NO 1390
<211> LENGTH: 25
<212> TYPE: DNA
<213> ORGANISM: Homo sapiens

<400> SEQUENCE: 1390
gtacagcaag aggagagagg tcaag 25

<210> SEQ ID NO 1391
<211> LENGTH: 25
<212> TYPE: DNA
<213> ORGANISM: Homo sapiens

<400> SEQUENCE: 1391
tacagcaaga ggagagaggt caagc 25

<210> SEQ ID NO 1392
<211> LENGTH: 25
<212> TYPE: DNA
<213> ORGANISM: Homo sapiens

<400> SEQUENCE: 1392
acagcaagag gagagaggtc aagcg 25

<210> SEQ ID NO 1393
<211> LENGTH: 25
<212> TYPE: DNA
<213> ORGANISM: Homo sapiens

<400> SEQUENCE: 1393
cagcaagagg agagaggtca agcga 25

<210> SEQ ID NO 1394
<211> LENGTH: 25
<212> TYPE: DNA
<213> ORGANISM: Homo sapiens

<400> SEQUENCE: 1394
agcaagagga gagaggtcaa gcgag 25

<210> SEQ ID NO 1395
<211> LENGTH: 25
<212> TYPE: DNA
<213> ORGANISM: Homo sapiens

<400> SEQUENCE: 1395
gcaagaggag agaggtcaag cgaga 25

-continued

<210> SEQ ID NO 1396
<211> LENGTH: 25
<212> TYPE: DNA
<213> ORGANISM: Homo sapiens

<400> SEQUENCE: 1396
caagaggaga gaggtcaagc gagaa 25

<210> SEQ ID NO 1397
<211> LENGTH: 25
<212> TYPE: DNA
<213> ORGANISM: Homo sapiens

<400> SEQUENCE: 1397
aagaggagag aggtcaagcg agaag 25

<210> SEQ ID NO 1398
<211> LENGTH: 25
<212> TYPE: DNA
<213> ORGANISM: Homo sapiens

<400> SEQUENCE: 1398
agaggagaga ggtcaagcga gaagc 25

<210> SEQ ID NO 1399
<211> LENGTH: 25
<212> TYPE: DNA
<213> ORGANISM: Homo sapiens

<400> SEQUENCE: 1399
gaggagagag gtcaagcgag aagcg 25

<210> SEQ ID NO 1400
<211> LENGTH: 25
<212> TYPE: DNA
<213> ORGANISM: Homo sapiens

<400> SEQUENCE: 1400
aggagagagg tcaagcgaga agcgt 25

<210> SEQ ID NO 1401
<211> LENGTH: 25
<212> TYPE: DNA
<213> ORGANISM: Homo sapiens

<400> SEQUENCE: 1401
ggagagaggt caagcgagaa gcgtg 25

<210> SEQ ID NO 1402
<211> LENGTH: 25
<212> TYPE: DNA
<213> ORGANISM: Homo sapiens

<400> SEQUENCE: 1402
gagagaggtc aagcgagaag cgtgc 25

<210> SEQ ID NO 1403
<211> LENGTH: 25
<212> TYPE: DNA
<213> ORGANISM: Homo sapiens

<400> SEQUENCE: 1403
agagaggtca agcgagaagc gtgcg 25

-continued

<210> SEQ ID NO 1404
<211> LENGTH: 25
<212> TYPE: DNA
<213> ORGANISM: Homo sapiens

<400> SEQUENCE: 1404
gagaggtcaa gcgagaagcg tgcgg 25

<210> SEQ ID NO 1405
<211> LENGTH: 25
<212> TYPE: DNA
<213> ORGANISM: Homo sapiens

<400> SEQUENCE: 1405
agaggtcaag cgagaagcgt gcggg 25

<210> SEQ ID NO 1406
<211> LENGTH: 25
<212> TYPE: DNA
<213> ORGANISM: Homo sapiens

<400> SEQUENCE: 1406
gaggtcaagc gagaagcgtg cggga 25

<210> SEQ ID NO 1407
<211> LENGTH: 25
<212> TYPE: DNA
<213> ORGANISM: Homo sapiens

<400> SEQUENCE: 1407
aggtcaagcg agaagcgtgc gggaa 25

<210> SEQ ID NO 1408
<211> LENGTH: 25
<212> TYPE: DNA
<213> ORGANISM: Homo sapiens

<400> SEQUENCE: 1408
ggtcaagcga gaagcgtgcg ggaag 25

<210> SEQ ID NO 1409
<211> LENGTH: 25
<212> TYPE: DNA
<213> ORGANISM: Homo sapiens

<400> SEQUENCE: 1409
gtcaagcgag aagcgtgcgg gaagc 25

<210> SEQ ID NO 1410
<211> LENGTH: 25
<212> TYPE: DNA
<213> ORGANISM: Homo sapiens

<400> SEQUENCE: 1410
tcaagcgaga agcgtgcggg aagca 25

<210> SEQ ID NO 1411
<211> LENGTH: 25
<212> TYPE: DNA
<213> ORGANISM: Homo sapiens

<400> SEQUENCE: 1411
caagcgagaa gcgtgcggga agcac 25

-continued

<210> SEQ ID NO 1412
<211> LENGTH: 25
<212> TYPE: DNA
<213> ORGANISM: Homo sapiens

<400> SEQUENCE: 1412
aagcgagaag cgtgcgggaa gcaca 25

<210> SEQ ID NO 1413
<211> LENGTH: 25
<212> TYPE: DNA
<213> ORGANISM: Homo sapiens

<400> SEQUENCE: 1413
agcgagaagc gtgcgggaag cacat 25

<210> SEQ ID NO 1414
<211> LENGTH: 25
<212> TYPE: DNA
<213> ORGANISM: Homo sapiens

<400> SEQUENCE: 1414
gcgagaagcg tgcgggaagc acatg 25

<210> SEQ ID NO 1415
<211> LENGTH: 25
<212> TYPE: DNA
<213> ORGANISM: Homo sapiens

<400> SEQUENCE: 1415
cgagaagcgt gcgggaagca catgc 25

<210> SEQ ID NO 1416
<211> LENGTH: 25
<212> TYPE: DNA
<213> ORGANISM: Homo sapiens

<400> SEQUENCE: 1416
gagaagcgtg cgggaagcac atgcc 25

<210> SEQ ID NO 1417
<211> LENGTH: 25
<212> TYPE: DNA
<213> ORGANISM: Homo sapiens

<400> SEQUENCE: 1417
agaagcgtgc gggaagcaca tgccc 25

<210> SEQ ID NO 1418
<211> LENGTH: 25
<212> TYPE: DNA
<213> ORGANISM: Homo sapiens

<400> SEQUENCE: 1418
gaagcgtgcg ggaagcacat gccct 25

<210> SEQ ID NO 1419
<211> LENGTH: 25
<212> TYPE: DNA
<213> ORGANISM: Homo sapiens

<400> SEQUENCE: 1419

-continued aagcgtgcgg gaagcacatg ccctg 25

<210> SEQ ID NO 1420
<211> LENGTH: 25
<212> TYPE: DNA
<213> ORGANISM: Homo sapiens

<400> SEQUENCE: 1420
agcgtgcggg aagcacatgc cctgg 25

<210> SEQ ID NO 1421
<211> LENGTH: 25
<212> TYPE: DNA
<213> ORGANISM: Homo sapiens

<400> SEQUENCE: 1421
gcgtgcggga agcacatgcc ctggg 25

<210> SEQ ID NO 1422
<211> LENGTH: 25
<212> TYPE: DNA
<213> ORGANISM: Homo sapiens

<400> SEQUENCE: 1422
cgtgcgggaa gcacatgccc tgggg 25

<210> SEQ ID NO 1423
<211> LENGTH: 25
<212> TYPE: DNA
<213> ORGANISM: Homo sapiens

<400> SEQUENCE: 1423
gtgcgggaag cacatgccct gggga 25

<210> SEQ ID NO 1424
<211> LENGTH: 25
<212> TYPE: DNA
<213> ORGANISM: Homo sapiens

<400> SEQUENCE: 1424
tgcgggaagc acatgccctg gggag 25

<210> SEQ ID NO 1425
<211> LENGTH: 25
<212> TYPE: DNA
<213> ORGANISM: Homo sapiens

<400> SEQUENCE: 1425
gcgggaagca catgccctgg ggagg 25

<210> SEQ ID NO 1426
<211> LENGTH: 25
<212> TYPE: DNA
<213> ORGANISM: Homo sapiens

<400> SEQUENCE: 1426
cgggaagcac atgccctggg gaggc 25

<210> SEQ ID NO 1427
<211> LENGTH: 25
<212> TYPE: DNA
<213> ORGANISM: Homo sapiens

<400> SEQUENCE: 1427

-continued gggaagcaca tgccctgggg aggca 25

<210> SEQ ID NO 1428
<211> LENGTH: 25
<212> TYPE: DNA
<213> ORGANISM: Homo sapiens

<400> SEQUENCE: 1428
ggaagcacat gccctgggga ggcat 25

<210> SEQ ID NO 1429
<211> LENGTH: 25
<212> TYPE: DNA
<213> ORGANISM: Homo sapiens

<400> SEQUENCE: 1429
gaagcacatg ccctggggag gcata 25

<210> SEQ ID NO 1430
<211> LENGTH: 25
<212> TYPE: DNA
<213> ORGANISM: Homo sapiens

<400> SEQUENCE: 1430
aagcacatgc cctggggagg catag 25

<210> SEQ ID NO 1431
<211> LENGTH: 25
<212> TYPE: DNA
<213> ORGANISM: Homo sapiens

<400> SEQUENCE: 1431
agcacatgcc ctggggaggc ataga 25

<210> SEQ ID NO 1432
<211> LENGTH: 25
<212> TYPE: DNA
<213> ORGANISM: Homo sapiens

<400> SEQUENCE: 1432
gcacatgccc tggggaggca tagaa 25

<210> SEQ ID NO 1433
<211> LENGTH: 25
<212> TYPE: DNA
<213> ORGANISM: Homo sapiens

<400> SEQUENCE: 1433
cacatgccct ggggaggcat agaag 25

<210> SEQ ID NO 1434
<211> LENGTH: 25
<212> TYPE: DNA
<213> ORGANISM: Homo sapiens

<400> SEQUENCE: 1434
acatgccctg gggaggcata gaagc 25

<210> SEQ ID NO 1435
<211> LENGTH: 25
<212> TYPE: DNA
<213> ORGANISM: Homo sapiens -continued

<400> SEQUENCE: 1435
catgccctgg ggaggcatag aagcc 25

<210> SEQ ID NO 1436
<211> LENGTH: 25
<212> TYPE: DNA
<213> ORGANISM: Homo sapiens

<400> SEQUENCE: 1436
atgccctggg gaggcataga agcca 25

<210> SEQ ID NO 1437
<211> LENGTH: 25
<212> TYPE: DNA
<213> ORGANISM: Homo sapiens

<400> SEQUENCE: 1437
tgccctgggg aggcatagaa gccac 25

<210> SEQ ID NO 1438
<211> LENGTH: 25
<212> TYPE: DNA
<213> ORGANISM: Homo sapiens

<400> SEQUENCE: 1438
gccctgggga ggcatagaag ccaca 25

<210> SEQ ID NO 1439
<211> LENGTH: 25
<212> TYPE: DNA
<213> ORGANISM: Homo sapiens

<400> SEQUENCE: 1439
ccctggggag gcatagaagc cacac 25

<210> SEQ ID NO 1440
<211> LENGTH: 25
<212> TYPE: DNA
<213> ORGANISM: Homo sapiens

<400> SEQUENCE: 1440
cctggggagg catagaagcc acact 25

<210> SEQ ID NO 1441
<211> LENGTH: 25
<212> TYPE: DNA
<213> ORGANISM: Homo sapiens

<400> SEQUENCE: 1441
ctggggaggc atagaagcca cactg 25

<210> SEQ ID NO 1442
<211> LENGTH: 25
<212> TYPE: DNA
<213> ORGANISM: Homo sapiens

<400> SEQUENCE: 1442
tggggaggca tagaagccac actgg 25

<210> SEQ ID NO 1443
<211> LENGTH: 25
<212> TYPE: DNA
<213> ORGANISM: Homo sapiens -continued

<400> SEQUENCE: 1443
ggggaggcat agaagccaca ctggc 25

<210> SEQ ID NO 1444
<211> LENGTH: 25
<212> TYPE: DNA
<213> ORGANISM: Homo sapiens

<400> SEQUENCE: 1444
gggaggcata gaagccacac tggca 25

<210> SEQ ID NO 1445
<211> LENGTH: 25
<212> TYPE: DNA
<213> ORGANISM: Homo sapiens

<400> SEQUENCE: 1445
ggaggcatag aagccacact ggcag 25

<210> SEQ ID NO 1446
<211> LENGTH: 25
<212> TYPE: DNA
<213> ORGANISM: Homo sapiens

<400> SEQUENCE: 1446
gaggcataga agccacactg gcaga 25

<210> SEQ ID NO 1447
<211> LENGTH: 25
<212> TYPE: DNA
<213> ORGANISM: Homo sapiens

<400> SEQUENCE: 1447
aggcatagaa gccacactgg cagag 25

<210> SEQ ID NO 1448
<211> LENGTH: 25
<212> TYPE: DNA
<213> ORGANISM: Homo sapiens

<400> SEQUENCE: 1448
ggcatagaag ccacactggc agagc 25

<210> SEQ ID NO 1449
<211> LENGTH: 25
<212> TYPE: DNA
<213> ORGANISM: Homo sapiens

<400> SEQUENCE: 1449
gcatagaagc cacactggca gagcg 25

<210> SEQ ID NO 1450
<211> LENGTH: 25
<212> TYPE: DNA
<213> ORGANISM: Homo sapiens

<400> SEQUENCE: 1450
catagaagcc acactggcag agcgg 25

<210> SEQ ID NO 1451
<211> LENGTH: 25
<212> TYPE: DNA

-continued

<213> ORGANISM: Homo sapiens

<400> SEQUENCE: 1451
atagaagcca cactggcaga gcggc 25

<210> SEQ ID NO 1452
<211> LENGTH: 25
<212> TYPE: DNA
<213> ORGANISM: Homo sapiens

<400> SEQUENCE: 1452
tagaagccac actggcagag cggcc 25

<210> SEQ ID NO 1453
<211> LENGTH: 25
<212> TYPE: DNA
<213> ORGANISM: Homo sapiens

<400> SEQUENCE: 1453
agaagccaca ctggcagagc ggcca 25

<210> SEQ ID NO 1454
<211> LENGTH: 25
<212> TYPE: DNA
<213> ORGANISM: Homo sapiens

<400> SEQUENCE: 1454
gaagccacac tggcagagcg gccag 25

<210> SEQ ID NO 1455
<211> LENGTH: 25
<212> TYPE: DNA
<213> ORGANISM: Homo sapiens

<400> SEQUENCE: 1455
aagccacact ggcagagcgg ccagc 25

<210> SEQ ID NO 1456
<211> LENGTH: 25
<212> TYPE: DNA
<213> ORGANISM: Homo sapiens

<400> SEQUENCE: 1456
agccacactg gcagagcggc cagca 25

<210> SEQ ID NO 1457
<211> LENGTH: 25
<212> TYPE: DNA
<213> ORGANISM: Homo sapiens

<400> SEQUENCE: 1457
gccacactgg cagagcggcc agcac 25

<210> SEQ ID NO 1458
<211> LENGTH: 25
<212> TYPE: DNA
<213> ORGANISM: Homo sapiens

<400> SEQUENCE: 1458
ccacactggc agagcggcca gcaca 25

<210> SEQ ID NO 1459
<211> LENGTH: 25

-continued

<212> TYPE: DNA
<213> ORGANISM: Homo sapiens

<400> SEQUENCE: 1459
cacactggca gagcggccag cacag 25

<210> SEQ ID NO 1460
<211> LENGTH: 25
<212> TYPE: DNA
<213> ORGANISM: Homo sapiens

<400> SEQUENCE: 1460
acactggcag agcggccagc acagg 25

<210> SEQ ID NO 1461
<211> LENGTH: 25
<212> TYPE: DNA
<213> ORGANISM: Homo sapiens

<400> SEQUENCE: 1461
cactggcaga gcggccagca caggt 25

<210> SEQ ID NO 1462
<211> LENGTH: 25
<212> TYPE: DNA
<213> ORGANISM: Homo sapiens

<400> SEQUENCE: 1462
actggcagag cggccagcac aggta 25

<210> SEQ ID NO 1463
<211> LENGTH: 25
<212> TYPE: DNA
<213> ORGANISM: Homo sapiens

<400> SEQUENCE: 1463
ctggcagagc ggccagcaca ggtag 25

<210> SEQ ID NO 1464
<211> LENGTH: 25
<212> TYPE: DNA
<213> ORGANISM: Homo sapiens

<400> SEQUENCE: 1464
tggcagagcg gccagcacag gtagc 25

<210> SEQ ID NO 1465
<211> LENGTH: 25
<212> TYPE: DNA
<213> ORGANISM: Homo sapiens

<400> SEQUENCE: 1465
ggcagagcgg ccagcacagg tagcc 25

<210> SEQ ID NO 1466
<211> LENGTH: 25
<212> TYPE: DNA
<213> ORGANISM: Homo sapiens

<400> SEQUENCE: 1466
gcagagcggc cagcacaggt agcca 25

<210> SEQ ID NO 1467

-continued

<211> LENGTH: 25
<212> TYPE: DNA
<213> ORGANISM: Homo sapiens

<400> SEQUENCE: 1467
cagagcggcc agcacaggta gccag 25

<210> SEQ ID NO 1468
<211> LENGTH: 25
<212> TYPE: DNA
<213> ORGANISM: Homo sapiens

<400> SEQUENCE: 1468
agagcggcca gcacaggtag ccagc 25

<210> SEQ ID NO 1469
<211> LENGTH: 25
<212> TYPE: DNA
<213> ORGANISM: Homo sapiens

<400> SEQUENCE: 1469
gagcggccag cacaggtagc cagca 25

<210> SEQ ID NO 1470
<211> LENGTH: 25
<212> TYPE: DNA
<213> ORGANISM: Homo sapiens

<400> SEQUENCE: 1470
agcggccagc acaggtagcc agcag 25

<210> SEQ ID NO 1471
<211> LENGTH: 25
<212> TYPE: DNA
<213> ORGANISM: Homo sapiens

<400> SEQUENCE: 1471
gcggccagca caggtagcca gcaga 25

<210> SEQ ID NO 1472
<211> LENGTH: 25
<212> TYPE: DNA
<213> ORGANISM: Homo sapiens

<400> SEQUENCE: 1472
cggccagcac aggtagccag cagag 25

<210> SEQ ID NO 1473
<211> LENGTH: 25
<212> TYPE: DNA
<213> ORGANISM: Homo sapiens

<400> SEQUENCE: 1473
ggccagcaca ggtagccagc agagg 25

<210> SEQ ID NO 1474
<211> LENGTH: 25
<212> TYPE: DNA
<213> ORGANISM: Homo sapiens

<400> SEQUENCE: 1474
gccagcacag gtagccagca gaggc 25

-continued

<210> SEQ ID NO 1475
<211> LENGTH: 25
<212> TYPE: DNA
<213> ORGANISM: Homo sapiens

<400> SEQUENCE: 1475
ccagcacagg tagccagcag aggca 25

<210> SEQ ID NO 1476
<211> LENGTH: 25
<212> TYPE: DNA
<213> ORGANISM: Homo sapiens

<400> SEQUENCE: 1476
cagcacaggt agccagcaga ggcat 25

<210> SEQ ID NO 1477
<211> LENGTH: 25
<212> TYPE: DNA
<213> ORGANISM: Homo sapiens

<400> SEQUENCE: 1477
agcacaggta gccagcagag gcatt 25

<210> SEQ ID NO 1478
<211> LENGTH: 25
<212> TYPE: DNA
<213> ORGANISM: Homo sapiens

<400> SEQUENCE: 1478
gcacaggtag ccagcagagg cattc 25

<210> SEQ ID NO 1479
<211> LENGTH: 25
<212> TYPE: DNA
<213> ORGANISM: Homo sapiens

<400> SEQUENCE: 1479
cacaggtagc cagcagaggc attct 25

<210> SEQ ID NO 1480
<211> LENGTH: 25
<212> TYPE: DNA
<213> ORGANISM: Homo sapiens

<400> SEQUENCE: 1480
acaggtagcc agcagaggca ttctt 25

<210> SEQ ID NO 1481
<211> LENGTH: 25
<212> TYPE: DNA
<213> ORGANISM: Homo sapiens

<400> SEQUENCE: 1481
caggtagcca gcagaggcat tcttg 25

<210> SEQ ID NO 1482
<211> LENGTH: 25
<212> TYPE: DNA
<213> ORGANISM: Homo sapiens

<400> SEQUENCE: 1482
aggtagccag cagaggcatt cttgg 25

-continued

<210> SEQ ID NO 1483
<211> LENGTH: 25
<212> TYPE: DNA
<213> ORGANISM: Homo sapiens

<400> SEQUENCE: 1483
ggtagccagc agaggcattc ttggg 25

<210> SEQ ID NO 1484
<211> LENGTH: 25
<212> TYPE: DNA
<213> ORGANISM: Homo sapiens

<400> SEQUENCE: 1484
gtagccagca gaggcattct tgggg 25

<210> SEQ ID NO 1485
<211> LENGTH: 25
<212> TYPE: DNA
<213> ORGANISM: Homo sapiens

<400> SEQUENCE: 1485
tagccagcag aggcattctt ggggc 25

<210> SEQ ID NO 1486
<211> LENGTH: 25
<212> TYPE: DNA
<213> ORGANISM: Homo sapiens

<400> SEQUENCE: 1486
agccagcaga ggcattcttg gggct 25

<210> SEQ ID NO 1487
<211> LENGTH: 25
<212> TYPE: DNA
<213> ORGANISM: Homo sapiens

<400> SEQUENCE: 1487
gccagcagag gcattcttgg ggcta 25

<210> SEQ ID NO 1488
<211> LENGTH: 25
<212> TYPE: DNA
<213> ORGANISM: Homo sapiens

<400> SEQUENCE: 1488
ccagcagagg cattcttggg gctat 25

<210> SEQ ID NO 1489
<211> LENGTH: 25
<212> TYPE: DNA
<213> ORGANISM: Homo sapiens

<400> SEQUENCE: 1489
cagcagaggc attcttgggg ctatt 25

<210> SEQ ID NO 1490
<211> LENGTH: 25
<212> TYPE: DNA
<213> ORGANISM: Homo sapiens

<400> SEQUENCE: 1490
agcagaggca ttcttggggc tattt 25

-continued

<210> SEQ ID NO 1491
<211> LENGTH: 25
<212> TYPE: DNA
<213> ORGANISM: Homo sapiens

<400> SEQUENCE: 1491
gcagaggcat tcttggggct atttg 25

<210> SEQ ID NO 1492
<211> LENGTH: 25
<212> TYPE: DNA
<213> ORGANISM: Homo sapiens

<400> SEQUENCE: 1492
cagaggcatt cttggggcta tttga 25

<210> SEQ ID NO 1493
<211> LENGTH: 25
<212> TYPE: DNA
<213> ORGANISM: Homo sapiens

<400> SEQUENCE: 1493
agaggcattc ttggggctat ttgaa 25

<210> SEQ ID NO 1494
<211> LENGTH: 25
<212> TYPE: DNA
<213> ORGANISM: Homo sapiens

<400> SEQUENCE: 1494
gaggcattct tggggctatt tgaaa 25

<210> SEQ ID NO 1495
<211> LENGTH: 25
<212> TYPE: DNA
<213> ORGANISM: Homo sapiens

<400> SEQUENCE: 1495
aggcattctt ggggctattt gaaaa 25

<210> SEQ ID NO 1496
<211> LENGTH: 25
<212> TYPE: DNA
<213> ORGANISM: Homo sapiens

<400> SEQUENCE: 1496
ggcattcttg gggctatttg aaaaa 25

<210> SEQ ID NO 1497
<211> LENGTH: 25
<212> TYPE: DNA
<213> ORGANISM: Homo sapiens

<400> SEQUENCE: 1497
gcattcttgg ggctatttga aaaag 25

<210> SEQ ID NO 1498
<211> LENGTH: 25
<212> TYPE: DNA
<213> ORGANISM: Homo sapiens

<400> SEQUENCE: 1498

-continued cattcttggg gctatttgaa aaagt 25

<210> SEQ ID NO 1499
<211> LENGTH: 25
<212> TYPE: DNA
<213> ORGANISM: Homo sapiens

<400> SEQUENCE: 1499
attcttgggg ctatttgaaa aagtt 25

<210> SEQ ID NO 1500
<211> LENGTH: 25
<212> TYPE: DNA
<213> ORGANISM: Homo sapiens

<400> SEQUENCE: 1500
ttcttggggc tatttgaaaa agttt 25

<210> SEQ ID NO 1501
<211> LENGTH: 25
<212> TYPE: DNA
<213> ORGANISM: Homo sapiens

<400> SEQUENCE: 1501
tcttggggct atttgaaaaa gtttg 25

<210> SEQ ID NO 1502
<211> LENGTH: 25
<212> TYPE: DNA
<213> ORGANISM: Homo sapiens

<400> SEQUENCE: 1502
cttggggcta tttgaaaaag tttgg 25

<210> SEQ ID NO 1503
<211> LENGTH: 25
<212> TYPE: DNA
<213> ORGANISM: Homo sapiens

<400> SEQUENCE: 1503
ttggggctat ttgaaaaagt ttggt 25

<210> SEQ ID NO 1504
<211> LENGTH: 25
<212> TYPE: DNA
<213> ORGANISM: Homo sapiens

<400> SEQUENCE: 1504
tggggctatt tgaaaaagtt tggtc 25

<210> SEQ ID NO 1505
<211> LENGTH: 25
<212> TYPE: DNA
<213> ORGANISM: Homo sapiens

<400> SEQUENCE: 1505
ggggctattt gaaaaagttt ggtct 25

<210> SEQ ID NO 1506
<211> LENGTH: 25
<212> TYPE: DNA
<213> ORGANISM: Homo sapiens

<400> SEQUENCE: 1506

-continued gggctatttg aaaaagtttg gtctg 25

<210> SEQ ID NO 1507
<211> LENGTH: 25
<212> TYPE: DNA
<213> ORGANISM: Homo sapiens

<400> SEQUENCE: 1507
ggctatttga aaaagtttgg tctgt 25

<210> SEQ ID NO 1508
<211> LENGTH: 25
<212> TYPE: DNA
<213> ORGANISM: Homo sapiens

<400> SEQUENCE: 1508
gctatttgaa aaagtttggt ctgtg 25

<210> SEQ ID NO 1509
<211> LENGTH: 25
<212> TYPE: DNA
<213> ORGANISM: Homo sapiens

<400> SEQUENCE: 1509
ctatttgaaa aagtttggtc tgtga 25

<210> SEQ ID NO 1510
<211> LENGTH: 25
<212> TYPE: DNA
<213> ORGANISM: Homo sapiens

<400> SEQUENCE: 1510
tatttgaaaa agtttggtct gtgaa 25

<210> SEQ ID NO 1511
<211> LENGTH: 25
<212> TYPE: DNA
<213> ORGANISM: Homo sapiens

<400> SEQUENCE: 1511
atttgaaaaa gtttggtctg tgaac 25

<210> SEQ ID NO 1512
<211> LENGTH: 25
<212> TYPE: DNA
<213> ORGANISM: Homo sapiens

<400> SEQUENCE: 1512
tttgaaaaag tttggtctgt gaaca 25

<210> SEQ ID NO 1513
<211> LENGTH: 25
<212> TYPE: DNA
<213> ORGANISM: Homo sapiens

<400> SEQUENCE: 1513
ttgaaaaagt ttggtctgtg aacaa 25

<210> SEQ ID NO 1514
<211> LENGTH: 25
<212> TYPE: DNA
<213> ORGANISM: Homo sapiens -continued

<400> SEQUENCE: 1514
tgaaaaagtt tggtctgtga acaaa 25

<210> SEQ ID NO 1515
<211> LENGTH: 25
<212> TYPE: DNA
<213> ORGANISM: Homo sapiens

<400> SEQUENCE: 1515
gaaaaagttt ggtctgtgaa caaaa 25

<210> SEQ ID NO 1516
<211> LENGTH: 25
<212> TYPE: DNA
<213> ORGANISM: Homo sapiens

<400> SEQUENCE: 1516
aaaaagtttg gtctgtgaac aaaac 25

<210> SEQ ID NO 1517
<211> LENGTH: 25
<212> TYPE: DNA
<213> ORGANISM: Homo sapiens

<400> SEQUENCE: 1517
aaaagtttgg tctgtgaaca aaaca 25

<210> SEQ ID NO 1518
<211> LENGTH: 25
<212> TYPE: DNA
<213> ORGANISM: Homo sapiens

<400> SEQUENCE: 1518
aaagtttggt ctgtgaacaa aacag 25

<210> SEQ ID NO 1519
<211> LENGTH: 25
<212> TYPE: DNA
<213> ORGANISM: Homo sapiens

<400> SEQUENCE: 1519
aagtttggtc tgtgaacaaa acagt 25

<210> SEQ ID NO 1520
<211> LENGTH: 25
<212> TYPE: DNA
<213> ORGANISM: Homo sapiens

<400> SEQUENCE: 1520
agtttggtct gtgaacaaaa cagtt 25

<210> SEQ ID NO 1521
<211> LENGTH: 25
<212> TYPE: DNA
<213> ORGANISM: Homo sapiens

<400> SEQUENCE: 1521
gtttggtctg tgaacaaaac agttt 25

<210> SEQ ID NO 1522
<211> LENGTH: 25
<212> TYPE: DNA
<213> ORGANISM: Homo sapiens

<400> SEQUENCE: 1522
tttggtctgt gaacaaaaca gtttc 25

<210> SEQ ID NO 1523
<211> LENGTH: 25
<212> TYPE: DNA
<213> ORGANISM: Homo sapiens

<400> SEQUENCE: 1523
ttggtctgtg aacaaaacag tttcc 25

<210> SEQ ID NO 1524
<211> LENGTH: 25
<212> TYPE: DNA
<213> ORGANISM: Homo sapiens

<400> SEQUENCE: 1524
tggtctgtga acaaaacagt ttccc 25

<210> SEQ ID NO 1525
<211> LENGTH: 25
<212> TYPE: DNA
<213> ORGANISM: Homo sapiens

<400> SEQUENCE: 1525
ggtctgtgaa caaaacagtt tccct 25

<210> SEQ ID NO 1526
<211> LENGTH: 25
<212> TYPE: DNA
<213> ORGANISM: Homo sapiens

<400> SEQUENCE: 1526
gtctgtgaac aaaacagttt ccctg 25

<210> SEQ ID NO 1527
<211> LENGTH: 25
<212> TYPE: DNA
<213> ORGANISM: Homo sapiens

<400> SEQUENCE: 1527
tctgtgaaca aaacagtttc cctgg 25

<210> SEQ ID NO 1528
<211> LENGTH: 25
<212> TYPE: DNA
<213> ORGANISM: Homo sapiens

<400> SEQUENCE: 1528
ctgtgaacaa aacagtttcc ctggt 25

<210> SEQ ID NO 1529
<211> LENGTH: 25
<212> TYPE: DNA
<213> ORGANISM: Homo sapiens

<400> SEQUENCE: 1529
tgtgaacaaa acagtttccc tggtg 25

<210> SEQ ID NO 1530
<211> LENGTH: 25
<212> TYPE: DNA

-continued

<213> ORGANISM: Homo sapiens

<400> SEQUENCE: 1530
gtgaacaaaa cagtttccct ggtga 25

<210> SEQ ID NO 1531
<211> LENGTH: 25
<212> TYPE: DNA
<213> ORGANISM: Homo sapiens

<400> SEQUENCE: 1531
tgaacaaaac agtttccctg gtgac 25

<210> SEQ ID NO 1532
<211> LENGTH: 25
<212> TYPE: DNA
<213> ORGANISM: Homo sapiens

<400> SEQUENCE: 1532
gaacaaaaca gtttccctgg tgact 25

<210> SEQ ID NO 1533
<211> LENGTH: 25
<212> TYPE: DNA
<213> ORGANISM: Homo sapiens

<400> SEQUENCE: 1533
aacaaaacag tttccctggt gactg 25

<210> SEQ ID NO 1534
<211> LENGTH: 25
<212> TYPE: DNA
<213> ORGANISM: Homo sapiens

<400> SEQUENCE: 1534
acaaaacagt ttccctggtg actgc 25

<210> SEQ ID NO 1535
<211> LENGTH: 25
<212> TYPE: DNA
<213> ORGANISM: Homo sapiens

<400> SEQUENCE: 1535
caaaacagtt tccctggtga ctgca 25

<210> SEQ ID NO 1536
<211> LENGTH: 25
<212> TYPE: DNA
<213> ORGANISM: Homo sapiens

<400> SEQUENCE: 1536
aaaacagttt ccctggtgac tgcaa 25

<210> SEQ ID NO 1537
<211> LENGTH: 25
<212> TYPE: DNA
<213> ORGANISM: Homo sapiens

<400> SEQUENCE: 1537
aaacagtttc cctggtgact gcaaa 25

<210> SEQ ID NO 1538
<211> LENGTH: 25

-continued

<212> TYPE: DNA
<213> ORGANISM: Homo sapiens

<400> SEQUENCE: 1538
aacagtttcc ctggtgactg caaat 25

<210> SEQ ID NO 1539
<211> LENGTH: 25
<212> TYPE: DNA
<213> ORGANISM: Homo sapiens

<400> SEQUENCE: 1539
acagtttccc tggtgactgc aaatc 25

<210> SEQ ID NO 1540
<211> LENGTH: 25
<212> TYPE: DNA
<213> ORGANISM: Homo sapiens

<400> SEQUENCE: 1540
cagtttccct ggtgactgca aatcc 25

<210> SEQ ID NO 1541
<211> LENGTH: 25
<212> TYPE: DNA
<213> ORGANISM: Homo sapiens

<400> SEQUENCE: 1541
agtttccctg gtgactgcaa atcca 25

<210> SEQ ID NO 1542
<211> LENGTH: 25
<212> TYPE: DNA
<213> ORGANISM: Homo sapiens

<400> SEQUENCE: 1542
gtttccctgg tgactgcaaa tccat 25

<210> SEQ ID NO 1543
<211> LENGTH: 25
<212> TYPE: DNA
<213> ORGANISM: Homo sapiens

<400> SEQUENCE: 1543
tttccctggt gactgcaaat ccatt 25

<210> SEQ ID NO 1544
<211> LENGTH: 25
<212> TYPE: DNA
<213> ORGANISM: Homo sapiens

<400> SEQUENCE: 1544
ttccctggtg actgcaaatc cattg 25

<210> SEQ ID NO 1545
<211> LENGTH: 25
<212> TYPE: DNA
<213> ORGANISM: Homo sapiens

<400> SEQUENCE: 1545
tccctggtga ctgcaaatcc attgc 25

<210> SEQ ID NO 1546

```
<211> LENGTH: 25
<212> TYPE: DNA
<213> ORGANISM: Homo sapiens

<400> SEQUENCE: 1546

ccctggtgac tgcaaatcca ttgct                                    25

<210> SEQ ID NO 1547
<211> LENGTH: 25
<212> TYPE: DNA
<213> ORGANISM: Homo sapiens

<400> SEQUENCE: 1547

cctggtgact gcaaatccat tgcta                                    25

<210> SEQ ID NO 1548
<211> LENGTH: 25
<212> TYPE: DNA
<213> ORGANISM: Homo sapiens

<400> SEQUENCE: 1548

ctggtgactg caaatccatt gctag                                    25

<210> SEQ ID NO 1549
<211> LENGTH: 25
<212> TYPE: DNA
<213> ORGANISM: Homo sapiens

<400> SEQUENCE: 1549

tggtgactgc aaatccattg ctagc                                    25

<210> SEQ ID NO 1550
<211> LENGTH: 25
<212> TYPE: DNA
<213> ORGANISM: Homo sapiens

<400> SEQUENCE: 1550

ggtgactgca aatccattgc tagct                                    25

<210> SEQ ID NO 1551
<211> LENGTH: 25
<212> TYPE: DNA
<213> ORGANISM: Homo sapiens

<400> SEQUENCE: 1551

gtgactgcaa atccattgct agctg                                    25

<210> SEQ ID NO 1552
<211> LENGTH: 25
<212> TYPE: DNA
<213> ORGANISM: Homo sapiens

<400> SEQUENCE: 1552

tgactgcaaa tccattgcta gctgc                                    25

<210> SEQ ID NO 1553
<211> LENGTH: 25
<212> TYPE: DNA
<213> ORGANISM: Homo sapiens

<400> SEQUENCE: 1553

gactgcaaat ccattgctag ctgcc                                    25
```

-continued

<210> SEQ ID NO 1554
<211> LENGTH: 25
<212> TYPE: DNA
<213> ORGANISM: Homo sapiens

<400> SEQUENCE: 1554
actgcaaatc cattgctagc tgcct 25

<210> SEQ ID NO 1555
<211> LENGTH: 25
<212> TYPE: DNA
<213> ORGANISM: Homo sapiens

<400> SEQUENCE: 1555
ctgcaaatcc attgctagct gcctc 25

<210> SEQ ID NO 1556
<211> LENGTH: 25
<212> TYPE: DNA
<213> ORGANISM: Homo sapiens

<400> SEQUENCE: 1556
tgcaaatcca ttgctagctg cctct 25

<210> SEQ ID NO 1557
<211> LENGTH: 25
<212> TYPE: DNA
<213> ORGANISM: Homo sapiens

<400> SEQUENCE: 1557
gcaaatccat tgctagctgc ctctt 25

<210> SEQ ID NO 1558
<211> LENGTH: 25
<212> TYPE: DNA
<213> ORGANISM: Homo sapiens

<400> SEQUENCE: 1558
caaatccatt gctagctgcc tcttt 25

<210> SEQ ID NO 1559
<211> LENGTH: 25
<212> TYPE: DNA
<213> ORGANISM: Homo sapiens

<400> SEQUENCE: 1559
aaatccattg ctagctgcct ctttc 25

<210> SEQ ID NO 1560
<211> LENGTH: 25
<212> TYPE: DNA
<213> ORGANISM: Homo sapiens

<400> SEQUENCE: 1560
aatccattgc tagctgcctc tttct 25

<210> SEQ ID NO 1561
<211> LENGTH: 25
<212> TYPE: DNA
<213> ORGANISM: Homo sapiens

<400> SEQUENCE: 1561
atccattgct agctgcctct ttctc 25

-continued

<210> SEQ ID NO 1562
<211> LENGTH: 25
<212> TYPE: DNA
<213> ORGANISM: Homo sapiens

<400> SEQUENCE: 1562
tccattgcta gctgcctctt tctcg 25

<210> SEQ ID NO 1563
<211> LENGTH: 25
<212> TYPE: DNA
<213> ORGANISM: Homo sapiens

<400> SEQUENCE: 1563
ccattgctag ctgcctcttt ctcgt 25

<210> SEQ ID NO 1564
<211> LENGTH: 25
<212> TYPE: DNA
<213> ORGANISM: Homo sapiens

<400> SEQUENCE: 1564
cattgctagc tgcctctttc tcgtc 25

<210> SEQ ID NO 1565
<211> LENGTH: 25
<212> TYPE: DNA
<213> ORGANISM: Homo sapiens

<400> SEQUENCE: 1565
attgctagct gcctctttct cgtct 25

<210> SEQ ID NO 1566
<211> LENGTH: 25
<212> TYPE: DNA
<213> ORGANISM: Homo sapiens

<400> SEQUENCE: 1566
ttgctagctg cctctttctc gtctg 25

<210> SEQ ID NO 1567
<211> LENGTH: 25
<212> TYPE: DNA
<213> ORGANISM: Homo sapiens

<400> SEQUENCE: 1567
tgctagctgc ctctttctcg tctgc 25

<210> SEQ ID NO 1568
<211> LENGTH: 25
<212> TYPE: DNA
<213> ORGANISM: Homo sapiens

<400> SEQUENCE: 1568
gctagctgcc tctttctcgt ctgcc 25

<210> SEQ ID NO 1569
<211> LENGTH: 25
<212> TYPE: DNA
<213> ORGANISM: Homo sapiens

<400> SEQUENCE: 1569
ctagctgcct ctttctcgtc tgccc 25

-continued

<210> SEQ ID NO 1570
<211> LENGTH: 25
<212> TYPE: DNA
<213> ORGANISM: Homo sapiens

<400> SEQUENCE: 1570
tagctgcctc tttctcgtct gccca 25

<210> SEQ ID NO 1571
<211> LENGTH: 25
<212> TYPE: DNA
<213> ORGANISM: Homo sapiens

<400> SEQUENCE: 1571
agctgcctct ttctcgtctg cccat 25

<210> SEQ ID NO 1572
<211> LENGTH: 25
<212> TYPE: DNA
<213> ORGANISM: Homo sapiens

<400> SEQUENCE: 1572
gctgcctctt tctcgtctgc ccatc 25

<210> SEQ ID NO 1573
<211> LENGTH: 25
<212> TYPE: DNA
<213> ORGANISM: Homo sapiens

<400> SEQUENCE: 1573
ctgcctcttt ctcgtctgcc catca 25

<210> SEQ ID NO 1574
<211> LENGTH: 25
<212> TYPE: DNA
<213> ORGANISM: Homo sapiens

<400> SEQUENCE: 1574
tgcctctttc tcgtctgccc atcac 25

<210> SEQ ID NO 1575
<211> LENGTH: 25
<212> TYPE: DNA
<213> ORGANISM: Homo sapiens

<400> SEQUENCE: 1575
gcctctttct cgtctgccca tcact 25

<210> SEQ ID NO 1576
<211> LENGTH: 25
<212> TYPE: DNA
<213> ORGANISM: Homo sapiens

<400> SEQUENCE: 1576
cctctttctc gtctgcccat cactc 25

<210> SEQ ID NO 1577
<211> LENGTH: 25
<212> TYPE: DNA
<213> ORGANISM: Homo sapiens

<400> SEQUENCE: 1577

-continued ctctttctcg tctgcccatc actct 25

<210> SEQ ID NO 1578
<211> LENGTH: 25
<212> TYPE: DNA
<213> ORGANISM: Homo sapiens

<400> SEQUENCE: 1578
tctttctcgt ctgcccatca ctctg 25

<210> SEQ ID NO 1579
<211> LENGTH: 25
<212> TYPE: DNA
<213> ORGANISM: Homo sapiens

<400> SEQUENCE: 1579
ctttctcgtc tgcccatcac tctgg 25

<210> SEQ ID NO 1580
<211> LENGTH: 25
<212> TYPE: DNA
<213> ORGANISM: Homo sapiens

<400> SEQUENCE: 1580
tttctcgtct gcccatcact ctggt 25

<210> SEQ ID NO 1581
<211> LENGTH: 25
<212> TYPE: DNA
<213> ORGANISM: Homo sapiens

<400> SEQUENCE: 1581
ttctcgtctg cccatcactc tggtg 25

<210> SEQ ID NO 1582
<211> LENGTH: 25
<212> TYPE: DNA
<213> ORGANISM: Homo sapiens

<400> SEQUENCE: 1582
tctcgtctgc ccatcactct ggtgt 25

<210> SEQ ID NO 1583
<211> LENGTH: 25
<212> TYPE: DNA
<213> ORGANISM: Homo sapiens

<400> SEQUENCE: 1583
ctcgtctgcc catcactctg gtgtg 25

<210> SEQ ID NO 1584
<211> LENGTH: 25
<212> TYPE: DNA
<213> ORGANISM: Homo sapiens

<400> SEQUENCE: 1584
tcgtctgccc atcactctgg tgtgg 25

<210> SEQ ID NO 1585
<211> LENGTH: 25
<212> TYPE: DNA
<213> ORGANISM: Homo sapiens

<400> SEQUENCE: 1585

-continued cgtctgccca tcactctggt gtggt 25

<210> SEQ ID NO 1586
<211> LENGTH: 25
<212> TYPE: DNA
<213> ORGANISM: Homo sapiens

<400> SEQUENCE: 1586
gtctgcccat cactctggtg tggta 25

<210> SEQ ID NO 1587
<211> LENGTH: 25
<212> TYPE: DNA
<213> ORGANISM: Homo sapiens

<400> SEQUENCE: 1587
tctgcccatc actctggtgt ggtac 25

<210> SEQ ID NO 1588
<211> LENGTH: 25
<212> TYPE: DNA
<213> ORGANISM: Homo sapiens

<400> SEQUENCE: 1588
ctgcccatca ctctggtgtg gtacc 25

<210> SEQ ID NO 1589
<211> LENGTH: 25
<212> TYPE: DNA
<213> ORGANISM: Homo sapiens

<400> SEQUENCE: 1589
tgcccatcac tctggtgtgg taccc 25

<210> SEQ ID NO 1590
<211> LENGTH: 25
<212> TYPE: DNA
<213> ORGANISM: Homo sapiens

<400> SEQUENCE: 1590
gcccatcact ctggtgtggt accca 25

<210> SEQ ID NO 1591
<211> LENGTH: 25
<212> TYPE: DNA
<213> ORGANISM: Homo sapiens

<400> SEQUENCE: 1591
cccatcactc tggtgtggta cccag 25

<210> SEQ ID NO 1592
<211> LENGTH: 25
<212> TYPE: DNA
<213> ORGANISM: Homo sapiens

<400> SEQUENCE: 1592
ccatcactct ggtgtggtac ccaga 25

<210> SEQ ID NO 1593
<211> LENGTH: 25
<212> TYPE: DNA
<213> ORGANISM: Homo sapiens -continued

<400> SEQUENCE: 1593
catcactctg gtgtggtacc cagaa 25

<210> SEQ ID NO 1594
<211> LENGTH: 25
<212> TYPE: DNA
<213> ORGANISM: Homo sapiens

<400> SEQUENCE: 1594
atcactctgg tgtggtaccc agaag 25

<210> SEQ ID NO 1595
<211> LENGTH: 25
<212> TYPE: DNA
<213> ORGANISM: Homo sapiens

<400> SEQUENCE: 1595
tcactctggt gtggtaccca gaagt 25

<210> SEQ ID NO 1596
<211> LENGTH: 25
<212> TYPE: DNA
<213> ORGANISM: Homo sapiens

<400> SEQUENCE: 1596
cactctggtg tggtacccag aagtt 25

<210> SEQ ID NO 1597
<211> LENGTH: 25
<212> TYPE: DNA
<213> ORGANISM: Homo sapiens

<400> SEQUENCE: 1597
actctggtgt ggtacccaga agttg 25

<210> SEQ ID NO 1598
<211> LENGTH: 25
<212> TYPE: DNA
<213> ORGANISM: Homo sapiens

<400> SEQUENCE: 1598
ctctggtgtg gtacccagaa gttga 25

<210> SEQ ID NO 1599
<211> LENGTH: 25
<212> TYPE: DNA
<213> ORGANISM: Homo sapiens

<400> SEQUENCE: 1599
tctggtgtgg tacccagaag ttgac 25

<210> SEQ ID NO 1600
<211> LENGTH: 25
<212> TYPE: DNA
<213> ORGANISM: Homo sapiens

<400> SEQUENCE: 1600
ctggtgtggt acccagaagt tgact 25

<210> SEQ ID NO 1601
<211> LENGTH: 25
<212> TYPE: DNA
<213> ORGANISM: Homo sapiens

<400> SEQUENCE: 1601
tggtgtggta cccagaagtt gactt 25

<210> SEQ ID NO 1602
<211> LENGTH: 25
<212> TYPE: DNA
<213> ORGANISM: Homo sapiens

<400> SEQUENCE: 1602
ggtgtggtac ccagaagttg acttc 25

<210> SEQ ID NO 1603
<211> LENGTH: 25
<212> TYPE: DNA
<213> ORGANISM: Homo sapiens

<400> SEQUENCE: 1603
gtgtggtacc cagaagttga cttct 25

<210> SEQ ID NO 1604
<211> LENGTH: 25
<212> TYPE: DNA
<213> ORGANISM: Homo sapiens

<400> SEQUENCE: 1604
tgtggtaccc agaagttgac ttctg 25

<210> SEQ ID NO 1605
<211> LENGTH: 25
<212> TYPE: DNA
<213> ORGANISM: Homo sapiens

<400> SEQUENCE: 1605
gtggtaccca gaagttgact tctgg 25

<210> SEQ ID NO 1606
<211> LENGTH: 25
<212> TYPE: DNA
<213> ORGANISM: Homo sapiens

<400> SEQUENCE: 1606
tggtacccag aagttgactt ctggt 25

<210> SEQ ID NO 1607
<211> LENGTH: 25
<212> TYPE: DNA
<213> ORGANISM: Homo sapiens

<400> SEQUENCE: 1607
ggtacccaga agttgacttc tggtt 25

<210> SEQ ID NO 1608
<211> LENGTH: 25
<212> TYPE: DNA
<213> ORGANISM: Homo sapiens

<400> SEQUENCE: 1608
gtacccagaa gttgacttct ggttc 25

<210> SEQ ID NO 1609
<211> LENGTH: 25
<212> TYPE: DNA

-continued

<213> ORGANISM: Homo sapiens

<400> SEQUENCE: 1609
tacccagaag ttgacttctg gttct 25

<210> SEQ ID NO 1610
<211> LENGTH: 25
<212> TYPE: DNA
<213> ORGANISM: Homo sapiens

<400> SEQUENCE: 1610
acccagaagt tgacttctgg ttctg 25

<210> SEQ ID NO 1611
<211> LENGTH: 25
<212> TYPE: DNA
<213> ORGANISM: Homo sapiens

<400> SEQUENCE: 1611
cccagaagtt gacttctggt tctgt 25

<210> SEQ ID NO 1612
<211> LENGTH: 25
<212> TYPE: DNA
<213> ORGANISM: Homo sapiens

<400> SEQUENCE: 1612
ccagaagttg acttctggtt ctgta 25

<210> SEQ ID NO 1613
<211> LENGTH: 25
<212> TYPE: DNA
<213> ORGANISM: Homo sapiens

<400> SEQUENCE: 1613
cagaagttga cttctggttc tgtag 25

<210> SEQ ID NO 1614
<211> LENGTH: 25
<212> TYPE: DNA
<213> ORGANISM: Homo sapiens

<400> SEQUENCE: 1614
agaagttgac ttctggttct gtaga 25

<210> SEQ ID NO 1615
<211> LENGTH: 25
<212> TYPE: DNA
<213> ORGANISM: Homo sapiens

<400> SEQUENCE: 1615
gaagttgact tctggttctg tagaa 25

<210> SEQ ID NO 1616
<211> LENGTH: 25
<212> TYPE: DNA
<213> ORGANISM: Homo sapiens

<400> SEQUENCE: 1616
aagttgactt ctggttctgt agaaa 25

<210> SEQ ID NO 1617
<211> LENGTH: 25

-continued

<212> TYPE: DNA
<213> ORGANISM: Homo sapiens

<400> SEQUENCE: 1617
agttgacttc tggttctgta gaaag 25

<210> SEQ ID NO 1618
<211> LENGTH: 25
<212> TYPE: DNA
<213> ORGANISM: Homo sapiens

<400> SEQUENCE: 1618
gttgacttct ggttctgtag aaaga 25

<210> SEQ ID NO 1619
<211> LENGTH: 25
<212> TYPE: DNA
<213> ORGANISM: Homo sapiens

<400> SEQUENCE: 1619
ttgacttctg gttctgtaga aagag 25

<210> SEQ ID NO 1620
<211> LENGTH: 25
<212> TYPE: DNA
<213> ORGANISM: Homo sapiens

<400> SEQUENCE: 1620
tgacttctgg ttctgtagaa agagc 25

<210> SEQ ID NO 1621
<211> LENGTH: 25
<212> TYPE: DNA
<213> ORGANISM: Homo sapiens

<400> SEQUENCE: 1621
gacttctggt tctgtagaaa gagct 25

<210> SEQ ID NO 1622
<211> LENGTH: 25
<212> TYPE: DNA
<213> ORGANISM: Homo sapiens

<400> SEQUENCE: 1622
acttctggtt ctgtagaaag agcta 25

<210> SEQ ID NO 1623
<211> LENGTH: 25
<212> TYPE: DNA
<213> ORGANISM: Homo sapiens

<400> SEQUENCE: 1623
cttctggttc tgtagaaaga gctag 25

<210> SEQ ID NO 1624
<211> LENGTH: 25
<212> TYPE: DNA
<213> ORGANISM: Homo sapiens

<400> SEQUENCE: 1624
ttctggttct gtagaaagag ctagg 25

<210> SEQ ID NO 1625

-continued

<211> LENGTH: 25
<212> TYPE: DNA
<213> ORGANISM: Homo sapiens

<400> SEQUENCE: 1625
tctggttctg tagaaagagc taggg 25

<210> SEQ ID NO 1626
<211> LENGTH: 25
<212> TYPE: DNA
<213> ORGANISM: Homo sapiens

<400> SEQUENCE: 1626
ctggttctgt agaaagagct agggg 25

<210> SEQ ID NO 1627
<211> LENGTH: 25
<212> TYPE: DNA
<213> ORGANISM: Homo sapiens

<400> SEQUENCE: 1627
tggttctgta gaaagagcta gggga 25

<210> SEQ ID NO 1628
<211> LENGTH: 25
<212> TYPE: DNA
<213> ORGANISM: Homo sapiens

<400> SEQUENCE: 1628
ggttctgtag aaagagctag gggag 25

<210> SEQ ID NO 1629
<211> LENGTH: 25
<212> TYPE: DNA
<213> ORGANISM: Homo sapiens

<400> SEQUENCE: 1629
gttctgtaga aagagctagg ggagg 25

<210> SEQ ID NO 1630
<211> LENGTH: 25
<212> TYPE: DNA
<213> ORGANISM: Homo sapiens

<400> SEQUENCE: 1630
ttctgtagaa agagctaggg gaggt 25

<210> SEQ ID NO 1631
<211> LENGTH: 25
<212> TYPE: DNA
<213> ORGANISM: Homo sapiens

<400> SEQUENCE: 1631
tctgtagaaa gagctagggg aggta 25

<210> SEQ ID NO 1632
<211> LENGTH: 25
<212> TYPE: DNA
<213> ORGANISM: Homo sapiens

<400> SEQUENCE: 1632
ctgtagaaag agctagggga ggtat 25

-continued

<210> SEQ ID NO 1633
<211> LENGTH: 25
<212> TYPE: DNA
<213> ORGANISM: Homo sapiens

<400> SEQUENCE: 1633
tgtagaaaga gctaggggag gtatg 25

<210> SEQ ID NO 1634
<211> LENGTH: 25
<212> TYPE: DNA
<213> ORGANISM: Homo sapiens

<400> SEQUENCE: 1634
gtagaaagag ctaggggagg tatga 25

<210> SEQ ID NO 1635
<211> LENGTH: 25
<212> TYPE: DNA
<213> ORGANISM: Homo sapiens

<400> SEQUENCE: 1635
tagaaagagc taggggaggt atgat 25

<210> SEQ ID NO 1636
<211> LENGTH: 25
<212> TYPE: DNA
<213> ORGANISM: Homo sapiens

<400> SEQUENCE: 1636
agaaagagct aggggaggta tgatg 25

<210> SEQ ID NO 1637
<211> LENGTH: 25
<212> TYPE: DNA
<213> ORGANISM: Homo sapiens

<400> SEQUENCE: 1637
gaaagagcta ggggaggtat gatgt 25

<210> SEQ ID NO 1638
<211> LENGTH: 25
<212> TYPE: DNA
<213> ORGANISM: Homo sapiens

<400> SEQUENCE: 1638
aaagagctag gggaggtatg atgtg 25

<210> SEQ ID NO 1639
<211> LENGTH: 25
<212> TYPE: DNA
<213> ORGANISM: Homo sapiens

<400> SEQUENCE: 1639
aagagctagg ggaggtatga tgtgc 25

<210> SEQ ID NO 1640
<211> LENGTH: 25
<212> TYPE: DNA
<213> ORGANISM: Homo sapiens

<400> SEQUENCE: 1640
agagctaggg gaggtatgat gtgct 25

-continued

<210> SEQ ID NO 1641
<211> LENGTH: 25
<212> TYPE: DNA
<213> ORGANISM: Homo sapiens

<400> SEQUENCE: 1641
gagctagggg aggtatgatg tgctt 25

<210> SEQ ID NO 1642
<211> LENGTH: 25
<212> TYPE: DNA
<213> ORGANISM: Homo sapiens

<400> SEQUENCE: 1642
agctagggga ggtatgatgt gctta 25

<210> SEQ ID NO 1643
<211> LENGTH: 25
<212> TYPE: DNA
<213> ORGANISM: Homo sapiens

<400> SEQUENCE: 1643
gctaggggag gtatgatgtg cttaa 25

<210> SEQ ID NO 1644
<211> LENGTH: 25
<212> TYPE: DNA
<213> ORGANISM: Homo sapiens

<400> SEQUENCE: 1644
ctaggggagg tatgatgtgc ttaaa 25

<210> SEQ ID NO 1645
<211> LENGTH: 25
<212> TYPE: DNA
<213> ORGANISM: Homo sapiens

<400> SEQUENCE: 1645
taggggaggt atgatgtgct taaag 25

<210> SEQ ID NO 1646
<211> LENGTH: 25
<212> TYPE: DNA
<213> ORGANISM: Homo sapiens

<400> SEQUENCE: 1646
aggggaggta tgatgtgctt aaaga 25

<210> SEQ ID NO 1647
<211> LENGTH: 25
<212> TYPE: DNA
<213> ORGANISM: Homo sapiens

<400> SEQUENCE: 1647
ggggaggtat gatgtgctta aagat 25

<210> SEQ ID NO 1648
<211> LENGTH: 25
<212> TYPE: DNA
<213> ORGANISM: Homo sapiens

<400> SEQUENCE: 1648
gggaggtatg atgtgcttaa agatc 25

-continued

<210> SEQ ID NO 1649
<211> LENGTH: 25
<212> TYPE: DNA
<213> ORGANISM: Homo sapiens

<400> SEQUENCE: 1649
ggaggtatga tgtgcttaaa gatcc 25

<210> SEQ ID NO 1650
<211> LENGTH: 25
<212> TYPE: DNA
<213> ORGANISM: Homo sapiens

<400> SEQUENCE: 1650
gaggtatgat gtgcttaaag atcct 25

<210> SEQ ID NO 1651
<211> LENGTH: 25
<212> TYPE: DNA
<213> ORGANISM: Homo sapiens

<400> SEQUENCE: 1651
aggtatgatg tgcttaaaga tccta 25

<210> SEQ ID NO 1652
<211> LENGTH: 25
<212> TYPE: DNA
<213> ORGANISM: Homo sapiens

<400> SEQUENCE: 1652
ggtatgatgt gcttaaagat cctaa 25

<210> SEQ ID NO 1653
<211> LENGTH: 25
<212> TYPE: DNA
<213> ORGANISM: Homo sapiens

<400> SEQUENCE: 1653
gtatgatgtg cttaaagatc ctaag 25

<210> SEQ ID NO 1654
<211> LENGTH: 25
<212> TYPE: DNA
<213> ORGANISM: Homo sapiens

<400> SEQUENCE: 1654
tatgatgtgc ttaaagatcc taaga 25

<210> SEQ ID NO 1655
<211> LENGTH: 25
<212> TYPE: DNA
<213> ORGANISM: Homo sapiens

<400> SEQUENCE: 1655
atgatgtgct taaagatcct aagaa 25

<210> SEQ ID NO 1656
<211> LENGTH: 25
<212> TYPE: DNA
<213> ORGANISM: Homo sapiens

<400> SEQUENCE: 1656

-continued tgatgtgctt aaagatccta agaat 25

<210> SEQ ID NO 1657
<211> LENGTH: 25
<212> TYPE: DNA
<213> ORGANISM: Homo sapiens

<400> SEQUENCE: 1657
gatgtgctta aagatcctaa gaata 25

<210> SEQ ID NO 1658
<211> LENGTH: 25
<212> TYPE: DNA
<213> ORGANISM: Homo sapiens

<400> SEQUENCE: 1658
atgtgcttaa agatcctaag aataa 25

<210> SEQ ID NO 1659
<211> LENGTH: 25
<212> TYPE: DNA
<213> ORGANISM: Homo sapiens

<400> SEQUENCE: 1659
tgtgcttaaa gatcctaaga ataag 25

<210> SEQ ID NO 1660
<211> LENGTH: 25
<212> TYPE: DNA
<213> ORGANISM: Homo sapiens

<400> SEQUENCE: 1660
gtgcttaaag atcctaagaa taagc 25

<210> SEQ ID NO 1661
<211> LENGTH: 25
<212> TYPE: DNA
<213> ORGANISM: Homo sapiens

<400> SEQUENCE: 1661
tgcttaaaga tcctaagaat aagcc 25

<210> SEQ ID NO 1662
<211> LENGTH: 25
<212> TYPE: DNA
<213> ORGANISM: Homo sapiens

<400> SEQUENCE: 1662
gcttaaagat cctaagaata agcct 25

<210> SEQ ID NO 1663
<211> LENGTH: 25
<212> TYPE: DNA
<213> ORGANISM: Homo sapiens

<400> SEQUENCE: 1663
cttaaagatc ctaagaataa gcctg 25

<210> SEQ ID NO 1664
<211> LENGTH: 25
<212> TYPE: DNA
<213> ORGANISM: Homo sapiens

<400> SEQUENCE: 1664

-continued ttaaagatcc taagaataag cctgg 25

<210> SEQ ID NO 1665
<211> LENGTH: 25
<212> TYPE: DNA
<213> ORGANISM: Homo sapiens

<400> SEQUENCE: 1665
taaagatcct aagaataagc ctggc 25

<210> SEQ ID NO 1666
<211> LENGTH: 25
<212> TYPE: DNA
<213> ORGANISM: Homo sapiens

<400> SEQUENCE: 1666
aaagatccta agaataagcc tggcg 25

<210> SEQ ID NO 1667
<211> LENGTH: 25
<212> TYPE: DNA
<213> ORGANISM: Homo sapiens

<400> SEQUENCE: 1667
aagatcctaa gaataagcct ggcga 25

<210> SEQ ID NO 1668
<211> LENGTH: 25
<212> TYPE: DNA
<213> ORGANISM: Homo sapiens

<400> SEQUENCE: 1668
agatcctaag aataagcctg gcgat 25

<210> SEQ ID NO 1669
<211> LENGTH: 25
<212> TYPE: DNA
<213> ORGANISM: Homo sapiens

<400> SEQUENCE: 1669
gatcctaaga ataagcctgg cgatt 25

<210> SEQ ID NO 1670
<211> LENGTH: 25
<212> TYPE: DNA
<213> ORGANISM: Homo sapiens

<400> SEQUENCE: 1670
atcctaagaa taagcctggc gattt 25

<210> SEQ ID NO 1671
<211> LENGTH: 25
<212> TYPE: DNA
<213> ORGANISM: Homo sapiens

<400> SEQUENCE: 1671
tcctaagaat aagcctggcg atttt 25

<210> SEQ ID NO 1672
<211> LENGTH: 25
<212> TYPE: DNA
<213> ORGANISM: Homo sapiens -continued

<400> SEQUENCE: 1672
cctaagaata agcctggcga ttttg 25

<210> SEQ ID NO 1673
<211> LENGTH: 25
<212> TYPE: DNA
<213> ORGANISM: Homo sapiens

<400> SEQUENCE: 1673
ctaagaataa gcctggcgat tttgg 25

<210> SEQ ID NO 1674
<211> LENGTH: 25
<212> TYPE: DNA
<213> ORGANISM: Homo sapiens

<400> SEQUENCE: 1674
taagaataag cctggcgatt ttggc 25

<210> SEQ ID NO 1675
<211> LENGTH: 25
<212> TYPE: DNA
<213> ORGANISM: Homo sapiens

<400> SEQUENCE: 1675
aagaataagc ctggcgattt tggct 25

<210> SEQ ID NO 1676
<211> LENGTH: 25
<212> TYPE: DNA
<213> ORGANISM: Homo sapiens

<400> SEQUENCE: 1676
agaataagcc tggcgatttt ggctg 25

<210> SEQ ID NO 1677
<211> LENGTH: 25
<212> TYPE: DNA
<213> ORGANISM: Homo sapiens

<400> SEQUENCE: 1677
gaataagcct ggcgattttg gctgg 25

<210> SEQ ID NO 1678
<211> LENGTH: 25
<212> TYPE: DNA
<213> ORGANISM: Homo sapiens

<400> SEQUENCE: 1678
aataagcctg gcgattttgg ctggg 25

<210> SEQ ID NO 1679
<211> LENGTH: 25
<212> TYPE: DNA
<213> ORGANISM: Homo sapiens

<400> SEQUENCE: 1679
ataagcctgg cgattttggc tgggt 25

<210> SEQ ID NO 1680
<211> LENGTH: 25
<212> TYPE: DNA
<213> ORGANISM: Homo sapiens -continued

<400> SEQUENCE: 1680
taagcctggc gattttggct gggtg 25

<210> SEQ ID NO 1681
<211> LENGTH: 25
<212> TYPE: DNA
<213> ORGANISM: Homo sapiens

<400> SEQUENCE: 1681
aagcctggcg attttggctg ggtgg 25

<210> SEQ ID NO 1682
<211> LENGTH: 25
<212> TYPE: DNA
<213> ORGANISM: Homo sapiens

<400> SEQUENCE: 1682
agcctggcga ttttggctgg gtggg 25

<210> SEQ ID NO 1683
<211> LENGTH: 25
<212> TYPE: DNA
<213> ORGANISM: Homo sapiens

<400> SEQUENCE: 1683
gcctggcgat tttggctggg tgggc 25

<210> SEQ ID NO 1684
<211> LENGTH: 25
<212> TYPE: DNA
<213> ORGANISM: Homo sapiens

<400> SEQUENCE: 1684
cctggcgatt ttggctgggt gggca 25

<210> SEQ ID NO 1685
<211> LENGTH: 25
<212> TYPE: DNA
<213> ORGANISM: Homo sapiens

<400> SEQUENCE: 1685
ctggcgattt tggctgggtg ggcac 25

<210> SEQ ID NO 1686
<211> LENGTH: 25
<212> TYPE: DNA
<213> ORGANISM: Homo sapiens

<400> SEQUENCE: 1686
tggcgatttt ggctgggtgg gcact 25

<210> SEQ ID NO 1687
<211> LENGTH: 25
<212> TYPE: DNA
<213> ORGANISM: Homo sapiens

<400> SEQUENCE: 1687
ggcgattttg gctgggtggg cactc 25

<210> SEQ ID NO 1688
<211> LENGTH: 25
<212> TYPE: DNA

-continued

<213> ORGANISM: Homo sapiens

<400> SEQUENCE: 1688
gcgattttgg ctgggtgggc actct 25

<210> SEQ ID NO 1689
<211> LENGTH: 25
<212> TYPE: DNA
<213> ORGANISM: Homo sapiens

<400> SEQUENCE: 1689
cgattttggc tgggtgggca ctctg 25

<210> SEQ ID NO 1690
<211> LENGTH: 25
<212> TYPE: DNA
<213> ORGANISM: Homo sapiens

<400> SEQUENCE: 1690
gattttggct gggtgggcac tctgt 25

<210> SEQ ID NO 1691
<211> LENGTH: 25
<212> TYPE: DNA
<213> ORGANISM: Homo sapiens

<400> SEQUENCE: 1691
attttggctg ggtgggcact ctgtt 25

<210> SEQ ID NO 1692
<211> LENGTH: 25
<212> TYPE: DNA
<213> ORGANISM: Homo sapiens

<400> SEQUENCE: 1692
ttttggctgg gtgggcactc tgttc 25

<210> SEQ ID NO 1693
<211> LENGTH: 25
<212> TYPE: DNA
<213> ORGANISM: Homo sapiens

<400> SEQUENCE: 1693
tttggctggg tgggcactct gttct 25

<210> SEQ ID NO 1694
<211> LENGTH: 25
<212> TYPE: DNA
<213> ORGANISM: Homo sapiens

<400> SEQUENCE: 1694
ttggctgggt gggcactctg ttctg 25

<210> SEQ ID NO 1695
<211> LENGTH: 25
<212> TYPE: DNA
<213> ORGANISM: Homo sapiens

<400> SEQUENCE: 1695
tggctgggtg ggcactctgt tctgc 25

<210> SEQ ID NO 1696
<211> LENGTH: 25

-continued

<212> TYPE: DNA
<213> ORGANISM: Homo sapiens

<400> SEQUENCE: 1696
ggctgggtgg gcactctgtt ctgcc 25

<210> SEQ ID NO 1697
<211> LENGTH: 25
<212> TYPE: DNA
<213> ORGANISM: Homo sapiens

<400> SEQUENCE: 1697
gctgggtggg cactctgttc tgcca 25

<210> SEQ ID NO 1698
<211> LENGTH: 25
<212> TYPE: DNA
<213> ORGANISM: Homo sapiens

<400> SEQUENCE: 1698
ctgggtgggc actctgttct gccaa 25

<210> SEQ ID NO 1699
<211> LENGTH: 25
<212> TYPE: DNA
<213> ORGANISM: Homo sapiens

<400> SEQUENCE: 1699
tgggtgggca ctctgttctg ccaac 25

<210> SEQ ID NO 1700
<211> LENGTH: 25
<212> TYPE: DNA
<213> ORGANISM: Homo sapiens

<400> SEQUENCE: 1700
gggtgggcac tctgttctgc caact 25

<210> SEQ ID NO 1701
<211> LENGTH: 25
<212> TYPE: DNA
<213> ORGANISM: Homo sapiens

<400> SEQUENCE: 1701
ggtgggcact ctgttctgcc aactc 25

<210> SEQ ID NO 1702
<211> LENGTH: 25
<212> TYPE: DNA
<213> ORGANISM: Homo sapiens

<400> SEQUENCE: 1702
gtgggcactc tgttctgcca actct 25

<210> SEQ ID NO 1703
<211> LENGTH: 25
<212> TYPE: DNA
<213> ORGANISM: Homo sapiens

<400> SEQUENCE: 1703
tgggcactct gttctgccaa ctctg 25

<210> SEQ ID NO 1704

-continued

<211> LENGTH: 25
<212> TYPE: DNA
<213> ORGANISM: Homo sapiens

<400> SEQUENCE: 1704
gggcactctg ttctgccaac tctga 25

<210> SEQ ID NO 1705
<211> LENGTH: 25
<212> TYPE: DNA
<213> ORGANISM: Homo sapiens

<400> SEQUENCE: 1705
ggcactctgt tctgccaact ctgag 25

<210> SEQ ID NO 1706
<211> LENGTH: 25
<212> TYPE: DNA
<213> ORGANISM: Homo sapiens

<400> SEQUENCE: 1706
gcactctgtt ctgccaactc tgagc 25

<210> SEQ ID NO 1707
<211> LENGTH: 25
<212> TYPE: DNA
<213> ORGANISM: Homo sapiens

<400> SEQUENCE: 1707
cactctgttc tgccaactct gagct 25

<210> SEQ ID NO 1708
<211> LENGTH: 25
<212> TYPE: DNA
<213> ORGANISM: Homo sapiens

<400> SEQUENCE: 1708
actctgttct gccaactctg agctg 25

<210> SEQ ID NO 1709
<211> LENGTH: 25
<212> TYPE: DNA
<213> ORGANISM: Homo sapiens

<400> SEQUENCE: 1709
ctctgttctg ccaactctga gctgg 25

<210> SEQ ID NO 1710
<211> LENGTH: 25
<212> TYPE: DNA
<213> ORGANISM: Homo sapiens

<400> SEQUENCE: 1710
tctgttctgc caactctgag ctggg 25

<210> SEQ ID NO 1711
<211> LENGTH: 25
<212> TYPE: DNA
<213> ORGANISM: Homo sapiens

<400> SEQUENCE: 1711
ctgttctgcc aactctgagc tgggc 25

-continued

<210> SEQ ID NO 1712
<211> LENGTH: 17
<212> TYPE: DNA
<213> ORGANISM: Homo sapiens

<400> SEQUENCE: 1712
gtcataagcc agttgtt 17

<210> SEQ ID NO 1713
<211> LENGTH: 17
<212> TYPE: DNA
<213> ORGANISM: Homo sapiens

<400> SEQUENCE: 1713
tcataagcca gttgttg 17

<210> SEQ ID NO 1714
<211> LENGTH: 17
<212> TYPE: DNA
<213> ORGANISM: Homo sapiens

<400> SEQUENCE: 1714
cataagccag ttgttgc 17

<210> SEQ ID NO 1715
<211> LENGTH: 17
<212> TYPE: DNA
<213> ORGANISM: Homo sapiens

<400> SEQUENCE: 1715
ataagccagt tgttgct 17

<210> SEQ ID NO 1716
<211> LENGTH: 17
<212> TYPE: DNA
<213> ORGANISM: Homo sapiens

<400> SEQUENCE: 1716
taagccagtt gttgctg 17

<210> SEQ ID NO 1717
<211> LENGTH: 17
<212> TYPE: DNA
<213> ORGANISM: Homo sapiens

<400> SEQUENCE: 1717
aagccagttg ttgctgc 17

<210> SEQ ID NO 1718
<211> LENGTH: 17
<212> TYPE: DNA
<213> ORGANISM: Homo sapiens

<400> SEQUENCE: 1718
agccagttgt tgctgct 17

<210> SEQ ID NO 1719
<211> LENGTH: 17
<212> TYPE: DNA
<213> ORGANISM: Homo sapiens

<400> SEQUENCE: 1719
gccagttgtt gctgctt 17

-continued

<210> SEQ ID NO 1720
<211> LENGTH: 17
<212> TYPE: DNA
<213> ORGANISM: Homo sapiens

<400> SEQUENCE: 1720
ccagttgttg ctgcttg 17

<210> SEQ ID NO 1721
<211> LENGTH: 17
<212> TYPE: DNA
<213> ORGANISM: Homo sapiens

<400> SEQUENCE: 1721
cagttgttgc tgcttgt 17

<210> SEQ ID NO 1722
<211> LENGTH: 17
<212> TYPE: DNA
<213> ORGANISM: Homo sapiens

<400> SEQUENCE: 1722
agttgttgct gcttgtg 17

<210> SEQ ID NO 1723
<211> LENGTH: 17
<212> TYPE: DNA
<213> ORGANISM: Homo sapiens

<400> SEQUENCE: 1723
gttgttgctg cttgtgt 17

<210> SEQ ID NO 1724
<211> LENGTH: 17
<212> TYPE: DNA
<213> ORGANISM: Homo sapiens

<400> SEQUENCE: 1724
ttgttgctgc ttgtgtt 17

<210> SEQ ID NO 1725
<211> LENGTH: 17
<212> TYPE: DNA
<213> ORGANISM: Homo sapiens

<400> SEQUENCE: 1725
tgttgctgct tgtgttc 17

<210> SEQ ID NO 1726
<211> LENGTH: 17
<212> TYPE: DNA
<213> ORGANISM: Homo sapiens

<400> SEQUENCE: 1726
gttgctgctt gtgttcc 17

<210> SEQ ID NO 1727
<211> LENGTH: 17
<212> TYPE: DNA
<213> ORGANISM: Homo sapiens

<400> SEQUENCE: 1727
ttgctgcttg tgttccc 17

-continued

<210> SEQ ID NO 1728
<211> LENGTH: 17
<212> TYPE: DNA
<213> ORGANISM: Homo sapiens

<400> SEQUENCE: 1728
tgctgcttgt gttccca 17

<210> SEQ ID NO 1729
<211> LENGTH: 17
<212> TYPE: DNA
<213> ORGANISM: Homo sapiens

<400> SEQUENCE: 1729
gctgcttgtg ttcccat 17

<210> SEQ ID NO 1730
<211> LENGTH: 17
<212> TYPE: DNA
<213> ORGANISM: Homo sapiens

<400> SEQUENCE: 1730
ctgcttgtgt tcccatt 17

<210> SEQ ID NO 1731
<211> LENGTH: 17
<212> TYPE: DNA
<213> ORGANISM: Homo sapiens

<400> SEQUENCE: 1731
tgcttgtgtt cccattg 17

<210> SEQ ID NO 1732
<211> LENGTH: 17
<212> TYPE: DNA
<213> ORGANISM: Homo sapiens

<400> SEQUENCE: 1732
gcttgtgttc ccattgt 17

<210> SEQ ID NO 1733
<211> LENGTH: 17
<212> TYPE: DNA
<213> ORGANISM: Homo sapiens

<400> SEQUENCE: 1733
cttgtgttcc cattgtc 17

<210> SEQ ID NO 1734
<211> LENGTH: 17
<212> TYPE: DNA
<213> ORGANISM: Homo sapiens

<400> SEQUENCE: 1734
ttgtgttccc attgtcc 17

<210> SEQ ID NO 1735
<211> LENGTH: 17
<212> TYPE: DNA
<213> ORGANISM: Homo sapiens

<400> SEQUENCE: 1735

-continued tgtgttccca ttgtccc 17

<210> SEQ ID NO 1736
<211> LENGTH: 17
<212> TYPE: DNA
<213> ORGANISM: Homo sapiens

<400> SEQUENCE: 1736
gtgttcccat tgtccca 17

<210> SEQ ID NO 1737
<211> LENGTH: 17
<212> TYPE: DNA
<213> ORGANISM: Homo sapiens

<400> SEQUENCE: 1737
tgttcccatt gtcccag 17

<210> SEQ ID NO 1738
<211> LENGTH: 17
<212> TYPE: DNA
<213> ORGANISM: Homo sapiens

<400> SEQUENCE: 1738
gttcccattg tcccagc 17

<210> SEQ ID NO 1739
<211> LENGTH: 17
<212> TYPE: DNA
<213> ORGANISM: Homo sapiens

<400> SEQUENCE: 1739
ttcccattgt cccagca 17

<210> SEQ ID NO 1740
<211> LENGTH: 17
<212> TYPE: DNA
<213> ORGANISM: Homo sapiens

<400> SEQUENCE: 1740
tcccattgtc ccagcaa 17

<210> SEQ ID NO 1741
<211> LENGTH: 17
<212> TYPE: DNA
<213> ORGANISM: Homo sapiens

<400> SEQUENCE: 1741
cccattgtcc cagcaag 17

<210> SEQ ID NO 1742
<211> LENGTH: 17
<212> TYPE: DNA
<213> ORGANISM: Homo sapiens

<400> SEQUENCE: 1742
ccattgtccc agcaaga 17

<210> SEQ ID NO 1743
<211> LENGTH: 17
<212> TYPE: DNA
<213> ORGANISM: Homo sapiens

<400> SEQUENCE: 1743

-continued cattgtccca gcaagaa 17

<210> SEQ ID NO 1744
<211> LENGTH: 17
<212> TYPE: DNA
<213> ORGANISM: Homo sapiens

<400> SEQUENCE: 1744
attgtcccag caagaac 17

<210> SEQ ID NO 1745
<211> LENGTH: 17
<212> TYPE: DNA
<213> ORGANISM: Homo sapiens

<400> SEQUENCE: 1745
ttgtcccagc aagaaca 17

<210> SEQ ID NO 1746
<211> LENGTH: 17
<212> TYPE: DNA
<213> ORGANISM: Homo sapiens

<400> SEQUENCE: 1746
tgtcccagca agaacac 17

<210> SEQ ID NO 1747
<211> LENGTH: 17
<212> TYPE: DNA
<213> ORGANISM: Homo sapiens

<400> SEQUENCE: 1747
gtcccagcaa gaacaca 17

<210> SEQ ID NO 1748
<211> LENGTH: 17
<212> TYPE: DNA
<213> ORGANISM: Homo sapiens

<400> SEQUENCE: 1748
tcccagcaag aacacac 17

<210> SEQ ID NO 1749
<211> LENGTH: 17
<212> TYPE: DNA
<213> ORGANISM: Homo sapiens

<400> SEQUENCE: 1749
cccagcaaga acacacg 17

<210> SEQ ID NO 1750
<211> LENGTH: 17
<212> TYPE: DNA
<213> ORGANISM: Homo sapiens

<400> SEQUENCE: 1750
ccagcaagaa cacacgt 17

<210> SEQ ID NO 1751
<211> LENGTH: 17
<212> TYPE: DNA
<213> ORGANISM: Homo sapiens -continued

<400> SEQUENCE: 1751
cagcaagaac acacgta 17

<210> SEQ ID NO 1752
<211> LENGTH: 17
<212> TYPE: DNA
<213> ORGANISM: Homo sapiens

<400> SEQUENCE: 1752
agcaagaaca cacgtat 17

<210> SEQ ID NO 1753
<211> LENGTH: 17
<212> TYPE: DNA
<213> ORGANISM: Homo sapiens

<400> SEQUENCE: 1753
gcaagaacac acgtatg 17

<210> SEQ ID NO 1754
<211> LENGTH: 17
<212> TYPE: DNA
<213> ORGANISM: Homo sapiens

<400> SEQUENCE: 1754
caagaacaca cgtatgc 17

<210> SEQ ID NO 1755
<211> LENGTH: 17
<212> TYPE: DNA
<213> ORGANISM: Homo sapiens

<400> SEQUENCE: 1755
aagaacacac gtatgct 17

<210> SEQ ID NO 1756
<211> LENGTH: 17
<212> TYPE: DNA
<213> ORGANISM: Homo sapiens

<400> SEQUENCE: 1756
agaacacacg tatgcta 17

<210> SEQ ID NO 1757
<211> LENGTH: 17
<212> TYPE: DNA
<213> ORGANISM: Homo sapiens

<400> SEQUENCE: 1757
gaacacacgt atgctac 17

<210> SEQ ID NO 1758
<211> LENGTH: 17
<212> TYPE: DNA
<213> ORGANISM: Homo sapiens

<400> SEQUENCE: 1758
aacacacgta tgctaca 17

<210> SEQ ID NO 1759
<211> LENGTH: 17
<212> TYPE: DNA
<213> ORGANISM: Homo sapiens -continued

<400> SEQUENCE: 1759
acacacgtat gctacat 17

<210> SEQ ID NO 1760
<211> LENGTH: 17
<212> TYPE: DNA
<213> ORGANISM: Homo sapiens

<400> SEQUENCE: 1760
cacacgtatg ctacata 17

<210> SEQ ID NO 1761
<211> LENGTH: 17
<212> TYPE: DNA
<213> ORGANISM: Homo sapiens

<400> SEQUENCE: 1761
acacgtatgc tacatat 17

<210> SEQ ID NO 1762
<211> LENGTH: 17
<212> TYPE: DNA
<213> ORGANISM: Homo sapiens

<400> SEQUENCE: 1762
cacgtatgct acatatc 17

<210> SEQ ID NO 1763
<211> LENGTH: 17
<212> TYPE: DNA
<213> ORGANISM: Homo sapiens

<400> SEQUENCE: 1763
acgtatgcta catatct 17

<210> SEQ ID NO 1764
<211> LENGTH: 17
<212> TYPE: DNA
<213> ORGANISM: Homo sapiens

<400> SEQUENCE: 1764
cgtatgctac atatctg 17

<210> SEQ ID NO 1765
<211> LENGTH: 17
<212> TYPE: DNA
<213> ORGANISM: Homo sapiens

<400> SEQUENCE: 1765
gtatgctaca tatctgc 17

<210> SEQ ID NO 1766
<211> LENGTH: 17
<212> TYPE: DNA
<213> ORGANISM: Homo sapiens

<400> SEQUENCE: 1766
tatgctacat atctgca 17

<210> SEQ ID NO 1767
<211> LENGTH: 17
<212> TYPE: DNA

-continued

<213> ORGANISM: Homo sapiens

<400> SEQUENCE: 1767
atgctacata tctgcaa 17

<210> SEQ ID NO 1768
<211> LENGTH: 17
<212> TYPE: DNA
<213> ORGANISM: Homo sapiens

<400> SEQUENCE: 1768
tgctacatat ctgcaat 17

<210> SEQ ID NO 1769
<211> LENGTH: 17
<212> TYPE: DNA
<213> ORGANISM: Homo sapiens

<400> SEQUENCE: 1769
gctacatatc tgcaatc 17

<210> SEQ ID NO 1770
<211> LENGTH: 17
<212> TYPE: DNA
<213> ORGANISM: Homo sapiens

<400> SEQUENCE: 1770
ctacatatct gcaatcc 17

<210> SEQ ID NO 1771
<211> LENGTH: 17
<212> TYPE: DNA
<213> ORGANISM: Homo sapiens

<400> SEQUENCE: 1771
tacatatctg caatcca 17

<210> SEQ ID NO 1772
<211> LENGTH: 17
<212> TYPE: DNA
<213> ORGANISM: Homo sapiens

<400> SEQUENCE: 1772
acatatctgc aatccaa 17

<210> SEQ ID NO 1773
<211> LENGTH: 17
<212> TYPE: DNA
<213> ORGANISM: Homo sapiens

<400> SEQUENCE: 1773
catatctgca atccaaa 17

<210> SEQ ID NO 1774
<211> LENGTH: 17
<212> TYPE: DNA
<213> ORGANISM: Homo sapiens

<400> SEQUENCE: 1774
atatctgcaa tccaaaa 17

<210> SEQ ID NO 1775
<211> LENGTH: 17

-continued

<212> TYPE: DNA
<213> ORGANISM: Homo sapiens

<400> SEQUENCE: 1775
tatctgcaat ccaaaat 17

<210> SEQ ID NO 1776
<211> LENGTH: 17
<212> TYPE: DNA
<213> ORGANISM: Homo sapiens

<400> SEQUENCE: 1776
atctgcaatc caaaatt 17

<210> SEQ ID NO 1777
<211> LENGTH: 17
<212> TYPE: DNA
<213> ORGANISM: Homo sapiens

<400> SEQUENCE: 1777
tctgcaatcc aaaattg 17

<210> SEQ ID NO 1778
<211> LENGTH: 17
<212> TYPE: DNA
<213> ORGANISM: Homo sapiens

<400> SEQUENCE: 1778
ctgcaatcca aaattgt 17

<210> SEQ ID NO 1779
<211> LENGTH: 17
<212> TYPE: DNA
<213> ORGANISM: Homo sapiens

<400> SEQUENCE: 1779
tgcaatccaa aattgtt 17

<210> SEQ ID NO 1780
<211> LENGTH: 17
<212> TYPE: DNA
<213> ORGANISM: Homo sapiens

<400> SEQUENCE: 1780
gcaatccaaa attgttg 17

<210> SEQ ID NO 1781
<211> LENGTH: 17
<212> TYPE: DNA
<213> ORGANISM: Homo sapiens

<400> SEQUENCE: 1781
caatccaaaa ttgttgc 17

<210> SEQ ID NO 1782
<211> LENGTH: 17
<212> TYPE: DNA
<213> ORGANISM: Homo sapiens

<400> SEQUENCE: 1782
aatccaaaat tgttgcc 17

<210> SEQ ID NO 1783

-continued

<211> LENGTH: 17
<212> TYPE: DNA
<213> ORGANISM: Homo sapiens

<400> SEQUENCE: 1783
atccaaaatt gttgccc 17

<210> SEQ ID NO 1784
<211> LENGTH: 17
<212> TYPE: DNA
<213> ORGANISM: Homo sapiens

<400> SEQUENCE: 1784
tccaaaattg ttgccct 17

<210> SEQ ID NO 1785
<211> LENGTH: 17
<212> TYPE: DNA
<213> ORGANISM: Homo sapiens

<400> SEQUENCE: 1785
ccaaaattgt tgccctt 17

<210> SEQ ID NO 1786
<211> LENGTH: 17
<212> TYPE: DNA
<213> ORGANISM: Homo sapiens

<400> SEQUENCE: 1786
caaaattgtt gcccttc 17

<210> SEQ ID NO 1787
<211> LENGTH: 17
<212> TYPE: DNA
<213> ORGANISM: Homo sapiens

<400> SEQUENCE: 1787
aaaattgttg cccttcc 17

<210> SEQ ID NO 1788
<211> LENGTH: 17
<212> TYPE: DNA
<213> ORGANISM: Homo sapiens

<400> SEQUENCE: 1788
aaattgttgc ccttcca 17

<210> SEQ ID NO 1789
<211> LENGTH: 17
<212> TYPE: DNA
<213> ORGANISM: Homo sapiens

<400> SEQUENCE: 1789
aattgttgcc cttccaa 17

<210> SEQ ID NO 1790
<211> LENGTH: 17
<212> TYPE: DNA
<213> ORGANISM: Homo sapiens

<400> SEQUENCE: 1790
attgttgccc ttccaag 17

-continued

<210> SEQ ID NO 1791
<211> LENGTH: 17
<212> TYPE: DNA
<213> ORGANISM: Homo sapiens

<400> SEQUENCE: 1791
ttgttgccct tccaagc 17

<210> SEQ ID NO 1792
<211> LENGTH: 17
<212> TYPE: DNA
<213> ORGANISM: Homo sapiens

<400> SEQUENCE: 1792
tgttgccctt ccaagca 17

<210> SEQ ID NO 1793
<211> LENGTH: 17
<212> TYPE: DNA
<213> ORGANISM: Homo sapiens

<400> SEQUENCE: 1793
gttgcccttc caagcaa 17

<210> SEQ ID NO 1794
<211> LENGTH: 17
<212> TYPE: DNA
<213> ORGANISM: Homo sapiens

<400> SEQUENCE: 1794
ttgcccttcc aagcaaa 17

<210> SEQ ID NO 1795
<211> LENGTH: 17
<212> TYPE: DNA
<213> ORGANISM: Homo sapiens

<400> SEQUENCE: 1795
tgcccttcca agcaaat 17

<210> SEQ ID NO 1796
<211> LENGTH: 17
<212> TYPE: DNA
<213> ORGANISM: Homo sapiens

<400> SEQUENCE: 1796
gcccttccaa gcaaatg 17

<210> SEQ ID NO 1797
<211> LENGTH: 25
<212> TYPE: DNA
<213> ORGANISM: Homo sapiens

<400> SEQUENCE: 1797
gtcataagcc agttgttgct gcttg 25

<210> SEQ ID NO 1798
<211> LENGTH: 25
<212> TYPE: DNA
<213> ORGANISM: Homo sapiens

<400> SEQUENCE: 1798
tcataagcca gttgttgctg cttgt 25

-continued

<210> SEQ ID NO 1799
<211> LENGTH: 25
<212> TYPE: DNA
<213> ORGANISM: Homo sapiens

<400> SEQUENCE: 1799
cataagccag ttgttgctgc ttgtg 25

<210> SEQ ID NO 1800
<211> LENGTH: 25
<212> TYPE: DNA
<213> ORGANISM: Homo sapiens

<400> SEQUENCE: 1800
ataagccagt tgttgctgct tgtgt 25

<210> SEQ ID NO 1801
<211> LENGTH: 25
<212> TYPE: DNA
<213> ORGANISM: Homo sapiens

<400> SEQUENCE: 1801
taagccagtt gttgctgctt gtgtt 25

<210> SEQ ID NO 1802
<211> LENGTH: 25
<212> TYPE: DNA
<213> ORGANISM: Homo sapiens

<400> SEQUENCE: 1802
aagccagttg ttgctgcttg tgttc 25

<210> SEQ ID NO 1803
<211> LENGTH: 25
<212> TYPE: DNA
<213> ORGANISM: Homo sapiens

<400> SEQUENCE: 1803
agccagttgt tgctgcttgt gttcc 25

<210> SEQ ID NO 1804
<211> LENGTH: 25
<212> TYPE: DNA
<213> ORGANISM: Homo sapiens

<400> SEQUENCE: 1804
gccagttgtt gctgcttgtg ttccc 25

<210> SEQ ID NO 1805
<211> LENGTH: 25
<212> TYPE: DNA
<213> ORGANISM: Homo sapiens

<400> SEQUENCE: 1805
ccagttgttg ctgcttgtgt tccca 25

<210> SEQ ID NO 1806
<211> LENGTH: 25
<212> TYPE: DNA
<213> ORGANISM: Homo sapiens

<400> SEQUENCE: 1806
cagttgttgc tgcttgtgtt cccat 25

-continued

<210> SEQ ID NO 1807
<211> LENGTH: 25
<212> TYPE: DNA
<213> ORGANISM: Homo sapiens

<400> SEQUENCE: 1807
agttgttgct gcttgtgttc ccatt 25

<210> SEQ ID NO 1808
<211> LENGTH: 25
<212> TYPE: DNA
<213> ORGANISM: Homo sapiens

<400> SEQUENCE: 1808
gttgttgctg cttgtgttcc cattg 25

<210> SEQ ID NO 1809
<211> LENGTH: 25
<212> TYPE: DNA
<213> ORGANISM: Homo sapiens

<400> SEQUENCE: 1809
ttgttgctgc ttgtgttccc attgt 25

<210> SEQ ID NO 1810
<211> LENGTH: 25
<212> TYPE: DNA
<213> ORGANISM: Homo sapiens

<400> SEQUENCE: 1810
tgttgctgct tgtgttccca ttgtc 25

<210> SEQ ID NO 1811
<211> LENGTH: 25
<212> TYPE: DNA
<213> ORGANISM: Homo sapiens

<400> SEQUENCE: 1811
gttgctgctt gtgttcccat tgtcc 25

<210> SEQ ID NO 1812
<211> LENGTH: 25
<212> TYPE: DNA
<213> ORGANISM: Homo sapiens

<400> SEQUENCE: 1812
ttgctgcttg tgttcccatt gtccc 25

<210> SEQ ID NO 1813
<211> LENGTH: 25
<212> TYPE: DNA
<213> ORGANISM: Homo sapiens

<400> SEQUENCE: 1813
tgctgcttgt gttcccattg tccca 25

<210> SEQ ID NO 1814
<211> LENGTH: 25
<212> TYPE: DNA
<213> ORGANISM: Homo sapiens

<400> SEQUENCE: 1814

-continued gctgcttgtg ttcccattgt cccag 25

<210> SEQ ID NO 1815
<211> LENGTH: 25
<212> TYPE: DNA
<213> ORGANISM: Homo sapiens

<400> SEQUENCE: 1815
ctgcttgtgt tcccattgtc ccagc 25

<210> SEQ ID NO 1816
<211> LENGTH: 25
<212> TYPE: DNA
<213> ORGANISM: Homo sapiens

<400> SEQUENCE: 1816
tgcttgtgtt cccattgtcc cagca 25

<210> SEQ ID NO 1817
<211> LENGTH: 25
<212> TYPE: DNA
<213> ORGANISM: Homo sapiens

<400> SEQUENCE: 1817
gcttgtgttc ccattgtccc agcaa 25

<210> SEQ ID NO 1818
<211> LENGTH: 25
<212> TYPE: DNA
<213> ORGANISM: Homo sapiens

<400> SEQUENCE: 1818
cttgtgttcc cattgtccca gcaag 25

<210> SEQ ID NO 1819
<211> LENGTH: 25
<212> TYPE: DNA
<213> ORGANISM: Homo sapiens

<400> SEQUENCE: 1819
ttgtgttccc attgtcccag caaga 25

<210> SEQ ID NO 1820
<211> LENGTH: 25
<212> TYPE: DNA
<213> ORGANISM: Homo sapiens

<400> SEQUENCE: 1820
tgtgttccca ttgtcccagc aagaa 25

<210> SEQ ID NO 1821
<211> LENGTH: 25
<212> TYPE: DNA
<213> ORGANISM: Homo sapiens

<400> SEQUENCE: 1821
gtgttcccat tgtcccagca agaac 25

<210> SEQ ID NO 1822
<211> LENGTH: 25
<212> TYPE: DNA
<213> ORGANISM: Homo sapiens

<400> SEQUENCE: 1822

-continued tgttcccatt gtcccagcaa gaaca 25

<210> SEQ ID NO 1823
<211> LENGTH: 25
<212> TYPE: DNA
<213> ORGANISM: Homo sapiens

<400> SEQUENCE: 1823
gttcccattg tcccagcaag aacac 25

<210> SEQ ID NO 1824
<211> LENGTH: 25
<212> TYPE: DNA
<213> ORGANISM: Homo sapiens

<400> SEQUENCE: 1824
ttcccattgt cccagcaaga acaca 25

<210> SEQ ID NO 1825
<211> LENGTH: 25
<212> TYPE: DNA
<213> ORGANISM: Homo sapiens

<400> SEQUENCE: 1825
tcccattgtc ccagcaagaa cacac 25

<210> SEQ ID NO 1826
<211> LENGTH: 25
<212> TYPE: DNA
<213> ORGANISM: Homo sapiens

<400> SEQUENCE: 1826
cccattgtcc cagcaagaac acacg 25

<210> SEQ ID NO 1827
<211> LENGTH: 25
<212> TYPE: DNA
<213> ORGANISM: Homo sapiens

<400> SEQUENCE: 1827
ccattgtccc agcaagaaca cacgt 25

<210> SEQ ID NO 1828
<211> LENGTH: 25
<212> TYPE: DNA
<213> ORGANISM: Homo sapiens

<400> SEQUENCE: 1828
cattgtccca gcaagaacac acgta 25

<210> SEQ ID NO 1829
<211> LENGTH: 25
<212> TYPE: DNA
<213> ORGANISM: Homo sapiens

<400> SEQUENCE: 1829
attgtcccag caagaacaca cgtat 25

<210> SEQ ID NO 1830
<211> LENGTH: 25
<212> TYPE: DNA
<213> ORGANISM: Homo sapiens -continued

<400> SEQUENCE: 1830
ttgtcccagc aagaacacac gtatg 25

<210> SEQ ID NO 1831
<211> LENGTH: 25
<212> TYPE: DNA
<213> ORGANISM: Homo sapiens

<400> SEQUENCE: 1831
tgtcccagca agaacacacg tatgc 25

<210> SEQ ID NO 1832
<211> LENGTH: 25
<212> TYPE: DNA
<213> ORGANISM: Homo sapiens

<400> SEQUENCE: 1832
gtcccagcaa gaacacacgt atgct 25

<210> SEQ ID NO 1833
<211> LENGTH: 25
<212> TYPE: DNA
<213> ORGANISM: Homo sapiens

<400> SEQUENCE: 1833
tcccagcaag aacacacgta tgcta 25

<210> SEQ ID NO 1834
<211> LENGTH: 25
<212> TYPE: DNA
<213> ORGANISM: Homo sapiens

<400> SEQUENCE: 1834
cccagcaaga acacacgtat gctac 25

<210> SEQ ID NO 1835
<211> LENGTH: 25
<212> TYPE: DNA
<213> ORGANISM: Homo sapiens

<400> SEQUENCE: 1835
ccagcaagaa cacacgtatg ctaca 25

<210> SEQ ID NO 1836
<211> LENGTH: 25
<212> TYPE: DNA
<213> ORGANISM: Homo sapiens

<400> SEQUENCE: 1836
cagcaagaac acacgtatgc tacat 25

<210> SEQ ID NO 1837
<211> LENGTH: 25
<212> TYPE: DNA
<213> ORGANISM: Homo sapiens

<400> SEQUENCE: 1837
agcaagaaca cacgtatgct acata 25

<210> SEQ ID NO 1838
<211> LENGTH: 25
<212> TYPE: DNA
<213> ORGANISM: Homo sapiens -continued

<400> SEQUENCE: 1838
gcaagaacac acgtatgcta catat 25

<210> SEQ ID NO 1839
<211> LENGTH: 25
<212> TYPE: DNA
<213> ORGANISM: Homo sapiens

<400> SEQUENCE: 1839
caagaacaca cgtatgctac atatc 25

<210> SEQ ID NO 1840
<211> LENGTH: 25
<212> TYPE: DNA
<213> ORGANISM: Homo sapiens

<400> SEQUENCE: 1840
aagaacacac gtatgctaca tatct 25

<210> SEQ ID NO 1841
<211> LENGTH: 25
<212> TYPE: DNA
<213> ORGANISM: Homo sapiens

<400> SEQUENCE: 1841
agaacacacg tatgctacat atctg 25

<210> SEQ ID NO 1842
<211> LENGTH: 25
<212> TYPE: DNA
<213> ORGANISM: Homo sapiens

<400> SEQUENCE: 1842
gaacacacgt atgctacata tctgc 25

<210> SEQ ID NO 1843
<211> LENGTH: 25
<212> TYPE: DNA
<213> ORGANISM: Homo sapiens

<400> SEQUENCE: 1843
aacacacgta tgctacatat ctgca 25

<210> SEQ ID NO 1844
<211> LENGTH: 25
<212> TYPE: DNA
<213> ORGANISM: Homo sapiens

<400> SEQUENCE: 1844
acacacgtat gctacatatc tgcaa 25

<210> SEQ ID NO 1845
<211> LENGTH: 25
<212> TYPE: DNA
<213> ORGANISM: Homo sapiens

<400> SEQUENCE: 1845
cacacgtatg ctacatatct gcaat 25

<210> SEQ ID NO 1846
<211> LENGTH: 25
<212> TYPE: DNA

-continued

<213> ORGANISM: Homo sapiens

<400> SEQUENCE: 1846
acacgtatgc tacatatctg caatc 25

<210> SEQ ID NO 1847
<211> LENGTH: 25
<212> TYPE: DNA
<213> ORGANISM: Homo sapiens

<400> SEQUENCE: 1847
cacgtatgct acatatctgc aatcc 25

<210> SEQ ID NO 1848
<211> LENGTH: 25
<212> TYPE: DNA
<213> ORGANISM: Homo sapiens

<400> SEQUENCE: 1848
acgtatgcta catatctgca atcca 25

<210> SEQ ID NO 1849
<211> LENGTH: 25
<212> TYPE: DNA
<213> ORGANISM: Homo sapiens

<400> SEQUENCE: 1849
cgtatgctac atatctgcaa tccaa 25

<210> SEQ ID NO 1850
<211> LENGTH: 25
<212> TYPE: DNA
<213> ORGANISM: Homo sapiens

<400> SEQUENCE: 1850
gtatgctaca tatctgcaat ccaaa 25

<210> SEQ ID NO 1851
<211> LENGTH: 25
<212> TYPE: DNA
<213> ORGANISM: Homo sapiens

<400> SEQUENCE: 1851
tatgctacat atctgcaatc caaaa 25

<210> SEQ ID NO 1852
<211> LENGTH: 25
<212> TYPE: DNA
<213> ORGANISM: Homo sapiens

<400> SEQUENCE: 1852
atgctacata tctgcaatcc aaaat 25

<210> SEQ ID NO 1853
<211> LENGTH: 25
<212> TYPE: DNA
<213> ORGANISM: Homo sapiens

<400> SEQUENCE: 1853
tgctacatat ctgcaatcca aaatt 25

<210> SEQ ID NO 1854
<211> LENGTH: 25

-continued

<212> TYPE: DNA
<213> ORGANISM: Homo sapiens

<400> SEQUENCE: 1854
gctacatatc tgcaatccaa aattg 25

<210> SEQ ID NO 1855
<211> LENGTH: 25
<212> TYPE: DNA
<213> ORGANISM: Homo sapiens

<400> SEQUENCE: 1855
ctacatatct gcaatccaaa attgt 25

<210> SEQ ID NO 1856
<211> LENGTH: 25
<212> TYPE: DNA
<213> ORGANISM: Homo sapiens

<400> SEQUENCE: 1856
tacatatctg caatccaaaa ttgtt 25

<210> SEQ ID NO 1857
<211> LENGTH: 25
<212> TYPE: DNA
<213> ORGANISM: Homo sapiens

<400> SEQUENCE: 1857
acatatctgc aatccaaaat tgttg 25

<210> SEQ ID NO 1858
<211> LENGTH: 25
<212> TYPE: DNA
<213> ORGANISM: Homo sapiens

<400> SEQUENCE: 1858
catatctgca atccaaaatt gttgc 25

<210> SEQ ID NO 1859
<211> LENGTH: 25
<212> TYPE: DNA
<213> ORGANISM: Homo sapiens

<400> SEQUENCE: 1859
atatctgcaa tccaaaattg ttgcc 25

<210> SEQ ID NO 1860
<211> LENGTH: 25
<212> TYPE: DNA
<213> ORGANISM: Homo sapiens

<400> SEQUENCE: 1860
tatctgcaat ccaaaattgt tgccc 25

<210> SEQ ID NO 1861
<211> LENGTH: 25
<212> TYPE: DNA
<213> ORGANISM: Homo sapiens

<400> SEQUENCE: 1861
atctgcaatc caaaattgtt gccct 25

<210> SEQ ID NO 1862

-continued

<211> LENGTH: 25
<212> TYPE: DNA
<213> ORGANISM: Homo sapiens

<400> SEQUENCE: 1862
tctgcaatcc aaaattgttg ccctt 25

<210> SEQ ID NO 1863
<211> LENGTH: 25
<212> TYPE: DNA
<213> ORGANISM: Homo sapiens

<400> SEQUENCE: 1863
ctgcaatcca aaattgttgc ccttc 25

<210> SEQ ID NO 1864
<211> LENGTH: 25
<212> TYPE: DNA
<213> ORGANISM: Homo sapiens

<400> SEQUENCE: 1864
tgcaatccaa aattgttgcc cttcc 25

<210> SEQ ID NO 1865
<211> LENGTH: 25
<212> TYPE: DNA
<213> ORGANISM: Homo sapiens

<400> SEQUENCE: 1865
gcaatccaaa attgttgccc ttcca 25

<210> SEQ ID NO 1866
<211> LENGTH: 25
<212> TYPE: DNA
<213> ORGANISM: Homo sapiens

<400> SEQUENCE: 1866
caatccaaaa ttgttgccct tccaa 25

<210> SEQ ID NO 1867
<211> LENGTH: 25
<212> TYPE: DNA
<213> ORGANISM: Homo sapiens

<400> SEQUENCE: 1867
aatccaaaat tgttgccctt ccaag 25

<210> SEQ ID NO 1868
<211> LENGTH: 25
<212> TYPE: DNA
<213> ORGANISM: Homo sapiens

<400> SEQUENCE: 1868
atccaaaatt gttgcccttc caagc 25

<210> SEQ ID NO 1869
<211> LENGTH: 25
<212> TYPE: DNA
<213> ORGANISM: Homo sapiens

<400> SEQUENCE: 1869
tccaaaattg ttgcccttcc aagca 25

-continued

<210> SEQ ID NO 1870
<211> LENGTH: 25
<212> TYPE: DNA
<213> ORGANISM: Homo sapiens

<400> SEQUENCE: 1870
ccaaaattgt tgcccttcca agcaa 25

<210> SEQ ID NO 1871
<211> LENGTH: 25
<212> TYPE: DNA
<213> ORGANISM: Homo sapiens

<400> SEQUENCE: 1871
caaaattgtt gcccttccaa gcaaa 25

<210> SEQ ID NO 1872
<211> LENGTH: 25
<212> TYPE: DNA
<213> ORGANISM: Homo sapiens

<400> SEQUENCE: 1872
aaaattgttg cccttccaag caaat 25

<210> SEQ ID NO 1873
<211> LENGTH: 25
<212> TYPE: DNA
<213> ORGANISM: Homo sapiens

<400> SEQUENCE: 1873
aaattgttgc ccttccaagc aaatg 25

<210> SEQ ID NO 1874
<211> LENGTH: 25
<212> TYPE: DNA
<213> ORGANISM: Homo sapiens

<400> SEQUENCE: 1874
aattgttgcc cttccaagca aatgg 25

<210> SEQ ID NO 1875
<211> LENGTH: 25
<212> TYPE: DNA
<213> ORGANISM: Homo sapiens

<400> SEQUENCE: 1875
attgttgccc ttccaagcaa atggt 25

<210> SEQ ID NO 1876
<211> LENGTH: 25
<212> TYPE: DNA
<213> ORGANISM: Homo sapiens

<400> SEQUENCE: 1876
ttgttgccct tccaagcaaa tggtt 25

<210> SEQ ID NO 1877
<211> LENGTH: 25
<212> TYPE: DNA
<213> ORGANISM: Homo sapiens

<400> SEQUENCE: 1877
tgttgccctt ccaagcaaat ggttg 25

-continued

<210> SEQ ID NO 1878
<211> LENGTH: 25
<212> TYPE: DNA
<213> ORGANISM: Homo sapiens

<400> SEQUENCE: 1878
gttgcccttc caagcaaatg gttgg 25

<210> SEQ ID NO 1879
<211> LENGTH: 25
<212> TYPE: DNA
<213> ORGANISM: Homo sapiens

<400> SEQUENCE: 1879
ttgcccttcc aagcaaatgg ttggt 25

<210> SEQ ID NO 1880
<211> LENGTH: 25
<212> TYPE: DNA
<213> ORGANISM: Homo sapiens

<400> SEQUENCE: 1880
tgcccttcca agcaaatggt tggtg 25

<210> SEQ ID NO 1881
<211> LENGTH: 25
<212> TYPE: DNA
<213> ORGANISM: Homo sapiens

<400> SEQUENCE: 1881
gcccttccaa gcaaatggtt ggtgt 25

ISOFORMS OF HUMAN PREGNANCY-ASSOCIATED PROTEIN-E

CROSS REFERENCE TO RELATED APPLICATIONS

The present application claims priority to U.S. provisional patent application Nos. 60/207,456, filled May 26, 2000, and 60/236,359, filed Sep. 27, 2000, the disclosures of which are incorporated herein by reference in their entireties.

REFERENCE TO SEQUENCE LISTING SUBMITTED ON COMPACT DISC

The present application includes a Sequence Listing filed on one (1) CD-R disc, provided in duplicate, containing a single file named pto_MDhMORF-8.txt, having 349 kilobytes, last modified on Apr. 3, 2001 and recorded Apr. 5, 2001. The Sequence Listing contained in said file on said disc is incorporated herein by reference in its entirety.

FIELD OF THE INVENTION

The present invention relates to novel isoforms of a human protein, and particularly relates to novel isoforms of human pregnancy-associated plasma protein-E.

BACKGROUND OF THE INVENTION

Pregnancy-Associated Plasma Protein-A (PAPP-A) was first identified as a component of a circulating protein complex uniquely present in the serum of pregnant women. Principally of placental, that is, fetal, origin, and detectable in maternal serum as early as 4 weeks into gestation, PAPP-A has proven useful as a readily sampled marker for prenatal monitoring of fetal health and diagnosis of a number of human fetal abnormalities.

Maternal serum PAPP-A levels normally increase throughout gestation. Failure of PAPP-A levels to increase at the normal rate—that is, PAPP-A levels lower than the average for the respective gestational age—has been associated with a variety of fetal disorders.

For example, PAPP-A levels have been shown to be significantly lower than normal at 10–14 weeks gestation in pregnancies that subsequently result in miscarriage, pregnancy-induced hypertension, growth restriction, and pre-existing or gestational diabetes mellitus. Ong et al., Brit. *J. Obstet. Gynaec.* 107: 1265–70 (2000).

As another example, a statistical measure of maternal serum PAPP-A levels (the median multiple of the median (MoM)) is significantly decreased (less than the 5th centile of normal in 78% of cases) during the first trimester in cases of fetal trisomy 18. Tul et al., *Prenat. Diagn.* 19: 1035–42 (1999). When measurement of PAPP-A is combined with measurement of maternal serum free βhCG, fetal nuchal translucency, and maternal age, 89% of cases of trisomy 18 can be detected with a 1% false-positive rate.

In the second trimester of pregnancy, maternal serum levels of PAPP-A are reduced more markedly than either alpha fetoprotein (αFP) or free beta-hCG in cases of trisomy 18; one study reports levels of PAPP-A lower than the 5% centile of normal in 93% of the cases. Spencer et al., *Prenat. Diagn.* 19: 1127–34 (1999).

Median maternal serum levels of PAPP-A are also significantly reduced at 8 to 14 weeks in trisomy 21 gestations. Screening using maternal age, serum-free β-hCG, and PAPP-A at 10 weeks of pregnancy has been demonstrated to provide better prediction of fetal trisomy 21 than one standard test (levels of alpha-fetoprotein and hCG, in conduction with maternal age), and equal predictive value to the test of αFP, unconjugated estriol, hCG, and maternal age at 15–22 weeks. Wald et al., Br. *J. Obstet. Gynaecol.* 103(5): 407–412 (1996).

Although first discovered based upon its primary expression in placental tissue, PAPP-A has also been detected in ovaries, with expression restricted to healthy antral follicles in granulosa cells and healthy corpora lutea (CL) in a subset of large luteal cells, a pattern of expression consistent with a role for PAPP-A at the very outset of pregnancy, through control of survival, growth, and/or differentiation of the dominant ovarian follicle. Hourvitz et al., *J. Clin. Endocrinol.* Metab. 85:4916–4920 (2000).

PAPP-A is a member of the metzincin superfamily of metalloproteinases.

The metzincin gene superfamily was first identified based upon topological and sequence relationships among the astacins, adamalysins, serralysins, and matrix metalloproteinases. These zinc endopeptidases share topological similarity with respect to a five-stranded beta-sheet and three alpha-helices arranged in typical sequential order. The common consensus motif, HEXXHXXGXXH, found in PAPP-A at residues 482–492, contains three histidine residues which are involved in binding of the catalytically essential zinc ion. Stocker et. al., *Protein Sci.* 4:823–40 (1995). Metzincins also possess a conserved methionine residue in spaced relationship to the zinc-binding motif; in PAPP-A, the conserved methionine is believed to be the methionine at residue 556.

PAPP-A has been demonstrated specifically to cleave insulin-like growth factor binding protein 4 (IGFBP-4), Lawrence et al., *Proc. Natl. Acad. Sci. USA* 96:3149–3153 (1999), and to be the dominating, if not sole, IGFBP-4 protease present in the circulation, Overgaard et al., *J. Biol. Chem.* 275:41128–31133 (2000). IGFBP-4 is one of six known inhibitors of IGF action in vitro; like other IGFBPs, cleavage of IGFBP-4 has been shown to abolish its ability to inhibit IGF activity. The cleavage specificity of PAPP-A for IGFBP-4 implicates PAPP-A in normal and pathological physiology of insulin-like growth factor (IGF). Overgaard et al., *J. Biol. Chem.* 275: 31128–33 (2000).

PAPP-A exists in pregnancy serum as a covalent, heterotetrameric 2:2 complex with the proform of eosinophil major basic protein (proMBP); pro-MBP appears to inhibit PAPP-A's protease activity. Overgaard et al., *J. Biol. Chem.* 275:31128–33 (2000). Conversely, IGF appears to be a necessary cofactor or agonist for PAPP-A protease activity, leading to a feedback network controlling IGF availability.

Reports in the literature of pregnancy-related proteins related in sequence to PAPP-A, termed PAPP-B, PAPP-C, and PAPP-D, have proven spurious. Farr et al., *Biochim. Biophys. Acta* 1493:356–362 (2000) recently identified a cDNA that encodes a protein related in primary sequence and protein domain structure to PAPP-A and that is expressed primarily in placenta, which they term PAPP-E. FARR et al. report that the cDNA encodes a complete open reading frame.

Recent reports suggest that at least one-third, and likely a higher percentage, of human genes are alternatively spliced. Hanke et al., *Trends Genet.* 15(1):389–390 (1999); Mironov et al., *Genome Res.* 9:1288–93 (1999); Brett et al., *FEBS Lett.* 474(1):83–6 (2000). Alternative splicing has been proposed to account for at least part of the difference between the number of genes recently called from the completed human genome draft sequence—30,000 to 40,000 (Genome International Sequencing Consortium, *Nature* 409:860–921 (Feb. 15 2001)—and earlier predictions of human gene number that routinely ranged as high as 120,000, Liang et al., *Nature Genet.* 25(2):239–240 (2000). With the Drosophila homolog of one human gene reported to have 38,000 potential alternatively spliced variants, Schmucker et al., *Cell* 101:671 (2000), it now appears that alternative splicing may permit the relatively small number of human coding regions to encode millions, perhaps tens of millions, of structurally distinct proteins and protein isoforms.

With increasing age, women experience decrease in ovarian reserve and, upon conception, an increased incidence of aneuploid gestations. Given a likely role of PAPP-A in controlling ovarian follicular maturation, and its proven clinical utility as a predictor of fetal abnormality during gestation, PAPP-A has potential therapeutic as well as diagnostic roles in clinical infertility practice.

With the recent identification of a protein that is related to the clinically useful prenatal diagnostic marker, human PAPP-A, and the recognition that alternatively spliced isoforms of proteins are as critical to metabolic and physiologic function as proteins that are separately encoded, there is a need to identify and to characterize additional isoforms of the PAPP-E protein.

SUMMARY OF THE INVENTION

The present invention solves these and other needs in the art by providing isolated nucleic acids that encode three novel isoforms of hPAPP-E, and fragments thereof.

In other aspects, the invention provides vectors for propagating and expressing the nucleic acids of the present invention, host cells comprising the nucleic acids and vectors of the present invention, proteins, protein fragments, and protein fusions of the novel PAPP-E isoforms, and antibodies thereto.

The invention further provides pharmaceutical formulations of the nucleic acids, proteins, and antibodies of the present invention.

In other aspects, the invention provides transgenic cells and non-human organisms comprising human PAPP-E isoform nucleic acids, and transgenic cells and non-human organisms with targeted disruption of the endogenous orthologue of the human PAPP-E gene.

The invention additionally provides diagnostic, investigational, and therapeutic methods based on the PAPP-E nucleic acids, proteins, and antibodies of the present invention.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIGS. 3A–3J present the nucleotide and predicted amino acid sequences of PAPP-Ea;

FIGS. 4A–4I present the nucleotide and predicted amino acid sequences of PAPP-Eb; and FIGS. 5A–5G present the nucleotide and predicted amino acid sequences of PAPP-Ec.

DETAILED DESCRIPTION OF THE INVENTION

Mining the sequence of the human genome for novel human genes, the present inventors have identified three novel isoforms of the recently cloned human pregnancy-associated protein E (PAPP-E), a protein expressed predominantly in placenta and related to the clinically useful prenatal diagnostic marker, human PAPP-A.

Figure 1:
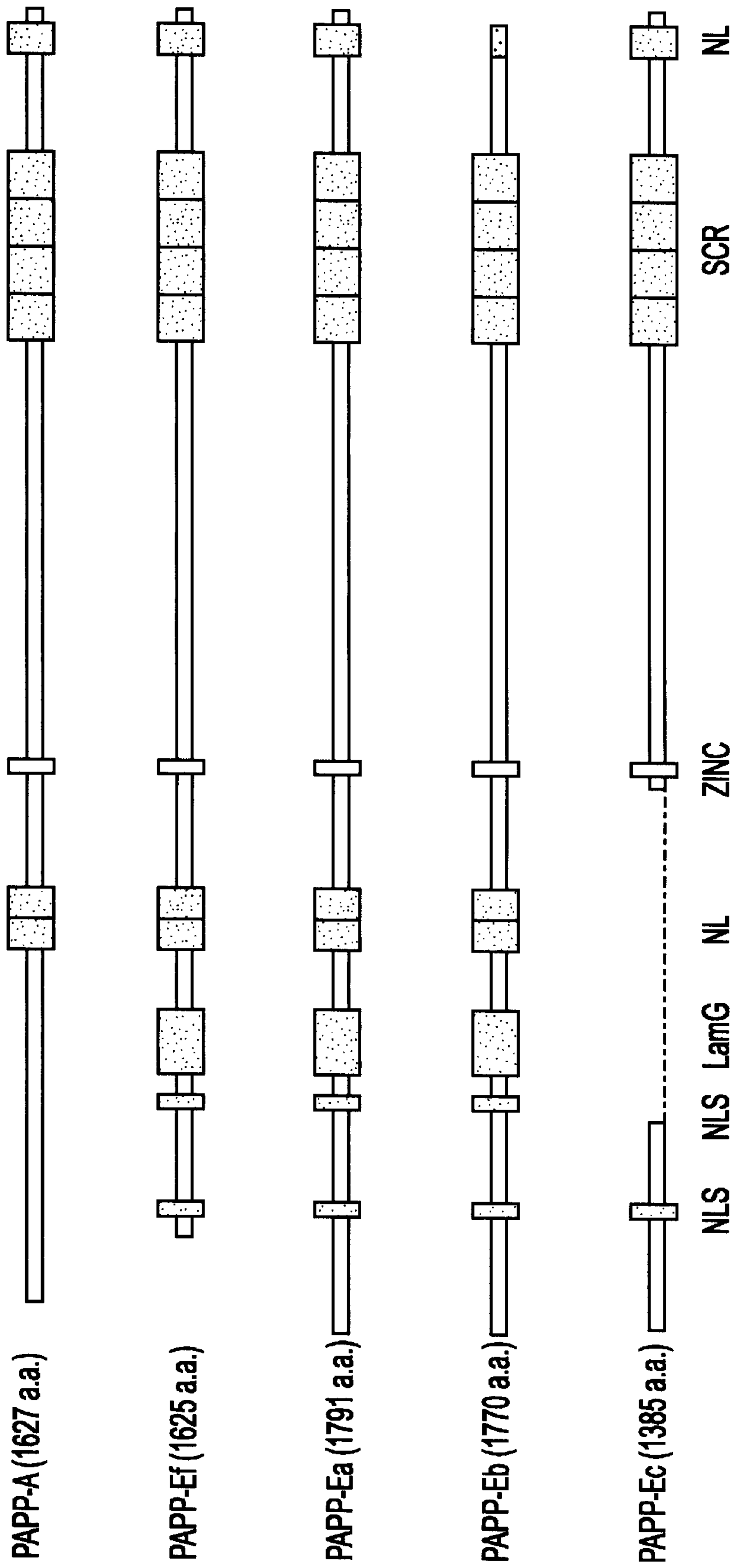
FIG. 1 schematizes the protein domain structure of the three novel isoforms of PAPP-E and the earlier-described PAPP-A.

As schematized in FIG. 1, the newly isolated isoforms—PAPP-Ea, PAPP-Eb, and PAPP-Ec—share certain protein domains and an overall structural organization with PAPP-A; in conjunction with a pattern of expression strikingly similar to that of PAPP-A, with high level expression in placenta, the shared structural features strongly imply that the three PAPP-E isoforms play a role similar to that of PAPP-A in regulating the activity of a plasma borne growth factor(s), likely IGF, which in turn is important for maintenance of pregnancy and/or normal fetal development, thus making the PAPP-E isoforms clinically useful diagnostic markers and potential therapeutic agents.

Like PAPP-A, all three novel isoforms have the zinc-binding domain ("zinc") characteristic of metzincin superfamily metalloproteases, defined by the degenerate motif " HEXXHXXGXXH", where invariant residues are shown underlined and variable residues are shown as "X"In PAPP-Ea, the longest isoform, the zinc binding domain occurs at residues 733–743 with sequence HEVGHVLGLYH.

In common with PAPP-A, all three novel isoforms of PAPP-E have an at least four-fold repetition near the C-terminus of the short consensus repeat ("SCR"; alternatively denominated "sushi" domain) (relaxation of certain bioinformatic parameters causes bioinformatic algorithms to suggest a potential five-fold repetition).

In common with PAPP-A, all three novel isoforms of PAPP-E also have at least one "NL" (notch-lin, also termed lin notch repeat, or "LNR") domain, so-called due to its presence in Notch and Lin-12 proteins, both of which proteins regulate early tissue differentiation. As shown in FIG. 1, PAPP-Ea possesses three NL domains in the same general spaced relationship to the zinc domain as is found in PAPP-A. PAPP-Eb, in contrast, lacks the C-terminal NL domain, whereas PAPPE-c, the shortest of the novel isoforms, lacks the two NL domains on the N-terminal side of the zinc-binding domain.

The four-fold repetition of SCR ("sushi") domains is characteristic of complement proteins and selectins. Five-fold repetition of SCR domains with further presence of at least one NL domain has been previously identified in complement decay-accelerating factor and P-selectin.

In contrast to PAPP-A, two of the novel isoforms of PAPP-E—PAPP-Ea and PAPP-Eb—have a laminin G domain. Laminin G domains are found in a number of extracellular and receptor proteins, and are implicated in interactions with cellular receptors (integrins, alpha-dystroglycan), sulfated carbohydrates and other extracellular ligands.

In contrast to PAPP-A, all three novel isoforms of PAPP-E contain nuclear localization signals ("NLS"); with concurrent presence of a leader sequence (not shown), these signals suggest that all three PAPP-E isoforms can be secreted and also localize to the cell nucleus.

Figure 2:
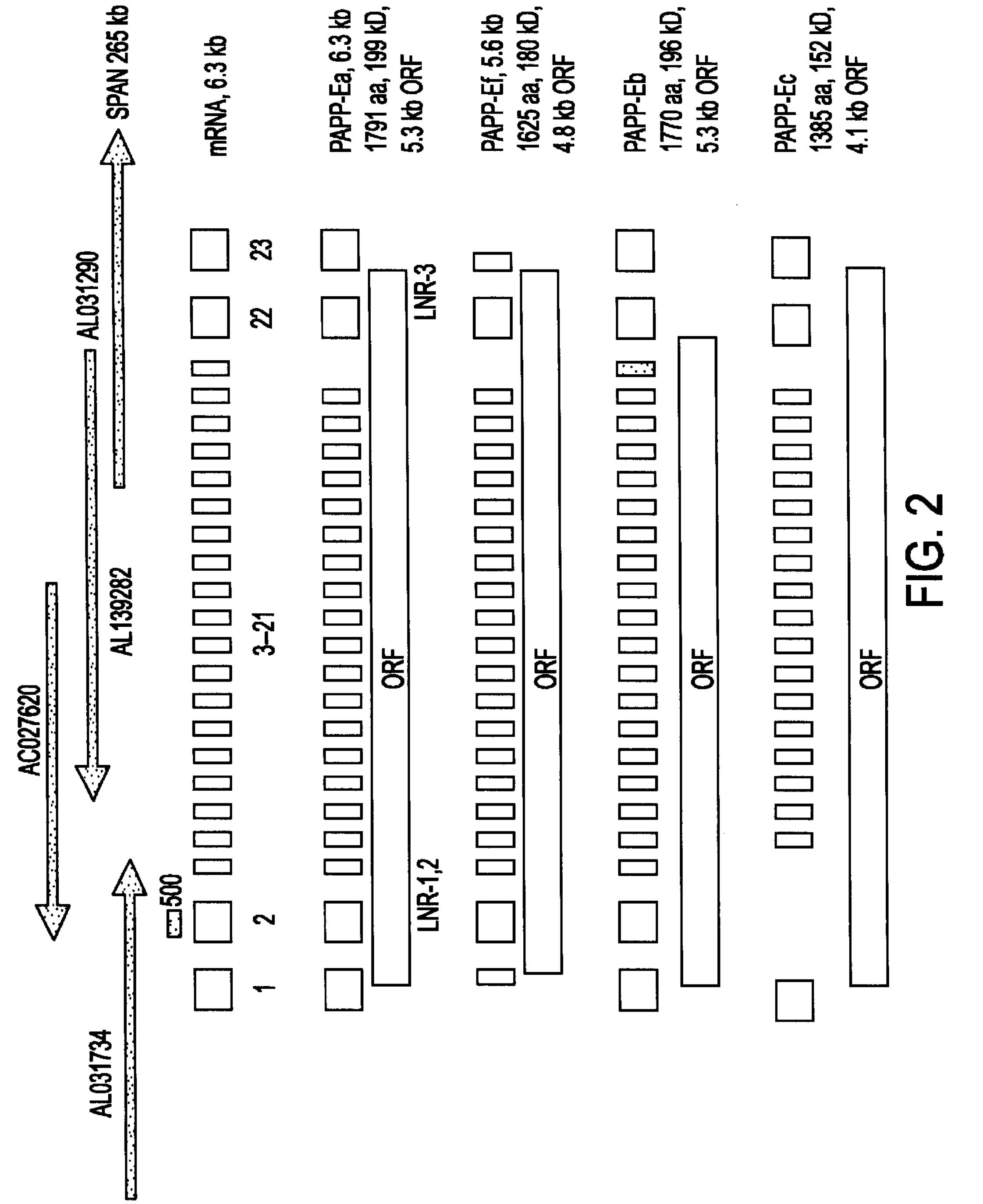
FIG. 2 is a map showing the genomic structure and alternative exon usage of three novel isoforms of human PAPP-E that are encoded at chromosome 1q24.1, termed PAPP-Ea, PAPP-Eb, and PAPP-Ec.

FIG. 2 shows the genomic organization of the three PAPP-E isoforms.

At the top is shown the four bacterial artificial chromosomes (BACs), with GenBank accession numbers, that span the PAPP-E locus. The genome-derived single-exon probe first used to demonstrate expression from this locus, as further described in commonly owned and copending provisional patent application No. 60/207,456, filed May 26, 2000, the disclosure of which is incorporated herein by reference in its entirety, is shown below the BACs and labeled "500". The 500 bp probe includes sequence drawn solely from exon two.

As shown in FIG. 2, PAPP-Ea, encoding a protein of 1791 amino acids, is the longest PAPP-E isoform, comprising exons 1–20, 22 and 23. Insertion of the 85 bp exon 21 in PAPP-Eb leads to a downstream frame shift and earlier termination, thus encoding a protein of 1770 amino acids. PAPP-Ec lacks exons 2, 3 and 21, encoding a protein of 1385 amino acids. Predicted molecular weights, prior to any post-translational modification, are 199 kD, 196 kD and 152 kD, respectively.

As further discussed in the examples herein, expression of PAPP-E was assessed using hybridization to genome-derived single exon microarrays and northern blot. Microarray analysis of the first two exons showed high level expression in placenta, and little expression in other tissues. This was confirmed by northern blot of 12 tissues (blood leukocyte, lung, placenta, small intestine, liver, kidney, spleen, thymus, colon, skeletal muscle, heart and brain).

As more fully described below, the present invention provides isolated nucleic acids that encode each of the novel isoforms of hPAPP-E, and fragments thereof. The invention further provides vectors for propagation and expression of the nucleic acids of the present invention, host cells comprising the nucleic acids and vectors of the present invention, proteins, protein fragments, and protein fusions of the present invention, and antibodies specific for all or any one of the isoforms. The invention provides pharmaceutical formulations of the nucleic acids, proteins, and antibodies of the present invention. The invention further provides transgenic cells and non-human organisms comprising human PAPP-E isoform nucleic acids, and transgenic cells and non-human organisms with targeted disruption of the endogenous orthologue of the human PAPP-E gene. The invention additionally provides diagnostic, investigational, and therapeutic methods based on the PAPP-E nucleic acids, proteins, and antibodies of the present invention.

Definitions

As used herein, "nucleic acid" includes polynucleotides having natural nucleotides in native 5'-3' phosphodiester linkage—e.g., DNA or RNA—as well as polynucleotides that have nonnatural nucleotide analogues, nonnative internucleoside bonds, or both, so long as the nonnatural polynucleotide is capable of sequence-discriminating basepairing under experimentally desired conditions. Unless otherwise specified, the term "nucleic acid" includes any topological conformation; the term thus explicitly comprehends single-stranded, double-stranded, partially duplexed, triplexed, hairpinned, circular, and padlocked conformations.

As used herein, an "isolated nucleic acid" is a nucleic acid molecule that exists in a physical form that is nonidentical to any nucleic acid molecule of identical sequence as found in nature; "isolated" does not require, although it does not prohibit, that the nucleic acid so described has itself been physically removed from its native environment.

For example, a nucleic acid can be said to be "isolated" when it includes nucleotides and/or internucleoside bonds not found in nature. When instead composed of natural nucleosides in phosphodiester linkage, a nucleic acid can be said to be "isolated" when it exists at a purity not found in nature, where purity can be adjudged with respect to the presence of nucleic acids of other sequence, with respect to the presence of proteins, with respect to the presence of lipids, or with respect the presence of any other component of a biological cell, or when the nucleic acid lacks sequence that flanks an otherwise identical sequence in an organism's genome, or when the nucleic acid possesses sequence not identically present in nature.

As so defined, "isolated nucleic acid" includes nucleic acids integrated into a host cell chromosome at a heterologous site, recombinant fusions of a native fragment to a heterologous sequence, recombinant vectors present as episomes or as integrated into a host cell chromosome.

As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

As used herein, the term "exon" refers to a nucleic acid sequence found in genomic DNA that is bioinformatically predicted and/or experimentally confirmed to contribute contiguous sequence to a mature mRNA transcript.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

As used herein, the term "microarray" and equivalent phrase "nucleic acid microarray" refer to a substrate-bound collection of plural nucleic acids, hybridization to each of the plurality of bound nucleic acids being separately detectable. The substrate can be solid or porous, planar or non-planar, unitary or distributed.

As so defined, the term "microarray" and phrase "nucleic acid microarray" include all the devices so called in Schena (ed.), *DNA Microarrays: A Practical Approach* (*Practical Approach Series*), Oxford University Press (1999) (ISBN: 0199637768); *Nature Genet.* 21(1)(suppl):1–60 (1999); and Schena (ed.), *Microarray Biochip: Tools and Technology,* Eaton Publishing Company/BioTechniques Books Division (2000) (ISBN: 1881299376), the disclosures of which are incorporated herein by reference in their entireties.

As so defined, the term "microarray" and phrase "nucleic acid microarray" also include substrate-bound collections of plural nucleic acids in which the plurality of nucleic acids are distributably disposed on a plurality of beads, rather than on a unitary planar substrate, as is described, inter alia, in Brenner et al., *Proc. Natl. Acad. Sci. USA* 97(4):166501670 (2000), the disclosure of which is incorporated herein by reference in its entirety; in such case, the term "microarray" and phrase "nucleic acid microarray" refer to the plurality of beads in aggregate.

As used herein with respect to solution phase hybridization, the term "probe", or equivalently, "nucleic acid probe" or "hybridization probe", refers to an isolated nucleic acid of known sequence that is, or is intended to be, detectably labeled. As used herein with respect to a nucleic acid microarray, the term "probe" (or equivalently "nucleic acid probe" or "hybridization probe") refers to the isolated nucleic acid that is, or is intended to be, bound to the substrate. In either such context, the term "target" refers to nucleic acid intended to be bound to probe by sequence complementarity.

As used herein, the expression "probe comprising SEQ ID NO:X", and variants thereof, intends a nucleic acid probe, at least a portion of which probe has either (i) the sequence directly as given in the referenced SEQ ID NO:X, or (ii) a sequence complementary to the sequence as given in the referenced SEQ ID NO:X, the choice as between sequence directly as given and complement thereof dictated by the requirement that the probe be complementary to the desired target.

As used herein, the phrases "expression of a probe" and "expression of an isolated nucleic acid" and their linguistic equivalents intend that the probe or, respectively, the isolated nucleic acid, can hybridize detectably under high stringency conditions to a sample of nucleic acids that derive from mRNA from a given source. For example, and by way of illustration only, expression of a probe in "liver" means that the probe can hybridize detectably under high stringency conditions to a sample of nucleic acids that derive from mRNA obtained from liver.

As used herein, the terms "protein", "polypeptide", and "peptide" are used interchangeably to refer to a naturally-occurring or synthetic polymer of amino acid monomers (residues), irrespective of length, where amino acid monomer here includes naturally-occurring amino acids, naturally-occurring amino acid structural variants, and synthetic non-naturally occurring analogs that are capable of participating in peptide bonds. The terms "protein", "polypeptide", and "peptide" explicitly permits of post-translational and post-synthetic modifications, such as glycosylation.

The term "oligopeptide" herein denotes a protein, polypeptide, or peptide having 25 or fewer monomeric subunits.

The phrases "isolated protein", "isolated polypeptide", "isolated peptide" and "isolated oligopeptide" refer to a protein (equally, to a polypeptide, peptide, or oligopeptide) that is nonidentical to any protein molecule of identical amino acid sequence as found in nature; "isolated" does not require, although it does not prohibit, that the protein so described has itself been physically removed from its native environment.

For example, a protein can be said to be "isolated" when it includes amino acid analogues or derivatives not found in nature, or includes linkages other than standard peptide bonds.

When instead composed entirely of natural amino acids linked by peptide bonds, a protein can be said to be "isolated" when it exists at a purity not found in nature—where purity can be adjudged with respect to the presence of proteins of other sequence, with respect to the presence of non-protein compounds, such as nucleic acids, lipids, or other components of a biological cell, or when it exists in a composition not found in nature, such as in a host cell that does not naturally express that protein.

A "purified protein" (equally, a purified polypeptide, peptide, or oligopeptide) is an isolated protein, as above described, present at a concentration of at least 95%, as measured on a mass basis with respect to total protein in a composition. A "substantially purified protein" (equally, a substantially purified polypeptide, peptide, or oligopeptide) is an isolated protein, as above described, present at a concentration of at least 70%, as measured on a mass basis with respect to total protein in a composition.

As used herein, the phrase "protein isoforms" refers to a plurality of proteins having nonidentical primary amino acid sequence but that share amino acid sequence encoded by at least one common exon.

As used herein, the phrase "alternative splicing" and its linguistic equivalents includes all types of RNA processing that lead to expression of plural protein isoforms from a single gene; accordingly, the phrase "splice variant(s)" and its linguistic equivalents embraces mRNAs transcribed from a given gene that, however processed, collectively encode plural protein isoforms. For example, and by way of illustration only, splice variants can include exon insertions, exon extensions, exon truncations, exon deletions, alternatives in the 5' untranslated region ("5' UT") and alternatives in the 3' untranslated region ("3' UT"). Such 3' alternatives include, for example, differences in the site of RNA transcript cleavage and site of poly(A) addition. See, e.g., Gautheret et al., *Genome Res.* 8:524–530 (1998).

As used herein, "orthologues" are separate occurrences of the same gene in multiple species. The separate occurrences have similar, albeit nonidentical, amino acid sequences, the degree of sequence similarity depending, in part, upon the evolutionary distance of the species from a common ancestor having the same gene.

As used herein, the term "paralogues" indicates separate occurrences of a gene in one species. The separate occurrences have similar, albeit nonidentical, amino acid sequences, the degree of sequence similarity depending, in part, upon the evolutionary distance from the gene duplication event giving rise to the separate occurrences.

As used herein, the term "homologues" is generic to "orthologues" and "paralogues".

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term include those produced by digestion with various proteases, those produced by chemical cleavage and/or chemical dissociation, and those produced recombinantly, so long as the fragment remains capable of specific binding to a target molecule. Among such fragments are Fab, Fab', Fv, $F(ab)'_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), *Intracellular Antibodies: Research and Disease Applications,* Springer-Verlag New York, Inc. (1998) (ISBN: 3540641513), the disclosure of which is incorporated herein by reference in its entirety).

As used herein, antibodies can be produced by any known technique, including harvest from cell culture of native B lymphocytes, harvest from culture of hybridomas, recombinant expression systems, and phage display.

As used herein, "antigen" refers to a ligand that can be bound by an antibody; an antigen need not itself be immunogenic. The portions of the antigen that make contact with the antibody are denominated "epitopes".

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample. Typically, the affinity or avidity of a specific binding reaction is least about $10^{-7}$ M, with specific binding reactions of greater specificity typically having affinity or avidity of at least $10^{-8}$ M to at least about $10^{-9}$ M.

As used herein, "molecular binding partners"—and equivalently, "specific binding partners"—refer to pairs of molecules, typically pairs of biomolecules, that exhibit specific binding. Nonlimiting examples are receptor and ligand, antibody and antigen, and biotin to any of avidin, streptavidin, neutrAvidin and captAvidin.

Nucleic Acid Molecules

In a first aspect, the invention provides isolated nucleic acids that encode three novel isoforms of the PAPP-E protein, variants having at least 90% sequence identity thereto, degenerate variants thereof, variants that encode PAPP-E proteins having conservative or moderately conservative substitutions, cross-hybridizing nucleic acids, and fragments thereof.

FIGS. 3A–3J, 4A–4I, and 5A–5G present the nucleotide sequences of PAPP-Ea, PAPP-Eb, and PAPP-Ec cDNA clones, with predicted amino acid translations; the nucleotide sequences are further presented, respectively, in SEQ ID NOs:1 (full length nucleotide sequence of PAPP-Ea cDNA), 3 (full length amino acid coding sequence of PAPP-Ea), 8 (nucleotide sequence encoding the entirety of PAPP-Eb), 10 (full length amino acid coding sequence of PAPP-Eb), 15 (nucleotide sequence encoding the entirety of PAPP-Ec), and 16 (full length amino acid coding sequence of PAPP-Ec).

Unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Unless otherwise indicated, nucleotide sequences of the isolated nucleic acids of the present invention were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA), or by reliance upon such sequence or upon genomic sequence prior-accessioned into a public database. Unless otherwise indicated, all amino acid sequences of the polypeptides of the present invention were predicted by translation from the nucleic acid sequences so determined.

As a consequence, any nucleic acid sequence presented herein may contain errors introduced by erroneous incorporation of nucleotides during polymerization, by erroroneous base calling by the automated sequencer (although such sequencing errors have been minimized for the nucleic acids directly determined herein, unless otherwise indicated, by the sequencing of each of the complementary strands of a duplex DNA), or by similar errors accessioned into the public database.

Accordingly, each of PAPP-Ea, PAPP-Eb, and PAPP-Ec cDNA clones described herein has been deposited in a public repository (American Type Culture Collection, Manassas, Va., USA) under accession numbers PTA-3399 (PAPP-Ea), PTA-3400 (PAPP-Eb), PTA-3401 (PAPP-Ec). Any errors in sequence reported herein can be determined and corrected by sequencing nucleic acids propagated from the deposited clones using standard techniques.

Single nucleotide polymorphisms (SNPS) occur frequently in eukaryotic genomes—more than 1.4 million SNPs have already identified in the human genome, International Human Genome Sequencing Consortium, *Nature* 409:860–921 (2001)—and the sequence determined from one individual of a species may differ from other allelic forms present within the population. Additionally, small deletions and insertions, rather than single nucleotide polymorphisms, are not uncommon in the general population, and often do not alter the function of the protein.

Accordingly, it is an aspect of the present invention to provide nucleic acids not only identical in sequence to those described with particularity herein, but also to provide isolated nucleic acids at least about 90% identical in sequence to those described with particularity herein, typically at least about 91%, 92%, 93%, 94%, or 95% identical in sequence to those described with particularity herein, usefully at least about 96%, 97%, 98%, or 99% identical in sequence to those described with particularity herein, and, most conservatively, at least about 99.5%, 99.6%, 99.7%, 99.8% and 99.9% identical in sequence to those described with particularity herein. These sequence variants can be naturally occurring or can result from human intervention, as by random or directed mutagenesis.

For purposes herein, percent identity of two nucleic acid sequences is determined using the procedure of Tatiana et al., "Blast 2 sequences—a new tool for comparing protein and nucleotide sequences", *FEMS Microbiol Lett.* 174:247–250 (1999), which procedure is effectuated by the computer program BLAST 2 SEQUENCES, available online at http://www.ncbi.nlm.nih.gov/blast/bl2seq/bl2.html.

To assess percent identity of nucleic acids, the BLASTN module of BLAST 2 SEQUENCES is used with default values of (i) reward for a match: 1; (ii) penalty for a mismatch: -2; (iii) open gap 5 and extension gap 2 penalties; (iv) gap X_dropoff 50 expect 10 word size 11 filter, and both sequences are entered in their entireties.

As is well known, the genetic code is degenerate, with each amino acid except methionine translated from a plurality of codons, thus permitting a plurality of nucleic acids of disparate sequence to encode the identical protein. As is also well known, codon choice for optimal expression varies from species to species. The isolated nucleic acids of the present invention being useful for expression of PAPP-E proteins and protein fragments, it is, therefore, another aspect of the present invention to provide isolated isolated nucleic acids that encode PAPP-E isoforms, and portions thereof, not only identical in sequence to those described with particularity herein, but degenerate variants thereof as well.

As is also well known, amino acid substitutions occur frequently among natural allelic variants, with conservative substitutions often occasioning only de minimis change in protein function.

Accordingly, it is an aspect of the present invention to provide nucleic acids not only identical in sequence to those described with particularity herein, but also to provide isolated nucleic acids that encode PAPP-E isoforms, and portions thereof, having conservative amino acid substitutions, and also to provide isolated nucleic acids that encode PAPP-E isoforms, and portions thereof, having moderately conservative amino acid substitutions.

Although there are a variety of metrics for calling conservative amino acid substitutions, based primarily on either observed changes among evolutionarily related proteins or on predicted chemical similarity, for purposes herein a conservative replacement is any change having a positive value in the PAM250 log-likelihood matrix reproduced herein below (see Gonnet et al., *Science* 256(5062):1443–5 (1992)):

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 2 | −1 | 0 | 0 | 0 | 0 | 0 | 0 | −1 | −1 | −1 | 0 | −1 | −2 | 0 | 1 | 1 | −4 | −2 | 0 |
| R | −1 | 5 | 0 | 0 | −2 | 2 | 0 | −1 | 1 | −2 | −2 | 3 | −2 | −3 | −1 | 0 | 0 | −2 | −2 | −2 |
| N | 0 | 0 | 4 | 2 | −2 | 1 | 1 | 0 | 1 | −3 | −3 | 1 | −2 | −3 | −1 | 1 | 0 | −4 | −1 | −2 |
| D | 0 | 0 | 2 | 5 | −3 | 1 | 3 | 0 | 0 | −4 | −4 | 0 | −3 | −4 | −1 | 0 | 0 | −5 | −3 | −3 |
| C | 0 | −2 | −2 | −3 | 12 | −2 | −3 | −2 | −1 | −1 | −2 | −3 | −1 | −1 | −3 | 0 | 0 | −1 | 0 | 0 |
| Q | 0 | 2 | 1 | 1 | −2 | 3 | 2 | −1 | 1 | −2 | −2 | 2 | −1 | −3 | 0 | 0 | 0 | −3 | −2 | −2 |
| E | 0 | 0 | 1 | 3 | −3 | 2 | 4 | −1 | 0 | −3 | −3 | 1 | −2 | −4 | 0 | 0 | 0 | −4 | −3 | −2 |
| G | 0 | −1 | 0 | 0 | −2 | −1 | −1 | 7 | −1 | −4 | −4 | −1 | −4 | −5 | −2 | 0 | −1 | −4 | −4 | −3 |
| H | −1 | 1 | 1 | 0 | −1 | 1 | 0 | −1 | 6 | −2 | −2 | 1 | −1 | 0 | −1 | 0 | 0 | −1 | 2 | −2 |
| I | −1 | −2 | −3 | −4 | −1 | −2 | −3 | −4 | −2 | 4 | 3 | −2 | 2 | 1 | −3 | −2 | −1 | −2 | −1 | 3 |
| L | −1 | −2 | −3 | −4 | −2 | −2 | −3 | −4 | −2 | 3 | 4 | −2 | 3 | 2 | −2 | −2 | −1 | −1 | 0 | 2 |
| K | 0 | 3 | 1 | 0 | −3 | 2 | 1 | −1 | 1 | −2 | −2 | 3 | −1 | −3 | −1 | 0 | 0 | −4 | −2 | −2 |
| M | −1 | −2 | −2 | −3 | −1 | −1 | −2 | −4 | −1 | 2 | 3 | −1 | 4 | 2 | −2 | −1 | −1 | −1 | 0 | 2 |
| F | −2 | −3 | −3 | −4 | −1 | −3 | −4 | −5 | 0 | 1 | 2 | −3 | 2 | 7 | −4 | −3 | −2 | 4 | 5 | 0 |
| P | 0 | −1 | −1 | −1 | −3 | 0 | 0 | −2 | −1 | −3 | −2 | −1 | −2 | −4 | 8 | 0 | 0 | −5 | −3 | −2 |
| S | 1 | 0 | 1 | 0 | 0 | 0 | 0 | 0 | 0 | −2 | −2 | 0 | −1 | −3 | 0 | 2 | 2 | −3 | −2 | −1 |
| T | 1 | 0 | 0 | 0 | 0 | 0 | 0 | −1 | 0 | −1 | −1 | 0 | −1 | −2 | 0 | 2 | 2 | −4 | −2 | 0 |
| W | −4 | −2 | −4 | −5 | −1 | −3 | −4 | −4 | −1 | −2 | −1 | −4 | −1 | 4 | −5 | −3 | −4 | 14 | 4 | −3 |
| Y | −2 | −2 | −1 | −3 | 0 | −2 | −3 | −4 | 2 | −1 | 0 | −2 | 0 | 5 | −3 | −2 | −2 | 4 | 8 | −1 |
| V | 0 | −2 | −2 | −3 | 0 | −2 | −2 | −3 | −2 | 3 | 2 | −2 | 2 | 0 | −2 | −1 | 0 | −3 | −1 | 3 |

For purposes herein, a "moderately conservative" replacement is any change having a nonnegative value in the PAM250 log-likelihood matrix reproduced herein above.

As is also well known in the art, relatedness of nucleic acids can also be characterized using a functional test, the ability of the two nucleic acids to base-pair to one another at defined hybridization stringencies.

It is, therefore, another aspect of the invention to provide isolated nucleic acids not only identical in sequence to those described with particularity herein, but also to provide isolated nucleic acids ("cross-hybridizing nucleic acids") that hybridize under high stringency conditions (as defined herein below) to all or to a portion of various of the isolated PAPP-E nucleic acids of the present invention ("reference nucleic acids"), as well as cross-hybridizing nucleic acids that hybridize under moderate stringency conditions to all or to a portion of various of the isolated PAPP-E nucleic acids of the present invention.

Such cross-hybridizing nucleic acids are useful, inter alia, as probes for, and to drive expression of, proteins related to the proteins of the present invention as alternative isoforms, homologues, paralogues, and orthologues. Particularly preferred orthologues are those from other primate species, such as chimpanzee, rhesus macaque, baboon, and gorilla, from rodents, such as rats, mice, guinea pigs, and from livestock, such as cow, pig, sheep, horse, goat.

For purposes herein, high stringency conditions are defined as aqueous hybridization (i.e., free of formamide) in 6×SSC (where 20×SSC contains 3.0 M NaCl and 0.3 M sodium citrate), 1% SDS at 65° C. for at least 8 hours, followed by one or more washes in 0.2×SSC, 0.1% SDS at 65° C. For purposes herein, moderate stringency conditions are defined as aqueous hybridization (i.e., free of formamide) in 6×SSC, 1% SDS at 65° C. for at least 8 hours, followed by one or more washes in 2×SSC, 0.1% SDS at room temperature.

The hybridizing portion of the reference nucleic acid is typically at least 15 nucleotides in length, often at least 17 nucleotides in length. Often, however, the hybridizing portion of the reference nucleic acid is at least 20 nucleotides in length, 25 nucleotides in length, and even 30 nucleotides, 35 nucleotides, 40 nucleotides, and 50 nucleotides in length. Of course, cross-hybridizing nucleic acids that hybridize to a larger portion of the reference nucleic acid—for example, to a portion of at least 50 nt, at least 100 nt, at least 150 nt, 200 nt, 250 nt, 300 nt, 350 nt, 400 nt, 450 nt, or 500 nt or more—or even to the entire length of the reference nucleic acid, are also useful.

The hybridizing portion of the cross-hybridizing nucleic acid is at least 75% identical in sequence to at least a portion of the reference nucleic acid. Typically, the hybridizing portion of the cross-hybridizing nucleic acid is at least 80%, often at least 85%, 86%, 87%, 88%, 89% or even at least 90% identical in sequence to at least a portion of the reference nucleic acid. Often, the hybridizing portion of the cross-hybridizing nucleic acid will be at least 91%, 92%, 93%, 94%, 95%, 96%, 97%, 98%, or 99% identical in sequence to at least a portion of the reference nucleic acid sequence. At times, the hybridizing portion of the cross-hybridizing nucleic acid will be at least 99.5% identical in sequence to at least a portion of the reference nucleic acid.

The invention also provides fragments of various of the isolated nucleic acids of the present invention.

By "fragments" of a reference nucleic acid is here intended isolated nucleic acids, however obtained, that have a nucleotide sequence identical to a portion of the reference nucleic acid sequence, which portion is at least 17 nucleotides and less than the entirety of the reference nucleic acid.

As so defined, "fragments" need not be obtained by physical fragmentation of the reference nucleic acid, although such provenance is not thereby precluded.

In theory, an oligonucleotide of 17 nucleotides is of sufficient length as to occur at random less frequently than once in the three gigabase human genome, and thus to provide a nucleic acid probe that can uniquely identify the reference sequence in a nucleic acid mixture of genomic complexity. As is well known, further specificity can be obtained by probing nucleic acid samples of subgenomic complexity, and/or by using plural fragments as short as 17 nucleotides in length collectively to prime amplification of nucleic acids, as, e.g., by polymerase chain reaction (PCR).

As further described herein below, nucleic acid fragments that encode at least 6 contiguous amino acids (i.e., fragments of 18 nucleotides or more) are useful in directing the expression or the synthesis of peptides that have utility in mapping the epitopes of the protein encoded by the reference nucleic acid. See, e.g., Geysen et al., "Use of peptide synthesis to probe viral antigens for epitopes to a resolution of a single amino acid," *Proc. Natl. Acad. Sci. USA* 81:3998–4002 (1984); and U.S. Pat. Nos. 4,708,871 and 5,595,915, the disclosures of which are incorporated herein by reference in their entireties.

As further described herein below, fragments that encode at least 8 contiguous amino acids (i.e., fragments of 24 nucleotides or more) are useful in directing the expression or the synthesis of peptides that have utility as immunogens. See, e.g., Lerner, "Tapping the immunological repertoire to produce antibodies of predetermined specificity," Nature 299:592–596 (1982); Shinnick et al., "Synthetic peptide immunogens as vaccines," *Annu. Rev. Microbiol.* 37:425–46 (1983); Sutcliffe et al., "Antibodies that react with predetermined sites on proteins," Science 219:660–6 (1983), the disclosures of which are incorporated herein by reference in their entireties.

The nucleic acid fragment of the present invention is thus at least 17 nucleotides in length, typically at least 18 nucleotides in length, and often at least 24 nucleotides in length. Often, the nucleic acid of the present invention is at least 25 nucleotides in length, and even 30 nucleotides, 35 nucleotides, 40 nucleotides, or 45 nucleotides in length. Of course, larger fragments having at least 50 nt, at least 100 nt, at least 150 nt, 200 nt, 250 nt, 300 nt, 350 nt, 400 nt, 450 nt, or 500 nt or more are also useful, and at times preferred.

Having been based upon the mining of genomic sequence, rather than upon surveillance of expressed message, the present invention further provides isolated genome-derived nucleic acids that include portions of the PAPP-E gene.

The invention particularly provides genome-derived single exon probes.

As further described in commonly owned and copending U.S. patent application Ser. Nos. 09/774,203, filed Jan. 29, 2001 and 09/632,366, filed Aug. 3, 2000, and provisional U.S. patent application Nos. 60/236,359, filed May 26, 2000 and 60/236,359, filed Sep. 27, 2000, the disclosures of which are incorporated herein by reference in their entireties, single exon probes comprise a portion of no more than one exon of the reference gene; the exonic portion is of sufficient length to hybridize under high stringency conditions to transcript-derived nucleic acids—such as mRNA or cDNA—that contain the exon or a portion thereof.

Genome-derived single exon probes typically further comprise, contiguous to a first end of the exon portion, a first intronic and/or intergenic sequence that is identically contiguous to the exon in the genome. Often, the genome-derived single exon probe further comprises, contiguous to a second end of the exonic portion, a second intronic and/or intergenic sequence that is identically contiguous to the exon in the genome.

The minimum length of genome-derived single exon probes is defined by the requirement that the exonic portion be of sufficient length to hybridize under high stringency conditions to transcript-derived nucleic acids. Accordingly, the exon portion is at least 17 nucleotides, typically at least 18 nucleotides, 20 nucleotides, 24 nucleotides, 25 nucleotides or even 30, 35, 40, 45, or 50 nucleotides in length, and can usefully include the entirety of the exon, up to 100 nt, 150 nt, 200 nt, 250 nt, 300 nt, 350 nt, 400 nt or even 500 nt or more in length.

The maximum length of genome-derived single exon probes is defined by the requirement that the probes contain portions of no more than one exon. Given variable spacing of exons through eukaryotic genomes, the maximum length is typically no more than 25 kb, often no more than 20 kb, 15 kb, 10 kb or 7.5 kb, or even no more than 5 kb, 4 kb, 3 kb, or even no more than about 2.5 kb in length.

Genome-derived single exon probes can usefully include at least a first terminal priming sequence not found in contiguity with the rest of the probe sequence in the genome, and often will contain a second terminal priming sequence not found in contiguity with the rest of the probe sequence in the genome.

The present invention also provides isolated genome-derived nucleic acids that include nucleic acid sequence elements that control transcription of the PAPP-E gene and its various isoforms.

The isolated nucleic acids of the present invention can be composed of natural nucleotides in native 5'-3' phosphodiester internucleoside linkage—e.g., DNA or RNA—or can contain any or all of nonnatural nucleotide analogues, nonnative internucleoside bonds, or post-synthesis modifications, either throughout the length of the nucleic acid or localized to one or more portions thereof. As is well known in the art, when the isolated nucleic acid is used as a hybridization probe, the range of such nonnatural analogues, nonnative internucleoside bonds, or post-synthesis modifications will be limited to those that permit sequence-discriminating basepairing of the resulting nucleic acid. When used to direct expression or RNA or protein in vitro or in vivo, the range of such nonnatural analogues, nonnative internucleoside bonds, or post-synthesis modifications will be limited to those that permit the nucleic acid to function properly as a polymerization substrate. When the isolated nucleic acid is used as a therapeutic agent, the range of such changes will be limited to those that do not confer toxicity upon the isolated nucleic acid.

For example, when desired to be used as probes, the isolated nucleic acids of the present invention can usefully include nucleotide analogues that incorporate labels that are directly detectable, such as radiolabels or fluorophores, or nucleotide analogues that incorporate labels that can be visualized in a subsequent reaction, such as biotin or various haptens.

Common radiolabeled analogues include those labeled with $^{33}P$, $^{32}P$, and $^{35}S$, such as $\alpha$-$^{32}P$-DATP, $\alpha$-$^{32}P$-dCTP, $\alpha$-$^{32}P$-dGTP, $\alpha$-$^{32}P$-dTTP, $\alpha$-$^{32}P$-3'dATP, $\alpha$-$^{32}P$-ATP, $\alpha$-$^{32}P$-CTP, $\alpha$-$^{32}P$-GTP, $\alpha$-$^{32}P$-UTP, $\alpha$-$^{35}S$-dATP, $\gamma$-$^{35}S$-GTP, $\gamma$-33P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6- dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA).

Protocols are available for custom synthesis of nucleotides having other fluorophores. Henegariu et al., "Custom Fluorecent-Nucleotide Synthesis as an Alternative Method for Nucleic Acid Labeling," *Nature Biotechnol.* 18:345–348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

As another example, when desired to be used for antisense inhibition of translation, the isolated nucleic acids of the present invention can usefully include altered, often nuclease-resistant, internucleoside bonds. See Hartmann et al. (eds.), *Manual of Antisense Methodology* (Perspectives in Antisense Science), Kluwer Law International (1999) (ISBN:079238539X); Stein et al. (eds.), *Applied Antisense Oligonucleotide Technology,* Wiley-Liss (cover (1998) (ISBN: 0471172790); Chadwick et al. (eds.), *Oligonucleotides as Therapeutic Agents—Symposium No.* 209, John Wiley & Son Ltd (1997) (ISBN: 0471972797), or for targeted gene correction, Gamper et al., *Nucl. Acids Res.* 28(21):4332–9 (2000), the disclosures of which are incorporated herein by reference in their entireties.

Modified oligonucleotide backbones often preferred when the nucleic acid is to be used for antisense purposes are, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, the disclosures of which are incorporated herein by reference in their entireties.

Preferred modified oligonucleotide backbones for antisense use that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, the disclosures of which are incorporated herein by reference in their entireties.

In other preferred oligonucleotide mimetics, both the sugar and the internucleoside linkage are replaced with novel groups, such as peptide nucleic acids (PNA).

In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages.

The uncharged nature of the PNA backbone provides PNA/DNA and PNA/RNA duplexes with a higher thermal stability than is found in DNA/DNA and DNA/RNA duplexes, resulting from the lack of charge repulsion between the PNA and DNA or RNA strand. In general, the Tm of a PNA/DNA or PNA/RNA duplex is 1° C. higher per base pair than the Tm of the corresponding DNA/DNA or DNA/RNA duplex (in 100 mM NaCl).

The neutral backbone also allows PNA to form stable DNA duplexes largely independent of salt concentration. At low ionic strength, PNA can be hybridized to a target sequence at temperatures that make DNA hybridization problematic or impossible. And unlike DNA/DNA duplex formation, PNA hybridization is possible in the absence of magnesium. Adjusting the ionic strength, therefore, is useful if competing DNA or RNA is present in the sample, or if the nucleic acid being probed contains a high level of secondary structure.

PNA also demonstrates greater specificity in binding to complementary DNA. A PNA/DNA mismatch is more destabilizing than DNA/DNA mismatch. A single mismatch in mixed a PNA/DNA 15-mer lowers the Tm by 8–20° C. (15° C. on average). In the corresponding DNA/DNA duplexes, a single mismatch lowers the Tm by 4–16° C. (11° C. on average). Because PNA probes can be significantly shorter than DNA probes, their specificity is greater.

Additionally, nucleases and proteases do not recognize the PNA polyamide backbone with nucleobase sidechains. As a result, PNA oligomers are resistant to degradation by enzymes, and the lifetime of these compounds is extended both in vivo and in vitro. In addition, PNA is stable over a wide pH range.

Because its backbone is formed from amide bonds, PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference; automated PNA synthesis is readily achievable on commercial synthesizers (see, e.g., "PNA User's Guide," Rev. 2, February 1998, Perseptive Biosystems Part No. 60138, Applied Biosystems, Inc., Foster City, Calif.).

PNA chemistry and applications are reviewed, inter alia, in Ray et al., *FASEB J.* 14(9):1041–60 (2000); Nielsen et al., *Pharmacol Toxicol.* 86(1):3–7 (2000); Larsen et al., *Biochim Biophys Acta.* 1489(1):159–66 (1999); Nielsen, *Curr. Opin. Struct. Biol.* 9(3):353–7 (1999), and Nielsen, *Curr. Opin. Biotechnol.* 10(1):71–5 (1999), the disclosures of which are incorporated herein by reference in their entireties.

Differences from nucleic acid compositions found in nature—e.g., nonnative bases, altered internucleoside linkages, post-synthesis modification—can be present throughout the length of the nucleic acid or can, instead, usefully be localized to discrete portions thereof. As an example of the latter, chimeric nucleic acids can be synthesized that have discrete DNA and RNA domains and demonstrated utility for targeted gene repair, as further described in U.S. Pat. Nos. 5,760,012 and 5,731,181, the disclosures of which are incorporated herein by reference in their entireties. As another example, chimeric nucleic acids comprising both DNA and PNA have been demonstrated to have utility in modified PCR reactions. See Misra et al., *Biochem.* 37: 1917–1925 (1998); see also Finn et al., *Nucl. Acids Res.* 24: 3357–3363 (1996), incorporated herein by reference.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utility are further described in Banér et al., *Curr. Opin. Biotechnol.* 12:11–15 (2001); Escude et al., Proc. Natl. Acad. Sci. USA 14;96(19):10603–7 (1999); Nilsson et al., *Science* 265(5181):2085–8 (1994), the disclosures of which are incorporated herein by reference in their entireties. Triplex and quadruplex conformations, and their utility, are reviewed in Praseuth et al., *Biochim. Biophys. Acta.* 1489(1):181–206 (1999); Fox, *Curr. Med. Chem.* 7(1):17–37 (2000); Kochetkova et al., *Methods Mol. Biol.* 130:189–201 (2000); Chan et al., *J. Mol. Med.* 75(4):267–82 (1997), the disclosures of which are incorporated herein by reference in their entireties.

The nucleic acids of the present invention can be detectably labeled. Commonly-used labels include radionuclides, such as $^{32}P$, $^{33}P$, $^{35}S$, $^{3}H$ (and for nmr detection, $^{13}C$ and $^{15}N$), haptens that can be detected by specific antibody or high affinity binding partner (such as avidin), and fluorophores.

As noted above, detectable labels can be incorporated by inclusion of labeled nucleotide analogues in the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach.

Analogues can also be incorporated during automated solid phase chemical synthesis.

As is well known, labels can also be incorporated after nucleic acid synthesis, with the 5' phosphate and 3' hydroxyl providing convenient sites for post-synthetic covalent attachment of detectable labels.

Various other post-synthetic approaches permit internal labeling of nucleic acids.

For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., *Genes, Chromosomes & Cancer,* Vol. 25, pp. 301–305 (1999); Jelsma et al., *J. NIH Res.* 5:82 (1994); Van Belkum et al., *BioTechniques* 16:148–153 (1994), incorporated herein by reference. As another example, nucleic acids can be labeled using a disulfide-containing linker (FastTag™ Reagent, Vector Laboratories, Inc., Burlingame, Calif., USA) that is photo- or thermally coupled to the target nucleic acid using aryl azide chemistry; after reduction, a free thiol is available for coupling to a hapten, fluorophore, sugar, affinity ligand, or other marker.

Multiple independent or interacting labels can be incorporated into the nucleic acids of the present invention. For example, both a fluorophore and a moiety that in proximity thereto acts to quench fluorescence can be included to report specific hybridization through release of fluorescence quenching, Tyagi et al., *Nature Biotechnol.* 14:303–308 (1996); Tyagi et al., *Nature Biotechnol.* 16, 49–53 (1998); Sokol et al., *Proc. Natl. Acad. Sci. USA* 95:11538–11543 (1998); Kostrikis et al., *Science* 279:1228–1229 (1998); Marras et al., *Genet. Anal.* 14:151–156 (1999); U.S. Pat. Nos. 5,846,726, 5,925,517, 5925517, or to report exonucleotidic excision, U.S. Pat. No. 5,538,848; Holland et al., *Proc. Natl. Acad. Sci. USA* 88:7276–7280 (1991); Heid et al., *Genome Res.* 6(10):986–94 (1996); Kuimelis et al., *Nucleic Acids Symp Ser.* (37):255–6 (1997); U.S. Pat. No. 5,723,591, the disclosures of which are incorporated herein by reference in their entireties.

So labeled, the isolated nucleic acids of the present invention can be used as probes, as further described below.

Nucleic acids of the present invention can also usefully be bound to a substrate. The substrate can porous or solid, planar or non-planar, unitary or distributed; the bond can be covalent or noncovalent. Bound to a substrate, nucleic acids of the present invention can be used as probes in their unlabeled state.

For example, the nucleic acids of the present invention can usefully be bound to a porous substrate, commonly a membrane, typically comprising nitrocellulose, nylon, or positively-charged derivatized nylon; so attached, the nucleic acids of the present invention can be used to detect PAPP-E nucleic acids present within a labeled nucleic acid sample, either a sample of genomic nucleic acids or a sample of transcript-derived nucleic acids, e.g. by reverse dot blot.

The nucleic acids of the present invention can also usefully be bound to a solid substrate, such as glass, although other solid materials, such as amorphous silicon, crystalline silicon, or plastics, can also be used. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof.

Typically, the solid substrate will be rectangular, although other shapes, particularly disks and even spheres, present certain advantages. Particularly advantageous alternatives to glass slides as support substrates for array of nucleic acids are optical discs, as described in Demers, "Spatially Addressable Combinatorial Chemical Arrays in CD-ROM Format," international patent publication WO 98/12559, incorporated herein by reference in its entirety.

The nucleic acids of the present invention can be attached covalently to a surface of the support substrate or applied to a derivatized surface in a chaotropic agent that facilitates denaturation and adherence by presumed noncovalent interactions, or some combination thereof.

The nucleic acids of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

The isolated nucleic acids of the present invention can be used as hybridization probes to detect, characterize, and quantify PAPP-E nucleic acids in, and isolate PAPP-E nucleic acids from, both genomic and transcript-derived nucleic acid samples. When free in solution, such probes are typically, but not invariably, detectably labeled; bound to a substrate, as in a microarray, such probes are typically, but not invariably unlabeled.

For example, the isolated nucleic acids of the present invention can be used as probes to detect and characterize gross alterations in the PAPP-E genomic locus, such as deletions, insertions, translocations, and duplications of the PAPP-E genomic locus through fluorescence in situ hybridization (FISH) to chromosome spreads. See, e.g., Andreeff et al. (eds.), *Introduction to Fluorescence In Situ Hybridization: Principles and Clinical Applications,* John Wiley & Sons (1999) (ISBN: 0471013455), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acids of the present invention can be used as probes to isolate genomic clones that include the nucleic acids of the present invention, which thereafter can be restriction mapped and sequenced to identify deletions, insertions, translocations, and substitutions (single nucleotide polymorphisms, SNPs) at the sequence level.

The isolated nucleic acids of the present invention can be also be used as probes to detect, characterize, and quantify PAPP-E nucleic acids in, and isolate PAPP-E nucleic acids from, transcript-derived nucleic acid samples.

For example, the isolated nucleic acids of the present invention can be used as hybridization probes to detect, characterize by length, and quantify PAPP-E mRNA by northern blot of total or poly-$A^+$-selected RNA samples. For example, the isolated nucleic acids of the present invention can be used as hybridization probes to detect, characterize by location, and quantify PAPP-E message by in situ hybridization to tissue sections (see, e.g., Schwarchzacher et al., *In Situ Hybridization,* Springer-Verlag New York (2000) (ISBN: 0387915966), the disclosure of which is incorporated herein by reference in its entirety). For example, the isolated nucleic acids of the present invention can be used as hybridization probes to measure the representation of PAPP-E clones in a cDNA library. For example, the isolated nucleic acids of the present invention can be used as hybridization probes to isolate PAPP-E nucleic acids from cDNA libraries, permitting sequence level characterization of PAPP-E messages, including identification of deletions, insertions, truncations—including deletions, insertions, and truncations of exons in alternatively spliced forms—and single nucleotide polymorphisms.

All of the aforementioned probe techniques are well within the skill in the art, and are described at greater length in standard texts such as Sambrook et al., *Molecular Cloning: A Laboratory Manual* ($3^{rd}$ ed.), Cold Spring Harbor Laboratory Press (2001) (ISBN: 0879695773); Ausubel et al. (eds.), *Short Protocols in Molecular Biology: A Compendium of Methods from Current Protocols in Molecular Biology* ($4^{th}$ ed.), John Wiley & Sons, 1999 (ISBN: 047132938X); and Walker et al. (eds.), *The Nucleic Acids Protocols Handbook,* Humana Press (2000) (ISBN: 0896034593), the disclosures of which are incorporated herein by reference in their entirety.

As described in the Examples herein below, the nucleic acids of the present invention can also be used to detect and quantify PAPP-E nucleic acids in transcript-derived samples—that is, to measure expression of the PAPP-E gene—when included in a microarray. Measurement of placental PAPP-E expression has particular utility in prenatal diagnosis, as further described in the Examples herein below.

As would be readily apparent to one of skill in the art, each PAPP-E nucleic acid probe—whether labeled, substrate-bound, or both—is thus currently available for use as a tool for measuring the level of PAPP-E expression in each of the tissues in which expression has already been confirmed, notably placenta. The utility is specific to the probe: under high stringency conditions, the probe reports the level of expression of message specifically containing that portion of the PAPP-E gene included within the probe.

Measuring tools are well known in many arts, not just in molecular biology, and are known to possess credible, specific, and substantial utility. For example, U.S. Pat. No. 6,016,191 describes and claims a tool for measuring characteristics of fluid flow in a hydrocarbon well; U.S. Pat. No. 6,042,549 describes and claims a device for measuring exercise intensity; U.S. Pat. No. 5,889,351 describes and claims a device for measuring viscosity and for measuring characteristics of a fluid; U.S. Pat. No. 5,570,694 describes and claims a device for measuring blood pressure; U.S. Pat. No. 5,930,143 describes and claims a device for measuring the dimensions of machine tools; U.S. Pat. No. 5,279,044 describes and claims a measuring device for determining an absolute position of a movable element; U.S. Pat. No. 5,186,042 describes and claims a device for measuring action force of a wheel; and U.S. Pat. No. 4,246,774 describes and claims a device for measuring the draft of smoking articles such as cigarettes.

As for tissues not yet demonstrated to express PAPP-E, the PAPP-E nucleic acid probes of the present invention are currently available as tools for surveying such tissues to detect the presence of PAPP-E nucleic acids.

Survey tools—i.e., tools for determining the presence and/or location of a desired object by search of an area—are well known in many arts, not just in molecular biology, and are known to possess credible, specific, and substantial utility. For example, U.S. Pat. No. 6,046,800 describes and claims a device for surveying an area for objects that move; U.S. Pat. No. 6,025,201 describes and claims an apparatus for locating and discriminating platelets from non-platelet particles or cells on a cell-by-cell basis in a whole blood sample; U.S. Pat. No. 5,990,689 describes and claims a device for detecting and locating anomalies in the electromagnetic protection of a system; U.S. Pat. No. 5,984,175 describes and claims a device for detecting and identifying wearable user identification units; U.S. Pat. No. 3,980,986 ("Oil well survey tool"), describes and claims a tool for finding the position of a drill bit working at the bottom of a borehole.

As noted above, the nucleic acid probes of the present invention are useful in constructing microarrays; the microarrays, in turn, are products of manufacture that are useful for measuring and for surveying gene expression.

When included on a microarray, each PAPP-E nucleic acid probe makes the microarray specifically useful for detecting that portion of the PAPP-E gene included within the probe, thus imparting upon the microarray device the ability to detect a signal where, absent such probe, it would have reported no signal. This utility makes each individual probe on such microarray akin to an antenna, circuit, firmware or software element included in an electronic apparatus, where the antenna, circuit, firmware or software element imparts upon the apparatus the ability newly and additionally to detect signal in a portion of the radio-frequency spectrum where previously it could not; such devices are known to have specific, substantial, and credible utility.

Changes in expression need not be observed for the measurement of expression to have utility.

For example, where gene expression analysis is used to assess toxicity of chemical agents on cells, the failure of the agent to change a gene's expression level is evidence that the drug likely does not affect the pathway of which the gene's expressed protein is a part. Analogously, where gene expression analysis is used to assess side effects of pharmacologic agents—whether in lead compound discovery or in subsequent screening of lead compound derivatives—the inability of the agent to alter a gene's expression level is evidence that the drug does not affect the pathway of which the gene's expressed protein is a part.

WO 99/58720, incorporated herein by reference in its entirety, provides methods for quantifying the relatedness of a first and second gene expression profile and for ordering the relatedness of a plurality of gene expression profiles, without regard to the identity or function of the genes whose expression is used in the calculation.

Gene expression analysis, including gene expression analysis by microarray hybridization, is, of course, principally a laboratory-based art. Devices and apparatus used principally in laboratories to facilitate laboratory research are well-established to possess specific, substantial, and credible utility. For example, U.S. Pat. No. 6,001,233 describes and claims a gel electrophoresis apparatus having a cam-activated clamp; for example, U.S. Pat. No. 6,051,831 describes and claims a high mass detector for use in time-of-flight mass spectrometers; for example, U.S. Pat. No. 5,824,269 describes and claims a flow cytometer—few gel electrophoresis apparatuses, TOF-MS devices, or flow cytometers are sold for consumer use.

Indeed, and in particular, nucleic acid microarrays, as devices intended for laboratory use in measuring gene expression, are well-established to have specific, substantial and credible utility. Thus, the microarrays of the present invention have at least the specific, substantial and credible utilities of the microarrays claimed as devices and articles of manufacture in the following U.S. patents, the disclosures of each of which is incorporated herein by reference: U.S. Pat. No. 5,445,934 ("Array of oligonucleotides on a solid substrate"); U.S. Pat. No. 5,744,305 ("Arrays of materials attached to a substrate"); and U.S. Pat. No. 6,004,752 ("Solid support with attached molecules").

Genome-derived single exon probes and genome-derived single exon probe microarrays have the additional utility, inter alia, of permitting high-throughput detection of splice variants of the nucleic acids of the present invention, as further described in copending and commonly owned U.S. patent application Ser. No. 09/632,366, filed Aug. 3, 2000, the disclosure of which is incorporated herein by reference in its entirety.

The isolated nucleic acids of the present invention can also be used to prime synthesis of nucleic acid, for purpose of either analysis or isolation, using mRNA, cDNA, or genomic DNA as template.

For use as primers, at least 17 contiguous nucleotides of the isolated nucleic acids of the present invention will be used. Often, at least 18, 19, or 20 contiguous nucleotides of the nucleic acids of the present invention will be used, and on occasion at least 20, 22, 24, or 25 contiguous nucleotides of the nucleic acids of the present invention will be used, and even 30 nucleotides or more of the nucleic acids of the present invention can be used to prime specific synthesis.

The nucleic acid primers of the present invention can be used, for example, to prime first strand cDNA synthesis on an mRNA template.

Such primer extension can be done directly to analyze the message. Alternatively, synthesis on an mRNA template can be done to produce first strand cDNA. The first strand cDNA can thereafter be used, inter alia, directly as a single-stranded probe, as above-described, as a template for sequencing—permitting identification of alterations, including deletions, insertions, and substitutions, both normal allelic variants and mutations associated with abnormal phenotypes—or as a template, either for second strand cDNA synthesis (e.g., as an antecedent to insertion into a cloning or expression vector), or for amplification.

The nucleic acid primers of the present invention can also be used, for example, to prime single base extension (SBE) for SNP detection (see, e.g., U.S. Pat. No. 6,004,744, the disclosure of which is incorporated herein by reference in its entirety).

As another example, the nucleic acid primers of the present invention can be used to prime amplification of PAPP-E nucleic acids, using transcript-derived or genomic DNA as template.

Primer-directed amplification methods are now well-established in the art. Methods for performing the polymerase chain reaction (PCR) are compiled, inter alia, in McPherson, *PCR* (*Basics: From Background to Bench*), Springer Verlag (2000) (ISBN: 0387916008); Innis et al. (eds.), *PCR Applications: Protocols for Functional Genomics,* Academic Press (1999) (ISBN: 0123721857); Gelfand et al. (eds.), *PCR Strategies,* Academic Press (1998) (ISBN: 0123721822); Newton et al., *PCR,* Springer-Verlag New York (1997) (ISBN: 0387915060); Burke (ed.), *PCR: Essential Techniques,* John Wiley & Son Ltd (1996) (ISBN: 047195697X); White (ed.), *PCR Cloning Protocols:* From Molecular Cloning to Genetic Engineering, Vol. 67, Humana Press (1996) (ISBN: 0896033430); McPherson et al. (eds.), *PCR 2: A Practical Approach,* Oxford University Press, Inc. (1995) (ISBN: 0199634254), the disclosures of which are incorporated herein by reference in their entireties. Methods for performing RT-PCR are collected, e.g., in Siebert et al. (eds.), *Gene Cloning and Analysis by RT-PCR,* Eaton Publishing Company/Bio Techniques Books Division, 1998 (ISBN: 1881299147); Siebert (ed.), *PCR Technique:RT-PCR,* Eaton Publishing Company/BioTechniques Books (1995) (ISBN:1881299139), the disclosure of which is incorporated herein by reference in its entirety.

Isothermal amplification approaches, such as rolling circle amplification, are also now well-described. See, e.g., Schweitzer et al., *Curr. Opin. Biotechnol.* 12(1):21–7 (2001); U.S. Pat. Nos. 5,854,033 and 5,714,320 and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3):225–32 (1998).

As further described below, nucleic acids of the present invention, inserted into vectors that flank the nucleic acid insert with a phage promoter, such as T7, T3, or SP6 promoter, can be used to drive in vitro expression of RNA complementary to either strand of the nucleic acid of the present invention. The RNA can be used, inter alia, as a single-stranded probe, to effect subtraction, or for in vitro translation.

As will be further discussed herein below, nucleic acids of the present invention that encode PAPP-E protein or portions thereof can be used, inter alia, to express the PAPP-E proteins or protein fragments, either alone, or as part of fusion proteins.

Expression can be from genomic nucleic acids of the present invention, or from transcript-derived nucleic acids of the present invention.

Where protein expression is effected from genomic DNA, expression will typically be effected in eukaryotic, typically mammalian, cells capable of splicing introns from the initial RNA transcript. Expression can be driven from episomal vectors, such as EBV-based vectors, or can be effected from genomic DNA integrated into a host cell chromosome. As will be more fully described below, where expression is from transcript-derived (or otherwise intron-less) nucleic acids of the present invention, expression can be effected in wide variety of prokaryotic or eukaryotic cells.

Expressed in vitro, the protein, protein fragment, or protein fusion can thereafter be isolated, to be used, inter alia, as a standard in immunoassays specific for the proteins, or protein isoforms, of the present invention; to be used as a therapeutic agent, e.g., to be administered as passive replacement therapy in individuals deficient in the proteins of the present invention, or to be administered as a vaccine; to be used for in vitro production of specific antibody, the antibody thereafter to be used, e.g., as an analytical reagent for detection and quantitation of the proteins of the present invention or to be used as an immunotherapeutic agent.

The isolated nucleic acids of the present invention can also be used to drive in vivo expression of the proteins of the present invention. In vivo expression can be driven from a vector—typically a viral vector, often a vector based upon a replication incompetent retrovirus, an adenovirus, or an adeno-associated virus (AAV)—for purpose of gene therapy. In vivo expression can also be driven from signals endogenous to the nucleic acid or from a vector, often a plasmid vector, for purpose of "naked" nucleic acid vaccination, as further described in U.S. Pat. Nos. 5,589,466; 5,679,647; 5,804,566; 5,830,877; 5,843,913; 5,880,104; 5,958,891; 5,985,847; 6,017,897; 6,110,898; 6,204,250, the disclosures of which are incorporated herein by reference in their entireties.

The nucleic acids of the present invention can also be used for antisense inhibition of translation. See Phillips (ed.), *Antisense Technology, Part B.* Methods in Enzymology Vol. 314, Academic Press, Inc. (1999) (ISBN: 012182215X); Phillips (ed.), *Antisense Technology, Part A,* Methods in Enzymology Vol. 313, Academic Press, Inc. (1999) (ISBN: 0121822141); Hartmann et al. (eds.), *Manual of Antisense Methodology* (Perspectives in Antisense Science), Kluwer Law International (1999) (ISBN:079238539X); Stein et al. (eds.), *Applied Antisense Oligonucleotide Technology,* Wiley-Liss (cover (1998) (ISBN: 0471172790); Agrawal et al. (eds.), *Antisense Research and Application,* Springer-Verlag New York, Inc. (1998) (ISBN: 3540638334); Lichtenstein et al. (eds.), *Antisense Technology: A Practical Approach,* Vol. 185, Oxford University Press, INC. (1998) (ISBN: 0199635838); Gibson (ed.), *Antisense and Ribozyme Methodology: Laboratory Companion,* Chapman & Hall (1997) (ISBN: 3826100794); Chadwick et al. (eds.), *Oligonucleotides as Therapeutic Agents—Symposium No.* 209, John Wiley & Son Ltd (1997) (ISBN: 0471972797), the disclosures of which are incorporated herein by reference in their entireties.

Nucleic acids of the present invention that encode full-length human PAPP-E protein isoforms, particularly cDNAs encoding full-length isoforms, have additional, well-recognized, utility as products of manufacture suitable for sale.

For example, cDNAs encoding full length human proteins have immediate, real world utility as commercial products suitable for sale. Invitrogen Corp. (Carlsbad, Calif., USA), through its Research Genetics subsidiary, sells full length human cDNAs cloned into one of a selection of expression vectors as GeneStorm® expression-ready clones; utility is specific for the gene, since each gene is capable of being ordered separately and has a distinct catalogue number, and utility is substantial, each clone selling for $650.00 US.

Nucleic acids of the present invention that include genomic regions encoding the human PAPP-E protein isoforms, or portions thereof, have yet further utilities.

For example, genomic nucleic acids of the present invention can be used as amplification substrates, e.g. for preparation of genome-derived single exon probes of the present invention, described above, and further described in copending and commonly-owned U.S. patent application Ser. Nos. 09/774,203, filed Jan. 29, 2001, and 09/632,366, filed Aug. 3, 2000 and commonly-owned and copending U.S. provisional patent application Nos. 60/207,456, filed May 26, 2000, 60/234,687, filed Sep. 21, 2000, 60/236,359, filed Sep. 27, 2000, the disclosures of which are incorporated herein by reference in their entireties.

As another example, genomic nucleic acids of the present invention can be integrated non-homologously into the genome of somatic cells, e.g. CHO cells, COS cells, or 293 cells, with or without amplification of the insertional locus, in order, e.g., to create stable cell lines capable of producing the proteins of the present invention.

As another example, more fully described herein below, genomic nucleic acids of the present invention can be integrated nonhomologously into embryonic stem (ES) cells to create transgenic non-human animals capable of producing the proteins of the present invention.

Genomic nucleic acids of the present invention can also be used to target homologous recombination to the human PAPP-E locus. See, e.g., U.S. Pat. Nos. 6,187,305; 6,204,061; 5,631,153; 5,627,059; 5,487,992; 5,464,764; 5,614,396; 5,527,695 and 6,063,630; and Kmiec et al. (eds.), *Gene Targeting Protocols,* Vol. 133, Humana Press (2000) (ISBN: 0896033600); Joyner (ed.), *Gene Targeting: A Practical Approach,* Oxford University Press, Inc. (2000) (ISBN: 0199637938); Sedivy et al., *Gene Targeting,* Oxford University Press (1998) (ISBN: 071677013X); Tymms et al.

(eds.), *Gene Knockout Protocols,* Humana Press (2000) (ISBN: 0896035727); Mak et al. (eds.), *The Gene Knockout FactsBook,* Vol. 2, Academic Press, Inc. (1998) (ISBN: 0124660444); Torres et al., *Laboratory Protocols for Conditional Gene Targeting,* Oxford University Press (1997) (ISBN: 019963677X); Vega (ed.), *Gene Targeting,* CRC Press, LLC (1994) (ISBN: 084938950X), the disclosures of which are incorporated herein by reference in their entireties.

Where the genomic region includes transcription regulatory elements, homologous recombination can be used to alter the expression of PAPP-E, both for purpose of in vitro production of PAPP-E protein from human cells, and for purpose of gene therapy. See, e.g., U.S. Pat. Nos. 5,981,214, 6,048,524; 5,272,071.

Fragments of the nucleic acids of the present invention smaller than those typically used for homologous recombination can also be used for targeted gene correction or alteration, possibly by cellular mechanisms different from those engaged during homologous recombination.

For example, partially duplexed RNA/DNA chimeras have been shown to have utility in targeted gene correction, U.S. Pat. Nos. 5,945,339, 5,888,983, 5,871,984, 5,795,972, 5,780,296, 5,760,012, 5,756,325, 5,731,181, the disclosures of which are incorporated herein by reference in their entireties. So too have small oligonucleotides fused to triplexing domains have been shown to have utility in targeted gene correction, Culver et al., "Correction of chromosomal point mutations in human cells with bifunctional oligonucleotides," *Nature Biotechnol.* 17(10):989–93 (1999), as have oligonucleotides having modified terminal bases or modified terminal internucleoside bonds, Gamper et al., *Nucl. Acids Res.* 28(21):4332–9 (2000), the disclosures of which are incorporated herein by reference.

Nucleic acids of the present invention can be obtained by using the labeled probes of the present invention to probe nucleic acid samples, such as genomic libraries, cDNA libraries, and mRNA samples, by standard techniques. Nucleic acids of the present invention can also be obtained by amplification, using the nucleic acid primers of the present invention, as further demonstrated in Example 1, herein below. Nucleic acids of the present invention of fewer than about 100 nt can also be synthesized chemically, typically by solid phase synthesis using commercially available automated synthesizers.

"Full Length" PAPP-E Isoform Nucleic Acids

In a first series of nucleic acid embodiments, the invention provides isolated nucleic acids that encode the entirety of a PAPP-E protein isoform. As discussed above, the "full-length" nucleic acids of the present invention can be used, inter alia, to express full length PAPP-Ea, PAPP-Eb, and PAPP-Ec isoforms. The full-length nucleic acids can also be used as nucleic acid probes; used as probes, the isolated nucleic acids of these embodiments will hybridize to all known isoforms of PAPP-E without discriminating thereamong.

In a first such embodiment, the invention provides an isolated nucleic acid comprising (i) the nucleotide sequence of the nucleic acid of ATCC deposit PTA-3399, (ii) the nucleotide sequence of SEQ ID NO:1, or (iii) the complement of (i) or (ii) . The ATCC deposit has, and SEQ ID NO:1 presents, the entire cDNA of PAPP-Ea, including the 5' untranslated (UT) region and 3' UT.

In a second embodiment, the invention provides an isolated nucleic acid comprising (i) the nucleotide sequence of SEQ ID NO:2, (ii) a degenerate variant of the nucleotide sequence of SEQ ID NO:2, or (iii) the complement (i) or (ii). SEQ ID NO:2 presents the open reading frame from SEQ ID NO:1.

In a third embodiment, the invention provides an isolated nucleic acid comprising (i) a nucleotide sequence that encodes a polypeptide with the amino acid sequence of SEQ ID NO:3 or (ii) the complement of a nucleotide sequence that encodes a polypeptide with the amino acid sequence of SEQ ID NO:3. SEQ ID NO:3 provides the 1791 amino acid sequence of PAPP-Ea.

In a fourth embodiment, the invention provides an isolated nucleic acid having a nucleotide sequence that (i) encodes a polypeptide having the sequence of SEQ ID NO:3, (ii) encodes a polypeptide having the sequence of SEQ ID NO:3 with conservative amino acid substitutions, or (iii) that is the complement of (i) or (ii), where SEQ ID NO:3 provides the 1791 amino acid sequence of PAPP-Ea.

In another embodiment, the invention provides an isolated nucleic acid comprising (i) the nucleotide sequence of the nucleic acid of ATCC deposit PTA-3400, (ii) the nucleotide sequence of SEQ ID NO:8 or (iii) the complement of (i) or (ii), where the referenced ATCC deposit has, and SEQ ID NO:8 provides, the nucleotide sequence of the entire PAPP-Eb ORF and portions of the 3' UT.

In another embodiment, the invention provides an isolated nucleic acid comprising (i) the nucleotide sequence of SEQ ID NO:9, (ii) a degenerate variant of the nucleotide sequence of SEQ ID NO:9, or (iii) the complement (i) or (ii), where SEQ ID NO:9 presents the nucleotide sequence of the open reading frame coding region of PAPP-Eb cDNA.

In a further embodiment, the invention provides an isolated nucleic acid comprising (i) a nucleotide sequence that encodes a polypeptide with the amino acid sequence of SEQ ID NO:10 or (ii) the complement of a nucleotide sequence that encodes a polypeptide with the amino acid sequence of SEQ ID NO:10, where SEQ ID NO:10 provides the full length amino acid coding sequence of PAPP-Eb. The invention further provides an isolated nucleic acid comprising a nucleotide sequence that (i) encodes a polypeptide having the sequence of SEQ ID NO:10, (ii) encodes a polypeptide having the sequence of SEQ ID NO:10 with conservative amino acid substitutions, or (iii) that is the complement of (i) or (ii).

The invention also provides isolated nucleic acids that encode the entirety of the PAPP-Ec isoform.

In a first such embodiment, the invention provides an isolated nucleic acid comprising (i) the nucleotide sequence of the nucleic acid of ATCC deposit PTA-3401, (ii) the nucleotide sequence of SEQ ID NO:15, (iii) a degenerate variant of SEQ ID NO:15, or (iv) the complement of (i) , (ii) or (iii) , where the referenced deposit has, and SEQ ID NO:15 provides, the nucleotide sequence of the PAPP-Ec open reading frame.

In another embodiment, the invention provides an isolated nucleic acid comprising (i) a nucleotide sequence that encodes a polypeptide with the amino acid sequence of SEQ ID NO:16 or (ii) the complement of a nucleotide sequence that encodes a polypeptide with the amino acid sequence of SEQ ID NO:16. SEQ ID NO:16 provides the entire amino acid sequence of PAPP-Ec. The invention further provides an isolated nucleic acid comprising a nucleotide sequence that (i) encodes a polypeptide having the sequence of SEQ ID NO:16, (ii) encodes a polypeptide having the sequence of SEQ ID NO:16 with conservative amino acid substitutions, or (iii) that is the complement of (i) or (ii).

Selected Partial Nucleic Acids

In a second series of nucleic acid embodiments, the invention provides isolated nucleic acids that encode select portions of one or more PAPP-E protein isoforms. As will be further discussed herein below, these "partial" nucleic acids can be used, inter alia, to express specific portions of the PAPP-E protein isoforms—both those portions that are shared by two or more isoforms, and those other portions that are unique to one or another of the isoforms—in vitro and in vivo. These "partial" nucleic acids can also be used, inter alia, as nucleic probes; used as probes, various of these embodiments are able to discriminate among the individual PAPP-E isoforms.

In a first such embodiment, the invention provides isolated nucleic acids comprising (i) the nucleotide sequence of SEQ ID NO:4 or (ii) the complement of the nucleotide sequence of SEQ ID NO:4, wherein the isolated nucleic acid is no more than about 100 kb in length, typically no more than about 75 kb in length, more typically no more than about 50 kb in length. SEQ ID NO:4 is the nucleotide sequence, drawn from both 5' UT and initial coding region, of the PAPP-Ea cDNA clone that is absent from the clone encoding the PAPP-Ef isoform. Often, the isolated nucleic acids of this embodiment are no more than about 25 kb in length, often no more than about 15 kb in length, and frequently no more than about 10 kb in length.

In another embodiment, the invention provides an isolated nucleic acid comprising (i) the nucleotide sequence of SEQ ID NO:5 or (ii) the complement of the nucleoide sequence of SEQ ID NO:5, wherein the isolated nucleic acid is no more than about 100 kb in length, typically no more than about 75 kb in length, more typically no more than about 50 kb in length. SEQ ID NO:5 presents the 5' untranslated region of the PAPP-Ea cDNA, which is not found in the PAPP-Ef cDNA. Often, the isolated nucleic acids of this embodiment are no more than about 25 kb in length, often no more than about 15 kb in length, and frequently no more than about 10 kb in length.

In another embodiment, the invention provides an isolated nucleic acid comprising (i) the nucleotide sequence of SEQ ID NO:6, (ii) a degenerate variant of the nucleotide sequence of SEQ ID NO:6, or (iii) the complement (i) or (ii), wherein the isolated nucleic acid is no more than about 100 kb in length, typically no more than about 75 kb in length, more typically no more than about 50 kb in length. SEQ ID NO:6 presents the nucleotide sequence of the 5' portion of the coding region of the PAPP-Ea cDNA not found in the PAPP-Ef cDNA. Often, the isolated nucleic acids of this embodiment are no more than about 25 kb in length, often no more than about 15 kb in length, and frequently no more than about 10 kb in length.

In yet another embodiment, the invention provides isolated nucleic acids comprising (i) a nucleotide sequence that encodes a polypeptide with the amino acid sequence of SEQ ID NO:7 or (ii) the complement of a nucleotide sequence that encodes a polypeptide with the amino acid sequence of SEQ ID NO:7, wherein the isolated nucleic acid is no more than about 100 kb in length, typically no more than about 75 kb in length, more typically no more than about 50 kb in length. SEQ ID NO:7 is the amino acid sequence of the N-terminal coding region of the PAPP-Ea isoform absent from the PAPP-Ef cDNA. Often, the isolated nucleic acids of this embodiment are no more than about 25 kb in length, often no more than about 15 kb in length, and frequently no more than about 10 kb in length.

In yet a further embodiment, the invention provides an isolated nucleic acid comprising a nucleotide sequence (i) that encodes a polypeptide having the sequence of SEQ ID NO:7, (ii) that encodes a polypeptide having the sequence of SEQ ID NO:7 with conservative amino acid substitutions, or (iii) the complement of (i) or (ii), wherein the isolated nucleic acid is no more than about 100 kb in length, typically no more than about 75 kb in length, more typically no more than about 50 kb in length. Often, the isolated nucleic acids of this embodiment are no more than about 25 kb in length, often no more than about 15 kb in length, and frequently no more than about 10 kb in length.

In a further embodiment, the invention provides an isolated nucleic acid comprising (i) the nucleotide sequence of SEQ ID NO:11, (ii) a degenerate variant of SEQ ID NO:11, or (iii) the complement of (i) or (ii), wherein the isolated nucleic acid is no more than about 100 kb in length, typically no more than about 75 kb in length, more typically no more than about 50 kb length. Often, the isolated nucleic acids of this embodiment are no more than about 25 kb in length, often no more than about 15 kb in length, and frequently no more than about 10 kb in length. SEQ ID NO:11 provides the portion of the PAPP-E cDNA sequence drawn from exon 21, which appears uniquely in the PAPP-Eb isoform; probes that include SEQ ID NO:11 and no other portions of the PAPP-E gene will be useful in discriminating expression of the PAPP-Eb isoform.

In another embodiment, the invention provides an isolated nucleic acid comprising (i) a nucleotide sequence that encodes SEQ ID NO:12 or (ii) the complement of a nucleotide sequence that encodes SEQ ID NO:12, wherein the isolated nucleic acid is no more than about 100 kb in length, typically no more than about 75 kb in length, frequently no more than about 50 kb in length. SEQ ID NO:12 provides the amino acid sequence encoded by exon 21 that is uniquely present in the PAPP-Eb isoform (aa 1735–1762). Often, the isolated nucleic acids of this embodiment are no more than about 25 kb in length, often no more than about 15 kb in length, and frequently no more than about 10 kb in length.

In another embodiment, the invention provides an isolated nucleic acid comprising (i) a nucleotide sequence that encodes SEQ ID NO:12, (ii) a nucleotide sequence that encodes SEQ ID NO:12 with conservative substititions, or (iii) the complement of (i) or (ii), wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In a further embodiment, the invention provides an isolated nucleic acid comprising (i) a nucleotide sequence that encodes a polypeptide with the amino acid sequence of SEQ ID NO:14 or (ii) the complement of a nucleotide sequence that encodes a polypeptide with the amino acid sequence of SEQ ID NO:14, wherein the isolated nucleic acid is no more than about 100 kb in length, typically no more than about 75 kb in length, often no more than about 50 kb in length. SEQ ID NO:14 is the amino acid sequence unique to the PAPP-Eb isoform, both that encoded by exon 21 and that caused by subsequent frameshift (aa 1735–1770). Often, the isolated nucleic acids of this embodiment are no more than about 25 kb in length, often no more than about 15 kb in length, and frequently no more than about 10 kb in length.

In yet another embodiment, the invention provides isolated nucleic acids comprising a nucleotide sequence (i) that encodes a polypeptide having the sequence of SEQ ID NO:14, (ii) that encodes a polypeptide having the sequence of SEQ ID NO:14 with conservative amino acid substitutions, or (iii) the complement of (i) or (ii), wherein the isolated nucleic acid is no more than about 100 kb in length, typically no more than about 75 kb in length, often no more than about 50 kb in length. Often, the isolated nucleic acids of this embodiment are no more than about 25 kb in length, often no more than about 15 kb in length, and frequently no more than about 10 kb in length.

In another embodiment, the invention provides an isolated nucleic acid comprising (i) the nucleotide sequence of SEQ ID NO:17, (ii) a degenerate variant of SEQ ID NO:17, or (iii) the complement of (i) or (ii). SEQ ID NO:17 provides the nucleotide sequence surrounding the junction of exons 1 and 4, a junction unique to PAPP-Ec among the PAPP-E isoforms.

In another embodiment, the invention provides isolated nucleic acids comprising (i) a nucleotide sequence that encodes SEQ ID NO:18, (ii) a nucleotide sequence that encodes SEQ ID NO:18 with conservative amino acid substititions, or (iii) the complement of (i) or (ii). SEQ ID NO:18 presents the 20 amino acid sequence centered at the junction between exons 1 and 4, a sequence unique to PAPP-Ec among the PAPP-E isoforms.

Cross-Hybridizing Nucleic Acids

In another series of nucleic acid embodiments, the invention provides isolated nucleic acids that hybridize to various of the PAPP-E nucleic acids of the present invention. These cross-hybridizing nucleic acids can be used, inter alia, as probes for, and to drive expression of, proteins that are related to the PAPP-E isoforms of the present invention as further isoforms, homologues, paralogues, or orthologues.

In a first such embodiment, the invention provides an isolated nucleic acid comprising a sequence that hybridizes under high stringency conditions to a probe the nucleotide sequence of which consists of SEQ ID NO:4 or the complement of SEQ ID NO:4, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In a further embodiment, the invention provides an isolated nucleic acid comprising a sequence that hybridizes under moderate stringency conditions to a probe the nucleotide sequence of which consists of SEQ ID NO:4 or the complement of SEQ ID NO:4, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In another embodiment, the invention provides an isolated nucleic acid comprising a sequence that hybridizes under high stringency conditions to a hybridization probe that consists of a nucleotide sequence that encodes SEQ ID NO:5, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In yet another embodiment, the invention provides an isolated nucleic acid comprising a sequence that hybridizes under moderate stringency conditions to a hybridization probe consisting of a nucleotide sequence that encodes SEQ ID NO:5, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In an additional embodiment, the invention provides an isolated nucleic acid comprising a sequence that hybridizes under high stringency conditions to a hybridization probe the nucleotide sequence of which consists of SEQ ID NO:6 or the complement of SEQ ID NO:6, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

The invention further provides an isolated nucleic acid comprising a sequence that hybridizes under moderate stringency conditions to a hybridization probe the nucleotide sequence of which consists of SEQ ID NO:6 or the complement of SEQ ID NO:6, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

The invention also provides an isolated nucleic acid comprising a sequence that hybridizes under high stringency conditions to a hybridization probe the nucleotide sequence of which (i) encodes a polypeptide having the sequence of SEQ ID NO:7, (ii) encodes a polypeptide having the sequence of SEQ ID NO:7 with conservative amino acid substitutions, or (iii) is the complement of (i) or (ii), wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

Additionally, the invention provides an isolated nucleic acid comprising a sequence that hybridizes under moderate stringency conditions to a hybridization probe the nucleotide sequence of which (i) encodes a polypeptide having the sequence of SEQ ID NO:7, (ii) encodes a polypeptide having the sequence of SEQ ID NO:7 with conservative amino acid substitutions, or (iii) is the complement of (i) or (ii), wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In a further embodiment, the invention provides an isolated nucleic acid comprising a sequence that hybridizes under high stringency conditions to a probe the nucleotide sequence of which consists of SEQ ID NO:11or the complement of SEQ ID NO:11, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In another embodiment, the invention provides an isolated nucleic acid comprising a sequence that hybridizes under moderate stringency conditions to a probe the nucleotide sequence of which consists of SEQ ID NO:11 or the complement of SEQ ID NO:11, wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In a further embodiment, the invention provides an isolated nucleic acid comprising a sequence that hybridizes under high stringency conditions to a hybridization probe the nucleotide sequence of which (i) encodes a polypeptide having the sequence of SEQ ID NO:12, (ii) encodes a polypeptide having the sequence of SEQ ID NO:12 with conservative amino acid substitutions, or (iii) is the complement of (i) or (ii), wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

In a yet further embodiment, the invention provides an isolated nucleic acid comprising a sequence that hybridizes under moderate stringency conditions to a hybridization probe the nucleotide sequence of which (i) encodes a polypeptide having the sequence of SEQ ID NO:12, (ii) encodes a polypeptide having the sequence of SEQ ID NO:12 with conservative amino acid substitutions, or (iii) is the complement of (i) or (ii), wherein the isolated nucleic acid is no more than about 100 kb in length, typically no more than about 75 kb in length, and often no more than about 50 kb in length. Often, the isolated nucleic acids of this embodiment are no more than about 25 kb in length, often no more than about 15 kb in length, and frequently no more than about 10 kb in length.

Preferred Nucleic Acids

Particularly preferred among the above-described nucleic acids are those that are expressed, or the complement of which are expressed, in placental tissue, preferably at a level greater than that in HeLa cells, typically at a level at least two-fold that in HeLa cells, often at least three-fold, four-fold, or even five-fold that in HeLa cells.

Also particularly preferred among the above-described nucleic acids are those that encode, or the complement of which encode, a polypeptide having metalloproteinase activity, particularly those having cleavage specificity for an IGF binding protein.

Other preferred embodiments of the nucleic acids above-described are those that encode, or the complement of which encode, a polypeptide having any or all of (i) at least one zinc binding domain, (ii) at least one notch domain, and (iii) tandemly repeated SCR domains.

Nucleic Acid Fragments

In another series of nucleic acid embodiments, the invention provides fragments of various of the isolated nucleic acids of the present invention which prove useful, inter alia, as nucleic acid probes, as amplification primers, and to direct expression or synthesis of epitopic or immunogenic protein fragments.

In a first such embodiment, the invention provides an isolated nucleic acid comprising at least 17 nucleotides, 18 nucleotides, 20 nucleotides, 24 nucleotides, or 25 nucleotides of (i) SEQ ID NO:4 or (ii) the complement of SEQ ID NO:4, wherein the isolated nucleic acid is no more than about 100 kb in length, typically no more than about 75 kb in length, more typically no more than about 50 kb in length. SEQ ID NO:4 is the nucleotide sequence of the 5' region of the PAPP-Ea cDNA absent from the PAPP-Ef cDNA; accordingly, these fragments can be used to identify PAPP-E isoforms other than PAPP-Ef. Often, the isolated nucleic acids of this embodiment are no more than about 25 kb in length, often no more than about 15 kb in length, and frequently no more than about 10 kb in length.

In another embodiment, the invention provides an isolated nucleic acid comprising at least 17 nucleotides, 18 nucleotides, 20 nucleotides, 24 nucleotides, or 25 nucleotides of (i) SEQ ID NO:5 or (ii) the complement of SEQ ID NO:5, wherein the isolated nucleic acid is no more than about 100 kb in length, typically no more than about 75 kb in length, more typically no more than about 50 kb in length. SEQ ID NO:5 is the nucleotide sequence of the 5' UT of the PAPP-Ea cDNA, which is absent from the PAPP-Ef cDNA; accordingly, these fragments can be used to identify PAPP-E isoforms other than PAPP-Ef. Often, the isolated nucleic acids of this embodiment are no more than about 25 kb in length, often no more than about 15 kb in length, and frequently no more than about 10 kb in length.

In a yet further embodiment, the invention provides an isolated nucleic acid comprising at least at least 17 nucleotides, 18 nucleotides, 20 nucleotides, 24 nucleotides, or 25 nucleotides of (i) SEQ ID NO:6, (ii) a degenerate variant of SEQ ID NO:6, or (ii) the complement of (i) or (ii), wherein the isolated nucleic acid is no more than about 100 kb in length, typically no more than about 75 kb in length, more typically no more than about 50 kb in length. SEQ ID NO:6 is the nucleotide sequence encoding the N-terminal amino acids absent from the PAPP-Ef isoform; accordingly, these fragments can be used to identify PAPP-E isoforms other than PAPP-Ef. Often, the isolated nucleic acids of this embodiment are no more than about 25 kb in length, often no more than about 15 kb in length, and frequently no more than about 10 kb in length.

In another embodiment, the invention provides an isolated nucleic acid comprising a nucleotide sequence that (i) encodes a polypeptide having the sequence of at least 8 contiguous amino acids of SEQ ID NO:7, (ii) encodes a polypeptide having the sequence of at least 8 contiguous amino acids of SEQ ID NO:7 with conservative amino acid substitutions, or (iii) is the complement of (i) or (ii), wherein the isolated nucleic acid is no more than about 100 kb in length, typically no more than about 75 kb in length, more typically no more than about 50 kb in length. SEQ ID NO:7 is the amino acid sequence of the 19 N-terminal amino acids absent from the PAPP-Ef isoform. Often, the isolated nucleic acids of this embodiment are no more than about 25 kb in length, often no more than about 15 kb in length, and frequently no more than about 10 kb in length.

In a further embodiment, the invention provides an isolated nucleic acid comprising at least 17 nucleotides, 18 nucleotides, 20 nucleotides, 24 nucleotides, or 25 nucleotides of (i) SEQ ID NO:11, (ii) a degenerate variant of SEQ ID NO:11, or (iii) the complement of (i) or (ii), wherein the isolated nucleic acid is no more than about 100 kb in length, typically no more than about 75 kb in length, more typically no more than about 50 kb in length. Often, the isolated nucleic acids of this embodiment are no more than about 25 kb in length, often no more than about 15 kb in length, and frequently no more than about 10 kb in length.

The invention also provides an isolated nucleic acid comprising (i) a nucleotide sequence that encodes a peptide of at least 8 contiguous amino acids of SEQ ID NO:12, or (ii) the complement of a nucleotide sequence that encodes a peptide of at least 8 contiguous amino acids of SEQ ID NO:12, wherein the isolated nucleic acid is no more than about 100 kb in length, typically no more than about 75 kb in length, more typically no more than about 50 kb in length. Often, the isolated nucleic acids of this embodiment are no more than about 25 kb in length, often no more than about 15 kb in length, and frequently no more than about 10 kb in length.

The invention also provides an isolated nucleic acid comprising a nucleotide sequence that (i) encodes a polypeptide having the sequence of at least 8 contiguous amino acids of SEQ ID NO:12, (ii) encodes a polypeptide having the sequence of at least 8 contiguous amino acids of SEQ ID NO:12 with conservative amino acid substitutions, or (iii) is the complement of (i) or (ii).

The structural chemical formulas of representative 17-mer nucleic acid fragments of the present invention as above-described are provided as SEQ ID NOs:[x–x'] and [z–z'] in the attached Sequence Listing, incorporated herein by reference in its entirety. The structural chemical formulas of representative 25-mer nucleic acid fragments of the present invention as above-described are reduced to drawings as SEQ ID Nos: [y–y'] and [*–*'] in the attached Sequence Listing, incorporated herein by reference in its entirety.

Single Exon Probes

The invention further provides genome-derived single exon probes having portions of no more than one exon of the PAPP-E gene. As further described in commonly owned and copending U.S. patent application Ser. No. 09/632,366 ("Methods and Apparatus for High Throughput Detection and Characterization of alternatively Spliced Genes"), the disclosure of which is incorporated herein by reference in its entirety, such single exon probes have particular utility in identifying and characterizing splice variants. In particular, such single exon probes are useful for identifying and discriminating the expression of PAPP-Ea, PAPP-Eb, and PAPP-Ec isoforms.

In a first embodiment, the invention provides an isolated nucleic acid comprising a nucleotide sequence of no more than one portion of SEQ ID NOs:19 to 41 or the complement of SEQ ID NOs:19 to 41, wherein the portion comprises at least 17 contiguous nucleotides, 18 contiguous nucleotides, 20 contiguous nucleotides, 24 contiguous nucleotides, 25 contiguous nucleotides, or 50 contiguous nucleotides of any one of SEQ ID NOs:19 to 41, or their complement, and hybridizes under high stringency conditions to a nucleic acid expressed in human placenta. In a further embodiment, the exonic portion comprises the entirety of the referenced SEQ ID NO: or its complement.

In other embodiments, the invention provides isolated single exon probes having the nucleotide sequence of any one of SEQ ID NOs:42–65.

In a particular embodiment, the invention provides a single exon probe having a portion of SEQ ID NO:39. SEQ ID NO:39 presents the exon (exon 21) that is unique to the PAPP-Eb isoform; single exon probes, including genome-derived single exon probes, having a portion drawn from exon 21 can be used to identify and or measure expression of PAPP-Eb.

Transcription Control Nucleic Acids

In another aspect, the present invention provides genome-derived isolated nucleic acids that include nucleic acid sequence elements that control transcription of the PAPP-E gene and its various isoforms. These nucleic acids can be used, inter alia, to drive expression of heterologous coding regions in recombinant constructs, thus conferring upon such hetereologous coding regions the expression pattern of the native PAPP-E gene. These nucleic acids can also be used, conversely, to target heterologous transcription control elements to the PAPP-E genomic locus, altering the expression pattern of the PAPP-E gene itself.

In a first such embodiment, the invention provides an isolated nucleic acid comprising the nucleotide sequence of SEQ ID NO:65 or its complement, wherein the isolated nucleic acid is no more than about 100 kb in length, typically no more than about 75 kb in length, more typically no more than about 50 kb in length. Often, the isolated nucleic acids of this embodiment are no more than about 25 kb in length, often no more than about 15 kb in length, and frequently no more than about 10 kb in length.

In another embodiment, the invention provides an isolated nucleic acid comprising at least 17, 18, 20, 24, or 25 nucleotides of the sequence of SEQ ID NO:65 or its complement, wherein wherein the isolated nucleic acid is no more than about 100 kb in length, typically no more than about 75 kb in length, more typically no more than about 50 kb in length. Often, the isolated nucleic acids of this embodiment are no more than about 25 kb in length, often no more than about 15 kb in length, and frequently no more than about 10 kb in length.

Vectors and Host Cells

In another aspect, the present invention provides vectors that comprise one or more of the isolated nucleic acids of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides. Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd 1998 (ISBN: 047196266X); Jones et al. (eds.), *Vectors: Expression Systems: Essential Techniques* (Essential Techniques Series), John Wiley & Son Ltd, 1998 (ISBN:0471962678); Gacesa et al., *Vectors: Essential Data,* John Wiley & Sons, 1995 (ISBN: 0471948411); Cid-Arregui (eds.), *Viral Vectors: Basic Science and Gene Therapy,* Eaton Publishing Co., 2000 (ISBN: 188129935X); Sambrook et al., *Molecular Cloning: A Laboratory Manual* (3rd ed.), Cold Spring Harbor Laboratory Press, 2001 (ISBN: 0879695773); Ausubel et al. (eds.), *Short Protocols in Molecular Biology: A Compendium of Methods from Current Protocols in Molecular Biology* (4th ed.), John Wiley & Sons, 1999 (ISBN: 047132938X), the disclosures of which are incorporated herein by reference in their entireties. Furthermore, an enormous variety of vectors are available commercially. Use of existing vectors and modifications thereof being well within the skill in the art, only basic features need be described here.

Typically, vectors are derived from virus, plasmid, prokaryotic or eukaryotic chromosomal elements, or some combination thereof, and include at least one origin of replication, at least one site for insertion of heterologous nucleic acid, typically in the form of a polylinker with multiple, tightly clustered, single cutting restriction sites, and at least one selectable marker, although some integrative vectors will lack an origin that is functional in the host to be chromosomally modified, and some vectors will lack selectable markers. Vectors of the present invention will further include at least one nucleic acid of the present invention inserted into the vector in at least one location.

Where present, the origin of replication and selectable markers are chosen based upon the desired host cell or host cells; the host cells, in turn, are selected based upon the desired application.

For example, prokaryotic cells, typically *E. coli,* are typically chosen for cloning. In such case, vector replication is predicated on the replication strategies of coliform-infecting phage—such as phage lambda, M13, T7, T3 and P1—or on the replication origin of autonomously replicating episomes, notably the ColE1 plasmid and later derivatives, including pBR322 and the pUC series plasmids. Where *E. coli* is used as host, selectable markers are, analogously, chosen for selectivity in gram negative bacteria: e.g., typical markers confer resistance to antibiotics, such as ampicillin, tetracycline, chlorampenicol, kanamycin, streptomycin, zeocin; auxotrophic markers can also be used.

As another example, yeast cells, typically *S. cerevisiae,* are chosen, inter alia, for eukaryotic genetic studies, due to the ease of targeting genetic changes by homologous recombination and to the ready ability to complement genetic defects using recombinantly expressed proteins, for identification of interacting protein components, e.g. through use of a two-hybrid system, and for protein expression. Vectors of the present invention for use in yeast will typically, but not invariably, contain an origin of replication suitable for use in yeast and a selectable marker that is functional in yeast.

Integrative YIp vectors do not replicate autonomously, but integrate, typically in single copy, into the yeast genome at low frequencies and thus replicate as part of the host cell chromosome; these vectors lack an origin of replication that is functional in yeast, although they typically have at least one origin of replication suitable for progation of the vector in bacterial cells. YEp vectors, in contrast, replicate episomally and autonomously due to presence of the yeast 2 micron plasmid origin (2 $\mu$m ori). The YCp yeast centromere plasmid vectors are autonomously replicating vectors containing centromere sequences, CEN, and autonomously replicating sequences, ARS; the ARS sequences are believed to correspond to the natural replication origins of yeast chromosomes. YACs are based on yeast linear plasmids, denoted YLp, containing homologous or heterologous DNA sequences that function as telomeres (TEL) in vivo, as well as containing yeast ARS (origins of replication) and CEN (centromeres) segments.

Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1, trp1-D1 and lys2-201. The URA3 and LYS2 yeast genes further permit negative selection based on specific inhibitors, 5-fluoro-orotic acid (FOA) and $\alpha$-aminoadipic acid ($\alpha$AA), respectively, that prevent growth of the prototrophic strains but allows growth of the ura3 and lys2 mutants, respectively. Other selectable markers confer resistance to, e.g., zeocin.

As yet another example, insect cells are often chosen for high efficiency protein expression. Where the host cells are from Spodoptera frugiperda—e.g., Sf9 and Sf21 cell lines, and express™ cells (Protein Sciences Corp., Meriden, Conn., USA)—the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following cotransfection with AcMNPV DNA, a homologous recombination event occurs between these sequences resulting in a recombinant virus carrying the gene of interest and the polyhedrin or p10 promoter. Selection can be based upon visual screening for lacZ fusion activity.

As yet another example, mammalian cells are often chosen for expression of proteins intended as pharmaceutical agents, and are also chosen as host cells for screening of potential agonist and antagonists of a protein or a physiological pathway.

Where mammalian cells are chosen as host cells, vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy.

Selectable markers for use in mammalian cells include resistance to neomycin (G418), blasticidin, hygromycin and to zeocin, and selection based upon the purine salvage pathway using HAT medium.

Vectors of the present invention will also often include elements that permit in vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Expression vectors of the present invention—that is, those vectors that will drive expression of polypeptides from the inserted heterologous nucleic acid—will often include a variety of other genetic elements operatively linked to the protein-encoding heterologous nucleic acid insert, typically genetic elements that drive transcription, such as promoters and enhancer elements, those that facilitate RNA processing, such as transcription termination and/or polyadenylation signals, and those that facilitate translation, such as ribosomal consensus sequences.

For example, vectors for expressing proteins of the present invention in prokaryotic cells, typically *E. coli,* will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), or the araBAD operon. Often, such prokaryotic expression vectors will further include transcription terminators, such as the aspA terminator, and elements that facilitate translation, such as a consensus ribosome binding site and translation termination codon, Schomer et al., *Proc. Natl. Acad. Sci. USA* 83:8506–8510 (1986).

As another example, vectors for expressing proteins of the present invention in yeast cells, typically *S. cerevisiae,* will include a yeast promoter, such as the CYC1 promoter, the GAL1 promoter, ADH1 promoter, or the GPD promoter, and will typically have elements that facilitate transcription termination, such as the transcription termination signals from the CYC1 or ADH1 gene.

As another example, vectors for expressing proteins of the present invention in mammalian cells will include a promoter active in mammalian cells. Such promoters are often drawn from mammalian viruses—such as the enhancer—promoter sequences from the immediate early gene of the human cytomegalovirus (CMV), the enhancer-promoter sequences from the Rous sarcoma virus long terminal repeat (RSV LTR), and the enhancer-promoter from SV40. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Vector-drive protein expression can be constitutive or inducible.

Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline.

As another example of inducible elements, hormone response elements, such as the glucocorticoid response element (GRE) and the estrogen response element (ERE), can confer hormone inducibility where vectors are used for expression in cells having the respective hormone receptors. To reduce background levels of expression, elements responsive to ecdysone, an insect hormone, can be used instead, with coexpression of the ecdysone receptor.

Expression vectors can be designed to fuse the expressed polypeptide to small protein tags that facilitate purification and/or visualization.

For example, proteins can be expressed with a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). As another example, the fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA).

Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides larger than purification and/or identification tags. Useful protein fusions include those that permit display of the encoded protein on the surface of a phage or cell, fusions to intrinsically fluorescent proteins, such as green fluorescent protein (GFP), fusions to the IgG Fc region, and fusions for use in two hybrid systems.

Vectors for phage display fuse the encoded polypeptide to, e.g., the gene III protein (pIII) or gene VIII protein (pVIII) for display on the surface of filamentous phage, such as M13. See Barbas et al., *Phase Display: A Laboratory Manual,* Cold Spring Harbor Laboratory Press (2001) (ISBN 0-87969-546-3); Kay et al. (eds.), *Phage Display of Peptides and Proteins: A Laboratory Manual,* San Diego: Academic Press, Inc., 1996; Abelson et al. (eds.), *Combinatorial Chemistry,* Methods in Enzymology vol. 267, Academic Press (May 1996).

Vectors for yeast display, e.g. the pYD1 yeast display vector (Invitrogen, Carlsbad, Calif., USA), use the α-agglutinin yeast adhesion receptor to display recombinant protein on the surface of *S. cerevisiae.* Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea victoria* ("GFP") and its variants. These proteins are intrinsically fluorescent: the GFP-like chromophore is entirely encoded by its amino acid sequence and can fluoresce without requirement for cofactor or substrate.

Structurally, the GFP-like chromophore comprises an 11-stranded β-barrel (β-can) with a central α-helix, the central α-helix having a conjugated Π-resonance system that includes two aromatic ring systems and the bridge between them. The Π-resonance system is created by autocatalytic cyclization among amino acids; cyclization proceeds through an imidazolinone intermediate, with subsequent dehydrogenation by molecular oxygen at the Cα-Cβ bond of a participating tyrosine.

The GFP-like chromophore can be selected from GFP-like chromophores found in naturally occurring proteins, such as *A. Victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. Li et al., "Deletions of the *Aequorea Victoria* Green Fluorescent Protein Define the Minimal Domain Required for Fluorescence," *J. Biol. Chem.* 272:28545–28549 (1997).

Alternatively, the GFP-like chromophore can be selected from GFP-like chromophores modified from those found in nature. Typically, such modifications are made to improve recombinant production in heterologous expression systems (with or without change in protein sequence), to alter the excitation and/or emission spectra of the native protein, to facilitate purification, to facilitate or as a consequence of cloning, or are a fortuitous consequence of research investigation.

The methods for engineering such modified GFP-like chromophores and testing them for fluorescence activity, both alone and as part of protein fusions, are well-known in the art. Early results of these efforts are reviewed in Heim et al., *Curr. Biol.* 6:178–182 (1996), incorporated herein by reference in its entirety; a more recent review, with tabulation of useful mutations, is found in Palm et al., "Spectral Variants of Green Fluorescent Protein," in *Green Fluorescent Proteins,* Conn (ed.), *Methods Enzymol.* vol. 302, pp. 378–394 (1999), incorporated herein by reference in its entirety. A variety of such modified chromophores are now commercially available and can readily be used in the fusion proteins of the present invention.

For example, EGFP ("enhanced GFP"), Cormack et al., *Gene* 173:33–38 (1996); U.S. Pat. Nos. 6,090,919 and 5,804,387, is a red-shifted, human codon-optimized variant of GFP that has been engineered for brighter fluorescence, higher expression in mammalian cells, and for an excitation spectrum optimized for use in flow cytometers. EGFP can usefully contribute a GFP-like chromophore to the fusion proteins of the present invention. A variety of EGFP vectors, both plasmid and viral, are available commercially (Clontech Labs, Palo Alto, Calif., USA), including vectors for bacterial expression, vectors for N-terminal protein fusion expression, vectors for expression of C-terminal protein fusions, and for bicistronic expression.

Toward the other end of the emission spectrum, EBFP ("enhanced blue fluorescent protein") and BFP2 contain four amino acid substitutions that shift the emission from green to blue, enhance the brightness of fluorescence and improve solubility of the protein, Heim et al., *Curr. Biol.* 6:178–182 (1996); Cormack et al., *Gene* 173:33–38 (1996). EBFP is optimized for expression in mammalian cells whereas BFP2, which retains the original jellyfish codons, can be expressed in bacteria; as is further discussed below, the host cell of production does not affect the utility of the resulting fusion protein. The GFP-like chromophores from EBFP and BFP2 can usefully be included in the fusion proteins of the present invention, and vectors containing these blue-shifted variants are available from Clontech Labs (Palo Alto, Calif., USA).

Analogously, EYFP ("enhanced yellow fluorescent protein"), also available from Clontech Labs, contains four amino acid substitutions, different from EBFP, Ormö et al., *Science* 273:1392–1395 (1996), that shift the emission from green to yellowish-green. Citrine, an improved yellow fluorescent protein mutant, is described in Heikal et al., *Proc. Natl. Acad. Sci. USA* 97:11996–12001 (2000). ECFP ("enhanced cyan fluorescent protein") (Clontech Labs, Palo Alto, Calif., USA) contains six amino acid substitutions, one of which shifts the emission spectrum from green to cyan. Heim et al., *Curr. Biol.* 6:178–182 (1996); Miyawaki et al., *Nature* 388:882–887 (1997). The GFP-like chromophore of each of these GFP variants can usefully be included in the fusion proteins of the present invention.

The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein,* Methods in Fusions to the IgG Fc region increase serum half life of protein pharmaceutical products through interaction with the FcRn receptor (also denominated the FcRp receptor and the Brambell receptor, FcRb), further described in international patent application Nos. WO 97/43316, WO 97/34631, WO 96/32478, WO 96/18412.

The present invention further includes host cells comprising the vectors of the present invention, either present episomally within the cell or integrated, in whole or in part, into the host cell chromosome.

As noted earlier, host cells can be prokaryotic or eukaryotic. Representative examples of appropriate host cells include, but are not limited to, bacterial cells, such as *E. coli, Caulobacter crescentus,* Streptomyces species, and *Salmonella typhimurium;* yeast cells, such as *Saccharomyces cerevisiae, Schizosaccharomyces pombe, Pichia pastoris, Pichia methanolica;* insect cell lines, such as those from *Spodoptera frugiperda*—e.g., Sf9 and Sf21 cell lines, and expresSF™ cells (Protein Sciences Corp., Meriden, Conn., USA)—Drosophila S2 cells, and Trichoplusia ni High Five® Cells (Invitrogen, Carlsbad, Calif., USA); and mammalian cells. Typical mammalian cells include COS1 and COS7 cells, chinese hamster ovary (CHO) cells, NIH 3T3 cells, 293 cells, HEPG2 cells, HeLa cells, L cells, murine ES cell lines (e.g., from strains 129/SV, C57/BL6, DBA-1, 129/SVJ), K562, Jurkat cells, and BW5147. Other mammalian cell lines are well known and readily available from the American Type Culture Collection (ATCC) (Manassas, Va., USA) and the National Institute of General medical Sciences (NIGMS) Human Genetic Cell Repository at the Coriell Cell Repositories (Camden, N.J., USA).

Methods for introducing the vectors and nucleic acids of the present invention into the host cells are well known in the art; the choice of technique will depend primarily upon the specific vector to be introduced.

For example, phage lambda vectors will typically be packaged using a packaging extract (e.g., Gigapack® packaging extract, Stratagene, La Jolla, Calif., USA), and the packaged virus used to infect *E. coli.* Plasmid vectors will typically be introduced into chemically competent or electrocompetent bacterial cells.

*E. coil* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, *J. Mol. Biol.* 166(4):557–80 (1983), and vectors introduced by heat shock. A wide variety of chemically competent strains are also available commercially (e.g., Epicurian Coli® XL10-Gold® Ultracompetent Cells (Stratagene, La Jolla, Calif., USA); DH5α competent cells (Clontech Laboratories, Palo Alto, Calif., USA);

TOP10 Chemically Competent *E. coli* Kit (Invitrogen, Carlsbad, Calif., USA)).

Bacterial cells can be rendered electrocompetent—that is, competent to take up exogenous DNA by electroporation—by various pre-pulse treatments; vectors are introduced by electroporation followed by subsequent outgrowth in selected media. An extensive series of protocols is provided online in *Electroprotocols* (BioRad, Richmond, Calif., USA) (http://www.bio-rad.com/LifeScience/pdf/New__Gene__Pulser.pdf).

Vectors can be introduced into yeast cells by spheroplasting, treatment with lithium salts, electroporation, or protoplast fusion.

Spheroplasts are prepared by the action of hydrolytic enzymes—a snail-gut extract, usually denoted Glusulase, or Zymolyase, an enzyme from *Arthrobacter luteus*—to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol. For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5–6):339–46 (1989). For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194:182–7 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means.

For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPOFECTAMINE™ Reagent, CELLFECTIN® Reagent, and LIPOFECTIN® Reagent (Invitrogen, Carlsbad, Calif., USA), DOTAP Liposomal Transfection Reagent, FUGENE 6, X-tremeGENE Q2, DOSPER, (Roche Molecular Biochemicals, Indianapolis, IN USA), Effectene™, PolyFect®, Superfect® (Qiagen, Inc., Valencia, Calif., USA). Protocols for electroporating mammalian cells can be found online in Electroprotocols (Bio-Rad, Richmond, Calif., USA) (http://www.bio-rad.com/LifeScience/pdf/New__Gene__Pulser.pdf). See also, Norton et al. (eds.), *Gene Transfer Methods: Introducing DNA into Living Cells and Organisms,* BioTechiques Books, Eaton Publishing Co. (2000) (ISBN 1-881299-34-1), incorporated herein by reference in its entirety.

Proteins

In another aspect, the present invention provides PAPP-E isoform proteins, various fragments thereof suitable for use as antigens (e.g., for epitope mapping) and for use as immunogens (e.g., for raising antibodies or as vaccines), fusions of PAPP-E isoform polypeptides and fragments to heterologous polypeptides, and conjugates of the proteins, fragments, and fusions of the present invention to other moieties (e.g., to carrier proteins, to fluorophores).

FIGS. 3A–3J, 4A–4I, and 5A–5G present the predicted amino acid sequences encoded by PAPP-Ea, PAPP-Eb, and PAPP-Ec cDNA clones. The amino acid sequences are further presented, respectively, in SEQ ID Nos: 3 (full length PAPP-Ea isoform), 7 (PAPPE-Ea isoform from aa 1–19), 10 (full length PAPP-Eb isoform) , 12 (amino acid sequence entirely within the novel exon of PAPP-Eb (aa 1735–1762)), 13 (amino acid sequence of PAPP-Eb resulting from the frame shift (aa 1763–1770)), 14 (amino acids present uniquely within PappE-b, due to exon insertion followed by frameshift (aa 1735–1770)), 16 (full length PAPP-Ec isoform), 18 (20 amino acids centered about deletion of exon 21 in PAPP-Ec (aa 298–317))

Unless otherwise indicated, amino acid sequences of the proteins of the present invention were determined as a predicted translation from a nucleic acid sequence. Accordingly, any amino acid sequence presented herein may contain errors due to errors in the nucleic acid sequence, as described in detail above. Furthermore, single nucleotide polymorphisms (SNPs) occur frequently in eukaryotic genomes—more than 1.4 million SNPs have already identified in the human genome, International Human Genome Sequencing Consortium, *Nature* 409:860–921 (2001)—and the sequence determined from one individual of a species may differ from other allelic forms present within the population. Small deletions and insertions can often be found that do not alter the function of the protein.

Accordingly, it is an aspect of the present invention to provide proteins not only identical in sequence to those described with particularity herein, but also to provide isolated proteins at least about 90% identical in sequence to those described with particularity herein, typically at least about 91%, 92%, 93%, 94%, or 95% identical in sequence to those decribed with particularity herein, usefully at least about 96%, 97%, 98%, or 99% identical in sequence to those described with particularity herein, and, most conservatively, at least about 99.5%, 99.6%, 99.7%, 99.8% and 99.9% identical in sequence to those described with particularity herein. These sequence variants can be naturally occurring or can result from human intervention by way of random or directed mutagenesis.

For purposes herein, percent identity of two amino acid sequences is determined using the procedure of Tatiana et al., "Blast 2 sequences—a new tool for comparing protein and nucleotide sequences", *FEMS Microbiol Lett.* 174:247–250 (1999), which procedure is effectuated by the computer program BLAST 2 SEQUENCES, available online at http://www.ncbi.nlm.nih.gov/blast/bl2seq/bl2.html, To assess percent identity of amino acid sequences, the BLASTP module of BLAST 2 SEQUENCES is used with default values of (i) BLOSUM62 matrix, Henikoff et al., *Proc. Natl. Acad. Sci USA* 89(22):10915–9 (1992); (ii) open gap 11 and extension gap 1 penalties; and (iii) gap x__dropoff 50 expect 10 word size 3 filter, and both sequences are entered in their entireties.

As is well known, amino acid substitutions occur frequently among natural allelic variants, with conservative substitutions often occasioning only de minimis change in protein function.

Accordingly, it is an aspect of the present invention to provide proteins not only identical in sequence to those described with particularity herein, but also to provide isolated proteins having the sequence of PAPP-E proteins, or portions thereof, with conservative amino acid substitutions, and to provide isolated proteins having the sequence of PAPP-E proteins, and portions thereof, with moderately conservative amino acid substitutions. These conservatively-sustituted or moderately conservatively-substituted variants can be naturally occurring or can result from human intervention.

Although there are a variety of metrics for calling conservative amino acid substitutions, based primarily on either observed changes among evolutionarily related proteins or on predicted chemical similarity, for purposes herein a conservative replacement is any change having a positive value in the PAM250 log-likelihood matrix reproduced herein below (see Gonnet et al., *Science* 256(5062):1443–5 (1992)):

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 2 | −1 | 0 | 0 | 0 | 0 | 0 | 0 | −1 | −1 | −1 | 0 | −1 | −2 | 0 | 1 | 1 | −4 | −2 | 0 |
| R | −1 | 5 | 0 | 0 | −2 | 2 | 0 | −1 | 1 | −2 | −2 | 3 | −2 | −3 | −1 | 0 | 0 | −2 | −2 | −2 |
| N | 0 | 0 | 4 | 2 | −2 | 1 | 1 | 0 | 1 | −3 | −3 | 1 | −2 | −3 | −1 | 1 | 0 | −4 | −1 | −2 |
| D | 0 | 0 | 2 | 5 | −3 | 1 | 3 | 0 | 0 | −4 | −4 | 0 | −3 | −4 | −1 | 0 | 0 | −5 | −3 | −3 |
| C | 0 | −2 | −2 | −3 | 12 | −2 | −3 | −2 | −1 | −1 | −2 | −3 | −1 | −1 | −3 | 0 | 0 | −1 | 0 | 0 |
| Q | 0 | 2 | 1 | 1 | −2 | 3 | 2 | −1 | 1 | −2 | −2 | 2 | −1 | −3 | 0 | 0 | 0 | −3 | −2 | −2 |
| E | 0 | 0 | 1 | 3 | −3 | 2 | 4 | −1 | 0 | −3 | −3 | 1 | −2 | −4 | 0 | 0 | 0 | −4 | −3 | −2 |
| G | 0 | −1 | 0 | 0 | −2 | −1 | −1 | 7 | −1 | −4 | −4 | −1 | −4 | −5 | −2 | 0 | −1 | −4 | −4 | −3 |
| H | −1 | 1 | 1 | 0 | −1 | 1 | 0 | −1 | 6 | −2 | −2 | 1 | −1 | 0 | −1 | 0 | 0 | −1 | 2 | −2 |
| I | −1 | −2 | −3 | −4 | −1 | −2 | −3 | −4 | −2 | 4 | 3 | −2 | 2 | 1 | −3 | −2 | −1 | −2 | −1 | 3 |
| L | −1 | −2 | −3 | −4 | −2 | −2 | −3 | −4 | −2 | 3 | 4 | −2 | 3 | 2 | −2 | −2 | −1 | −1 | 0 | 2 |
| K | 0 | 3 | 1 | 0 | −3 | 2 | 1 | −1 | 1 | −2 | −2 | 3 | −1 | −3 | −1 | 0 | 0 | −4 | −2 | −2 |
| M | −1 | −2 | −2 | −3 | −1 | −1 | −2 | −4 | −1 | 2 | 3 | −1 | 4 | 2 | −2 | −1 | −1 | −1 | 0 | 2 |
| F | −2 | −3 | −3 | −4 | −1 | −3 | −4 | −5 | 0 | 1 | 2 | −3 | 2 | 7 | −4 | −3 | −2 | 4 | 5 | 0 |
| P | 0 | −1 | −1 | −1 | −3 | 0 | 0 | −2 | −1 | −3 | −2 | −1 | −2 | −4 | 8 | 0 | 0 | −5 | −3 | −2 |
| S | 1 | 0 | 1 | 0 | 0 | 0 | 0 | 0 | 0 | −2 | −2 | 0 | −1 | −3 | 0 | 2 | 2 | −3 | −2 | −1 |
| T | 1 | 0 | 0 | 0 | 0 | 0 | 0 | −1 | 0 | −1 | −1 | 0 | −1 | −2 | 0 | 2 | 2 | −4 | −2 | 0 |
| W | −4 | −2 | −4 | −5 | −1 | −3 | −4 | −4 | −1 | −2 | −1 | −4 | −1 | 4 | −5 | −3 | −4 | 14 | 4 | −3 |
| Y | −2 | −2 | −1 | −3 | 0 | −2 | −3 | −4 | 2 | −1 | 0 | −2 | 0 | 5 | −3 | −2 | −2 | 4 | 8 | −1 |
| V | 0 | −2 | −2 | −3 | 0 | −2 | −2 | −3 | −2 | 3 | 2 | −2 | 2 | 0 | −2 | −1 | 0 | −3 | −1 | 3 |

For purposes herein, a "moderately conservative" replacement is any change having a nonnegative value in the PAM250 log-likelihood matrix reproduced herein above.

As is also well known in the art, relatedness of proteins can also be characterized using a functional test, the ability of the encoding nucleic acids to base-pair to one another at defined hybridization stringencies.

It is, therefore, another aspect of the invention to provide isolated proteins not only identical in sequence to those described with particularity herein, but also to provide isolated proteins ("hybridization related proteins") that are encoded by nucleic acids that hybridize under high stringency conditions (as defined herein above) to all or to a portion of various of the isolated PAPP-E nucleic acids of the present invention ("reference nucleic acids"). It is a further aspect of the invention to provide isolated proteins ("hybridization related proteins") that are encoded by nucleic acids that hybridize under moderate sringency conditions (as defined herein above) to all or to a portion of various of the isolated PAPP-E nucleic acids of the present invention.

The hybridization related proteins can be alternative isoforms, homologues, paralogues, and orthologues of the PAPP-E proteins of the present invention. Particularly preferred orthologues are those from other primate species, such as chimpanzee, rhesus macaque, baboon, and gorilla, from rodents, such as rats, mice, guinea pigs, and from livestock, such as cow, pig, sheep, horse, goat.

Relatedness of proteins can also be characterized using a second functional test, the ability of a first protein competitively to inhibit the binding of a second protein to an antibody.

It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated PAPP-E proteins of the present invention ("reference proteins"). Such competitive inhibition can readily be determined using immunoassays well known in the art.

Among the proteins of the present invention that differ in amino acid sequence from those described with particularity herein—including those that have deletions and insertions causing up to 10% non-identity, those having conservative or moderately conservative substitutions, hybridization related proteins, and cross-reactive proteins—those that substantially retain one or more PAPP-E activities are preferred. As described above, those activities include metalloprotease activity, specifically an ability to cleave an IGFBF, ability to heteromultimerize with serum proteins, such as eosinophil major basic protein (proMBP), and the ability to control survival, growth, and/or differentiation of the dominant ovarian follicle.

Residues that are tolerant of change while retaining function can be identified by altering the protein at known residues using methods known in the art, such as alanine scanning mutagenesis, Cunningham et al., *Science* 244 (4908):1081–5 (1989); transposon linker scanning mutagenesis, Chen et al., *Gene* 263(1–2):39–48 (2001); combinations of homolog- and alanine-scanning mutagenesis, Jin et al., J. Mol. Biol. 226(3):851–65 (1992); combinatorial alanine scanning, Weiss et al., Proc. Natl. Acad. Sci USA 97(16):8950–4 (2000), followed by functional assay. Transposon linker scanning kits are available commercially (New England Biolabs, Beverly, Mass., USA, catalog. No. E7-102S; EZ::TN™ In-Frame Linker Insertion Kit, catalogue No. EZI04KN, Epicentre Technologies Corporation, Madison, Wis., USA).

As further described below, the isolated proteins of the present invention can readily be used as specific immunogens to raise antibodies that specifically recognize PAPP-E proteins, their isoforms, homologues, paralogues, and/or orthologues. The antibodies, in turn, can be used, inter alia, specifically to assay for the PAPP-E proteins of the present invention—e.g. by ELISA for detection of protein fluid samples, such as serum, by immunohistochemistry or laser scanning cytometry, for detection of protein in tissue samples, or by flow cytometry, for detection of intracellular protein in cell suspensions—for specific antibody-mediated isolation and/or purification of PAPP-E proteins, as for example by immunoprecipitation, and for use as specific agonists or antagonists of PAPP-E action.

The isolated proteins of the present invention are also immediately available for use as specific standards in assays used to determine the concentration and/or amount specifically of the PAPP-E proteins of the present invention. For example, ELISA kits for detection and quantitation of protein analytes include purified protein of known concentration for use as a measurement standard (e.g., the human interferon-γ OptEIA kit, catalog No. 555142, Pharmingen, San Diego, Calif., USA includes human recombinant gamma interferon, baculovirus produced).

The isolated proteins of the present invention are also immediately available for use as specific biomolecule capture probes for surface-enhanced laser desorption ionization (SELDI) detection of protein-protein interactions, WO 98/59362; WO 98/59360; WO 98/59361; and Merchant et al., *Electrophoresis* 21(6):1164–77 (2000), the disclosures of which are incorporated herein by reference in their entireties. The isolated proteins of the present invention are also immediately available for use as specific biomolecule capture probes on BIACORE surface plasmon resonance probes.

The isolated proteins of the present invention are also useful as a therapeutic supplement in patients having a specific deficiency in PAPP-E production.

In another aspect, the invention also provides fragments of various of the proteins of the present invention. The protein fragments are useful, inter alia, as antigenic and immunogenic fragments of a PAPP-E isoform.

By "fragments" of a protein is here intended isolated proteins (equally, polypeptides, peptides, oligopeptides), however obtained, that have an amino acid sequence identical to a portion of the reference amino acid sequence, which portion is at least 6 amino acids and less than the entirety of the reference nucleic acid. As so defined, "fragments" need not be obtained by physical fragmentation of the reference protein, although such provenance is not thereby precluded.

Fragments of at least 6 contiguous amino acids are useful in mapping B cell and T cell epitopes of the reference protein. See, e.g., Geysen et al., "Use of peptide synthesis to probe viral antigens for epitopes to a resolution of a single amino acid," *Proc. Natl. Acad. Sci. USA* 81:3998–4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, have utility as immunogens for raising antibodies that recognize the proteins of the present invention. See, e.g., Lerner, "Tapping the immunological repertoire to produce antibodies of predetermined specificity," Nature 299:592–596 (1982); Shinnick et al., "Synthetic peptide immunogens as vaccines," *Annu. Rev. Microbiol.* 37:425–46 (1983); Sutcliffe et al., "Antibodies that react with predetermined sites on proteins," Science 219:660–6 (1983), the disclosures of which are incorporated herein by reference in their entireties. As further described in the above-cited references, virtually all 8-mers, conjugated to a carrier, such as a protein, prove immunogenic—that is, prove capable of eliciting antibody for the conjugated peptide; accordingly, all fragments of at least 8 amino acids of the proteins of the present invention have utility as immunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multerimic complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein or the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

The present invention further provides fusions of the proteins and protein fragments of the present invention to heterologous polypeptides.

By fusion is here intended that the protein or protein fragment of the present invention is linearly contiguous to the heterologous polypeptide in a peptide-bonded polymer of amino acids or amino acid analogues; by "heterologous polypeptide" is here intended a polypeptide that does not naturally occur in contiguity with the protein or protein fragment of the present invention. As so defined, the fusion can consist entirely of a plurality of fragments of the PAPP-E protein in altered arrangement; in such case, any of the PAPP-E fragments can be considered heterologous to the other PAPP-E fragments in the fusion protein. More typically, however, the heterologous polypeptide is not drawn from the PAPP-E protein itself.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins), have particular utility.

As described above in the description of vectors and expression vectors of the present invention, which discussion is incorporated herein by reference in its entirety, heterologous polypeptides to be included in the fusion proteins of the present invention can usefully include those designed to facilitate purification and/or visualization of recombinantly-expressed proteins. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of PAPP-E presence.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences.

Other useful protein fusions of the present invention include those that permit use of the protein of the present invention as bait in a yeast two-hybrid system. See Bartel et al. (eds.), *The Yeast Two-Hybrid System,* Oxford University Press (1997) (ISBN: 0195109384); Zhu et al., *Yeast Hybrid Technologies,* Eaton Publishing, (2000) (ISBN 1-881299-15-5); Fields et al., *Trends Genet.* 10(8):286–92 (1994); Mendelsohn et al., *Curr. Opin. Biotechnol.* 5(5):482–6 (1994); Luban et al., *Curr. Opin. Biotechnol.* 6(1):59–64 (1995); Allen et al., Trends Biochem. Sci. 20(12):511–6 (1995); Drees, *Curr. Opin. Chem. Biol.* 3(1):64–70 (1999); Topcu et al., *Pharm. Res.* 17(9) :1049–55 (2000); Fashena et al., *Gene* 250(1–2):1–14 (2000), the disclosures of which are incorporated herein by reference in their entireties. Typically, such fusion is to either *E. Coli* LexA or yeast GAL4 DNA binding domains. Related bait plasmids are available that express the bait fused to a nuclear localization signal.

Other useful protein fusions include those that permit display of the encoded protein on the surface of a phage or cell, fusions to intrinsically fluorescent proteins, such as green fluorescent protein (GFP), and fusions to the IgG Fc region.

The proteins and protein fragments of the present invention can also usefully be fused to protein toxins, such as Pseudomonas exotoxin A, diphtheria toxin, shiga toxin A, anthrax toxin lethal factor, ricin, in order to effect ablation of cells that bind or take up the proteins of the present invention.

The isolated proteins, protein fragments, and protein fusions of the present invention can be composed of natural amino acids linked by native peptide bonds, or can contain any or all of nonnatural amino acid analogues, nonnative bonds, and post-synthetic (post translational) modifications, either throughout the length of the protein or localized to one or more portions thereof.

As is well known in the art, when the isolated protein is used, e.g., for epitope mapping, the range of such nonnatural analogues, nonnative inter-residue bonds, or post-synthesis modifications will be limited to those that permit binding of the peptide to antibodies. When used as an immunogen for the preparation of antibodies in a non-human host, such as a mouse, the range of such nonnatural analogues, nonnative inter-residue bonds, or post-synthesis modifications will be limited to those that do not interfere with the immunogenicity of the protein. When the isolated protein is used as a therapeutic agent, such as a vaccine or for replacement therapy, the range of such changes will be limited to those that do not confer toxicity upon the isolated protein.

Non-natural amino acids can be incorporated during solid phase chemical synthesis or by recombinant techniques, although the former is typically more common.

For example, D-enantiomers of natural amino acids can readily be incorporated during chemical peptide synthesis: peptides assembled from D-amino acids are more resistant to proteolytic attack; incorporation of D-enantiomers can also be used to confer specific three dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (Kole et al., *Biochem. Biophys. Res. Com.* 209:817–821 (1995)), and various halogenated phenylalanine derivatives.

Amino acid analogues having detectable labels are also usefully incorporated during synthesis to provide a labeled polypeptide.

Biotin, for example, can be added using biotinoyl—(9-fluorenylmethoxycarbonyl)-L-lysine (FMOC biocytin) (Molecular Probes, Eugene, Oreg., USA). The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS—FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)—TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio)butyric acid, Fmoc-L-buthionine, Fmoc-S-methyl-L-Cysteine, Fmoc-2-aminobenzoic acid (anthranillic acid), Fmoc-3-aminobenzoic acid, Fmoc-4-aminobenzoic acid, Fmoc-2-aminobenzophenone-2'-carboxylic acid, Fmoc-N-

(4-aminobenzoyl)-b-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino-4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-?-amino-2-thiophenacetic acid, Fmoc-4-(carboxymethyl) piperazine, Fmoc-4-carboxypiperazine, Fmoc-4-(carboxymethyl)homopiperazine, Fmoc-4-phenyl-4-piperidinecarboxylic acid, Fmoc-L-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid and. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl Acad. Sci. USA* 96(9):4780–5 (1999).

The isolated proteins, protein fragments and fusion proteins of the present invention can also include nonnative inter-residue bonds, including bonds that lead to circular and branched forms.

The isolated proteins and protein fragments of the present invention can also include post-translational and post-synthetic modifications, either throughout the length of the protein or localized to one or more portions thereof.

For example, when produced by recombinant expression in eukaryotic cells, the isolated proteins, fragments, and fusion proteins of the present invention will typically include N-linked and/or O-linked glycosylation, the pattern of which will reflect both the availability of glycosylation sites on the protein sequence and the identity of the host cell. Further modification of glycosylation pattern can be performed enzymatically.

As another example, recombinant polypeptides of the invention may also include an initial modified methionine residue, in some cases resulting from host-mediated processes.

When the proteins, protein fragments, and protein fusions of the present invention are produced by chemical synthesis, post-synthetic modification can be performed before deprotection and cleavage from the resin or after deprotection and cleavage. Modification before deprotection and cleavage of the synthesized protein often allows greater control, e.g. by allowing targeting of the modifying moiety to the N-terminus of a resin-bound synthetic peptide.

Useful post-synthetic (and post-translational) modifications include conjugation to detectable labels, such as fluorophores.

A wide variety of amine-reactive and thiol-reactive fluorophore derivatives have been synthesized that react under nondenaturating conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yello, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents.

Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The proteins, protein fragments, and protein fusions of the present invention can be conjugated, using such cross-linking reagents, to fluorophores that are not amine- or thiol-reactive.

Other labels that usefully can be conjugated to the proteins, protein fragments, and fusion proteins of the present invention include radioactive labels, echosonographic contrast reagents, and MRI contrast agents.

The proteins, protein fragments, and protein fusions of the present invention can also usefully be conjugated using cross-linking agents to carrier proteins, such as KLH, bovine thyroglobulin, and even bovine serum albumin (BSA), to increase immunogenicity for raising anti-PAPP-E antibodies.

The proteins, protein fragments, and protein fusions of the present invention can also usefully be conjugated to polyethylene glycol (PEG); PEGylation increases the serum half life of proteins administered intravenously for replacement therapy. Delgado et al., Crit. Rev. Ther. Drug Carrier Syst.

9(3–4):249–304 (1992); Scott et al., Curr. Pharm. Des. 4(6):423–38 (1998); DeSantis et al., *Curr. Opin. Biotechnol.* 10(4):324–30 (1999), incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

The isolated proteins of the present invention, including fusions thereof, can be produced by recombinant expression, typically using the expression vectors of the present invention as above-described or, if fewer than about 100 amino acids, by chemical synthesis (typically, solid phase synthesis), and, on occasion, by in vitro translation.

Production of the isolated proteins of the present invention can optionally be followed by purification.

Purification of recombinantly expressed proteins is now well within the skill in the art. See, e.g., Thorner et al. (eds.), *Applications of Chimeric Genes and Hybrid Proteins, Part A: Gene Expression and Protein Purification* (Methods in Enzymology, Volume 326), Academic Press (2000), (ISBN: 0121822273); Harbin (ed.), *Cloning, Gene Expression and Protein Purification: Experimental Procedures and Process Rationale,* Oxford Univ. Press (2001) (ISBN: 0195132947); Marshak et al., *Strategies for Protein Purification and Characterization: A Laboratory Course Manual,* Cold Spring Harbor Laboratory Press (1996) (ISBN: 0-87969-385-1); and Roe (ed.), *Protein Purification Applications,* Oxford University Press (2001), the disclosures of which are incorporated herein by reference in their entireties, and thus need not be detailed here.

Briefly, however, if purification tags have been fused through use of an expression vector that appends such tag, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Purification of chemically-synthesized peptides can readily be effected, e.g., by HPLC.

Accordingly, it is an aspect of the present invention to provide the isolated proteins of the present invention in pure or substantially pure form.

A purified protein of the present invention is an isolated protein, as above described, that is present at a concentration of at least 95%, as measured on a mass basis with respect to total protein in a composition. Such purities can often be obtained during chemical synthesis without further purification, as, e.g., by HPLC. Purified proteins of the present invention can be present at a concentration (measured on a mass basis with respect to total protein in a composition) of 96%, 97%, 98%, and even 99%. The proteins of the present invention can even be present at levels of 99.5%, 99.6%, and even 99.7%, 99.8%, or even 99.9% following purification, as by HPLC.

Although high levels of purity are preferred when the isolated proteins of the present invention are used as therapeutic agents—such as vaccines, or for replacement therapy—the isolated proteins of the present invention are also useful at lower purity. For example, partially purified proteins of the present invention can be used as immunogens to raise antibodies in laboratory animals.

Thus, in another aspect, the present invention provides the isolated proteins of the present invention in substantially purified form. A "substantially purified protein" of the present invention is an isolated protein, as above described, present at a concentration of at least 70%, measured on a mass basis with respect to total protein in a composition. Usefully, the substantially purified protein is present at a concentration, measured on a mass basis with respect to total protein in a composition, of at least 75%, 80%, or even at least 85%, 90%, 91%, 92%, 93%, 94%, 94.5% or even at least 94.9%.

In preferred embodiments, the purified and substantially purified proteins of the present invention are in compositions that lack detectable ampholytes, acrylamide monomers, bis-acrylamide monomers, and polyacrylamide.

The proteins, fragments, and fusions of the present invention can usefully be attached to a substrate. The substrate can porous or solid, planar or non-planar; the bond can be covalent or noncovalent.

For example, the proteins, fragments, and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g. in serum, that bind specifically to the immobilized protein of the present invention.

As another example, the proteins, fragments, and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in standard microtiter dish, the plastic is typically polystyrene.

The proteins, fragments, and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction therebetween. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction therebetween.

PAPP-E Isoform Proteins

In a first series of protein embodiments, the invention provides an isolated PAPP-E polypeptide having an amino acid sequence encoded by the cDNA in ATCC Deposit No. PTA-3399, or the amino acid sequence in SEQ ID NO:3, which are full length human PAPP-Ea isoforms. The invention further provides isolated PAPP-E polypeptides having an amino acid sequence encoded by the cDNA in ATCC Deposit No. PTA-3400, or the amino acid sequence in SEQ ID NO:10, which are full length human PAPP-Eb isoforms. The invention also provides isolated PAPP-E polypeptides having an amino acid sequence encoded by the cDNA in ATCC Deposit No. PTA-3401, or the amino acid sequence in SEQ ID NO:16, which are full length human PAPP-Ec isoforms.

When used as immunogens, the full length proteins of the present invention can be used, inter alia, to elicit antibodies that bind to epitopes that are common to all known PAPP-E isoforms. Such epitopes are encoded by any of exons 2–20, and by that portion of exon 1 translated in the PAPP-Ef isoform. When such antibodies are used for analytical assay of PAPP-E—e.g., in an ELISA intended to report the presence and/or amount of all isoforms, without distinction thereamong—any of the full length proteins can be used as a standard.

When used as immunogens, the full length proteins of the present invention can be used, inter alia, to elicit antibodies that bind to an epitope that is shared by PAPP-Ea, PAPP-Eb, and PAPP-Ec but absent from PAPP-Ef: such epitopes are encoded by that portion of exon 1 not translated in PAPP-Ef. Such antibodies are identified by counterscreening using PAPP-Ef protein. When such antibodies are used for analytical assay of PAPP-E—e.g., an ELISA intended to report the amount of PAPP-Ea, PAPP-Eb, and PAPP-Ec, but not PAPP-Ef—any of the full length proteins can be used as a standard.

When used as an immunogen, the full length PAPP-Eb protein can be used, inter alia, as an immunogen to elicit antibodies that bind to an epitope unique to the PAPP-Eb isoform. Such epitopes are encoded by exon 21 and the translated portion of exon 22. Such antibodies are identified by counterscreening using PAPP-Ea, PAPP-Ec, and/or PAPP-Ef isoforms. When such antibodies are used for analytical assay of PAPP-E—e.g., an ELISA intended to report the presence and/or amount of PAPP-Eb—the full length PAPP-Eb protein can be used uniquely among the isoforms as a standard.

The invention further provides fragments of the above-described polypeptides, particularly fragments having at least 6 amino acids, typically at least 8 amino acids, often at least 15 amino acids, and even the entirety of the sequence given in SEQ ID NO:7. This fragment (amino acids 1–19 of PAPP-Ea, -Eb, and Ec) is common to PAPP-Ea, PAPP-Eb and PAPP-Ec isoforms but absent from PAPP-Ef. These protein fragments can thus be used to identify and/or generate antibodies that recognize PAPP-Ea, PAPP-Eb, and PAPP-Ec isoforms without distinction thereamong, but that do not recognize PAPP-Ef.

The invention further provides fragments of at least 6 amino acids, typically at least 8 amino acids, often at least 15 amino acids, and even the entirety of the sequence given in SEQ ID NO:12, which is encoded by the exon that is novel in PAPP-Eb. The fragments have particular utility in identifying and in generating antibodies that recognize epitopes unique to the PAPP-Eb isoform.

The invention further provides fragments of at least 6 amino acids, typically at least 8 amino acids, often at least 15 amino acids, and even the entirety of the sequence given in SEQ ID NO:13, the coding sequence of the PAPP-Eb isoform that results from frameshift relative to PAPP-Ea isoform. These fragments have particular utility in identifying and in generating antibodies that recognize epitopes unique to the PAPP-Eb isoform.

The invention further provides fragments of at least 6 amino acids, typically at least 8 amino acids, often at least 15 amino acids, and even the entirety of the sequence given in SEQ ID NO:14, the coding sequence present uniquely in the PAPP-Eb isoform. These fragments have particular utility in dientifying and in generating antibodies that recognize epitopes unique to the PAPP-Eb isoform.

The invention further provides fragments of at least 6 amino acids, typically at least 8 amino acids, often at least 15 amino acids, and even the entirety of the sequence given in SEQ ID NO:18, the twenty amino acids centered about the exon 21 deletion in PAPP-Ec. These fragments have particular utility in identifying and generating antibodies that recognize epitopes created in the PAPP-Ec isoform due to absence of exon 21.

As described above, the invention further provides proteins that differ in sequence from those described with particularity in the above-referenced SEQ ID NOs., whether by way of insertion or deletion, by way of conservative or moderately conservative substitutions, as hybridization related proteins, or as cross-hybridizing proteins, with those that substantially retain a PAPP-E activity preferred.

The invention further provides fusions of the proteins and protein fragments herein described to heterologous polypeptides.

Antibodies and Antibody-producing Cells

In another aspect, the invention provides antibodies, including fragments and derivatives thereof, that bind specifically to one or more of the PAPP-E proteins and protein fragments of the present invention or to one or more of the proteins and protein fragments encoded by the isolated PAPP-E nucleic acids of the present invention. The antibodies of the present invention specifically recognize any or all of linear epitopes, discontinuous epitopes, or conformational epitopes of such proteins or protein fragments, either as present on the protein in its native conformation or, in some cases, as present on the proteins as denatured, as, e.g., by solubilization in SDS.

In other embodiments, the invention provides antibodies, including fragments and derivatives thereof, the binding of which can be competitively inhibited by one or more of the PAPP-E proteins and protein fragments of the present invention, or by one or more of the proteins and protein fragments encoded by the isolated PAPP-E nucleic acids of the present invention.

As used herein, the term "antibody" refers to a polypeptide, at least a portion of which is encoded by at least one immunoglobulin gene, which can bind specifically to a first molecular species, and to fragments or derivatives thereof that remain capable of such specific binding.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies of the present invention will discriminate over adventitious binding to non-PAPP-E proteins by at least two-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in human serum.

Typically, the affinity or avidity of an antibody (or antibody multimer, as in the case of an IgM pentamer) of the present invention for a protein or protein fragment of the present invention will be at least about $1\times10^{-6}$ molar (M), typically at least about $5\times10^{-7}$ M, usefully at least about $1\times10^{-7}$ M, with affinities and avidities of at least $1\times10^{-8}$ M, $5\times10^{-9}$ M, and $1\times10^{-10}$ M proving especially useful.

The antibodies of the present invention can be naturally-occurring forms, such as IgG, IgM, IgD, IgE, and IgA, from any mammalian species.

Human antibodies can, but will infrequently, be drawn directly from human donors or human cells. In such case, antibodies to the proteins of the present invention will typically have resulted from fortuitous immunization, such as autoimmune immunization, with the protein or protein fragments of the present invention. Such antibodies will typically, but will not invariably, be polyclonal.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described, inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE and IgA antibodies of the present invention are also usefully obtained from other mammalian species, including rodents—typically mouse, but also rat, guinea pig, and hamster—lagomorphs, typically rabbits, and also larger mammals, such as sheep, goats, cows, and horses. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thryoglobulin, keyhole limpet hemocyanin, or bovine serum albumin, conveniently using a bifunctional linker such as those described elsewhere above, which discussion is incorporated by reference here.

Immunogenicity can also be conferred by fusion of the proteins and protein fragments of the present invention to other moieties.

For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al., Proc. Natl. Acad. Sci. USA 85:5409–5413 (1988); Posnett et al., *J. Biol. Chem.* 263, 1719–1725 (1988).

Protocols for immunizing non-human mammals are well-established in the art, Harlow et al. (eds.), *Antibodies: A Laboratory Manual,* Cold Spring Harbor Laboratory (1998) (ISBN: 0879693142); Coligan et al. (eds.), *Current Protocols in Immunology,* John Wiley & Sons, Inc. (2001) (ISBN: 0-471-52276-7); Zola, *Monoclonal Antibodies: Preparation and Use of Monoclonal Antibodies and Engineered Antibody Derivatives* (*Basics: From Background to Bench*), Springer Verlag (2000) (ISBN: 0387915907), the disclosures of which are incorporated herein by reference, and often include multiple immunizations, either with or without adjuvants such as Freund's complete adjuvant and Freund's incomplete adjuvant.

Antibodies from nonhuman mammals can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention.

Following immunization, the antibodies of the present invention can be produced using any art-accepted technique. Such techniques are well known in the art, Coligan et al. (eds.), *Current Protocols in Immunology,* John Wiley & Sons, Inc. (2001) (ISBN: 0-471-52276-7); Zola, *Monoclonal Antibodies: Preparation and Use of Monoclonal Antibodies and Engineered Antibody Derivatives* (*Basics: From Background to Bench*), Springer Verlag (2000) (ISBN: 0387915907); Howard et al. (eds.), *Basic Methods in Antibody Production and Characterization,* CRC Press (2000) (ISBN: 0849394457); Harlow et al. (eds.), *Antibodies: A Laboratory Manual,* Cold Spring Harbor Laboratory (1998) (ISBN: 0879693142); Davis (ed.), *Monoclonal Antibody Protocols,* Vol. 45, Humana Press (1995) (ISBN: 0896033082); Delves (ed.), *Antibody Production: Essential Techniques,* John Wiley & Son Ltd (1997) (ISBN: 0471970107); Kenney, *Antibody Solution: An Antibody Methods Manual,* Chapman & Hall (1997) (ISBN: 0412141914), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S. Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant antibody production—either whole antibodies, antibody fragments, or antibody derivatives—can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (pVIII) for display on the surface of filamentous phage, such as M13, is by now well-established, Sidhu, *Curr. Opin. Biotechnol.* 11(6):610–6 (2000); Griffiths et al., *Curr. Opin. Biotechnol.*

9(1):102–8 (1998); Hoogenboom et al., *Immunotechnology,* 4(1):1–20 (1998); Rader et al., *Current Opinion in Biotechnology* 8:503–508 (1997); Aujame et al., *Human Antibodies* 8:155–168 (1997); Hoogenboom, *Trends in Biotechnol.* 15:62–70 (1997); de Kruif et al., 17:453–455 (1996); Barbas et al., *Trends in Biotechnol.* 14:230–234 (1996); Winter et al., *Ann. Rev. Immunol.* 433–455 (1994), and techniques and protocols required to generate, propagate, screen (pan), and use the antibody fragments from such libraries have recently been compiled, Barbas et al., *Phage Display: A Laboratory Manual,* Cold Spring Harbor Laboratory Press (2001) (ISBN 0-87969-546-3); Kay et al. (eds.), *Phage Display of Peptides and Proteins: A Laboratory Manual,* Academic Press, Inc. (1996); Abelson et al. (eds.), *Combinatorial Chemistry,* Methods in Enzymology vol. 267, Academic Press (May 1996), the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in *Pichia pastoris,* Takahashi et al., *Biosci. Biotechnol. Biochem.* 64(10):2138–44 (2000); Freyre et al., J. Biotechnol. 76(2–3):157–63 (2000); Fischer et al., *Biotechnol. Appl. Biochem.* 30 (Pt 2):117–20 (1999); Pennell et al., *Res. Immunol.* 149(6):599–603 (1998); Eldin et al., *J. Immunol. Methods.* 201(1):67–75 (1997); and in *Saccharomyces cerevisiae,* Frenken et al., *Res. Immunol.* 149(6):589–99 (1998); Shusta et al., *Nature Biotechnol.* 16(8):773–7 (1998), the disclosures of which are incorporated herein by reference in their entireties.

Antibodies, including antibody fragments and derivatives, of the present invention can also be produced in insect cells, Li et al., *Protein Expr. Purif.* 21(1):121–8 (2001); Ailor et al., *Biotechnol. Bioeng.* 58(2–3):196–203 (1998); Hsu et al., *Biotechnol. Prog.* 13(1):96–104 (1997); Edelman et al., *Immunology* 91(1):13–9 (1997); and Nesbit et al., *J. Immunol. Methods.* 151(1–2):201–8 (1992), the disclosures of which are incorporated herein by reference in their entireties.

Antibodies and fragments and derivatives thereof of the present invention can also be produced in plant cells, Giddings et al., *Nature Biotechnol.* 18(11):1151–5 (2000); Gavilondo et al., *Biotechniques* 29(1):128–38 (2000); Fischer et al., *J. Biol. Regul. Homeost. Agents* 14(2):83–92 (2000); Fischer et al., *Biotechnol. Appl. Biochem.* 30 (Pt 2):113–6 (1999); Fischer et al., *Biol. Chem.* 380(7–8):825–39 (1999); Russell, *Curr. Top. Microbiol. Immunol.* 240:119–38 (1999); and Ma et al., Plant Physiol. 109(2):341–6 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al., *J. Immunol. Methods* 216(1–2):165–81 (1998), review and compare bacterial, yeast, insect and mammalian expression systems for expression of antibodies.

Antibodies of the present invention can also be prepared by cell free translation, as further described in Merk et al., J. Biochem. (Tokyo). 125(2):328–33 (1999) and Ryabova et al., *Nature Biotechnol.* 15(1):79–84 (1997), and in the milk of transgenic animals, as further described in Pollock et al., *J. Immunol. Methods* 231(1–2):147–57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, $F(ab)'_2$, and single chain Fv (scFv) fragments. Other useful fragments are described in Hudson, *Curr. Opin. Biotechnol.* 9(4):395–402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA.*81(21):6851–5 (1984); Sharon et al., *Nature* 309(5966):364–7 (1984); Takeda et al., *Nature* 314(6010):452–4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162):323–7 (1988); Co et al., *Nature* 351(6326):501–2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label can usefully be an enzyme that catalyzes production and local deposition of a detectable product.

Enzymes typically conjugated to antibodies to permit their immunohistochemical visualization are well known, and include alkaline phosphatase, β-galactosidase, glucose oxidase, horseradish peroxidase (HRP), and urease. Typical substrates for production and deposition of visually detectable products include o-Nitrophenyl-beta-D-galactopyranoside (ONPG); o-Phenylenediamine Dihydrochloride (OPD); p-Nitrophenyl Phosphate (PNPP); p-Nitrophenyl-beta-D-galactopryanoside (PNPG); 3',3' Diaminobenzidine (DAB); 3-Amino-9-ethylcarbazole (AEC); 4-Chloro-1-naphthol (CN); 5-Bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., Methods Enzymol. 133:331–53 (1986); Kricka et al., *J. Immunoassay* 17(1):67–83 (1996); and Lundqvist et al., *J. Biolumin. Chemilumin.* 10(6):353–9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yello, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g., for western blotting applications, they can usefully be labeled with radioisotopes, such as $^{33}P$, $^{32}P$, $^{35}s$, $^{3}H$, and $^{125}I$.

As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$ , $^{211}At$ , $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}y$, $^{72}Se$, $^{67}Cu$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2):529–38 (1998), or by radioisotopic labeling As would be understood, use of the labels described above is not restricted to the application as for which they were mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to Pseudomonas exotoxin A, diphtheria toxin, shiga toxin A, anthrax toxin lethal factor, or ricin. See Hall (ed.), *Immunotoxin Methods and Protocols* (Methods in Molecular Biology, Vol 166), Humana Press (2000) (ISBN:0896037754); and Frankel et al. (eds.), *Clinical Applications of Immunotoxins,* Springer-Verlag New York, Incorporated (1998) (ISBN:3540640975), the disclosures of which are incorporated herein by reference in their entireties, for review.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microsphere can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Papp-E Antibodies

In a first series of antibody embodiments, the invention provides antibodies, both polyclonal and monoclonal, and fragments and derivatives thereof, that bind specifically to polypeptides comprising an amino acid sequence as provided in SEQ ID NO:7—the N-terminal portion of PAPP-Ea, PAPP-Eb, and PAPP-Ec that is absent from the PAPP-Ef isoform—and the binding of which can be competitively inhibited by a polypeptide the sequence of which is given in SEQ ID NO:7. Such antibodies can be used to discriminate the novel isoforms described herein from the PAPP-Ef isoform, but will not be able to discriminate as among PAPP-Ea, -Eb, and -Ec isoforms.

Such antibodies are useful in in vitro immunoassays, such as ELISA of maternal serum, western blot of maternal serum, or immunohistochemical assay of chorionic villus samples, in which the collective concentration and/or quantity of PAPP-Ea, -Eb, and -Ec protein isoforms provides diagnostic and/or prognostic information on pregnancy status. Such antibodies are also useful in isolating and purifying PAPP-E isoforms other than PAPP-Ef by immunoprecipitation, immunoaffinity chromatography, or magnetic bead-mediated purification.

In another series of embodiments, the invention provides antibodies, both polyclonal and monoclonal, and fragments and derivatives thereof, that bind specifically to polypeptides comprising an amino acid sequence as provided in SEQ ID NO:12—the region encoded by exon 21, unique to the PAPP-Eb isoform—and the binding of which can be competitively inhibited by a polypeptide the sequence of which is given in SEQ ID NO:12. In a further series of embodiments, the invention provides antibodies, both polyclonal and monoclonal, and fragments and derivatives thereof, that bind specifically to polypeptides comprising an amino acid sequence as provided in SEQ ID NO:13—the region C-terminal to exon 21 that is unique to PAPP-Eb isoform due to frameshift relative to the reading frame in PAPP-Ea, PAPP-Ec, and PAPP-Ef—and the binding of which can be competitively inhibited by a polypeptide the sequence of which is given in SEQ ID NO:13. In yet another series of embodiments, the invention provides antibodies, both polyclonal and monoclonal, and fragments and derivatives thereof, that bind specifically to polypeptides comprising an amino acid sequence as provided in SEQ ID NO:14—the region that is uniquely found in PAPP-Eb—and the binding of which can be competitively inhibited by a polypeptide the sequence of which is given in SEQ ID NO:14.

All of the antibodies of these latter three series of embodiments can be used to discriminate the PAPP-Eb isoform from all other isoforms. Such antibodies are useful in in vitro immunoassays, such as ELISA of maternal serum, western blot of maternal serum, or immunohistochemical assay of chorionic villus samples, in which the collective concentration and/or quantity of the PAPP-Eb isoform provides diagnostic and/or prognostic information on pregnancy status. Such antibodies are also useful in isolating and purifying the PAPP-Eb isoform by immunoprecipitation, immunoaffinity chromatography, or magnetic bead-mediated purification.

In yet a further series of embodiments, the invention provides antibodies, both polyclonal and monoclonal, and fragments and derivatives thereof, that bind specifically to polypeptides comprising an amino acid sequence as provided in SEQ ID NO:18—a 20 amino acid region of PAPP-Ec centered about the deletion of exons 2 and 3—and the binding of which can be competitively inhibited by a polypeptide the amino acid sequence of which is given in SEQ ID NO:18 and cannot be competitively inhibited by a polypeptide having the amino acid sequence of SEQ ID NO:1 (the full-length PAPP-Ea protein).

Such antibodies can be used to discriminate the PAPP-EC isoform from the other known isoforms, and are useful in in vitro immunoassays, such as ELISA of maternal serum, western blot of maternal serum, or immunohistochemical assay of chorionic villus samples, in which the concentration and/or quantity of PAPP-Ec isoform provides diagnostic and/or prognostic information on pregnancy status. Such antibodies are also useful in isolating and purifying the PAPP-Ec isoform by immunoprecipitation, immunoaffinity chromatography, or magnetic bead-mediated purification.

In other embodiments, the invention further provides the above-described antibodies detectably labeled, and in yet other embodiments, provides the above-described antibodies attached to a substrate.

Pharmaceutical Compositions

PAPP-E isoforms are important for maintenance of pregnancy and maturation of ovarian follicles. Thus, compositions comprising nucleic acids and proteins of the present invention can be administered as contraceptive vaccines and antibodies of the present invention can be administered for passive immunization, and thus reversible contraception. Alternatively, proteins of the present invention can be administered by nonimmunogenic routes as replacement therapy in patients with decreased levels of PAPP-E isoforms, thus supporting at-risk pregnancies.

Accordingly, in another aspect, the invention provides pharmaceutical compositions comprising the nucleic acids, nucleic acid fragments, proteins, protein fusions, protein fragments, antibodies, antibody derivatives, and antibody fragments of the present invention.

Such a composition typically contains from about 0.1 to 90% by weight (such as 1 to 20% or 1 to 10%) of a therapeutic agent of the invention in a pharmaceutically accepted carrier. Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch and ethylcellulose. Lubricants that can be used include magnesium stearates, stearic acid, silicone fluid, talc, waxes, oils, and colloidal silica.

Liquid formulations of the compositions for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweetners, and coloring and flavoring agents. Various liquid and powder formulations can be prepared by conventional methods for inhalation into the lungs of the mammal to be treated.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 1 to 20%, e.g., 5 to 10%, in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic regimens.

Inhalation and transdermal formulations can also readily be prepared.

Pharmaceutical formulation is a well-established art, and is further described in Gennaro (ed.), *Remington: The Science and Practice of Pharmacy,* 20$^{th}$ ed., Lippincott, Williams & Wilkins (2000) (ISBN: 0683306472); and Ansel et al., *Pharmaceutical Dosaqe Forms and Drug Delivery Systems,* 7$^{th}$ ed., Lippincott Williams & Wilkins Publishers (1999) (ISBN: 0683305727), the disclosures of which are incorporated herein by reference in their entireties.

Conventional methods, known to those of ordinary skill in the art of medicine, can be used to administer the pharmaceutical formulation(s) to the patient.

Typically, the pharmaceutical formulation will be administered to the patient by applying to the skin of the patient a transdermal patch containing the pharmaceutical formulation, and leaving the patch in contact with the patient's skin (generally for 1 to 5 hours per patch). Other transdermal routes of administration (e.g., through use of a topically applied cream, ointment, or the like) can be used by applying conventional techniques. The pharmaceutical formulation(s) can also be administered via other conventional routes (e.g., enteral, subcutaneous, intrapulmonary, transmucosal, intraperitoneal, intrauterine, sublingual, intrathecal, or intramuscular routes) by using standard methods. In addition, the pharmaceutical formulations can be administered to the patient via injectable depot routes of administration such as by using 1-, 3-, or 6-month depot injectable or biodegradable materials and methods.

Regardless of the route of administration, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

The effectiveness of the method of treatment can be assessed by monitoring the patient for known signs or symptoms of a disorder.

Transgenic Animals and Cells

In another aspect, the invention provides transgenic cells and non-human organisms comprising human PAPP-E isoform nucleic acids, and transgenic cells and non-human organisms with targeted disruption of the endogenous orthologue of the human PAPP-E gene.

The cells can be embryonic stem cells or somatic cells. The transgenic non-human organisms can be chimeric, nonchimeric heterozygotes, and nonchimeric homozygotes.

Diagnostic Methods

The nucleic acids of the present invention can be used as nucleic acid probes to assess the levels of PAPP-E isoform mRNA in chorionic villus samples, and antibodies of the present invention can be used to assess the expression levels of PAPP-E isoform proteins in chorionic villus samples, to diagnose dysgenetic pregnancies antenatally.

EXAMPLE 1

Identification and Characterization of cDNAs Encoding Multiple Isoforms of Human PAPP-E Predicating our gene discovery efforts on use of genome-derived single exon probes and hybridization to genome-derived single exon microarrays—an approach that we have previously demonstrated will readily identify novel genes that have proven refractory to mRNA-based identification efforts—we identified an exon in raw human genomic sequence that is particularly expressed in human placenta.

Briefly, bioinformatic algorithms were applied to human genomic sequence data to identify putative exons. Each of the predicted exons was amplified from genomic DNA, typically centering the putative coding sequence within a larger amplicon that included flanking noncoding sequence. These genome-derived single exon probes were arrayed on a support and expression of the bioinformatically predicted exons assessed through a series of simultaneous two-color hybridizations to the genome-derived single exon microarrays.

The approach and procedures are further described in detail in Penn et al., "Mining the Human Genome using Microarrays of Open Reading Frames," *Nature Genetics* 26:315–318 (2000); commonly owned and copending U.S. patent application Ser. Nos. 09/774,203, filed Jan. 29, 2001

("Methods and Apparatus for Predicting, Confirming, and Displaying Functional Information Derived from Genomic Sequence") and 09/632,366, filed Aug. 3, 2000 ("Methods and Apparatus for High-throughput Detection and Characterization of Alternatively Spliced Genes"), and commonly owned and copending U.S. provisional patent application Nos. 60/207,456, filed May 26, 2000 ("Human Genome-derived Single Exon Nucleic Acid Probes Useful for Gene Expression Analysis by Microarray"), the disclosures of which are incorporated herein by reference in their entireties.

Using a graphical display particularly designed to facilitate computerized query of the resulting exon-specific expression data, as further described in commonly owned and copending U.S. patent application Ser. No. 09/774,203, filed Jan. 29, 2001 ("Methods and Apparatus for Predicting, Confirming, and Displaying Functional Information Derived from Genomic Sequence"), two exons were identified that are expressed at high levels in human placenta, but that are expressed, if at all, at low levels in human heart, brain, adult liver, HeLa cells, lung, fetal liver, HBL100 cells, bone marrow, and BT474 cells; subsequent analysis revealed that the two exons belong to the same gene. Further details of procedures and results are set forth in commonly owned and copending U.S. provisional patent application No. 60/207,456, filed May 26, 2000 ("Human Genome-derived Single Exon Nucleic Acid Probes Useful for Gene Expression Analysis by Microarray").

Table 1 summarizes the microarray expression data obtained using genome-derived single exon probes corresponding to exons 1 and 2. Each probe was completely sequenced on both strands prior to its use on a genome-derived single exon microarray; sequencing confirmed the exact chemical structure of each probe. An added benefit of sequencing is that it placed us in possession of a set of single base-incremented fragments of the sequenced nucleic acid, starting from the sequencing primer's 3' OH. (Since the single exon probes were first obtained by PCR amplification from genomic DNA, we were of course additionally in possession of an even larger set of single base incremented fragments of each of the single exon probes, each fragment corresponding to an extension product from one of the two amplification primers.)

Signals and expression ratios are normalized values measured and calculated as further described in commonly owned and copending U.S. patent application Ser. No. 09/774,203, filed Jan. 29, 2001 ("Methods and Apparatus for Predicting, Confirming, and Displaying Functional Information Derived from Genomic Sequence"),and U.S. provisional patent application Nos. 60/207,456, filed May 26, 2000 ("Human Genome-derived Probes Useful for Gene Expression Analysis by Microarray").

TABLE 1

Expression Analysis
Genome-Derived Single Exon Microarray

| | Amplicon 7403 (exon 1) | | Amplicon 7409 (exon 2) | |
|---|---|---|---|---|
| | Signal | Expression Ratio | Signal | Expression Ratio |
| Heart | 1.01 | — | 4.64 | — |
| Brain | 0.79 | — | 1.11 | −7.46 |
| Adult Liver | 0.80 | −12.73 | 1.40 | — |
| HeLa | 0.89 | −7.18 | 1.29 | — |
| Lung | 0.90 | — | 1.81 | — |
| Fetal Liver | 0.82 | — | 1.56 | −8.27 |
| Bone Marrow | 1.02 | — | 1.86 | — |
| Placenta | 74.34 | 8.08 | 43.62 | 6.05 |

As shown in Table 1, significant expression of exons 1 and 2 was seen only in placenta. Placenta-specific expression was further confirmed by northern blot analysis (see below).

Marathon-Ready™ placenta cDNA (Clontech Laboratories, Palo Alto, Calif., USA, catalogue No. 7411-1) was used as a substrate for standard RACE (rapid amplification of cDNA ends) to obtain a cDNA clone that spans 6.3 kilobases and appears to contain the entire coding region of the gene to which the two exons contribute; for reasons described below, we termed this cDNA PAPP-Ea. Marathon-Ready cDNAs are adaptor-ligated double stranded cDNAs suitable for 3' and 5' RACE. Chenchik et al., *BioTechniques* 21:526–532 (1996); Chenchik et al., *CLONTECHniques X*(1):5–8 (January 1995). RACE techniques are described, inter alia, in the Marathon-Ready™ cDNA User Manual (Clontech Labs., Palo Alto, Calif., USA, Mar. 30, 2000, Part No. PT1156-1 (PR03517)), Ausubel et al. (eds.), *Short Protocols in Molecular Biology: A Compendium of Methods from Current Protocols in Molecular Biology,* $4^{th}$ edition (April 1999), John Wiley & Sons (ISBN: 047132938X) and Sambrook et al. (eds.), *Molecular Cloning: A Laboratory Manual* (3rd ed.), Cold Spring Harbor Laboratory Press (2000) (ISBN: 0879695773), the disclosures of which are incorporated herein by reference in their entireties.

The PAPP-Ea cDNA was sequenced on both strands using a MegaBace™ sequencer (Molecular Dynamics, Inc., Sunnyvale, Calif., USA). Sequencing both strands provided us with the exact chemical structure of the cDNA, which is shown in FIGS. 3A–3J and further presented in the SEQUENCE LISTING as SEQ ID NO:1, and placed us in actual physical possession of the entire set of single-base incremented fragments of the sequenced clone, starting at the 5' and 3' termini.

A 398 bp fragment of PAPP-Ea cDNA (nt 2314 to 2711, including part of exon 4, the whole of exon 5, and part of exon 6) was prepared by PCR using PAPP-Ea cDNA as template; the fragment was thereafter labeled by random priming and used to probe a northern blot of 12 tissues (leukocyte, lung, placenta, small intestine, liver, kidney, spleen, thymus, colon, skeletal muscle, heart and brain). Blot (not shown) confirmed the placenta-specific expression pattern. In addition, the random priming placed us in possession of a near complete set of fragments of the 398 bp PAPP-Ea cDNA fragment.

Further cDNA clones were obtained from the same cDNA library using primers designed to capture the entire PAPP-Ea ORF; these efforts identified two splice variants that we designated PAPP-Eb and PAPP-Ec, respectively.

The PAPP-Eb and PAPP-Ec cDNAs were sequenced on both strands using a MegaBace™ sequencer (Molecular Dynamics, Inc., Sunnyvale, Calif., USA). Sequencing both strands provided us with the exact chemical structure of the PAPP-Eb cDNA, shown in FIGS. 4A–4I and further presented in the SEQUENCE LISTING as SEQ ID NO:8, and of the PAPP-Ec cDNA, shown in FIGS. 5A–5G and further presented in the SEQUENCE LISTING as SEQ ID NO:10. Sequencing further placed us in actual physical possession of the entire set of single-base incremented fragments of the sequenced clones, starting at the 5' and 3' termini.

pAPP-Ea, PAPP-Eb, and PAPP-Ec cDNAs were deposited at the American Type Culture Collection on May 23, 2001, under accession numbers PTA-3399, PTA-3400, and PTA-3401, respectively.

As shown in FIGS. 3A–3J, the PAPP-Ea cDNA spans 6719 nucleotides and contains an open reading frame from nucleotide 767 through and including nt 6142 (inclusive of termination codon), predicting a protein of 1791 amino acids with a (posttranslationally unmodified) molecular weight of 198.6 kD. The clone appears full length, with the reading frame opening with a methionine and terminating with a stop codon before a 3' poly-A tail.

As further shown in FIGS. 4A–4I and 5A–5G, respectively, splice variants PAPP-Eb and PAPP-Ec are 5461 and 4158 nt, respectively. Because the two clones were obtained using a 5' primer designed to amplify only the PAPP-Ea coding region, the clones lack 5' untranslated region (5' UT) ; we presume that the 5' UT of these two clones, both of which start with the same exon as PAPP-Ea, should be identical to that for the PAPP-Ea clone. The PAPP-Eb and PAPP-Ec clones encode proteins of 1770 (PAPP-Eb) and 1385 (PAPP-Ec) amino acids, respectively, with predicted (post-translationally unmodified) molecular weights of 196 kD and 152 kD, respectively.

BLAST query of genomic sequence identified four BACs, spanning 265 kb, that constitute the minimum set of clones encompassing the three cDNA sequences. Based upon the known origin of the four BACs (GenBank accession numbers AL031734, AC027620, AL139282, and AL031290), the PAPP-E gene can be mapped to human chromosome 1q24.1–1q25.2.

Comparison of the cDNA and genomic sequences identified 23 exons. Exon organization is listed in Table 2.

TABLE 2 hPAPP-E Exon Structure

| Exon no. | cDNA range (PAPP-Ea) | genomic range | BAC accession |
|---|---|---|---|
| 1 | 1–1685 | 102055–103564 | AL031734.9 |
| 2 | 1686–2757 | 140847–141918 | |
| 3 | 2758–2903 | 122946–120931 | AC027620.4 |
| 4 | 2904–3197 | 172521–172228 | |
| 5 | 3198–3390 | 170533–170341 | |
| 6 | 3391–3512 | 166922–166801 | |
| 7 | 3513–4002 | 163562–163073 | |
| 8 | 4003–4131 | 160055–159927 | |
| 9 | 4132–4223 | 156303–156212 | |
| 10 | 4224–4417 | 16422–16229 | |
| 11 | 4418–4564 | 115036–114890 | AL039282.4 |
| 12 | 4565–4700 | 87245–87110 | |
| 13 | 4701–4917 | 86891–86675 | |
| 14 | 4918–5089 | 60806–60635 | |
| 15 | 5090–5267 | 56865–56688 | |
| 16 | 5268–5481 | 55505–55292 | |
| 17 | 5482–5650 | 10208–10376 | AL031290.1 |
| 18 | 5651–5786 | 11746–11881 | |
| 19 | 5787–5896 | 13959–14068 | |
| 20 | 5897–5968 | 20460–20531 | |

TABLE 2-continued hPAPP-E Exon Structure

| Exon no. | cDNA range (PAPP-Ea) | genomic range | BAC accession |
|---|---|---|---|
| 21 | 85bp* (PAPP-Eb only) | 23336–23420 | |
| 22 | 5969–6067 | 60572–60670 | |
| 23 | 6068–6707 | 62779–63418 | |

FIG. 2 schematizes the exon organization of the PAPP-Ea, Eb, and Ec clones.

Insertion of the 85 bp exon 21 uniquely in PAPP-Eb leads to a downstream frame shift, shown by shading of exon 21, with earlier termination of translation. PAPP-Ec lacks exons 2, 3 and 21.

The sequence of the PAPP-Ea cDNA was used as a BLAST query into the GenBank nr and dbEst databases. The nr database includes all non-redundant GenBank coding sequence translations, sequences derived from the 3-dimensional structures in the Brookhaven Protein Data Bank (PDB), sequences from SwissProt, sequences from the protein information resource (PIR), and sequences from protein research foundation (PRF). The dbEst (database of expressed sequence tags) includes ESTs, short, single pass read cDNA (mRNA) sequences, and cDNA sequences from differential display experiments and RACE experiments.

BLAST search identified multiple human ESTs, mainly from placental sources, one EST from mouse (AI157031), one from rat (AW916144), and one from cow (AW660476) as having sequence closely related to PAPP-Ea. BLAST search also identified as closely related a newly described human gene, termed PAPP-E, further described in Farr et al., *Biochim. Biophys. Acta* 1493:356–362 (October 2000), and human pregnancy-associated protein-A (PAPP-A).

Because the PAPP-E clone described by Farr et al. appears to be either another isoform, or an incomplete clone, of the gene that we have identified, we have named our gene PAPP-E and termed the Farr et al. clone PAPP-Ef ("f" in deference to the authors).

As shown in FIG. 2, the PAPP-Ef cDNA includes only a portion of exon 1, and is thereafter identical (with a single nucleotide change) to PAPP-Ea, including all of exons 2–20, 22 and 23. The exact start of the PAPP-Ef and PAPP-Ef translations are shown on each of FIGS. 3A and 3B, 4A, and 5A. We detect only a single nucleotide difference between PAPP-Ea and PAPP-Ef in the region in which they are coextensive.

Globally, PAPP-Ea resembles human (44% amino acid identity and 63% amino acid similarity) and mouse (46% amino acid identity and 63% amino acid similarity) PAPP-A protein.

Motif searches using Pfam (http://pfam.wustl.edu), SMART (http://smart.embl-heidelberg.de), and PROSITE pattern and profile databases (http://www.expasy.ch/prosite), identified several known domains shared with PAPP-A.

FIG. 1 shows the domain structure of PAPP-A and all known isoforms of the PAPP-E protein.

As schematized in FIG. 1, our newly isolated isoforms—PAPP-Ea, PAPP-Eb, and PAPP-Ec—share certain protein domains and an overall structural organization with PAPP-A; in conjunction with a pattern of expression strikingly similar to that of PAPP-A, with high level expression in placenta, the shared structural features strongly imply that the three PAPP-E isoforms play a similar role in regulating the activity of a plasma borne growth factor(s), possibly IGF, which in turn is important for maintenance of pregnancy and/or normal fetal development, making the PAPP-E isoforms clinically useful diagnostic markers and potential therapeutic agents.

Like PAPP-A, all three novel isoforms have the zinc-binding domain ("zinc") characteristic of metzincin superfamily metalloproteases, defined by the degenerate motif "<u>HE</u>XX<u>H</u>XX<u>G</u>XX<u>H</u>", where invariant residues are shown underlined and variable residues are shown as "X". In PAPP-Ea, the longest isoform, the zinc binding domain occurs at residues 733–743 with sequence <u>HE</u>VG<u>H</u>VL<u>G</u>LY<u>H</u>; the sequence is underlined in FIG. 3E.

In common with PAPP-A, all three novel isoforms of PAPP-E have an at least four-fold repetition near the C-terminus of the short consensus repeat ("SCR"; alternatively denominated "sushi"domain) (residues 1396–1459, 1464–1521, 1525–1590, and 1595–1646, numbered as in PAPP-Ea). Relaxation of certain bioinformatic parameters suggests the presence of a fifth SCR domain.

In common with PAPP-A, all three novel isoforms of PAPP-E also have at least one "NL" (notch-lin, also termed lin notch repeat, or "LNR") domain, so-called due to its presence in Notch and Lin-12 proteins, both of which proteins regulate early tissue differentiation. As shown in FIG. 1, PAPP-Ea possesses three NL domains in the same general spaced relationship to the zinc domain as is found in PAPP-A. PAPP-Eb, in contrast, lacks the C-terminal NL domain, whereas PAPPE-c, the shortest of the novel isoforms, lacks the two NL domains on the N-terminal side of the zinc-binding domain.

The four-fold repetition of SCR ("sushi") domains is characteristic of complement proteins and selectins. Five-fold repetition of SCR domains with further presence of at least one NL domain has been previously identified in complement decay-accelerating factor and P-selectin.

In contrast to PAPP-A, two of the novel isoforms of PAPP-E—PAPP-Ea and PAPP-Eb—have a laminin G domain. Laminin G domains are found in a number of extracellular and receptor proteins, and are implicated in interactions with cellular receptors (integrins, alpha-dystroglycan), sulfated carbohydrates and other extracellular ligands.

In contrast to PAPP-A, all three novel isoforms of PAPP-E contain nuclear localization signals ("NLS"); with concurrent presence of a leader sequence (not shown), these signals suggest that all three PAPP-E isoforms can be secreted and also localize to the cell nucleus.

Possession of the genomic sequence permitted search for promoter and other control sequences for the hPAPP-E gene.

A putative transcriptional control region, inclusive of promoter and downstream elements, was defined as 1 kb around the transcription start site, itself defined as the first nucleotide of the PAPP-Ea cDNA clone. The region, drawn from sequence of BAC AL031734.9, has the following sequence, where nucleotide number 1001 is the transcription start site:

```
                                      [SEQ ID NO:65]
tcttccccatcctttccatccatttcaaatcaattggaaa     40
catggttccttgggtctagctgttcatttttgtaaattac     80
ttattttgaacatctcattgtttatttgctcactcagcat    120
atggtgacttttagtaacttcagattgagaaacttctgag    160
ataaaaaggagacctatgtagtatgaattcatggcatttc    200
catttagtacttctcacagcaggatacttgatttctcctt    240
tctcccatgtccgatttaaagtgaatttaagatattgttc    280
ttttaaatccccaatgattgaacaaagtaagaaaaaatac    320
tttgttttgtttgtgacaaaacaaaagaaaaatacaaggg    360
atccctaaaaggttagtgtgggcttattaggcagtaggta    400
gatctgttcacagtaagtgtgtgtgtgtgtgtgtgtgtgt    440
gtgtgagagagagagagagagagagagggagaatacacac    480
agagaagagtactccaaaacactattgatttttttgctatt   520
gattgtgtaggctgcggctgctgaaagagaaagcccgaga    560
tgtttactggggaaaccaagagtagcgtctgtcccctgtg    600
ccttggtgaggtgggtaggttttcaggaggaaggagggga    640
cagggaggagtaggtggagtgatgcattgaacttactagc    680
tttgacatcatcattgtctttaaatgaaaacaaaaacaaa    720
aacaaaaacaaaaaacaagaagatatttacaggcagacag    760
aaagggagccaaggggagcaggagagactggagagaacag    800
gtcccctgaagtgtatgctcttctttttgctcttttcccg    840
atcttcccaggaacccacaagactcccagaaggtgaagtt    880
aagagctcccagactcataaggttattagaacagcaaact    920
ggcaccccaaagaactttacggagacttgcaacctatcaa    960
caagttggatgagggattaaaagccttcaacaaccaacaa   1000.
```

Using PROSCAN, (http://bimas.dcrt.nih.gov/molbio/proscan/), no significant promoter was identified in the putative promoter region. However, transcription factor binding sites were identified using a web site at http://motif.genome.ad.jp/, including a group of SRY (sex-determining region Y gene product) binding sites (726.732; 714.720; 339.345 bp, with numbering according to SEQ ID NO:65).

We have thus identified three novel isoforms of a newly described human gene, PAPP-E, which share certain protein domains and an overall structural organization with PAPP-A; in conjunction with a pattern of expression strikingly similar to that of PAPP-A, with high level expression in placenta, the shared structural features strongly imply that the three PAPP-E isoforms play a role similar to PAPP-A, regulating the activity of a plasma-borne growth factor(s), possibly IGF, which in turn is important for maintenance of pregnancy and/or normal fetal development, making the PAPP-E isoforms clinically useful diagnostic markers and potential therapeutic agents.

EXAMPLE 2

Preparation and Labeling of Useful Fragments of Human PAPP-E Isoforms

Useful fragments of PAPP-Ea, PAPP-Eb, and PAPP-Ec clones are produced by PCR, using standard techniques, or solid phase chemical synthesis using an automated nucleic acid synthesizer. Each fragment is sequenced, confirming the exact chemical structure thereof.

The exact chemical structure of preferred fragments is provided in the attached SEQUENCE LISTING, the disclosure of which is incorporated herein by reference in its entirety. The following summary identifies the fragments whose structures are more fully described in the SEQUENCE LISTING:

| | | |
|---|---|---|
| SEQ ID NO:1 | nt | full length PAPP-Ea cDNA |
| SEQ ID NO:2 | nt | coding region of PAPP-Ea |
| SEQ ID NO:3 | aa | full length coding sequence of PAPP-Ea |
| SEQ ID NO:4 | nt | 5' sequence absent from PAPP-Ef clone |
| SEQ ID NO:5 | nt | 5' UT absent from PAPP-Ef clone (nt 1–766) |
| SEQ ID NO:6 | nt | N-terminal coding region absent from PAPP-Ef clone |
| SEQ ID NO:7 | aa | coding region of PAPPE-Ea from aa 1–19 [N terminal coding region absent from PAPP-Ef clone] |
| SEQ ID NO:8 | nt | full length PAPP-Eb cDNA |
| SEQ ID NO:9 | nt | coding region of PAPP-Eb cDNA |
| SEQ ID NO:10 | aa | full length coding sequence of PAPP-Eb (aa 1–1770) |
| SEQ ID NO:11 | nt | exon novel in PAPP-Eb (nt 5203–5287) |
| SEQ ID NO:12 | aa | CDS entirely within novel exon (aa 1735–1762) |
| SEQ ID NO:13 | aa | CDS due to frame shift (aa 1763–1770) |
| SEQ ID NO:14 | aa | CDS novel within PappE-b (aa 1735–1770) (inclusive of old nt) |
| SEQ ID NO:15 | nt | coding region of PAPP-Ec cDNA |
| SEQ ID NO:16 | aa | full length coding sequence of PAPP-Ec |
| SEQ ID NO:17 | nt | nt 892–951 (around splice junction) |
| SEQ ID NO:18 | aa | 20 amino acids centered about deletion: aa 298–317 |
| SEQ ID NO:19 | nt | exon 1 (from genomic sequence) |
| SEQ ID NO:20 | nt | exon 2 |
| SEQ ID NO:21 | nt | exon 3 |
| SEQ ID NO:22 | nt | exon 4 |
| SEQ ID NO:23 | nt | exon 5 |
| SEQ ID NO:24 | nt | exon 6 |
| SEQ ID NO:25 | nt | exon 7 |
| SEQ ID NO:26 | nt | exon 8 |
| SEQ ID NO:27 | nt | exon 9 |
| SEQ ID NO:28 | nt | exon 10 |
| SEQ ID NO:29 | nt | exon 11 |
| SEQ ID NO:30 | nt | exon 12 |
| SEQ ID NO:31 | nt | exon 13 |
| SEQ ID NO:32 | nt | exon 14 |
| SEQ ID NO:33 | nt | exon 15 |
| SEQ ID NO:34 | nt | exon 16 |
| SEQ ID NO:35 | nt | exon 17 |
| SEQ ID NO:36 | nt | exon 18 |
| SEQ ID NO:37 | nt | exon 19 |
| SEQ ID NO:38 | nt | exon 20 |
| SEQ ID NO:39 | nt | exon 21 |
| SEQ ID NO:40 | nt | exon 22 |
| SEQ ID NO:41 | nt | exon 23 |
| SEQ ID NO:42 | nt | 500 bp genomic amplicon centered about exon 1 |
| SEQ ID NO:43 | nt | 500 bp genonic amplicon centered about exon 2 |
| SEQ ID NO:44 | nt | 500 bp genoinic amplicon centered about exon 3 |
| SEQ ID NO:45 | nt | 500 bp genomic amplicon centered about exon 4 |
| SEQ ID NO:46 | nt | 500 bp genomic amplicon centered about exon 5 |
| SEQ ID NO:47 | nt | 500 bp genomic amplicon centered about exon 6 |
| SEQ ID NO:48 | nt | 500 bp genomic amplicon centered about exon 7 |
| SEQ ID NO:49 | nt | 500 bp genornic amplicon centered about exon 8 |
| SEQ ID NO:50 | nt | 500 bp genomic amplicon centered about exon 9 |
| SEQ ID NO:51 | nt | 500 bp genonic araplicon centered about exon 10 |
| SEQ ID NO:52 | nt | 500 bp genomic amplicon centered about exon 11 |
| SEQ ID NO:53 | nt | 500 bp genornic amplicon centered about exon 12 |
| SEQ ID NO:54 | nt | 500 bp genomic amplicon centered about exon 13 |
| SEQ ID NO:55 | nt | 500 bp genomic amplicon centered about exon 14 |
| SEQ ID NO:56 | nt | 500 bp genomic amplicon centered about exon 15 |
| SEQ ID NO:57 | nt | 500 bp genomic amplicon centered about exon 16 |
| SEQ ID NO:58 | nt | 500 bp genomic amplicon centered about exon 17 |
| SEQ ID NO:59 | nt | 500 bp genomic amplicon centered about exon 18 |
| SEQ ID NO:60 | nt | 500 bp genomic amplicon centered about exon 19 |
| SEQ ID NO:61 | nt | 500 bp genornic amplicon centered about exon 20 |
| SEQ ID NO:62 | nt | 500 bp genomic amplicon centered about exon 21 |
| SEQ ID NO:63 | nt | 500 bp genomic amplicon centered about exon 22 |
| SEQ ID NO:64 | nt | 500 bp genomic amplicon centered about exon 23 |
| SEQ ID NO:65 | nt | 1000 bp putative promoter |
| SEQ ID NOs:66–888 | nt | 17-mers scanning nt 1–823 of PAPP-Ea |
| SEQ ID NOs: 889–1711 | nt | 25-mers scanning nt 1–823 of PAPP-Ea |
| SEQ ID NOs: 1712–1796 | nt | 17-mers scanning SEQ ID NO:11 |
| SEQ ID NOs: 1787–1881 | nt | 25-mers scanning SEQ ID NO:25 |

Upon confirmation of the exact structure, each of the above-described nucleic acids of confirmed structure is recognized to be immediately useful as a PAPP-E-specific probe.

For use as labeled nucleic acid probes, the above-described PAPP-E nucleic acids are separately labeled by random priming. As is well known in the art of molecular biology, random priming places the investigator in possession of a near-complete set of labeled fragments of the template of varying length and varying starting nucleotide.

The labeled probes are used to identify the PAPP-E gene on a Southern blot, and are used to measure expression of PAPP-E isoforms on a northern blot and by RT-PCR, using standard techniques.

EXAMPLE 3

Production of PAPP-E Protein

In parallel, each of the full length PAPP-Ea, PAPP-Eb, and PAPP-Ec cDNA clones is separately cloned into the mammalian expression vector pcDNA3.1/HISA (Invitrogen, Carlsbad, Calif., USA), transfected into COS7 cells, transfectants selected with G418, and protein expression in transfectants confirmed by detection of the anti-Xpress™ epitope according to manufacturer's instructions. Protein is purified using immobilized metal affinity chromatography and vector-encoded protein sequence is then removed with enterokinase, per manufacturer's instructions, followed by gel filtration and/or HPLC.

Following epitope tag removal, each of PAPP-Ea, PAPP-Eb, and PAPP-Ec proteins is present at a concentration of at least 70%, measured on a weight basis with respect to total protein, and is free of acrylamide monomers, bis acrylamide monomers, polyacrylamide and ampholytes. Further HPLC purification provides PAPP-Ea, PAPP-Eb, and PAPP-Ec proteins at concentrations, respectively, of at least 95%, measured on a weight basis with respect to total protein.

EXAMPLE 4

Production of Anti-PAPP-E Antibody

Purified proteins prepared as in Example 3 are conjugated to carrier proteins and used to prepare murine monoclonal antibodies by standard techniques. Initial screening with the unconjugated purified proteins, followed by competitive inhibition screening using peptide fragments of the PAPP-E isoforms, identifies monoclonal antibodies with specificities in each of the following categories: antibodies that recognize all PAPP-E isoforms, antibodies that recognize PAPP-Eb alone, and antibodies that recognize PAPP-Ec alone.

EXAMPLE 5

Use of hPAPP-E Probes and Antibodies for Antenatal Diagnosis of Aneuploidy

After informed consent is obtained, peripheral blood samples are drawn from pregnant women at 14 weeks gestation and tested for PAPP-A levels by standard techniques and tested additionally for PAPP-E levels using anti-PAPP-E antibodies in a standard ELISA.

After pregnancy outcome is fully determined for all patients, tabulated results demonstrate a statistically significant decrease in the circulating maternal level of PAPP-E correlated with adverse outcome, and specifically with presence of either trisomy 18 or trisomy 21. Results further demonstrate that determination of concurrent PAPP-A and PAPP-E levels provides greater predictive value than either marker alone.

In a second series of experiments, chorionic villus samples obtained for purpose of antenatal fetal karyotyping are further examined for expression of PAPP-E isoforms.

In a first series of tests, total RNA is separately extracted from each CVS using a commercial kit and poly-$A^+$ RNA isolated with a commercial kit. A northern blot is prepared and probed with a radiolabeled PAPP-E nucleic acid probe. Specific hybridization is quantitated using a PhosphorImager (Molecular Dynamics, Inc., Sunnyvale, Calif., USA). RNA levels are normalized to expression levels of β-actin.

After pregnancy outcome is fully determined for all patients, tabulated results demonstrate that a statistically significant decrease in chorionic villus PAPP-E expression is correlated with adverse outcome, and specifically with presence of either trisomy 18 or trisomy 21. Results further demonstrate that determination of maternal serum PAPP-E levels in conjunction with fetal chorionic villus expression provides greater predictive value than either marker alone.

In a second series of tests, chorionic villus samples are prepared for immunohistochemical analysis by standard techniques. Anti-PAPP-E antibodies labeled with alkaline phosphatase are used to visualize PAPP-E protein in the CVS samples by enhanced chemiluminescence.

After pregnancy outcome is fully determined for all patients, tabulated results demonstrate a statistically significant decrease in chorionic villus PAPP-E protein expression is correlated with adverse outcome, and specifically with presence of either trisomy 18 or trisomy 21. Results further demonstrate that determination of maternal serum PAPP-E levels in conjunction with fetal chorionic villus expression provides greater predictive value than either marker alone.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. An isolated nucleic acid comprising a nucleotide sequence selected from the group consisting of:

(i) the nucleotide sequence of SEQ ID NO:1; (ii) the nucleotide sequence of SEQ ID NO:2; (iii) a nucleotide sequence that is a degenerate variant of the nucleotide sequence of SEQ ID NO:2; (iv) a sequence of a polynucleotide that encodes a polypeptide with the amino acid sequence of SEQ ID NO:3; and (v) a nucleotide sequence that is the complete complement of the nucleotide sequence of any one of (i)–(iv).

2. The isolated nucleic acid of claim 1, wherein said nucleic acid encodes a polypeptide having metalloproteinase activity.

3. The isolated nucleic acid of claim 1, wherein said nucleic acid is expressed in placental tissue.

4. The isolated nucleic acid of claim 1, further comprising at least one expression control element, wherein said polynucleotide is operably linked to said at least one expression control element.

5. The isolated nucleic acid of claim 1, wherein said isolated nucleic acid is detectably labeled.

6. The isolated nucleic acid of claim 1, wherein said isolated nucleic acid is attached to a substrate.

7. A microarray wherein at least one probe of said microarray is a nucleic acid according to claim 1.

8. A replicable vector comprising the isolated nucleic acid of claim 1.

9. A replicable vector comprising the isolated nucleic acid of claim 4.

10. An expression vector comprising the isolated nucleic acid of claim 1.

11. A host cell transformed to contain the nucleic acid of claim 1, or the progeny thereof.

12. A host cell transformed to contain the replicable vector of claim 8, or the progeny thereof.

13. A host cell transformed to contain the replicable vector of claim 9, or the progeny thereof.

14. A host cell transformed to contain the expression vector of claim 10, or the progeny thereof.

* * * * *